(12) United States Patent
Cappuccilli et al.

(10) Patent No.: US 8,716,195 B2
(45) Date of Patent: May 6, 2014

(54) ANTIBODY ULTRAHUMANIZATION BY PREDICTED MATURE CDR BLASTING AND COHORT LIBRARY GENERATION AND SCREENING

(75) Inventors: Guido Cappuccilli, San Mateo, CA (US); Roberto Crea, San Mateo, CA (US); Takeuchi Toshihilo, Oakland, CA (US); Randy Shen, Sunnyvale, CA (US); Ramesh R. Bhatt, Belmont, CA (US); Nurten Beyaz-Kavuncu, Chesterfield, MO (US)

(73) Assignee: Bioren, Inc., Chesterfield, MO (US)

( * ) Notice: Subject to any disclaimer, the term of this patent is extended or adjusted under 35 U.S.C. 154(b) by 1281 days.

(21) Appl. No.: 12/085,175

(22) PCT Filed: Nov. 10, 2006

(86) PCT No.: PCT/IB2006/003288
§ 371 (c)(1),
(2), (4) Date: Sep. 2, 2009

(87) PCT Pub. No.: WO2007/054816
PCT Pub. Date: May 18, 2007

(65) Prior Publication Data
US 2009/0318297 A1 Dec. 24, 2009

Related U.S. Application Data

(60) Provisional application No. 60/736,726, filed on Nov. 14, 2005.

(51) Int. Cl.
*C40B 50/06* (2006.01)
(52) U.S. Cl.
USPC ........................................................ 506/26

(58) Field of Classification Search
None
See application file for complete search history.

(56) References Cited

U.S. PATENT DOCUMENTS

| | | | |
|---|---|---|---|
| 5,667,988 A | 9/1997 | Barbas et al. |
| 5,798,208 A | 8/1998 | Crea |
| 5,830,650 A | 11/1998 | Crea |
| 5,852,186 A | 12/1998 | Sodroski et al. |
| 6,096,551 A | 8/2000 | Barbas et al. |
| 6,537,776 B1 | 3/2003 | Short |
| 6,649,340 B1 | 11/2003 | Crea |
| 2005/0136428 A1 | 6/2005 | Crea |

FOREIGN PATENT DOCUMENTS

WO　　WO91/15581　　10/1991

OTHER PUBLICATIONS

Knappik et al. (Feb. 11, 2000) Journal of Molecular Biology vol. 296 pp. 57 to 86.*
Knappik et al. (Feb. 11, 2000) Journal of Molecular Biology vol. 296 pp. 57 to 86 including supplementary table 1.*
26-10 anti-digoxin Fab structure summary from RCSB Protein Data Bank Downloaded Mar. 23, 2012 from http://www.rcsb.org/pdb/explore/explore.do?structureId=1IGJ.*

(Continued)

Primary Examiner — Christian Boesen
(74) Attorney, Agent, or Firm — Pfizer Inc.

(57) ABSTRACT

Methods and compositions directed to improved universal antibody libraries that rationally exploit human diversity information contained within reference antibody libraries, such as universal antibody libraries, are disclosed. The disclosed processes involve use of a query CDR sequence to guide incorporation of human antibody diversity present within the reference library into cohort libraries of the invention. Methods for making and screening such cohort libraries for isolating therapeutics suitable for treating disease are also disclosed.

2 Claims, 194 Drawing Sheets

(56) References Cited

OTHER PUBLICATIONS 26-10 anti-digoxin Fab structure sequence from RCSB Protein Data Bank Downloaded Mar. 23, 2012 from http://www.rcsb.org/pdb/explore/remediatedSequence.do?structureId=1IGJ.*

Burks, et al., In vitro scanning saturation mutagenesis of an antibody binding pocket, Proc. Natl. Acad. Sci, 1997 94:412-417.

Hanes, et al., Picomolar affinity antibodies from a fully synthetic naive library selected and evolved by ribosome display, Nature Biotechnology 2000, 18:1287-1292.

Crameri, et al., Construction and Evolution of Antibody-Phage Libraries by DNA shuffling, Nature Medicine, 1996 2:100-102.

Gerstner, et al., Sequence Plasticity in the Antigen-Binding Site of a Therapeutic Anti-HER2 antibody, J Mol. Biol., 2002 321:851-862.

Glaser et al., Antibody Engineering by Codon-based Mutagenesis in a Filamentous Phage Vector System, The Journal of Immunology 1992 149(12)3903-13.

Roberts, et al., Antibody Remodeling: A General Solution to the Design of a Metal-Coodination Site in an antibody Binding Pocket, PNAS 1990, 87:6654-58.

Chatellier, et al., Combinatorial Scanning Site-Directed Mutagenesis, Gene Cloning and Analysis:Current Innovations 1997, 117-132.

Rajpal, et al., A general method for greatly improving the affinity of antibodies by using combinatorial libraries, PNAS 2005, 102(24):8466-71.

Fellhouse, et al., Synthetic antibodies from a four-amino-acid code:A dominant role for tyrosine in antigen recognition, PNAS 2004 V101 p. 12467-72.

Sidhu, et al., Phage-displayed Antibody Libraries of Synthetic Heavy Chain Complementarity Determining Regions, J Mol. Biol. 2004 V338 p. 299-10.

* cited by examiner

FIG. 3

- Generate all combinatorial CDR sequences predicted from CDR positional frequency analysis
  - Heavy chains: CDR1s, CDR2s, & CDR3s
  - Light chains: (κ & λ) CDR1s, CDR2s, & CDR3s
- Assemble CDR sequences as framework and isotype matched polypeptides individually for all Heavy and Light Chains
  -- Heavy: VH-1 & VH-3
  -- Light:
    • kappa (VK-1 & VK-3)
    • lambda (VL-1, VL-2, & VL-3)
  -- Alternatively assemble CDR sequences and framework shuffle
    • Ex.) CDRL1 – Vk1, CDRL2 – Vk3
- Generate all combinations of Heavy and Light Chains as a complete collated UAL

| | FR1 | CDR1 | FR2 | CDR2 | FR3 |
|---|---|---|---|---|---|
| 1-e | QVQLVQSGAEVKKPGSSVKVSCKASGGTF | SS----YAIS | WVRQAPGQGLE | WMGGIIPIFGTAN | YAQKFQGRVTITADKSTSTAYMELSSLRSEDTAVYYC |
| 3-07 | EVQLVESGGGLVQPGGSLRLSCAASGFTF | SS----YWMS | WVRQAPGKGLE | WVANIKQDGSEKY | YVDSVKGRFTISRDNAKNSLYLQMNSLRAEDTAVYYC |
| 3-11 | QVQLVESGGGLVKPGGSLRLSCAASGFTF | SD----YYMS | WIRQAPGKGLE | WVSYISSSGSTIY | YADSVKGRFTISRDNAKNSLYLQMNSLRAEDTAVYYC |
| 3-23 | EVQLLESGGGLVQPGGSLRLSCAASGFTF | SS----YAMS | WVRQAPGKGLE | WVSAISGSGGSTY | YADSVKGRFTISRDNSKNTLYLQMNSLRAEDTAVYYC |
| 3-30* | QVQLVESGGGVVQPGRSLRLSCAASGFTF | SS----YGMH | WVRQAPGKGLE | WVAVISYDGSNKY | YADSVKGRFTISRDNSKNTLYLQMNSLRAEDTAVYYC |

$V_\kappa$

| | FR1 | CDR1 | FR2 | CDR2 | FR3 |
|---|---|---|---|---|---|
| I-L1 | DIQMTQSPSSLSASVGDRVTITCRASQGI | SN----YLAWF | QQKPGKAPK | SLIYAASSLQ | SGVPSRFSGSGSGTDFTLTISSLQPEDFATYYC |
| III-A27 | EIVLTQSPGTLSLSPGERATLSCRASQSV | SSS---YLAWY | QQKPGQAPR | LLIYGASSRA | TGIPDRFSGSGSGTDFTLTISRLEPEDFAVYYC |
| III-L20 | EIVLTQSPATLSLSPGERATLSCRASQGV | SS----YLAWY | QQKPGQAPR | LLIYDASNRA | TGIPARFSGSGPGTDFTLTISSLEPEDFAVYYC |

$V_\lambda$

| | FR1 | CDR1 | FR2 | CDR2 | FR3 |
|---|---|---|---|---|---|
| 1b | QSVLTQPPSVSAAPGQKVTISCSGSSSN | IGN-NYVSWY | QQLPGTAPK | LLIYDNNKRP | SGIPDRFSGSKSGTSATLGITGLQTGDEADYYC |
| 2a2* | QSALTQPASVSGSPGQSITISCTGTSSD | VGGYNYVSWY | QQHPGKAPK | LMIYEVSNRP | SGVSNRFSGSKSGNTASLTISGLQAEDEADYYC |
| 3r | SYELTQPPSVSVSPGQTASITCSGDKLG | D---KYACWY | QQKPGQSPV | LVIYQDSKRP | SGIPERFSGSNSGNTATLTISGTQAMDEADYYC |
| 31 | SSELTQDPAVSVALGQTVRITCQGDSLR | S----YYASWY | QQKPGQAPV | LVIYGKNNRP | SGIPDRFSGSSSGNTASLIITGAQAEDEADYYC |

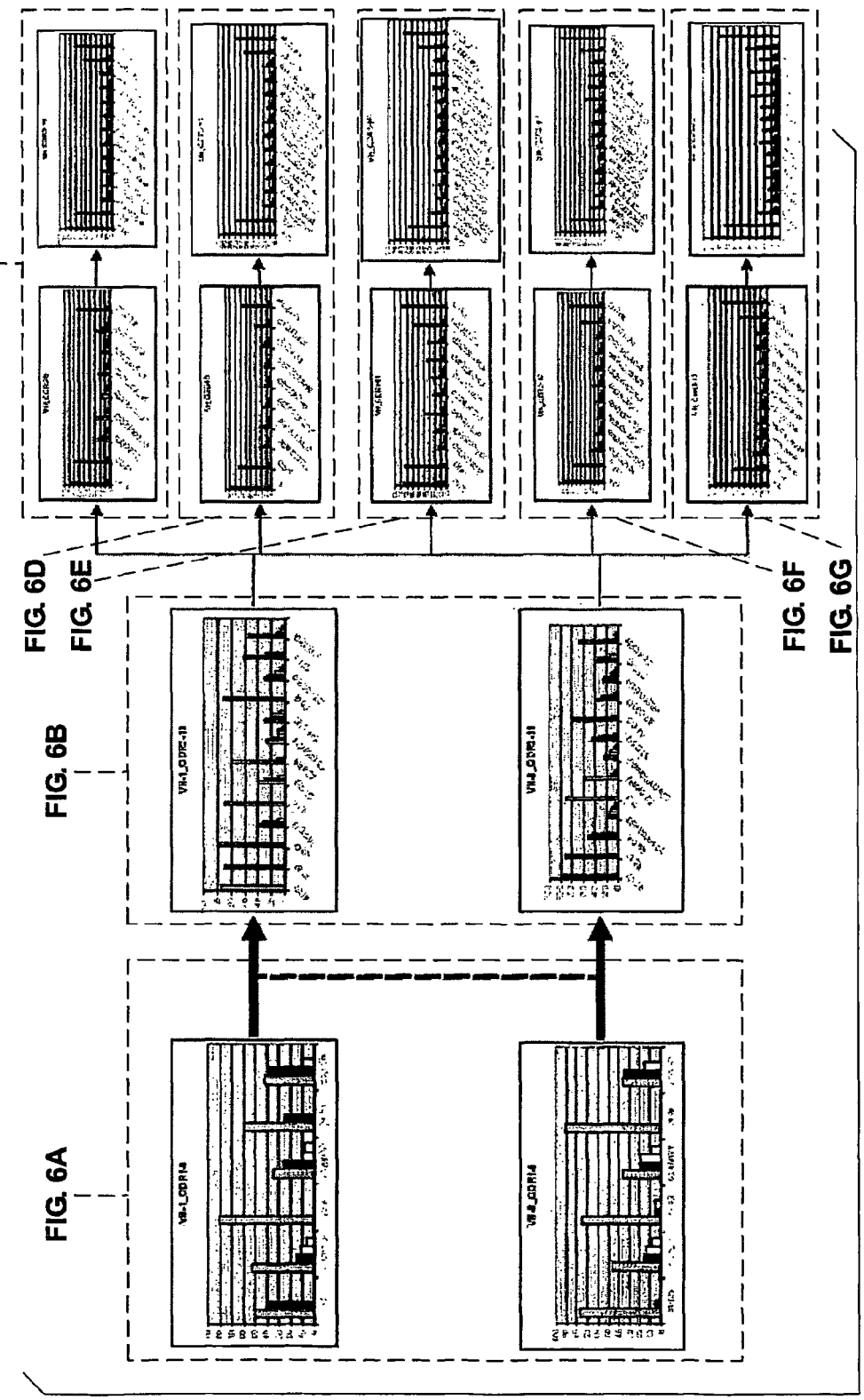

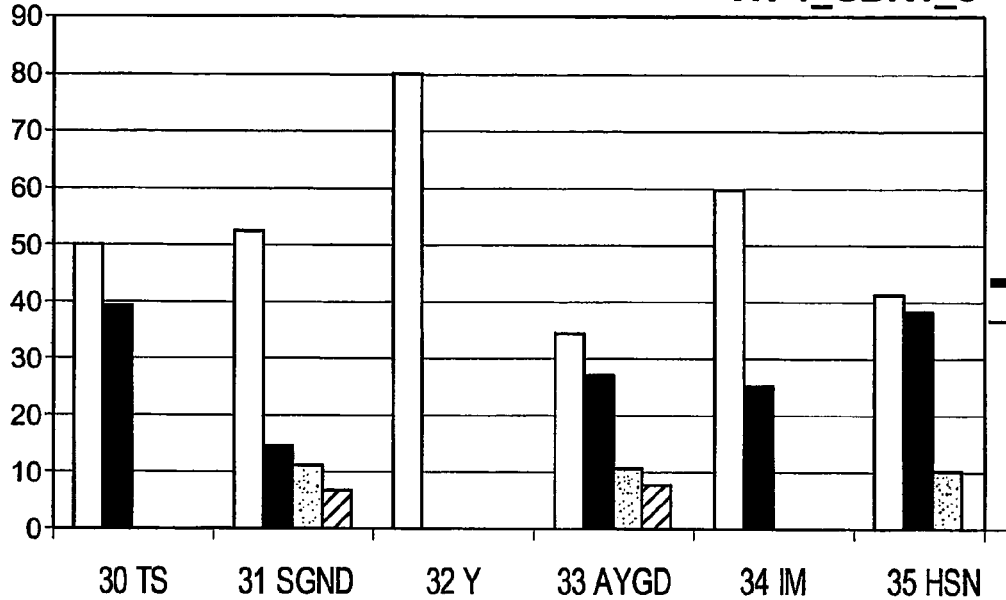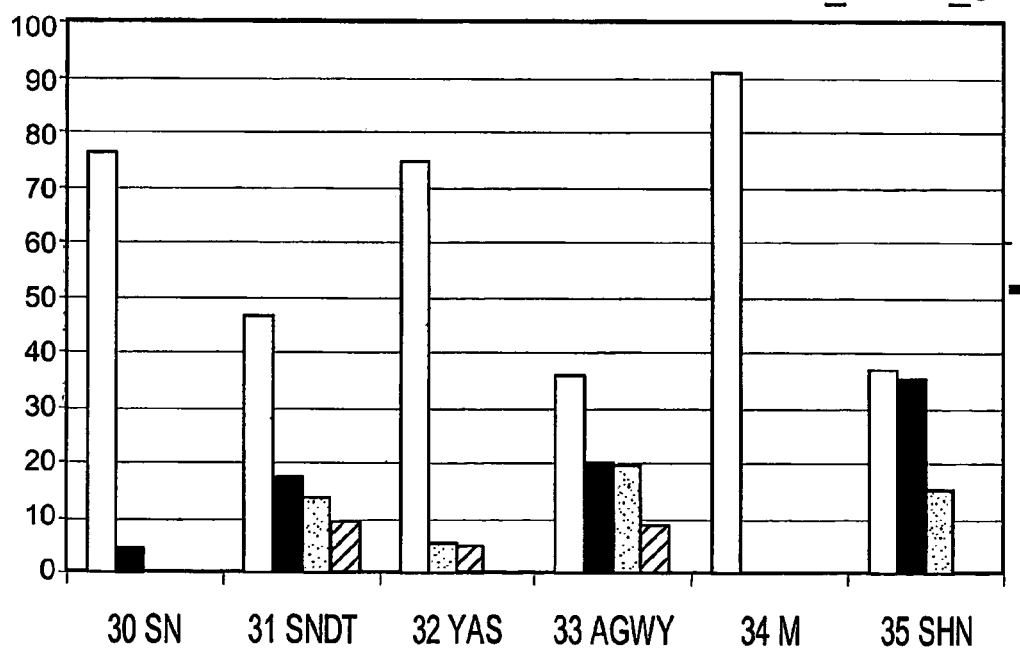

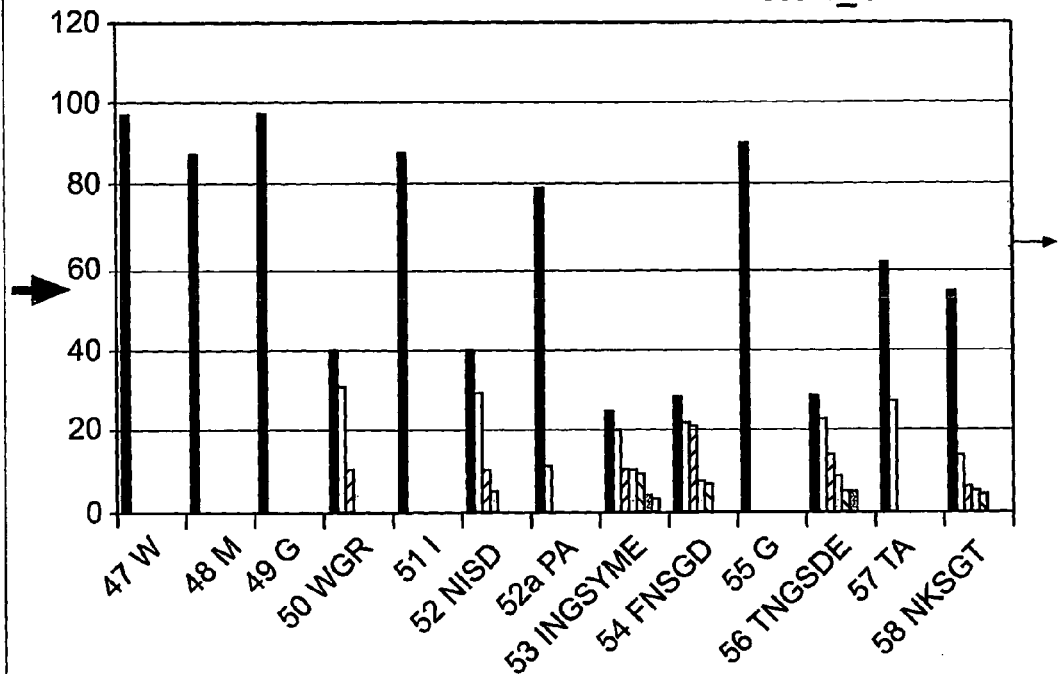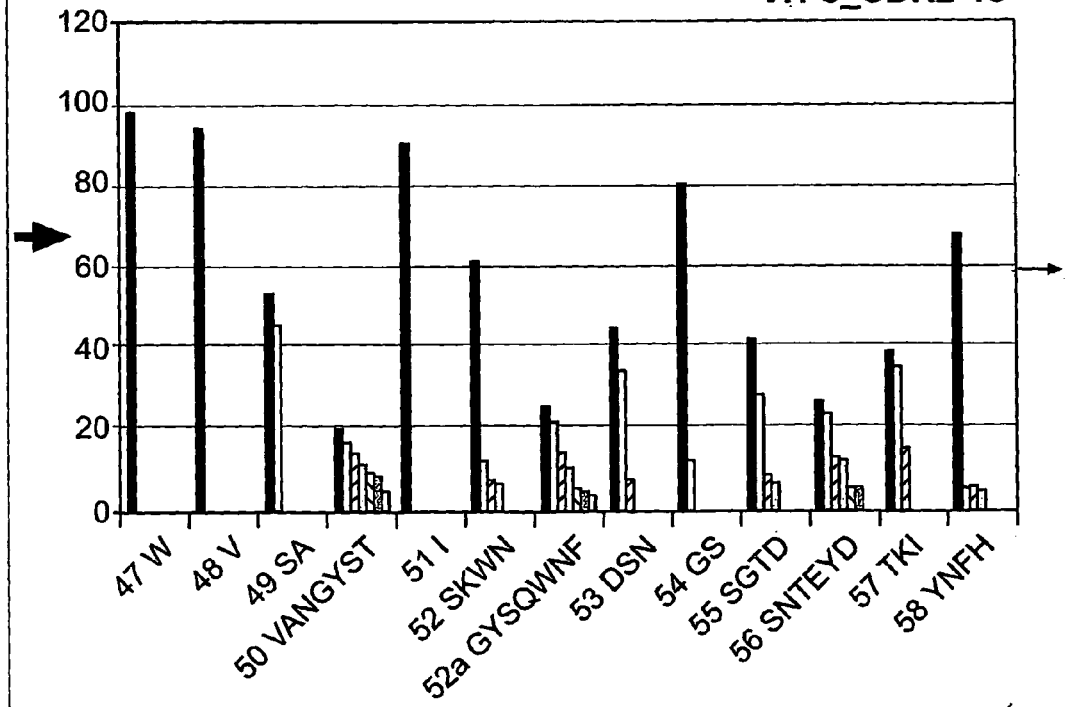
FIG. 6B

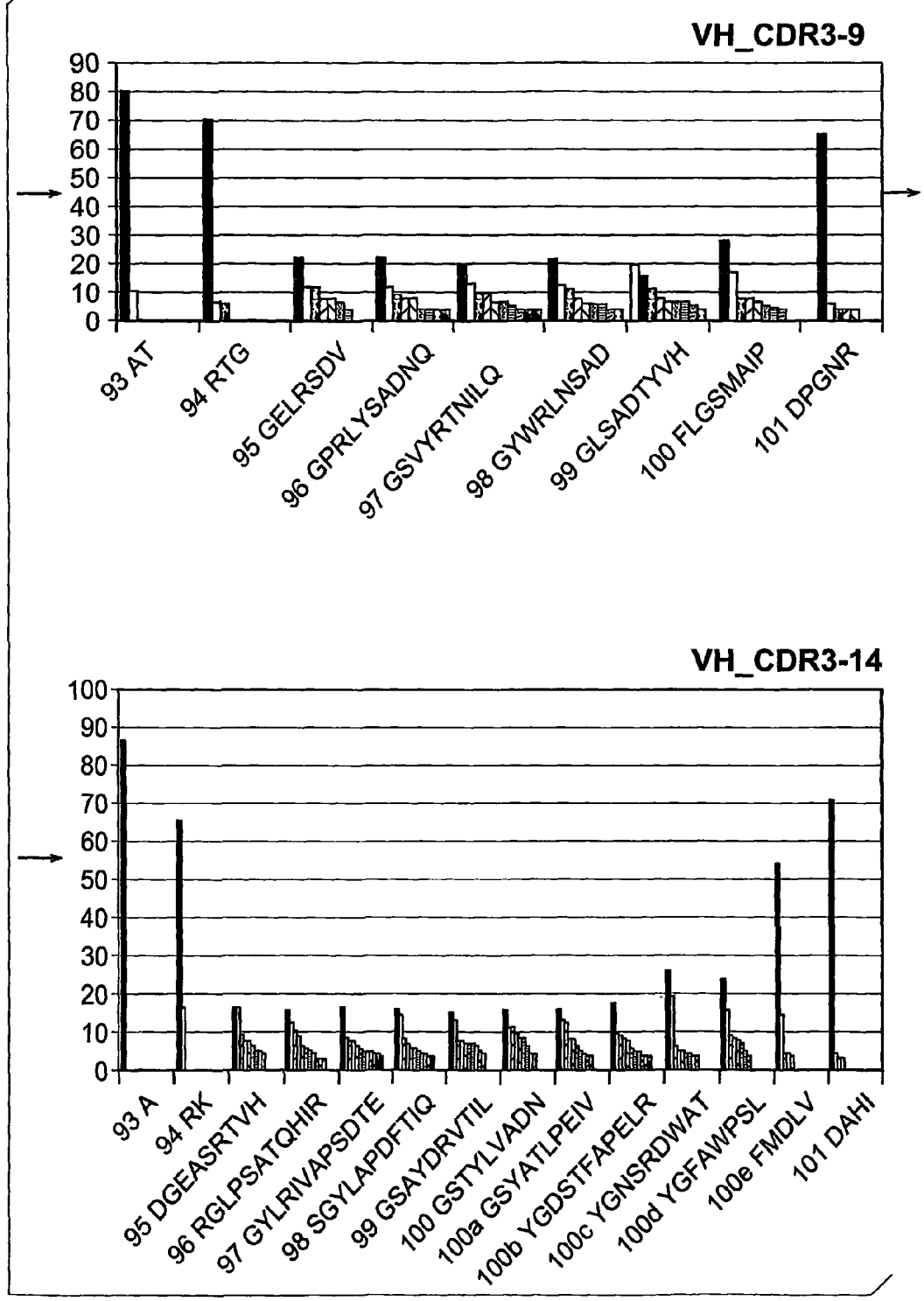

FIG. 6E
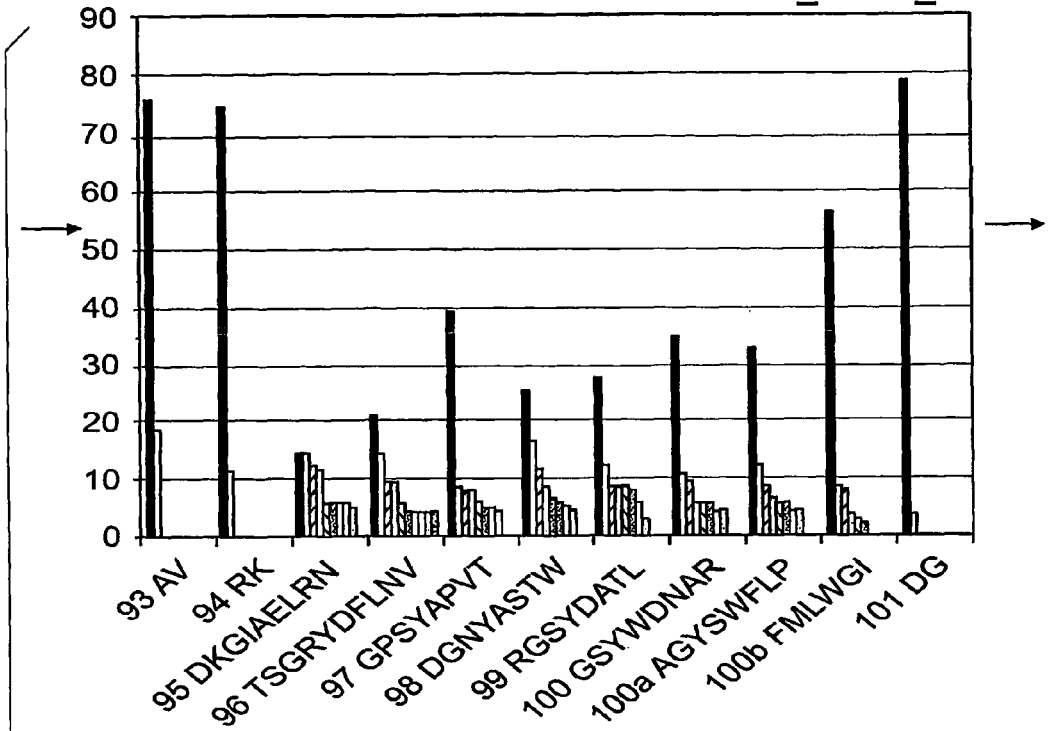
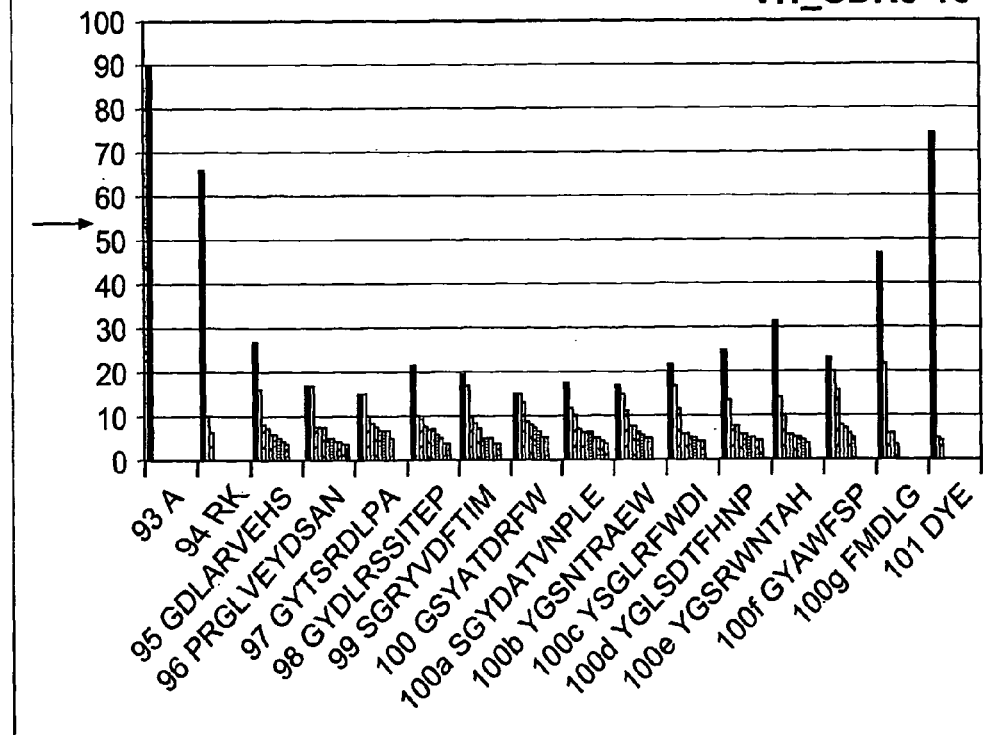

FIG. 6F
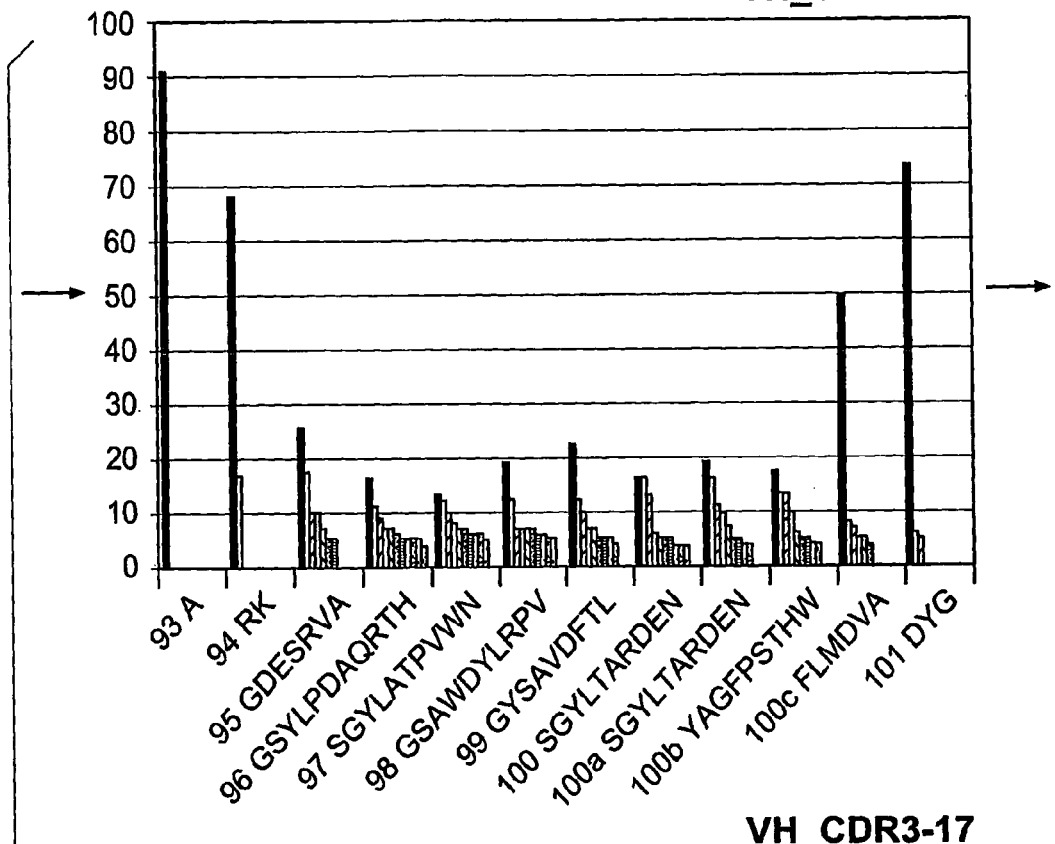
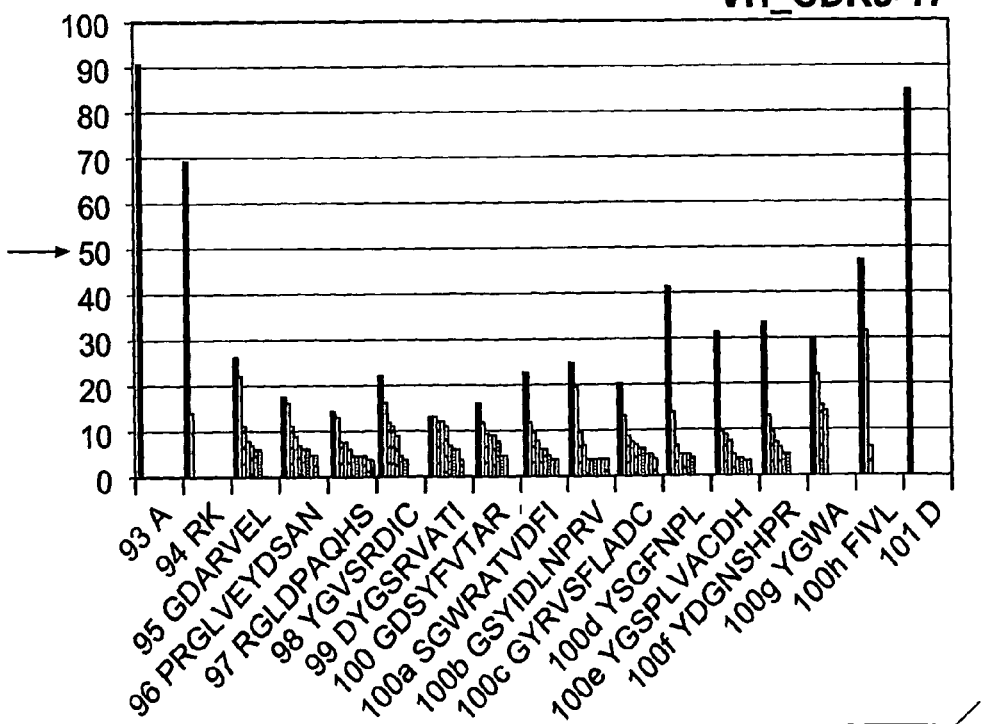

FIG. 7 (Key)
FIG. 7A
FIG. 7B
FIG. 7C
FIG. 7D
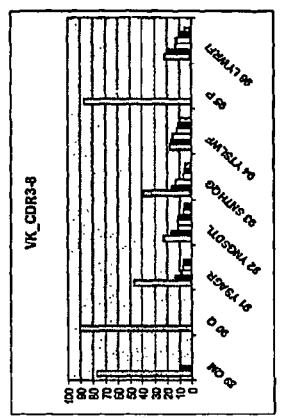
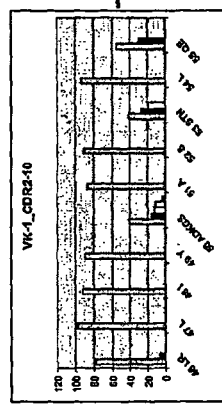
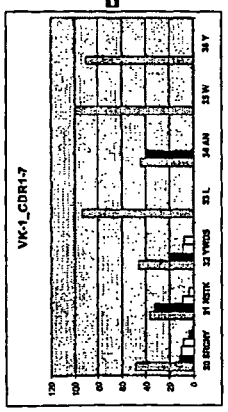
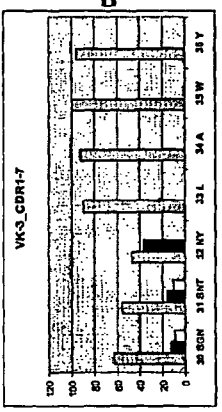

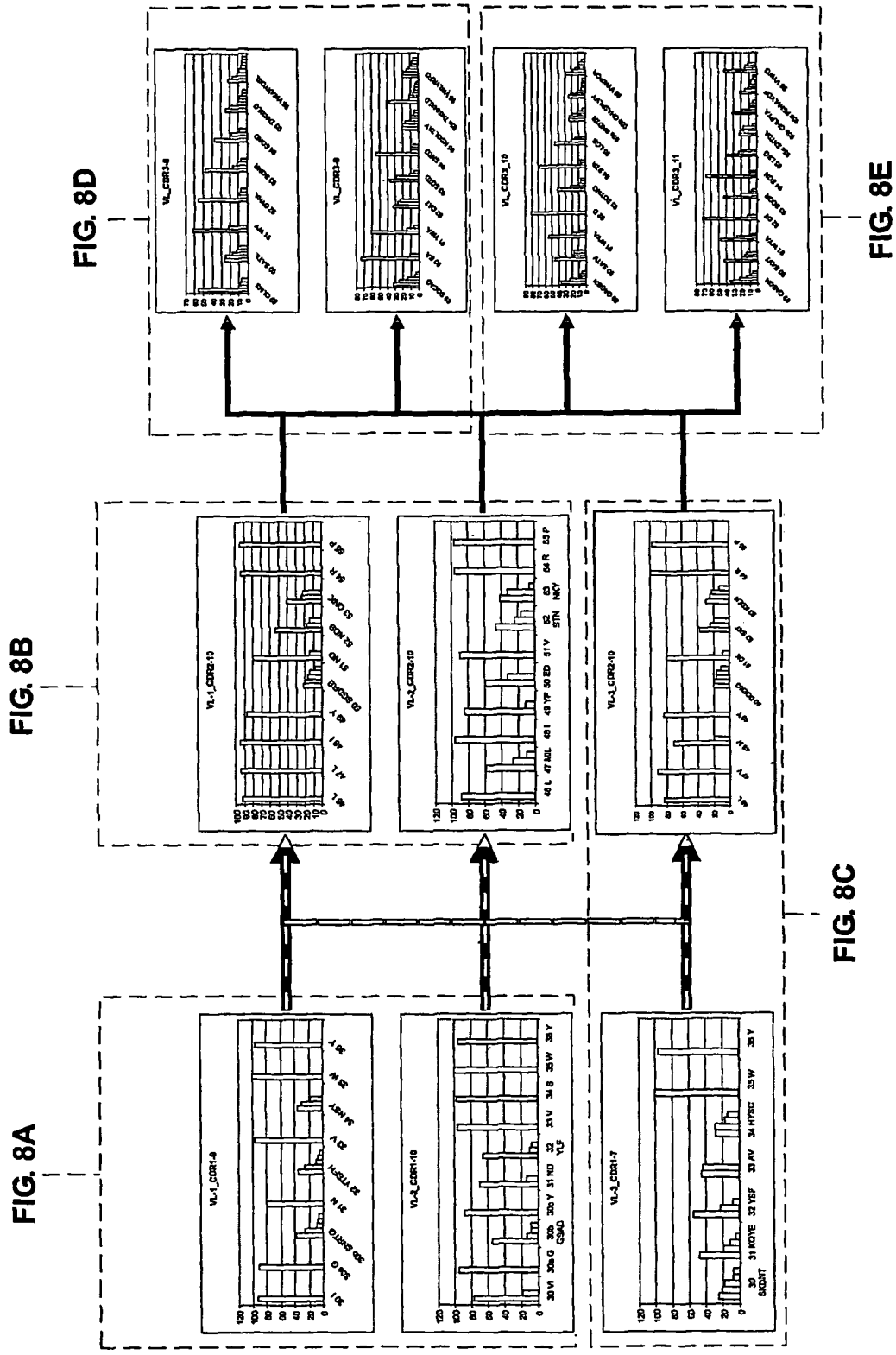
FIG. 8 (Key)

FIG. 9B
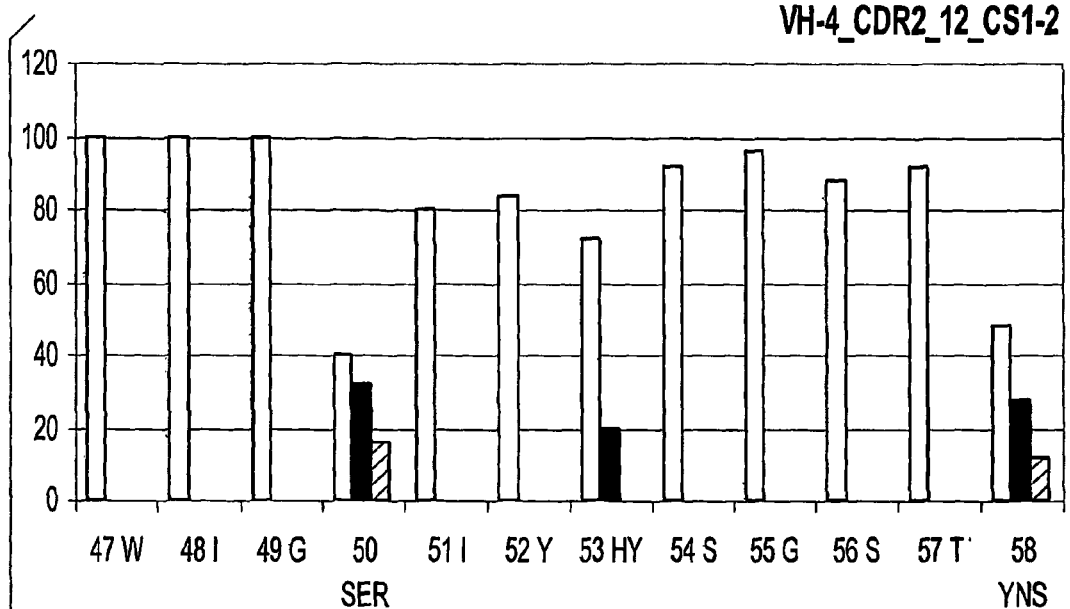
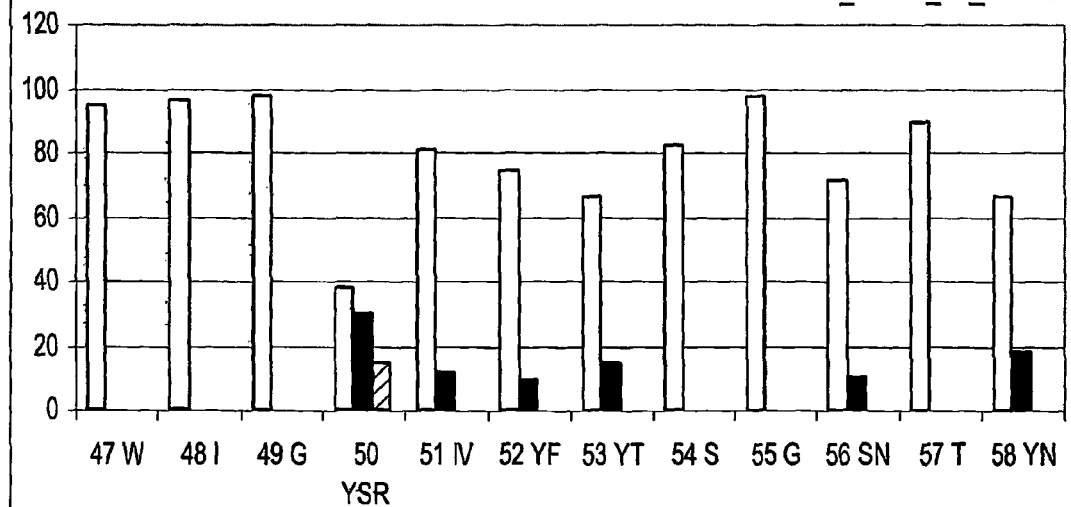

FIG. 10

VH-1 CDR1

| UAL constituents | | | | | | |
|---|---|---|---|---|---|---|
| | | | | S | A | |
| | | | | G | Y | H |
| | | | | N | G | I | S |
| | T | | | D | D | M | N |
| mouse probe | T | S | | Y | G | M | N |
| library encodes | T | | N | Y | G | M | N |
| possible residues | 1 | 1 | 1 | 1 | 1 | 1 | 1 | No Diversity |
| | | | | | | | | Product 1 |

VH-3 CDR1

| UAL constituents | | | | | | |
|---|---|---|---|---|---|---|
| | | | | | A | |
| | | S | Y | | G | S |
| | | N | A | | W | H |
| | | D | S | | Y | N |
| mouse probe | | T | N | | Y | N |
| library encodes | S or N | T | N | N | Y | G | M | N |
| possible residues | 2 | 1 | 1 | 1 | 1 | 1 | 1 | Diversity 2 |

↑ Positional mismatch

CDR1
Library diversity
"Product of possible residues"

Steps
- Determine contact CDRs in probe mAb
- Query UAL for positional matches with probe sequence
- Generate libraries where
  - Positional matches are fixed with probe sequences
  - Positional mismatches are enc

FIG. 11

VH-1 CDR2 Library Diversity 320

| VH-1 CDR2 | | | | | | | | | | | |
|---|---|---|---|---|---|---|---|---|---|---|---|
| UAL constituents | | | | W G R | I | N S Y G M Y | P A T | F S N G T | T N G S D E | N K S G T | |
| mouse probe | W | M | G | W | I | N | P | S | N | A | K | |
| library encodes | W | M | G | W | – | N | P/A | Y F/S/N/G | Y T/N/G/S/D | T/A | N/K/S/G | |
| possible residues | 1 | 1 | 1 | 1 | 1 | 1 | 2 | 4 | 5 | 2 | 4 | |

VH-3 CDR2 Library Diversity 7056

| VH-3 CDR2 | | | | | | | | | | |
|---|---|---|---|---|---|---|---|---|---|---|
| UAL constituents | V A N | S A | V A N G Y S T | S K Y W N | D S N Y | G S T D G | S N T E Y D E | T K I P | Y N F H T | |
| mouse probe | V | S | G | S | N | G | S | E | T | K |
| library encodes | W V | S/A | V/A/N/G Y/S/T | N | W/N/F D/S/N | G/S | G | E | T/K/I | Y/N/F/H |
| possible residues | 2 | 2 | 7 | 1 | 3 | 2 | 1 | 1 | 3 | 4 |

Result
- VH-1 matches at 8 positions
  - Library would be fixed with probe sequence at these 8 positions
  - The library would encode for human preferred residues at remaining 5 positions
- VH-3 matches at 5 positions
  - Library would be fixed with probe sequence at these 5 positions
  - The library would encode for human preferred residues at remaining 8 positions

FIG. 12

Results
- Smallest "best fit" cohort library is VH1 X VK3 = 30,720
- Largest "best fit" cohort library is VH3 X VK1 = 13,547,520

Quantitative Diversity by CDR

| | Frame | CDR1 | CDR2 | CDR3 | residue mismatches | | Frame | CDR1 | CDR2 | CDR3 | residue mismatches |
|---|---|---|---|---|---|---|---|---|---|---|---|
| A4.6.1 | H1 | 0 | 5 | 1 | 6 | | K1 | 0 | 4 | 1 | 5 |
| | H3 | 1 | 8 | 1 | 10 | | K3 | 1 | 4 | 1 | 6 |

Heavy Chain combinations

| | Frame | CDR1 | CDR2 | CDR3 | | | Frame | CDR1 | CDR2 | CDR3 | Light Chain combinations |
|---|---|---|---|---|---|---|---|---|---|---|---|
| A4.6.1 | H1 | 1 | 320 | 8 | 2560 | | K1 | 1 | 20 | 6 | 120 |
| | H3 | 2 | 7056 | 8 | 112896 | | K3 | 1 | 2 | 6 | 12 |

Calculated combinatorial cross Product library

| | K1 | K3 |
|---|---|---|
| H1 | 307200 | 30720 |
| H3 | 13547520 | 1354752 |

FIG. 13A-1

| Chain Diversity | | |
|---|---|---|
| H1 | H3 | K1 | K3 |
| 2560 | 112896 | 120 | 12 |
| mAb diversity | K1 | K3 | |
| H1 | 3.1E+05 | 3.1E+04 | |
| H3 | 1.4E+07 | 1.4E+06 | |

A4.6.1
VH-3 CDR1

| UAL constituents | S | S | A | S | H |
| | N | N | Y | G | N |
| | | D | A | W | M |
| | | T | S | Y | N |
| mouse probe | T | N | Y | G | M | N |
| library encodes | S or N | N | Y | G | M | N |
| possible residues | 2 | 1 | 1 | 1 | 1 | 1 | Product 2

VH-1 CDR1

| UAL constituents | S | A | H |
| | G | Y | S |
| | N | G | N |
| | D | D | M |
| mouse probe | T | N | Y | G | M | N |
| library encodes | T | N | Y | G | M | N | No Diversity |
| possible residues | 1 | 1 | 1 | 1 | 1 | 1 | Product 1

FIG. 13A-2

A4.6.1
VH-1 CDR2

| UAL constituents | | | | | | | | | | |
|---|---|---|---|---|---|---|---|---|---|---|
| W | M | G | W | N | | | | | N | |
| | | | R | I | | | | | K | |
| | | | | S | | | | T | S | T |
| | | | | | | F | | N | | A |
| | | | | | | S | | G | | |
| | | | | | | N | | S | | |
| | | | | | | G | | D | | |
| W | M | G | W | I | | | G | | | |
| W | M | G | W | N | P | Y | T | E | P | T |
| | | | | | A | | | | | |
| W | M | G | W | I | N | Y | T | G | | |

| | mouse probe | library encodes | possible residues |
|---|---|---|---|
| W | W | W | 1 |
| M | M | M | 1 |
| G | G | G | 1 |
| W | W | W | 1 |
| N/S | I/S | N | 1 |
| P/A | P/A | P/A | 2 |
| Y | Y/M | Y | 1 |
| F/S/N/G | T/G | F/S/N/G | 4 |
| G | G | G | 1 |
| T/N/G/S/D | E | T/N/G/S/D | 5 |
| T/A | P | T/A | 2 |
| N/K/S/G | T | N/K/S/G | 4 |

Product 320

FIG. 13A-3

| A4.6.1 | | | | | | | | | | | |
|---|---|---|---|---|---|---|---|---|---|---|---|
| VH-3 CDR2 | | | | | | | | | | | |
| UAL constituents | | | V | | S | G | | | | Y | |
| | | | A | | K | Y | | | | N | |
| | | | N | | W | S | | D | S | T | |
| | | | G | | | Q | | S | N | Y | T |
| | | V | Y | I | N | W | | N | S | K | |
| | W | M | A | S | T | N | Y | S | G | T | N |
| mouse probe | W | G | T | I | W | F | T | Y | T | D | F |
| | | | | N | | | | | | D | H |
| | | | | | | | | | | E | |
| | | | | | | | | | | G | |
| | | | | | | | | | P | E | T |
| library encodes | W | V | V/A/N/G/ | S/A | I | G/Y/S/Q/ | D/S/N | G/S | G | T/K/I | Y/N/F/H |
| | | | Y/S/T | | N | W/N/F | | | | E | |
| possible residues | 1 | 2 | 7 | 1 | 1 | 7 | 3 | 2 | 1 | 3 | 4 |

Product 7056

FIG. 13A-4

A4.6.1
VH - CDR3

| | | | | | | | | | | | | | | | | |
|---|---|---|---|---|---|---|---|---|---|---|---|---|---|---|---|---|
| | R | | G | G | G | G | | | | | | | | | | |
| A | K | | D | R | Y | R | S | | | | | | | Y | F | D |
| A | K | | E | S | A | S | Y | G | S | S | G | Y | G | N | L | P |
| | | | R | P | S | R | G | Y | G | S | T | G | S | G | M | G |
| | | | A | W | R | E | D | T | D | P | Y | S | N | S | H |
| | | | H | L | E | T | E | Y | R | L | T | N | R | W | P | D |
| | | | V | Y | T | F | A | T | P | F | R | R | V | H | A | H |
| | | | T | A | L | L | C | W | A | N | A | V | A | D | F | |
| | | | Y | T | V | W | T | A | D | | C | | | R | L | |
| | | | | V | | I | F | L | R | L | K | A | Q | A | | |
| | | | | | | | N | E | T | | D | | D | L | | |
| | | | | | | | - | W | W | M | W | | H | | | |
| | | | | | | | | | A | W | | | | | | |

UAL constituents mouse probe: A K Y P H Y G S H W Y F D library encodes: A K G/D/E/R/N/H/V/T P H Y G S H W Y F D possible residues: 1 1 8 1 1 1 1 1 1 1 1 1 1 1

Product 8

FIG. 13B-1

A4.6.1 VK-1 CDR1

| UAL constituents | S | R | Y | | | |
| --- | --- | --- | --- | --- | --- | --- |
| | | G | W | | | |
| | | N | D | A | | |
| | | Y | S | | L | W Y |
| mouse probe | S | N | Y | | L | W Y |
| library encodes | S | N | Y | L | N | W Y | No diversity |
| possible residues | 1 | 1 | 1 | 1 | 1 | 1 1 | Product 1 |

A4.6.1 VK-3 CDR1

| UAL constituents | S | | | | | |
| --- | --- | --- | --- | --- | --- | --- |
| | | G | | | | |
| | | N | N | | | |
| | | T | Y | A | | |
| | | | S | | L | W Y |
| mouse probe | S | N | Y | | L | W Y |
| library encodes | S | N | Y | L | A | W Y | Product 1 |
| possible residues | 1 | 1 | 1 | 1 | 1 | 1 1 | |

FIG. 13B-2

A4.6.1
VK-1 CDR2

| UAL constituents | | L<br>R | | | | A<br>D<br>K<br>G | | | | Q | |
|---|---|---|---|---|---|---|---|---|---|---|---|
| | | V | L<br>I<br>Y | L<br>I<br>Y | | S | A | S | I<br>S<br>T | L<br>N | E |
| mouse probe | | | L | L | | F | T | S | S | S | L | H |
| library encodes | | L/R | L<br>I<br>Y | L<br>I<br>Y | | A/D/K/G<br>/S | A | S | S | L | Q/E | |
| possible residues | | 2 | 1 | 1 | | 5 | 1 | 1 | 1 | 1 | 2 | Product 20 |

VK-3 CDR2

| UAL constituents | | L | | | | G | | | | | A | |
|---|---|---|---|---|---|---|---|---|---|---|---|
| | | V | L<br>I<br>Y | L<br>I<br>Y | | D | A | S | S<br>T | N | |
| mouse probe | | | L | L | | F | T | S | T | L | H |
| library encodes | | L | L<br>I<br>Y | L<br>I<br>Y | | G/D | T | S | S | R | A |
| possible residues | 1 | 1 | 1 | 2 | | 1 | 1 | 1 | 1 | 1 | Product 2 |

FIG. 14A

CDR BLAST with mouse probe anti-HIV gp41 monoclonal 41-S-2-L

DIVMTQATPSVSVTPGESVFISCRSSKSLLYSNGNTYLYWFLQRPGQSP
QLLIYRLFHLASGVPDRFSGSGSGTAFTLRISRVEAEDVGVYYCMQH

LEYPYTFGGTKLEIKRAD

>> (Catalytic TRIAD residues are underlined)

• Kappa light Chain sequences
 – CDR1: LYSNGNTYLYWF
 – CDR2: LLIYRLFHLA
 – CDR3: MQHLEYPYT

FIG. 14B

Human VK-1 CDR size 7 Blast library result

| VK-1 CDR1-7 | | | | | | | | | |
|---|---|---|---|---|---|---|---|---|---|
| UAL constituents | S | | N | Y | | | | | |
| | R | | S | W | | | | | |
| | G | | T | D | | A | | | |
| | N | | K | S | L | N | W | Y | |
| mouse probe | L | YSNGN | T | Y | L | Y | W | F | |
| library encodes | S/R/G/N/Y | YSNGN | N | Y | L | A/N | W | Y | diversity |
| possible residues | 5 | 1 | 1 | 1 | 1 | 2 | 1 | 1 | Product |
| | | | | | | | | | 10 |

FIG. 14C

Human VK-3 CDR1 size 7 library result

| VK-3 CDR1-7 | | | | | | | |
|---|---|---|---|---|---|---|---|
| mouse probe | S G N | S N T | | Y | L | A Y | Y W F |
| library encodes | L | YSNGN | T | Y | L | Y | W |
| possible residues | S/G/N | YSNGN | T | Y | L | A | W Y |
| | 3 | 1 | 1 | 1 | 1 | 1 | 1 | Product 3 |

Human VK-3 CDR1 size 8 library result

| | | N | S | | | | A | Y |
|---|---|---|---|---|---|---|---|---|
| mouse probe | S | S | S | T | Y | L | Y | W F |
| library encodes | | YSNG | YSNG | N | | | | |
| possible residues | S | YSNG | YSNG | N | T | Y | L | A | W | Y |
| | 1 | 1 | 1 | 1 | 1 | 1 | 1 | 1 | Product 1 diversity 1 |

| VK-3 CDR1 | S | | S | N | | | | |
|---|---|---|---|---|---|---|---|---|
| UAL constituents | G | | | N | | | | |

FIG. 14D

Human VK-1 CDR2 library result

| VK-1 CDR2 | | | | | | | | | | VK-1 CDR2 Cohort Diversity 20 |
|---|---|---|---|---|---|---|---|---|---|---|
| UAL constituents | | | | A<br>D<br>K<br>G | | | I<br>S<br>T<br>N | Q<br>E | | |
| mouse probe | R | L | Y | S<br>R | A<br>L | S<br>F | N<br>H | L<br>L | A | |
| library encodes | L | L | Y | A/D/K/<br>G/S | A | S | I/S/T/N/L | Q/E | | |
| possible residues | 1 | 1 | 1 | 5 | 1 | 1 | 4 | 1 | 2 | Product 40 |

Human VK-3 CDR2 library result

| VK-3 CDR2 | | | | | | | | | | VK-3 CDR2 Cohort Diversity 2 |
|---|---|---|---|---|---|---|---|---|---|---|
| UAL constituents | | | | G<br>D | A<br>T | T<br>S | S<br>N | S<br>T<br>N<br>H | A | |
| mouse probe | L | L | L | Y | D | T | S | N | R | A |
| | L | L | L | Y | R | L | F | H | L | A |
| library encodes | L | L | L | Y | G/D | A/T | S | S/T/N | R | A |
| possible residues | 1 | 1 | 1 | 1 | 2 | 2 | 1 | 3 | 1 | 1 | Product 12 |

FIG. 14E

Human VK CDR3 library result

| VK - CDR3-9 | | | | | | | | | |
|---|---|---|---|---|---|---|---|---|---|
| UAL constituents | | | Q | S | D | | T | I | |
| | | H | Y | D | G | Y | S | Y | |
| | | Q | S | Y | T | T | R | T | |
| | | | N | N | S | S | L | L | |
| | | | G | G | E | W | P | W | |
| mouse probe | Q | M | Q | H | | | | | |
| library encodes | | Q | Q | H | S/D/Y/N/G | D/G/T/N/S | Y | P | P/L/R/S/T | T |
| possible residues | 1 | 1 | 1 | 1 | 5 | 5 | 1 | 1 | 5 | 1 | Product |
| | | | | | | | | | | | 125 |

Result

In this case, the essential catalytic H is NOT replaced by the UAL library constituents.

FIG. 15A

VIPase human monoclonal HK14.

DIVMTQSPSS LSASVGDRVT ITCRASLKII NFLSWYQQKP GKAPKLVLYA ASTLQSGVPS RFSGSGSGTD FTLTISSLQP

EDLATYYCQQ SYILPPTFGG GTKVDIL

- Kappa light Chain sequences
  - CDR1: IFNLSWY
  - CDR2: LVLYAASTLQ
  - CDR3: QQSYILPPT

FIG. 15B

Human VK-3 CDR1 size 7 library result

| VK-3 CDR1-7 | | | | | | | | VK-3 CDR2 |
|---|---|---|---|---|---|---|---|---|
| | S | G | T | Y | L | A | W | Y |
| | | N | F | N | L | S | W | Y |
| human probe | | | | | | | | |
| library encodes | S/G/N | S/N/T | N | L | A | W | Y | |
| possible residues | 3 | 3 | 1 | 1 | 1 | 1 | 1 | |
| | | | | | | | Product | Cohort Diversity |
| | | | | | | | 9 | 9 |

FIG. 15C

Human VK-3 CDR2 library result

| VK-3 CDR2 | | | | | | | | | | | VK-3 CDR2 Cohort Diversity 2 |
|---|---|---|---|---|---|---|---|---|---|---|---|
| UAL constituents | L | | | | G | A | | S | | | |
| Human probe | L | V | I | Y | D | T | S | N | R | A | |
| library encodes | L | L | F | Y | G/D | A | S | T | R | A | Product |
| possible residues | 1 | 1 | 1 | 1 | 2 | 1 | 1 | 1 | 1 | 1 | 2 |

FIG. 15D

Human VK CDR3 library result

| VK - CDR3-9 | | | | | | | | | | |
|---|---|---|---|---|---|---|---|---|---|---|
| UAL constituents | | H | R | S | D | Y | | | T | I |
| | | Q | S | D | G | Y | | S | S | Y |
| | Q | Q | Y | Y | T | T | L | R | R | T |
| | Q | Q | S | N | N | S | P | L | L | L |
| mouse probe | Q | Q | Y | G | S | W | P | P | P | W |
| library encodes | Q | Q | S | Y | D/G/T/N/S | Y/T/S/W | P | P | P | T |
| possible residues | 1 | 1 | 1 | 1 | 5 | 4 | 1 | 1 | 1 | 1 | Product | 20 |

Result

VK-CDR3 matches at 7 of 9 positions

AAV293

| VH-1 CDR2 | | | | | | | | | | |
|---|---|---|---|---|---|---|---|---|---|---|
| UAL constituents | W | M | G | W<br>G<br>R | N | N<br>I<br>S | P<br>A | –<br>N<br>S<br>Y<br>G<br>M | F<br>S<br>N<br>G | T<br>N<br>G<br>S<br>D | T<br>A | N<br>K<br>S<br>G |
| human probe | W | V | A | N | I | E | Q | D | G | E | K | Y |
| library encodes | W | M | G | WGR | I | NIS | PA | INSYGM | G | G | TNGSE | TA | NKSG |
| minimal degenerates | 1 | 1 | 1 | 1 | 1 | 1 | 1 | 1 | 1 | 1 | 1 | 1 |
| possible residues | 1 | 1 | 1 | 3 | 1 | 3 | 2 | 6 | 1 | 1 | 5 | 2 | 4 | oligos needed 2
Product 4320

FIG. 16A-4

AAV293

| VH - CDR3 | | | | | | | | |
|---|---|---|---|---|---|---|---|---|
| UAL constituents | T<br>A | G<br>T<br>R | G<br>E<br>L<br>R<br>S<br>D<br>V | G<br>P<br>R<br>L<br>Y<br>S<br>A<br>D<br>N<br>Q | G<br>S<br>V<br>Y<br>R<br>T<br>N<br>I<br>L<br>Q | G<br>Y<br>W<br>R<br>L<br>N<br>S<br>A<br>D<br>H | G<br>G<br>L<br>S<br>A<br>D<br>T<br>Y<br>V<br>H | F<br>L<br>G<br>S<br>M<br>A<br>I<br>P | D<br>P<br>G<br>N<br>R |
| human probe | A | R | D | L | D | G | G | T | D |
| library encodes | A | R | D | L | GSVYRTNILQ | G | Y | FLGSMAIP | D |
| possible residues | 1 | 1 | 1 | 1 | 10 | 1 | 1 | 8 | 1 |
| oligos needed | 1 | 1 | 1 | 1 | 1 | 1 | 1 | 1 | 1 |

Product 80

FIG. 16B-1

AAV/293

VK-1 CDR1

| UAL constituents | S<br>R<br>G<br>N<br>Y | S<br>N<br>T<br>K | Y<br>W<br>D<br>S | | | A | L<br>L | N<br>A | W<br>W | Y<br>Y | | |
|---|---|---|---|---|---|---|---|---|---|---|---|---|
| human probe | S | S | A | | | | | | | | | |
| library encodes | S | S | YWDS | | | L | A | W | Y | | | |
| minimal degenerates | 1 | 1 | 1 | | | 1 | 1 | 1 | 1 | | oligos needed | 1 |
| possible residues | 1 | 1 | 4 | | | 1 | 1 | 1 | 1 | | Product | 4 |

VK-3 CDR1

| UAL constituents | S | S<br>G<br>N | N<br>Y | | | A | L<br>L | A<br>A | W<br>W | Y<br>Y | | |
|---|---|---|---|---|---|---|---|---|---|---|---|---|
| human probe | S | S | A | | | | | | | | | |
| library encodes | S | S | NY | | | L | A | W | Y | | | |
| minimal degenerates | 1 | 1 | 1 | | | 1 | 1 | 1 | 1 | | oligos needed | 1 |
| possible residues | 1 | 1 | 2 | | | 1 | 1 | 1 | 1 | | Product | 2 |

FIG. 17A-1

ACZ885

VH-3 CDR1

| | | | | | | | |
|---|---|---|---|---|---|---|---|
| UAL constituents | | S | S<br>N | Y<br>A<br>S | A<br>G<br>W | | S<br>H |
| mouse probe | | | N | Y | Y | | N |
| | S | S | T | Y | G | M | N |
| library encodes | S | S/N/D/<br>T | Y | G | M | N | |
| possible residues | 1 | 1 | 2 | 4 | 1 | 1 | 1 | 1 | oligos 2
Product 4

VH-1 CDR1

| | | | | | | | |
|---|---|---|---|---|---|---|---|
| UAL constituents | | T<br>S | S<br>G<br>N | Y<br>A<br>S | A<br>Y<br>G | | H<br>S |
| mouse probe | | | N | Y | D | I | N |
| | S | S | D | Y | G | M | N |
| library encodes | S | S/G/N/<br>D | Y | G | M | N | |
| possible residues | 1 | 1 | 2 | 4 | 1 | 1 | 1 | 1 | oligos 2
Product 4

| Chain Diversity | | | |
|---|---|---|---|
| H1 | H3 | K1 | K3 |
| 8640 | 840 | 800 | 24 |

| mAb diversity | K1 | K3 |
|---|---|---|
| H1 | 6912000 | 207360 |
| H3 | 672000 | 20160 |

FIG. 17B-1

VK-1 CDR1

| UAL constituents | S<br>R<br>G<br>N<br>Y | N<br>S<br>T<br>K | Y<br>W<br>D<br>S | | | A<br>N<br>H | W<br>W | Y<br>Y |
|---|---|---|---|---|---|---|---|---|
| mouse probe | G | S | S | | | H | W | Y |
| library encodes | S/R/G/<br>N/Y | S | S | L | A/N | W | Y | |
| possible residues | 5 | 1 | 1 | 1 | 2 | 1 | 1 | |
| | | | | | | | oligos | 1 |
| | | | | | | | Product | 10 |

VK-3 CDR1

| UAL constituents | S<br>G<br>N<br>Y | S<br>N<br>T | N<br>Y<br>S | | A<br>H | W<br>W | Y<br>Y |
|---|---|---|---|---|---|---|---|
| mouse probe | G | S | S | | H | W | Y |
| library encodes | G | S | N/Y | L | A | W | Y |
| possible residues | 1 | 1 | 2 | 1 | 1 | 1 | 1 |
| | | | | | | oligos | 1 |
| | | | | | | Product | 2 |

| VK-1 CDR2 | | | | | | | |
|---|---|---|---|---|---|---|---|
| UAL constituents | L<br>R | L | Y | A<br>D<br>K<br>G<br>S | A | I<br>S<br>T<br>N | | Q |
| human probe | S | L | Y | A | S | | L | E |
| library encodes | L/R | L | Y | A | S | S | L | Q |
| minimal degenerates | 1 | 1 | 1 | 1 | 1 | 1 | 1 | 1 |
| possible residues | 2 | 1 | 1 | 1 | 1 | 1 | 1 | 1 |
| | | | | | | | o

FIG. 19A-1

| Chain Diversity | | |
|---|---|---|
| H1 | H3 | K3 |
| 32 | 84672 | 144 |
| mAb diversity | | |
| H1 | K3 | |
| H3 | 4608 | |
| | 12192768 | | scFvgp120

| VH-3 CDR1 | | | | | |
|---|---|---|---|---|---|
| UAL constituents | S | | A/Y | A/G/W/Y | S/H/N |
| | N/D/T | S/N | | M/V/I | H/N |
| human probe | S | N | F | V | I |
| library enc

FIG. 19A-3

| scFv gp120 VH-3 CDR2 | | | | | | | | | | | | | | | |
|---|---|---|---|---|---|---|---|---|---|---|---|---|---|---|---|
| UAL constituents | W | W | | | V | | | G | S | Y | P | Y | | |

FIG. 19A-4

FIG. 19B-1 scFv gp120

| VK-3 CDR1 | | | | | | | | | | |
|---|---|---|---|---|---|---|---|---|---|---|
| UAL constituents | S<br>N | S<br>N | S<br>N<br>T | Y | L | A | W | Y | | |
| human probe | R | S | R | R | V | A | W | Y | | |
| library encodes | S/N | S/N | S/N/T | Y | L | A | W | Y | No diversity | |
| | | | | | | | | | oligos | |
| minimal degenerates | 1 | 1 | 1 | 1 | 1 | 1 | 1 | 1 | needed | 1 |
| possible residues | 2 | 2 | 3 | 1 | 1 | 1 | 1 | 1 | Product | 12 |

| VK-1 CDR2 | | | | | | | | | | | | |
|---|---|---|---|---|---|---|---|---|---|---|---|---|
| UAL constituents | L<br>R | L | I | Y | A<br>D<br>K<br>G<br>S | A | S | I<br>S<br>T<br>N | L | Q<br>E | | |
| human probe | L | L | I | Y | G | V | S | N | R | A | | |
| library encodes | L | L | I | Y | G | A | S | N | L | Q/E | | |
| | | | | | | | | | | | oligos | |
| minimal degenerates | 1 | 1 | 1 | 1 | 1 | 1 | 1 | 1 | 1 | 1 | needed | 1 |
| possible residues | 1 | 1 | 1 | 1 | 1 | 1 | 1 | 1 | 1 | 2 | Product | 2 |

| 4D5 | VH-1 CDR2 | | | | | | | | | | |
|---|---|---|---|---|---|---|---|---|---|---|---|
| UAL constituents | W | M | G | R | I | N | P | I | F | T | N | N |
| | W | I | G | R | I | S | A | N S Y G M | N S N G | N G S D | T A | K S G |
| | | | G | | | Y | P | G M | G | Y | T | R |
| | | | | | | | | T | | | | |
| human probe | W | M | G | R | I | S | P | I N S Y G M | N G | T N G S D | T | N K S G |
| library encodes | W | M | G | R | I | N I S | P | I N S Y G M | N G | T N G S D | T | N K S G |
| minimal degenerates | 1 | 1 | 1 | 1 | 1 | 3 | 1 | 1 | 1 | 1 | 1 | 2 |
| possible residues | 1 | 1 | 1 | 1 | 1 | 3 | 1 | 6 | 1 | 5 | 1 | 4 | oligos needed 2
Product 360

| VH - CDR3 | | | | | | | | | | | | | | |
|---|---|---|---|---|---|---|---|---|---|---|---|---|---|---|
| | | | | | | | | | | | | | D | G |
| | | | | | | | | | | F | | | Y | |
| | | | | | | | | | | L | | | | |
| | | | | | | | Y | | | M | | | | |
| | | | | | | G | A | | G | D | | | | |
| | | | | G | | Y | G | | Y | V | | | | |
| | | | | Y | S | S | F | | S | A | | | | |
| | | G | | L | A | D | P | | D | G | | | | |
| | | D | S | A | W | T | S | | A | F | | | | |
| | | E | Y | T | D | A | A | | V | P | | | | |
| | | R | L | P | Y | R | W | | D | T | | | | |
| R | | V | P | V | L | D | P | | F | H | | | | |
| K | | A | D | W | R | F | H | | T | W | | | | |

UAL constituents human probe: A S R W

| Chain Diversity | | | | |
|---|---|---|---|---|
| | H1 | H3 | K1 | K3 |
| | 1296 | 5292 | 20 | 6 |
| mAb diversity | H1 | K1 | 7776 | |
| | | 25920 | | |
| | H3 | 105840 | 31752 | |

HD37

| VH-3 CDR1 | | | | | | | oligos | |
|---|---|---|---|---|---|---|---|---|
| UAL constituents | S | S | A | S | | needed | Product |
| | N | N | N | G | H | | | |
| | | Y | A | W | S | | | |
| | | D | S | Y | N | | | |
| | | T | | | M | | | |
| human probe | S | S | Y | W | M | N | 1 | 1 |
| library encodes | S | S | Y | W | M | N | 1 | 1 |
| minimal degenerates | 1 | 1 | 1 | 1 | 1 | 1 | | |
| possible residues | 1 | 1 | 1 | 1 | 1 | 1 | | |

HD37

| VH-1 CDR1 | | | | | | | oligos | |
|---|---|---|---|---|---|---|---|---|
| UAL constituents | T | S | A | H | | needed | Product |
| | S | G | Y | Y | S | | | |
| | | N | G | G | I | | | |
| | | D | D | M | | | | |
| | | Y | | | M | | | |
| human probe | S | S | Y | W | M | N | 2 | 4 |
| library encodes | S | S | Y | AYGD | M | N | | |
| minimal degenerates | 1 | 1 | 1 | 4 | 1 | 1 | | |
| possible residues | 1 | 1 | 1 | 4 | 1 | 1 | | |

FIG. 21A-3

| VH-3 CDR2 | | | | | | | | | | | | |
|---|---|---|---|---|---|---|---|---|---|---|---|---|
| UAL constituents | | S | | V A N G Y S T | | S K W N | G Y S Q W N F | D S N | G S | S G T D | S N T E Y D | I T K | Y N F H |
| | W | V | G A | Q | I | W | P | G | D | G | G D | D T | N |
| human probe | W | W | SA | T | | I | W | | | | | | |
| library encodes | W | W | SA | VANGYS T | GYSQW FN | I W | SDN | GS | G | D T | N | | |
| possible residues | 1 | 1 | 2 | 7 | 1 | 1 | 7 | 1 | 3 | 1 | 2 | 1 | 1 | 1 | 1 | 1 |
| oligos needed | 1 | 1 | 2 | 7 | 1 | 1 | 7 | 1 | 3 | 1 | 2 | 1 | 1 | 1 | 1 | 1 |

Product 588

FIG. 21A-4

HD37 VH - CDR3

| | | | | | | | | | | | | | | | | |
|---|---|---|---|---|---|---|---|---|---|---|---|---|---|---|---|---|
| | | | | | | | | | | | | | | | | |

UAL constituents:

| | | | | | | | | | | | | | | |
|---|---|---|---|---|---|---|---|---|---|---|---|---|---|---|
| | | | | | | | | | | | | | S | |
| | | | | | | | | | | | | | G | |
| | | | | | | | | | | | | Y | Y | |
| | | | | | | | | | | | Y | G | D | |
| | | | | | | | | | | G | G | S | A | |
| | | | | S | G | G | P | | | S | S | N | T | D |
| | | | | G | Y | Y | R | | | D | L | T | V | |
| | | | R | R | D | T | G | | | R | R | D | N | M |
| | G | P | G | Y | L | S | L | | | W | F | F | R | F |
| | D | R | G | V | R | R | V | | | N | W | F | P | D |
| A | L | G | L | D | S | D | E | | | T | D | N | A | L |
| R | A | L | V | L | I | L | H | | | A | I | T | L | Y |
| K | V | Y | E | R | P | R | A | | | W | P | A | E | G |
| S | E | D | R | S | A | S | S | | | F | F | H | W | E |
| | R | E | T | T | M | T | T | | | P | S | P | | |
| A | R | E | T | T | V | GSYATDRFW | G | R | Y | Y | Y | A | M | D | human probe: GSYATDRFW library encodes: A R E T T V | G R Y Y Y A M D possible residues: 1 1 1 1 1 1 1 1 1 1 1 1 1 1 1 1 1 | 1 9 | 1 1 1 1 1 1 1 1 oligos needed: 1
Product: 9

FIG. 21B-1

| VK-1 CDR1 | | | | | | |
|---|---|---|---|---|---|---|
| UAL constituents | S R G N Y V | N S T K T | Y W D S Y | L V | A N S | W W | Y Y |
| human probe | | | | | | | |
| library encodes | SRGNY | T | Y | L | AN | W | Y | oligos needed |
| minimal degenerates | 1 | 1 | 1 | 1 | 1 | 1 | 1 | 1 |
| possible residues | 5 | 1 | 1 | 1 | 2 | 1 | 1 | Product 10 |

| VK-3 CDR1 | | | | | | |
|---|---|---|---|---|---|---|
| UAL constituents | S G N V | S N T T | N Y Y | L V | A S | W W | Y Y |
| human probe | | | | | | | |
| library encodes | SGN | T | Y | L | A | W | Y | oligos needed |
| minimal degenerates | 1 | 1 | 1 | 1 | 1 | 1 | 1 | 1 |
| possible residues | 3 | 1 | 1 | 1 | 1 | 1 | 1 | Product 3 |

FIG. 21B-2

| VK-1 CDR2 | | | | | | | |
|---|---|---|---|---|---|---|---|
| UAL constituents | L R | L | I | Y | A D K G S | A | – S T N | Q E |
| human probe | L | L | I | Y | G | A | S | N R Y |
| library encodes | L | L | I | Y | G | A | S | Q E |
| minimal degenerates | 1 | 1 | 1 | 1 | 1 | 1 | 1 | 1 |
| possible residues | 1 | 1 | 1 | 1 | 1 | 1 | 1 | 2 |
| No Diversity oligos needed Product | | | | | | | | 1 / 1 |

| VK-3 CDR2 | | | | | | | |
|---|---|---|---|---|---|---|---|
| UAL constituents | L R | L | I | Y | G D | A T | S T N | R A |
| human probe | L | L | I | Y | G | A | S | N R Y |
| library encodes | L | L | I | Y | G | A | S | N R A |
| minimal degenerates | 1 | 1 | 1 | 1 | 1 | 1 | 1 | 1 |
| possible residues | 1 | 1 | 1 | 1 | 1 | 1 | 1 | 1 |
| oligos needed Product | | | | | | | | 1 / 1 |

FIG. 22A-1

Human CD8 g10-1

VH-3 CDR1

| UAL constituents | | | | | |
|---|---|---|---|---|---|
| S | S | Y | A | | |
| N | N | A | G | | S |
| | D | S | W | M | H |
| | T | | Y | | N |
| mouse probe | T | D | Y | Y | K |
| library encodes | S or N | D | Y | Y | M | S/H/N |
| possible residues | 1 | 1 | 1 | 1 | 1 | 1 |
| | 2 | 1 | 1 | 1 | 1 | | oligos 1
Product 2

VH-1 CDR1

| UAL constituents | | | | | |
|---|---|---|---|---|---|
| | S | | A | | H |
| T | G | | Y | | S |
| | N | | G | I | |
| | D | Y | D | M | N |
| mouse probe | T | D | Y | Y | K |
| library encodes | S | D | Y | Y | M | S/H/N |
| possible residues | 1 | 1 | 1 | 1 | 1 | 3 |
| | 1 | 1 | 1 | 1 | 1 | | oligos 1
Product 3

Chain Diversity

| | H1 | H3 | K1 | K3 |
|---|---|---|---|---|
| | 72 | 784 | 70 | 28 |
| mAb diversity | H1 | K1 | | |
| | 5040 | 2016 | | |
| H3 | 54880 | 21952 | | |

FIG. 22A-2

VH-1 CDR2

| UAL constituents | | | | | | | | | | |
|---|---|---|---|---|---|---|---|---|---|---|
| W | I | G | | | N | - | I | P | N | N K S G |
| | M | | | | | S | S | A | G | |
| | | | | | | Y | G | M | | |
| | | | | | | N | | | | |
| | | | | | | | F | | T | |
| | | | | | | | | | N | |
| | | | | | | | | | G | |
| | | | | | | | | | S | |
| | | | | | | | | | A | |
| mouse probe | W | M | G | | | I | N | P | N | D | T | F |
| library encodes | W | M | G | | | I | N | P | N | D | D | N/K/S/G |
| possible residues | W | 1 | W/G/R | | | 1 | 1 | 1 | 1 | D | T | 1 |
| | 1 | 1 | 3 | | | 1 | 1 | 3 | 1 | 2 | 1 | 4 | oligos 6
Product 12

VH-3 CDR2

| UAL constituents | | | | | | | | | | |
|---|---|---|---|---|---|---|---|---|---|---|
| | | V | V | G | S | W | G | N | S | Y N F |
| | | | A | Y | K | Y | S | T | K I |
| | | | N | W | Q | | E | Y H |
| | | | G | | W | | Y | |
| | | | Y | | N | | | |
| | | | S | | F | | | |
| | | | T | | | | | |
| mouse probe | W | V | G | S | I | N | G | D | S | G D T F |
| library encodes | W | V | G | S/A | I | N | P | N | N | D D T F |
| possible residues | 1 | 1 | 1 | V/A/N/G/Y/ | 1 | G/Y/S/Q/ | N | G/S | D D T F |
| | | | | S/T | | W/N/F | | | |
| | 1 | 1 | 2 | 7 | 1 | 4 | 1 | 1 | 1 1 1 1 |
| | 1 | 1 | 2 | 7 | 1 | 7 | 2 | 1 | 1 1 1 1 | oligos 8
Product 196

FIG. 22A-3

VH - CDR3

| UAL constituents | | | | | | | | | | | mouse probe | library encodes | possible residues |
|---|---|---|---|---|---|---|---|---|---|---|---|---|---|
| V | | | | | | | | | | | V | V | 1 |
| A | R | | | | | | | | | | R | R | 1 |
| | K | | | | | | | | | | D | D | 1 |
| | N | A | | | | | | | | | D | D | 1 |
| | R | E | L | | | | | | | | Y | Y | 1 |
| | V | L | F | P | V | T | N | A | F | | D | D | 1 |
| | T | N | L | V | T | W | Y | R | L | | G | G | 1 |
| | W | R | Y | A | S | A | D | S | W | | G | G | 1 |
| | | P | T | S | A | D | Y | W | L | | W | W | 1 |
| | | R | N | V | P | Y | S | D | F | | F | F | 1 |
| | | | D | W | T | S | W | Y | M | | | | |
| | | | L | A | N | D | A | G | L | | | | |
| | | | F | E | D | A | D | S | W | | | | |
| | | | M | L | A | R | L | Y | G | | | | |
| | | | W | R | Y | G | Y | W | | | | | |
| | | | G | P | | G | S | G | | | | | |
| | | | | | | | | | | | D | D/G | 2 |
| | | | | | | | | | | | G | | |
| | | | | | | | | | | | A | A | 1 | oligos 1
Product 2

FIG. 22B-1

VK-1 CDR1

| UAL constituents | | | | | | | |
|---|---|---|---|---|---|---|---|
| S | R | | | | | | |
| | N | Y | | | | | |
| G | S | W | | | A | | |
| N | T | D | | L | N | W | Y |
| Y | K | S | | | | | |
| mouse probe | N | N | N | | L | N | W | Y |
| library encodes | N | N | Y | | L | N | W | Y |
| possible residues | 1 | 1 | 1 | | 1 | 1 | 1 | 1 | oligos 1
Product 1
no diversity

VK-3 CDR1

| UAL constituents | | | | | | | |
|---|---|---|---|---|---|---|---|
| S | S | | | | | | |
| G | N | | | | | | |
| N | T | | | | A | | |
| | | | | Y | L | N | W | Y |
| mouse probe | N | N | N | | Y | L | A | W | Y |
| library encodes | N | N | Y | | Y | L | N | W | Y |
| possible residues | 1 | 1 | 1 | | 1 | 1 | 1 | 1 | oligos 1
Product 1

FIG. 22B-2

VK-1 CDR2

| UAL constituents | | | | | A<br>D<br>K<br>G<br>S | A<br>S | I<br>S<br>T<br>N | Q<br>E |
|---|---|---|---|---|---|---|---|---|
| mouse probe | | L | R | Y | | | | |
| library encodes | L | L | I | Y | A/D/K/G/<br>S | A | S | Q/E |
| | L | L | I | Y | S | S | S | Y |
| possible residues | 1 | 1 | 1 | 1 | 1 | 1 | 1 | 1 |
| | 1 | 1 | 1 | 1 | 3 | 1 | 1 | 2 |
| | 1 | 1 | 1 | 1 | 5 | 1 | 1 | | oligos 3
Product 10

VK-3 CDR2

| UAL constituents | | | | | G<br>D | A<br>T | S<br>N | Y<br>A |
|---|---|---|---|---|---|---|---|---|
| mouse probe | L | L | Y | | | | R | |
| library encodes | L | L | I | Y | G/D | T/A | S | R |
| | L | L | I | Y | T | S | S | Y |
| possible residues | 1 | 1 | 1 | 1 | 1 | 1 | 1 | 1 |
| | 1 | 1 | 1 | 1 | 2 | 2 | 1 | 1 | oligos 1
Product 4

FIG. 22B-3

VK - CDR3

| UAL constituents | | | | | | | | mouse probe | library encodes | possible residues | |
|---|---|---|---|---|---|---|---|---|---|---|---|
| Q | Q | Y | Y | S | Y | | L | Q | Q | 1 | |
| M | Q | S | N | N | T | | Y | Q | Q | 1 | |
| Q | G | A | G | T | S | | W | G | G | 1 | |
| | | G | S | H | L | | R | K | Y/N/G/S/D/T/L | 7 | |
| | | R | D | Q | W | | F | F | T | 1 | |
| | | G | T | G | F | P | I | L | I | 1 | |
| | | | L | F | L | | W | P | P | 1 | |
| | | | | | | | | W | W | 1 | | oligos 4
Product 7

VK-1 CDR1

| UAL constituents | S R G N Y | | N S T K | Y W D S | | | A | L N W | L N W Y |
|---|---|---|---|---|---|---|---|---|---|
| mouse probe | | T | G | A | | | | | |
| library encodes | S/R/G/ N/Y | | N/S/T/ K | Y/W/D/ S | | | A | L N W | L N W Y |
| possible residues | 5 | | 4 | 4 | | | 1 | 1 | 1 |
| | | | | | | | | oligos | 0 |
| | | | | | | | | Product | 80 |

VK-3 CDR1

| UAL constituents | S G N | | S N T | N Y | | L | A | L N W | L N W Y |
|---|---|---|---|---|---|---|---|---|---|
| mouse probe | | T | | G | | | A | | |
| library encodes | S/G/N | | S/N/T | N/Y | | L | A | L N W | L N W Y |
| possible residues | 3 | | 3 | 2 | | 1 | 1 | 1 | 1 |
| | | | | | | | | oligos | 0 |
| | | | | | | | | Product | 18 |

FIG. 23B-2

VK-1 CDR2

| UAL constituents | | | | A<br>D<br>K | | | I<br>S<br>T | Q<br>E |
| --- | --- | --- | --- | --- | --- | --- | --- | --- |
| | L<br>R | L<br>I<br>Y | G<br>S | A<br>T | S | N<br>L | A |
| mouse probe | L | I | Y | G | A | S | N | L |
| library encodes | L | I | Y | A | T | S | N | L | Q/E |
| possible residues | 1 | 1 | 1 | 1 | 1 | 1 | 1 | 1 | 1 | oligos 1
| | 1 | 1 | 1 | 1 | 1 | 1 | 1 | 1 | 2 | Product 2

VK-3 CDR2

| UAL constituents | | | | | S<br>T | | | A |
| --- | --- | --- | --- | --- | --- | --- | --- | --- |
| | L | I | Y | G<br>D | A<br>T | S | N<br>L | A |
| mouse probe | L | I | Y | G | A | S | N | L | A |
| library encodes | L | I | Y | G<br>A | A<br>T | S | S<br>N<br>L | R<br>L | A |
| possible residues | 1 | 1 | 1 | 1 | 1 | 1 | 1 | 1 | 1 | oligos 1
| | 1 | 1 | 1 | 1 | 1 | 1 | 1 | 1 | 1 | Product 1

FIG. 24A-1

| Chain Diversity | | | | |
|---|---|---|---|---|
| | H1 | H3 | K1 | K3 |
| | 3240 | 508032 | 2240 | 56 |
| mAb diversity | H1 | K1 | 181440 | |
| | 7257600 | 1137991 | 2844979 | |
| | H3 | K3 | | |
| | 680 | 2 | | |

7E3

VH-3 CDR1

| UAL constituents | S | S | A | | | |
|---|---|---|---|---|---|---|
| | | N | Y | G | | S |
| | | | | | | H |
| | N | | | W | M | N |
| mouse probe | K | D | T | D | Y | H |
| library encodes | S or N | D | Y/A/S | Y | Y | M |
| | | | | | Y | H |
| possible residues | 1 | 1 | 2 | 1 | 1 | 1 | oligos 2
| | 2 | 1 | 3 | 1 | 1 | 1 | Product 6

VH-1 CDR1

| UAL constituents | | | | A | | |
|---|---|---|---|---|---|---|
| | | G | Y | | | |
| | S | N | | G | I | S |
| | T | | | | M | H |
| | S | | T | D | V | N |
| mouse probe | K | D | | Y | Y | H |
| library encodes | T/S | D | Y | Y | Y | M/I |
| | | | | | | H |
| possible residues | 1 | 1 | 1 | 1 | 2 | 1 | oligos 1
| | 2 | 1 | 1 | 1 | 2 | 1 | Product 4

FIG. 24A-2

VH-1 CDR2

| UAL constituents | | | | | | | | | | | |
|---|---|---|---|---|---|---|---|---|---|---|---|
| | | | | | | | | | | K | |
| | | | W | | | I | | | F | N | |
| | | | G | R | N | S | | G | S | S | N |
| | W | M | G | R | S | Y | P | N | G | A | S |
| mouse probe | W | I | G | R | D | A | P | M | G | G | T |
| | | | | | | | | | N | T | K |
| | | | | | | | | | G | A | G |
| | | | | | | | | Y | | | | mouse probe: W I G R I D S A P M A G N G Y A K T

| library encodes | | | | | | | | | | | |
|---|---|---|---|---|---|---|---|---|---|---|---|
| | | | | | I/N/S | | | I/N/S | | | T/N |
| | W | M | G | R | S | N/I | P/A | Y/G/M | N | G | G/S/Y | T/A | K | possible residues: 1 1 1 1 1 3 1 6 1 1 5 1 1 oligos: 1 1 1 1 1 3 1 3 1 1 2 1 1

Product 90

VH - CDR3

| UAL constituents | | | | | | | | | | | mouse probe | library encodes | possible residues | oligos | Product |
|---|---|---|---|---|---|---|---|---|---|---|---|---|---|---|---|
| V | | | | | | | | | | | V | V | 1 | 1 | 1 |
| A | R | | | | | | | | | | R | R | 1 | 1 | 1 |
| K | D | T | | | | | | | | | P | D/K/G/ A/E/L | 9 | 4 | 1 |
| | K | S | | | | | | | | | | R/N | | | |
| | G | G | | | | | | | | | | | | | |
| | I | R | G | D | T | R | S | A | F | | L | L | 1 | 1 | 1 |
| | A | Y | D | G | S | G | G | G | M | D | Y | Y | 1 | 1 | 1 |
| | E | D | S | N | Y | S | Y | Y | L | G | D | D | 1 | 1 | 1 |
| | L | F | Y | Y | D | W | W | S | W | | Y | Y | 1 | 1 | 1 |
| | R | L | A | A | A | D | D | W | F | | A | A | 1 | 1 | 1 |
| | N | N | P | S | L | N | N | F | L | | M | M | 1 | 1 | 1 |
| | V | V | V | T | W | A | A | L | P | | D | D | 1 | 1 | 1 |
| | | T | T | W | | R | R | P | I | G | | | | | |

FIG. 24B-1

VK-1 CDR1

| UAL constituents | S | R<br>G | N<br>S<br>K | Y<br>W<br>D<br>S | L<br>I<br>N | A<br>N<br>G | W | Y | | |
|---|---|---|---|---|---|---|---|---|---|---|
| mouse probe | | | S | T/W/D | S | G | W | L | | |
| library encodes | | | S | S | L | A/N | W | Y | oligos | 3 |
| | | | | | | | | | Product | 8 |
| possible residues | 1 | 1 | 1 | 3 | 1 | 1 | 1 | 1 | | |
| | | | 1 | 4 | 1 | 2 | 1 | 1 | | |

VK-3 CDR1

| UAL constituents | S | G<br>N | S<br>N<br>T | N<br>Y | L | A<br>G | W | Y | | |
|---|---|---|---|---|---|---|---|---|---|---|
| mouse probe | | | S | N | L | G | W | L | | |
| library encodes | | | S | N | L | A | W | Y | oligos | 1 |
| | | | | | | | | | Product | 1 |
| possible residues | 1 | 1 | 1 | 1 | 1 | 1 | 1 | 1 | | |
| | | | 1 | 1 | 1 | 1 | 1 | 1 | | |

FIG. 24B-2

VK-1 CDR2

| UAL constituents | | | | A<br>D<br>K<br>G<br>S | | A<br>S | I<br>S<br>T | Q<br>E |
|---|---|---|---|---|---|---|---|---|
| mouse probe | L<br>R | L<br>I<br>Y | L<br>I<br>Y | Y | G | T | N<br>L | L |
| library encodes | G | L/R | L | V/S | A/D/K/G<br>V/S | A | S | N | L | Q/E |
| possible residues | 1 | 2 | 1 | 1 | 3 | 1 | 1 | 1 | 2 |
| | | | | 5 | | | | | oligos 3 |
| | | | | | | | | | Product 20 |

VK-3 CDR2

| UAL constituents | | | | G<br>D | A<br>T | S | S<br>N | R<br>A |
|---|---|---|---|---|---|---|---|---|
| mouse probe | L | L<br>I<br>Y | L<br>Y | Y | D | T | N | R |
| library encodes | G | L | L<br>I<br>Y | G/D | T/A | S | N | R | A |
| possible residues | 1 | 1 | 1 | 2 | 2 | 1 | 1 | 1 | 1 |
| | | | | | | | | | oligos 1 |
| | | | | | | | | | Product 4 |

FIG. 24B-3

| VK - CDR3 | | | | | | | | | |
|---|---|---|---|---|---|---|---|---|---|
| UAL constituents | | Q | | | Y | | | L | |
| | | M | | Y | N | S | Y | Y | |
| | | V | Q | S | G | N | T | W | |
| | | | Q | A | S | T | S | R | |
| | | | | G | D | H | L | F | |
| | | | | R | T | Q | W | I | |
| | | | | Y | L | G | F | | |
| | | | | | A | | | | |
| mouse probe | | Q/M | Q | Y | A | Q | L | P | Y |
| library encodes | | Q/M | Q | Y | Y/N/G/S/ D/T/I/L | Q | L | P | Y |
| possible residues | | 2 | 1 | 1 | 4 | 1 | 1 | 1 | 1 |
| oligos | | 2 | 1 | 1 | 7 | 1 | 1 | 1 | 1 | 8 |
| Product | | 2 | 1 | 1 | 1 | 1 | 1 | 1 | 1 | 14 |

FIG. 25A-1

MHM24

| Chain Diversity | | | | |
|---|---|---|---|---|
| H1 | H3 | K1 | K3 |
| 259200 | 6773760 | 30 | 360 |
| mAb diversity | H1 | K1 | K3 |
| | H3 | 7776000 | 93312000 |
| | | 203212800 | 2438553600 |

VH-3 CDR1

| UAL constituents | | | | | | |
|---|---|---|---|---|---|---|
| S | | | Y | A | | S |
| N | N | D | A | G | W | H |
| | T | G | S | | Y | |
| mouse probe | | | | W | | |
| library encodes | S or N | S/N/D/T | Y/A/S | W | Y | N |
| | | | | | M | M |
| | | | | | M | M |
| possible residues | 2 | 4 | 3 | 1 | 1 | 1 |
| oligos | | | | | | 0 |
| Product | | | | | | 24 |

VH-1 CDR1

| UAL constituents | | | | | | |
|---|---|---|---|---|---|---|
| | S | | A | | H |
| | G | N | Y | I | S |
| T | S | D | G | | |
| | | Y | D | | |
| mouse probe | T | G | H | W | | |
| library encodes | T | G Y | A/Y/G/D | W | N | N |
| | | | | | M | M |
| | | | | | M | M |
| possible residues | 1 | 1 | 4 | 1 | 1 | 1 |
| oligos | | | | | | 0 |
| Product | | | | | | 4 |

VK-1 CDR2

| UAL constituents | | | | | | | | | | |
|---|---|---|---|---|---|---|---|---|---|---|
| | | | | A | | | | | | |
| | | | | D | | | | | | |
| | | | | K | | | I | | | Q |
| | | | | G | A | | S | | | |
| | | L | | Y | S | | N | | T | |
| mouse probe | R | L | I | Y | A | | N | L | | Q |
| library encodes | | L | L | I | Y | S | G | S | T | L | Q |
| library encodes | | L | L | I | Y | A | S | T | L | Q |
| oligos | 1 | 1 | 1 | 1 | 1 | 1 | 1 | 1 | 1 | 1 |
| Product 1 | 1 | 1 | 1 | 1 | 1 | 1 | 1 | 1 | 1 | 1 |
| possible residues | 1 | 1 | 1 | 1 | 1 | 1 | 1 | 1 | 1 | 1 |

VK-3 CDR2

| UAL constituents | | | | | | | | | | |
|---|---|---|---|---|---|---|---|---|---|---|
| | | | | | | | S | | | Q |
| | | | | | G | A | T | | | |
| | | | | | D | | N | | | |
| | | | | Y | S | G | T | S | | R |
| mouse probe | L | L | I | Y | G | A | T | S | L | Q |
| library encodes | L | L | I | Y | G/D | T/A | S | T | R | A |
| oligos | 1 | 1 | 1 | 1 | 2 | 2 | 1 | 1 | 1 | 1 |
| Product 4 | 1 | 1 | 1 | 1 | 2 | 2 | 1 | 1 | 1 | 1 |
| possible residues | 1 | 1 | 1 | 1 | 1 | 1 | 1 | 1 | 1 | 1 |

FIG. 26A-1

| Chain Diversity | |
|---|---|
| H1 | 583200 |
| mAb diversity | |
| H1 | H3 |
| H3 | 45722880 |
| K3 | 41990400 |
| | 3292047360 |
| | K3 72 |

OVA
VH-3 CDR1

| UAL constituents | S | S | | A | S | |
| | N | N | Y | G | H | |
| | | D | A | W | N | |
| | | T | S | Y | D | |
| mouse probe | T | D | Y | N | | |
| library encodes | S/N | N | Y | AG/W/Y | M | N/H/N |
| minimal | | | | | | |
| degenerates | 1 | 1 | 1 | 3 | 1 | 1 |
| possible residues | 2 | 1 | 1 | 4 | 1 | 3 | oligos needed 3
Product 24

VH-1 CDR1

| UAL constituents | S | | A | | H | |
| | G | | Y | I | S | |
| | N | Y | G | M | N | |
| | D | | D | | D | |
| human probe | T | D | Y | N | | |
| library encodes | T/S | Y | A/Y/G/D | M | H/S/N | |
| minimal | | | | | | |
| degenerates | 1 | 1 | 2 | 1 | 1 | |
| possible residues | 1 | 1 | 4 | 1 | 3 | | oligos needed 2
Product 12

| VH - CDR3 | | | | | | | | | | | | | | | |
|---|---|---|---|---|---|---|---|---|---|---|---|---|---|---|---|
| | | | H | | | | | | | | | | | | |
| | | | V | T | | | | | | | | | V | | |
| | | | T | D | | | | | | | | | I | | L |
| | | K | R | S | Q | | | | | | | | E | | S |
| | | | S | P | T | | | | | N | | | P | | P |
| | | | A | A | A | L | | | | D | V | R | L | | W |
| | | | E | V | S | I | | | | A | I | L | T | A | A |
| | | | G | I | P | T | | | | V | E | E | A | F | | | | H |
| | | | D | R | A | V | | | | L | P | P | Y | T | | | L | D | A |
| A | R | K | R | L | L | R | | | | Y | L | A | S | S | | G | D | M | |
| | | | S | G | G | D | | | | T | T | F | D | D | | Y | P | F | A |
| A | R | R | G | S | Y | G | | | | S | A | T | G | G | | G | F | G | D |
| (human probe) | A | R | S | G | Y | G | S | | | G | Y | S | P | Y | | G | F | A |
| library encodes | A | R | S | G | Y | G | S | R N/D/A/ V/L/Y/T/ S/G | H V/I/E/P/ L/L/T/A /Y/S/G | P | P T/A/W/D /R/N/S/G /Y | G | F | A |
| | 1 | 1 | 1 | 1 | 1 | 1 | 1 | 9 | 10 | 1 | 9 | 1 | 1 | 1 |
| possible residues | 1 | 1 | 1 | 1 | 1 | 1 | 1 | 9 | 10 | 1 | 9 | 1 | 1 | 1 |

No diversity oligos needed 1
Product 810

VK-3 CDR2

| UAL constituents | | | | | | | |
|---|---|---|---|---|---|---|---|
| | | | | | | S | |
| | | | | G | A | T | |
| | L | L | Y | D | T | S | N | R | A |
| human probe | L | I | Y | G | V | S | N | R | A |
| library encodes | L | L | Y | G | A/T | S | R | A |
| minimal degenerates | 1 | 1 | 1 | 1 | 1 | 1 | 1 | 1 |
| possible residues | 1 | 1 | 1 | 1 | 2 | 1 | 1 | 1 | oligos needed  1
Product        2

VK - CDR3

| UAL constituents | | | | | | | |
|---|---|---|---|---|---|---|---|
| | | | Y | | Y | | L | |
| | | Y | N | S | T | S | Y | |
| | | S | G | N | H | L | W | |
| | Q | A | D | T | Q | W | R | |
| M | V | R | L | G | P | F | Y |
| human probe | Q | Y | G | A | S | S | Y |
| library encodes | Q | Q | Y | G | S/N/T/H | S | P | Y |
| | | | | /Q/G | | | | |
| minimal degenerates | 1 | 1 | 1 | 1 | 3 | 1 | 1 | 1 |
| possible residues | 1 | 1 | 1 | 1 | 6 | 1 | 1 | 1 | oligos needed  3
Product        6

VK-1 CDR1

| UAL constituents | S | R | Y | | | | |
|---|---|---|---|---|---|---|---|
| | | | N | | | | |
| | G | S | W | | A | | |
| | N | T | D | L | N | W | Y |
| | Y | K | S | | | | |
| mouse probe | S | N | D | V | N | W | Y |
| library encodes | S | N | D | L | A/N | W | Y |
| possible residues | 1 | 1 | 1 | 1 | 2 | 1 | 1 | oligos 0
Product 2

VK-3 CDR1

| UAL constituents | S | S | N | | | | |
|---|---|---|---|---|---|---|---|
| | G | N | Y | L | A | W | Y |
| | N | T | | | | | |
| mouse probe | S | N | D | V | V | W | Y |
| library encodes | S | N | Y/N | L | A | W | Y |
| possible residues | 1 | 1 | 2 | 1 | 1 | 1 | 1 | oligos 0
Product 2

FIG. 27B-2

VK-1 CDR2

| UAL constituents | | | | | | | | | | |
|---|---|---|---|---|---|---|---|---|---|---|
| | | | | A | | | I | | | Q |
| L | | | | D | | | S | | | |
| | | | | K | | | | | | |
| R | | | | G | | | | | S | L |
| mouse probe | M | L | I | Y | S | A | T | | | |
| library encodes | L/R | L | M | Y | S | A | F | N | R | E |
| | | | | A | | | | | | |
| possible residues | 2 | 1 | 1 | 1 | 1 | 1 | 1 | 1 | 1 | 2 | oligos 1
Product 4

VK-3 CDR2

| UAL constituents | | | | | | | | | | |
|---|---|---|---|---|---|---|---|---|---|---|
| | | | | G | | | S | | | A |
| L | | | | D | A | T | | N | R | |
| mouse probe | M | L | I | Y | S | A | F | N | R | Y |
| library encodes | L | L | I | Y | G/D | A | F | S | N | A |
| | | | | | | | | | R | |
| possible residues | 1 | 1 | 1 | 1 | 2 | 1 | 1 | 1 | 1 | 1 | oligos 1
Product 2

FIG. 27B-3

VK - CDR3

| UAL constituents | | | | | | | |
|---|---|---|---|---|---|---|---|
| Q | Q | | | | | | |
| M | | Y | Y | S | Y | | L |
| | | S | N | N | T | | Y |
| | | A | G | T | S | | W |
| | | G | S | H | L | | R |
| | | R | D | Q | W | | F |
| | | | T | G | F | P | I |
| | | | L | | | | |

| mouse probe | Q | Q | D | Y | N | S | | R |
| library encodes | Q | Q | Y/S/A/G/R | Y | N | S | P | R |
| possible residues | 1 | 1 | 5 | 1 | 1 | 1 | 1 | 1 | oligos 0
Product 5

FIG. 28

| Side Chain Chemistry | Residues | | | | |
|---|---|---|---|---|---|
| Small | G | A | | | |
| Nucleophilic | S | T | C | H | |
| Hydrophobic | V | L | I | M | P |
| Aromatic | F | Y | W | | |
| Acidic | D | E | | | |
| Amide | N | Q | | | |
| Basic | K | R | | | |

FIG. 30B $V_H1$

| mouse probe | W | M | G | W | I | N | T | Y | T | G | E | P | T | Diversity | Mismatched positions |
|---|---|---|---|---|---|---|---|---|---|---|---|---|---|---|---|
| Similar | W | M | G | W | I | N | P/A | Y | S | G | D | T/A | S | 4 | 2 |
| Identity | W | M | G | W | I | N | P/A | Y/F/S/N | G | Y/N/G/S/D | T/A | N/K/S/G | | 320 | 5 |

$V_H3$

| mouse probe | W | M | G | W | I | N | T | Y | T | G | E | P | T | Diversity | Mismatched positions |
|---|---|---|---|---|---|---|---|---|---|---|---|---|---|---|---|
| Similar | W | V | A | Y | I | N | S | D/S/N | S | G | E | L | H | 3 | 2 |
| Identity | W | V | S/A | V/A/N/G | I | N | G/Y/S/Q | D/S/N | G/S | G | E | T/K/I | Y/N/F/H | 7056 | 8 |

FIG. 30C

| mouse probe | A | K | Y | P | H | Y | Y | G | S | S | H | W | Y | F | D | Diversity | Mismatched positions |
|---|---|---|---|---|---|---|---|---|---|---|---|---|---|---|---|---|---|
| Similar | A | K | Q/D/E/R/A H/V/T | P | H | Y | Y | G | S | S | H | W | Y | F | D | 8 | 1 |
| Identity | A | K | Q/D/E/R/A H/V/T | P | H | Y | Y | G | S | S | H | W | Y | F | D | 8 | 1 |

FIG. 30D $V_L\kappa 1$

| mouse probe | S | N | Y | L | N | W | Y | Diversity | Mismatched positions |
|---|---|---|---|---|---|---|---|---|---|
| Similar | S | N | Y | L | N | W | Y | 1 | 0 |
| Identity | S | N | Y | L | N | W | Y | 1 | 0 |

$V_L\kappa 3$

| mouse probe | S | N | Y | L | N | W | Y | Diversity | Mismatched positions |
|---|---|---|---|---|---|---|---|---|---|
| Similar | S | N | Y | L | A | W | Y | 1 | 1 |
| Identity | S | N | Y | L | A | W. | Y | 1 | 1 |

$V_L\lambda 3$

| mouse probe | S | N | Y | L | N | W | Y | Diversity | Mismatched positions |
|---|---|---|---|---|---|---|---|---|---|
| Similar | S | KQYE | Y | V | HYSC | W | Y | 16 | 2 |
| Identity | S | KQYE | Y | AV | HYSC | W | Y | 32 | 3 |

FIG. 30E

$V_L\kappa 1$

| mouse probe | V | L | I | Y | F | T | S | S | L | H | Diversity | Mismatched positions |
|---|---|---|---|---|---|---|---|---|---|---|---|---|
| Similar | L | L | I | Y | A/D/K/ G/S | A | S | S | L | Q/E | 10 | 3 |
| Identity | L/R | L | I | Y | A/D/K/ G/S | A | S | S | L | Q/E | 20 | 4 |

$V_L\kappa 3$

| mouse probe | V | L | I | Y | F | T | S | S | L | H | Diversity | Mismatched positions |
|---|---|---|---|---|---|---|---|---|---|---|---|---|
| Similar | L | L | I | Y | G/D | T | S | S | R | A | 2 | 4 |
| Identity | L | L | I | Y | G/D | T | S | S | R | A | 2 | 4 |

$V_L\lambda 3$

| mouse probe | V | L | I | Y | F | T | S | S | L | H | Diversity | Mismatched positions |
|---|---|---|---|---|---|---|---|---|---|---|---|---|
| Similar | L | V | I | Y | DQEK | DK | S | KDEN | R | P | 40 | 7 |
| Identity | L | V | I | Y | DQEK | DK | S | KDEN | R | P | 40 | 7 |

FIG. 30F

| $V_L\kappa$ mouse probe | Q | Q | Y | S | T | V | P | W | Diversity | Mismatched positions |
|---|---|---|---|---|---|---|---|---|---|---|
| Similar | Q | Q | Y | S | T | L | P | W | 1 | 0 |
| Identity | Q | Q | Y | S | T | Y/T/S/L/W/F | P | W | 6 | 1 |

| $V_L\lambda$ mouse probe | Q | Q | Y | S | T | V | P | W | Diversity | Mismatched positions |
|---|---|---|---|---|---|---|---|---|---|---|
| Similar | Q | SATIL | Y | DYHA | S | SGND | IL | W | 160 | 3 |
| Identity | Q | SATIL | Y | DYHA | SGNR | SGND | TANISLG | W | 2240 | 5 |

FIG. 30G

| Chain Diversity Identity criteria | | | |
|---|---|---|---|
| H1 | H3 | K1 | K3 | L3 |
| 2560 | 112896 | 120 | 12 | 2867200 |

| Identity criteria | | | |
|---|---|---|---|
| mAb diversity | K1 | K3 | L3 |
| H1 | 3.1E+05 | 3.1E+04 | 7.3E+09 |
| H3 | 1.4E+07 | 1.4E+06 | 3.2E+11 |

| Chain Diversity Similarity criteria | | | |
|---|---|---|---|
| H1 | H3 | K1 | K3 | L3 |
| 32 | 72 | 10 | 2 | 102400 |

| similar criteria | | | |
|---|---|---|---|
| mAb diversity | K1 | K3 | L3 |
| H1 | 320 | 64 | 3276800 |
| H3 | 720 | 144 | 7372800 |

| fold reduction | | | |
|---|---|---|---|
| mAb diversity | K1 | K3 | L3 |
| H1 | 960 | 480 | 2240 |
| H3 | 18816 | 9408 | 43904 |

FIG. 31A $V_H 1$

| mouse probe | T | N | Y | G | M | N | Diversity | Mismatched positions |
|---|---|---|---|---|---|---|---|---|
| Similar | T | N | Y | G | M | N | 1 | 0 |
| Identity | T | N | Y | G | M | N | 1 | 0 |
| all similar | TS | N | Y | G | M | N | 2 | |
| Database | TS | SGND | Y | AYGD | IM | HSN | | |

$V_H 3$

| mouse probe | T | N | Y | G | M | N | Diversity | Mismatched positions |
|---|---|---|---|---|---|---|---|---|
| Similar | S | N | Y | G | M | N | 1 | 0 |
| Identity | S or N | N | Y | G | M | N | 2 | 1 |
| all similar | S | N | Y | GA | M | N | 2 | |
| Database | SN | SNDT | YAS | AGWY | M | SHN | | |

| mouse probe | W | M | G | W | I | N | T | Y | T | G | E | P | T | Diversity | Mismatched positions |
|---|---|---|---|---|---|---|---|---|---|---|---|---|---|---|---|
| Similar | W | M | G | W | I | N | P/A | Y | S | G | D | T/A | S | 4 | 2 |
| Identity | W | M | G | W | I | N | P/A | Y | FSNG | G | T/N/G/S/D | T/A | N/K/S/G | 320 | 5 |
| all similar | W | M | G | W | I | N | PA | Y | S | G | D | TA | S | 4 | |
| Database | W | M | G | WGR | INSYGMFSNG | NIS | PA | INSYGMFSNG | FSNG | G | TNGSZ | TA | NKSG | | |

V_H3

| mouse probe | W | V | G | W | I | N | T | Y | T | G | E | P | T | Diversity | Mismatched positions |
|---|---|---|---|---|---|---|---|---|---|---|---|---|---|---|---|
| Similar | W | V | A | Y | I | N | S | D/S/N | S | G | E | I | H | 3 | 4 |
| Identity | W | V | S/A | V/A/N/G /Y/S/T | I | N | G/Y/S/ W/N/F | D/S/N | G/S | G | E | T/K/I | Y/N/F/H | 7056 | 8 |
| all similar | W | V | A | Y | I | N | S | DSN | S | G | F/D | I | H | 6 | |
| Database | W | V | SA | VANGY ST | SKWN | I | GYSCW NE | DSN | GS | SGTD | SNTEYD | TKI | YNFH | | |

FIG. 31C

| mouse probe | A | K | Y | P | H | Y | Y | G | S | S | H | W | Y | F | D | Diversity | Mismatched positions |
|---|---|---|---|---|---|---|---|---|---|---|---|---|---|---|---|---|---|
| Similar | A | K | G/D/E/R/A/H/V/T | P | H | Y | Y | G | S | S | H | W | Y | F | D | 8 | 1 |
| Identity | A | K | G/D/E/R/A/H/V/T | P | H | Y | Y | G | S | S | H | W | Y | F | D | 8 | 1 |
| all similar | A | RK | GDERAHVT | PVL | STH | YF | YW | GA | ST | ST | SH | YW | YW | F | D | 36864 | |
| Database | A | RK | GDERAHVT | GRSPWG LYATV | YASRES TFLWHI | YGDE ACTFNI | SGYDR TWAL | SYGTYD RPAE | GSYTPL AVDW | YGSNRV FVHMW | ACKDH HDRAQ | YNGSW FALH | YGWP | FLMDDPGH | | | |

FIG. 31D

$V_L\kappa 1$

| mouse probe | S | N | Y | L | N | W | Y | Diversity | Mismatched positions |
|---|---|---|---|---|---|---|---|---|---|
| Similar | S | N | Y | L | N | W | Y | 1 | 0 |
| Identity | S | N | Y | L | N | W | Y | 1 | 0 |
| all similar | S | N | AW | L | N | W | Y | 2 | |
| Database | SRGN Y | NSTK | YWDS | L | AN | W | Y | | |

$V_L\kappa 3$

| mouse probe | S | N | Y | L | N | W | Y | Diversity | Mismatched positions |
|---|---|---|---|---|---|---|---|---|---|
| Similar | S | N | Y | L | N | W | Y | 1 | 0 |
| Identity | S | N | Y | L | A | W | Y | 1 | 1 |
| all similar | S | N | Y | L | A | W | Y | 1 | |
| Database | SGN | SNT | NY | L | A | W | Y | | |

$V_L\lambda 3$

| mouse probe | S | N | Y | L | N | W | Y | Diversity | Mismatched positions |
|---|---|---|---|---|---|---|---|---|---|
| Similar | S | KQYE | Y | V | HYSC | W | Y | 16 | 2 |
| Identity | S | KQYE | Y | AV | HYSC | W | Y | 32 | 3 |
| all similar | ST | KQYE | YF | V | HYSC | W | Y | 64 | |
| Database | SKDNT | KQYE | YSF | AV | HYSC | W | Y | | |

FIG. 31E $V_L\kappa1$

| mouse probe | V | L | I | Y | F | T | S | S | L | H | Diversity | Mismatched positions |
|---|---|---|---|---|---|---|---|---|---|---|---|---|
| Similar | L | L | I | Y | A/D/K/G/S | A | S | S | L | Q/E | 10 | 3 |
| Identity | L/R | L | I | Y | A/D/K/G/S | A | S | S | L | Q/E | 20 | 4 |
| all similar | L | L | I | Y | ADKGS | A | S | ST | L | QE | 20 | |
| Database | LR | L | I | Y | ADKGS | A | S | STN | L | QE | | |

$V_L\kappa3$

| mouse probe | V | L | I | Y | F | T | S | S | L | H | Diversity | Mismatched positions |
|---|---|---|---|---|---|---|---|---|---|---|---|---|
| Similar | L | L | I | Y | G/D | T | S | S | R | A | 2 | 4 |
| Identity | L | L | I | Y | G/D | T | S | S | R | A | 2 | 4 |
| all similar | L | L | I | Y | GD | T | S | ST | R | A | 4 | |
| Database | L | L | IV | Y | GD | AT | S | STN | R | A | | |

$V_L\lambda3$

| mouse probe | V | L | I | Y | F | T | S | S | L | H | Diversity | Mismatched positions |
|---|---|---|---|---|---|---|---|---|---|---|---|---|
| Similar | L | V | I | Y | DQEKGDK | T | S | KDEN | R | P | 40 | 7 |
| Identity | L | V | I | Y | DQEKGDK | T | S | KDEN | R | P | 40 | 7 |
| all similar | L | V | IV | Y | DQEKGDK | T | ST | KDEN | R | P | 160 | |
| Database | L | V | IV | Y | DQEKGDK | AT | SNT | KDEN | R | P | | |

FIG. 31F $V_L\kappa$

| mouse probe | Q | Q | Y | S | T | V | P | W | Diversity | Mismatched positions |
|---|---|---|---|---|---|---|---|---|---|---|
| Similar | Q | Q | Y | S | T | L | P | W | 1 | 0 |
| Identity | Q | Q | Y | S | T | Y/T/S/L/W/F | P | W | 6 | 1 |
| all similar | Q | Q | Y | ST | STH | L | P | Y/W/F | 18 | |
| Database | QM | YSAGR | YNGSD L | TSNTHQ G | YTSL | P | LYWRFI | | | |

$V_L\lambda$

| mouse probe | Q | Y | S | T | V | P | W | Diversity | Mismatched positions |
|---|---|---|---|---|---|---|---|---|---|
| Similar | SATIL | Y | H | S | SGND | IL | W | 40 | 3 |
| Identity | SATIL | Y | DYHA | SGNR | SGND | TANISLG | W | 2240 | 5 |
| all similar | SATIL | WX | H | S | SGND | IL | W | 80 | |
| Database | QLMS | WY | DYHA | SGNR | SGND | TANISLG | VWARYQSL | | |

FIG. 36

| | L1 | | | | | | | | | | L2 | | | | | | L3 | | | | | | | | | |
|---|---|---|---|---|---|---|---|---|---|---|---|---|---|---|---|---|---|---|---|---|---|---|---|---|---|---|
| Test Reference | R | A | S | Q | G | I | R | N | Y | L | A | A | S | T | L | Q | S | Q | R | Y | N | R | A | P | Y | T |
| Clone 24 | | | | | E | | | | | | | | | | | | | | | | | | | | | | |
| | | | | L | | | | | | | | | | | | | | | | | | | | | P | |
| Clone 29 | | | | L | | | | | | | | | | | | | | | | | | | | | | P | |
| Clone F4 | | | | | | | | | | | | | S | F | | Q | | | | | | | | D | | P | |
| Clone 28 | | | | | | | | | | | | | | | | | | | | | | | | | | | |
| LB-H1 | H | | R | K | L | | | | | | | | | | L | H | | | | | | | D | R | P | |
| LB-E2 | H | | R | R | L | | | | | | | | S | F | L | P | | | | | | | D | | P | |
| LB-F4 | H | | | K | | | | | | | | | S | | L | | | | | | | | D | K | | |
| 3ss-35 | | | | | | | | | | | | | | | | | | | | | | | | K | | |
| Clone 26 | | | | L | | | | | | | | | | | | | | | | | | | | | | P | |
| Clone G1 | | | | | | | | | | | | | | | | | | | | | | | | D | | | |

| | H1 | | | | | H2 | | | | | | | | | | | | | | H3 | | | | | | | | | | |
|---|---|---|---|---|---|---|---|---|---|---|---|---|---|---|---|---|---|---|---|---|---|---|---|---|---|---|---|---|---|---|
| Test Reference | D | Y | A | M | H | T | W | N | S | G | H | I | D | Y | A | D | S | V | E | V | S | Y | L | S | T | A | S | S | L | D | Y |
| Clone 24 | Q | | | | | | | | | | | | | | | | | | | | | | | | | | | | | | |
| | Q | | | | | | | | | | | | | | | | | | | | | | | | | | | | | | |
| Clone 29 | Q | | | | | | | | | | | | | | | | | | | | | | | | | | | | | | |
| Clone F4 | Q | | | | | | | | | | | | | | | | | | | | | | | | | | | | | | |
| Clone 28 | Q | | | | | | | | | | | | | | | | | | | Q | | | | | | | | Q | H | H | |
| LB-H1 | | | | | | | | | | | | | | | | | | | | | | | | | | | | | | | |
| LB-E2 | | | | | | | | | | | | | | | | | | | | | | | | | | | | | | | |
| LB-F4 | | | | | | | | | | | | | | | | | | | | | | | | | | | | | | | |
| 3ss-35 | | S | | L | | | | | | | | | | | | | | | | | | | K | | | | | | | | |
| Clone 26 | Q | | | | | | | | | | | | | | | | | | | | | | | | | | | | | | |
| Clone G1 | | S | | | | | | | | | | | | | | | | | | | | | | | | | | | | | |

Pre-sort: 0.6% of Total
Library population

Post-sort: 25% of Total
Library population

Fig 44 KEY / Fig 44A / Fig 44B / Fig 44C / Fig 44D / Fig 44E / Fig 44F

Fig 44A

| | DIVERSITY | 30 | 31 | 32 | 33 | 34 | 35 | | | |
|---|---|---|---|---|---|---|---|---|---|---|
| VH1-CDR1 | 192 | TS | SGND | Y | AYGD | IM | HSN | | | |
| VH3-CDR1 | 288 | SN | SNDT | YAS | AGWY | M | SHN | | | |
| VH4_1-CDR1 | 162 | ST | GSD | YDS | YFS | W | STN | | | |
| VH4_2-CDR1 | 24 | S | S | SG | YND | YW | W | SG | | |
| VH4_3-CDR1 | 144 | SN | SNT | GST | SGDN | Y | Y | W | | |

| | | 47 | 48 | 49 | 50 | 51 | 52 | 52a | 53 | 54 |
|---|---|---|---|---|---|---|---|---|---|---|
| VH1-CDR2 | 17280 | W | M | G | WGR | I | NIS | PA | INSYGM | FSNG |
| VH3-CDR2 | 677376 | W | V | SA | VANGYST | I | SKWN | GYSQWNF | DSN | GS |
| VH4_1-CDR2 | 512 | W | I | G | EY | IL | NYSD | | HQYD | SR |
| VH4_2-CDR2 | 48 | W | I | G | SERY | I | Y | | HY | S |
| VH4_3-CDR2 | 144 | W | I | G | YSR | IV | YF | | YT | S |

| | | 93 | 94 | 95 | 96 | 97 | 98 | 99 | 100 | 100a |
|---|---|---|---|---|---|---|---|---|---|---|
| H3-9 | 1.4E+07 | AT | RTG | GELRSDV | GPRLYSADNQ | GSVYRTNILQ | GYWRLNSAD | GLSADTYVH | FLGSMAIP | |
| H3-10 | 3.3E+08 | AV | RTK | DGRESLNPVM | GRLDPVYKANQ | GTDSERALVQWY | GSADLYVIPQ | AYGDTESWHLP | YASGLFIP | FMLDSAIP |
| H3-11 | 1.4E+08 | AV | RK | DKGIAELRN | TSGRYDFLNV | GDSYAPVT | DGNYASTW | RGSYDATL | GSYWDNAR | AGYSWFLP |
| H3-12 | 2.0E+09 | A | RK | GDESRVA | GSYLPDAQRTH | SGYLATPVWN | GSAWDYLRPV | GYSAVDFTL | SGYLTARDEN | GYSDTAWPF |
| H3-13 | 2.5E+10 | A | RKT | DGSEVALK | GRSPAILQK | GSADRYLVKMP | GSTYDPRILV | GSTDWAIRYLQ | GYSDVLRAENT | YSRLVPTWGA |
| H3-14 | 3.7E+11 | A | RK | DGEASRTVH | RGLPSATQHIK | GYLRIVAPSDTE | SGYLAPDFTIQ | GSAYDRVTIL | GSTYLVADN | GSYATLPEIV |
| H3-15 | 2.4E+12 | A | RK | GDERAHVT | GRSPWLYATV | GYASRETFLWHI | SYGDEACTFNI | SGYDRTWAL | SGTYDRPAE | GSYTRAVDW |
| H3-16 | 2.0E+13 | A | RKS | GDLARVEHS | PRGLVEYDSAN | GYTSRDLPAVAM | GYDLRSITEP | SGRYVDFTIM | GSYATDRFW | SGYDATVNPLE |
| H3-17 | 6.6E+12 | A | RK | GDARVEL | RGLDPAQHS | YGRSILHPTVAM | YGVSRDIC | DYGSRVATI | GDSYFVTAR | SGWRATVDFI |

Fig 44B

| | | | | | | | | | | | | |
|---|---|---|---|---|---|---|---|---|---|---|---|---|
| H3-18 | 8.16717E+13 | A | RK | DGEVRAL | GRLPISADK | RGTYSVDLAF | YGSVPRADT | YGSCDRFIKLM | GSVYDFTWC | GSTYRWFA | | |
| H3-19 | 1.75649E+13 | A | R | GDVA | LRGSQY | SYGRVIP | GDYANSWVPT | TSGYRDMNI | AGSVWPDFQ | GASWITVD | | |
| H3-20 | 1.48157E+16 | A | RK | DVAGREHL | GLRPVADNST | YPGDLRTHS | DYGPSRCFA | YFDGAPRSCI | SGWYPRTVD | SGNDEVTA FIL | | |
| | DIVERSITY | 30 | 30a | 31 | 32 | 33 | 34 | 35 | 36 | | | |
| VK1-CDR1 | 160 | SRGNY | | NSTK | YWDS | L | AN | W | Y | | | |
| VK3 7-CDR1 | 18 | SGN | | SNT | NY | | A | W | Y | | | |
| VK3 8-CDR1 | 12 | SN | SN | SNT | Y | L | A | W | Y | 54 L R | | |
| VK1-CDR2 | 60 | LR | L | — | Y | L | A | S | STN | | | |
| VK3-CDR2 | 12 | L | L | — | Y | GD | AT | S | STN | | | |
| | | 89 | 90 | 91 | 92 | 93 | 94 | 95 | 95a | 96 | | |
| VK_CDR3 8 | 15120 | QM | Q | YSAGR | YNGSDTL | SNTHQG | YTSLWF | P | LYWRFI | WLTYI | | |
| VK_CDR3 9 | 30000 | Q | QH | YSR | GNYDS | SNTGD | WSTY | PL | PLRST | | | |
| | | 30 | 30a | 30b | 30c | 31 | 32 | 33 | 34 | 35 | | |
| VL1-CDR1 | 75 | — | — | SNRTG | | N | YTSFH | V | NSY | W | | |
| VL2-CDR1 | 48 | VI | G | GSAD | Y | ND | YLF | V | S | W | | |
| VL3-CDR1 | 480 | SKDNT | | | | KQYE | YSF | AV | HYSC | W | | |
| | | 46 | 47 | 48 | 49 | 50 | 51 | 52 | 53 | 54 | | |
| VL1-CDR2 | 90 | L | L | — | Y | SGDRE | ND | NDS | QNK | R | | |
| VL2-CDR2 | 108 | L | M/L | I | YF | ED | V | STN | NKY | R | | |
| VL3-CDR2 | 240 | L | V | IV | Y | DQEKG | DK | SNT | KDEN | R | | |
| | | 89 | 90 | 91 | 92 | 93 | 94 | 95 | 95a | 95b | | |
| VL-CDR3 8 | 143360 | QLMS | SATIL | WY | DYHA | SGNR | SGND | TANISLG | | | | |

Fig 44C

| VL-CDR3_9 | 564480 | SQCAG | SA | YWA | DAT | SGTD | SNTG | NSGLTAY | TNSIHALD | |
|---|---|---|---|---|---|---|---|---|---|---|
| VL-CDR3_10 | 648000 | QAGSN | SATV | WYA | D | SDTNG | STR | LGS | SNDTR | GHASPLVY |
| VL-CDR3_11 | 4147200 | QASGN | SAVT | WYA | DT | SDGR | SGN | LSG | SNTDA | GHLPYA |

Fig 44F

| | VWLYRFG | | |
|---|---|---|---|
| | VYWPGR | | |
| PSHVLYDF | VYWG | | |

Fig 44D

| 55 | 56 | 57 | 58 | 100b | 100c | 100d | 100e | 100f | 100g | 100h | 100i | 100j | 100k | 101 |
|---|---|---|---|---|---|---|---|---|---|---|---|---|---|---|
| G | TNGSD | TA | NKSG | | | | | | | | | | | |
| SGTD | SNTEYD | TKI | YNFH | | | | | | | | | | | |
| G | STAN | T | NI | | | | | | | | | | | |
| G | S | T | YNS | | | | | | | | | | | |
| G | SNT | T | YN | | | | | | | | | | | |
| FMLWGI YAGFPS THW | FLMDVA | | | | | | | | | | | | | DPGNR |
| GYNPSA DRF | YGAPFS WT | FLMDIS | | | | | | | | | | | | DPRISA |
| YGDSTF APELR | YGSNRD WAT | YGFAWP SL | FMDLV | | | | | | | | | | | DG |
| GYSTPL FVHMW | YGSNRV ACKDH | YNGSW HDRAQ | YGWPFA LH | FLMD | | | | | | | | | | DYG |
| YGSNTR AEW | YSGLRF WDI | YGLSDT FHNP | YGSRW NTAH | GYAWFS P | FMDLG | | | | | | | | | DG |
| GSYIDLN PRV | GYRVSF LADC | YSGFNP L | YGSPLV ACDH | YDGNSH PR | YGWA | FML | | | | | | | | DAHI |
| | | | | | | | | | | | | | | DPGH |
| | | | | | | | | | | | | | | DYE |
| | | | | | | | | | | | | | | D |

Fig 44E

| | GSYDIW VAF | SGYNAR LVD | YRGCLA DSPFH | YFGRWN PAS | YGHSTL RFN | YDSGW NR | YGAWPT | YNKDGRS | | | |
|---|---|---|---|---|---|---|---|---|---|---|---|
| | RSTGVD YL | RSYPGD T | GYRSDL PV | PYSRAG Q | PYGRLD H | AYTPNV R | | YDFGNR VEK | FML | | | D |
| | GSDVTA LYP | GYLSIPR VC | YSGATN QCPRV | YSGVTD PWAC | YGRSTA DEFI | YSGLHA DFN | | | AYGFT | MFL | | D |
| | | | | | | | | | YDTS | GYWAS | MFYL | DG |
| | | | | | | | | | | | | |
| | | | | | | | | | | | | |
| 55 | | | | | | | | | | | | |
| QE | | | | | | | | | | | | |
| A | | | | | | | | | | | | |
| | | | | | | | | | | | | |
| 36 | | | | | | | | | | | | |
| Y | | | | | | | | | | | | |
| Y | | | | | | | | | | | | |
| Y | | | | | | | | | | | | |
| 55 | | | | | | | | | | | | |
| P | | | | | | | | | | | | |
| P | | | | | | | | | | | | |
| P | | | | | | | | | | | | |
| | | | | | | | | | | | | |
| 95c | 96 | | | | | | | | | | | |
| | VWARYQ SL | | | | | | | | | | | |

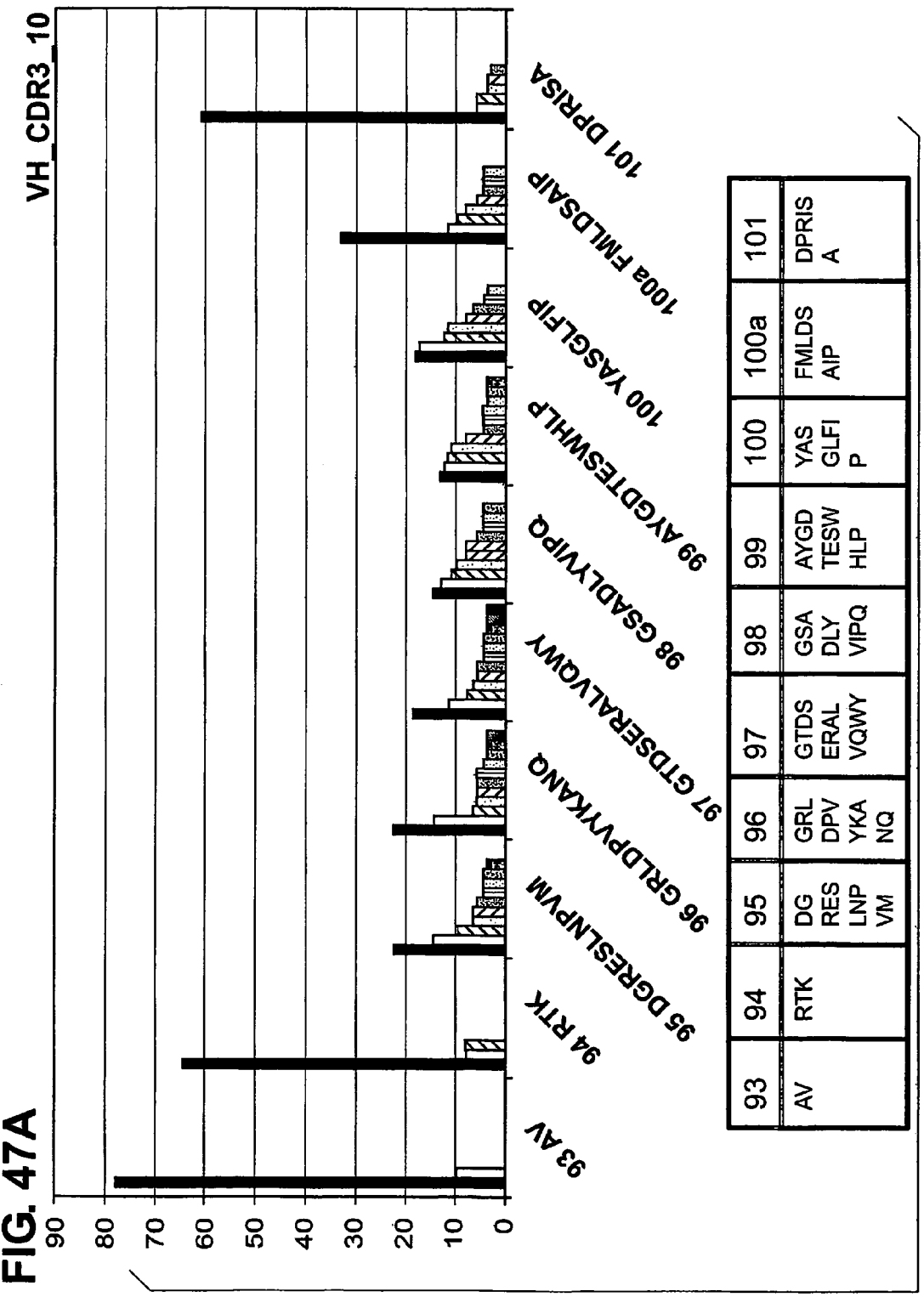

FIG. 58

Multiple oligonucleotide anneal

Step 1:

Annealing of LTM oligonucleotide(s) (dark bars) to uridinylated single stranded template (dotted line) at target codons.

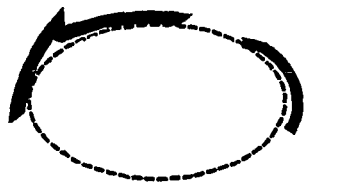

Step 2:

Synthesis of complementary strand (solid line) to uridinylated single stranded template to form double stranded duplex.

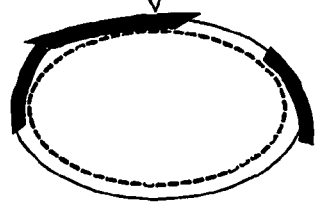

Step 3:

Degradation of uridinylated strand to form single stranded template with incorporated codon change(s).

Step 4:

Synthesis of complementary strand to form double stranded DNA duplex incorporating LTM replacement codon(s).

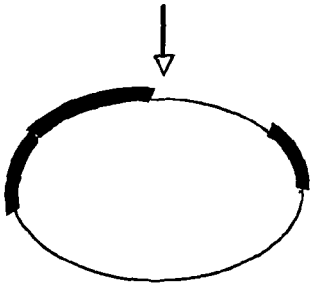

Step 5:

Regeneration of single stranded template to anneal another LTM oligonucleotide (dashed bar) and repeat Step 1.

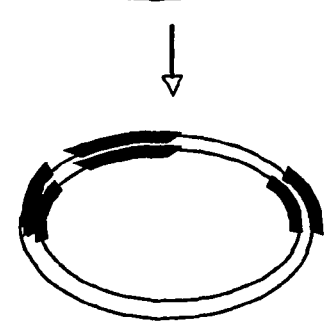

FIG. 62A

Oligonucleotide listings for $V_H1$, $V_H3$, $V_\lambda1$, $V_\lambda2$, $V_\lambda3$ and $V_k3$ scFv framework constructs.

$V_H1$, 1e sub-family

| | |
|---|---|
| H-1-E-S1 | caggtgcagctggtgcagagcggtgccgaa |
| H-1-E-S2 | gtgaagaaaccaggctctagcgtgaaagtgagctgcaaa |
| H-1-E-S3 | gccagcggtggcaccttctccagctacgccatcagctgggtgagacaggcccca |
| H-1-E-S4 | ggtcagggcctggaatggatgggtggcattatcccaatcttcggcaccgccaacta cgcccagaaattccag |
| H-1-E-S5 | ggcagagtgacaatcaccgccgataaaagcaccagcacc |
| H-1-E-S6 | gcctacatggaactgtctagcctgagaagcgaagat |
| H-1-E-S7 | accgccgtgtattactgcgccagagatggttctggcagcggctacgccttcgatta ctggggtcagggcacc |
| | |
| H-1-E-A1 | ctggttcagtctggtgccgaagtgaaaaagccaggttctagc |
| H-1-E-A2 | gtgaaagtgagctgcaaagcttccggtggcaccttc |
| H-1-E-A3 | tgggtgagacaggctccaggtcagggcctggag |
| H-1-E-A4 | tacgctcagaaattccagggcagagtgacaatcaccgcc |
| H-1-E-A5 | gataaaagcaccagcaccgcctacatggaactgtct |
| H-1-E-A6 | agcctgagaagcgaagataccgccgtgtattactgt |
| H-1-E-A7 | tactggggtcagggcaccctggttaccgtgtccagc |

$V_H3$, 3-07 sub-family

| | |
|---|---|
| H-3-07-S1 | gaagtgcagctggtggaatctggtggc |
| H-3-07-S2 | ggtctggtgcagccaggtggcagcttgagactgagctgcgct |
| H-3-07-S3 | gccagcggctttaccttctctagctattggatgagctgggttagacaggcacct |
| H-3-07-S4 | ggcaaaggtttggaatggtggccaacatcaaacaggatggcagcgaaaaatatta cgtggatagcgtgaaa |
| H-3-07-S5 | ggcagattcaccatcagcagagataacgccaaaaacagc |
| H-3-07-S6 | ctgtacttgcagatgaacagcctgagagccgaagat |
| H-3-07-S7 | accgccgtgtattactgtgctagagatggttctggttccggctacgccttcgatta ctggggtcagggcaca |
| | |
| H-3-07-A1 | ctggtggaatctggtggcggtttggtgcagcctggcggt |
| H-3-07-A2 | agcttgagactgtcttgcgctgccagcggctttaccttc |
| H-3-07-A3 | tgggttagacaggcacctggcaaaggtttggaa |
| H-3-07-A4 | tatgtggatagcgtgaaaggcagattcaccatcagcaga |
| H-3-07-A5 | gataacgccaaaaacagcctgtacttgcagatgaac |
| H-3-07-A6 | agcctgagagccgaagataccgctgtgtattactgt |
| H-3-07-A7 | tactggggtcagggcacactggttaccgtgtctagc |

FIG. 62B

V_H3, 3-11 sub-family

H-3-11-S1  caggtgcagctggtggaatctggtgga
H-3-11-S2  ggtttggtgaaacctggcggtagcttgagactgtcttgtgct
H-3-11-S3  gccagcggctttaccttctctgattattatatgagctggatcagacaggcacct
H-3-11-S4  ggcaagggtttggaatgggtgagctacatctctagctccggcagcaccatctacta
           tgccgatagcgtcaaa
H-3-11-S5  ggcagattcaccatcagcagagataacgccaaaaacagc
H-3-11-S6  ctgtacttgcagatgaacagcctgagagccgaagat
H-3-11-S7  accgctgtgtattactgtgctagagatggttctggttccggctacgccttcgatta
           ctggggtcagggcaca H-3-11-A1  ctggtggaatctggtggaggattggtgaaacctggcggt
H-3-11-A2  agcttgagactgtcttgtgctgccagtggctttaccttc
H-3-11-A3  tggatcagacaggcacctggcaagggtttggaa
H-3-11-A4  tatgctgatagcgtcaaaggcagattcaccatcagcaga
H-3-11-A5  gataacgccaaaaacagcctgtacttgcagatgaac
H-3-11-A6  agcctgagagccgaagataccgctgtgtattactgt
H-3-11-A7  tactggggtcagggcacactggttaccgtctctagc V_H3, 3-23 sub-family H-3-23-S2  ggattggtgcagcctggcggtagcttgagactgtcttgtgct
H-3-23-S3  gccagtggctttaccttctccagctatgccatgagctgggttagacaggcacct
H-3-23-S4  ggcaagggtttggaatgggtgagcgccatcagcggctctggcggtagcacctacta
           atgcagatagcgtcaaa
H-3-23-S5  ggcagattcaccatcagcagagataacagcaaaaacacc
H-3-23-S6  ctgtacttgcagatgaacagcctgagagccgaagat
H-3-23-S7  accgctgtgtattactgtgctaaagatggttctggttccggctacgccttcgatta
           ctggggtcagggcaca H-3-23-A1  ctgttggagtctggtggaggattggtgcagcctggcggt
H-3-23-A2  agcttgagactgtcttgtgctgccagtggctttaccttc
H-3-23-A3  tgggttagacaggctcctggcaagggtttggaa
H-3-23-A4  tatgcagatagcgtcaaaggcagattcaccatcagcaga
H-3-23-A5  gataacagcaaaaacaccctgtacttgcagatgaac
H-3-23-A6  agcctgagagccgaagataccgctgtgtattactgt
H-3-23-A7  tactggggtcagggcacactggttaccgtctctagc

FIG. 62C

V<sub>H</sub>3, 3-30 sub-family

```
H-3-33-S1   caggtgcagctggtggagtctggtgga
H-3-33-S2   ggagttgtgcagcctggcagaagcttgagactgtcttgtgct
H-3-33-S3   gccagtggctttaccttctcctcctatggtatgcactgggttagacaggcacct
H-3-33-S4   ggcaagggtttggaatgggtggctgtgatctggtacgatggcagcaacaaatacta
            tgcagatagcgtcaaa
H-3-33-S5   ggcagattcaccatcagcagagataacagcaaaaacacc
H-3-33-S6   ctgtacttgcagatgaacagcctgagagccgaagat
H-3-33-S7   accgctgtgtattactgtgctagagatggttctggttccggctacgccttcgatta
            ctggggtcagggcaca H-3-33-A1   ctggtggagtctggtggaggagttgtccagcctggcaga
H-3-33-A2   agcttgagactgtcttgtgctgcctctggctttaccttc
H-3-33-A3   tgggttagacaggcacctggcaagggtttggaa
H-3-33-A4   tatgcagatagcgtcaaaggcagattcaccatcagcaga
H-3-33-A5   gataacagcaaaaacaccctgtacttgcagatgaac
H-3-33-A6   agcctgagagccgaagataccgctgtgtattactgt
H-3-33-A7   tactggggtcagggcacactggttaccgtctctagc
```

V<sub>λ</sub>1 1b, sub-family

```
L-1-1B-S1   cagagcgtgctgacccagcctccaagcgtg
L-1-1B-S2   tccgctgccccaggccagaaagtgaccatctcttgc
L-1-1B-S3   agcggctccagctctaacatcggcaataactacgtgagctggtatcaacagctgcca
L-1-1B-S4   ggcaccgcccccaaaattgctgatctacgataataacaaaagaccaagcggcatccc
            agataga
L-1-1B-S5   ttctccggtagcaaatctggcacaagcgcc
L-1-1B-S6   actctgggcatcaccggcttgcagaccggc
L-1-1B-S7   gatgaagccgattactattgccagagctgggattctagcctgaacggcgttgtgtt
            cggcggtggcacaaaa L-1-1B-A1   ctgacccagcctccaagcgtgtccgctgccccaggccagaaa
L-1-1B-A2   gtgaccatctcttgcagcggctccagctctaac
L-1-1B-A3   caacagctgccaggcaccgcccccaaaa
L-1-1B-A4   agcggcatcccagatagattctccggtagcaaa
L-1-1B-A5   tctggcacaagcgctactctgggtatcACC
L-1-1B-A6   ggcttgcagacaggcgatgaagctgattactattgc
L-1-1B-A7   gtgttcggcggtggcaccaaaactgacagtgctgggccag
```

FIG. 62D

V$_\lambda$2 2a2 sub-family

| | |
|---|---|
| L-2-2A2-S1 | cagagcgccctgacccagccagcctccgtg |
| L-2-2A2-S2 | agcggctctccaggccagagcattaccatcagctgc |
| L-2-2A2-S3 | acaggcacaagctccgatgtgggtggctacaactatgtgagctggtatcaacagc atcca |
| L-2-2A2-S4 | ggcaaagccccaaagctgatgatctacgaagtgagcaacagaccaagcggcgtga gcaacaga |
| L-2-2A2-S5 | ttctccggtagcaaatctggcaacacagcc |
| L-2-2A2-S6 | agcctgaccatcagcggtttgcaggccgag |
| L-2-2A2-S7 | gatgaagctgattactattgccagagctgggattctagcctgaacggtgttgtgt tcggcggtggcaccaaa |
| | |
| L-2-2A2-A1 | ctgacccagccagcctccgtgagcggttccccaggccagagc |
| L-2-2A2-A2 | attaccatcagctgcacaggcacaagctccgac |
| L-2-2A2-A3 | caacagcatccaggcaaagcccccaaag |
| L-2-2A2-A4 | agcggcgtgagcaacagattctccggtagcaaa |
| L-2-2A2-A5 | tctggcaacacagctagtctgaccatcagt |
| L-2-2A2-A6 | ggtttgcaggccgaggatgaagctgattactattgc |
| L-2-2A2-A7 | gtgttcggcggtggcaccaaactgacagttctgggacag |

V$_\lambda$3 3r sub-family

| | |
|---|---|
| L-3-3R-S1 | agctacgaactgacccagcctccaagcgtg |
| L-3-3R-S2 | agcgttagcccaggccagaccgccagcattacatgc |
| L-3-3R-S3 | agcggcgataagttgggcgataaatacgcctgctggtatcaacagaaacct |
| L-3-3R-S4 | ggccagagccctgtgttggtgatctaccaggatagcaaaagaccaagcggcatcc ctgaaaga |
| L-3-3R-S5 | ttctccggtagcaactctggcaacacagca |
| L-3-3R-S6 | accctgaccatcagcggcacccaggctatg |
| L-3-3R-S7 | gatgaagctgattactattgccagagctgggattctagcctgaacggtgttgtgt tcggcggtggcaccaaa |
| | |
| L-3-3R-A1 | ctgacccagcctccaagcgtgagcgttagcccaggtcagacc |
| L-3-3R-A2 | gccagcattacatgtagcggtgataagttgggt |
| L-3-3R-A3 | caacagaaacctggccagagcccagtg |
| L-3-3R-A4 | agcggcatccctgaaagattctccggtagcaac |
| L-3-3R-A5 | tctggcaacacagcaaccctgaccatcagc |
| L-3-3R-A6 | ggcacccaggctatggatgaagctgattactattgc |
| L-3-3R-A7 | gtgttcggcggtggcaccaaactgacagttctgggacag |

FIG. 62E

V$_\lambda$3  31 sub-family

| | |
|---|---|
| L-3-3L-S1 | agctccgaactgacccaggacccagccgtg |
| L-3-3L-S2 | agcgtggccctgggccagaccgtgagaatcacctgc |
| L-3-3L-S3 | cagggcgatagcctgagaagctactatgccagctggtatcaacagaaacca |
| L-3-3L-S4 | ggccaggccccagttctggtgatctacggcaaaaataacagaccaagcggcatcccagataga |
| L-3-3L-S5 | ttctccggtagctctagcggcaacacagcc |
| L-3-3L-S6 | agcctgaccatcaccggtgcccaggccgag |
| L-3-3L-S7 | gatgaagctgattactattgccagagctgggattctagcctgaacggtgttgtgttcggcggtggcaccaaa |
| | |
| L-3-3L-A1 | ctgacccaggacccagccgtgagcgttgccctgggccagacc |
| L-3-3L-A2 | gtgagaatcacctgccagggcgattctctgaga |
| L-3-3L-A3 | caacagaaacctggccaggccccagtg |
| L-3-3L-A4 | agcggcatcccagatagattctctggtagctct |
| L-3-3L-A5 | agcggcaacacagcatctctgaccatcaca |
| L-3-3L-A6 | ggtgcccaggccgaggatgaagctgattactattgc |
| L-3-3L-A7 | gtgttcggcggtggcaccaaactgacagttctgggacag |

V$_\kappa$3  L6 sub-family

K-III-L6-S1 gaaatcgtgctgacacagtctccagccacc
K-III-L6-S2 ttgtctctgtccccaggcgaaagagctacactgtcctgc
K-III-L6-S3 agagcttctcagtccgtgtctagttatctggcctggtatcaacagaaacct
K-III-L6-S4 ggtcaggcccctagattgctgatctacgatgcttctaacagagccacaggcatccctgccaga
K-III-L6-S5 ttctctggtagcggctctggcacagatttc
K-III-L6-S6 acactgactatctctagcttggaaccagaa
K-III-L6-S7 gatttcgccgtttactattgccaacagtacaacagcacccattgacattcggtcagggcaccaaa K-III-L6-A1 ttgacacagtctccagccaccttgtctctgtccccaggcgaa
K-III-L6-A2 agagctacactgtcctgcagagcttctcagtccgtg
K-III-L6-A3 caacagaaacctggtcaggcccctaga
K-III-L6-A4 acaggtatccctgccagattctctggtagcggc
K-III-L6-A5 tctggcacagatttcacactgactatctct
K-III-L6-A6 agcttggaaccagaagatttcgccgtttactattgc
K-III-L6-A7 acattcggtcagggcaccaaagtggaaatcaaaagaac

FIG. 62F

VH3_1_6_WAGCCAGGCGGCTTTACCTTC

| 30 | 31 | 32 | 33 | 34 | 35 | TGGGTTAGACAGGCACCT |
|----|----|----|----|----|----|---|
| T  | T  | C  | G  | A  | K  | |
| C  | C  | T  | C  | T  | C  | |
|    |    | A  | C  | G  | C  | |

VK3_18_WAAGAGCTTCTCAGTCCGTG

| 30 | 30A | 31 | 32 | 33 | 34 | 35 | 36 | CAACAGAAACCT |
|----|-----|----|----|----|----|----|----|---|
| T  | A   | K  | C  | C  | G  | G  | T  | |
| C  | R   | C  | C  | T  | C  | C  | A  | |
|    | C   |    | T  |    | T  | T  | C  | |
|    |     |    | A  |    | G  | G  | |  |

FIG. 62G

Avastin A4.6.1 anti-VEGF: V_L kappa 1, kappa 3 and V_H1 1e, CDRs 1, 2, and 3 oligonucleotides

```
K1_1_C01 GCAGAGCTTCTCAGGGTATCAGCAACTACCTGAACTGGTACCAACAGAAGCCTGGTAAA
K3_1_C01 GCAGAGCTTCTCAGTCCGTGAGCAACTACCTGCCTGTACCAACAGAAACCTGGTCAGGC
H1e_2_C01 CACCTGGTCAGGGCTTGGATGGGCTGGATCAACCCTACTTCGGCACCAGCTACACGCTCAGAAATTCCAGGG
H1e_2_C02 CACCTGGTCAGGGCTTGGAGTGGCTGGATGGGCTGGATCAACCCCTACTTCGGCACCAGCTACACGCTCAGAAATTCCAGGG
H1e_2_C03 CACCTGGTCAGGGCTTGGAGTGGCTGGATGGGCTGGATCAACCCCTACACAGCGGCACCAGCTACACGCTCAGAAATTCCAGGG
H1e_2_C04 CACCTGGTCAGGGCTTGGAGTGGCTGGATGGGCTGGATCAACCCCTACACAGCGGCACCAACGGCACCAGCTACACGCTCAGAAATTCCAGGG
H1e_2_C05 CACCTGGTCAGGGCTTGGAGTGGCTGGATGGGCTGGATCAACCCCTACAACAGCGGCACCAACGGCACCAGCTACACGCTCAGAAATTCCAGGG
H1e_2_C06 CACCTGGTCAGGGCTTGGAGTGGCTGGATGGGCTGGATCAACCCCTACAACAGCGGCACCAACGGCACCAACACCAGCTACACGCTCAGAAATTCCAGGG
H1e_2_C07 CACCTGGTCAGGGCTTGGAGTGGCTGGATGGGCTGGATCAACCCCTACTTCGGCAACAACCAGCTACACGCTCAGAAATTCCAGGG
H1e_2_C08 CACCTGGTCAGGGCTTGGAGTGGCTGGATGGGCTGGATCAACCCCTACTTCGGCAACAACCAGCTACACGCTCAGAAATTCCAGGG
H1e_2_C09 CACCTGGTCAGGGCTTGGAGTGGCTGGATGGGCTGGATCAACCCCTACTTCGGCAACAACACCAGCTACACGCTCAGAAATTCCAGGG
H1e_2_C10 CACCTGGTCAGGGCTTGGAGTGGCTGGATGGGCTGGATCAACCCCTACAACAGCGGCGGCAACAACGGCAACAACCAGCTACACGCTCAGAAATTCCAGGG
H1e_2_C11 CACCTGGTCAGGGCTTGGAGTGGCTGGATGGGCTGGATCAACCCCTACAACAGCGGCGGCAACAACGGCAACAACACCAGCTACACGCTCAGAAATTCCAGGG
H1e_2_C12 CACCTGGTCAGGGCTTGGAGTGGCTGGATGGGCTGGATGGGCTGGATCAACCCCTACAACAGCGGCGGCAACAACGGCAACAACACCAGCTACACGCTCAGAAATTCCAGGG
H1e_3_C01 ATACCGCCGTGTATTACTGTGCCAAGAGACCCCACTACGGCAGCAGCAGCAGCAGCAGCTGGTACTTCGACTACTTCGACTACTGGGGTCAGGGCACTCT
H1e_3_C02 ATACCGCCGTGTATTACTGTGCCAAGAGCACCACTACGGCCAAGGACCCCACTACTACGGCAGCAGCAGCAGCAGCAGCTGGTACTTCGACTACTTCGACTACTGGGGTCAGGGCACTCT
H1e_3_C03 ATACCGCCGTGTATTACTGTGCCAAGAGCACCACTACTGTGCCAAGGAGCCCCACTACTACGGCAGCAGCAGCAGCAGCAGCTGGTACTTCGACTACTTCGACTACTGGGGTCAGGGCACTCT
H1e_3_C04 ATACCGCCGTGTATTACTGTGCCAAGAGCACCACTACTGTGCCAAGGAGACCCCACTACTACGGCAGCAGCAGCAGCAGCAGCTGGTACTTCGACTACTTCGACTACTGGGGTCAGGGCACTCT
K1_3_C01 ATTTCGCCACCTACTATTGCCAGCAGTACAGCACACCTGGCCCCTGGACACCTTCGGTCAGGGCACCAA
K1_3_C02 ATTTCGCCACCTACTATTGCCAGCAGTACAGCACACCTACCCCCTGGACATTCGGTCAGGGCACCAA
K1_3_C03 ATTTCGCCACCTACTATTGCCAGCAGTACAGCACACCTACCCCTGGACATTCGGTCAGGGCACCAA
K3_3_C01 ATTTCGCCGTTTACTATTGCCAGCAGTACAGCACACCTGGCCCCTGGACATTCGGTCAGGGCACCAA
```

FIG. 62H

```
K3_3_C02    ATTTCGCCGTTTACTATTGCCAGCAGTACACAGCACCCCCTGGACATTCGGTCAGGGCACCAA
K3_3_C03    ATTTCGCCGTTTACTATTGCCAGCAGTACAGCACCACCCCTGGACATTCGGTCAGGGCACCAA
H1e_1_VEGF01

CDR1 H1 oligoC
            AGGCTTCCGGTGGCAGATTCACCAACTACGGGATGAACTGGGTTAGACAGGCACCTGG CDR2 G1 oligoC
            AGGCCTGGTAAAGCCCCCTAAGCGGCTGGCTGTGATCTACAAGGCCAGCAGCCTGCAGTCCGGCGTTCCTAGCAGATT
            AGGCCTGGTAAAGCCCCCTAAGCGGCTGGCTGTGATCTACGCGCCAGCAGCCTGCAGTCCGGCGTTCCTAGCAGATT
            AGGCCTGGTAAAGCCCCCTAAGCGGCTGGCTGTGATCTACAAGCAGCAGCAGCCTGCAGTCCGGCGTTCCTAGCAGATT CDR2 G3 oligoC L6  AACCTGGTCAGGCCCCTAGACTGCTGATCTACGACAGCAGGGCCACAGGTATCCCTGCCAGATT Avastin A4.6.1 anti-VEGF: V_L and V_H, CDRs 1, 2, and 3 stop codon oligonucleotides CDR1 H1 STOP
H1e_1_VEGFstop   AGGCTTCCGGTGGCACATTCCACCAACTAATAAATGAACTGGGTTAGACAGGCACCTGG
CDR2 H1 STOP
H1e_2_VEGFstop   CACCTGGTCAGGGCTTCAGGGTTGGAGTTGATGGGCTTGATCTAATAATACTTCGGCACCRCCRGCTACGCTCAGAAATTCCAGGG
CDR1 K1 STOP
K1_1_VEGFstop    GCAGAGCTTCTCAGGGTATCAGCAGGGCCTGATCTAGTAAAACTTGTACCAACAGAAGCCTGGTAAAGC
CDR2 K1 STOP
K1_2_VEGFstop    AGCCTGGTAAAGCCCCTAAGCGGCTGATCTAGTAAGCCAGCAGCCTGSAGTCCGGGCGTTCCTAGCAGATT
CDR1 K3 STOP shared for both A27 and L6 kappa 3 frameworks
K3_2_VEGFstop    GCAGAGCTTCTCAGTCCGTGAGCAACTAGTAAGCCTTGTACCAACAGAAACCTGGTCAGGC
```

FIG. 62I

```
                   CDR2 K3 STOP A27 1st and L6 2nd
K3A27_1_VEGFstop   AACCTGGTCAGGCCCCTCGCCTGCTGATCTAGTAAACCAGCAGCAGGGCCACAGGCATCCCTGATATATT
K3L6_1_VEGFstop    AACCTGGTCAGGCCCCTAGACTGCTGATCTAGTAATAACCAGCAGCAGGTATCCCTGCCAGATT Avastin A4.6.1 anti-VEGF: V_H3 CDRs 1, 2, and 3 oligonucleotides:

See Table 30

MCP-1: V_L and V_H, CDRs 1, 2, and 3

H3_1_MCP101   CTGCCAGTGGCTTTACCTTCAGCASCTACTGGATGAGCTGGGTTAGACAGGCTCCTGG
H3_1_MCP102   CTGCCAGTGGCTTTACCTTCAGCACTACTGGATGAGCTGGGTTAGACAGGCTCCTGG
H3_2_MCP101   CTCCTGCCAAGGGTTTGGAATGGGTGGCCAACATCAASCAGGACGGCAGCAGGACTACTATGCAGATAGCGTCAAAGG
H3_2_MCP102   CTCCTGCCAAGGGTTTGGAATGGGTGGCCAACATCTSGCAGGACGGCAGCAGGACTACTATGCAGATAGCGTCAAAGG
H3_3_MCP101   ATACCGCTGTGTATTACTGTGCCAGGAGACCTGRKCGGCTACWTSGACTACTGGGTCAGGGCACACT
H3_3_MCP102   ATACCGCTGTGTATTACTGTGCCAGGAGACCTGRKCGGCTACSCCGACTACTGGGTCAGGGCACACT
H3_3_MCP103   ATACCGCTGTGTATTACTGTGCCAGGAGACCTGCWGGGCTACWTSGACTACTGGGTCAGGGCACACT
H3_3_MCP104   ATACCGCTGTGTATTACTGTGCCAGGAGACCTGCWGGGCTACSCCGACTACTGGGTCAGGGCACACT
H3_3_MCP105   ATACCGCTGTGTATTACTGTGCCAGGAGACCTGCMGGGCTACKGCGACTACTGGGTCAGGGCACACT
H3_3_MCP106   ATACCGCTGTGTATTACTGTGCCAGGAGACCTGWACGGCTACWTSGACTACTGGGTCAGGGCACACT
H3_3_MCP107   ATACCGCTGTGTATTACTGTGCCAGGAGACCTGWACGGCTACSCCGACTACTGGGTCAGGGCACACT
H3_3_MCP108   ATACCGCTGTGTATTACTGTGCCAGGAGACCTGWACGGCTACKGCGACTACTGGGTCAGGGCACACT
H3_3_MCP109   ATACCGCTGTGTATTACTGTGCCAGGAGACCTGASCGGCTACWTSGACTACTGGGTCAGGGCACACT
H3_3_MCP110   ATACCGCTGTGTATTACTGTGCCAGGAGACCTGASCGGCTACSCCGACTACTGGGTCAGGGCACACT
H3_3_MCP111   ATACCGCTGTGTATTACTGTGCCAGGAGACCTGASCGGCTACKGCGACTACTGGGTCAGGGCACACT
H3_3_MCP112   ATACCGCTGTGTATTACTGTGCCAGGAGACCTGASCGGCTACKGCGACTACTGGGTCAGGGCACACT
```

FIG. 62J

```
K1_1_MCP101  GCAGAGCTTCTCAGGGTATCAGCAGCKACCTGGCCTGGTACCAACAGAAGCCTGGTAAAGC
K1_1_MCP102  GCAGAGCTTCTCAGGGTATCAGCAGCTSGCTGGCCTGGTACCAACAGAAGCCTGGTAAAGC
K1_2_MCP101  AGCCTGGTAAAGCCCCTAAGCTGCTGATCTACGACGCCAGCACTCCCCCTGGAGTCCGGCGTTCCTAGCAGATT
K1_3_MCP101  ATTTCGCCACCTACTATTGCCAGCAGGSCAACAGCTACCCCCTGACATTCGGTCAGGGCACCAA
K1_3_MCP102  ATTTCGCCACCTACTATTGCCAGCAGSAACAGCTACCCCCTGACATTCGGTCAGGGCACCAA
K1_3_MCP103  ATTTCGCCACCTACTATTGCCAGCAGTACAACAGCTACCCCCTGACATTCGGTCAGGGCACCAA
K3_1_MCP101  GCAGAGCTTCTCAGTCCGTGAGCAGCWACCTGGCCTGATCTACGACGCAGGCCACAGGCCATCCCTGATAGATT
K3_2_MCP101  AACCTGGTCAGGCCCCTCGCCGTTTACTATTGCCAGCAGSCAACAGCTACCCCCTGACATTCGGTCAGGGCACCAA
K3_2_MCP102  ATTTCGCCGTTTACTATTGCCAGCAGSAACAGCTACCCCCTGACATTCGGTCAGGGCACCAA
K3_3_MCP101  ATTTCGCCGTTTACTATTGCCAGCAGTACAACAGCTACCCCCTGACATTCGGTCAGGGCACCAA
K3_3_MCP102  ATTTCGCCGTTTACTATTGCCAGCAGTACAACAGCTACCCCCTGACATTCGGTCAGGGCACCAA
K3_3_MCP103  ATTTCGCCCGTTTACTATTGCCAGCAGTACAACAGCTACCCCCTGACATTCGGTCAGGGCACCAA
```

CTLA-4: V$_L$ and V$_H$, CDRs 1, 2, and 3

SEQUENCE LISTING

```
<160> NUMBER OF SEQ ID NOS: 641

<210> SEQ ID NO 1
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60
```

```
Gln Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

<210> SEQ ID NO 2
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
                 20                  25                  30

Trp Met Ser Trp Val Arg Gln Ala Pro Gly Lys Gly Leu Glu Trp Val
             35                  40                  45

Ala Asn Ile Lys Gln Asp Gly Ser Glu Lys Tyr Tyr Val Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

<210> SEQ ID NO 3
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gln Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Ser Asp Tyr
                 20                  25                  30

Tyr Met Ser Trp Ile Arg Gln Ala Pro Gly Lys Gly Leu Glu Trp Val
             35                  40                  45

Ser Tyr Ile Ser Ser Ser Gly Ser Thr Ile Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

<210> SEQ ID NO 4
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
                 20                  25                  30
```

```
Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

<210> SEQ ID NO 5
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

<210> SEQ ID NO 6
<211> LENGTH: 88
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Asn Tyr
                20                  25                  30

Leu Ala Trp Phe Gln Gln Lys Pro Gly Lys Ala Pro Lys Ser Leu Ile
        35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys
                 85

<210> SEQ ID NO 7
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide
```

-continued

```
<400> SEQUENCE: 7

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys
                85

<210> SEQ ID NO 8
<211> LENGTH: 88
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Pro Gly Thr Asp Phe Thr Leu Thr Ile Ser Ser Leu Glu Pro
65                  70                  75                  80

Glu Asp Phe Ala Val Tyr Tyr Cys
                85

<210> SEQ ID NO 9
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys
                85

<210> SEQ ID NO 10
```

```
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Glu Val Ser Asn Arg Pro Ser Gly Val Ser Asn Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys
                85                  90

<210> SEQ ID NO 11
<211> LENGTH: 87
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
                20                  25                  30

Cys Trp Tyr Gln Gln Lys Pro Gly Gln Ser Pro Val Leu Val Ile Tyr
            35                  40                  45

Gln Asp Ser Lys Arg Pro Ser Gly Ile Pro Glu Arg Phe Ser Gly Ser
50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys
                85

<210> SEQ ID NO 12
<211> LENGTH: 87
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
                20                  25                  30

Ser Trp Tyr Gln Gln Lys Pro Gly Gln Ala Pro Val Leu Val Ile Tyr
            35                  40                  45

Gly Lys Asn Asn Arg Pro Ser Gly Ile Pro Asp Arg Phe Ser Gly Ser
50                  55                  60

Ser Ser Gly Asn Thr Ala Ser Leu Thr Ile Thr Gly Ala Gln Ala Glu
```

-continued

```
              65                  70                  75                  80

Asp Glu Ala Asp Tyr Tyr Cys
                85

<210> SEQ ID NO 13
<211> LENGTH: 6
<212> TYPE: PRT
<213> ORGANISM: Mus musculus

<400> SEQUENCE: 13

Thr Asn Tyr Gly Met Asn
1               5

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Thr Asn Tyr Gly Met Asn
1               5

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ser or Asn

<400> SEQUENCE: 15

Xaa Asn Tyr Gly Met Asn
1               5

<210> SEQ ID NO 16
<211> LENGTH: 13
<212> TYPE: PRT
<213> ORGANISM: Mus musculus

<400> SEQUENCE: 16

Trp Met Gly Trp Ile Asn Thr Tyr Thr Gly Glu Pro Thr
1               5                   10

<210> SEQ ID NO 17
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Pro or Ala
<220> FEATURE:
<221> NAME/KEY: MOD_RES
<222> LOCATION: (9)..(9)
<223> OTHER INFORMATION: Phe, Ser, Asn or Gly
<220> FEATURE:
<221> NAME/KEY: MOD_RES
<222> LOCATION: (11)..(11)
<223> OTHER INFORMATION: Thr, Asn, Gly, Ser or Asp
<220> FEATURE:
```

```
<221> NAME/KEY: MOD_RES
<222> LOCATION: (12)..(12)
<223> OTHER INFORMATION: Thr or Ala
<220> FEATURE:
<221> NAME/KEY: MOD_RES
<222> LOCATION: (13)..(13)
<223> OTHER INFORMATION: Asn, Lys, Ser or Gly

<400> SEQUENCE: 17

Trp Met Gly Trp Ile Asn Xaa Tyr Xaa Gly Xaa Xaa Xaa
1               5                   10

<210> SEQ ID NO 18
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ser or Ala
<220> FEATURE:
<221> NAME/KEY: MOD_RES
<222> LOCATION: (4)..(4)
<223> OTHER INFORMATION: Val, Ala, Asn, Gly, Tyr, Ser or Thr
<220> FEATURE:
<221> NAME/KEY: MOD_RES
<222> LOCATION: (7)..(7)
<223> OTHER INFORMATION: Gly, Tyr, Ser, Gln, Trp, Asn or Phe
<220> FEATURE:
<221> NAME/KEY: MOD_RES
<222> LOCATION: (8)..(8)
<223> OTHER INFORMATION: Asp, Ser or Asn
<220> FEATURE:
<221> NAME/KEY: MOD_RES
<222> LOCATION: (9)..(9)
<223> OTHER INFORMATION: Gly or Ser
<220> FEATURE:
<221> NAME/KEY: MOD_RES
<222> LOCATION: (12)..(12)
<223> OTHER INFORMATION: Thr, Lys or Ile
<220> FEATURE:
<221> NAME/KEY: MOD_RES
<222> LOCATION: (13)..(13)
<223> OTHER INFORMATION: Tyr, Asn, Phe or His

<400> SEQUENCE: 18

Trp Val Xaa Xaa Ile Asn Xaa Xaa Xaa Gly Glu Xaa Xaa
1               5                   10

<210> SEQ ID NO 19
<211> LENGTH: 15
<212> TYPE: PRT
<213> ORGANISM: Mus musculus

<400> SEQUENCE: 19

Ala Lys Tyr Pro His Tyr Tyr Gly Ser Ser His Trp Tyr Phe Asp
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Gly, Asp, Glu, Arg, Ala, His, Val or Thr

<400> SEQUENCE: 20
```

```
Ala Lys Xaa Pro His Tyr Tyr Gly Ser Ser His Trp Tyr Phe Asp
1               5                   10                  15

<210> SEQ ID NO 21
<211> LENGTH: 7
<212> TYPE: PRT
<213> ORGANISM: Mus musculus

<400> SEQUENCE: 21

Ser Asn Tyr Leu Asn Trp Tyr
1               5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ser Asn Tyr Leu Asn Trp Tyr
1               5

<210> SEQ ID NO 23
<211> LENGTH: 10
<212> TYPE: PRT
<213> ORGANISM: Mus musculus

<400> SEQUENCE: 23

Val Leu Ile Tyr Phe Thr Ser Ser Leu His
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Leu or Arg
<220> FEATURE:
<221> NAME/KEY: MOD_RES
<222> LOCATION: (5)..(5)
<223> OTHER INFORMATION: Ala, Asp, Lys, Gly or Ser
<220> FEATURE:
<221> NAME/KEY: MOD_RES
<222> LOCATION: (10)..(10)
<223> OTHER INFORMATION: Gln or Glu

<400> SEQUENCE: 24

Xaa Leu Ile Tyr Xaa Ala Ser Ser Leu Xaa
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Gly or Asp

<400> SEQUENCE: 25
```

```
Leu Leu Ile Tyr Xaa Thr Ser Ser Arg Ala
1               5                   10
```

<210> SEQ ID NO 26
<211> LENGTH: 8
<212> TYPE: PRT
<213> ORGANISM: Mus musculus

<400> SEQUENCE: 26

```
Gln Gln Tyr Ser Thr Val Pro Trp
1               5
```

<210> SEQ ID NO 27
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Tyr, Thr, Ser, Leu, Trp or Phe

<400> SEQUENCE: 27

```
Gln Gln Tyr Ser Thr Xaa Pro Trp
1               5
```

<210> SEQ ID NO 28
<211> LENGTH: 114
<212> TYPE: PRT
<213> ORGANISM: Mus musculus

<400> SEQUENCE: 28

```
Asp Ile Val Met Thr Gln Ala Thr Pro Ser Val Ser Val Thr Pro Gly
1               5                   10                  15

Glu Ser Val Phe Ile Ser Cys Arg Ser Ser Lys Ser Leu Leu Tyr Ser
                20                  25                  30

Asn Gly Asn Thr Tyr Leu Tyr Trp Phe Leu Gln Arg Pro Gly Gln Ser
            35                  40                  45

Pro Gln Leu Leu Ile Tyr Arg Leu Phe His Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Tyr Thr Phe Gly Gly Thr Lys Leu Glu Ile Lys Arg
                100                 105                 110

Ala Asp
```

<210> SEQ ID NO 29
<211> LENGTH: 12
<212> TYPE: PRT
<213> ORGANISM: Mus musculus

<400> SEQUENCE: 29

```
Leu Tyr Ser Asn Gly Asn Thr Tyr Leu Tyr Trp Phe
1               5                   10
```

<210> SEQ ID NO 30
<211> LENGTH: 10
<212> TYPE: PRT
<213> ORGANISM: Mus musculus

```
<400> SEQUENCE: 30

Leu Leu Ile Tyr Arg Leu Phe His Leu Ala
1               5                   10

<210> SEQ ID NO 31
<211> LENGTH: 9
<212> TYPE: PRT
<213> ORGANISM: Mus musculus

<400> SEQUENCE: 31

Met Gln His Leu Glu Tyr Pro Tyr Thr
1               5

<210> SEQ ID NO 32
<211> LENGTH: 8
<212> TYPE: PRT
<213> ORGANISM: Mus musculus
<220> FEATURE:
<221> NAME/KEY: MOD_RES
<222> LOCATION: (2)..(2)
<223> OTHER INFORMATION: Tyr, Ser, Asn or Gly

<400> SEQUENCE: 32

Leu Xaa Thr Tyr Leu Tyr Trp Phe
1               5

<210> SEQ ID NO 33
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ser, Arg, Gly, Asn or Tyr
<220> FEATURE:
<221> NAME/KEY: MOD_RES
<222> LOCATION: (2)..(2)
<223> OTHER INFORMATION: Tyr, Ser, Asn or Gly
<220> FEATURE:
<221> NAME/KEY: MOD_RES
<222> LOCATION: (6)..(6)
<223> OTHER INFORMATION: Ala or Asn

<400> SEQUENCE: 33

Xaa Xaa Asn Tyr Leu Xaa Trp Tyr
1               5

<210> SEQ ID NO 34
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ser, Gly or Asn
<220> FEATURE:
<221> NAME/KEY: MOD_RES
<222> LOCATION: (2)..(2)
<223> OTHER INFORMATION: Tyr, Ser, Asn or Gly

<400> SEQUENCE: 34

Xaa Xaa Thr Tyr Leu Ala Trp Tyr
1               5
```

```
<210> SEQ ID NO 35
<211> LENGTH: 9
<212> TYPE: PRT
<213> ORGANISM: Mus musculus
<220> FEATURE:
<221> NAME/KEY: MOD_RES
<222> LOCATION: (2)..(2)
<223> OTHER INFORMATION: Tyr, Ser, Asn or Gly

<400> SEQUENCE: 35

Ser Xaa Asn Thr Tyr Leu Tyr Trp Phe
 1               5

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Tyr, Ser, Asn or Gly

<400> SEQUENCE: 36

Ser Xaa Asn Thr Tyr Leu Ala Trp Tyr
 1               5

<210> SEQ ID NO 37
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Ala, Asp, Lys, Gly or Ser
<220> FEATURE:
<221> NAME/KEY: MOD_RES
<222> LOCATION: (8)..(8)
<223> OTHER INFORMATION: Ile, Ser, Thr or Asn
<220> FEATURE:
<221> NAME/KEY: MOD_RES
<222> LOCATION: (10)..(10)
<223> OTHER INFORMATION: Gln or Glu

<400> SEQUENCE: 37

Leu Leu Ile Tyr Xaa Ala Ser Xaa Leu Xaa
 1               5                  10

<210> SEQ ID NO 38
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Gly or Asp
<220> FEATURE:
<221> NAME/KEY: MOD_RES
<222> LOCATION: (6)..(6)
<223> OTHER INFORMATION: Ala or Thr
<220> FEATURE:
<221> NAME/KEY: MOD_RES
<222> LOCATION: (8)..(8)
<223> OTHER INFORMATION: Ser, Thr or Asn
```

```
<400> SEQUENCE: 38

Leu Leu Ile Tyr Xaa Xaa Ser Xaa Arg Ala
1               5                   10

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Ser, Asp, Tyr, Asn or Gly
<220> FEATURE:
<221> NAME/KEY: MOD_RES
<222> LOCATION: (5)..(5)
<223> OTHER INFORMATION: Asp, Gly, Thr, Asn or Ser
<220> FEATURE:
<221> NAME/KEY: MOD_RES
<222> LOCATION: (8)..(8)
<223> OTHER INFORMATION: Pro, Leu, Arg, Ser or Thr

<400> SEQUENCE: 39

Gln Gln His Xaa Xaa Tyr Pro Xaa Thr
1               5

<210> SEQ ID NO 40
<211> LENGTH: 107
<212> TYPE: PRT
<213> ORGANISM: Homo sapiens

<400> SEQUENCE: 40

Asp Ile Val Met Thr Gln Ser Pro Ser Ser Leu Ser Ala Ser Val Gly
1               5                   10                  15

Asp Arg Val Thr Ile Thr Cys Arg Ala Ser Leu Lys Ile Ile Asn Phe
                20                  25                  30

Leu Ser Trp Tyr Gln Gln Lys Pro Gly Lys Ala Pro Lys Leu Val Leu
            35                  40                  45

Tyr Ala Ala Ser Thr Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Leu Ala Thr Tyr Tyr Cys Gln Gln Ser Tyr Ile Leu Pro Pro
                85                  90                  95

Thr Phe Gly Gly Gly Thr Lys Val Asp Ile Leu
            100                 105

<210> SEQ ID NO 41
<211> LENGTH: 7
<212> TYPE: PRT
<213> ORGANISM: Homo sapiens

<400> SEQUENCE: 41

Ile Phe Asn Leu Ser Trp Tyr
1               5

<210> SEQ ID NO 42
<211> LENGTH: 10
<212> TYPE: PRT
<213> ORGANISM: Homo sapiens

<400> SEQUENCE: 42

Leu Val Leu Tyr Ala Ala Ser Thr Leu Gln
```

<210> SEQ ID NO 43
<211> LENGTH: 9
<212> TYPE: PRT
<213> ORGANISM: Homo sapiens

<400> SEQUENCE: 43

Gln Gln Ser Tyr Ile Leu Pro Pro Thr
1               5

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ser, Gly or Asn
<220> FEATURE:
<221> NAME/KEY: MOD_RES
<222> LOCATION: (2)..(2)
<223> OTHER INFORMATION: Ser, Asn or Thr

<400> SEQUENCE: 44

Xaa Xaa Asn Leu Ala Trp Tyr
1               5

<210> SEQ ID NO 45
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Gly or Asp

<400> SEQUENCE: 45

Leu Leu Ile Tyr Xaa Ala Ser Thr Arg Ala
1               5                   10

<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Asp, Gly, Thr, Asn or Ser
<220> FEATURE:
<221> NAME/KEY: MOD_RES
<222> LOCATION: (6)..(6)
<223> OTHER INFORMATION: Tyr, Thr, Ser or Trp

<400> SEQUENCE: 46

Gln Gln Ser Tyr Xaa Xaa Pro Pro Thr
1               5

<210> SEQ ID NO 47
<211> LENGTH: 6
<212> TYPE: PRT
<213> ORGANISM: Homo sapiens

```
<400> SEQUENCE: 47

Ser His Tyr Trp Met Ser
1               5

<210> SEQ ID NO 48
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ser, Asn, Asp or Thr

<400> SEQUENCE: 48

Ser Xaa Tyr Trp Met Ser
1               5

<210> SEQ ID NO 49
<211> LENGTH: 6
<212> TYPE: PRT
<213> ORGANISM: Homo sapiens

<400> SEQUENCE: 49

Ser His Tyr Trp Met Ser
1               5

<210> SEQ ID NO 50
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ser, Gly, Asp or Asn
<220> FEATURE:
<221> NAME/KEY: MOD_RES
<222> LOCATION: (4)..(4)
<223> OTHER INFORMATION: Ala, Tyr, Gly or Asp

<400> SEQUENCE: 50

Ser Xaa Tyr Xaa Met Ser
1               5

<210> SEQ ID NO 51
<211> LENGTH: 13
<212> TYPE: PRT
<213> ORGANISM: Homo sapiens

<400> SEQUENCE: 51

Trp Val Ala Asn Ile Glu Gln Asp Gly Ser Glu Lys Tyr
1               5                   10

<210> SEQ ID NO 52
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Trp, Gly or Arg
```

```
<220> FEATURE:
<221> NAME/KEY: MOD_RES
<222> LOCATION: (6)..(6)
<223> OTHER INFORMATION: Asn, Ile or Ser
<220> FEATURE:
<221> NAME/KEY: MOD_RES
<222> LOCATION: (7)..(7)
<223> OTHER INFORMATION: Pro or Ala
<220> FEATURE:
<221> NAME/KEY: MOD_RES
<222> LOCATION: (8)..(8)
<223> OTHER INFORMATION: Ile, Asn, Ser, Tyr, Gly or Met
<220> FEATURE:
<221> NAME/KEY: MOD_RES
<222> LOCATION: (11)..(11)
<223> OTHER INFORMATION: Thr, Asn, Gly, Ser or Glu
<220> FEATURE:
<221> NAME/KEY: MOD_RES
<222> LOCATION: (12)..(12)
<223> OTHER INFORMATION: Thr or Ala
<220> FEATURE:
<221> NAME/KEY: MOD_RES
<222> LOCATION: (13)..(13)
<223> OTHER INFORMATION: Asn, Lys, Ser or Gly

<400> SEQUENCE: 52

Trp Met Gly Xaa Ile Xaa Xaa Xaa Gly Gly Xaa Xaa Xaa
1               5                   10

<210> SEQ ID NO 53
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser, Lys, Trp or Asn

<400> SEQUENCE: 53

Trp Val Ala Asn Ile Xaa Gln Asp Gly Ser Glu Lys Tyr
1               5                   10

<210> SEQ ID NO 54
<211> LENGTH: 9
<212> TYPE: PRT
<213> ORGANISM: Homo sapiens

<400> SEQUENCE: 54

Ala Arg Asp Leu Asp Gly Tyr Thr Asp
1               5

<210> SEQ ID NO 55
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Gly, Ser, Val, Tyr, Arg, Thr, Asn, Ile, Leu or
      Gln
<220> FEATURE:
<221> NAME/KEY: MOD_RES
<222> LOCATION: (8)..(8)
<223> OTHER INFORMATION: Phe, Leu, Gly, Ser, Met, Ala, Ile or Pro

<400> SEQUENCE: 55

Ala Arg Asp Leu Xaa Gly Tyr Xaa Asp
```

```
<210> SEQ ID NO 56
<211> LENGTH: 7
<212> TYPE: PRT
<213> ORGANISM: Homo sapiens

<400> SEQUENCE: 56

Ser Ser Ala Leu Ala Trp Tyr
1               5

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Tyr, Trp, Asp or Ser

<400> SEQUENCE: 57

Ser Ser Xaa Leu Ala Trp Tyr
1               5

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Asn or Tyr

<400> SEQUENCE: 58

Ser Ser Xaa Leu Ala Trp Tyr
1               5

<210> SEQ ID NO 59
<211> LENGTH: 10
<212> TYPE: PRT
<213> ORGANISM: Homo sapiens

<400> SEQUENCE: 59

Leu Leu Ile Tyr Asp Ala Ser Ser Leu Glu
1               5                   10

<210> SEQ ID NO 60
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Leu Leu Ile Tyr Asp Ala Ser Ser Leu Glu
1               5                   10

<210> SEQ ID NO 61
<211> LENGTH: 8
<212> TYPE: PRT
<213> ORGANISM: Homo sapiens
```

-continued

```
<400> SEQUENCE: 61

Gln Gln Phe Asn Ser Tyr Pro Leu
1               5

<210> SEQ ID NO 62
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Tyr, Ser, Ala, Gly or Arg

<400> SEQUENCE: 62

Gln Gln Xaa Asn Ser Tyr Pro Leu
1               5

<210> SEQ ID NO 63
<211> LENGTH: 6
<212> TYPE: PRT
<213> ORGANISM: Mus musculus

<400> SEQUENCE: 63

Ser Val Tyr Gly Met Asn
1               5

<210> SEQ ID NO 64
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ser, Asn, Asp or Thr

<400> SEQUENCE: 64

Ser Xaa Tyr Gly Met Asn
1               5

<210> SEQ ID NO 65
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ser, Gly, Asn or Asp

<400> SEQUENCE: 65

Ser Xaa Tyr Gly Met Asn
1               5

<210> SEQ ID NO 66
<211> LENGTH: 13
<212> TYPE: PRT
<213> ORGANISM: Mus musculus

<400> SEQUENCE: 66

Trp Val Ala Ile Ile Trp Tyr Asp Gly Asp Asn Gln Tyr
1               5                   10
```

```
<210> SEQ ID NO 67
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Trp, Gly or Arg
<220> FEATURE:
<221> NAME/KEY: MOD_RES
<222> LOCATION: (6)..(6)
<223> OTHER INFORMATION: Asn, Ile or Ser
<220> FEATURE:
<221> NAME/KEY: MOD_RES
<222> LOCATION: (7)..(7)
<223> OTHER INFORMATION: Pro or Ala
<220> FEATURE:
<221> NAME/KEY: MOD_RES
<222> LOCATION: (8)..(8)
<223> OTHER INFORMATION: Ile, Asn, Ser, Tyr, Gly or Met
<220> FEATURE:
<221> NAME/KEY: MOD_RES
<222> LOCATION: (12)..(12)
<223> OTHER INFORMATION: Thr or Ala
<220> FEATURE:
<221> NAME/KEY: MOD_RES
<222> LOCATION: (13)..(13)
<223> OTHER INFORMATION: Asn, Lys, Ser or Gly

<400> SEQUENCE: 67

Trp Met Gly Xaa Ile Xaa Xaa Xaa Gly Asp Asn Xaa Xaa
1               5                   10

<210> SEQ ID NO 68
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Val, Ala, Asn, Gly, Tyr, Ser or Thr
<220> FEATURE:
<221> NAME/KEY: MOD_RES
<222> LOCATION: (12)..(12)
<223> OTHER INFORMATION: Thr, Lys or Ile
<220> FEATURE:
<221> NAME/KEY: MOD_RES
<222> LOCATION: (13)..(13)
<223> OTHER INFORMATION: Tyr, Asn, Phe or His

<400> SEQUENCE: 68

Trp Val Ala Xaa Ile Trp Tyr Asp Gly Asp Asn Xaa Xaa
1               5                   10

<210> SEQ ID NO 69
<211> LENGTH: 10
<212> TYPE: PRT
<213> ORGANISM: Mus musculus

<400> SEQUENCE: 69

Ala Arg Asp Leu Arg Thr Gly Pro Phe Asp
1               5                   10

<210> SEQ ID NO 70
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Gly, Ser, Ala, Asp, Leu, Tyr, Val, Ile, Pro or
      Gln

<400> SEQUENCE: 70

Ala Arg Asp Leu Arg Xaa Gly Pro Phe Asp
1               5                   10

<210> SEQ ID NO 71
<211> LENGTH: 7
<212> TYPE: PRT
<213> ORGANISM: Mus musculus

<400> SEQUENCE: 71

Gly Ser Ser Leu His Trp Tyr
1               5

<210> SEQ ID NO 72
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ser, Arg, Gly, Asn or Tyr
<220> FEATURE:
<221> NAME/KEY: MOD_RES
<222> LOCATION: (5)..(5)
<223> OTHER INFORMATION: Ala or Asn

<400> SEQUENCE: 72

Xaa Ser Ser Leu Xaa Trp Tyr
1               5

<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Asn or Tyr

<400> SEQUENCE: 73

Gly Ser Xaa Leu Ala Trp Tyr
1               5

<210> SEQ ID NO 74
<211> LENGTH: 10
<212> TYPE: PRT
<213> ORGANISM: Mus musculus

<400> SEQUENCE: 74

Leu Leu Ile Lys Tyr Ala Ser Gln Ser Phe
1               5                   10

<210> SEQ ID NO 75
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Ala, Asp, Lys, Gly or Ser
<220> FEATURE:
<221> NAME/KEY: MOD_RES
<222> LOCATION: (8)..(8)
<223> OTHER INFORMATION: Ile, Ser, Thr or Asn
<220> FEATURE:
<221> NAME/KEY: MOD_RES
<222> LOCATION: (10)..(10)
<223> OTHER INFORMATION: Gln or Glu

<400> SEQUENCE: 75

Leu Leu Ile Tyr Xaa Ala Ser Xaa Leu Xaa
1               5                   10

<210> SEQ ID NO 76
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Gly or Asp
<220> FEATURE:
<221> NAME/KEY: MOD_RES
<222> LOCATION: (8)..(8)
<223> OTHER INFORMATION: Ser, Thr or Asn

<400> SEQUENCE: 76

Leu Leu Ile Tyr Xaa Ala Ser Xaa Arg Ala
1               5                   10

<210> SEQ ID NO 77
<211> LENGTH: 8
<212> TYPE: PRT
<213> ORGANISM: Mus musculus

<400> SEQUENCE: 77

His Gln Ser Ser Ser Leu Pro Phe
1               5

<210> SEQ ID NO 78
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gln or Met

<400> SEQUENCE: 78

Xaa Gln Tyr Ser Ser Leu Pro Phe
1               5

<210> SEQ ID NO 79
<211> LENGTH: 6
<212> TYPE: PRT
<213> ORGANISM: Homo sapiens
```

```
<400> SEQUENCE: 79

Ser Asp Tyr Gly Val Ser
1               5

<210> SEQ ID NO 80
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Ser Asp Tyr Gly Met Ser
1               5

<210> SEQ ID NO 81
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Ile or Met

<400> SEQUENCE: 81

Ser Asp Tyr Gly Xaa Ser
1               5

<210> SEQ ID NO 82
<211> LENGTH: 13
<212> TYPE: PRT
<213> ORGANISM: Homo sapiens

<400> SEQUENCE: 82

Trp Leu Ser Gly Ile Ser Gly Gly Gly Ser Thr Val Tyr
1               5                   10

<210> SEQ ID NO 83
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Pro or Ala
<220> FEATURE:
<221> NAME/KEY: MOD_RES
<222> LOCATION: (12)..(12)
<223> OTHER INFORMATION: Thr or Ala
<220> FEATURE:
<221> NAME/KEY: MOD_RES
<222> LOCATION: (13)..(13)
<223> OTHER INFORMATION: Asn, Lys, Ser or Gly

<400> SEQUENCE: 83

Trp Met Gly Gly Ile Ser Xaa Gly Gly Gly Thr Xaa Xaa
1               5                   10

<210> SEQ ID NO 84
<211> LENGTH: 13
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Asp, Ser or Asn
<220> FEATURE:
<221> NAME/KEY: MOD_RES
<222> LOCATION: (12)..(12)
<223> OTHER INFORMATION: Thr, Lys or Ile

<400> SEQUENCE: 84

Trp Val Ser Gly Ile Ser Gly Xaa Gly Ser Thr Xaa Tyr
1               5                   10

<210> SEQ ID NO 85
<211> LENGTH: 9
<212> TYPE: PRT
<213> ORGANISM: Homo sapiens

<400> SEQUENCE: 85

Ala Arg Gly Arg Gly Gly Tyr Tyr Asp
1               5

<210> SEQ ID NO 86
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Phe, Leu, Gly, Ser, Met, Ala, Ile or Pro

<400> SEQUENCE: 86

Ala Arg Gly Arg Gly Gly Tyr Xaa Asp
1               5

<210> SEQ ID NO 87
<211> LENGTH: 7
<212> TYPE: PRT
<213> ORGANISM: Homo sapiens

<400> SEQUENCE: 87

Gly Ser Tyr Leu Ala Trp Tyr
1               5

<210> SEQ ID NO 88
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Gly Ser Tyr Leu Ala Trp Tyr
1               5

<210> SEQ ID NO 89
<211> LENGTH: 10
<212> TYPE: PRT
<213> ORGANISM: Homo sapiens

<400> SEQUENCE: 89

Ser Leu Ile Tyr Ala Ala Ser Ser Leu Gln
1               5                   10
```

<210> SEQ ID NO 90
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Leu or Arg

<400> SEQUENCE: 90

Xaa Leu Ile Tyr Ala Ala Ser Ser Leu Gln
1               5                   10

<210> SEQ ID NO 91
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Gly or Asp

<400> SEQUENCE: 91

Leu Leu Ile Tyr Xaa Ala Ser Ser Arg Ala
1               5                   10

<210> SEQ ID NO 92
<211> LENGTH: 8
<212> TYPE: PRT
<213> ORGANISM: Homo sapiens

<400> SEQUENCE: 92

Gln Gln Tyr Asn Ser Tyr Pro Ile
1               5

<210> SEQ ID NO 93
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Gln Gln Tyr Asn Ser Tyr Pro Ile
1               5

<210> SEQ ID NO 94
<211> LENGTH: 6
<212> TYPE: PRT
<213> ORGANISM: Homo sapiens

<400> SEQUENCE: 94

Ser Asn Phe Val Ile His
1               5

<210> SEQ ID NO 95
<211> LENGTH: 6
<212> TYPE: PRT
<213> ORGANISM: Artificial Sequence
<220> FEATURE:
<223> OTHER INFORMATION: Description of Artificial Sequence: Synthetic

```
        peptide
<220> FEATURE:
<221> NAME/KEY: MOD_RES
<222> LOCATION: (3)..(3)
<223> OTHER INFORMATION: Tyr, Ala or Ser
<220> FEATURE:
<221> NAME/KEY: MOD_RES
<222> LOCATION: (4)..(4)
<223> OTHER INFORMATION: Ala, Gly, Trp or Tyr

<400> SEQUENCE: 95

Ser Asn Xaa Xaa Met Asn
1               5

<210> SEQ ID NO 96
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Ala, Tyr, Gly or Asp

<400> SEQUENCE: 96

Ser Asn Tyr Xaa Ile His
1               5

<210> SEQ ID NO 97
<211> LENGTH: 13
<212> TYPE: PRT
<213> ORGANISM: Homo sapiens

<400> SEQUENCE: 97

Trp Val Gly Trp Ile Asn Pro Tyr Asn Gly Asn Lys Glu
1               5                   10

<210> SEQ ID NO 98
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Thr or Ala
<220> FEATURE:
<221> NAME/KEY: MOD_RES
<222> LOCATION: (13)..(13)
<223> OTHER INFORMATION: Asn, Lys, Ser or Gly

<400> SEQUENCE: 98

Trp Met Gly Trp Ile Asn Pro Tyr Asn Gly Asn Xaa Xaa
1               5                   10

<210> SEQ ID NO 99
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ser or Ala
<220> FEATURE:
<221> NAME/KEY: MOD_RES
```

```
<222> LOCATION: (4)..(4)
<223> OTHER INFORMATION: Val, Ala, Asn, Gly, Tyr, Ser or Thr
<220> FEATURE:
<221> NAME/KEY: MOD_RES
<222> LOCATION: (7)..(7)
<223> OTHER INFORMATION: Gly, Tyr, Ser, Gln, Trp, Asn or Phe
<220> FEATURE:
<221> NAME/KEY: MOD_RES
<222> LOCATION: (8)..(8)
<223> OTHER INFORMATION: Asp, Ser or Asn
<220> FEATURE:
<221> NAME/KEY: MOD_RES
<222> LOCATION: (9)..(9)
<223> OTHER INFORMATION: Gly or Ser
<220> FEATURE:
<221> NAME/KEY: MOD_RES
<222> LOCATION: (13)..(13)
<223> OTHER INFORMATION: Tyr, Asn, Phe or His

<400> SEQUENCE: 99

Trp Val Xaa Xaa Ile Asn Xaa Xaa Xaa Gly Asn Lys Xaa
1               5                   10

<210> SEQ ID NO 100
<211> LENGTH: 19
<212> TYPE: PRT
<213> ORGANISM: Homo sapiens

<400> SEQUENCE: 100

Ala Arg Val Gly Pro Tyr Ser Trp Asp Asp Ser Pro Gln Asp Asn Tyr
1               5                   10                  15

Tyr Met Asp

<210> SEQ ID NO 101
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Ala Arg Val Gly Pro Tyr Ser Trp Asp Asp Ser Pro Gln Asp Asn Tyr
1               5                   10                  15

Tyr Met Asp

<210> SEQ ID NO 102
<211> LENGTH: 8
<212> TYPE: PRT
<213> ORGANISM: Homo sapiens

<400> SEQUENCE: 102

Arg Ser Arg Arg Val Ala Trp Tyr
1               5

<210> SEQ ID NO 103
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Ser or Asn
<220> FEATURE:
<221> NAME/KEY: MOD_RES
<222> LOCATION: (3)..(3)
<223> OTHER INFORMATION: Ser, Asn or Thr
```

<400> SEQUENCE: 103

Xaa Xaa Xaa Tyr Leu Ala Trp Tyr
1               5

<210> SEQ ID NO 104
<211> LENGTH: 10
<212> TYPE: PRT
<213> ORGANISM: Homo sapiens

<400> SEQUENCE: 104

Leu Leu Ile Tyr Gly Val Ser Asn Arg Ala
1               5                   10

<210> SEQ ID NO 105
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Gln or Glu

<400> SEQUENCE: 105

Leu Leu Ile Tyr Gly Ala Ser Asn Leu Xaa
1               5                   10

<210> SEQ ID NO 106
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ala or Thr

<400> SEQUENCE: 106

Leu Leu Ile Tyr Gly Xaa Ser Asn Arg Ala
1               5                   10

<210> SEQ ID NO 107
<211> LENGTH: 8
<212> TYPE: PRT
<213> ORGANISM: Homo sapiens

<400> SEQUENCE: 107

Gln Val Tyr Gly Ala Ser Ser Tyr
1               5

<210> SEQ ID NO 108
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Ser, Asn, Thr, His, Gln or Gly

<400> SEQUENCE: 108

Gln Gln Tyr Gly Xaa Ser Pro Tyr

-continued

```
<210> SEQ ID NO 109
<211> LENGTH: 6
<212> TYPE: PRT
<213> ORGANISM: Homo sapiens

<400> SEQUENCE: 109

Lys Asp Thr Tyr Ile His
1               5

<210> SEQ ID NO 110
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ser or Asn
<220> FEATURE:
<221> NAME/KEY: MOD_RES
<222> LOCATION: (3)..(3)
<223> OTHER INFORMATION: Tyr, Ala or Ser

<400> SEQUENCE: 110

Xaa Asp Xaa Tyr Met His
1               5

<210> SEQ ID NO 111
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Thr or Ser

<400> SEQUENCE: 111

Xaa Asp Tyr Tyr Ile His
1               5

<210> SEQ ID NO 112
<211> LENGTH: 13
<212> TYPE: PRT
<213> ORGANISM: Homo sapiens

<400> SEQUENCE: 112

Trp Ile Gly Arg Ile Tyr Pro Thr Asn Gly Tyr Thr Arg
1               5                   10

<210> SEQ ID NO 113
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Asn, Ile or Ser
<220> FEATURE:
<221> NAME/KEY: MOD_RES
<222> LOCATION: (8)..(8)
<223> OTHER INFORMATION: Ile, Asn, Ser, Tyr, Gly or Met
```

```
<220> FEATURE:
<221> NAME/KEY: MOD_RES
<222> LOCATION: (11)..(11)
<223> OTHER INFORMATION: Thr, Asn, Gly, Ser or Asp
<220> FEATURE:
<221> NAME/KEY: MOD_RES
<222> LOCATION: (13)..(13)
<223> OTHER INFORMATION: Asn, Lys, Ser or Gly

<400> SEQUENCE: 113

Trp Met Gly Arg Ile Xaa Pro Xaa Asn Gly Xaa Thr Xaa
1               5                   10

<210> SEQ ID NO 114
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ser or Ala
<220> FEATURE:
<221> NAME/KEY: MOD_RES
<222> LOCATION: (4)..(4)
<223> OTHER INFORMATION: Val, Ala, Asn, Gly, Tyr, Ser or Thr
<220> FEATURE:
<221> NAME/KEY: MOD_RES
<222> LOCATION: (6)..(6)
<223> OTHER INFORMATION: Ser, Lys, Trp or Asn
<220> FEATURE:
<221> NAME/KEY: MOD_RES
<222> LOCATION: (7)..(7)
<223> OTHER INFORMATION: Gly, Tyr, Ser, Gln, Trp, Asn or Phe
<220> FEATURE:
<221> NAME/KEY: MOD_RES
<222> LOCATION: (8)..(8)
<223> OTHER INFORMATION: Asp, Ser or Asn
<220> FEATURE:
<221> NAME/KEY: MOD_RES
<222> LOCATION: (9)..(9)
<223> OTHER INFORMATION: Gly or Ser
<220> FEATURE:
<221> NAME/KEY: MOD_RES
<222> LOCATION: (13)..(13)
<223> OTHER INFORMATION: Tyr, Asn, Phe or His

<400> SEQUENCE: 114

Trp Val Xaa Xaa Ile Xaa Xaa Xaa Xaa Gly Tyr Thr Xaa
1               5                   10

<210> SEQ ID NO 115
<211> LENGTH: 12
<212> TYPE: PRT
<213> ORGANISM: Homo sapiens

<400> SEQUENCE: 115

Ser Arg Trp Gly Gly Asp Gly Phe Tyr Ala Met Asp
1               5                   10

<210> SEQ ID NO 116
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Gly, Asp, Glu, Arg, Val or Ala
```

```
<400> SEQUENCE: 116

Ala Arg Xaa Gly Gly Asp Gly Phe Tyr Ala Met Asp
1               5                   10

<210> SEQ ID NO 117
<211> LENGTH: 7
<212> TYPE: PRT
<213> ORGANISM: Homo sapiens

<400> SEQUENCE: 117

Asn Thr Ala Val Ala Trp Tyr
1               5

<210> SEQ ID NO 118
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Tyr, Trp, Asp or Ser

<400> SEQUENCE: 118

Asn Thr Xaa Leu Ala Trp Tyr
1               5

<210> SEQ ID NO 119
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Asn or Tyr

<400> SEQUENCE: 119

Asn Thr Xaa Leu Ala Trp Tyr
1               5

<210> SEQ ID NO 120
<211> LENGTH: 10
<212> TYPE: PRT
<213> ORGANISM: Homo sapiens

<400> SEQUENCE: 120

Leu Leu Ile Tyr Ser Ala Ser Phe Arg Tyr
1               5                   10

<210> SEQ ID NO 121
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Ile, Ser, Thr or Asn
<220> FEATURE:
<221> NAME/KEY: MOD_RES
<222> LOCATION: (10)..(10)
<223> OTHER INFORMATION: Gln or Glu
```

```
<400> SEQUENCE: 121

Leu Leu Ile Tyr Ser Ala Ser Xaa Leu Xaa
1               5                   10

<210> SEQ ID NO 122
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Gly or Asp
<220> FEATURE:
<221> NAME/KEY: MOD_RES
<222> LOCATION: (8)..(8)
<223> OTHER INFORMATION: Ser, Thr or Asn

<400> SEQUENCE: 122

Leu Leu Ile Tyr Xaa Ala Ser Xaa Arg Ala
1               5                   10

<210> SEQ ID NO 123
<211> LENGTH: 8
<212> TYPE: PRT
<213> ORGANISM: Homo sapiens

<400> SEQUENCE: 123

Gln Gln His Tyr Thr Thr Pro Pro
1               5

<210> SEQ ID NO 124
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Tyr, Ser, Ala, Gly or Arg
<220> FEATURE:
<221> NAME/KEY: MOD_RES
<222> LOCATION: (8)..(8)
<223> OTHER INFORMATION: Leu, Tyr, Trp, Arg, Phe or Ile

<400> SEQUENCE: 124

Gln Gln Xaa Tyr Thr Thr Pro Xaa
1               5

<210> SEQ ID NO 125
<211> LENGTH: 6
<212> TYPE: PRT
<213> ORGANISM: Homo sapiens

<400> SEQUENCE: 125

Ser Ser Tyr Trp Met Asn
1               5

<210> SEQ ID NO 126
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 126

Ser Ser Tyr Trp Met Asn
1               5

<210> SEQ ID NO 127
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Ala, Tyr, Gly or Asp

<400> SEQUENCE: 127

Ser Ser Tyr Xaa Met Asn
1               5

<210> SEQ ID NO 128
<211> LENGTH: 13
<212> TYPE: PRT
<213> ORGANISM: Homo sapiens

<400> SEQUENCE: 128

Trp Ile Gly Gln Ile Trp Pro Gly Asp Gly Asp Thr Asn
1               5                   10

<210> SEQ ID NO 129
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Trp, Gly or Arg
<220> FEATURE:
<221> NAME/KEY: MOD_RES
<222> LOCATION: (6)..(6)
<223> OTHER INFORMATION: Ser, Ile or Asn
<220> FEATURE:
<221> NAME/KEY: MOD_RES
<222> LOCATION: (9)..(9)
<223> OTHER INFORMATION: Phe, Ser, Asn or Gly

<400> SEQUENCE: 129

Trp Met Gly Xaa Ile Xaa Pro Gly Xaa Gly Asp Thr Asn
1               5                   10

<210> SEQ ID NO 130
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ser or Ala
<220> FEATURE:
<221> NAME/KEY: MOD_RES
<222> LOCATION: (4)..(4)
<223> OTHER INFORMATION: Val, Ala, Asn, Gly, Tyr, Ser or Thr
<220> FEATURE:
<221> NAME/KEY: MOD_RES
<222> LOCATION: (7)..(7)
<223> OTHER INFORMATION: Gly, Tyr, Ser, Gln, Trp, Phe or Asn
```

```
<220> FEATURE:
<221> NAME/KEY: MOD_RES
<222> LOCATION: (8)..(8)
<223> OTHER INFORMATION: Ser, Asp or Asn
<220> FEATURE:
<221> NAME/KEY: MOD_RES
<222> LOCATION: (9)..(9)
<223> OTHER INFORMATION: Gly or Ser

<400> SEQUENCE: 130

Trp Val Xaa Xaa Ile Trp Xaa Xaa Xaa Gly Asp Thr Asn
1               5                   10

<210> SEQ ID NO 131
<211> LENGTH: 16
<212> TYPE: PRT
<213> ORGANISM: Homo sapiens

<400> SEQUENCE: 131

Ala Arg Arg Glu Thr Thr Thr Val Gly Arg Tyr Tyr Tyr Ala Met Asp
1               5                   10                  15

<210> SEQ ID NO 132
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Gly, Ser, Tyr, Ala, Thr, Asp, Arg, Phe or Trp

<400> SEQUENCE: 132

Ala Arg Arg Glu Thr Thr Thr Xaa Gly Arg Tyr Tyr Tyr Ala Met Asp
1               5                   10                  15

<210> SEQ ID NO 133
<211> LENGTH: 7
<212> TYPE: PRT
<213> ORGANISM: Homo sapiens

<400> SEQUENCE: 133

Val Thr Tyr Val Ser Trp Tyr
1               5

<210> SEQ ID NO 134
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ser, Arg, Gly, Asn or Tyr
<220> FEATURE:
<221> NAME/KEY: MOD_RES
<222> LOCATION: (5)..(5)
<223> OTHER INFORMATION: Ala or Asn

<400> SEQUENCE: 134

Xaa Thr Tyr Leu Xaa Trp Tyr
1               5

<210> SEQ ID NO 135
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ser, Gly or Asn

<400> SEQUENCE: 135

Xaa Thr Tyr Leu Ala Trp Tyr
1               5

<210> SEQ ID NO 136
<211> LENGTH: 10
<212> TYPE: PRT
<213> ORGANISM: Homo sapiens

<400> SEQUENCE: 136

Leu Leu Ile Tyr Gly Ala Ser Asn Arg Tyr
1               5                   10

<210> SEQ ID NO 137
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Gln or Glu

<400> SEQUENCE: 137

Leu Leu Ile Tyr Gly Ala Ser Asn Leu Xaa
1               5                   10

<210> SEQ ID NO 138
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Leu Leu Ile Tyr Gly Ala Ser Asn Arg Ala
1               5                   10

<210> SEQ ID NO 139
<211> LENGTH: 8
<212> TYPE: PRT
<213> ORGANISM: Homo sapiens

<400> SEQUENCE: 139

Gly Gln Gly Tyr Ser Tyr Pro Tyr
1               5

<210> SEQ ID NO 140
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gln or Met
```

<400> SEQUENCE: 140

Xaa Gln Gly Tyr Ser Tyr Pro Tyr
1               5

<210> SEQ ID NO 141
<211> LENGTH: 6
<212> TYPE: PRT
<213> ORGANISM: Mus musculus

<400> SEQUENCE: 141

Thr Asp Tyr Tyr Met Lys
1               5

<210> SEQ ID NO 142
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ser or Asn
<220> FEATURE:
<221> NAME/KEY: MOD_RES
<222> LOCATION: (6)..(6)
<223> OTHER INFORMATION: Ser, His or Asn

<400> SEQUENCE: 142

Xaa Asp Tyr Tyr Met Xaa
1               5

<210> SEQ ID NO 143
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser, His or Asn

<400> SEQUENCE: 143

Thr Asp Tyr Tyr Met Xaa
1               5

<210> SEQ ID NO 144
<211> LENGTH: 13
<212> TYPE: PRT
<213> ORGANISM: Mus musculus

<400> SEQUENCE: 144

Trp Ile Gly His Ile Asn Pro Asn Asn Asp Asp Thr Phe
1               5                   10

<210> SEQ ID NO 145
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Trp, Gly or Arg

```
<220> FEATURE:
<221> NAME/KEY: MOD_RES
<222> LOCATION: (13)..(13)
<223> OTHER INFORMATION: Asn, Lys, Ser or Gly

<400> SEQUENCE: 145

Trp Met Gly Xaa Ile Asn Pro Asn Asn Gly Asp Thr Xaa
1               5                   10

<210> SEQ ID NO 146
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ser or Ala
<220> FEATURE:
<221> NAME/KEY: MOD_RES
<222> LOCATION: (4)..(4)
<223> OTHER INFORMATION: Val, Ala, Asn, Gly, Tyr, Ser or Thr
<220> FEATURE:
<221> NAME/KEY: MOD_RES
<222> LOCATION: (7)..(7)
<223> OTHER INFORMATION: Gly, Thr, Ser, Gln, Trp, Asn or Phe
<220> FEATURE:
<221> NAME/KEY: MOD_RES
<222> LOCATION: (9)..(9)
<223> OTHER INFORMATION: Gly or Ser

<400> SEQUENCE: 146

Trp Val Xaa Xaa Ile Asn Xaa Asn Xaa Asp Asp Thr Phe
1               5                   10

<210> SEQ ID NO 147
<211> LENGTH: 11
<212> TYPE: PRT
<213> ORGANISM: Mus musculus

<400> SEQUENCE: 147

Val Arg Asp Asp Tyr Asp Gly Gly Trp Phe Ala
1               5                   10

<210> SEQ ID NO 148
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Asp or Gly

<400> SEQUENCE: 148

Val Arg Asp Asp Tyr Asp Gly Gly Trp Phe Xaa
1               5                   10

<210> SEQ ID NO 149
<211> LENGTH: 7
<212> TYPE: PRT
<213> ORGANISM: Mus musculus

<400> SEQUENCE: 149

Asn Asn Tyr Leu Asn Trp Tyr
1               5
```

<210> SEQ ID NO 150
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Asn Asn Tyr Leu Asn Trp Tyr
1               5

<210> SEQ ID NO 151
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Asn Asn Tyr Leu Ala Trp Tyr
1               5

<210> SEQ ID NO 152
<211> LENGTH: 10
<212> TYPE: PRT
<213> ORGANISM: Mus musculus

<400> SEQUENCE: 152

Leu Leu Ile Tyr Thr Ser Arg Ser Ser Tyr
1               5                   10

<210> SEQ ID NO 153
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Ala, Asp, Lys, Gly or Ser
<220> FEATURE:
<221> NAME/KEY: MOD_RES
<222> LOCATION: (10)..(10)
<223> OTHER INFORMATION: Gln or Glu

<400> SEQUENCE: 153

Leu Leu Ile Tyr Xaa Ala Ser Ser Leu Xaa
1               5                   10

<210> SEQ ID NO 154
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Gly or Asp
<220> FEATURE:
<221> NAME/KEY: MOD_RES
<222> LOCATION: (6)..(6)
<223> OTHER INFORMATION: Thr or Ala

<400> SEQUENCE: 154

```
Leu Leu Ile Tyr Xaa Xaa Ser Ser Arg Ala
1               5                   10

<210> SEQ ID NO 155
<211> LENGTH: 8
<212> TYPE: PRT
<213> ORGANISM: Mus musculus

<400> SEQUENCE: 155

Gln Gln Gly Lys Thr Leu Pro Trp
1               5

<210> SEQ ID NO 156
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Tyr, Asn, Gly, Ser, Asp, Thr or Leu

<400> SEQUENCE: 156

Gln Gln Gly Xaa Thr Ile Pro Trp
1               5

<210> SEQ ID NO 157
<211> LENGTH: 6
<212> TYPE: PRT
<213> ORGANISM: Mus musculus

<400> SEQUENCE: 157

Ser Asn Tyr Trp Ile Gln
1               5

<210> SEQ ID NO 158
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ser, His or Asn

<400> SEQUENCE: 158

Ser Asn Tyr Trp Met Xaa
1               5

<210> SEQ ID NO 159
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Ala, Tyr, Gly or Asp
<220> FEATURE:
<221> NAME/KEY: MOD_RES
<222> LOCATION: (6)..(6)
<223> OTHER INFORMATION: His, Ser or Asn

<400> SEQUENCE: 159
```

```
Ser Asn Tyr Xaa Ile Xaa
1               5
```

<210> SEQ ID NO 160
<211> LENGTH: 13
<212> TYPE: PRT
<213> ORGANISM: Mus musculus

<400> SEQUENCE: 160

```
Trp Ile Gly Glu Ile Leu Pro Gly Ser Gly Ser Thr Glu
1               5                   10
```

<210> SEQ ID NO 161
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Trp, Gly or Arg
<220> FEATURE:
<221> NAME/KEY: MOD_RES
<222> LOCATION: (6)..(6)
<223> OTHER INFORMATION: Asn, Ile or Ser
<220> FEATURE:
<221> NAME/KEY: MOD_RES
<222> LOCATION: (13)..(13)
<223> OTHER INFORMATION: Asn, Lys, Ser or Gly

<400> SEQUENCE: 161

```
Trp Met Gly Xaa Ile Xaa Pro Gly Ser Gly Ser Thr Xaa
1               5                   10
```

<210> SEQ ID NO 162
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ser or Ala
<220> FEATURE:
<221> NAME/KEY: MOD_RES
<222> LOCATION: (4)..(4)
<223> OTHER INFORMATION: Val, Ala, Asn, Gly, Tyr, Ser or Thr
<220> FEATURE:
<221> NAME/KEY: MOD_RES
<222> LOCATION: (6)..(6)
<223> OTHER INFORMATION: Ser, Lys, Trp or Asn
<220> FEATURE:
<221> NAME/KEY: MOD_RES
<222> LOCATION: (7)..(7)
<223> OTHER INFORMATION: Gly, Tyr, Ser, Gln, Trp, Asn or Phe
<220> FEATURE:
<221> NAME/KEY: MOD_RES
<222> LOCATION: (8)..(8)
<223> OTHER INFORMATION: Asp, Ser or Asn
<220> FEATURE:
<221> NAME/KEY: MOD_RES
<222> LOCATION: (12)..(12)
<223> OTHER INFORMATION: Thr, Lys or Ile
<220> FEATURE:
<221> NAME/KEY: MOD_RES
<222> LOCATION: (13)..(13)
<223> OTHER INFORMATION: Tyr, Asn, Phe or His

<400> SEQUENCE: 162

Trp Val Xaa Xaa Ile Xaa Xaa Xaa Ser Gly Ser Xaa Xaa

```
1               5                   10

<210> SEQ ID NO 163
<211> LENGTH: 14
<212> TYPE: PRT
<213> ORGANISM: Mus musculus

<400> SEQUENCE: 163

Ala Arg Tyr Phe Phe Gly Ser Ser Pro Asn Trp Tyr Phe Asp
1               5                   10

<210> SEQ ID NO 164
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Asp, Gly, Glu, Ala, Ser, Arg, Thr, Val or His
<220> FEATURE:
<221> NAME/KEY: MOD_RES
<222> LOCATION: (4)..(4)
<223> OTHER INFORMATION: Arg, Gly, Leu, Pro, Ser, Ala, Thr, Gln, His,
      Ile or Lys
<220> FEATURE:
<221> NAME/KEY: MOD_RES
<222> LOCATION: (5)..(5)
<223> OTHER INFORMATION: Gly, Tyr, Leu, Arg, Ile, Val, Ala, Pro, Ser,
      Asp Thr or Glu
<220> FEATURE:
<221> NAME/KEY: MOD_RES
<222> LOCATION: (10)..(10)
<223> OTHER INFORMATION: Tyr, Gly, Asp, Ser, Thr, Phe, Ala, Pro, Glu,
      Leu or Arg

<400> SEQUENCE: 164

Ala Arg Xaa Xaa Xaa Gly Ser Ser Pro Xaa Trp Tyr Phe Asp
1               5                   10

<210> SEQ ID NO 165
<211> LENGTH: 7
<212> TYPE: PRT
<213> ORGANISM: Mus musculus

<400> SEQUENCE: 165

Thr Gly Ala Leu Asn Trp Tyr
1               5

<210> SEQ ID NO 166
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ser, Arg, Gly, Asn or Tyr
<220> FEATURE:
<221> NAME/KEY: MOD_RES
<222> LOCATION: (2)..(2)
<223> OTHER INFORMATION: Asn, Ser, Thr or Lys
<220> FEATURE:
<221> NAME/KEY: MOD_RES
<222> LOCATION: (3)..(3)
<223> OTHER INFORMATION: Tyr, Trp, Asp or Ser

<400> SEQUENCE: 166
```

```
Xaa Xaa Xaa Leu Asn Trp Tyr
1               5

<210> SEQ ID NO 167
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ser, Gly or Asn
<220> FEATURE:
<221> NAME/KEY: MOD_RES
<222> LOCATION: (2)..(2)
<223> OTHER INFORMATION: Ser, Asn or Thr
<220> FEATURE:
<221> NAME/KEY: MOD_RES
<222> LOCATION: (3)..(3)
<223> OTHER INFORMATION: Asn or Tyr

<400> SEQUENCE: 167

Xaa Xaa Xaa Leu Ala Trp Tyr
1               5

<210> SEQ ID NO 168
<211> LENGTH: 10
<212> TYPE: PRT
<213> ORGANISM: Mus musculus

<400> SEQUENCE: 168

Leu Leu Ile Tyr Gly Ala Thr Asn Leu Ala
1               5                   10

<210> SEQ ID NO 169
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Gln or Glu

<400> SEQUENCE: 169

Leu Leu Ile Tyr Gly Ala Ser Asn Leu Xaa
1               5                   10

<210> SEQ ID NO 170
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Leu Leu Ile Tyr Gly Ala Ser Ser Arg Ala
1               5                   10

<210> SEQ ID NO 171
<211> LENGTH: 8
<212> TYPE: PRT
<213> ORGANISM: Mus musculus

<400> SEQUENCE: 171
```

```
Gln Asn Val Leu Asn Thr Pro Leu
1               5

<210> SEQ ID NO 172
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Tyr, Ser, Ala, Gly or Arg

<400> SEQUENCE: 172

Gln Gln Xaa Leu Asn Thr Pro Leu
1               5

<210> SEQ ID NO 173
<211> LENGTH: 6
<212> TYPE: PRT
<213> ORGANISM: Mus musculus

<400> SEQUENCE: 173

Lys Asp Thr Tyr Val His
1               5

<210> SEQ ID NO 174
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ser or Asn
<220> FEATURE:
<221> NAME/KEY: MOD_RES
<222> LOCATION: (3)..(3)
<223> OTHER INFORMATION: Tyr, Ala or Ser

<400> SEQUENCE: 174

Xaa Asp Xaa Tyr Met His
1               5

<210> SEQ ID NO 175
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Thr or Ser
<220> FEATURE:
<221> NAME/KEY: MOD_RES
<222> LOCATION: (5)..(5)
<223> OTHER INFORMATION: Met or Ile

<400> SEQUENCE: 175

Xaa Asp Tyr Tyr Xaa His
1               5

<210> SEQ ID NO 176
<211> LENGTH: 13
<212> TYPE: PRT
```

<213> ORGANISM: Mus musculus

<400> SEQUENCE: 176

Trp Ile Gly Arg Ile Asp Pro Ala Asn Gly Tyr Thr Lys
1               5                   10

<210> SEQ ID NO 177
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Asn, Ile or Ser
<220> FEATURE:
<221> NAME/KEY: MOD_RES
<222> LOCATION: (7)..(7)
<223> OTHER INFORMATION: Pro or Ala
<220> FEATURE:
<221> NAME/KEY: MOD_RES
<222> LOCATION: (8)..(8)
<223> OTHER INFORMATION: Ile, Asn, Ser, Tyr, Gly or Met
<220> FEATURE:
<221> NAME/KEY: MOD_RES
<222> LOCATION: (11)..(11)
<223> OTHER INFORMATION: Thr, Asn, Gly, Ser or Tyr
<220> FEATURE:
<221> NAME/KEY: MOD_RES
<222> LOCATION: (12)..(12)
<223> OTHER INFORMATION: Thr or Ala

<400> SEQUENCE: 177

Trp Met Gly Arg Ile Xaa Xaa Xaa Asn Gly Xaa Xaa Lys
1               5                   10

<210> SEQ ID NO 178
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ser or Ala
<220> FEATURE:
<221> NAME/KEY: MOD_RES
<222> LOCATION: (4)..(4)
<223> OTHER INFORMATION: Val, Ala, Asn, Gly, Tyr, Ser or Thr
<220> FEATURE:
<221> NAME/KEY: MOD_RES
<222> LOCATION: (6)..(6)
<223> OTHER INFORMATION: Ser, Lys, Trp or Asn
<220> FEATURE:
<221> NAME/KEY: MOD_RES
<222> LOCATION: (7)..(7)
<223> OTHER INFORMATION: Gly, Tyr, Ser, Gln, Trp, Asn or Phe
<220> FEATURE:
<221> NAME/KEY: MOD_RES
<222> LOCATION: (8)..(8)
<223> OTHER INFORMATION: Asp, Ser or Asn
<220> FEATURE:
<221> NAME/KEY: MOD_RES
<222> LOCATION: (9)..(9)
<223> OTHER INFORMATION: Gly or Ser
<220> FEATURE:
<221> NAME/KEY: MOD_RES
<222> LOCATION: (13)..(13)
<223> OTHER INFORMATION: Thr, Asn, Phe or His

<400> SEQUENCE: 178

```
Trp Val Xaa Xaa Ile Xaa Xaa Xaa Xaa Gly Tyr Thr Xaa
1               5                   10
```

<210> SEQ ID NO 179
<211> LENGTH: 11
<212> TYPE: PRT
<213> ORGANISM: Mus musculus

<400> SEQUENCE: 179

```
Val Arg Pro Leu Tyr Asp Tyr Tyr Ala Met Asp
1               5                   10
```

<210> SEQ ID NO 180
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Asp, Lys, Gly, Ile, Ala, Glu, Leu, Arg or Asn

<400> SEQUENCE: 180

```
Val Arg Xaa Leu Tyr Asp Tyr Tyr Ala Met Asp
1               5                   10
```

<210> SEQ ID NO 181
<211> LENGTH: 7
<212> TYPE: PRT
<213> ORGANISM: Mus musculus

<400> SEQUENCE: 181

```
Ser Ser Asn Ile Gly Trp Leu
1               5
```

<210> SEQ ID NO 182
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Thr, Trp, Asp or Ser
<220> FEATURE:
<221> NAME/KEY: MOD_RES
<222> LOCATION: (5)..(5)
<223> OTHER INFORMATION: Ala or Asn

<400> SEQUENCE: 182

```
Ser Ser Xaa Leu Xaa Trp Tyr
1               5
```

<210> SEQ ID NO 183
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

```
Ser Ser Asn Leu Ala Trp Tyr
1               5
```

```
<210> SEQ ID NO 184
<211> LENGTH: 10
<212> TYPE: PRT
<213> ORGANISM: Mus musculus

<400> SEQUENCE: 184

Gly Leu Ile Tyr Tyr Gly Thr Asn Leu Val
1               5                   10

<210> SEQ ID NO 185
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Leu or Arg
<220> FEATURE:
<221> NAME/KEY: MOD_RES
<222> LOCATION: (5)..(5)
<223> OTHER INFORMATION: Ala, Asp, Lys, Gly or Ser
<220> FEATURE:
<221> NAME/KEY: MOD_RES
<222> LOCATION: (10)..(10)
<223> OTHER INFORMATION: Gln or Glu

<400> SEQUENCE: 185

Xaa Leu Ile Tyr Xaa Ala Ser Asn Leu Xaa
1               5                   10

<210> SEQ ID NO 186
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Gly or Asp
<220> FEATURE:
<221> NAME/KEY: MOD_RES
<222> LOCATION: (6)..(6)
<223> OTHER INFORMATION: Thr or Ala

<400> SEQUENCE: 186

Leu Leu Ile Tyr Xaa Xaa Ser Asn Arg Ala
1               5                   10

<210> SEQ ID NO 187
<211> LENGTH: 8
<212> TYPE: PRT
<213> ORGANISM: Mus musculus

<400> SEQUENCE: 187

Val Gln Tyr Ala Gln Leu Pro Tyr
1               5

<210> SEQ ID NO 188
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
```

```
<223> OTHER INFORMATION: Gln or Met
<220> FEATURE:
<221> NAME/KEY: MOD_RES
<222> LOCATION: (4)..(4)
<223> OTHER INFORMATION: Tyr, Asn, Gly, Ser, Asp, Thr or Leu

<400> SEQUENCE: 188

Xaa Gln Tyr Xaa Gln Leu Pro Tyr
1               5

<210> SEQ ID NO 189
<211> LENGTH: 6
<212> TYPE: PRT
<213> ORGANISM: Mus musculus

<400> SEQUENCE: 189

Thr Gly His Trp Met Asn
1               5

<210> SEQ ID NO 190

<400> SEQUENCE: 190

000

<210> SEQ ID NO 191
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Ala, Tyr, Gly or Asp

<400> SEQUENCE: 191

Thr Gly Tyr Xaa Met Asn
1               5

<210> SEQ ID NO 192
<211> LENGTH: 13
<212> TYPE: PRT
<213> ORGANISM: Mus musculus

<400> SEQUENCE: 192

Trp Ile Gly Met Ile His Pro Ser Asp Ser Glu Thr Arg
1               5                   10

<210> SEQ ID NO 193
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Trp, Gly or Arg
<220> FEATURE:
<221> NAME/KEY: MOD_RES
<222> LOCATION: (6)..(6)
<223> OTHER INFORMATION: Asn, Ile or Ser
<220> FEATURE:
<221> NAME/KEY: MOD_RES
<222> LOCATION: (7)..(7)
<223> OTHER INFORMATION: Pro or Ala
<220> FEATURE:
<221> NAME/KEY: MOD_RES
```

```
<222> LOCATION: (9)..(9)
<223> OTHER INFORMATION: Phe, Ser, Asn or Gly
<220> FEATURE:
<221> NAME/KEY: MOD_RES
<222> LOCATION: (11)..(11)
<223> OTHER INFORMATION: Thr, Asn, Gly, Ser or Asp
<220> FEATURE:
<221> NAME/KEY: MOD_RES
<222> LOCATION: (13)..(13)
<223> OTHER INFORMATION: Lys, Asn, Ser or Gly

<400> SEQUENCE: 193

Trp Met Gly Xaa Ile Xaa Xaa Ser Xaa Gly Xaa Thr Xaa
1               5                   10

<210> SEQ ID NO 194
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ser or Ala
<220> FEATURE:
<221> NAME/KEY: MOD_RES
<222> LOCATION: (4)..(4)
<223> OTHER INFORMATION: Val, Ala, Asn, Gly, Tyr, Ser or Thr
<220> FEATURE:
<221> NAME/KEY: MOD_RES
<222> LOCATION: (6)..(6)
<223> OTHER INFORMATION: Ser, Lys, Trp or Asn
<220> FEATURE:
<221> NAME/KEY: MOD_RES
<222> LOCATION: (7)..(7)
<223> OTHER INFORMATION: Gly, Tyr, Ser, Gln, Trp, Asn or Phe
<220> FEATURE:
<221> NAME/KEY: MOD_RES
<222> LOCATION: (9)..(9)
<223> OTHER INFORMATION: Gly or Ser
<220> FEATURE:
<221> NAME/KEY: MOD_RES
<222> LOCATION: (13)..(13)
<223> OTHER INFORMATION: Tyr, Asn, Phe or His

<400> SEQUENCE: 194

Trp Val Xaa Xaa Ile Xaa Xaa Ser Xaa Ser Glu Thr Xaa
1               5                   10

<210> SEQ ID NO 195
<211> LENGTH: 13
<212> TYPE: PRT
<213> ORGANISM: Mus musculus

<400> SEQUENCE: 195

Ala Arg Gly Ile Tyr Phe Tyr Gly Thr Thr Tyr Phe Asp
1               5                   10

<210> SEQ ID NO 196
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Gly, Ser, Thr, Tyr, Asp, Pro, Ile, Leu, Val
      or Arg
<220> FEATURE:
<221> NAME/KEY: MOD_RES
```

```
<222> LOCATION: (10)..(10)
<223> OTHER INFORMATION: Gly, Tyr, Asn, Pro, Ser, Ala, Asp, Arg or Phe

<400> SEQUENCE: 196

Ala Arg Gly Ile Tyr Xaa Tyr Gly Thr Xaa Tyr Phe Asp
1               5                   10

<210> SEQ ID NO 197
<211> LENGTH: 7
<212> TYPE: PRT
<213> ORGANISM: Mus musculus

<400> SEQUENCE: 197

Ser Lys Tyr Leu Ala Trp Tyr
1               5

<210> SEQ ID NO 198
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Ser Lys Tyr Leu Ala Trp Tyr
1               5

<210> SEQ ID NO 199
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Asn, Ser or Thr

<400> SEQUENCE: 199

Ser Xaa Tyr Leu Ala Trp Tyr
1               5

<210> SEQ ID NO 200
<211> LENGTH: 10
<212> TYPE: PRT
<213> ORGANISM: Mus musculus

<400> SEQUENCE: 200

Leu Leu Ile Tyr Ser Gly Ser Thr Leu Gln
1               5                   10

<210> SEQ ID NO 201
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Leu Leu Ile Tyr Ser Ala Ser Thr Leu Gln
1               5                   10

<210> SEQ ID NO 202
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Gly or Asp
<220> FEATURE:
<221> NAME/KEY: MOD_RES
<222> LOCATION: (6)..(6)
<223> OTHER INFORMATION: Thr or Ala

<400> SEQUENCE: 202

Leu Leu Ile Tyr Xaa Xaa Ser Thr Arg Ala
1               5                   10

<210> SEQ ID NO 203
<211> LENGTH: 8
<212> TYPE: PRT
<213> ORGANISM: Mus musculus

<400> SEQUENCE: 203

Gln Gln His Asn Glu Tyr Pro Leu
1               5

<210> SEQ ID NO 204
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Tyr, Ser, Ala, Gly or Arg
<220> FEATURE:
<221> NAME/KEY: MOD_RES
<222> LOCATION: (5)..(5)
<223> OTHER INFORMATION: Ser, Asn, Thr, His, Gln or Gly

<400> SEQUENCE: 204

Gln Gln Xaa Asn Xaa Tyr Pro Leu
1               5

<210> SEQ ID NO 205
<211> LENGTH: 6
<212> TYPE: PRT
<213> ORGANISM: Mus musculus

<400> SEQUENCE: 205

Thr Asp Tyr Asn Met Asp
1               5

<210> SEQ ID NO 206

<400> SEQUENCE: 206

000

<210> SEQ ID NO 207
<211> LENGTH: 6
<212> TYPE: PRT
<213> ORGANISM: Homo sapiens

<400> SEQUENCE: 207

Thr Asp Tyr Asn Met Asp
1               5
```

```
<210> SEQ ID NO 208
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Ala, Tyr, Gly or Asp
<220> FEATURE:
<221> NAME/KEY: MOD_RES
<222> LOCATION: (6)..(6)
<223> OTHER INFORMATION: His, Ser or Asn

<400> SEQUENCE: 208

Thr Asn Tyr Xaa Met Xaa
1               5

<210> SEQ ID NO 209
<211> LENGTH: 13
<212> TYPE: PRT
<213> ORGANISM: Homo sapiens

<400> SEQUENCE: 209

Trp Ile Gly Asp Ile Asn Pro Ser Asn Gly Tyr Thr Ile
1               5                   10

<210> SEQ ID NO 210
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Trp, Gly or Arg
<220> FEATURE:
<221> NAME/KEY: MOD_RES
<222> LOCATION: (11)..(11)
<223> OTHER INFORMATION: Thr, Asn, Gly, Ser or Asp
<220> FEATURE:
<221> NAME/KEY: MOD_RES
<222> LOCATION: (13)..(13)
<223> OTHER INFORMATION: Asn, Lys, Ser or Gly

<400> SEQUENCE: 210

Trp Met Gly Xaa Ile Asn Pro Ser Asn Gly Xaa Thr Xaa
1               5                   10

<210> SEQ ID NO 211
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ser or Ala
<220> FEATURE:
<221> NAME/KEY: MOD_RES
<222> LOCATION: (4)..(4)
<223> OTHER INFORMATION: Val, Ala, Asn, Gly, Tyr, Ser or Thr
<220> FEATURE:
<221> NAME/KEY: MOD_RES
<222> LOCATION: (7)..(7)
<223> OTHER INFORMATION: Gly, Tyr, Ser, Gln, Trp, Asn or Phe
<220> FEATURE:
```

```
<221> NAME/KEY: MOD_RES
<222> LOCATION: (9)..(9)
<223> OTHER INFORMATION: Gly or Ser
<220> FEATURE:
<221> NAME/KEY: MOD_RES
<222> LOCATION: (12)..(12)
<223> OTHER INFORMATION: Lys, Ile or Thr
<220> FEATURE:
<221> NAME/KEY: MOD_RES
<222> LOCATION: (13)..(13)
<223> OTHER INFORMATION: Tyr, Asn, Phe or His

<400> SEQUENCE: 211

Trp Val Xaa Xaa Ile Asn Xaa Ser Xaa Gly Tyr Xaa Xaa
1               5                   10

<210> SEQ ID NO 212
<211> LENGTH: 14
<212> TYPE: PRT
<213> ORGANISM: Homo sapiens

<400> SEQUENCE: 212

Ala Arg Ser Gly Tyr Gly Ser Arg His Pro Pro Gly Phe Ala
1               5                   10

<210> SEQ ID NO 213
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Asn, Asp, Ala, Val, Leu, Tyr, Thr, Ser or Gly
<220> FEATURE:
<221> NAME/KEY: MOD_RES
<222> LOCATION: (9)..(9)
<223> OTHER INFORMATION: Val, Ile, Glu, Pro, Leu, Thr, Ala, Tyr, Ser or
      Gly
<220> FEATURE:
<221> NAME/KEY: MOD_RES
<222> LOCATION: (11)..(11)
<223> OTHER INFORMATION: Thr, Ala, Trp, Asp, Arg, Asn, Ser, Gly or Tyr

<400> SEQUENCE: 213

Ala Arg Ser Gly Tyr Gly Ser Xaa Xaa Pro Xaa Gly Phe Ala
1               5                   10

<210> SEQ ID NO 214
<211> LENGTH: 8
<212> TYPE: PRT
<213> ORGANISM: Homo sapiens

<400> SEQUENCE: 214

Asp Ser Tyr Gly Asn Ser Phe Met
1               5

<210> SEQ ID NO 215
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ser or Asn
<220> FEATURE:
<221> NAME/KEY: MOD_RES
```

```
<222> LOCATION: (3)..(3)
<223> OTHER INFORMATION: Ser, Asn or Thr

<400> SEQUENCE: 215

Xaa Ser Xaa Tyr Leu Ala Trp Tyr
1               5

<210> SEQ ID NO 216
<211> LENGTH: 10
<212> TYPE: PRT
<213> ORGANISM: Homo sapiens

<400> SEQUENCE: 216

Leu Leu Ile Tyr Gly Val Ser Asn Arg Ala
1               5                   10

<210> SEQ ID NO 217
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Gln or Glu

<400> SEQUENCE: 217

Leu Leu Ile Tyr Gly Ala Ser Asn Leu Xaa
1               5                   10

<210> SEQ ID NO 218
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ala or Thr

<400> SEQUENCE: 218

Leu Leu Ile Tyr Gly Xaa Ser Ser Arg Ala
1               5                   10

<210> SEQ ID NO 219
<211> LENGTH: 8
<212> TYPE: PRT
<213> ORGANISM: Homo sapiens

<400> SEQUENCE: 219

Gln Val Tyr Gly Ala Ser Ser Tyr
1               5

<210> SEQ ID NO 220
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Ser, Asn, Thr, His, Gln or Gly

<400> SEQUENCE: 220
```

```
Gln Gln Tyr Gly Xaa Ser Pro Tyr
1               5

<210> SEQ ID NO 221
<211> LENGTH: 6
<212> TYPE: PRT
<213> ORGANISM: Mus musculus

<400> SEQUENCE: 221

Thr His Tyr Gly Met Asn
1               5

<210> SEQ ID NO 222
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ser or Asn
<220> FEATURE:
<221> NAME/KEY: MOD_RES
<222> LOCATION: (2)..(2)
<223> OTHER INFORMATION: Ser, Asn, Asp or Thr

<400> SEQUENCE: 222

Xaa Xaa Tyr Gly Met Asn
1               5

<210> SEQ ID NO 223
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ser, Gly, Asn or Asp

<400> SEQUENCE: 223

Thr Xaa Tyr Gly Met Asn
1               5

<210> SEQ ID NO 224
<211> LENGTH: 13
<212> TYPE: PRT
<213> ORGANISM: Mus musculus

<400> SEQUENCE: 224

Trp Met Gly Trp Ile Asn Thr Tyr Thr Gly Glu Pro Thr
1               5                   10

<210> SEQ ID NO 225
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Pro or Ala
<220> FEATURE:
<221> NAME/KEY: MOD_RES
```

```
<222> LOCATION: (9)..(9)
<223> OTHER INFORMATION: Phe, Ser, Asn or Gly
<220> FEATURE:
<221> NAME/KEY: MOD_RES
<222> LOCATION: (11)..(11)
<223> OTHER INFORMATION: Thr, Asn, Gly, Ser or Asp
<220> FEATURE:
<221> NAME/KEY: MOD_RES
<222> LOCATION: (12)..(12)
<223> OTHER INFORMATION: Thr or Ala
<220> FEATURE:
<221> NAME/KEY: MOD_RES
<222> LOCATION: (13)..(13)
<223> OTHER INFORMATION: Asn, Lys, Ser or Gly

<400> SEQUENCE: 225

Trp Met Gly Trp Ile Asn Xaa Tyr Xaa Gly Xaa Xaa Xaa
1               5                   10

<210> SEQ ID NO 226
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ser or Ala
<220> FEATURE:
<221> NAME/KEY: MOD_RES
<222> LOCATION: (4)..(4)
<223> OTHER INFORMATION: Val, Ala, Asn, Gly, Tyr, Ser or Thr
<220> FEATURE:
<221> NAME/KEY: MOD_RES
<222> LOCATION: (7)..(7)
<223> OTHER INFORMATION: Gly, Tyr, Ser, Gln, Trp, Asn or Phe
<220> FEATURE:
<221> NAME/KEY: MOD_RES
<222> LOCATION: (8)..(8)
<223> OTHER INFORMATION: Asp, Ser or Asn
<220> FEATURE:
<221> NAME/KEY: MOD_RES
<222> LOCATION: (9)..(9)
<223> OTHER INFORMATION: Gly or Ser
<220> FEATURE:
<221> NAME/KEY: MOD_RES
<222> LOCATION: (12)..(12)
<223> OTHER INFORMATION: Thr, Lys or Ile
<220> FEATURE:
<221> NAME/KEY: MOD_RES
<222> LOCATION: (13)..(13)
<223> OTHER INFORMATION: Tyr, Asn, Phe or His

<400> SEQUENCE: 226

Trp Val Xaa Xaa Ile Asn Xaa Xaa Xaa Gly Glu Xaa Xaa
1               5                   10

<210> SEQ ID NO 227
<211> LENGTH: 9
<212> TYPE: PRT
<213> ORGANISM: Homo sapiens

<400> SEQUENCE: 227

Ala Arg Glu Arg Gly Asp Ala Met Asp
1               5

<210> SEQ ID NO 228
<211> LENGTH: 9
<212> TYPE: PRT
<213> ORGANISM: Artificial Sequence
<220> FEATURE:
<223> OTHER INFORMATION: Description of Artificial Sequence: Synthetic
```

```
                       peptide

<400> SEQUENCE: 228

Ala Arg Glu Arg Gly Asp Ala Met Asp
1               5

<210> SEQ ID NO 229
<211> LENGTH: 7
<212> TYPE: PRT
<213> ORGANISM: Mus musculus

<400> SEQUENCE: 229

Ser Asn Asp Val Val Trp Tyr
1               5

<210> SEQ ID NO 230
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Ala or Asn

<400> SEQUENCE: 230

Ser Asn Asp Leu Xaa Trp Tyr
1               5

<210> SEQ ID NO 231
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Tyr or Asn

<400> SEQUENCE: 231

Ser Asn Xaa Leu Ala Trp Tyr
1               5

<210> SEQ ID NO 232
<211> LENGTH: 10
<212> TYPE: PRT
<213> ORGANISM: Mus musculus

<400> SEQUENCE: 232

Met Leu Met Tyr Ser Ala Phe Asn Arg Tyr
1               5                   10

<210> SEQ ID NO 233
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Leu or Arg
<220> FEATURE:
<221> NAME/KEY: MOD_RES
<222> LOCATION: (10)..(10)
```

<223> OTHER INFORMATION: Gln or Glu

<400> SEQUENCE: 233

Xaa Leu Ile Tyr Ser Ala Ser Asn Leu Xaa
1               5                   10

<210> SEQ ID NO 234
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Gly or Asp

<400> SEQUENCE: 234

Leu Leu Ile Tyr Xaa Ala Ser Asn Arg Ala
1               5                   10

<210> SEQ ID NO 235
<211> LENGTH: 8
<212> TYPE: PRT
<213> ORGANISM: Mus musculus

<400> SEQUENCE: 235

Gln Gln Asp Tyr Asn Ser Pro Arg
1               5

<210> SEQ ID NO 236
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Tyr, Ser, Ala, Gly, Arg

<400> SEQUENCE: 236

Gln Gln Xaa Tyr Asn Ser Pro Arg
1               5

<210> SEQ ID NO 237
<211> LENGTH: 6
<212> TYPE: PRT
<213> ORGANISM: Mus musculus

<400> SEQUENCE: 237

Thr Ser Tyr Gly Val His
1               5

<210> SEQ ID NO 238
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Tyr, Phe or Ser
<220> FEATURE:
<221> NAME/KEY: MOD_RES
<222> LOCATION: (6)..(6)

```
<223> OTHER INFORMATION: Ser or Thr

<400> SEQUENCE: 238

Thr Ser Tyr Xaa Trp Xaa
1               5

<210> SEQ ID NO 239
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Tyr, Phe or Ser
<220> FEATURE:
<221> NAME/KEY: MOD_RES
<222> LOCATION: (6)..(6)
<223> OTHER INFORMATION: Ser, Thr or Asn

<400> SEQUENCE: 239

Thr Ser Tyr Xaa Trp Xaa
1               5

<210> SEQ ID NO 240
<211> LENGTH: 12
<212> TYPE: PRT
<213> ORGANISM: Mus musculus

<400> SEQUENCE: 240

Trp Leu Gly Val Ile Trp Ala Val Gly Ser Thr Asn
1               5                   10

<210> SEQ ID NO 241
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Glu or Tyr
<220> FEATURE:
<221> NAME/KEY: MOD_RES
<222> LOCATION: (7)..(7)
<223> OTHER INFORMATION: His, Gln, Tyr or Asp
<220> FEATURE:
<221> NAME/KEY: MOD_RES
<222> LOCATION: (8)..(8)
<223> OTHER INFORMATION: Ser or Arg

<400> SEQUENCE: 241

Trp Ile Gly Xaa Ile Tyr Xaa Xaa Gly Ser Thr Asn
1               5                   10

<210> SEQ ID NO 242
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Glu or Tyr
<220> FEATURE:
<221> NAME/KEY: MOD_RES
```

```
<222> LOCATION: (6)..(6)
<223> OTHER INFORMATION: Asn, Tyr, Ser or Asp
<220> FEATURE:
<221> NAME/KEY: MOD_RES
<222> LOCATION: (7)..(7)
<223> OTHER INFORMATION: His, Gln, Tyr or Asp
<220> FEATURE:
<221> NAME/KEY: MOD_RES
<222> LOCATION: (8)..(8)
<223> OTHER INFORMATION: Ser or Arg

<400> SEQUENCE: 242

Trp Ile Gly Xaa Ile Xaa Xaa Xaa Gly Ser Thr Asn
1               5                   10

<210> SEQ ID NO 243
<211> LENGTH: 20
<212> TYPE: PRT
<213> ORGANISM: Mus musculus

<400> SEQUENCE: 243

Ala Arg Glu Gly Glu Phe Asp Tyr Tyr Gly Ser Ser Leu Leu Ser Tyr
1               5                   10                  15

His Ser Met Asn
            20

<210> SEQ ID NO 244
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (20)..(20)
<223> OTHER INFORMATION: Asp or Gly

<400> SEQUENCE: 244

Ala Arg Glu Gly Asp Phe Asp Tyr Phe Gly Ser Ser Val Ile Ser Tyr
1               5                   10                  15

Ser Ser Met Xaa
            20

<210> SEQ ID NO 245
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Tyr, Pro, Gly, Asp, Leu, Arg, Thr, His or Ser
<220> FEATURE:
<221> NAME/KEY: MOD_RES
<222> LOCATION: (9)..(9)
<223> OTHER INFORMATION: Ser, Gly, Asn, Asp, Glu, Val, Thr, Ala, Phe,
      Ile or Leu
<220> FEATURE:
<221> NAME/KEY: MOD_RES
<222> LOCATION: (13)..(13)
<223> OTHER INFORMATION: Tyr, Ser, Gly, Val, Thr, Asp, Pro, Trp, Ala
      or Cys
<220> FEATURE:
<221> NAME/KEY: MOD_RES
<222> LOCATION: (14)..(14)
<223> OTHER INFORMATION: Thr, Gly, Arg, Ser, Ala, Asp, Glu, Phe or Ile
<220> FEATURE:
<221> NAME/KEY: MOD_RES
<222> LOCATION: (17)..(17)
```

```
<223> OTHER INFORMATION: Tyr, Asp, Thr or Ser
<220> FEATURE:
<221> NAME/KEY: MOD_RES
<222> LOCATION: (20)..(20)
<223> OTHER INFORMATION: Asp or Gly

<400> SEQUENCE: 245

Ala Arg Glu Gly Xaa Phe Asp Tyr Xaa Gly Ser Ser Xaa Xaa Ser Tyr
1               5                   10                  15

Xaa Ser Met Xaa
            20

<210> SEQ ID NO 246
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Ser Asn Tyr Gly Met Asn
1               5

<210> SEQ ID NO 247
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Pro or Ala
<220> FEATURE:
<221> NAME/KEY: MOD_RES
<222> LOCATION: (12)..(12)
<223> OTHER INFORMATION: Thr or Ala

<400> SEQUENCE: 247

Trp Met Gly Trp Ile Asn Xaa Tyr Ser Gly Asp Xaa Ser
1               5                   10

<210> SEQ ID NO 248
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Asp, Ser or Asn

<400> SEQUENCE: 248

Trp Val Ala Tyr Ile Asn Ser Xaa Ser Gly Glu Ile His
1               5                   10

<210> SEQ ID NO 249
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Ser Asn Tyr Leu Ala Trp Tyr
```

```
<210> SEQ ID NO 250
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Lys, Gln, Tyr or Glu
<220> FEATURE:
<221> NAME/KEY: MOD_RES
<222> LOCATION: (5)..(5)
<223> OTHER INFORMATION: His, Tyr, Ser or Cys

<400> SEQUENCE: 250

Ser Xaa Tyr Val Xaa Trp Tyr
1               5

<210> SEQ ID NO 251
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Lys, Gln, Tyr or Glu
<220> FEATURE:
<221> NAME/KEY: MOD_RES
<222> LOCATION: (4)..(4)
<223> OTHER INFORMATION: Ala or Val
<220> FEATURE:
<221> NAME/KEY: MOD_RES
<222> LOCATION: (5)..(5)
<223> OTHER INFORMATION: His, Tyr, Ser or Cys

<400> SEQUENCE: 251

Ser Xaa Tyr Xaa Xaa Trp Tyr
1               5

<210> SEQ ID NO 252
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Ala, Asp, Lys, Gly or Ser
<220> FEATURE:
<221> NAME/KEY: MOD_RES
<222> LOCATION: (10)..(10)
<223> OTHER INFORMATION: Gln or Glu

<400> SEQUENCE: 252

Leu Leu Ile Tyr Xaa Ala Ser Ser Leu Xaa
1               5                   10

<210> SEQ ID NO 253
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (5)..(5)
<223> OTHER INFORMATION: Gly or Asp

<400> SEQUENCE: 253

Leu Leu Ile Tyr Xaa Thr Ser Ser Arg Ala
1               5                   10

<210> SEQ ID NO 254
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Asp, Gln, Glu or Lys
<220> FEATURE:
<221> NAME/KEY: MOD_RES
<222> LOCATION: (6)..(6)
<223> OTHER INFORMATION: Asp or Lys
<220> FEATURE:
<221> NAME/KEY: MOD_RES
<222> LOCATION: (8)..(8)
<223> OTHER INFORMATION: Lys, Asp, Glu or Asn

<400> SEQUENCE: 254

Leu Val Ile Tyr Xaa Xaa Ser Xaa Arg Pro
1               5                   10

<210> SEQ ID NO 255
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Asp, Gln, Glu or Lys
<220> FEATURE:
<221> NAME/KEY: MOD_RES
<222> LOCATION: (6)..(6)
<223> OTHER INFORMATION: Asp or Lys
<220> FEATURE:
<221> NAME/KEY: MOD_RES
<222> LOCATION: (8)..(8)
<223> OTHER INFORMATION: Lys, Asp, Glu or Asn

<400> SEQUENCE: 255

Leu Val Ile Tyr Xaa Xaa Ser Xaa Arg Pro
1               5                   10

<210> SEQ ID NO 256
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Gln Gln Tyr Ser Thr Leu Pro Trp
1               5

<210> SEQ ID NO 257
<211> LENGTH: 8
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ser, Ala, Thr, Ile or Leu
<220> FEATURE:
<221> NAME/KEY: MOD_RES
<222> LOCATION: (4)..(4)
<223> OTHER INFORMATION: Asp, Tyr, His or Ala
<220> FEATURE:
<221> NAME/KEY: MOD_RES
<222> LOCATION: (6)..(6)
<223> OTHER INFORMATION: Ser, Gly, Asn or Asp
<220> FEATURE:
<221> NAME/KEY: MOD_RES
<222> LOCATION: (7)..(7)
<223> OTHER INFORMATION: Ile or Leu

<400> SEQUENCE: 257

Gln Xaa Tyr Xaa Ser Xaa Xaa Trp
1               5

<210> SEQ ID NO 258

<400> SEQUENCE: 258

000

<210> SEQ ID NO 259
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Thr or Ser

<400> SEQUENCE: 259

Xaa Asn Tyr Gly Met Asn
1               5

<210> SEQ ID NO 260

<400> SEQUENCE: 260

000

<210> SEQ ID NO 261
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Gly or Ala

<400> SEQUENCE: 261

Ser Asn Tyr Xaa Met Asn
1               5

<210> SEQ ID NO 262

<400> SEQUENCE: 262
```

```
000

<210> SEQ ID NO 263
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Pro or Ala
<220> FEATURE:
<221> NAME/KEY: MOD_RES
<222> LOCATION: (12)..(12)
<223> OTHER INFORMATION: Thr or Ala

<400> SEQUENCE: 263

Trp Met Gly Trp Ile Asn Xaa Tyr Ser Gly Asp Xaa Ser
1               5                   10

<210> SEQ ID NO 264
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Trp, Gly or Arg
<220> FEATURE:
<221> NAME/KEY: MOD_RES
<222> LOCATION: (6)..(6)
<223> OTHER INFORMATION: Asn, Ile or Ser
<220> FEATURE:
<221> NAME/KEY: MOD_RES
<222> LOCATION: (7)..(7)
<223> OTHER INFORMATION: Pro or Ala
<220> FEATURE:
<221> NAME/KEY: MOD_RES
<222> LOCATION: (8)..(8)
<223> OTHER INFORMATION: Ile, Asn, Ser, Tyr, Gly or Met
<220> FEATURE:
<221> NAME/KEY: MOD_RES
<222> LOCATION: (9)..(9)
<223> OTHER INFORMATION: Phe, Ser, Asn or Gly
<220> FEATURE:
<221> NAME/KEY: MOD_RES
<222> LOCATION: (11)..(11)
<223> OTHER INFORMATION: Thr, Asn, Gly, Ser or Asp
<220> FEATURE:
<221> NAME/KEY: MOD_RES
<222> LOCATION: (12)..(12)
<223> OTHER INFORMATION: Thr or Ala
<220> FEATURE:
<221> NAME/KEY: MOD_RES
<222> LOCATION: (13)..(13)
<223> OTHER INFORMATION: Asn, Lys, Ser or Gly

<400> SEQUENCE: 264

Trp Met Gly Xaa Ile Xaa Xaa Xaa Xaa Gly Xaa Xaa Xaa
1               5                   10

<210> SEQ ID NO 265
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (8)..(8)
<223> OTHER INFORMATION: Asp, Ser or Asn
<220> FEATURE:
<221> NAME/KEY: MOD_RES
<222> LOCATION: (11)..(11)
<223> OTHER INFORMATION: Glu or Asp

<400> SEQUENCE: 265

Trp Val Ala Tyr Ile Asn Ser Xaa Ser Gly Xaa Ile His
1               5                   10

<210> SEQ ID NO 266

<400> SEQUENCE: 266

000

<210> SEQ ID NO 267

<400> SEQUENCE: 267

000

<210> SEQ ID NO 268

<400> SEQUENCE: 268

000

<210> SEQ ID NO 269
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Tyr or Trp

<400> SEQUENCE: 269

Ser Asn Xaa Leu Asn Trp Tyr
1               5

<210> SEQ ID NO 270

<400> SEQUENCE: 270

000

<210> SEQ ID NO 271
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

Ser Asn Tyr Leu Ala Trp Tyr
1               5

<210> SEQ ID NO 272
<211> LENGTH: 7
<212> TYPE: PRT
<213> ORGANISM: Artificial Sequence
<220> FEATURE:
<223> OTHER INFORMATION: Description of Artificial Sequence: Synthetic
```

```
                    peptide
<220> FEATURE:
<221> NAME/KEY: MOD_RES
<222> LOCATION: (1)..(1)
<223> OTHER INFORMATION: Ser, Gly or Asn
<220> FEATURE:
<221> NAME/KEY: MOD_RES
<222> LOCATION: (2)..(2)
<223> OTHER INFORMATION: Ser, Asn or Thr
<220> FEATURE:
<221> NAME/KEY: MOD_RES
<222> LOCATION: (3)..(3)
<223> OTHER INFORMATION: Asn or Tyr

<400> SEQUENCE: 272

Xaa Xaa Xaa Leu Ala Trp Tyr
1               5

<210> SEQ ID NO 273

<400> SEQUENCE: 273

000

<210> SEQ ID NO 274

<400> SEQUENCE: 274

000

<210> SEQ ID NO 275
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Ala, Asp, Lys, Gly or Ser
<220> FEATURE:
<221> NAME/KEY: MOD_RES
<222> LOCATION: (8)..(8)
<223> OTHER INFORMATION: Ser or Thr
<220> FEATURE:
<221> NAME/KEY: MOD_RES
<222> LOCATION: (10)..(10)
<223> OTHER INFORMATION: Gln or Glu

<400> SEQUENCE: 275

Leu Leu Ile Tyr Xaa Ala Ser Xaa Leu Xaa
1               5                   10

<210> SEQ ID NO 276
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Leu or Arg
<220> FEATURE:
<221> NAME/KEY: MOD_RES
<222> LOCATION: (5)..(5)
<223> OTHER INFORMATION: Ala, Asp, Lys, Gly or Ser
<220> FEATURE:
<221> NAME/KEY: MOD_RES
<222> LOCATION: (8)..(8)
<223> OTHER INFORMATION: Ser, Thr or Asn
<220> FEATURE:
```

```
<221> NAME/KEY: MOD_RES
<222> LOCATION: (10)..(10)
<223> OTHER INFORMATION: Gln or Glu

<400> SEQUENCE: 276

Xaa Leu Ile Tyr Xaa Ala Ser Xaa Leu Xaa
1               5                   10

<210> SEQ ID NO 277
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Gly or Asp
<220> FEATURE:
<221> NAME/KEY: MOD_RES
<222> LOCATION: (8)..(8)
<223> OTHER INFORMATION: Ser or Thr

<400> SEQUENCE: 277

Leu Leu Ile Tyr Xaa Thr Ser Xaa Arg Ala
1               5                   10

<210> SEQ ID NO 278
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Gly or Asp
<220> FEATURE:
<221> NAME/KEY: MOD_RES
<222> LOCATION: (6)..(6)
<223> OTHER INFORMATION: Ala or Thr
<220> FEATURE:
<221> NAME/KEY: MOD_RES
<222> LOCATION: (8)..(8)
<223> OTHER INFORMATION: Ser, Thr or Asn

<400> SEQUENCE: 278

Leu Leu Ile Tyr Xaa Xaa Ser Xaa Arg Ala
1               5                   10

<210> SEQ ID NO 279
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ile or Val
<220> FEATURE:
<221> NAME/KEY: MOD_RES
<222> LOCATION: (5)..(5)
<223> OTHER INFORMATION: Asp, Gln, Glu, Lys or Gly
<220> FEATURE:
<221> NAME/KEY: MOD_RES
<222> LOCATION: (6)..(6)
<223> OTHER INFORMATION: Asp or Lys
<220> FEATURE:
<221> NAME/KEY: MOD_RES
<222> LOCATION: (7)..(7)
```

```
<223> OTHER INFORMATION: Ser or Thr
<220> FEATURE:
<221> NAME/KEY: MOD_RES
<222> LOCATION: (8)..(8)
<223> OTHER INFORMATION: Lys, Asp, Glu or Asn

<400> SEQUENCE: 279

Leu Val Xaa Tyr Xaa Xaa Xaa Xaa Arg Pro
1               5                   10

<210> SEQ ID NO 280
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ile or Val
<220> FEATURE:
<221> NAME/KEY: MOD_RES
<222> LOCATION: (5)..(5)
<223> OTHER INFORMATION: Asp, Gln, Glu, Lys or Gly
<220> FEATURE:
<221> NAME/KEY: MOD_RES
<222> LOCATION: (6)..(6)
<223> OTHER INFORMATION: Asp or Lys
<220> FEATURE:
<221> NAME/KEY: MOD_RES
<222> LOCATION: (7)..(7)
<223> OTHER INFORMATION: Ser, Asn or Thr
<220> FEATURE:
<221> NAME/KEY: MOD_RES
<222> LOCATION: (8)..(8)
<223> OTHER INFORMATION: Lys, Asp, Glu or Asn

<400> SEQUENCE: 280

Leu Val Xaa Tyr Xaa Xaa Xaa Xaa Arg Pro
1               5                   10

<210> SEQ ID NO 281
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Ser or Thr
<220> FEATURE:
<221> NAME/KEY: MOD_RES
<222> LOCATION: (5)..(5)
<223> OTHER INFORMATION: Ser, Thr or His
<220> FEATURE:
<221> NAME/KEY: MOD_RES
<222> LOCATION: (8)..(8)
<223> OTHER INFORMATION: Tyr, Trp or Phe

<400> SEQUENCE: 281

Gln Gln Tyr Xaa Xaa Leu Pro Xaa
1               5

<210> SEQ ID NO 282

<400> SEQUENCE: 282

000

<210> SEQ ID NO 283
```

```
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ser, Ala, Thr, Ile or Leu
<220> FEATURE:
<221> NAME/KEY: MOD_RES
<222> LOCATION: (3)..(3)
<223> OTHER INFORMATION: Trp or Tyr
<220> FEATURE:
<221> NAME/KEY: MOD_RES
<222> LOCATION: (6)..(6)
<223> OTHER INFORMATION: Ser, Gly, Asn or Asp
<220> FEATURE:
<221> NAME/KEY: MOD_RES
<222> LOCATION: (7)..(7)
<223> OTHER INFORMATION: Ile or Leu

<400> SEQUENCE: 283

Gln Xaa Xaa His Ser Xaa Xaa Trp
1               5

<210> SEQ ID NO 284

<400> SEQUENCE: 284

000

<210> SEQ ID NO 285
<211> LENGTH: 123
<212> TYPE: PRT
<213> ORGANISM: Artificial Sequence
<220> FEATURE:
<223> OTHER INFORMATION: Description of Artificial Sequence: Synthetic
      protein sequence

<400> SEQUENCE: 285

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Thr Pro Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Tyr Pro His Tyr Tyr Gly Ser Ser His Trp Tyr Phe Asp Tyr
            100                 105                 110

Trp Gly Gln Gly Thr Leu Val Thr Val Ser Ser
        115                 120

<210> SEQ ID NO 286
<211> LENGTH: 109
<212> TYPE: PRT
<213> ORGANISM: Artificial Sequence
<220> FEATURE:
<223> OTHER INFORMATION: Description of Artificial Sequence: Synthetic
      protein sequence

<400> SEQUENCE: 286
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65              70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr
            100                 105

<210> SEQ ID NO 287
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 287

Arg Ala Ser Gln Gly Ile Arg Asn Tyr Leu Ala
1               5                   10

<210> SEQ ID NO 288
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 288

Arg Ala Ser Gln Glu Ile Arg Asn Tyr Leu Ala
1               5                   10

<210> SEQ ID NO 289
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 289

Arg Ala Ser Leu Gly Ile Arg Asn Tyr Leu Ala
1               5                   10

<210> SEQ ID NO 290
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 290

Arg Ala Ser Leu Gly Ile Arg Asn Tyr Leu Ala
1               5                   10

<210> SEQ ID NO 291
```

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 291

Arg Ala Ser Gln Gly Ile Arg Asn Tyr Leu Ala
1               5                   10

<210> SEQ ID NO 292
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292

Arg Ala Ser Gln Gly Ile Arg Asn Tyr Leu Ala
1               5                   10

<210> SEQ ID NO 293
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 293

His Ala Ser Arg Lys Leu Arg Asn Tyr Leu Ala
1               5                   10

<210> SEQ ID NO 294
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 294

His Ala Ser Arg Arg Leu Arg Asn Tyr Leu Ala
1               5                   10

<210> SEQ ID NO 295
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 295

His Ala Ser Gln Lys Ile Arg Asn Tyr Leu Ala
1               5                   10

<210> SEQ ID NO 296
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 296

Arg Ala Ser Gln Gly Ile Arg Asn Tyr Leu Ala
```

```
1               5                   10

<210> SEQ ID NO 297
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 297

Arg Ala Ser Leu Gly Ile Arg Asn Tyr Leu Ala
1               5                   10

<210> SEQ ID NO 298
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 298

Arg Ala Ser Gln Gly Ile Arg Asn Tyr Leu Ala
1               5                   10

<210> SEQ ID NO 299
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 299

Ala Ser Thr Leu Gln Ser
1               5

<210> SEQ ID NO 300
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 300

Ala Ser Thr Leu Gln Ser
1               5

<210> SEQ ID NO 301
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 301

Ala Ser Thr Leu Gln Ser
1               5

<210> SEQ ID NO 302
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 302

Ala Ser Thr Leu Gln Ser
1               5

<210> SEQ ID NO 303
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 303

Ala Ser Ser Phe Gln Gln
1               5

<210> SEQ ID NO 304
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 304

Ala Ser Thr Leu Gln Ser
1               5

<210> SEQ ID NO 305
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 305

Ala Ser Thr Leu Leu His
1               5

<210> SEQ ID NO 306
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 306

Ala Ser Ser Phe Leu Pro
1               5

<210> SEQ ID NO 307
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 307

Ala Ser Ser Leu Leu Ser
1               5

<210> SEQ ID NO 308
<211> LENGTH: 6
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 308

Ala Ser Thr Leu Gln Ser
1               5

<210> SEQ ID NO 309
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 309

Ala Ser Thr Leu Gln Ser
1               5

<210> SEQ ID NO 310
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 310

Ala Ser Thr Leu Gln Ser
1               5

<210> SEQ ID NO 311
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 311

Gln Arg Tyr Asn Arg Ala Pro Tyr Thr
1               5

<210> SEQ ID NO 312
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 312

Gln Arg Tyr Asn Arg Ala Pro Tyr Thr
1               5

<210> SEQ ID NO 313
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 313

Gln Arg Tyr Asn Arg Pro Pro Tyr Thr
1               5
```

<210> SEQ ID NO 314
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 314

Gln Arg Tyr Asn Arg Pro Pro Tyr Thr
1               5

<210> SEQ ID NO 315
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 315

Gln Arg Tyr Asp Arg Pro Pro Tyr Thr
1               5

<210> SEQ ID NO 316
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 316

Gln Arg Tyr Asn Arg Ala Pro Tyr Thr
1               5

<210> SEQ ID NO 317
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 317

Gln Arg Tyr Asp Arg Pro Pro Tyr Thr
1               5

<210> SEQ ID NO 318
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 318

Gln Arg Tyr Asp Arg Pro Pro Tyr Thr
1               5

<210> SEQ ID NO 319
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 319

```
Gln Arg Tyr Asp Lys Ala Pro Tyr Thr
1               5

<210> SEQ ID NO 320
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 320

Gln Arg Tyr Asn Lys Ala Pro Tyr Thr
1               5

<210> SEQ ID NO 321
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 321

Gln Arg Tyr Asn Arg Pro Pro Tyr Thr
1               5

<210> SEQ ID NO 322
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 322

Gln Arg Tyr Asn Asp Ala Pro Tyr Thr
1               5

<210> SEQ ID NO 323
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 323

Asp Tyr Ala Met His
1               5

<210> SEQ ID NO 324
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 324

Gln Tyr Ala Met His
1               5

<210> SEQ ID NO 325
<211> LENGTH: 5
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 325

Gln Tyr Ala Met His
1               5

<210> SEQ ID NO 326
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 326

Gln Tyr Ala Met His
1               5

<210> SEQ ID NO 327
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 327

Gln Tyr Ala Met His
1               5

<210> SEQ ID NO 328
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 328

Gln Tyr Ala Met His
1               5

<210> SEQ ID NO 329
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 329

Asp Tyr Ala Met His
1               5

<210> SEQ ID NO 330
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 330

Asp Tyr Ala Met His
1               5

<210> SEQ ID NO 331

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 331

Asp Tyr Ala Met His
1               5

<210> SEQ ID NO 332
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 332

Asp Ser Ala Leu His
1               5

<210> SEQ ID NO 333
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 333

Gln Tyr Ala Met His
1               5

<210> SEQ ID NO 334
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 334

Asp Ser Ala Met His
1               5

<210> SEQ ID NO 335
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 335

Thr Trp Asn Ser Gly His Ile Asp Tyr Ala Asp Ser Val Glu
1               5                   10

<210> SEQ ID NO 336
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 336

Thr Trp Asn Ser Gly His Ile Asp Tyr Ala Asp Ser Val Glu
```

<210> SEQ ID NO 337
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 337

Thr Trp Asn Ser Gly His Ile Asp Tyr Ala Asp Ser Val Glu
1               5                   10

<210> SEQ ID NO 338
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 338

Thr Trp Asn Ser Gly His Ile Asp Tyr Ala Asp Ser Val Glu
1               5                   10

<210> SEQ ID NO 339
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 339

Thr Trp Asn Ser Gly His Ile Asp Tyr Ala Asp Ser Val Glu
1               5                   10

<210> SEQ ID NO 340
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 340

Thr Trp Asn Ser Gly His Ile Asp Tyr Ala Asp Ser Val Glu
1               5                   10

<210> SEQ ID NO 341
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 341

Thr Trp Asn Ser Gly His Ile Asp Tyr Ala Asp Ser Val Glu
1               5                   10

<210> SEQ ID NO 342
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 342

Thr Trp Asn Ser Gly His Ile Asp Tyr Ala Asp Ser Val Glu
1               5                   10

<210> SEQ ID NO 343
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 343

Thr Trp Asn Ser Gly His Ile Asp Tyr Ala Asp Ser Val Glu
1               5                   10

<210> SEQ ID NO 344
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 344

Thr Trp Asn Ser Gly His Ile Asp Tyr Ala Asp Ser Val Glu
1               5                   10

<210> SEQ ID NO 345
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 345

Thr Trp Asn Ser Gly His Ile Asp Tyr Ala Asp Ser Val Glu
1               5                   10

<210> SEQ ID NO 346
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 346

Thr Trp Asn Ser Gly His Ile Asp Tyr Ala Asp Ser Val Glu
1               5                   10

<210> SEQ ID NO 347
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 347

Val Ser Tyr Leu Ser Thr Ala Ser Ser Leu Asp Tyr
1               5                   10

<210> SEQ ID NO 348
<211> LENGTH: 12
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 348

Val Ser Tyr Leu Ser Thr Ala Ser Ser Leu Asp Tyr
1               5                   10

<210> SEQ ID NO 349
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 349

Val Ser Tyr Leu Ser Thr Ala Ser Ser Leu Asp Tyr
1               5                   10

<210> SEQ ID NO 350
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 350

Val Ser Tyr Leu Ser Thr Ala Ser Ser Leu Asp Tyr
1               5                   10

<210> SEQ ID NO 351
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 351

Val Ser Tyr Leu Ser Thr Ala Ser Ser Leu Asp Tyr
1               5                   10

<210> SEQ ID NO 352
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 352

Val Gln Tyr Leu Ser Thr Ala Ser Gln His His Tyr
1               5                   10

<210> SEQ ID NO 353
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 353

Val Ser Tyr Leu Ser Thr Ala Ser Ser Leu Asp Tyr
1               5                   10
```

<210> SEQ ID NO 354
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 354

Val Ser Tyr Leu Ser Thr Ala Ser Ser Leu Asp Tyr
1               5                   10

<210> SEQ ID NO 355
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 355

Val Ser Tyr Leu Ser Thr Ala Ser Ser Leu Asp Tyr
1               5                   10

<210> SEQ ID NO 356
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 356

Val Lys Tyr Leu Ser Thr Ala Ser Ser Leu Asp Tyr
1               5                   10

<210> SEQ ID NO 357
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 357

Val Ser Tyr Leu Ser Thr Ala Ser Ser Leu Asp Tyr
1               5                   10

<210> SEQ ID NO 358
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 358

Val Ser Tyr Leu Ser Thr Ala Ser Ser Leu Asp Tyr
1               5                   10

<210> SEQ ID NO 359
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 359
caggtgcagc tggtgcagag cggtgccgaa                                  30

<210> SEQ ID NO 360
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 360
gtgaagaaac caggctctag cgtgaaagtg agctgcaaa                        39

<210> SEQ ID NO 361
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 361
gccagcggtg gcaccttctc cagctacgcc atcagctggg tgagacaggc ccca       54

<210> SEQ ID NO 362
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 362
ggtcagggcc tggaatggat gggtggcatt atcccaatct tcggcaccgc caactacgcc  60
cagaaattcc ag                                                     72

<210> SEQ ID NO 363
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 363
ggcagagtga caatcaccgc cgataaaagc accagcacc                        39

<210> SEQ ID NO 364
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 364
gcctacatgg aactgtctag cctgagaagc gaagat                           36

<210> SEQ ID NO 365
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 365

```
accgccgtgt attactgcgc cagagatggt tctggcagcg gctacgcctt cgattactgg    60
ggtcagggca cc                                                        72
```

<210> SEQ ID NO 366
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 366

```
ctggttcagt ctggtgccga agtgaaaaag ccaggttcta gc                       42
```

<210> SEQ ID NO 367
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 367

```
gtgaaagtga gctgcaaagc ttccggtggc accttc                              36
```

<210> SEQ ID NO 368
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 368

```
tgggtgagac aggctccagg tcagggcctg gag                                 33
```

<210> SEQ ID NO 369
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 369

```
tacgctcaga aattccaggg cagagtgaca atcaccgcc                           39
```

<210> SEQ ID NO 370
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 370

```
gataaaagca ccagcaccgc ctacatggaa ctgtct                              36
```

<210> SEQ ID NO 371
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 371

-continued agcctgagaa gcgaagatac cgccgtgtat tactgt 36

<210> SEQ ID NO 372
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 372
tactggggtc agggcaccct ggttaccgtg tccagc 36

<210> SEQ ID NO 373
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 373
gaagtgcagc tggtggaatc tggtggc 27

<210> SEQ ID NO 374
<211> LENGTH: 42
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 374
ggtctggtgc agccaggtgg cagcttgaga ctgagctgcg ct 42

<210> SEQ ID NO 375
<211> LENGTH: 54
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 375
gccagcggct ttaccttctc tagctattgg atgagctggg ttagacaggc acct 54

<210> SEQ ID NO 376
<211> LENGTH: 72
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 376
ggcaaaggtt tggaatgggt ggccaacatc aaacaggatg gcagcgaaaa atattacgtg 60
gatagcgtga aa 72

<210> SEQ ID NO 377
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 377

```
ggcagattca ccatcagcag agataacgcc aaaaacagc                       39
```

<210> SEQ ID NO 378
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 378

```
ctgtacttgc agatgaacag cctgagagcc gaagat                          36
```

<210> SEQ ID NO 379
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 379

```
accgccgtgt attactgtgc tagagatggt tctggttccg gctacgcctt cgattactgg    60
ggtcagggca ca                                                        72
```

<210> SEQ ID NO 380
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 380

```
ctggtggaat ctggtggcgg tttggtgcag cctggcggt                       39
```

<210> SEQ ID NO 381
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 381

```
agcttgagac tgtcttgcgc tgccagcggc tttaccttc                       39
```

<210> SEQ ID NO 382
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 382

```
tgggttagac aggcacctgg caaaggtttg gaa                             33
```

<210> SEQ ID NO 383
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 383
tatgtggata gcgtgaaagg cagattcacc atcagcaga                                    39

<210> SEQ ID NO 384
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 384
gataacgcca aaacagcct gtacttgcag atgaac                                        36

<210> SEQ ID NO 385
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 385
agcctgagag ccgaagatac cgctgtgtat tactgt                                       36

<210> SEQ ID NO 386
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 386
tactggggtc agggcacact ggttaccgtg tctagc                                       36

<210> SEQ ID NO 387
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 387
caggtgcagc tggtggaatc tggtgga                                                 27

<210> SEQ ID NO 388
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 388
ggtttggtga aacctggcgg tagcttgaga ctgtcttgtg ct                                42

<210> SEQ ID NO 389
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 389
gccagcggct ttaccttctc tgattattat atgagctgga tcagacaggc acct                   54

<210> SEQ ID NO 390
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 390
ggcaagggtt tggaatgggt gagctacatc tctagctccg gcagcaccat ctactatgcc    60
gatagcgtca aa                                                        72

<210> SEQ ID NO 391
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 391
ggcagattca ccatcagcag agataacgcc aaaaacagc                            39

<210> SEQ ID NO 392
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 392
ctgtacttgc agatgaacag cctgagagcc gaagat                               36

<210> SEQ ID NO 393
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 393
accgctgtgt attactgtgc tagagatggt tctggttccg gctacgcctt cgattactgg    60
ggtcagggca ca                                                        72

<210> SEQ ID NO 394
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 394
ctggtggaat ctggtggagg attggtgaaa cctggcggt                            39

<210> SEQ ID NO 395
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 395

```
agcttgagac tgtcttgtgc tgccagtggc tttaccttc                              39
```

<210> SEQ ID NO 396
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 396

```
tggatcagac aggcacctgg caagggtttg gaa                                    33
```

<210> SEQ ID NO 397
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 397

```
tatgctgata gcgtcaaagg cagattcacc atcagcaga                              39
```

<210> SEQ ID NO 398
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 398

```
gataacgcca aaaacagcct gtacttgcag atgaac                                 36
```

<210> SEQ ID NO 399
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 399

```
agcctgagag ccgaagatac cgctgtgtat tactgt                                 36
```

<210> SEQ ID NO 400
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 400

```
tactggggtc agggcacact ggttaccgtc tctagc                                 36
```

<210> SEQ ID NO 401
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 401

```
ggattggtgc agcctggcgg tagcttgaga ctgtcttgtg ct                          42
```

```
<210> SEQ ID NO 402
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 402
gccagtggct ttaccttctc cagctatgcc atgagctggg ttagacaggc acct          54

<210> SEQ ID NO 403
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 403
ggcaagggtt tggaatgggt gagcgccatc agcggctctg gcggtagcac ctactatgca    60
gatagcgtca aa                                                        72

<210> SEQ ID NO 404
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 404
ggcagattca ccatcagcag agataacagc aaaaacacc                           39

<210> SEQ ID NO 405
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 405
ctgtacttgc agatgaacag cctgagagcc gaagat                              36

<210> SEQ ID NO 406
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 406
accgctgtgt attactgtgc taaagatggt tctggttccg gctacgcctt cgattactgg    60
ggtcagggca ca                                                        72

<210> SEQ ID NO 407
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 407
```
ctgttggagt ctggtggagg attggtgcag cctggcggt                          39

<210> SEQ ID NO 408
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 408
agcttgagac tgtcttgtgc tgccagtggc tttaccttc                          39

<210> SEQ ID NO 409
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 409
tgggttagac aggctcctgg caagggtttg gaa                                33

<210> SEQ ID NO 410
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 410
tatgcagata gcgtcaaagg cagattcacc atcagcaga                          39

<210> SEQ ID NO 411
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 411
gataacagca aaaacaccct gtacttgcag atgaac                             36

<210> SEQ ID NO 412
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 412
agcctgagag ccgaagatac cgctgtgtat tactgt                             36

<210> SEQ ID NO 413
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 413
tactggggtc agggcacact ggttaccgtc tctagc                             36

<210> SEQ ID NO 414
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 414
caggtgcagc tggtggagtc tggtgga                                              27

<210> SEQ ID NO 415
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 415
ggagttgtgc agcctggcag aagcttgaga ctgtcttgtg ct                             42

<210> SEQ ID NO 416
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 416
gccagtggct ttaccttctc ctcctatggt atgcactggg ttagacaggc acct               54

<210> SEQ ID NO 417
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 417
ggcaagggtt tggaatgggt ggctgtgatc tggtacgatg cagcaacaa atactatgca          60 gatagcgtca aa                                                              72

<210> SEQ ID NO 418
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 418
ggcagattca ccatcagcag agataacagc aaaaacacc                                 39

<210> SEQ ID NO 419
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 419
ctgtacttgc agatgaacag cctgagagcc gaagat                                    36

<210> SEQ ID NO 420
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 420
accgctgtgt attactgtgc tagagatggt tctggttccg gctacgcctt cgattactgg    60
ggtcagggca ca                                                        72

<210> SEQ ID NO 421
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 421
ctggtggagt ctggtggagg agttgtccag cctggcaga                           39

<210> SEQ ID NO 422
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 422
agcttgagac tgtcttgtgc tgcctctggc tttaccttc                           39

<210> SEQ ID NO 423
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 423
tgggttagac aggcacctgg caagggtttg gaa                                 33

<210> SEQ ID NO 424
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 424
tatgcagata gcgtcaaagg cagattcacc atcagcaga                           39

<210> SEQ ID NO 425
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 425
gataacagca aaaacaccct gtacttgcag atgaac                              36

<210> SEQ ID NO 426
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 426
agcctgagag ccgaagatac cgctgtgtat tactgt				36

<210> SEQ ID NO 427
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 427
tactggggtc agggcacact ggttaccgtc tctagc				36

<210> SEQ ID NO 428
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 428
cagagcgtgc tgacccagcc tccaagcgtg				30

<210> SEQ ID NO 429
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 429
tccgctgccc caggccagaa agtgaccatc tcttgc				36

<210> SEQ ID NO 430
<211> LENGTH: 57
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 430
agcggctcca gctctaacat cggcaataac tacgtgagct ggtatcaaca gctgcca				57

<210> SEQ ID NO 431
<211> LENGTH: 63
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 431
ggcaccgccc caaaattgct gatctacgat aataacaaaa gaccaagcgg catcccagat				60 aga				63

<210> SEQ ID NO 432
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 432
ttctccggta gcaaatctgg cacaagcgcc                                         30

<210> SEQ ID NO 433
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 433
actctgggca tcaccggctt gcagaccggc                                         30

<210> SEQ ID NO 434
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 434
gatgaagccg attactattg ccagagctgg gattctagcc tgaacggcgt tgtgttcggc        60
ggtggcacaa aa                                                            72

<210> SEQ ID NO 435
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 435
ctgacccagc ctccaagcgt gtccgctgcc ccaggccaga aa                           42

<210> SEQ ID NO 436
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 436
gtgaccatct cttgcagcgg ctccagctct aac                                     33

<210> SEQ ID NO 437
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 437
caacagctgc caggcaccgc cccaaaa                                            27

<210> SEQ ID NO 438
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 438
agcggcatcc cagatagatt ctccggtagc aaa                                 33

<210> SEQ ID NO 439
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 439
tctggcacaa gcgctactct gggtatcacc                                     30

<210> SEQ ID NO 440
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 440
ggcttgcaga caggcgatga agctgattac tattgc                              36

<210> SEQ ID NO 441
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 441
gtgttcggcg gtggcaccaa actgacagtg ctgggccag                           39

<210> SEQ ID NO 442
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 442
cagagcgccc tgacccagcc agcctccgtg                                     30

<210> SEQ ID NO 443
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 443
agcggctctc caggccagag cattaccatc agctgc                              36

<210> SEQ ID NO 444
<211> LENGTH: 60
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 444
acaggcacaa gctccgatgt gggtggctac aactatgtga gctggtatca acagcatcca      60

<210> SEQ ID NO 445
<211> LENGTH: 63
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 445
ggcaaagccc caaagctgat gatctacgaa gtgagcaaca gaccaagcgg cgtgagcaac      60
aga                                                                   63

<210> SEQ ID NO 446
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 446
ttctccggta gcaaatctgg caacacagcc                                      30

<210> SEQ ID NO 447
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 447
agcctgacca tcagcggttt gcaggccgag                                      30

<210> SEQ ID NO 448
<211> LENGTH: 72
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 448
gatgaagctg attactattg ccagagctgg gattctagcc tgaacggtgt tgtgttcggc      60
ggtggcacca aa                                                         72

<210> SEQ ID NO 449
<211> LENGTH: 42
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 449
ctgacccagc cagcctccgt gagcggttcc ccaggccaga gc                        42

<210> SEQ ID NO 450
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 450
attaccatca gctgcacagg cacaagctcc gac                                  33

<210> SEQ ID NO 451
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 451
caacagcatc caggcaaagc cccaaag                                         27

<210> SEQ ID NO 452
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 452
agcggcgtga gcaacagatt ctccggtagc aaa                                  33

<210> SEQ ID NO 453
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 453
tctggcaaca cagctagtct gaccatcagt                                      30

<210> SEQ ID NO 454
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 454
ggtttgcagg ccgaggatga agctgattac tattgc                               36

<210> SEQ ID NO 455
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 455
gtgttcggcg gtggcaccaa actgacagtt ctgggacag                            39

<210> SEQ ID NO 456
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 456
agctacgaac tgacccagcc tccaagcgtg                                        30

<210> SEQ ID NO 457
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 457
agcgttagcc caggccagac cgccagcatt acatgc                                 36

<210> SEQ ID NO 458
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 458
agcggcgata agttgggcga taaatacgcc tgctggtatc aacagaaacc t                51

<210> SEQ ID NO 459
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 459
ggccagagcc ctgtgttggt gatctaccag gatagcaaaa gaccaagcgg catccctgaa       60
aga                                                                     63

<210> SEQ ID NO 460
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 460
ttctccggta gcaactctgg caacacagca                                        30

<210> SEQ ID NO 461
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 461
accctgacca tcagcggcac ccaggctatg                                        30

```
<210> SEQ ID NO 462
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 462
gatgaagctg attactattg ccagagctgg gattctagcc tgaacggtgt tgtgttcggc      60
ggtggcacca aa                                                          72

<210> SEQ ID NO 463
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 463
ctgacccagc ctccaagcgt gagcgttagc ccaggtcaga cc                         42

<210> SEQ ID NO 464
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 464
gccagcatta catgtagcgg tgataagttg ggt                                   33

<210> SEQ ID NO 465
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 465
caacagaaac ctggccagag cccagtg                                          27

<210> SEQ ID NO 466
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 466
agcggcatcc ctgaaagatt ctccggtagc aac                                   33

<210> SEQ ID NO 467
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 467
tctggcaaca cagcaaccct gaccatcagc                                       30
```

```
<210> SEQ ID NO 468
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 468
ggcacccagg ctatggatga agctgattac tattgc                              36

<210> SEQ ID NO 469
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 469
gtgttcggcg gtggcaccaa actgacagtt ctgggacag                           39

<210> SEQ ID NO 470
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 470
agctccgaac tgacccagga cccagccgtg                                     30

<210> SEQ ID NO 471
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 471
agcgtggccc tgggccagac cgtgagaatc acctgc                              36

<210> SEQ ID NO 472
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 472
cagggcgata gcctgagaag ctactatgcc agctggtatc aacagaaacc a             51

<210> SEQ ID NO 473
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 473
ggccaggccc cagttctggt gatctacggc aaaaataaca gaccaagcgg catcccagat    60
aga                                                                  63
```

```
<210> SEQ ID NO 474
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 474
ttctccggta gctctagcgg caacacagcc                                          30

<210> SEQ ID NO 475
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 475
agcctgacca tcaccggtgc ccaggccgag                                          30

<210> SEQ ID NO 476
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 476
gatgaagctg attactattg ccagagctgg gattctagcc tgaacggtgt tgtgttcggc         60
ggtggcacca aa                                                             72

<210> SEQ ID NO 477
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 477
ctgacccagg acccagccgt gagcgttgcc ctgggccaga cc                            42

<210> SEQ ID NO 478
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 478
gtgagaatca cctgccaggg cgattctctg aga                                      33

<210> SEQ ID NO 479
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 479
caacagaaac ctggccaggc cccagtg                                             27
```

```
<210> SEQ ID NO 480
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 480
agcggcatcc cagatagatt ctctggtagc tct                                  33

<210> SEQ ID NO 481
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 481
agcggcaaca cagcatctct gaccatcaca                                      30

<210> SEQ ID NO 482
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 482
ggtgcccagg ccgaggatga agctgattac tattgc                               36

<210> SEQ ID NO 483
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 483
gtgttcggcg gtggcaccaa actgacagtt ctgggacag                            39

<210> SEQ ID NO 484
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 484
gaaatcgtgc tgacacagtc tccagccacc                                      30

<210> SEQ ID NO 485
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 485
ttgtctctgt ccccaggcga aagagctaca ctgtcctgc                            39

<210> SEQ ID NO 486
<211> LENGTH: 51
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 486
agagcttctc agtccgtgtc tagttatctg gcctggtatc aacagaaacc t           51

<210> SEQ ID NO 487
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 487
ggtcaggccc ctagattgct gatctacgat gcttctaaca gagccacagg catccctgcc    60
aga                                                                  63

<210> SEQ ID NO 488
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 488
ttctctggta gcggctctgg cacagatttc                                     30

<210> SEQ ID NO 489
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 489
acactgacta tctctagctt ggaaccagaa                                     30

<210> SEQ ID NO 490
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 490
gatttcgccg tttactattg ccaacagtac aacagcaccc cattgacatt cggtcagggc    60
accaaa                                                               66

<210> SEQ ID NO 491
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 491
ttgacacagt ctccagccac cttgtctctg tccccaggcg aa                       42
```

```
<210> SEQ ID NO 492
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 492
agagctacac tgtcctgcag agcttctcag tccgtg                                 36

<210> SEQ ID NO 493
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 493
caacagaaac ctggtcaggc ccctaga                                           27

<210> SEQ ID NO 494
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 494
acaggtatcc ctgccagatt ctctggtagc ggc                                    33

<210> SEQ ID NO 495
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 495
tctggcacag atttcacact gactatctct                                        30

<210> SEQ ID NO 496
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 496
agcttggaac cagaagattt cgccgtttac tattgc                                 36

<210> SEQ ID NO 497
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 497
acattcggtc agggcaccaa agtggaaatc aaaagaacc                              39

<210> SEQ ID NO 498
<211> LENGTH: 54
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 498
gccagcggct ttaccttctc ctcctacgcc atgkcctggg ttagacaggc acct         54

<210> SEQ ID NO 499
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 499
agagcttctc agtccgtgtc carckcctac ctggcctggt accaacagaa acct         54

<210> SEQ ID NO 500
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 500
gcagagcttc tcagggtatc agcaactacc tgaactggta ccaacagaag cctggtaaag   60
c                                                                   61

<210> SEQ ID NO 501
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 501
gcagagcttc tcagtccgtg agcaactacc tggcctggta ccaacagaaa cctggtcagg   60
c                                                                   61

<210> SEQ ID NO 502
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 502
cacctggtca gggcttggag tggatgggct ggatcaaccc ctacttcggc accaccagct   60
acgctcagaa attccaggg                                                79

<210> SEQ ID NO 503
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 503
cacctggtca gggcttggag tggatgggct ggatcaaccc ctacttcggc accaccaact   60
```

```
acgctcagaa attccaggg                                              79

<210> SEQ ID NO 504
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 504
cacctggtca gggcttggag tggatgggct ggatcaaccc ctacagcggc accaccagct    60
acgctcagaa attccaggg                                              79

<210> SEQ ID NO 505
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 505
cacctggtca gggcttggag tggatgggct ggatcaaccc ctacagcggc accaccaact    60
acgctcagaa attccaggg                                              79

<210> SEQ ID NO 506
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 506
cacctggtca gggcttggag tggatgggct ggatcaaccc ctacaacggc accaccagct    60
acgctcagaa attccaggg                                              79

<210> SEQ ID NO 507
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 507
cacctggtca gggcttggag tggatgggct ggatcaaccc ctacaacggc accaccaact    60
acgctcagaa attccaggg                                              79

<210> SEQ ID NO 508
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 508
cacctggtca gggcttggag tggatgggct ggatcaaccc ctacttcggc aacaccagct    60
acgctcagaa attccaggg                                              79

<210> SEQ ID NO 509
```

<211> LENGTH: 79
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 509
cacctggtca gggcttggag tggatgggct ggatcaaccc ctacttcggc aacaccaact    60
acgctcagaa attccaggg                                                 79

<210> SEQ ID NO 510
<211> LENGTH: 79
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 510
cacctggtca gggcttggag tggatgggct ggatcaaccc ctacagcggc aacaccagct    60
acgctcagaa attccaggg                                                 79

<210> SEQ ID NO 511
<211> LENGTH: 79
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 511
cacctggtca gggcttggag tggatgggct ggatcaaccc ctacagcggc aacaccaact    60
acgctcagaa attccaggg                                                 79

<210> SEQ ID NO 512
<211> LENGTH: 79
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 512
cacctggtca gggcttggag tggatgggct ggatcaaccc ctacaacggc aacaccagct    60
acgctcagaa attccaggg                                                 79

<210> SEQ ID NO 513
<211> LENGTH: 79
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 513
cacctggtca gggcttggag tggatgggct ggatcaaccc ctacaacggc aacaccaact    60
acgctcagaa attccaggg                                                 79

<210> SEQ ID NO 514
<211> LENGTH: 85
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 514
ataccgccgt gtattactgt gccaagagac cccactacta cggcagcagc cactggtact    60
tcgactactg gggtcagggc actct                                          85

<210> SEQ ID NO 515
<211> LENGTH: 85
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 515
ataccgccgt gtattactgt gccaagcacc cccactacta cggcagcagc cactggtact    60
tcgactactg gggtcagggc actct                                          85

<210> SEQ ID NO 516
<211> LENGTH: 85
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 516
ataccgccgt gtattactgt gccaaggagc cccactacta cggcagcagc cactggtact    60
tcgactactg gggtcagggc actct                                          85

<210> SEQ ID NO 517
<211> LENGTH: 85
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 517
ataccgccgt gtattactgt gccaagaccc cccactacta cggcagcagc cactggtact    60
tcgactactg gggtcagggc actct                                          85

<210> SEQ ID NO 518
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 518
atttcgccac ctactattgc cagcagtaca gcacctggcc ctggacattc ggtcagggca    60
ccaa                                                                 64

<210> SEQ ID NO 519
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 519
atttcgccac ctactattgc cagcagtaca gcaccacccc ctggacattc ggtcagggca    60

```
ccaa                                                                64

<210> SEQ ID NO 520
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 520
atttcgccac ctactattgc cagcagtaca gcacctaccc ctggacattc ggtcagggca      60
ccaa                                                                64

<210> SEQ ID NO 521
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 521
atttcgccgt ttactattgc cagcagtaca gcacctggcc ctggacattc ggtcagggca      60
ccaa                                                                64

<210> SEQ ID NO 522
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 522
atttcgccgt ttactattgc cagcagtaca gcaccacccc ctggacattc ggtcagggca      60
ccaa                                                                64

<210> SEQ ID NO 523
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 523
atttcgccgt ttactattgc cagcagtaca gcacctaccc ctggacattc ggtcagggca      60
ccaa                                                                64

<210> SEQ ID NO 524
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 524
aggcttccgg tggcagattc accaactacg ggatgaactg ggttagacag gcacctgg        58

<210> SEQ ID NO 525
<211> LENGTH: 71
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 525
aggcctggta aagcccctaa gcggctgatc tacaaggcca gcagcctgca gtccggcgtt    60
cctagcagat t                                                        71

<210> SEQ ID NO 526
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 526
aggcctggta aagcccctaa gcggctgatc tacgccgcca gcagcctgca gtccggcgtt    60
cctagcagat t                                                        71

<210> SEQ ID NO 527
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 527
aggcctggta aagcccctaa gcggctgatc tacaagagca gcagcctgca gtccggcgtt    60
cctagcagat t                                                        71

<210> SEQ ID NO 528
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 528
aacctggtca ggcccctaga ctgctgatct acgacaccag cagcagggcc acaggtatcc    60
ctgccagatt                                                          70

<210> SEQ ID NO 529
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 529
aggcttccgg tggcacattc accaactaat aaatgaactg ggttagacag gcacctgg      58

<210> SEQ ID NO 530
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 530
```

```
cacctggtca gggcttggag ttgatgggct tgatctaata atacttcggc accrccrgct    60
acgctcagaa attccaggg                                                 79
```

<210> SEQ ID NO 531
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 531

```
gcagagcttc tcagggtatc agcaactagt aaaacttgta ccaacagaag cctggtaaag    60
c                                                                    61
```

<210> SEQ ID NO 532
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 532

```
agcctggtaa agccccctaag cggctgatct agtaagccag cagcctgsag tccggcgttc    60
ctagcagatt                                                           70
```

<210> SEQ ID NO 533
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 533

```
gcagagcttc tcagtccgtg agcaactagt aagccttgta ccaacagaaa cctggtcagg    60
c                                                                    61
```

<210> SEQ ID NO 534
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 534

```
aacctggtca ggcccctcgc ctgctgatct agtaaaccag cagcagggcc acaggcatcc    60
ctgatatatt                                                           70
```

<210> SEQ ID NO 535
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 535

```
aacctggtca ggcccctaga ctgctgatct agtaaaccag cagcagggcc acaggtatcc    60
ctgccagatt                                                           70
```

```
<210> SEQ ID NO 536
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 536
ctgccagtgg ctttaccttc agcasctact ggatgagctg ggttagacag gctcctgg     58

<210> SEQ ID NO 537
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 537
ctgccagtgg ctttaccttc agcractact ggatgagctg ggttagacag gctcctgg     58

<210> SEQ ID NO 538
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 538
ctcctggcaa gggtttggaa tgggtggcca acatcaasca ggacggcagc gagaagtact   60
atgcagatag cgtcaaagg                                                79

<210> SEQ ID NO 539
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 539
ctcctggcaa gggtttggaa tgggtggcca acatctsgca ggacggcagc gagaagtact   60
atgcagatag cgtcaaagg                                                79

<210> SEQ ID NO 540
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 540
ataccgctgt gtattactgt gccagggacc tgrkcggcta cwtsgactac tggggtcagg   60
gcacact                                                             67

<210> SEQ ID NO 541
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 541
```

```
ataccgctgt gtattactgt gccagggacc tgrkcggcta csccgactac tggggtcagg    60
gcacact                                                              67

<210> SEQ ID NO 542
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 542
ataccgctgt gtattactgt gccagggacc tgrkcggcta ckgcgactac tggggtcagg    60
gcacact                                                              67

<210> SEQ ID NO 543
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 543
ataccgctgt gtattactgt gccagggacc tgcwgggcta cwtsgactac tggggtcagg    60
gcacact                                                              67

<210> SEQ ID NO 544
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 544
ataccgctgt gtattactgt gccagggacc tgcwgggcta csccgactac tggggtcagg    60
gcacact                                                              67

<210> SEQ ID NO 545
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 545
ataccgctgt gtattactgt gccagggacc tgcwgggcta ckgcgactac tggggtcagg    60
gcacact                                                              67

<210> SEQ ID NO 546
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 546
ataccgctgt gtattactgt gccagggacc tgwacggcta cwtsgactac tggggtcagg    60
gcacact                                                              67
```

<210> SEQ ID NO 547
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 547
ataccgctgt gtattactgt gccagggacc tgwacggcta csccgactac tggggtcagg     60
gcacact                                                              67

<210> SEQ ID NO 548
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 548
ataccgctgt gtattactgt gccagggacc tgwacggcta ckgcgactac tggggtcagg     60
gcacact                                                              67

<210> SEQ ID NO 549
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 549
ataccgctgt gtattactgt gccagggacc tgascggcta cwtsgactac tggggtcagg     60
gcacact                                                              67

<210> SEQ ID NO 550
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 550
ataccgctgt gtattactgt gccagggacc tgascggcta csccgactac tggggtcagg     60
gcacact                                                              67

<210> SEQ ID NO 551
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 551
ataccgctgt gtattactgt gccagggacc tgascggcta ckgcgactac tggggtcagg     60
gcacact                                                              67

<210> SEQ ID NO 552
<211> LENGTH: 61
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 552
gcagagcttc tcagggtatc agcagckacc tggcctggta ccaacagaag cctggtaaag    60
c                                                                    61

<210> SEQ ID NO 553
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 553
gcagagcttc tcagggtatc agcagctsgc tggcctggta ccaacagaag cctggtaaag    60
c                                                                    61

<210> SEQ ID NO 554
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 554
agcctggtaa agcccctaag ctgctgatct acgacgccag cagcctggag tccggcgttc    60
ctagcagatt                                                           70

<210> SEQ ID NO 555
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 555
atttcgccac ctactattgc cagcaggsca acagctaccc cctgacattc ggtcagggca    60
ccaa                                                                 64

<210> SEQ ID NO 556
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 556
atttcgccac ctactattgc cagcagagsa acagctaccc cctgacattc ggtcagggca    60
ccaa                                                                 64

<210> SEQ ID NO 557
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 557
```

```
atttcgccac ctactattgc cagcagtaca acagctaccc cctgacattc ggtcagggca    60
ccaa                                                                 64
```

<210> SEQ ID NO 558
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 558

```
gcagagcttc tcagtccgtg agcagcwacc tggcctggta ccaacagaaa cctggtcagg    60
c                                                                    61
```

<210> SEQ ID NO 559
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 559

```
aacctggtca ggcccctcgc ctgctgatct acgacgccag cagcagggcc acaggcatcc    60
ctgatagatt                                                           70
```

<210> SEQ ID NO 560
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 560

```
atttcgccgt ttactattgc cagcaggsca acagctaccc cctgacattc ggtcagggca    60
ccaa                                                                 64
```

<210> SEQ ID NO 561
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 561

```
atttcgccgt ttactattgc cagcagagsa acagctaccc cctgacattc ggtcagggca    60
ccaa                                                                 64
```

<210> SEQ ID NO 562
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 562

```
atttcgccgt ttactattgc cagcagtaca acagctaccc cctgacattc ggtcagggca    60
ccaa                                                                 64
```

```
<210> SEQ ID NO 563
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 563

Ser Tyr Ala Met His
1               5

<210> SEQ ID NO 564
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 564

Ser Tyr Tyr Met His
1               5

<210> SEQ ID NO 565
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 565

Ser Tyr Ala Met Tyr
1               5

<210> SEQ ID NO 566
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 566

Ser Tyr Tyr Met Tyr
1               5

<210> SEQ ID NO 567
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 567

Gly Ile Ser Gly Gly Thr Thr Tyr Tyr Ala Asp Ser Val Lys Gly
1               5                   10                  15

<210> SEQ ID NO 568
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (1)..(1)
<223> OTHER INFORMATION: Variable amino acid
<220> FEATURE:
<221> NAME/KEY: MOD_RES
<222> LOCATION: (3)..(5)
<223> OTHER INFORMATION: Variable amino acid
<220> FEATURE:
<221> NAME/KEY: MOD_RES
<222> LOCATION: (8)..(9)
<223> OTHER INFORMATION: Variable amino acid

<400> SEQUENCE: 568

Xaa Ile Xaa Xaa Xaa Gly Gly Xaa Xaa Tyr Tyr Ala Asp Ser Val Lys
1               5                   10                  15
Gly

<210> SEQ ID NO 569
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(5)
<223> OTHER INFORMATION: Variable amino acid
<220> FEATURE:
<221> NAME/KEY: MOD_RES
<222> LOCATION: (8)..(9)
<223> OTHER INFORMATION: Variable amino acid

<400> SEQUENCE: 569

Tyr Ile Xaa Xaa Xaa Gly Gly Xaa Xaa Tyr Tyr Ala Asp Ser Val Lys
1               5                   10                  15
Gly

<210> SEQ ID NO 570
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Variable amino acid
<220> FEATURE:
<221> NAME/KEY: MOD_RES
<222> LOCATION: (4)..(5)
<223> OTHER INFORMATION: Variable amino acid
<220> FEATURE:
<221> NAME/KEY: MOD_RES
<222> LOCATION: (8)..(9)
<223> OTHER INFORMATION: Variable amino acid

<400> SEQUENCE: 570

Xaa Ile Tyr Xaa Xaa Gly Gly Xaa Xaa Tyr Tyr Ala Asp Ser Val Lys
1               5                   10                  15
Gly

<210> SEQ ID NO 571
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (4)..(5)
<223> OTHER INFORMATION: Variable amino acid
<220> FEATURE:
<221> NAME/KEY: MOD_RES
<222> LOCATION: (8)..(9)
<223> OTHER INFORMATION: Variable amino acid

<400> SEQUENCE: 571

Tyr Ile Tyr Xaa Xaa Gly Gly Xaa Xaa Tyr Tyr Ala Asp Ser Val Lys
1               5                   10                  15

Gly

<210> SEQ ID NO 572
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(4)
<223> OTHER INFORMATION: Variable amino acid
<220> FEATURE:
<221> NAME/KEY: MOD_RES
<222> LOCATION: (8)..(9)
<223> OTHER INFORMATION: Variable amino acid

<400> SEQUENCE: 572

Tyr Ile Xaa Xaa Tyr Gly Gly Xaa Xaa Tyr Tyr Ala Asp Ser Val Lys
1               5                   10                  15

Gly

<210> SEQ ID NO 573
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(4)
<223> OTHER INFORMATION: Variable amino acid
<220> FEATURE:
<221> NAME/KEY: MOD_RES
<222> LOCATION: (9)..(9)
<223> OTHER INFORMATION: Variable amino acid

<400> SEQUENCE: 573

Tyr Ile Xaa Xaa Tyr Gly Gly Tyr Xaa Tyr Tyr Ala Asp Ser Val Lys
1               5                   10                  15

Gly

<210> SEQ ID NO 574
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(9)
<223> OTHER INFORMATION: Variable amino acid

<400> SEQUENCE: 574

Tyr Ile Tyr Tyr Tyr Gly Gly Xaa Xaa Tyr Tyr Ala Asp Ser Val Lys
1               5                   10                  15
```

```
<210> SEQ ID NO 575
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Variable amino acid
<220> FEATURE:
<221> NAME/KEY: MOD_RES
<222> LOCATION: (9)..(9)
<223> OTHER INFORMATION: Variable amino acid

<400> SEQUENCE: 575

Tyr Ile Xaa Tyr Tyr Gly Gly Tyr Xaa Tyr Tyr Ala Asp Ser Val Lys
1               5                   10                  15
Gly

<210> SEQ ID NO 576
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Variable amino acid

<400> SEQUENCE: 576

Tyr Ile Xaa Tyr Tyr Gly Gly Tyr Tyr Tyr Tyr Ala Asp Ser Val Lys
1               5                   10                  15
Gly

<210> SEQ ID NO 577
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 577

Tyr Ile Tyr Tyr Tyr Gly Gly Tyr Tyr Tyr Ala Asp Ser Val Lys
1               5                   10                  15
Gly

<210> SEQ ID NO 578
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Variable amino acid
<220> FEATURE:
<221> NAME/KEY: MOD_RES
<222> LOCATION: (3)..(3)
<223> OTHER INFORMATION: Variable amino acid
<220> FEATURE:
<221> NAME/KEY: MOD_RES
```

```
<222> LOCATION: (5)..(8)
<223> OTHER INFORMATION: Variable amino acid
<220> FEATURE:
<221> NAME/KEY: MOD_RES
<222> LOCATION: (10)..(11)
<223> OTHER INFORMATION: Variable amino acid

<400> SEQUENCE: 578

Xaa Gly Xaa Ser Xaa Xaa Xaa Xaa Tyr Xaa Xaa Asp Tyr
1               5                   10

<210> SEQ ID NO 579
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 579

Asn Asn Tyr Gly Met Asn
1               5

<210> SEQ ID NO 580
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 580

Tyr Ser Asn Gly Asn
1               5

<210> SEQ ID NO 581
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ser, Arg, Gly, Asn or Tyr
<220> FEATURE:
<221> NAME/KEY: MOD_RES
<222> LOCATION: (3)..(3)
<223> OTHER INFORMATION: Tyr, Trp, Asp or Ser
<220> FEATURE:
<221> NAME/KEY: MOD_RES
<222> LOCATION: (5)..(5)
<223> OTHER INFORMATION: Ala or Asn

<400> SEQUENCE: 581

Xaa Asn Xaa Leu Xaa Trp Tyr
1               5

<210> SEQ ID NO 582
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 582

Leu Leu Ile Tyr Asp Ala Ser Ser Arg Ala
1               5                   10
```

```
<210> SEQ ID NO 583
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Val, Ala, Asn, Gly, Tyr, Ser or Thr
<220> FEATURE:
<221> NAME/KEY: MOD_RES
<222> LOCATION: (12)..(12)
<223> OTHER INFORMATION: Thr, Lys or Ile

<400> SEQUENCE: 583

Trp Val Ala Xaa Ile Trp Tyr Asp Gly Asp Asn Xaa Tyr
1               5                   10

<210> SEQ ID NO 584

<400> SEQUENCE: 584

000

<210> SEQ ID NO 585
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Ala, Tyr, Gly or Asp
<220> FEATURE:
<221> NAME/KEY: MOD_RES
<222> LOCATION: (6)..(6)
<223> OTHER INFORMATION: His, Ser or Asn

<400> SEQUENCE: 585

Thr Asp Tyr Xaa Met Xaa
1               5

<210> SEQ ID NO 586
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 586

Asp Ser Tyr Gly Asn Ser Phe Met His Trp Tyr
1               5                   10

<210> SEQ ID NO 587
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 587

Leu Leu Ile Tyr Leu Ala Ser Asn Leu Glu
1               5                   10
```

```
<210> SEQ ID NO 588
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 588

Gln Gln Asn Ile Glu Asp Pro Phe
1               5

<210> SEQ ID NO 589
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 589

Ser Asn Tyr Leu Ala Trp Phe
1               5

<210> SEQ ID NO 590
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 590

Gly Gly Gly Gly Ser Gly Gly Gly Ser Gly Gly Gly Gly Ser
1               5                   10                  15

<210> SEQ ID NO 591
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 591
aggcttccgg tggcacattc accaactacg ggatgaactg ggttagacag gcacctgg       58

<210> SEQ ID NO 592
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 592
aggcttccgg tggcacattc accaactacg ggatgaactg ggttagacag gcacctgg       58

<210> SEQ ID NO 593
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 593
accaactacg ggatgaac                                                   18
```

<210> SEQ ID NO 594
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 594
aggcttccgg tggcacattc                                             20

<210> SEQ ID NO 595
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 595
tgggttagac aggcacctgg                                             20

<210> SEQ ID NO 596
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 596
gccagcggct ttaccttctc t                                           21

<210> SEQ ID NO 597
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 597
gctgggttag acaggcacct                                             20

<210> SEQ ID NO 598
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 598
ttgatgggat tgataaaccc atacttcgga acaaac                           36

<210> SEQ ID NO 599
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 599
cacctggtca gggcttggag                                             20

<210> SEQ ID NO 600

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 600
tacgctcaga aattccaggg                                                    20

<210> SEQ ID NO 601
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Pro or Ala
<220> FEATURE:
<221> NAME/KEY: MOD_RES
<222> LOCATION: (9)..(9)
<223> OTHER INFORMATION: Phe, Ser, Asn or Thr
<220> FEATURE:
<221> NAME/KEY: MOD_RES
<222> LOCATION: (11)..(11)
<223> OTHER INFORMATION: Thr, Asn, Gly, Ser or Asp
<220> FEATURE:
<221> NAME/KEY: MOD_RES
<222> LOCATION: (12)..(12)
<223> OTHER INFORMATION: Thr or Ala
<220> FEATURE:
<221> NAME/KEY: MOD_RES
<222> LOCATION: (13)..(13)
<223> OTHER INFORMATION: Asn, Lys, Ser or Gly

<400> SEQUENCE: 601

Trp Met Gly Trp Ile Asn Xaa Tyr Xaa Gly Xaa Xaa Xaa
1               5                   10

<210> SEQ ID NO 602
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 602
cacctggtca gggcttggag ttgatgggct tgatcaacsc ctacttcggc accrccrgct        60
acgctcagaa attccaggg                                                    79

<210> SEQ ID NO 603
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 603
cacctggtca gggcttggag ttgatgggct tgatcaacsc ctacttcggc accrccaast        60
acgctcagaa attccaggg                                                    79

<210> SEQ ID NO 604
<211> LENGTH: 79
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 604
cacctggtca gggcttggag ttgatgggct tgatcaacsc ctacrgcggc accrccrgct      60
acgctcagaa attccaggg                                                   79

<210> SEQ ID NO 605
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 605
cacctggtca gggcttggag ttgatgggct tgatcaacsc ctacrgcggc accrccaast      60
acgctcagaa attccaggg                                                   79

<210> SEQ ID NO 606
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 606
cacctggtca gggcttggag ttgatgggct tgatcaacsc ctacaacggc accrccrgct      60
acgctcagaa attccaggg                                                   79

<210> SEQ ID NO 607
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 607
cacctggtca gggcttggag ttgatgggct tgatcaacsc ctacaacggc accrccaast      60
acgctcagaa attccaggg                                                   79

<210> SEQ ID NO 608
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 608
cacctggtca gggcttggag ttgatgggct tgatcaacsc ctacttcggc rrcrccrgct      60
acgctcagaa attccaggg                                                   79

<210> SEQ ID NO 609
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 609
```
cacctggtca gggcttggag ttgatgggct tgatcaacsc ctacttcggc rrcrccaast    60
acgctcagaa attccaggg                                                79

<210> SEQ ID NO 610
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 610
cacctggtca gggcttggag ttgatgggct tgatcaacsc ctacrgcggc rrcrccrgct    60
acgctcagaa attccaggg                                                79

<210> SEQ ID NO 611
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 611
cacctggtca gggcttggag ttgatgggct tgatcaacsc ctacrgcggc rrcrccaast    60
acgctcagaa attccaggg                                                79

<210> SEQ ID NO 612
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 612
cacctggtca gggcttggag ttgatgggct tgatcaacsc ctacaacggc rrcrccrgct    60
acgctcagaa attccaggg                                                79

<210> SEQ ID NO 613
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 613
cacctggtca gggcttggag ttgatgggct tgatcaacsc ctacaacggc rrcrccaast    60
acgctcagaa attccaggg                                                79

<210> SEQ ID NO 614
<211> LENGTH: 85
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 614
ataccgccgt gtattactgt gccaagrgac cccactacta cggcagcagc cacttgtact    60
tcgactactg gggtcagggc actct                                         85

<210> SEQ ID NO 615
<211> LENGTH: 85
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 615
ataccgccgt gtattactgt gccaagsacc cccactacta cggcagcagc cacttgtact      60
tcgactactg gggtcagggc actct                                           85

<210> SEQ ID NO 616
<211> LENGTH: 85
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 616
ataccgccgt gtattactgt gccaaggwgc cccactacta cggcagcagc cacttgtact      60
tcgactactg gggtcagggc actct                                           85

<210> SEQ ID NO 617
<211> LENGTH: 85
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 617
ataccgccgt gtattactgt gccaagrccc cccactacta cggcagcagc cacttgtact      60
tcgactactg gggtcagggc actct                                           85

<210> SEQ ID NO 618
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(9)
<223> OTHER INFORMATION: This region may encompass RGA, SAC, GWG or RCC

<400> SEQUENCE: 618
gccaagnnnc cccactacta cggcagcagc cacttgtact tcgac                     45

<210> SEQ ID NO 619
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 619
ataccgccgt gtattactgt                                                 20

<210> SEQ ID NO 620
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 620
tactggggtc agggcactct                                                    20

<210> SEQ ID NO 621
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 621
gcagagcttc tcagggtatc agcaactacc tgaacttgta ccaacagaag cctggtaaag        60
c                                                                        61

<210> SEQ ID NO 622
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 622
gcagagcttc tcagtccgtg agcaactacc tggccttgta ccaacagaaa cctggtcagg        60
c                                                                        61

<210> SEQ ID NO 623
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 623
agcctggtaa agcccctaag                                                    20

<210> SEQ ID NO 624
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 624
tccggcgttc ctagcagatt                                                    20

<210> SEQ ID NO 625
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 625
agcctggtaa agcccctaag ckgctgatct acaaggccag cagcctgsag tccggcgttc        60
ctagcagatt                                                               70

```
<210> SEQ ID NO 626
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 626
agcctggtaa agcccctaag ckgctgatct acgmcgccag cagcctgsag tccggcgttc    60
ctagcagatt                                                          70

<210> SEQ ID NO 627
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 627
agcctggtaa agcccctaag ckgctgatct acaagrgcag cagcctgsag tccggcgttc    60
ctagcagatt                                                          70

<210> SEQ ID NO 628
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 628
ctgctgatct acgrcaccag cagcagggcc                                    30

<210> SEQ ID NO 629
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 629
aacctggtca ggcccctcgc                                               20

<210> SEQ ID NO 630
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 630
caggcatccc tgatatatt                                                19

<210> SEQ ID NO 631
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 631
aacctggtca ggcccctaga                                               20
```

```
<210> SEQ ID NO 632
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 632
caggtatccc tgccagatt                                                   19

<210> SEQ ID NO 633
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 633
aacctggtca ggcccctcgc ctgctgatct acgrcaccag cagcagggcc acaggcatcc     60
ctgatatatt                                                             70

<210> SEQ ID NO 634
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 634
aacctggtca ggcccctaga ctgctgatct acgrcaccag cagcagggcc acaggtatcc     60
ctgccagatt                                                             70

<210> SEQ ID NO 635
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 635

Leu Leu Ile Tyr Ala Ala Ser Thr Leu Gln
1               5                   10

<210> SEQ ID NO 636
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Glu, Tyr, Ser or Arg
<220> FEATURE:
<221> NAME/KEY: MOD_RES
<222> LOCATION: (6)..(6)
<223> OTHER INFORMATION: Tyr, Asn or Ser
<220> FEATURE:
<221> NAME/KEY: MOD_RES
<222> LOCATION: (7)..(7)
<223> OTHER INFORMATION: His, Tyr, Gln or Thr
<220> FEATURE:
<221> NAME/KEY: MOD_RES
```

```
<222> LOCATION: (8)..(8)
<223> OTHER INFORMATION: Ser or Thr
<220> FEATURE:
<221> NAME/KEY: MOD_RES
<222> LOCATION: (10)..(10)
<223> OTHER INFORMATION: Ser, Thr or Asn
<220> FEATURE:
<221> NAME/KEY: MOD_RES
<222> LOCATION: (12)..(12)
<223> OTHER INFORMATION: Asn, Tyr, Ile

<400> SEQUENCE: 636

Trp Ile Gly Xaa Ile Xaa Xaa Xaa Gly Xaa Thr Xaa
1               5                   10

<210> SEQ ID NO 637
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Glu or Tyr
<220> FEATURE:
<221> NAME/KEY: MOD_RES
<222> LOCATION: (6)..(6)
<223> OTHER INFORMATION: Asn, Tyr or Ser
<220> FEATURE:
<221> NAME/KEY: MOD_RES
<222> LOCATION: (7)..(7)
<223> OTHER INFORMATION: His, Gln or Tyr
<220> FEATURE:
<221> NAME/KEY: MOD_RES
<222> LOCATION: (8)..(8)
<223> OTHER INFORMATION: Ser or Thr
<220> FEATURE:
<221> NAME/KEY: MOD_RES
<222> LOCATION: (10)..(10)
<223> OTHER INFORMATION: Ser, Thr or Asn
<220> FEATURE:
<221> NAME/KEY: MOD_RES
<222> LOCATION: (12)..(12)
<223> OTHER INFORMATION: Asn or Ile

<400> SEQUENCE: 637

Trp Ile Gly Xaa Ile Xaa Xaa Xaa Gly Xaa Thr Xaa
1               5                   10

<210> SEQ ID NO 638
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Ser, Glu or Arg
<220> FEATURE:
<221> NAME/KEY: MOD_RES
<222> LOCATION: (7)..(7)
<223> OTHER INFORMATION: His or Tyr
<220> FEATURE:
<221> NAME/KEY: MOD_RES
<222> LOCATION: (12)..(12)
<223> OTHER INFORMATION: Tyr, Asn or Ser

<400> SEQUENCE: 638

Trp Ile Gly Xaa Ile Tyr Xaa Ser Gly Ser Thr Xaa
1               5                   10
```

```
<210> SEQ ID NO 639
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Tyr, Ser or Arg
<220> FEATURE:
<221> NAME/KEY: MOD_RES
<222> LOCATION: (5)..(5)
<223> OTHER INFORMATION: Ile or Val
<220> FEATURE:
<221> NAME/KEY: MOD_RES
<222> LOCATION: (6)..(6)
<223> OTHER INFORMATION: Tyr or Phe
<220> FEATURE:
<221> NAME/KEY: MOD_RES
<222> LOCATION: (7)..(7)
<223> OTHER INFORMATION: Tyr or Thr
<220> FEATURE:
<221> NAME/KEY: MOD_RES
<222> LOCATION: (10)..(10)
<223> OTHER INFORMATION: Ser or Asn
<220> FEATURE:
<221> NAME/KEY: MOD_RES
<222> LOCATION: (12)..(12)
<223> OTHER INFORMATION: Tyr or Asn

<400> SEQUENCE: 639

Trp Ile Gly Xaa Xaa Xaa Xaa Ser Gly Xaa Thr Xaa
1               5                   10

<210> SEQ ID NO 640
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Ser, Gly, Asp, Arg or Glu
<220> FEATURE:
<221> NAME/KEY: MOD_RES
<222> LOCATION: (6)..(6)
<223> OTHER INFORMATION: Asn or Asp
<220> FEATURE:
<221> NAME/KEY: MOD_RES
<222> LOCATION: (7)..(7)
<223> OTHER INFORMATION: Asn, Asp or Ser
<220> FEATURE:
<221> NAME/KEY: MOD_RES
<222> LOCATION: (8)..(8)
<223> OTHER INFORMATION: Gln, Asn or Lys

<400> SEQUENCE: 640

Leu Leu Ile Tyr Xaa Xaa Xaa Xaa Arg Pro
1               5                   10

<210> SEQ ID NO 641
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Met, Ile or Leu
```

-continued

```
<220> FEATURE:
<221> NAME/KEY: MOD_RES
<222> LOCATION: (4)..(4)
<223> OTHER INFORMATION: Tyr or Phe
<220> FEATURE:
<221> NAME/KEY: MOD_RES
<222> LOCATION: (5)..(5)
<223> OTHER INFORMATION: Glu or Asp
<220> FEATURE:
<221> NAME/KEY: MOD_RES
<222> LOCATION: (7)..(7)
<223> OTHER INFORMATION: Ser, Thr or Asn
<220> FEATURE:
<221> NAME/KEY: MOD_RES
<222> LOCATION: (8)..(8)
<223> OTHER INFORMATION: Asn, Lys or Tyr

<400> SEQUENCE: 641

Leu Xaa Ile Xaa Xaa Val Xaa Xaa Arg Pro
1               5                   10
```

ANTIBODY ULTRAHUMANIZATION BY PREDICTED MATURE CDR BLASTING AND COHORT LIBRARY GENERATION AND SCREENING

RELATED INFORMATION

This application is the U.S. national phase under 35 U.S.C. §371 of PCT International Application Number PCT/IB2006/003181, filed Nov. 10, 2006; which claims priority to U.S. Provisional Application No. 60/736,726, filed Nov. 14, 2005. The contents of all patents, patent applications, and references cited throughout this specification are hereby incorporated herein by reference in their entireties.

BACKGROUND OF THE INVENTION

Antibodies have profound relevance as research tools and in diagnostic and therapeutic applications. However, the identification of such useful antibodies is difficult and frequently, especially if therapeutic applications are envisioned, requires considerable redesign or 'humanization' before the antibody is suitable for administration.

Previous methods for identifying desirable antibodies have typically involved phage display of representative antibodies, for example human libraries or synthetic libraries, however, these approaches have limitations. For example, most human libraries contain only the antibody sequence diversity that can be experimentally captured or cloned from the source tissue. Accordingly, the human library may lack or under represent other valuable antibody sequences. Synthetic or consensus libraries have other limitations such as the potential to encode non-naturally occurring sequence that has the potential to be immunogenic. In addition, synthetic libraries, in an effort to be comprehensive, frequently contain too much diversity and are difficult to screen. Moreover, these libraries, when used to identify a candidate antibody that binds to a particular target, are not amenable to rational, follow-up, affinity maturation techniques to improve the binding of the candidate molecule. For example, methods for subsequent antibody improvement often involve in vitro mutagenesis such as random mutagenesis, saturation mutagenesis, error-prone PCR, gene shuffling, and antibody chain shuffling. These strategies are inherently stochastic and often require the construction of exceedingly large libraries to explore any meaningful sequence diversity. As the number of positions to be mutated in a given antibody becomes larger, the size of the resultant library becomes larger than what can be feasibly screened.

A recently identified method has described in silico (and optionally in vitro) construction of universal antibody libraries that systematically represent non-immunogenic, naturally-occurring candidate antibodies that possess desired properties, e.g., libraries that are fully representative of known, prevalent (e.g., >10% frequency in a surveyed population), naturally-occurring CDR diversity in the germline (e.g., antibodies derived from the V BASE database) and/or in mature antibodies (e.g., antibodies derived from the Kabat database).

A need exists for a rational, efficient process by which the information regarding naturally-occurring sequence diversity that is contained within reference libraries, such as universal antibody libraries, may be optimally exploited to enhance antibody design (e.g., design of novel human antibodies possessing optimal affinity and minimal immunogenicity).

SUMMARY OF THE INVENTION

The present invention solves the above problem by providing a process by which at least one CDR sequence of a query antibody may be used to search a reference antibody library (e.g., a universal antibody library) to identify novel candidate CDR sequences for use in novel antibodies and/or fragments thereof.

In one embodiment, the invention features methods of generating sequence libraries (cohort libraries) that comprise at least one CDR sequence that represents only known, prevalent, naturally-occurring diversity present in the reference library (e.g., a universal antibody library) at any selected CDR residue. The aligned residue-by-residue sequence diversity present within CDR domain sequences of the reference library may be independently sorted to generate novel CDR sequences as members of such cohort CDR libraries.

While the output (cohort) CDR libraries of the invention are predominately comprised of residue-by-residue human sequence diversity selected from a reference (diversity) library, the methods of the invention also allow for the "fixing" of certain CDR residues in the output library sequence(s) to match the residue present in, e.g., an aligned query sequence at that residue position. Fixing certain output (cohort library) sequence residues as query sequence residues may involve performance of the methods of the invention using a "gapped alignment" strategy. Such a gapped alignment strategy may also be employed to provide sufficient flexibility to the methods of the invention to allow for the presence of nucleotide insertions and/or deletions (in/dels) of one or more nucleotides in length, upon alignment of query and reference (diversity) library sequences and/or during generation of output (cohort library) sequences.

The methods of the invention also allow for use of similarity comparisons between query and library sequence residues to adjust the overall diversity of an output (cohort) CDR library in a rational manner. In such embodiments, the twenty naturally-occurring mammalian amino acid residues are assigned to seven distinct groups on the basis of side chain characteristics. Should a query residue at a given CDR position fall to match a human diversity library residue at the same position, us of such a similarity comparison may allow for selection of one or more similar residues as a component of the output (cohort) library at that residue position, should such a similar residue be present in the reference (diversity) library. Implementation of a similarity criteria for selection of output (cohort) CDR residues may produce cohort libraries of reduced complexity, as compared to use of an identity criteria (wherein non-identity between a query sequence residue and the reference (diversity) library residue(s) at that position results in the use of all CDR residues present in the reference (diversity) library at that position in the resulting output (cohort) library at the corresponding position). Such similarity criteria may also be implemented in a permissive or constrictive manner for any selected CDR residue position. In certain embodiments, implementation of similarity criteria may result in selection of only one amino acid residue from the reference (diversity) library that is similar to the corresponding query sequence residue for incorporation in the output (cohort) library sequences at that position. In other embodiments, more than one reference (diversity) library amino acid residue similar to a query sequence residue at a given position may be selected for use in the output (cohort) library sequences of the invention. In the most permissive of such embodiments, all similar residues present in the reference (diversity) library at a given non-identical (between query sequence and reference library) residue are represented in the output (cohort) sequence library at that residue (referred to as an "all similar" criteria). The methods of the invention may be performed using the above criteria (fixed residues/gapped alignments, in/dels, similarity criteria of any degree of permissiveness, and/or identity criteria) in any combination, at any selected residue position for generation of output (cohort) library sequence(s). (The criteria applied to one residue position of a query sequence may therefore be distinct from those applied to a neighboring residue within the same sequence.)

Selected cohort CDR libraries and/or selected sequences derived from the cohort CDR libraries of the invention may be combined with one another (and with selected framework domain sequences; e.g., via gene SOE (single overlap extension)) to produce completely novel antibody libraries that comprise at least one antibody or fragment thereof that predominately incorporates naturally-occurring CDR variation when examined residue-by-residue, thus minimizing the probability that such novel antibodies or fragments are immunogenic.

Because the complexity of any selected CDR library of the invention is minimized relative to randomized or other forms of synthetic CDR libraries, the selected CDR libraries of the invention (e.g., independent $V_H$CDR1, $V_H$CDR2, $V_H$CDR3, etc. libraries) may also be independently sorted with one another to produce novel antibody libraries that, e.g., represent all human diversity across all CDR sequences at the amino acid residues where a query CDR sequence is not identical to any reference library CDR amino acid residue at that position, yet are still of a size that can be readily screened using current technologies (e.g., library complexities of less than about $10^{12}$ to $10^{15}$ more preferably 10 to $10^{12}$ or intervals or ranges therein.). The present invention also features compositions produced by the processes of the present invention, as well as devices for performing the processes featured in the present invention.

The present invention therefore features a method of producing a library of polynucleotides encoding at least one complementarity determining region (CDR), wherein the method comprises determining the CDR amino acid sequence variation present in a reference antibody library that comprises naturally-occurring CDR amino acid regions, wherein the CDR sequence variation is determined at each amino acid residue position of the CDR; aligning a query CDR peptide sequence from an antibody against a target antigen with the CDR sequences of a reference antibody library; and synthesizing a library of polynucleotides encoding CDR sequences, wherein for the majority of library CDR sequences synthesized the amino acid residue encoded at any single position within a CDR sequence is identical to an amino acid residue at the corresponding aligned position of the query CDR peptide sequence from an antibody against a candidate antigen; or is a predetermined amino acid residue(s) if an identical amino acid residue for the query CDR peptide sequence at the position being aligned does not occur in the reference library, whereby a library of polynucleotides is provided that encodes CDR analogs of the query CDR peptide sequence from an antibody against a target antigen, the CDR analogs being enriched for naturally occurring amino acid residues at one or more residue positions. In one embodiment, the amino acid length of the query CDR being aligned is 4, 5, 6, 7, 8, 9, 10, 11, 12, 13, 14, 15, 16, 17, 18, 19, 20, 21, 22, 23, 24 or 25. In another embodiment, the predetermined amino acid residue is a small side chain amino add residue selected from the group consisting of Glycine (G) and Alanine (A); a nucleophilic side chain amino add residue selected from the group consisting of Serine (S), Threonine (T), Cysteine (C), and Histidine (H); a hydrophobic side chain amino acid residue selected from the group consisting of Valine (V), Leucine (L), Isoleucine (I), Methionine (M), and Proline (P); an aromatic side chain amino acid residue selected from the group consisting of Phenylalanine (F), Tyrosine (Y), and Tryptophan (W); an acidic side chain amino acid residue selected from the group consisting of Aspartate (D), and Glutamate (E); an amide side chain amino acid residue selected from the group consisting of Asparagine (N) and Glutamine (Q); or a basic side chain amino add residue selected from the group consisting of Lysine (K), and Arginine (R). In certain embodiments, aligning is performed by a process selected from the group consisting of gapped alignment, complete alignment, discontinuous alignment, or combinations thereof. In another embodiment, the CDR is defined according to the EU Index, Kabat, Chothia, or based on contact-point definition. An additional embodiment features a library produced by the method above.

In an additional aspect, the invention features a library of antigen binding regions comprising at least one complementarity determining region (CDR) wherein for a majority of library CDR sequences the amino acid residue at any single position within the CDR sequence is identical to an amino acid residue at a corresponding aligned position of a query CDR peptide sequence from an antibody against a target antigen; or a predetermined amino acid residue(s) if an identical amino acid residue for the query CDR peptide sequence at the position being aligned does not occur in a reference library, whereby a library of CDR analogs of the query CDR peptide sequence from an antibody against a candidate antigen is provided, the CDR analogs being enriched for naturally occurring amino acid sequence at one or more residue positions. In one embodiment, the reference antibody library target antigen is a protein, peptide, small molecule, lipid, polysaccharide, or polynucleotide. In another embodiment, the query CDR peptide sequence is a synthetic CDR sequence or a vertebrate CDR sequence. In an additional embodiment, the vertebrate CDR sequence is human, primate, murine, rat, rabbit, or chicken.

In certain embodiments, the query CDR peptide sequence binds a target antigen. In related embodiments, the target antigen is a protein, peptide, small molecule, polysaccharide, or polynucleotide. In further embodiments, greater than 10%, greater than 50%, or greater than 80% of the library sequences comprise known, naturally-occurring CDR sequences. In one embodiment, the library comprises only known, naturally-occurring diversity for any given CDR. In another embodiment, the library comprises all known CDR diversity for a human CDR. In an additional embodiment, the library comprises all known CDR diversity for an antigen class. In certain embodiments, the CDR analog is selected from the group consisting of CDR-H1, CDR-H2, CDR-H3, CDR-L1, CDR-L2, CDR-L3, and combinations thereof. In other embodiments, the query CDR sequence is selected from the group consisting of CDR-H1, CDR-H2, CDR-H3, CDR-L1, CDR-L2, and CDR-L3. In a further embodiment, more than one CDR is aligned, wherein the sequence diversity of one synthetic CDR library is defined, expanded, or restricted based on the variability of a linearly linked CDR.

In one embodiment, CDR-H1 comprises a cohort library amino acid sequence shown in any of FIG. 13 or 16-27. In another embodiment, CDR-H2 comprises a cohort library amino acid sequence shown in any of FIG. 13 or 16-27. In an additional embodiment, CDR-H3 comprises a cohort library amino add sequence shown in any of FIG. 13 or 16-27. In a further embodiment, CDR-L1 comprises a cohort library amino acid sequence shown in any of FIG. 13 or 16-27. In another embodiment, CDR-L2 comprises a cohort-library amino acid sequence shown in any of FIG. 13 or 16-27. In an additional embodiment, CDR-L3 comprises a cohort library amino acid sequence shown in any of FIG. 13 or 16-27.

In certain embodiments, the light chain CDR-L1 (lambda (L)) comprises an amino acid sequence set forth in FIG. 44. In other embodiments, the light chain CDR-L1 (kappa (K)) comprises an amino acid sequence set forth in FIG. 44. In additional embodiments, the light chain CDR-L2 comprises an amino add sequence set forth in FIG. 44. In another embodiment, the light chain CDR-L3 comprises an amino acid sequence set forth in FIG. 44.

In one embodiment, the CDR analog comprises an amino acid sequence set forth in any of FIG. 9-31, 34-36 or 44-61. In another embodiment, the CDR analogs comprise a diversity wherein one or more residues within the CDR analogs is represented using degenerate codons, walk-through mutagenesis, or look-though mutagenesis. In an additional embodiment, the antibody binding regions further comprise one or more amino add substitutions, insertions, or deletions. In a further embodiment, the antigen binding regions further comprise naturally occurring framework regions from human, primate, murine, rat, rabbit, or chicken. In certain embodiments, the naturally occurring framework regions are VH1, VH3, or VH4. In a related embodiment, the human framework regions are light chain framework regions, heavy chain framework regions, cross-cloned framework regions, consensus framework regions or combinations thereof. In another embodiment, the human framework regions have been selected according to their frequency of occurrence in linear connection with one or more human CDR regions. In other embodiments, the human framework regions between the CDRs are isotype matched.

In one embodiment, the library of the invention is an expression library. In certain embodiments, the expression library is selected from the group consisting of a ribosome display library, a polysome display library, a phage display library, viral display library, a bacterial expression library, yeast display library, and a mammalian display library. In an additional embodiment, the library is produced by synthesizing polynucleotides encoding one or more framework regions and one or more CDR regions wherein the polynucleotides are predetermined, wherein the polynucleotides encoding said regions further comprise sufficient overlapping sequence whereby the polynucleotide sequences, under polymerase chain reaction (PCR) conditions, are capable of assembly into polynucleotides encoding complete antibody binding regions. Another embodiment of the invention features an antibody binding region encoded by a polynucleotide of the library of the invention. A further embodiment features a method of identifying a polypeptide having a desired binding affinity comprising expressing the expression library of the invention to produce antibody binding regions, and screening the antibody binding regions to select for an antibody binding region having a desired binding affinity. In one embodiment, the screening comprises contacting the antigen binding region with a target substrate, the antibody binding region being associated with the polynucleotide encoding the antibody binding region. In another embodiment, the method further comprises the step of identifying the polynucleotide that encodes the selected antibody binding region. In an additional embodiment, the polynucleotide is associated with the antibody binding region using an expression display selected from the group consisting of a ribosome display library, a polysome display library, a phage display library, viral display library, a bacterial expression library, yeast display library, and a mammalian display library. A further embodiment features an antibody binding region identified according to the preceding methods.

In one embodiment, one or more steps of the featured methods of the invention is computer-assisted. A related embodiment features medium suitable for use in an electronic device having instructions for carrying out one or more steps of the methods of the invention. Another embodiment features a device for carrying out one or more steps of the methods of the invention.

A final aspect features a library of polynucleotides encoding antibody binding regions comprising one or more framework regions having a sequence set forth in any of the figures or tables; and one or more CDR regions having a sequence set forth in any of the figures or tables wherein the framework regions of a) and CDR regions of b) together form an antibody binding region against a predetermined antigen.

BRIEF DESCRIPTION OF THE FIGURES

FIG. 3 shows an overview of the process by which a collated universal antibody library may be constructed, for use in cohort searching.

FIG. 5 shows an exemplary partitioning of UAL framework and CDR sequences among $V_H$ (SEQ ID NOS 1-5, respectively, in order or appearance), $V_□$ (SEQ ID NOS 6-8, respectively, in order of appearance) and $V_□$ (SEQ ID NOS 9-12, respectively, in order or appearance) classes.

FIG. 10 (BLASTing UAL with mouse CDR1 probe $V_H$ CDR1 "TNYGMN" (SEQ ID NO: 13)) shows the exemplary use of a CDR1 peptide sequence derived from a mouse antibody to identify sequence diversity present at each CDR1 amino acid position in human CDR1 sequences present in VH-1 CDR1 (SEQ ID NO: 14) and VH-3 CDR1 (SEQ ID NO:15) reference universal antibody libraries.

FIG. 11 (BLASTing UAL with mouse CDR2 probe $V_H$ CDR2 "WMGWINTYTGEPT" (SEQ ID NO: 16)) shows the exemplary use of a CDR2 peptide sequence derived from a mouse antibody to identify sequence diversity present at each CDR2 amino acid position in human CDR2 sequences present in VH-1 CDR2 (SEQ ID NO: 17) and VH-3 CDR2 (SEQ ID NO: 18) reference universal antibody libraries.

FIG. 12 shows exemplary quantitated cohort libraries, in which the diversity of cohort libraries generated by independent assortment of reference library diversity to generate novel antibody sequences is calculated.

FIG. 13 shows tabulated cohort library CDR selections for heavy (FIG. 13A-1 to 13A-4) and light (kappa, FIG. 13B-1 to 13B-3) chains using query sequence derived from a mouse Avastin A4.6.1 antibody. In FIG. 13A-1, mouse probe and library encodes sequences are disclosed as SEQ ID NOS 13 and 15, respectively, in the first table and SEQ ID NOS 13 and 14, respectively, in the second table. In FIG. 13A-2 mouse probe and library encodes sequences are disclosed as SEQ ID NOS 16 and 17, respectively. In FIG. 13A-3 mouse probe and library encodes sequences are disclosed as SEQ ID NOS 16 and 18, respectively. In FIG. 13A-4 mouse probe and library encodes sequences are disclosed as SEQ ID NOS 19 and 20, respectively. In FIG. 13B-1 mouse probe and library encodes sequences are disclosed as SEQ ID NOS 21 and 22, respectively, in the first table and SEQ ID NOS 21 and 249, respectively, in the second table. In FIG. 13B-2 mouse probe and library encodes sequences are disclosed as SEQ ID NOS 23 and 24, respectively, in the first table and SEQ ID NOS 23 and 25, respectively, in the second table. In FIG. 13B-3 mouse probe and library encodes sequences are disclosed as SEQ ID NOS 26 and 27, respectively.

FIG. 14 (panels A-E) depicts the selection of cohort library CDR sequences for heavy and light chains using query sequence derived from a mouse anti-HIV gp41 monoclonal antibody. Catalytic triad residues are underlined. In FIG. 14A, the sequences are disclosed as SEQ ID NOS 28-31, respectively, in order or appearance. In FIG. 14B, mouse probe and library encodes sequences are disclosed as SEQ ID NOS 32 and 33, respectively. In FIG. 14C, mouse probe and library encodes sequences are disclosed as SEQ ID NOS 32 and 34, respectively, in the first table and SEQ ID NOS 35 and 36, respectively in the second table. In FIG. 14D, mouse probe and library encodes sequences are disclosed as SEQ ID NOS 30 and 37, respectively, in the first table and SEQ ID NOS 30 and 38, respectively, in the second table. In FIG. 14E, mouse probe and library encodes sequences are disclosed as SEQ ID NOS 31 and 39, respectively.

FIG. 15 (panels A-D) depicts the selection of cohort library CDR sequences for heavy and light chains using query sequence derived from a human HK14 antibody. In FIG. 15A, the sequences are disclosed as SEQ ID NOS: 40-43, respectively, in order or appearance. In FIG. 15B, human probe and library encodes sequences are disclosed as SEQ ID NOS 41 and 44, respectively. In FIG. 15C, human probe and library encodes sequences are disclosed as SEQ ID NOS 42 and 45, respectively. In FIG. 15D, mouse probe and library encodes sequences are disclosed as SEQ ID NOS 43 and 46, respectively.

FIG. 16 shows tabulated cohort library CDR selections for heavy (FIG. 16A-1 to 16A-4) and light (kappa, FIG. 16B-1 to 16B-3) chains using query sequence derived from a human AAV293 MCP-1 antibody. In FIG. 16A-1, human probe and library encodes sequences are disclosed as SEQ ID NOS 47 and 48, respectively in the first table and SEQ ID NOS 49 and 50, respectively, in the second table. In FIG. 16A-2, human probe and library encodes sequences are disclosed as SEQ ID NOS 51 and 52, respectively. In FIG. 16A-3, human probe and library encodes sequences are disclosed as SEQ ID NOS 51 and 53, respectively. In FIG. 16A-4, human probe and library encodes sequences are disclosed as SEQ ID NOS 54 and 55, respectively. In FIG. 16B-1, human probe and library encodes sequences are disclosed as SEQ ID NOS 56 and 57, respectively, in the first table and SEQ ID NOS 56 and 58, respectively, in the second table. In FIG. 16B-2, human probe and library encodes sequences are disclosed as SEQ ID NOS 59 and 60, respectively, in the first table, and SEQ ID NOS 59 and 60, respectively, in the second table. In FIG. 16B-3, human probe and library encodes sequences are disclosed as SEQ ID NOS 59 and 582, respectively, in the first table and SEQ ID NOS 61 and 62, respectively, in the second table.

FIG. 17 shows tabulated cohort library CDR selections for heavy (FIG. 17A-1 to 17A-4 and light (kappa, FIG. 17B-1 to 17B-3) chains using query sequence derived from a mouse ACZ885 antibody. In FIG. 17A-1, mouse probe and library encodes sequences are disclosed as SEQ ID NOS 63 and 64, respectively, in the first table and SEQ ID NOS 63 and 65, respectively, in the second table. In FIG. 17A-2, mouse probe and library encodes sequences are disclosed as SEQ ID NOS 66 and 67, respectively. In FIG. 17A-3, mouse probe and library encodes sequences are disclosed as SEQ ID NOS 66 and 68, respectively. In FIG. 17A-4, mouse probe and library encodes sequences are disclosed as SEQ ID NOS 69 and 70, respectively. In FIG. 17B-1, mouse probe and library encodes sequences are disclosed as SEQ ID NOS 71 and 72, respectively, in the first table and SEQ ID NOS 71 and 73, respectively, in the second table. In FIG. 17B-2, mouse probe and library encodes sequences are disclosed as SEQ ID NOS 74 and 75, respectively, in the first table and SEQ ID NOS 74 and 76, respectively, in the second table. In FIG. 17B-3, mouse probe and library encodes sequences are disclosed as SEQ ID NOS 77 and 78, respectively.

FIG. 18 shows tabulated cohort library CDR selections for heavy (FIG. 18A-1 to 18A-4) and light (kappa, FIG. 18B-1 to 18B-3) chains using query sequence derived from a human gp120 ITH52 antibody. In FIG. 18A-1, human probe and library encodes sequences are disclosed as SEQ ID NOS 79 and 80, respectively, in the first table and SEQ ID NOS 79 and 81, respectively, in the second table. In FIG. 18A-2, human probe and library encodes sequences are disclosed as SEQ ID NOS 82 and 83, respectively. In FIG. 18A-3, human probe and library encodes sequences are disclosed as SEQ ID NOS 82 and 84, respectively. In FIG. 18A-4, human probe and library encodes sequences are disclosed as SEQ ID NOS 85 and 86, respectively. In FIG. 18B-1, human probe and library encodes sequences are disclosed as SEQ ID NOS 87 and 88, respectively, in both tables. In FIG. 18B-2, human probe and library encodes sequences are disclosed as SEQ ID NOS 89 and 90, respectively, in the first table and SEQ ID NOS 89 and 91, respectively, in the second table. In FIG. 18B-3, human probe and library encodes sequences are disclosed as SEQ ID NOS 92 and 93, respectively.

FIG. 19 shows tabulated cohort library CDR selections for heavy (FIG. 19A-1 to 19A-4) and light (kappa, FIG. 19B-1 to 19B-2) chains using query sequence derived from a human scFv gp120 ITH52 antibody. In FIG. 19A-1, human probe and library encodes sequences are disclosed as SEQ ID NOS 94 and 95, respectively, in the first table and SEQ ID NOS 94 and 96, respectively, in the second table. In FIG. 19A-2, human probe and library encodes sequences are disclosed as SEQ ID NOS 97 and 98, respectively. In FIG. 19A-3, human probe and library encodes sequences are disclosed as SEQ ID NOS 97 and 99, respectively. In FIG. 19A-4, human probe and library encodes sequences are disclosed as SEQ ID NOS 100 and 101, respectively. In FIG. 19B-1, human probe and library encodes sequences are disclosed as SEQ ID NOS 102 and 103, respectively, in the first table and SEQ ID NOS 104 and 105, respectively, in the second table. In FIG. 19B-2, human probe and library encodes sequences are disclosed as SEQ ID NOS 104 and 106, respectively, in the first table and SEQ ID NOS 107 and 108, respectively, in the second table.

FIG. 20 shows tabulated cohort library CDR selections for heavy (FIG. 20A-1 to 20A-4) and light (kappa, FIG. 20B-1 to 20B-3) chains using query sequence derived from a human 4D5 Herceptin antibody. In FIG. 20A-1, human probe and library encodes sequences are disclosed as SEQ ID NOS 109 and 110, respectively, in the first table and SEQ ID NOS 109 and 111, respectively, in the second table. In FIG. 20A-2, human probe and library encodes sequences are disclosed as SEQ ID NOS 112 and 113, respectively. In FIG. 20A-3, human probe and library encodes-sequences are disclosed as SEQ ID NOS 112 and 114, respectively. In FIG. 20A-4, human probe and library encodes sequences are disclosed as SEQ ID NOS 115 and 116, respectively. In FIG. 20B-1, human probe and library encodes sequences are disclosed as SEQ ID NOS 117 and 118, respectively. In the first table and SEQ ID NOS 117 and 119, respectively, in the second table. In FIG. 20B-2, human probe and library encodes sequences are disclosed as SEQ ID NOS 120 and 121, respectively, in the first table and SEQ ID NOS: 120 and 122, respectively, in the second table. In FIG. 20B-3, human probe and library encodes sequences are disclosed as SEQ ID NOS 123 and 124, respectively.

FIG. 21 shows tabulated cohort library CDR selections for heavy (FIG. 21A-1 to 21A-4) and light (kappa, FIG. 21B-1 to 21B-3) chains using query sequence derived from a human HD37 CD19 antibody. In FIG. 21A-1, human probe and library encodes sequences are disclosed as SEQ ID NOS 125 and 126, respectively, in the first table and SEQ ID NOS 125 and 127, respectively, in the second table. In FIG. 21A-2, human probe and library encodes sequences are disclosed as SEQ ID NOS 128 and 129, respectively. In FIG. 21A-3, human probe and library encodes sequences are disclosed as SEQ ID NOS 128 and 130, respectively. In FIG. 21A-4, human probe and library encodes sequences are disclosed as SEQ ID NOS 131 and 132, respectively. In FIG. 21B-1, human probe and library encodes sequences are disclosed as SEQ ID NOS 133 and 134, respectively, in the first table and SEQ ID NOS 133 and 135, respectively, in the second table. In FIG. 21B-2, human probe and library encodes sequences are disclosed as SEQ ID NOS 136 and 137, respectively, in the first table and SEQ ID NOS 136 and 138, respectively. In the second table. In FIG. 21B-3, human probe and library encodes sequences are disclosed as SEQ ID NOS 139 and 140, respectively.

FIG. 22 shows tabulated cohort library CDR selections for heavy (FIG. 22A-1 to 22A-3) and light (kappa, FIG. 22B-1 to 22B-3) chains using query sequence derived from a human CD8 g10-1 antibody. In FIG. 22A-1, mouse probe and library encodes sequences are disclosed as SEQ ID NOS 141 and 142, respectively, in the first table and SEQ ID NOS 141 and 143, respectively, in the second table. In FIG. 22A-2, mouse probe and library encodes sequences are disclosed as SEQ ID NOS 144 and 145, respectively, in the first table and SEQ ID NOS 144 and 146, respectively, in the second table. In FIG. 22A-3, mouse probe and library encodes sequences are disclosed as SEQ ID NOS 147 and 148, respectively. In FIG. 22B-1, mouse probe and library encodes sequences are disclosed as SEQ ID NOS 149 and 150, respectively, in the first table and SEQ ID NOS 149 and 151, respectively, in the second table. In FIG. 22B-2, mouse probe and library encodes sequences are disclosed as SEQ ID NOS 152 and 153, respectively, in the first table and SEQ ID NOS 152 and 154, respectively, in the second table. In FIG. 22B-3, mouse probe and library encodes sequences are disclosed as SEQ ID NOS 155 and 156, respectively.

FIG. 23 shows tabulated cohort library CDR selections for heavy (FIG. 23A-1 to 23A-3) and light (kappa, FIG. 23B-1 to 23B-3) chains using query sequence derived from a mouse 5G1.1 C5 antibody. In FIG. 23A-1, mouse probe and library encodes sequences are disclosed as SEQ ID NOS 157 and 158, respectively, in the first table and SEQ ID NOS 157 and 159, in the second table. In FIG. 23A-2, mouse probe and library encodes sequences are disclosed as SEQ ID NOS 160 and 161, respectively, in the first table and SEQ ID NOS 160 and 162, respectively, in the second table. In FIG. 23A-3, mouse probe and library encodes sequences are disclosed as SEQ ID NOS 163 and 164, respectively. In FIG. 23B-1, mouse probe and library encodes sequences are disclosed as SEQ ID NOS 165 and 166, respectively, in the first table and SEQ ID NOS 165 and 167, respectively, in the second table. In FIG. 23B-2, mouse probe and library encodes sequences are disclosed as SEQ ID NOS 168 and 169, respectively, in the first table and SEQ ID NOS 168 and 170, respectively, in the second table. In FIG. 23B-3, mouse probe and library encodes sequences are disclosed as SEQ ID NOS 171 and 172, respectively.

FIG. 24 shows tabulated cohort library CDR selections for heavy (FIG. 24A-1 to 24A-4) and light (kappa, FIG. 24B-1 to 24B-3) chains using query sequence derived from a mouse Reopro 7E3 antibody. In FIG. 24A-1, mouse probe and library encodes sequences are disclosed as SEQ ID NOS 173 and 174, respectively, in the first table and SEQ ID NOS 173 and 175, respectively in the second table. In FIG. 24A-2, mouse probe and library encodes sequences are disclosed as SEQ ID NOS 176 and 177, respectively. In FIG. 24A-3, mouse probe and library encodes sequences are disclosed as SEQ ID NOS 176 and 178, respectively. In FIG. 24A-4, mouse probe and library encodes sequences are disclosed as SEQ ID NOS 179 and 180, respectively. In FIG. 24B-1, mouse probe and library encodes sequences are disclosed as SEQ ID NOS 181 and 182, respectively, in the first table and SEQ ID NOS 181 and 183, respectively, in the second table. In FIG. 24B-2, mouse probe and library encodes sequences are disclosed as SEQ ID NOS 184 and 185, respectively, in the first table and SEQ ID NOS 184 and 186, respectively, in the second table. In FIG. 24B-3, mouse probe and library encodes sequences are disclosed as SEQ ID NOS 187 and 188, respectively.

FIG. 25 shows tabulated cohort library CDR selections for heavy (FIG. 25A-1 to 25A-3) and light (kappa, FIG. 25B-1 to 25B-3) chains using query sequence derived from a mouse Raptiva MHM24 antibody. In FIG. 25A-1, mouse probe sequence is disclosed as SEQ ID NO: 189 in the first table and mouse probe and library encodes sequences are disclosed as SEQ ID NOS 189 and 191, respectively, in the second table. In FIG. 25A-2, mouse probe and library encodes sequences are disclosed as SEQ ID NOS 192 and 193, respectively, in the first table and SEQ ID NOS 192 and 194, respectively, in the second table. In FIG. 25A-3, mouse probe and library encodes sequences are disclosed as SEQ ID NOS 195 and 196, respectively. In FIG. 25B-1, mouse probe and library encodes sequences are disclosed as SEQ ID NOS 197 and 198, respectively, in the first table and SEQ ID NOS 197 and 198, respectively, in the second table. In FIG. 25B-2, mouse probe and library encodes sequences are disclosed as SEQ ID NOS 200 and 201, respectively, in the first table and SEQ ID NOS 200 and 202, respectively, in the second table. In FIG. 25B-3, mouse probe and library encodes sequences are disclosed as SEQ ID NOS 203 and 204, respectively.

Figure 26A-2:
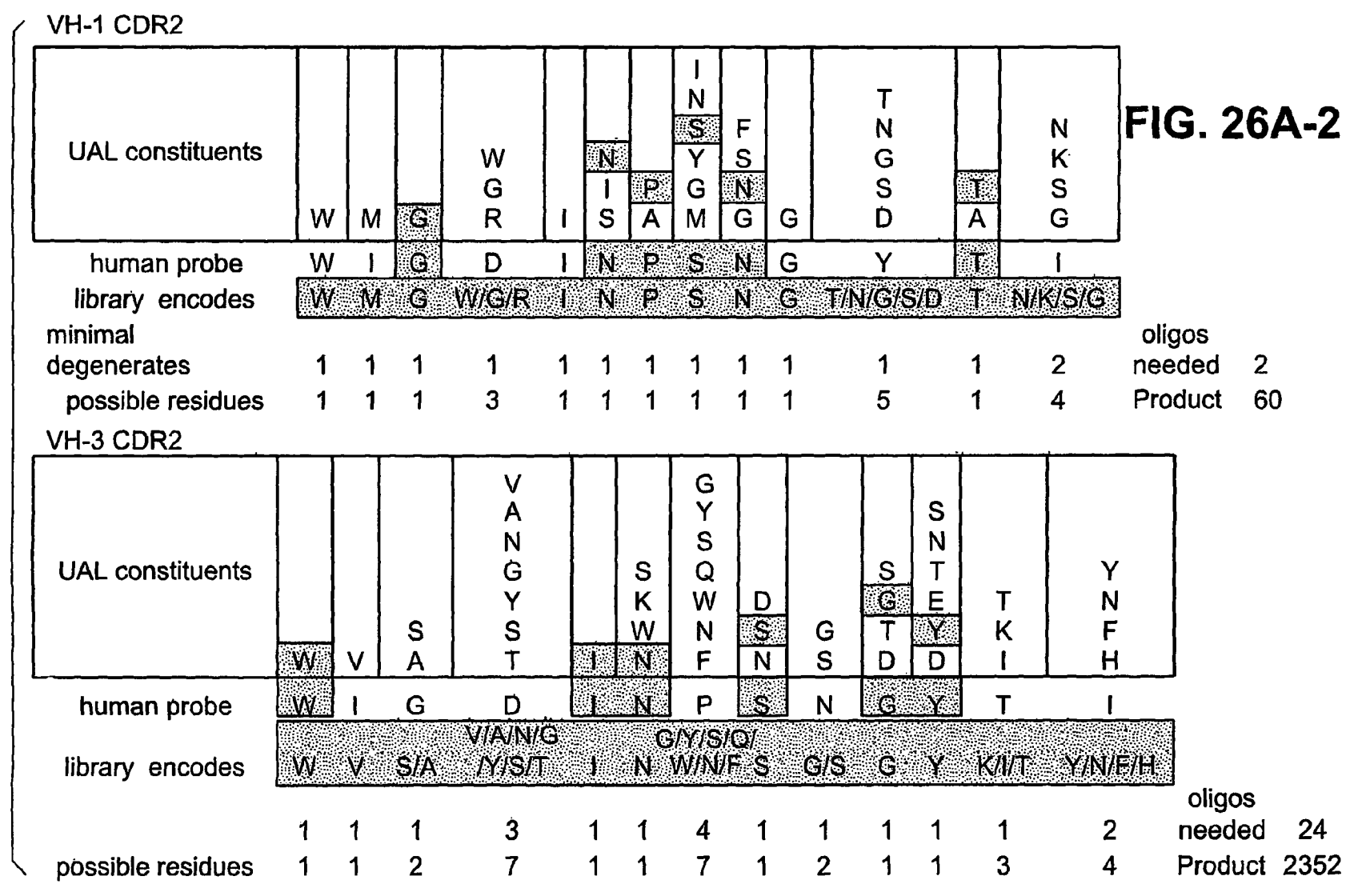

FIG. 26 shows tabulated cohort library CDR selections for heavy (FIG. 26A-1 to 26A-3) and light (kappa, FIG. 26B-1 to 26B-2) chains using query sequence derived from a mouse OVA antibody. In FIG. 26A-1, mouse probe sequence is disclosed as SEQ ID NO: 205, in the first table and human probe and library encodes sequences are disclosed as SEQ ID NOS 207 and 208, respectively, in the second table. In FIG. 26A-2, human probe and library encodes sequences are disclosed as SEQ ID NOS 209 and 210, respectively, in the first table and SEQ ID NOS 209 and 211, respectively, in the second table. In FIG. 26A-3, human probe and library encodes sequences are disclosed as SEQ ID NOS 212 and 213, respectively. In FIG. 26B-1, human probe and library encodes sequences are disclosed as SEQ ID NOS 214 and 215, respectively, in the first table and SEQ ID NOS 216 and 217, respectively, in the second table. In FIG. 26B-2, human probe and library encodes sequences are disclosed as SEQ ID NOS 216 and 218, respectively, in the first table and SEQ ID NOS 219 and 220, respectively, in the second table.

FIG. 27 shows tabulated cohort library CDR selections for heavy (FIG. 27A-1 to 27A-3) and light (kappa, FIG. 27B-1 to 27B-3) chains using query sequence derived from a mouse TNF-☐ monoclonal antibody. In FIG. 27A-1, mouse probe and library encodes sequences are disclosed as SEQ ID NOS 221 and 222, respectively, in the first table and SEQ ID NOS 221 and 223, respectively, in the second table. In FIG. 27A-2, mouse probe and library encodes sequences are disclosed as SEQ ID NOS 224 and 225, respectively, in the first table and SEQ ID NOS 224 and 226, respectively, in the second table. In FIG. 27A-3, human probe and library encodes sequences are disclosed as SEQ ID NOS 227 and 228, respectively. In FIG. 27B-1, mouse probe and library encodes sequences are disclosed as SEQ ID NOS 229 and 230, respectively, in the first table and SEQ ID NOS 229 and 231, respectively, in the second table. In FIG. 27B-2, mouse probe and library encodes sequences are disclosed as SEQ ID NOS 232 and 233, respectively, in the first table and SEQ ID NOS 232 and 234, respectively, in the second table. In FIG. 27B-3, mouse probe and library encodes sequences are disclosed as SEQ ID NOS 235 and 236, respectively.

FIG. 28 shows groupings of amino adds classified as similar on the basis of side chain chemistry, as employed in exemplary embodiments of the present invention.

FIG. 31 (panels A-F) shows the cohort library sequences obtained for the ant-VEGF A4.6.1 antibody when "all similar" criteria were used in addition to similarity and identity criteria. Panel A: Mouse Probe $V_H$ CDR1 "TNYGMN." (SEQ ID NO: 13). Similar, identity and all similar sequences disclosed as SEQ ID NOS 14, 14 and 259, respectively, in the first table and SEQ ID NOS 246, 15 and 261, respectively, in the second table. Panel B: Mouse Probe $V_H$ CDR2 "WMG-WINTYTGEPT." (SEQ ID NO: 16). Similar, identity, all similar and database sequences disclosed as SEQ ID NOS 247, 17, 263 and 264, respectively, in the first table. Similar, identity and all similar sequences disclosed as SEQ ID NOS 248, 18 and 265, respectively, in the second table. Panel C: Mouse Probe $V_H$ CDR3 "AKYPHYYGSSHWYFD." (SEQ ID NO: 19). Similar and identity sequences disclosed as SEQ ID NO: 20. Panel D: Mouse Probe $V_L$ CDR1 "SNYLNWY." (SEQ ID NO: 21). Similar, identity and all similar sequences disclosed as SEQ ID NOS 22, 22 and 269, respectively, in the first table. Similar, identity, all similar and database sequences are disclosed as SEQ ID NOS 249, 249, 271 and 272, respectively, in the second table. Similar and identity sequences disclosed as SEQ ID NOS 250 and 251, respectively, in the third table. Panel E: Mouse Probe $V_L$ CDR2 "VLIYFTSSLH." (SEQ ID NO: 23). Similar, identity, all similar and database sequences disclosed as SEQ ID NOS 252, 24, 275 and 276, respectively, in the first table, SEQ ID NOS 253, 25, 277 and 278, respectively, in the second table and SEQ ID NOS 254, 255, 279 and 280, in the third table. Panel F: Mouse Probe $V_L$ CDR3 "QQYSTVPW." (SEQ ID NO: 26). Similar, identity and all similar sequences disclosed as SEQ ID NOS 256, 27 and 281, respectively, in the first table. Similar and all similar sequences disclosed as SEQ ID NOS 257 and 283, respectively, in the second table.

FIG. 36 shows an array of scFv clones exhibiting combinatorial beneficial mutations (CBM). There are multiple mutations in the $V_L$ and $V_H$ CDR regions incorporated within the test reference scFv human antibody which are associated with superior $K_{off}$ binding values to the target antigen. These positional substitutions for CBM building were previously identified as individual Look Through Mutations (LTM) clones with enhanced $K_{off}$ and $K_{on}$ binding characteristics. L1 sequences disclosed as SEQ ID NOS 287-298, respectively, in order or appearance. L2 sequences disclosed as SEQ ID NOS 299-310, respectively, in order or appearance. L3 sequences disclosed as SEQ ID NOS 311-322, respectively, in order or appearance. H1 sequences disclosed as SEQ ID NOS 323-334, respectively, in order or appearance. H2 sequences disclosed as SEQ ID NOS 335-346, respectively, in order or appearance. H3 sequences disclosed as SEQ ID NOS 347-358, respectively, in order or appearance.

FIG. 44 shows a diversity table for heavy and light chain CDR1, CDR2, and CDR3 libraries of various lengths. VL1-CDR2, VL2-CDR2 and VL3-CDR2 sequences disclosed as SEQ ID NOS 640, 641 and 280, respectively.

FIG. 58 illustrates the Kunkel mutagenesis method as applied using multiple oligonucleotides to generate three distinct CDR mutations in a single linear sequence. These iterations were then repeated until the desired VL and VH CDR mutations were all incorporated.

FIG. 62A-J shows oligonucleotide sequences for constructs of the present invention (SEQ ID NOS 359-562, respectively, in order or appearance).

DETAILED DESCRIPTION OF THE INVENTION

Figure 1:
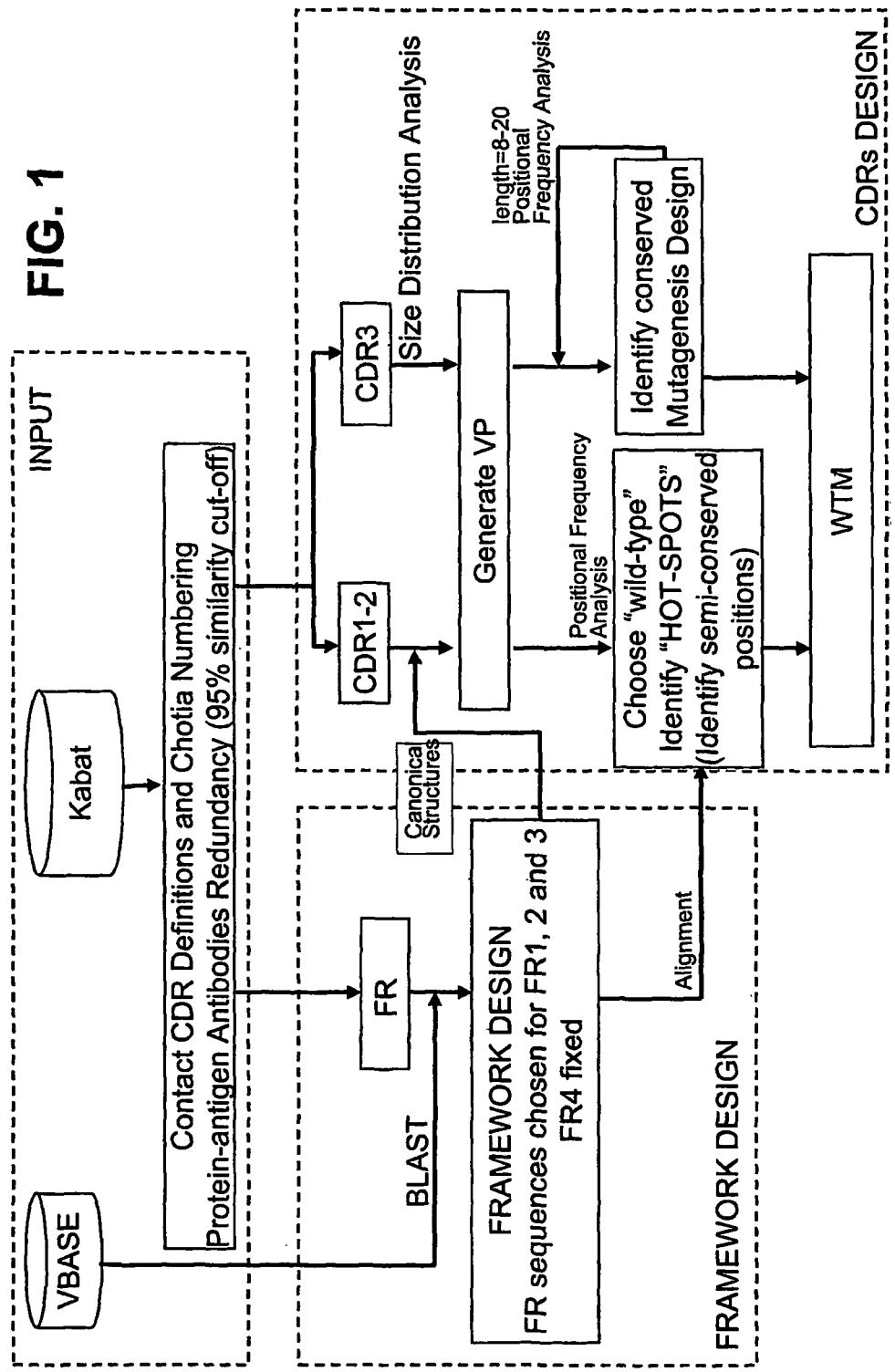
FIG. 1 shows a schematic for performing the construction of a universal antibody library featured in certain embodiments of the invention using computer-assisted database biomining.
Figure 2:
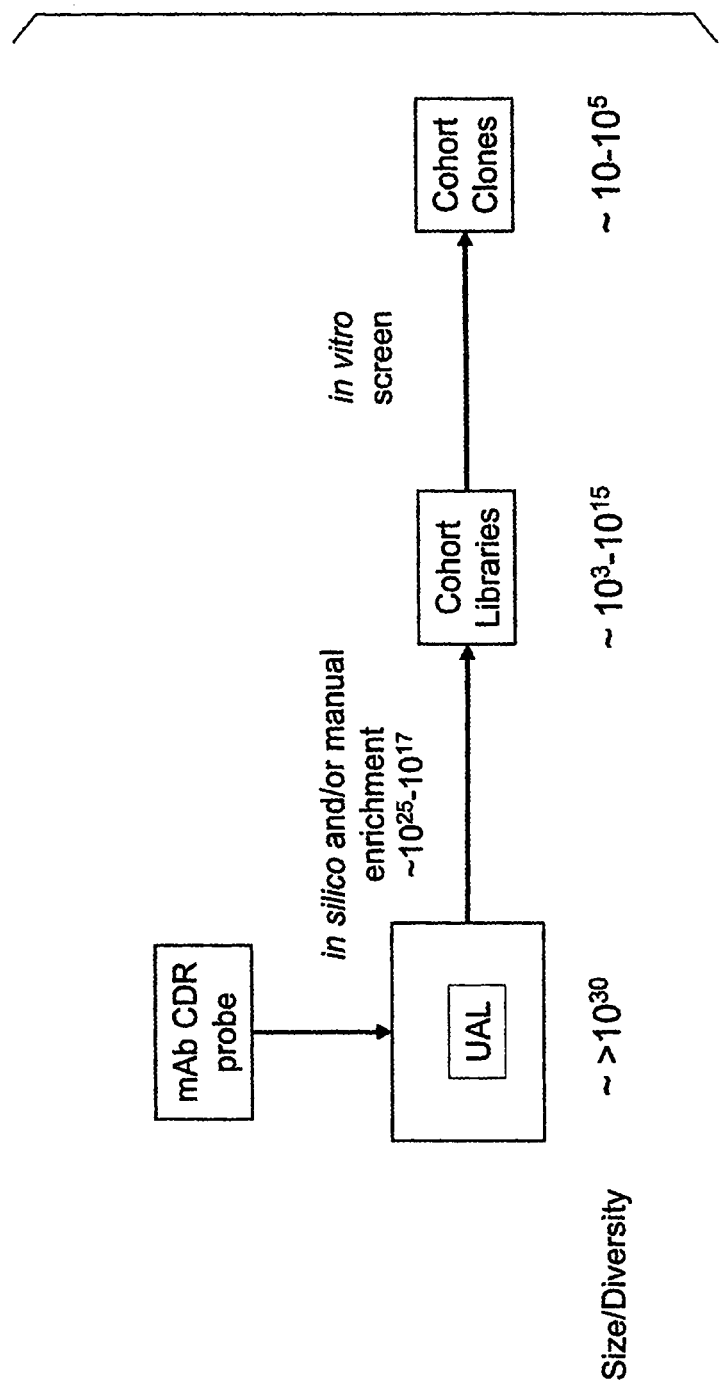
FIG. 2 highlights the selection process of the current invention by which a query mAb CDR probe is used for in silico identification of cohort libraries, which may then be used for in vitro screening approaches to identify optimized cohort clones.

In order to provide a clear understanding of the specification and claims, the following definitions are provided below.

DEFINITIONS

As used herein the term "universal antibody library" refers to an antibody library as described in U.S. Patent Application No. 60/585,931, the contents of which are incorporated in their entirety herein by this reference. The universal antibody library can be a reference library. A reference library can be in silico information representing naturally-occurring CDR diversity, for example, human CDR diversity, in particular, CDR diversity found in expressed antibodies responsive to a predetermined antigen class.

The term "cohort library" refers to a subset library, sublibrary, or analog library representing the CDR diversity that can be assembled, according to the methods of the invention, that is representative and/or comprises a given query CDR sequence or probe CDR sequence and, preferably, is enriched for human amino acid residues at a majority of amino acid positions when aligned to the query/probe CDR sequence.

The term "candidate antigen" refers to a well defined target or target antigen which is known, and typically, for which an antibody, for example, a murine antibody, is available which is capable of binding to the antigen. Such antibodies can be exploited as a source of query CDR sequence(s). A target antigen can be belong, e.g., to a particular antigen class, for example, protein antigen class, peptide antigen class, small molecule antigen class, polysaccharide antigen class, lipid antigen class, or polynucleotide antigen class. An antigen class may be further defined, e.g., a protein or polypeptide antigen class, as comprising soluble antigens, cell surface antigens, extracellular antigens, intracellular antigens, etc.

The term "query CDR sequence" or "probe CDR sequence" refers a CDR sequence that typically is derived from an antibody with known binding specificity but for which human or nearly human analog CDR sequences are desirable.

The term "antibody binding regions" refers to one or more portions of an immunoglobulin or antibody variable region capable of binding an antigen(s). Typically, the antibody binding region is, for example, an antibody light chain (VL) (or variable region thereof), an antibody heavy chain (VH) (or variable region thereof), an heavy chain Fd region, a combined antibody light and heavy chain (or variable region thereof) such as a Fab, F(ab')$_2$, single domain, or single chain antibody (scFv), or a full length antibody, for example, an IgG (e.g., an IgG1, IgG2, IgG3, or IgG4 subtype), IgA1, IgA2, IgD, IgE, or IgM antibody. It is understood that the query CDR sequence derived from an antibody against a target antigen can be derived from a full length antibody or antigen binding fragment comprising at one CDR, either naturally occurring or synthetic, e.g., a Fab, a scFv, a heavy chain, a light chain, a Fd, a DAb, or the like.

The term "framework region" refers to the art recognized portions of an antibody variable region that exist between the more divergent CDR regions. Such framework regions are typically referred to as frameworks 1 through 4 (FR1, FR2, FR3, and FR4) and provide a scaffold for holding, in three-dimensional space, the three CDRs found in a heavy or light chain antibody variable region, such that the CDRs can form an antigen-binding surface. It is understood that, as desired, the framework region(s) used to support the one or more CDR sequences determined or obtained as described herein can be, e.g., naturally occurring, or synthetic, or combinations thereof, e.g., a framework sequence can be naturally occurring or derived in part but be idealized in whole or in part to form a consensus sequence, e.g., for allowing for or accommodating a consensus or canonical CDR, or be cross-cloned, i.e., represent portions of frameworks which may be naturally occurring but are then juxtaposed linearly.

The term "threshold frequency of occurrence" refers to a criterion of certain embodiments of the invention which requires that a selected sequence for use in the reference universal antibody library be derived from a sequence which has been determined to be a sequence favored to be expressed by immune cells when, for example, responding to a particular class of antigens. Typically, such expressed (rearranged) sequences determined to meet the threshold frequency of occurrence are sequences which are expressed at a percent occurrence of about 10% or more.

The term "threshold frequency of germline origin" refers to a criterion of certain embodiments of the invention which requires that a selected sequence (i.e., expressed or rearranged sequence) for use in the reference universal antibody library be derived from a sequence which has been determined to be a germline sequence favored to be expressed by immune cells when, for example, responding to a particular class of antigens. Typically, sequences determined to meet the threshold frequency of germline origin are sequences which are derived or originate from a germline sequence at a percent occurrence of about 10% or more.

The term "predetermined antigen class", or "class of antigens" or "antigen class" refers to antigens which are structurally/chemically similar in terms of their basic composition. Typical antigen classes are proteins (polypeptides), peptides, polysaccharides, polynucleotides, and small molecules.

The term "canonical structure" includes considerations as to the linear sequence of the antibody, for example, as catalogued in the Kabat database. The Kabat numbering scheme is a widely adopted standard for numbering the amino acid residues of an antibody variable in a consistent manner. Additional structural considerations, for example, those differences not fully reflected by Kabat numbering, for example, as described by Chothia et al. and revealed by, for example, crystallography and three-dimensional modeling, can also be used to determine the canonical structure of an antibody. Accordingly, a given antibody sequence may be placed into a canonical class which allows for, among other things, identifying appropriate acceptor sequences. Kabat numbering of antibody amino acid sequence and structural considerations, for example, as described by Chothia et al., and its implication for construing canonical aspects of a given antibody, are described in the literature (see also, e.g., Materials and Methods, below).

The term "defined CDR region" refers to a complementarity determining region (CDR) of which three make up the binding character of a light chain variable region and/or heavy chain variable region of a binding molecule. Defined CDR regions contribute to the functional activity of an antibody molecule and may be separated by amino acid sequences that are merely scaffolding or framework regions. CDR regions are typically defined according to the EU Index, Kabat (see, e.g., Kabat et al., in "Sequences of Proteins of Immunological Interest," U.S. Department of Health and Human Services, 1983), Chothia (see, e.g., Chothia et al., *J. Mol. Biol.* 196: 901-917, 1987), or contact-point definition (see, e.g., MacCallum et al., *J. Mol. Biol.* 262:732-745 (1996)), although it is understood that any other system where the framework and antigen contact variable regions can be identified and demarcated can also be employed. In addition, the amino add residues/positions within defined CDR regions can be numbered according to a convention selected from the group consisting of EU Index, numbering Kabat numbering, Chothia numbering, contact-point definition and linear amino acid residue position numbering.

The term "library" refers to one or more CDR or antibody molecules (or antibody fragments thereof) having a diversity as described herein, mutagenized according to the method of the invention. The antibodies of the library can be in the form of polynucleotides, polypeptides, polynucleotides and polypeptides, polynucleotides and polypeptides in a cell free extract, or as polynucleotides and/or polypeptides in the context of a phage, prokaryotic cells, or in eukaryotic cells. A library of the invention, for example a library of CDR analogs, can also be in the form of a virtual library, i.e., a library of polynucleotide or amino add residue sequence information that can be used to design or synthesize an actual library or that can be queried or modeled, either in silico or otherwise.

The term "polynucleotide(s)" refers to nucleic acids such as DNA molecules and RNA molecules and analogs thereof (e.g., DNA or RNA generated using nucleotide analogs or using nucleic add chemistry). As desired, the polynucleotides may be made synthetically, e.g., using art-recognized nucleic acid chemistry or enzymatically using, e.g., a polymerase, and, if desired, be modified. Typical modifications include methylation, biotinylation, and other art-known modifications. In addition, the nucleic acid molecule can be single-stranded or double-stranded and, where desired, linked to a detectable moiety.

The term "mutagenesis" refers to, unless otherwise specified, any art recognized technique for altering a polynucleotide or polypeptide sequence. Preferred types of mutagenesis include walk-through mutagenesis (WTM), beneficial walk-through mutagenesis, look-through mutagenesis (LTM), improved look-through mutagenesis (LTM2), or combinations thereof.

The term "combinatorial beneficial mutagenesis" refers to a combination library of coding sequences that encode degenerate mixtures of $V_L$ and/or $V_H$ CDR amino-add sequence variations initially identified from the predetermined LTM amino add mutagenesis screen as having an alteration on a measurable property. In the combinatorial beneficial mutation approach, oligonucleotide coding sequences are generated which represent combinations of these beneficial mutations identified by LTM. These combinations may be combinations of different beneficial mutations within a single CDR, mutations within two or more CDRs within a single antibody chain, or mutations within the CDRs of different antibody chains.

The term "gapped alignment" refers to an alignment of at least two nucleotide or peptide sequences wherein alignment of the sequences is optimized such that one or more sequences are allowed to contain gaps in their sequence, e.g., where optimal alignment of the sequences occurs if the alignment algorithm assumes the presence of an insertion or deletion of sequence in any of the compared sequences. Gapping is most prevalently used in cross-species sequence comparisons (e.g., mouse-human), as insertion/deletion ("in/del") polymorphisms are rare relative to single nucleotide polymorphisms ("SNPs") in the human population, yet such features (in/dels) do exist in certain human sequences. In certain embodiments of the instant invention, a "gapped BLAST" alignment is performed. The term "gapped BLAST" alignment as used herein refers to a form of gapped alignment in which one or more residues of a query polypeptide (or polynucleotide) may be designated by one or more spacer residues (generally represented as dashes "-" within sequences of such alignments), wherein such spacer residues have no impact on the ensuing BLAST alignment other than providing spacing to the surrounding residues during alignment. For purposes of the instant invention, such gapped BLAST alignments are often performed in instances where the gapped residue(s) of the query sequence is fixed in the output (cohort library) sequence(s) as the same residue present at the corresponding position within the query sequence. Database searching/sequence alignment tools commonly used to generate gapped alignments include, e.g., FASTA (Wilbur and Lipman, *Proc. Natl Acad. Sci. USA*, 80: 726-730; Lipman and Pearson, *Science*, 227: 1435-1441; Pearson and Lipman, *Proc. Natl Acad. Sci. USA*, 85:2444-2448; Pearson, *Methods Enzymol.*, 183: 63-98) and BLAST (Altschul et al., *J. Mol. Biol.*, 215: 403-41; Altschul et al., *Nucleic Acids Res.*, 25: 3389-3402).

The term "discontinuous alignment", as used herein, refers to an alignment of at least two peptide sequences, wherein at least one residue of a linear query sequence is "fixed", meaning that the fixed residue need not be compared with reference sequence residues. The term "partial alignment" refers to a related form of alignment, wherein at least one N- or C-terminal residue of the linear query sequence is fixed and therefore need not be compared with reference sequence residues. As will be recognized by one of ordinary skill in the art, the preceding forms of alignment may also be performed to similar effect on nucleotide sequences comprised of codons, that may substitute for a direct alignment of peptide sequences.

The term "similar amino acid" refers to an amino acid that is of the same class of side chain chemistry as an initial amino acid. In exemplary embodiments of the instant invention, naturally-occurring amino acids are placed within the following classes on the basis of side chain chemistry.

Small Side Chains: Glycine (G), Alanine (A)
Nucleophilic: Serine (S), Threonine (T), Cysteine (C), Histidine (H)
Hydrophobic: Valine (V), Leucine (L), Isoleucine (I), Methionine (M), Proline (P)
Aromatic: Phenylalanine (F), Tyrosine (Y), Tryptophan (W)
Acidic: Aspartate (D), Glutamate (E)
Amide: Asparagine (N), Glutamine (Q)
Basic: Lysine (K), Arginine (R)

Thus, Glycine and Alanine are similar amino acids to one another, as are: Serine, Threonine, Cysteine, and Histidine; Valine, Leucine, Isoleucine, Methionine, and Proline; Phenylalanine, Tyrosine, and Tryptophan; Aspartate and Glutamate; Asparagine and Glutamine; and Lysine and Arginine. One of skill in the art will recognize that alternative classifications of similarity for naturally-occurring and/or synthetic amino adds (e.g., by charge, hydrophobicity, active groups, steric criteria, etc.) are also possible and within the scope of the instant invention. However, for purposes of the invention, partitioning of amino acids into similar groupings involves the designation of at least two groups, wherein each group comprises at least one amino add.

DETAILED DESCRIPTION

Overview

Antibodies are powerful diagnostic and therapeutic tools. Antibody libraries comprising candidate binding molecules that can be readily screened against targets are desirable. The present invention, at least in part, seeks to exploit the promise of a recently-described approach for constructing comprehensive universal antibody libraries (UALs). The methods of the present invention allow for rational synthesis of diverse cohort libraries of CDRs and/or antibodies that predominately or exclusively contain naturally-occurring human diversity at any selected amino add residue position (thus rendering such sequences non-immunogenic yet significantly more diverse than assemblages of only known CDR and/or antibody sequences). The cohort libraries featured in the methods and compositions of the present invention therefore have the advantage of representing a broad range of human sequence diversity (e.g., through independent assortment of residue-by-residue diversity of CDR sequences) in a library of relatively small size relative to, e.g., synthetic libraries prepared via random mutagenesis approaches across the same span of sequence. The vast majority of synthetic libraries (e.g., libraries produced via random mutagenesis) suffer from noise and too much diversity that is not naturally occurring. Entirely human libraries are biased against certain antigen classes and only as diverse as capture techniques allow.

The present invention, at least in part provides a method by which reference antibody libraries such as universal antibody libraries (UALs) may be "BLASTed" (e.g., aligned, optionally gap aligned) with query antibody CDR sequences to identify human cohort antibody libraries. Applications for such a strategy include:

(1) Identification of human-biased monoclonal antibody cohort libraries using existing non-human (e.g., mouse) monoclonal antibodies.

(2) Rational (re)generation of a human-biased cohort antibody library around an existing monoclonal antibody or family of monoclonal antibodies.

Such CDR "BLASTed" cohort antibody libraries may then be used to:

(1) Generate human-like antibodies that are based upon non-human antibodies.

(2) Regenerate human diversity from an existing human antibody or antibodies for specific selection of improved qualities (e.g., immunogenicity, affinity, specificity, expression, stability, etc.).

(3) Prospectively identify productive sublibraries of reference antibody libraries (e.g., UAL sublibraries; because UALs are a composite of many sublibraries, analysis of CDR BLASTing results for numerous antigens could be used to guide de novo screening efforts on productive UAL sublibraries).

In certain embodiments, the present invention employs universal antibody libraries as reference libraries that are comprehensive and may thus be used to identify/generate cohort CDR and/or antibody libraries that benefit from the comprehensive nature of such libraries. Both reference antibody libraries such as UALs and the cohort libraries of the invention can be readily screened using, for example, high throughput methods to obtain new therapeutics.

In particular, reference libraries such as UALs have the potential to recognize any antigen. Other significant advantages of such reference libraries include greater diversity, for example, to self antigens that are usually lost in an expressed human library because self reactive antibodies are removed by the donor's immune system by negative selection. Another advantageous feature of both cohort and reference (e.g., UAL) libraries described herein is that screening such libraries using positive done selection by FACS (florescence activated cell sorter) bypasses the standard and tedious methodology of generating a hybridoma library and supernatant screening. Still further, a reference library such as a UAL library can be re-screened to discover additional antibodies against other desired targets.

1.1 Featured Reference Antibody Libraries

The reference antibody libraries, and specifically universal antibody libraries (UALs) employed in certain methods of the present invention are capable of representing all desirable candidate antibodies against a given antigen class. An exemplary universal antibody library that may be employed by the methods of the invention is derived from human sequence, and is therefore nonimmunogenic, rendering antibodies selected from such a library suitable for therapeutic applications—for example, for administering to human patents for preventing or treating human disorders or disease.

The libraries featured in the invention have a diversity that is efficiently introduced using, for example, mutagenesis techniques such as walk-through mutagenesis (WTM) or look-through mutagenesis (LTM) (see respectively, e.g., U.S. Pat. Nos. 6,649,340; 5,830,650; 5,798,208; and U.S. Ser. No. 60/483,282) depending on whether multiple residue diversity or a single residue diversity needs to be introduced at a given site, e.g., within one or more complementarity determining regions (CDRs). Importantly, these techniques allow for maximizing the amount of productive diversity and minimizing the amount of non-productive diversity, i.e., mere noise or randomness. Accordingly, both the reference and cohort libraries featured in the present invention can be smaller than existing antibody libraries yet comprise more rational diversity in order to identity candidate antibody binding molecules more efficiently. Such reference antibody library efficiencies are effectively exploited to generate cohort CDR and antibody libraries using the methods of the instant invention.

In certain embodiments, the cohort and/or reference (e.g., universal antibody library) libraries of the invention result from application of the WTM or LTM technology to create a completely synthetic library that displays a desired diversity in one or more CDRs of the light and/or heavy chains. The antibody sequences, for example, the frameworks and CDRs of reference libraries are selected according to certain criteria. Criteria for selecting cohort libraries from reference libraries largely involve comparison of query sequences with reference library sequences, followed by mutagenic approaches to create the cohort CDR/antibody libraries of the invention. Such reference libraries are selected and/or assembled by various criteria. For example, one criterion is that the reference antibody sequence must have a minimum threshold frequency (e.g., about 10% or more) of occurring within expressed (rearranged) antibody sequences, e.g., human antibody sequences, and preferably, in response to a particular class of antigens. Optionally, yet another criterion, is that the expressed (rearranged) antibody sequence originates with (or is derived from) a minimum threshold frequency (e.g., about 10% or more) from a germlne sequence. The diversity is identified and then engineered into a conventional gene format, e.g., a single chain antibody format (scFv), fab, or whole Ig, using oligonucleotides which allow for the complete assembly of individual frameworks by PCR and diverse CDR sequences by kunkel mutagenesis, in a systematic manner.

Importantly, the libraries of the invention minimize any mutations that may lead to non-functional proteins by avoiding unwarranted mutations that typically occur when using random oligo degeneracy or error-prone PCR. In addition, the level of precision capable when using WTM contrasts with random mutagenesis and/or gene shuffling technologies. Moreover, by controlling framework selection and the level of sequence diversity in terms of position and amino acid type, the library's recognition of "antigen" classes is optimized. Furthermore, this in vitro methodology circumvents immunological negative selection of self-antigens and any gene bias due to the organism's environmental exposure.

Accordingly, the invention provides the advantage of being able to start with a screening library sized to be informative without being unnecessarily large. After the identification of the first set of clones, subsequent affinity maturation libraries can share common sets of LTM and/or WTM oligonucleotides saving time and reagent costs. Still further, reference libraries (e.g., universal antibody libraries), and cohort libraries derived therefrom via the methods of the invention, are capable of rapidly and effectively producing very specific antibodies against a variety of antigens, especially, e.g., self-antigens which are difficult to obtain by any other method.

The reference universal antibody libraries of the invention may be generated and screened by first synthesizing individual polynucleotides encoding a defined region or regions of an antibody where, collectively, the polynucleotides represent all possible variant antibodies according to the criteria described herein. Similarly, the cohort CDR and antibody libraries of the invention may be generated and screened by first synthesizing individual polynucleotides encoding a defined region or regions of an antibody where, collectively, the polynucleotides represent a selection of variant CDR positions according to the criteria of the present invention. The antibodies may be expressed, for example, using in vitro transcription and translation and/or using a display technology, such as ribosome display, phage display, bacterial display, or yeast display.

Alternatively, the reference universal antibody libraries of the invention may be generated and screened by first synthesizing individual polypeptides corresponding to a defined region or regions of an antibody where, collectively, the polypeptides represent all possible variant antibodies according to the criteria described herein. Similarly, the cohort CDR and antibody libraries of the invention may be generated and screened by first synthesizing individual polypeptides encoding a defined region or regions of an antibody where, collectively, the polypeptides represent a selection of variant CDR positions according to the criteria of the present invention. The antibodies may be generated and/or reverse translated from polypeptides and expressed, for example, using in vitro transcription and translation and/or using a display technology, such as ribosome display, phage display, bacterial display, or yeast display. Virtual reference (universal or filtered)

antibody and/or CDR libraries may also be used in the methods of the invention, with such libraries generated via manual and/or in silico compilation of human peptide sequence diversity information into a virtual reference library of the invention. Component sequences of such virtual reference libraries (e.g., single sequences, cohort libraries, or entire reference libraries) may be expressed using techniques widely known in the art (e.g., synthesis of nucleic acid sequences encoding for a peptide sequence, followed by in vivo (e.g., cell line-mediated) and/or in vitro transcription and translation and/or using a display technology, such as ribosome display, phage display, bacterial display, or yeast display).

Expressed antibodies may then be screened and selected using functional assays, such as binding assays. For example, the polypeptides may be expressed in association with the polynucleotide that encodes the antibody binding molecule, e.g., a single chain antibody (scFv), thereby allowing for identification of the polynucleotide sequence that encodes the antibody binding molecule (e.g., scFv). The antibodies may also be secreted and displayed on the membrane of a prokaryote such as E. coli, using, e.g., the technology as described in, e.g., US20040072740A1; US20030036092A1; and US20030100023A1.

The methods of the invention can be used to identify human antibody sequences to develop new or improved antibodies or fragments thereof, e.g., single chain antibodies (scFv). In addition, the method can be performed with the benefit of a priori information, e.g., via computer modeling and electronic database biomining, that can be used to prepare a reference library representing an initial subset of sequences to be diversified, e.g., according to the criterion described herein, using, e.g., WTM or LTM mutagenesis.

Other advantages and aspects of the present invention will be readily apparent from the following description and examples.

1.2 Identification and Selection of Universal Antibody Library Components Using Bioinformatics The first step in building a universal antibody library (UAL) as employed in certain embodiments of the present invention is selecting sequences that meet certain predetermined criteria. For example, the Kabat database, a electronic database containing non-redundant rearranged antibody sequences can be queried for those sequences that are most frequently represented, in particular, against a particular antigen class. The antigen class can include, for example, protein and peptide antigens but also small molecules, polysaccharides, and polynucleotides. A clustering analysis of the framework sequences of these antibodies is performed followed by a comparison (using the BLAST search algorithm) with germline sequences (V BASE database) to determine the most frequently used germline families that subsequently rearrange to generate functional antibodies that recognize a given antigen class, for example, proteinaceous antigens or targets.

The candidate framework sequences that represent the largest and most structurally diverse groups of functional antibodies are then chosen, and the canonical structures of CDR1 and CDR2 are then determined, to determine the length of the CDRs and thus, the diversity that can be accommodated within the frameworks. For CDR3, a size distribution of lengths is performed to identify a frequency analysis of rearranged antibody sequences.

The method for deriving amino acid sequences of the CDRs includes a frequency analysis of existing rearranged antibody sequences. As a rule, amino acid usage is tallied for a CDR residue position, and the most frequently used (prevalent) amino acids at the position within a population or subpopulation (e.g., panel of database-derived CDR sequences) are noted until the sum of frequencies reaches a predetermined limit. Once the predetermined limit is reached, amino adds are then added to the reference library only if their frequency (prevalence) is equal to or above a predetermined threshold. For the reference library of Example 4, the limit was set to 80% and the prevalence threshold set for individual amino adds was 10%.

The universal library construction strategy involves selection of framework sequences followed by design of the hypervariable CDR loops. For framework sequence selection, a subset of all available framework scaffolds determined to have been expressed in response to a particular antigen are arrayed. By determining the frameworks that are most frequently expressed in nature in response to a given antigen class an appropriate framework acceptor is selected. For example, to determine the preferred acceptor frameworks expressed in response to protein-based antigens, the Kabat database (a subscription antibody sequence database which can be accessed, e.g., at http://www.kabatdatabase.com/) is searched for "protein-directed" frameworks. If preferred acceptor sequences are needed for presenting CDRs against a different antigen class, and/or, acceptor sequences of a particular species, the Kabat protein sequence filter is set accordingly. For example, to determine sequences for use as human therapeutics against protein-based targets, the filter is set to focus only on human antibody sequences (not mouse, rat, or chicken sequences, etc.) that recognize protein/peptide antigens. This greatly reduces redundancy in the dataset and sequence information that would bias results.

The above step minimizes the need to generate numerous different synthetic framework scaffolds and typically results in a data set of potential acceptors of about 600 sequences or less. Accordingly, the resultant number of sequences is easily manageable for further analysis to determine the germline precursor sequences that give rise to the rearranged gene sequences that are selected by antigen class. This second determination of germline origin refines the selection of the antibody sequences that have been selected by an antigen class because it identifies if there are optimal (or high frequency) germline framework sequences that are overrepresented. Indeed, it has been observed that in some polyclonal responses against certain antigens, where a large number of rearranged antibody sequence are produced, that only a few acceptor framework sequences are used. In such a case, the antibody sequence and binding diversity for the antigens is chiefly localized to the CDRs not the frameworks. The above bioinformatic analysis focuses on $V_H$ genes for descriptive purposes, but it will be understood that genes for both $V\lambda$ and $V_K$ are similarly evaluated. Framework regions used in the cohort antibody libraries of the invention may be selected from those employed during design of the reference antibody libraries employed by the invention or by any art-recognized method of framework selection.

1.3 Design Strategies for Maximizing CDR Diversity

The choice of candidate frameworks used in exemplary reference Universal Antibody Libraries (UALs) dictates both the CDR sizes and the initial amino acid sequence diversity of the UALs. When the antibody sequences are identified for 1) frequency of occurrence against an antigen class and 2) germline frequency, the sequences can then be arrayed according to their canonical class. The canonical class is determined using the conventions as described by Chothia (see Materials and Methods, below). Of a given set of antibody sequences, the majority of the antibody sequences identified may fall within a certain canonical class. The canonical class then dictates the number of amino acid residues that can be accommodated in the CDRs. For example, if the canonical class is 1-3, then CDR1 would have a 5 amino acid loop and CDR2 would have a 17 amino acid loop. For the heavy chain variable sequence the J segment sequence contribution is relatively well conserved such that typically, only the best fit sequence from a subset of only six sequences need be considered. A CDR amino acid frequency analysis of the Kabat and V BASE databases allows identification of CDR amino acid residue positions that fall within three categories, i.e., 1) positions that should be conserved, 2) positions that are suitable for diversity generation, and 3) positions that can be mutated to mimic somatic hypermutation.

Accordingly, in designing $V_H$-CDR1 diversity of a reference UAL, the amino acid residues within the CDR are grouped into three different categories: 1) positions conserved in both the germline and rearranged genes that are therefore left unchanged, 2) positions conserved in the germline but variant in rearranged genes that are therefore initially fixed but mutated during affinity maturation, and 3) positions that have diversity in the germline and rearranged sequences and therefore are identified as positions for incorporation of diversity using WTM™ during initial library construction.

In designing VH-CDR2, diversity analysis in the V BASE and Kabat databases is approached in an similar manner as was performed for VH-CDR1 above.

In designing $V_H$ CDR3 diversity, CDR3 sequences of antibodies from the Kabat database are aligned according to their size and antigen class. Lengths of CDR3s of antibodies recognizing non-protein and protein/peptide antigens are compared and a frequency analysis is performed and a threshold frequency of 10% is used to identify the most favorable sequences to be used in designating the CDR3 diversity. Because CDR3 size and amino acid residue frequency analysis is performed using, e.g., the immunoglobulin D and J gene rearranged sequences, there are no "CDR3" germline equivalents for direct filtered Kabat and V BASE comparisons. However, a filtered Kabat frequency analysis for each rearranged CDR3 size can be performed which reveals, for each size classification, the most frequent amino acid throughout the CDR3 positions and results in a consensus "wild type" sequence. Surprisingly, this "consensus" approach identifies particular amino acids under high selective pressure. Accordingly, these residue position are typically fixed with diversity being introduced into remaining amino acid positions (taking into account the identified preference for certain amino acids to be present at these positions).

When designing the diversity of a reference UAL or cohort CDR or antibody library derived therefrom for any of the above-mentioned CDRs, modified amino acid residues, for example, residues outside the traditional 20 amino acids used in most polypeptides, e.g., homocysteine, can be incorporated into the CDRs as desired. This is carried out using art recognized techniques which typically introduce stop codons into the polynucleotide where the modified amino acid residue is desired. The technique then provides a modified tRNA linked to the modified amino add to be incorporated (a so-called suppressor tRNA of, e.g., the stop codon amber, opal, or ochre) into the polypeptide (see, e.g., Köhrer et al., import of amber and ochre suppressors tRNAs into mammalian cells: A general approach to site-specific insertion of amino acid analogues into proteins, *PNAS*, 98, 14310-14315 (2001)).

2. Cohort Antibody Library and Reference Universal Antibody Library (UAL) Construction The generation of cohort antibody libraries and reference universal antibody libraries of the invention and their construction are conducted with the benefit of sequence and structural information concerning the antibody diversity to be generated, such that the potential for generating improved antibodies is increased. Modeling information can also be used to guide the selection of amino acid diversity to be introduced into the defined regions, e.g., CDRs. Still further, actual results obtained with the antibodies of the invention can guide the selection (or exclusion), e.g., affinity maturation, of subsequent antibodies to be made and screened in an iterative manner.

In specific embodiments, modeling is used to eliminate the production of any antibodies predicted to have poor or undesired structure and/or function. In this way, the number of antibodies to be produced can be sharply reduced thereby increasing signal-to-noise in subsequent screening assays. In another particular embodiment, the modeling is continually updated with additional information, from any relevant source, e.g., from gene and protein sequence and three-dimensional databases and/or results from previously tested antibodies, so that the virtual (in certain embodiments, in silico) database becomes more precise in its predictive ability (FIG. 1).

In yet another embodiment, the virtual database is provided with the assay results, e.g., binding affinity/avidity of previously tested antibodies and categorizes the antibodies, based on the assay criterion or criteria, as responders or nonresponders, e.g., as antibodies that bind well or not so well. In this way, the affinity maturation of the invention can equate a range of functional responses with particular sequence and structural information and use such information to guide the production of future antibodies to be tested. The method is especially suitable for screening antibody or antibody fragments for a particular binding affinity to a target antigen using, e.g., a Biacore assay.

Accordingly, mutagenesis of noncontiguous residues within a region can be desirable if it is known, e.g., through in silico modeling, that certain residues in the region will not participate in the desired function. The coordinate structure and spatial interrelationship between the defined regions, e.g., the functional amino acid residues in the defined regions of the antibody, e.g., the diversity that has been introduced, can be considered and modeled. Such modeling criteria include, e.g., amino acid residue side group chemistry, atom distances, crystallography data, etc. Accordingly, the number antibodies to be produced can be intelligently minimized.

For synthesis of a reference UAL, one or more of the above steps may be computer-assisted. The computer-assisted step may comprise, e.g., mining the Kabat database and, optionally, cross-referencing the results against V BASE, whereby certain criteria of the invention are determined and used to design the desired CDR diversity (FIG. 1). Synthesis of a reference library (UAL) may also involve the compilation of sequence information (optionally computer-assisted) from a rescued done collection. Selection of cohort CDR and antibody libraries from the reference libraries employed by the methods of the invention may also be computer-assisted. Such methods are also amenable to being carried out, in part or in whole, by a device, e.g., a computer driven device. For example, sequence alignments, sequence comparisons, position-specific residue selections, calculations of library diversities, database mining antibody sequence selection, diversity design, oligonucleotide synthesis, PCR-mediated or kunkel mutagenesis assembly of the foregoing, and expression and selection of candidate antibodies that bind a given target, can be carried out in part or entirely, by interlaced devices. In addition, instructions for carrying out the method, in part or in whole, can be conferred to a medium suitable for use in an electronic device for carrying out the instructions. In sum, the methods of the invention are amendable to a high throughput approach comprising software (e.g., computer-readable instructions) and hardware (e.g., computers, robotics, and chips).

Figure 32:
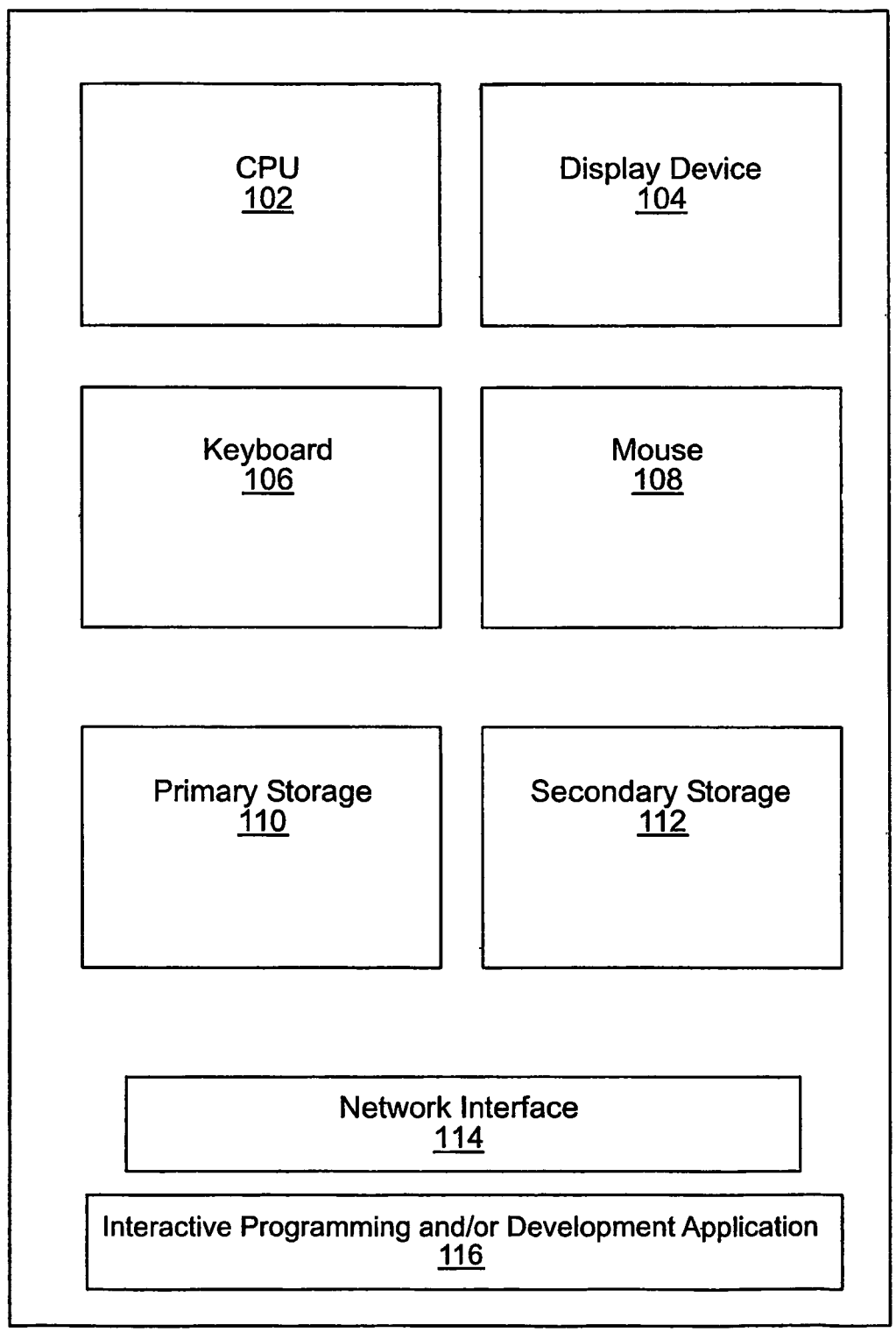
FIG. 32 illustrates one example embodiment of an electronic device 500 suitable for practicing the illustrative embodiments of the present invention.

Certain embodiments of the invention may be aided via use of a computer or other electronic device capable of performing and/or aiding performance of the featured methods of the invention. One example embodiment of an electronic device 500 suitable for practicing the illustrative embodiments of the present invention is shown in FIG. 32. The electronic device 500 is representative of a number of different technologies, such as personal computers (PCs), laptop computers, workstations, personal digital assistants (PDAs), Internet appliances, cellular telephones, and the like. In the illustrated embodiment, the electronic device 500 includes a central processing unit (CPU) 502 and a display device 504. The display device 504 enables the electronic device 500 to communicate directly with a user through a visual display. The electronic device 500 further includes a keyboard 506 and a mouse 508. Other potential input devices not depicted include a stylus, trackball, joystick, touch pad, touch screen, and the like. The electronic device 500 includes primary storage 510 and secondary storage 512 for storing data and instructions. The storage devices 510 and 512 can include such technologies as a floppy drive, hard drive, tape drive, optical drive, read only memory (ROM), random access memory (RAM), and the like. Applications such as browsers, JAVA virtual machines, and other utilities and applications can be resident on one or both of the storage devices 510 and 512. The electronic device 500 can also include a network interface 514 for communicating with one or more electronic devices external to the electronic device 500 depicted. A modem is one form of network interface 514 for establishing a connection with an external electronic device or network. The CPU 502 has either internally, or externally, attached thereto one or more of the aforementioned components. In addition to applications previously mentioned, modeling applications, such as Simulink® 516, can be installed and operated on the electronic device 500.

It should be noted that the electronic device 500 is merely representative of a structure for implementing the present invention. However, one of ordinary skill in the art will appreciate that the present invention is not limited to implementation on only the described device 500. Other implementations can be utilized, including an implementation based partially or entirely in embedded code, where no user inputs or display devices are necessary. Rather, a processor can communicate directly with another processor or other device.

3. Synthesizing Selected Cohort CDR and Antibody Libraries

In one embodiment, the selected cohort CDR and antibody libraries of the invention are generated for screening by synthesizing individual oligonucleotides that encode the defined region of the polypeptide and have no more than one codon for the predetermined amino acid. This is accomplished by incorporating, at each codon position within the oligonucleotide either the codon required for synthesis of the wild-type polypeptide or a codon for the predetermined amino add and is referred to as look-through mutagenesis (LTM) (see, e.g., U.S. Ser. No. 60/483,282).

In another embodiment, when diversity at multiple amino acid positions is required, oligonucleotide degeneracy, or walk-through mutagenesis (WTM) can be used (see e.g., U.S. Pat. Nos. 6,649,340; 5,830,650; and 5,798,208; and U.S. Ser. No. 60/483,282). WTM allows for multiple mutations to be made with a minimum number of oligonucleotides. The oligonucleotides can be produced individually, in batches, using, e.g., doping techniques, and then mixed or pooled as desired.

The mixture of oligonucleotides for generation of the library can be synthesized readily by known methods for DNA synthesis. The preferred method involves use of solid phase beta-cyanoethyl phosphoramidite chemistry (e.g., see U.S. Pat. No. 4,725,677). For convenience, an instrument for automated DNA synthesis can be used containing specified reagent vessels of nucleotides. The polynucleotides may also be synthesized to contain restriction sites or primer hybridization sites to facilitate the introduction or assembly of the polynucleotides representing, e.g., a defined region, into a larger gene context.

The synthesized polynucleotides can be inserted into a larger gene context, e.g., a single chain antibody (scFv), fab or whole Ig using standard genetic engineering techniques. For example, the polynucleotides can be made to contain flanking recognition sites for restriction enzymes (e.g., see U.S. Pat. No. 4,888,286). The recognition sites can be designed to correspond to recognition sites that either exist naturally or are introduced in the gene proximate to the DNA encoding the region. After conversion into double stranded form, the polynucleotides are ligated into the gene or gene vector by standard techniques. By means of an appropriate vector (including, e.g., phage vectors, plasmids) the genes can be introduced into a cell-free extract, phage, prokaryotic cell, or eukaryotic cell suitable for expression of the antibodies.

Alternatively, partially overlapping polynucleotides, typically about 20-60 nucleotides in length, are designed. The internal polynucleotides are then annealed to their complementary partner to give a double-stranded DNA molecule with single-stranded extensions useful for further annealing. The annealed pairs can then be mixed together, extended, and ligated to form full-length double-stranded molecules using PCR. Convenient restriction sites can be designed near the ends of the synthetic gene for cloning into a suitable vector. The full-length molecules can then be ligated into a suitable vector.

When partially overlapping polynucleotides are used in the gene assembly, a set of degenerate nucleotides can also be directly incorporated in place of one of the polynucleotides. The appropriate complementary strand is synthesized during the extension reaction from a partially complementary polynucleotide from the other strand by enzymatic extension with a polymerase. Incorporation of the degenerate polynucleotides at the stage of synthesis also simplifies cloning where more than one domain or defined region of a gene is mutagenized or engineered to have diversity.

In another approach, the antibody is present on a single stranded plasmid. For example, the gene can be cloned into a phage vector or a vector with a filamentous phage origin of replication that allows propagation of single-stranded molecules with the use of a helper phage. The single-stranded template can be annealed with a set of degenerate polynucleotides representing the desired mutations and elongated and ligated, thus incorporating each analog strand into a population of molecules that can be introduced into an appropriate host (see, e.g., Sayers, J. R. et al., Nucleic Adds Res. 16: 791-802 (1980)). This approach can circumvent multiple cloning steps where multiple domains are selected for mutagenesis.

Polymerase chain reaction (PCR) methodology can also be used to incorporate polynucleotides into a gene, for example, CDR diversity into framework regions. For example, the polynucleotides themselves can be used as primers for extension. In this approach, polynucleotides encoding the mutagenic cassettes corresponding to the defined region (or portion thereof) are complementary to each other, at least in part, and can be extended to form a large gene cassette (e.g., a scFv) using a polymerase, e.g., using PCR amplification.

The size of the library will vary depending upon the CDR length and the amount of CDR diversity which needs to be represented using, e.g., WTM or LTM. Preferably, the library will be designed to contain less than $10^{15}$, $10^{14}$, $10^{13}$, $10^{12}$, $10^{11}$, $10^{10}$, $10^9$, $10^8$, $10^7$, and more preferably, $10^6$ antibodies or less.

The description above has centered on representing antibody diversity by altering the polynucleotide that encodes the corresponding polypeptide. It is understood, however, that the scope of the invention also encompasses methods of representing the antibody diversity disclosed herein by direct synthesis of the desired polypeptide regions using protein chemistry. In carrying out this approach, the resultant polypeptides still incorporate the features of the invention except that the use of a polynucleotide intermediate can be eliminated.

For the libraries described above, whether in the form of polynucleotides and/or corresponding polypeptides, it is understood that the libraries may be also attached to a solid support, such as a microchip, and preferably arrayed, using art recognized techniques.

The method of this invention is especially useful for modifying candidate antibody molecules by way of affinity maturation. Alterations can be introduced into the variable region and/or into the framework (constant) region of an antibody. Modification of the variable region can produce antibodies with better antigen binding properties, and, if desired, catalytic properties. Modification of the framework region can also lead to the improvement of chemo-physical properties, such as solubility or stability, which are especially useful, for example, in commercial production, bioavailability, and affinity for the antigen. Typically, the mutagenesis will target the Fv region of the antibody molecule, i.e., the structure responsible for antigen-binding activity which is made up of variable regions of two chains, one from the heavy chain (VH) and one from the light chain (VL). Once the desired antigen-binding characteristics are identified, the variable region(s) can be engineered into an appropriate antibody class such as IgG, IgM, IgA, IgD, or IgE. In a preferred embodiment, an identified candidate binding molecule is subjected to affinity maturation to increase the affinity/avidity of the binding molecule to a target/antigen.

4. Expression and Screening Systems

Libraries of polynucleotides, generated by any of the above techniques or other suitable techniques can be expressed and screened to identify antibodies having desired structure and/or activity. Expression of the antibodies can be carried out using cell-free extracts (and e.g., ribosome display), phage display, prokaryotic cells, or eukaryotic cells (e.g., yeast display).

In one embodiment, the polynucleotides are engineered to serve as templates that can be expressed in a cell free extract. Vectors and extracts as described, for example in U.S. Pat. Nos. 5,324,637; 5,492,817; 5,665,563, can be used and many are commercially available. Ribosome display and other cell-free techniques for linking a polynucleotide (i.e., a genotype) to a polypeptide (i.e., a phenotype) can be used, e.g., Profusion™ (see, e.g., U.S. Pat. Nos. 6,348,315; 6,261,804; 6,258,558; and 6,214,553).

Alternatively, the polynucleotides of the invention can be expressed in a convenient E. coli expression system, such as that described by Pluckthun and Skerra. (Pluckthun, A. and Skerra, A., Meth. Enzymol. 178: 476-515 (1989); Skerra, A. et al., Biotechnology 9: 273-278 (1991)). The mutant proteins can be expressed for secretion in the medium and/or in the cytoplasm of the bacteria, as described by M. Better and A. Horwitz, Meth. Enzymol. 178: 476 (1989). In one embodiment, the single domains encoding VH and VL are each attached to the 3' end of a sequence encoding a signal sequence, such as the ompA, phoA or pelB signal sequence (Lel, S. P. et al., J. Bacteriol. 169: 4379 (1987)). These gene fusions are assembled in a dicistronic construct, so that they can be expressed from a single vector, and secreted into the periplasmic space of E. coli where they will refold and can be recovered in active form. (Skerra, A. et al., Biotechnology 9: 273-278 (1991)). For example, antibody heavy chain genes can be concurrently expressed with antibody light chain genes to produce antibody or antibody fragments.

In another embodiment, the antibody sequences are expressed on the membrane surface of a prokaryote, e.g., E. coli, using a secretion signal and lipidaeton moiety as described, e.g., in US20040072740A1; US20030100023A1; and US20030036092A1.

In still another embodiment, the polynucleotides can be expressed in eukaryotic cells such as yeast using, for example, yeast display as described, e.g., in U.S. Pat. Nos. 6,423,538; 6,331,391; and 6,300,065. In this approach, the antibodies of the library (e.g., scFvs) are fused to a polypeptide that is expressed and displayed on the surface of the yeast.

Higher eukaryotic cells for expression of the antibodies of the invention can also be used, such as mammalian cells, for example myeloma cells (e.g., NS/0 cells), hybridoma cells, or Chinese hamster ovary (CHO) cells. Typically, the antibodies when expressed in mammalian cells are designed to be expressed into the culture medium, or expressed on the surface of such a cell. The antibody or antibody fragments can be produced, for example, as entire antibody molecules or as individual VH and VL fragments, Fab fragments, single domains, or as single chains (sFv) (see e.g., Huston, J. S. et al., Proc. Natl. Acad. Sci. USA 85: 5879-5883 (1988)).

The screening of the expressed antibodies (or antibodies produced by direct synthesis) can be done by any appropriate means. For example, binding activity can be evaluated by standard immunoassay and/or affinity chromatography. Screening of the antibodies of the invention for catalytic function, e.g., proteolytic function can be accomplished using a standard hemoglobin plaque assay as described, for example, in U.S. Pat. No. 5,798,208. Determining the ability of candidate antibodies to bind therapeutic targets can be assayed in vitro using, e.g., a Biacore instrument, which measures binding rates of an antibody to a given target or antigen. In vivo assays can be conducted using any of a number of animal models and then subsequently tested, as appropriate, in humans.

EXEMPLIFICATION

Throughout the examples, the following materials and methods were used unless otherwise stated.

Materials and Methods

In general, the practice of the present invention employs, unless otherwise indicated, conventional techniques of chemistry, molecular biology, recombinant DNA technology, PCR technology, immunology (especially, e.g., antibody technology), expression systems (e.g., cell-free expression, phage display, ribosome display, and Profusion™), and any necessary cell culture that are within the skill of the art and are explained in the literature. See, e.g., Sambrook, Fritsch and Maniatis, *Molecular Cloning: Cold Spring Harbor Laboratory Press* (1989); *DNA Cloning*, Vols. 1 and 2, (D. N. Glover, Ed. 1985); *Oligonucleotide Synthesis* (M. J. Gait, Ed. 1984); *PCR Handbook Current Protocols in Nucleic Acid Chemis-*

*try*, Beaucage, Ed. John Wiley & Sons (1999) (Editor); *Oxford Handbook of Nucleic Acid Structure*, Neidle, Ed., Oxford Univ Press (1999); *PCR Protocols: A Guide to Methods and Applications*, Innis et al, Academic Press (1990); *PCR Essential Techniques: Essential Techniques*, Burke, Ed., John Wiley & Son Ltd (1996); *The PCR Technique: RT-PCR*, Siebert, Ed., Eaton Pub. Co. (1998); *Antibody Engineering Protocols (Methods in Molecular Biology)*, 510, Paul, S., Humana Pr (1996); *Antibody Engineering: A Practical Approach (Practical Approach Series,* 169), McCafferty, Ed., Irl Pr (1996); *Antibodies: A Laboratory Manual*, Harlow et al., C.S.H.L. Press, Pub. (1999); *Current Protocols in Molecular Biology*, ads. Ausubel et al., John Wiley & Sons (1992); *Large-Scale Mammalian Cell Culture Technology*, Lubiniecki, A., Ed., Marcel Dekker, Pub., (1990). *Phage Display: A Laboratory Manual*, C. Barbas (Ed.), CSHL Press, (2001); *Antibody Phage Display*, P O'Brien (Ed.), Humana Press (2001); Border et at, Yeast surface display for screening combinatorial polypeptide libraries, *Nature Biotechnology,* 15(6):553-7 (1997); Border et at, Yeast surface display for directed evolution of protein expression, affinity, and stability, *Methods Enzymol.,* 328:430-44 (2000); ribosome display as described by Pluckthun et al. in U.S. Pat. No. 6,348,315, and Profusion™ as described by Szostak et al. in U.S. Pat. Nos. 6,258,558; 6,261,804; and 6,214,553.

Further details regarding antibody sequence analysis using Kabat conventions may be found, e.g., in Johnson et al., The Kabat database and a bioinformatics example, *Methods Mol Biol.* 2004; 248:11-25; Johnson et al., Preferred CDRH3 lengths for antibodies with defined specificities, *Int Immunol.* 1998, December; 10(12):1801-5; Johnson et at, SEQHUNT. A program to screen aligned nucleotide and amino acid sequences, *Methods Mol Biol.* 1995; 51:1-15. and Wu et al., Length distribution of CDRH3 in antibodies; and Johnson et al., *Proteins.* 1993 May; 16(1):1-7. Review).

Further details regarding antibody sequence analysis using Chothia conventions may be found, e.g., in Chothia et at, Structural determinants in the sequences of immunoglobulin variable domain, *J Mol Biol.* 1998 May 1; 278(2):457-79; Morea et al., Antibody structure, prediction and redesign, *Biophys Chem.* 1997 October; 68(1-3):9-16.; Morea et al., Conformations of the third hypervariable region in the VH domain of immunoglobulins; *J Mol Bol. Jan.* 16, 1998; 275 (2):269-94; Al-Lazikani et al., Standard conformations for the canonical structures of immunoglobulins, *J Mol Biol. Nov.* 7, 1997; 273(4):927-48. Barre et al., Structural conservation of hypervariable regions in immunoglobulins evolution, Nat Struct Biol. 1994 December; 1(12):915-20; Chothia et al, Structural repertoire of the human VH segments, *J Mol Biol. Oct.* 5, 1992; 227(3):799817 Conformations of Immunoglobulin hypervariable regions, Nature. Dec. 21-28, 1989; 342(6252):877-83; and Chothia et al, Review Canonical structures for the hypervariable regions of immunoglobulins, *J Mol Biol. Aug.* 20, 1987; 196(4):901-17).

Further details regarding Chothia analysis are described, for example, in Morea V, Tramontano A, Rustici M, Chothia C, Lesk A M. Conformations of the third hypervariable region in the VH domain of immunoglobulins. J Mol Biol. Jan. 16, 1998; 275(2):269-94; Chothia C, Lesk A M, Gherardi E, Tomlinson I M, Walter G, Marks J D, Llewelyn M B, Winter G. Structural repertoire of the human VH segments. J Mol Biol. Oct. 5, 1992; 227(3):799-817; Chothia C, Lesk A M, Tramontano A, Levitt M, Smith-Gill S J, Air G, Sheriff S, Padlan E A, Davies D, Tulip W R, et al. Conformations of immunoglobulin hypervariable regions. Nature. Dec. 21-28, 1989; 342(6252):877-83; Chothia C, Lesk A M. Canonical structures for the hypervariable regions of immunoglobulins.

J Mol Biol. Aug. 20, 1987; 196(4):901-17; and Chothia C, Lesk A M. The evolution of protein structures. Cold Spring Harb Symp Quant Biol. 1987; 52:399-405.

Further details regarding CDR contact considerations are described, for example, in MacCallum R M, Martin A C, Thornton J M. Antibody-antigen interactuons: contact analysis and binding site. Topography. J Mol Biol. Oct. 11, 1996; 262(5):732-45.

Further details regarding the antibody sequences and databases referred to herein are found, e.g., in Tomlinson I M, Walter G, Marks J D, Llewelyn M B, Winter G. The repertoire of human germline VH sequences reveals about fifty groups of VH segments with different hypervariable loops. J Mol Biol. Oct. 5, 1992; 227(3):776-98; Li W, Jaroszewski L, Gocizik A. Clustering of highly homologous sequences to reduce the size of large protein databases. Bioinformatics. 2001 March; 17(3):282-3; [VBDB] www.mrc-coe.cam.ac.uk/V BASE-ok.phD?menu=901; [KBTDB] www.kabatdatabase.com: [BLST] www.ncbi.nlm.nih.oov/BLAST/ [CDHIT] bioinformatics.ljcrf.edu/cd-hi/; [EMBOSS] www.hgmp.mrc.ac.uk/Software/EMBOSS/; [PHYLIP] evolution.genetics.washington.edu/phylip.html; and [FASTA] fasta.bioch.virginia.edu.

Example 1

Methods for Identification and Selection of Reference Universal Antibody Library Sequences In this example, reference universal antibody library sequences are identified and selected using bioinformatics and selection criteria as disclosed in U.S. Patent Application No. 60/585,931, the contents of which are incorporated herein in their entirety by reference.

Briefly, the Kabat electronic database containing expressed, i.e., rearranged immunoglobulin sequences, was searched using certain filter algorithms. In particular, the filter algorithms were designed to identify only human sequences that were expressed in response to a particular antigen class. The antigen class selected was protein-based antigens/targets because this is a tractable set of targets for the development of human therapeutics. It is understood, however, that the database is just as easily queried for other antigen classes, e.g., peptides, polysaccharides, polynucleotides, and small molecules as well as for antibody sequences derived from other species such as primate, mouse, rat, or chicken sequences, etc., for the development of, e.g., therapeutics for veterinary application. The foregoing criteria were applied to an initial set of 3319 $V_H$ sequences (it is noted, however, that this set of sequences can increase in number as additional sequences are cloned and entered into the database).

The above search and filter analysis returned a dataset of ~600 $V_H$ gene sequences that represent non-redundant rearranged human antibody clones recognizing protein antigens. The next step involved the designation of the germline precursor that generated these rearranged gene sequences, followed by a frequency analysis of these candidate germline sequences. In other words, a determination as to whether there are optimal or high frequency germline framework sequences for protein antigens. In order to determine the germline sequences employed by the rearranged genes in the filtered $V_H$ sequences (from Kabat), V BASE was used. V BASE is a comprehensive directory of all human germline variable region sequences compiled from over a thousand published sequences, including those in the current releases of the Genbank and EMBL data libraries (see respectively, e.g., Altschul, S. F., Gish, W., Miller, W., Myers, E. W. &

Lipman, D. J. (1990) "Basic local alignment search tool." J. Mol. Biol. 215:403-410 and www.mrc-cpe.cam.ac.uk/V BASE-ok run by the Centre for Protein Engineering MRC Centre, Hills Rd, Cambridge, UK, CB2 2QH). Currently there are 51 functional $V_H$ segments grouped into 7 families: (i.e., $V_H$ 1-7), 40 functional $V_K$ segments grouped into 7 families: (i.e., $V_K$ I-VII), and 31 functional $V_\lambda$ segments grouped into 10 families: (i.e., $V_\lambda$ 1-10). A batch BLAST of V BASE germline sequences with the filtered Kabat sequences (~600 $V_H$) was performed to identify $V_H$ germline genes (and families) that most frequently contribute sequences that are expressed (rearranged). The analysis for, example, identified that six of the eight most highly represented frameworks (frameworks 1, 2, and 3) belong to the $V_H$3 germline family, and members of the $V_H$4 family formed a group of intermediate representation. A frequency analysis was performed on the germline $V_H$ frameworks (1,2, and 3) sequences that are represented in the filtered Kabat database. For this analysis up to 4 somatic mutations were permitted during the classification of the rearranged sequences to a germline gene. The threshold line was set to identify those germline genes that are most frequently represented in rearranged sequences of antibodies that recognize protein/peptide antigens.

The identification of highest frequency $V_H$3 frameworks has an important consequence. Selection of the $V_H$3 initial framework sequence dictates the corresponding CDR sequence diversity and size limitations as defined by standard canonical structures (see, e.g., Chothia, C., et al., Structural repertoire of the human VH segments. J Mol Biol, 1992. 227(3): p. 799-817 and Tomlinson, I. M., et al., The Structural repertoire of the human V kappa domain. Embo J, 1995. 14(18): p. 4628-38). The V BASE-filtered Kabat BLAST search also identifies positions that are so-called 'hotspot' for somatic hyper-mutation that can be mutated during affinity maturation of candidate molecules. The preliminary Kabat-V BASE results identified six highly utilized $V_H$3 frameworks; 3-07, 3-21, 3-23, 3-30.5, 3-48, and 3-74. In choosing multiple starting frameworks added structural diversity was created outside of the CDRs for potential antigen binding. Comparative analysis of all six $J_H$ sequences (that encode framework 4) indicates that four of these sequences are identical and there exist only two amino acid differences in the other two sequences. This sequence conservation allows for the use of a common framework 4 for all six framework families minimizing the generation of non-functional diversity.

Thus, it was demonstrated that a manageable set of antibody framework sequences can be rationally identified using the criteria of the invention and using a bioinformatic approach and existing antibody databases. Moreover, the identification of these sequences provides the foundation for maximizing intelligent CDR diversity within the universal antibody library and cohort libraries of the invention selected therefrom, as discussed below.

Example 2

Methods for Designing CDR Diversity for Reference Universal Antibody Libraries

In this example, methods for optimizing the CDR diversity of a reference universal antibody library are presented.

The choice of candidate frameworks, as previously noted, dictates both the CDR sizes to be introduced and the initial amino acid sequence selection. All six chosen $V_H$3 gene families have the same canonical structures of 1-3. Canonical structure 1-3 requires CDR1 and CDR2 to have, respectively, 5 and 17 amino acid loops. A CDR amino acid frequency analysis of the Kabat and V BASE databases allows identification of the CDR amino acids for 1) absolute sequence conservation, 2) the first round of diversity generation, and 3) subsequent affinity maturation by mimicking somatic hypermutation. The design of each CDR in the heavy and right chain variable regions are discussed sequentially, below.

To design the first CDR of the heavy chain, hereafter "VH-CDR1", the above criteria are considered as follows: CDR positions that are conserved in both the germline and rearranged genes are fixed; CDR positions conserved in the germline but variant in rearranged genes are fixed in the initial library construction but allowed to be mutated during affinity maturation; and CDR positions that exhibit diversity in the germline and rearranged sequences are positions for incorporating diversity using mutagenesis, for example, walk-through mutagenesis (WTM™). Starting with the six identified $V_H$3 gene families (i.e., 3-07, 3-21, 3-23, 3-30.5, 3-48, and 3-74), comparative V BASE analysis of the germline 5 amino acid CDR1 sequence revealed that S31, Y32 and M34 are conserved among the six genes. A frequency analysis of all rearranged 5 amino acid CDR1 sequences in the filtered Rabat dataset illustrated three important findings: first, Y32 is highly conserved, second, the conserved germline S31 and M34 positions are subject to subsequent somatic mutations, and third, CDR1 positions 33 and 35 are neither conserved in the germline nor in rearranged antibody sequences.

Accordingly, in VH-CDR1, Y32 is fixed and never subject to any alteration as the strict conservation of Y32 indicates strong selective pressures for its preservation. CDR1 positions, 33 and 35 are sites for creation of initial CDR1 sequence diversity by mutagenesis, e.g., WTM™. Positions S31 and M34 are initially "fixed" but are identified as sites for mutagenesis during affinity maturation in any scFv candidate clones. The reason for not creating diversity at all sites is to restrict the initial diversity of the library to facilitate expression and display.

From the above Kabat frequency analysis, CDR1 has a "wild type" consensus sequence of SYAMH (SEQ ID NO: 563). The residues A33 and H35 are chosen as wild-type sequences due to their highest frequency. In introducing subsequent amino acid diversity, the CDR1 sequence would then be SYXMX, where X denotes the position where mutagenesis, e.g., WTM, is conducted. For example, when mutagenesis, e.g., WTM, is conducted on the tyrosine residue in CDR1 positions 33 and 35, the desired resulting CDR1 sequences are SYYMH (SEQ ID NO: 564), SYAMY (SEQ ID NO: 565) and SYYMY (SEQ ID NO: 566). In this instance, the effects of introducing an aromatic side chain are explored. The oligonucleotide codon sequence for the wild type A33 position is GCX. If replaced by Y33, the needed corresponding oligonucleotide sequence would be TAY. Thus for an A33→Y33 oligonucleotide mix, the resulting codon sequences are (G/T)(A/C)C. The generated A33→Y33 oligonucleotides in this case can also have codon permutations coding for glycine (GCC), aspartate (GAC) and serine (TCC). These additional "by-products" contribute to additional diversity at position 33. For the next WTM™ position 35, the wild type codon sequence for H35 would be CAY and if replaced with Y35, the oligonucleotide sequence required would be TAY. Thus for an H35→Y35 mix the resulting codon sequence is (C/T)AC. In this case, there would be no additional amino acid "by-products" being formed.

In another approach, byproducts are avoided by employing look-through mutagenesis (LTM) which typically requires the synthesis of an oligonucleotide for each desired change but eliminates any by-products (noise).

To design the second CDR of the heavy chain, hereafter "VH-CDR2", the above sequence analysis in the V BASE and Kabat databases was approached in a similar manner as for VH-CDR1 above. A frequency analysis was performed for VH-CDR2 sequences and an alignment of germline CDR2 sequences from the six candidate frameworks was constructed and a threshold frequency of 10% was selected.

Starting with the same $V_H3$ gene families (3-07, 3-21, 3-23, 3-30.5, 3-48, and 3-74), V BASE and filtered Kabat frequency analysis shows that CDR2 positions I51, Y59, A60 and G65 are conserved in all germline and most rearranged genes and therefore must be invariant in a synthetic CDR2. The above Kabat frequency analysis indicates that VH-CDR2 would have a "wild type" consensus sequence of GISGGTTYY-ADSVKG (SEQ ID NO: 567). Because VH-CDR2 positions 54, 55, 58, 61, 62, 63, 64 display sequence conservation in the germline but are subject to subsequent somatic mutations, and are therefore "fixed" but allowed to be mutated during affinity maturation. For initial CDR2 diversity, investigational amino acids (underlined) are incorporated at positions 50, 52, 52a, 53, 56 and 57 (XIXXXGGXXYYADSVKG) (SEQ ID NO: 568) and introduced by mutagenesis, e.g., WTM™.

WTM, unlike random mutagenesis, allows predetermined placement of particular amino acids. For example, to perform WTM™ of CDR2 with a tyrosine (Y) residue at positions 50, 52, 53, 56 and 57 (underlined), the desired resulting WTM™ CDR2 sequences include the following (alterations are underlined): single substitutions (YIXXXGGXXYYADSVKG (SEQ ID NO: 569), XIYXXGGXXYYADSVKG (SEQ ID NO: 570) and etc.), double substitutions (YIYXXGGXXYYADSVKG (SEQ ID NO: 571), YIXXYGGXXYYADSVKG (SEQ ID NO: 572) and etc), triple substitutions (YIXXYGGYXYYADSVKG (SEQ ID NO: 573) and etc.), quadruple substitutions (YIYYYGGXXYYADSVKG (SEQ ID NO: 574) or YIXYYGGYXYYADSVKG (SEQ ID NO: 575)) quintuple substitutions (YIXYYGGYYYYADSVKG) (SEQ ID NO: 576), and sextuplet substitutions (YIYYYGGYYYYADSVKG) (SEQ ID NO: 577). Typically, 2-3 substitutions per CDR are preferred and this can be readily achieved by oligonucleotide synthesis doping (see, e.g., US20040033569A1 for technical details).

WTM™ for CDR2 using the nine pre-chosen WTM™ amino acids produces a library diversity of $9 \times 2^6$ or 576 members. For comparative purposes, CDR2 saturation mutagenesis of six positions with all twenty amino acids would be $20^6$ or $6.4 \times 10^7$. Accordingly, performing saturation mutagenesis on the 12 "non-fixed" positions of CDR2 alone, the library diversity would be $20^{12}$ or $4 \times 10^{15}$ which is beyond the capabilities of current library display and screening technology. This illustrates an advantage of the invention which, by contrast, allows for a smaller but more representative library to be constructed. Indeed, the methods of the invention provide for, a manageable library in some CDR positions in order to identify the first generation of binding molecules. Subsequent affinity maturation mutagenesis in the other CDR positions then optimizes those identified binding molecules.

To design the $V_H$ CDR3 diversity, CDR3 sequences of antibodies from the Kabat database were aligned according to their size and antigen class. Lengths of CDR3s of antibodies recognizing non-protein and protein/peptide antigens were fitted to trend lines. A frequency analysis of the 13 amino acid CDR3 sequences from the filtered Kabat dataset was also performed and a threshold frequency of 10% was selected. Because CDR3 size and amino acid residue frequency analysis is performed using, e.g., the immunoglobulin D and J gene rearranged sequences, there are no CDR3 germline equivalents for direct filtered Kabat and V BASE comparisons. Nonetheless, a filtered Kabat database was examined and search results indicated that, in terms of CDR3 loop size, there is a normal distribution curve ranging from 6 to 24 amino acids with a peak at approximately 13 amino acids. Interestingly, the analysis also indicated that antibodies recognizing other antigen types (i.e. non-protein/peptide) approaches a bimodal size distribution. This split distribution is due to the heterogeneous population of having some antibodies biased toward small molecules (e.g. haptens) and others targeted against larger antigens (complex polysaccharides, DNA).

Without a parallel V BASE-to-Kabat comparative analysis for CDR3 positions, a filtered Kabat frequency analysis for each rearranged CDR3 size was performed. Within each size classification, enumerating the most frequent amino add at that CDR3 position results in a consensus wild types sequence. Surprisingly, this "consensus" approach identifies particular amino adds under high selective pressures. For example, in a 13 amino add sized CDR3, position 101 was highly conserved as an aspartate. Therefore, as above in designing the diversity of VH-CDR1 and VH-CDR2, D101 is maintained as a "fixed" residue position in the synthetic 13 amino add VH-CDR3. The VH-CDR3 positions 96, 98, 100c, and 102, however, show a higher preference for some amino acids and are therefore preliminarily "fixed" but then mutagenized during affinity maturation. The frequency distribution indicates that CDR3 positions 95, 97, 99, 100, 100a, 100b, 100d, and 100e did not show any preferential amino acids. Thus in the 13 amino add CDR3 sequence, the formula XGXSXXXXYXXDY (SEQ ID NO: 578) represents the positions (underlined) that are sites of diversity using, e.g., mutagenesis such as WTM. A similar analysis can be conducted for all sizes of CDR3 sequences between 8 and 20 amino acids. This size range encompasses a majority of length diversity found in CDR3 of antibodies that recognize proteinaceous targets/antigens.

Example 3

Assembly of Fully Collated UAL Repertoire

Figures 3, 13B:
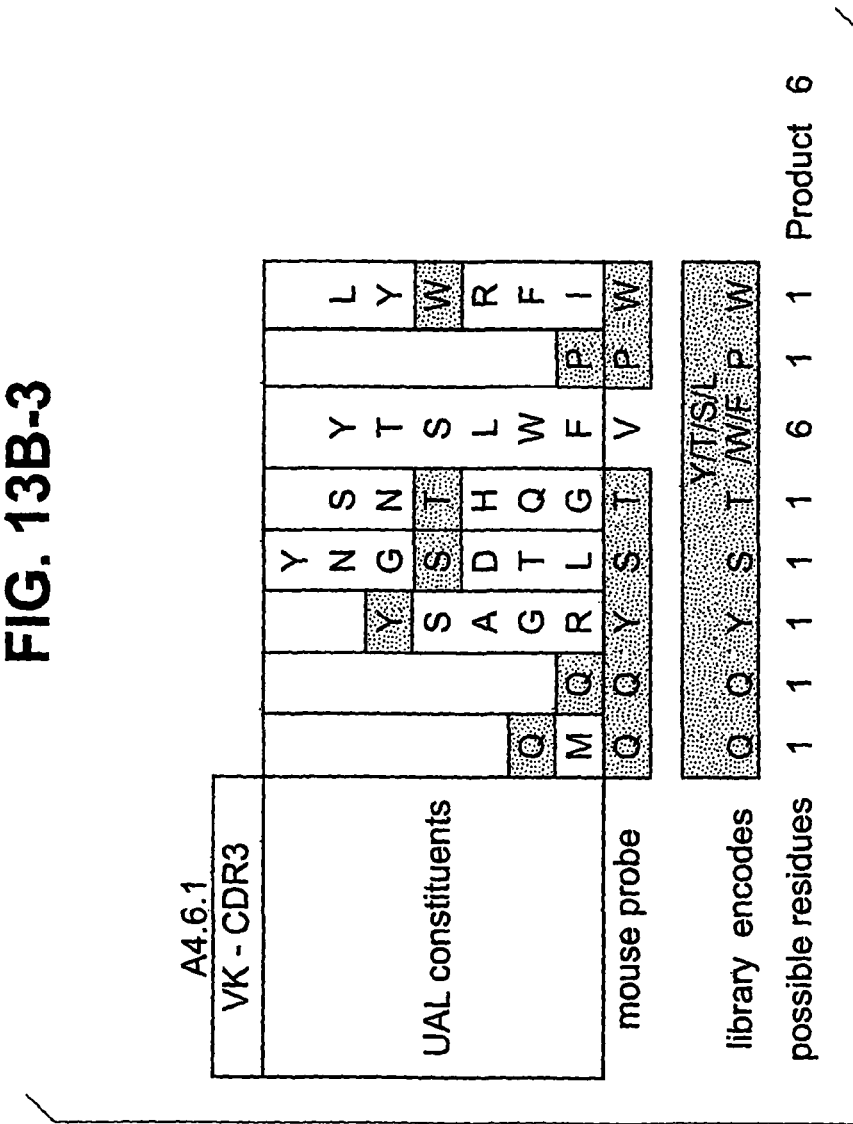

As described in the above examples, CDR positional frequency analysis may be used to assemble a reference library for use in the methods of the present invention. Production of a fully collated UAL repertoire initially involves the generation of all combinatorial CDR sequences that are predicted from such CDR frequency positional analyses. Such positional frequency analysis is performed for each CDR (CDR1, CDR2 and CDR3) of each applicable antibody chain, heavy or light (of kappa or lambda classes for light chains). These combinatorial CDR sequences may then be assembled as framework and isotype matched polypeptides individually for all heavy and light chains. Isotypes for heavy chains include VH-1, VH-3 and VH4, while isotypes for light kappa chains include VK-1 and VK-3 and isotypes for light lambda chains include VL-1, VL-2 and VL-3. Alternative to isotype matching across a UAL, CDR sequences may be "framework shuffled", meaning that a UAL may comprise a CDR1 derived from one type of isotype class that is fused to a CDR2 derived from a distinct isotype class (e.g., CDRL1 from Vk1 and CDRL2 from Vk3 within an single, assembled UAL). Assembly of a complete collated UAL then involves generation of all combinations of heavy and light antibody chains derived as described above (refer to FIG. 3).

Figure 6D:
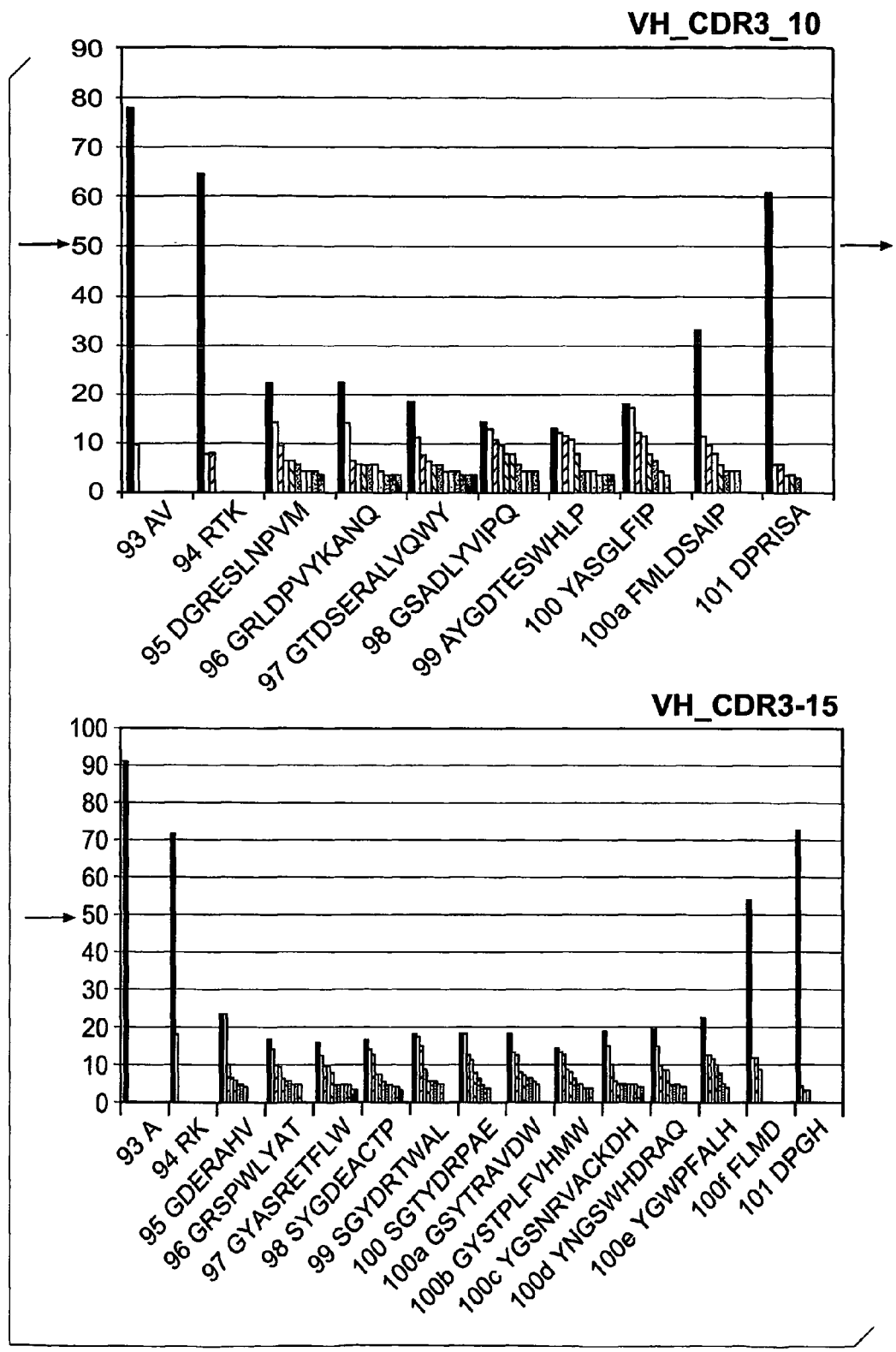
FIG. 6 shows the exemplary assembly of UAL heavy chains, allowing for CDR1 and CDR2 framework crosses.
Figure 6G:
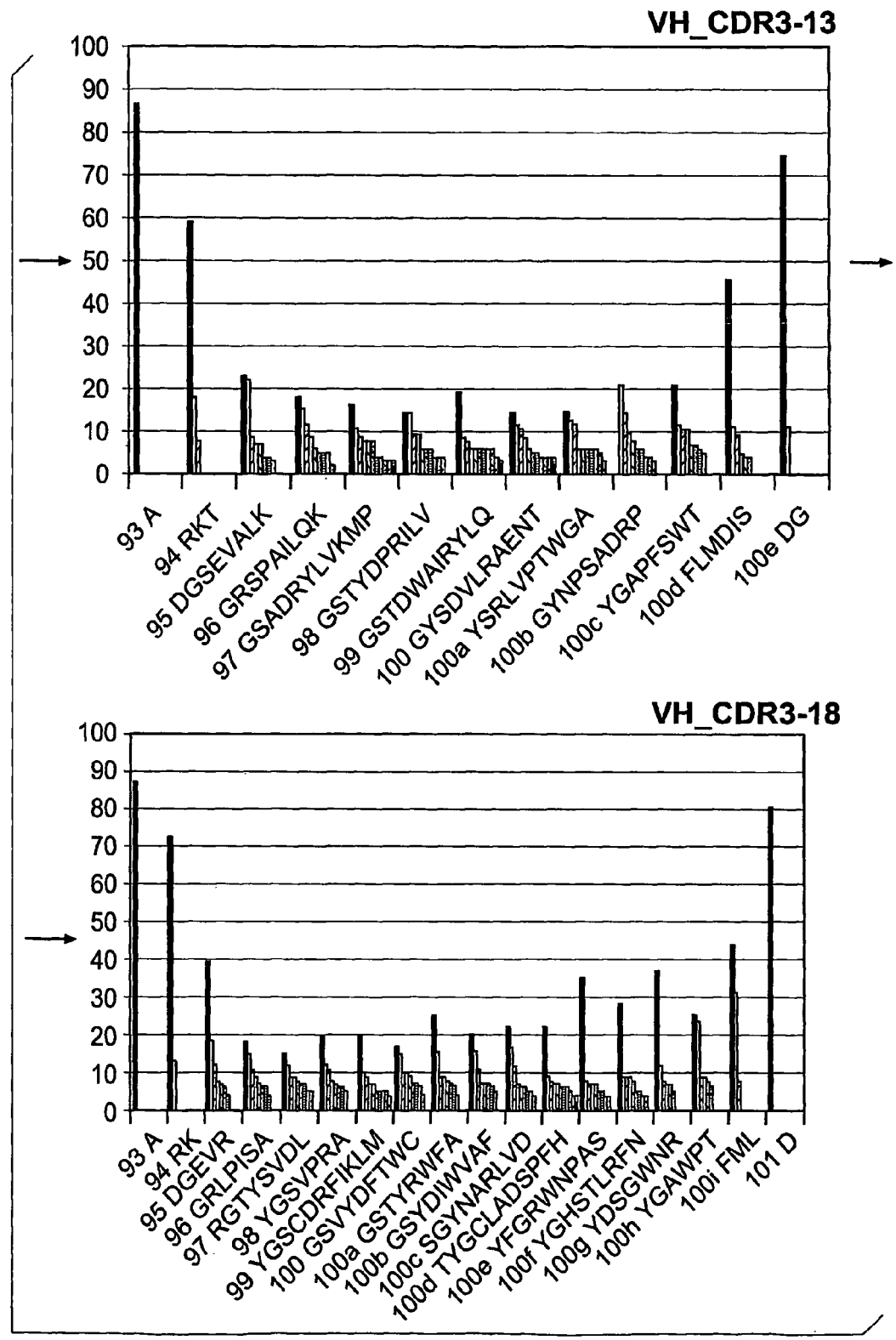
Figure 7A:
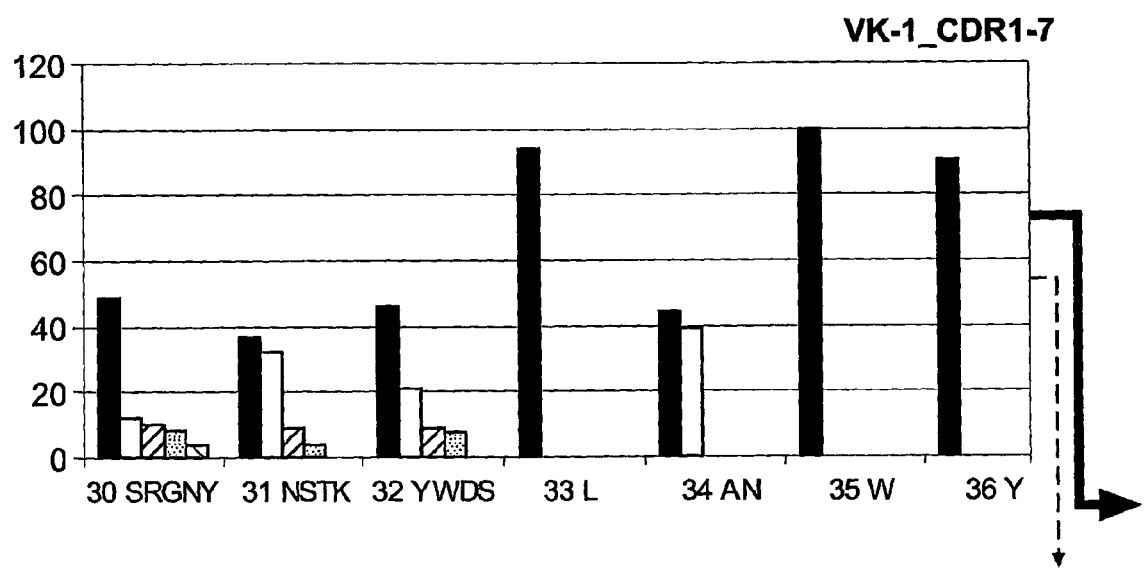
FIG. 7 shows the exemplary assembly of UAL kappa light chains, allowing for CDR1 and CDR2 framework crosses. VK-3_CDR1-7, VK-1_CDR2-10 and VK-3_CDR2-10 sequences disclosed as SEQ ID NOS 167, 276 and 278, respectively.
Figure 7B:
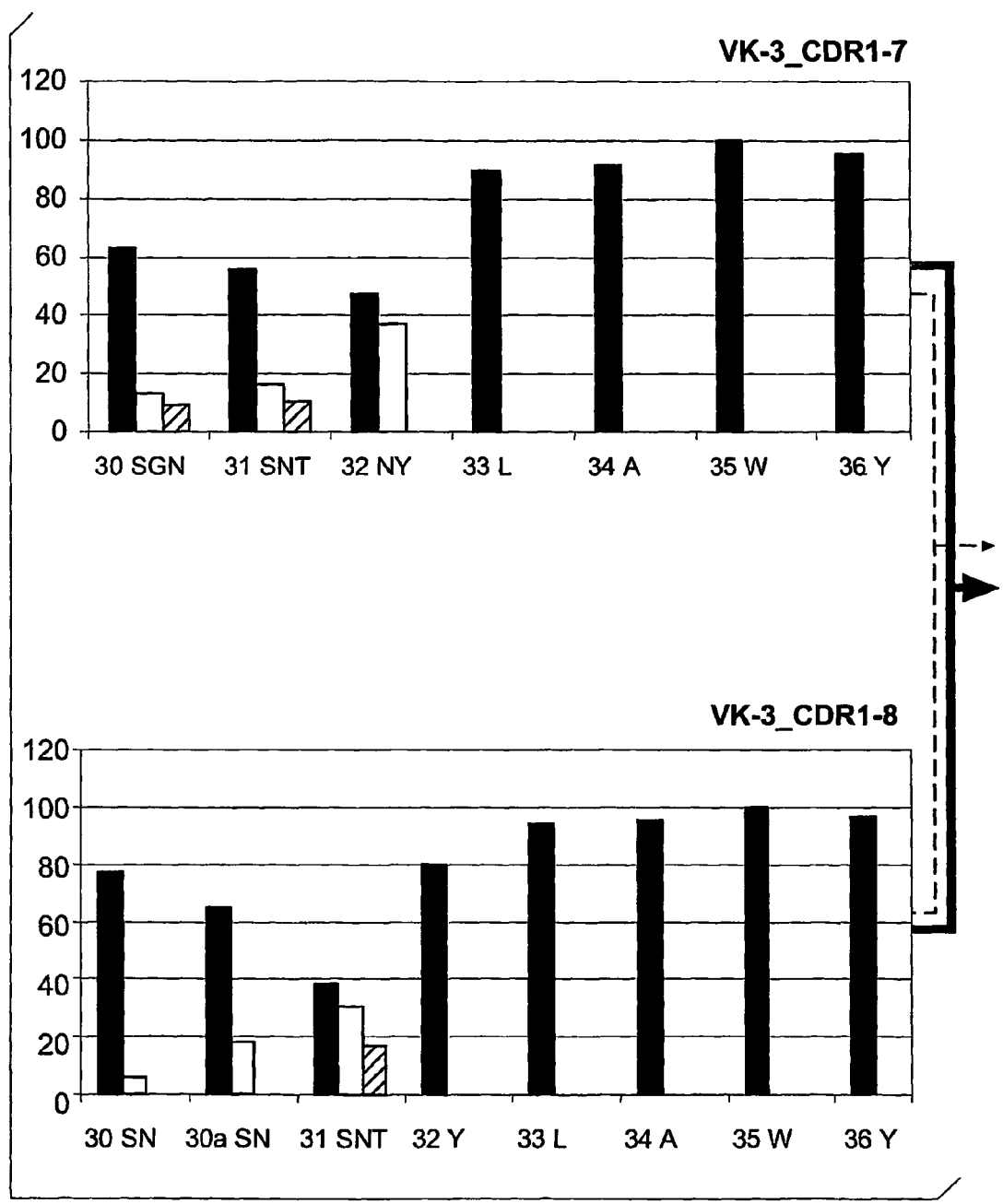
Figure 7C:
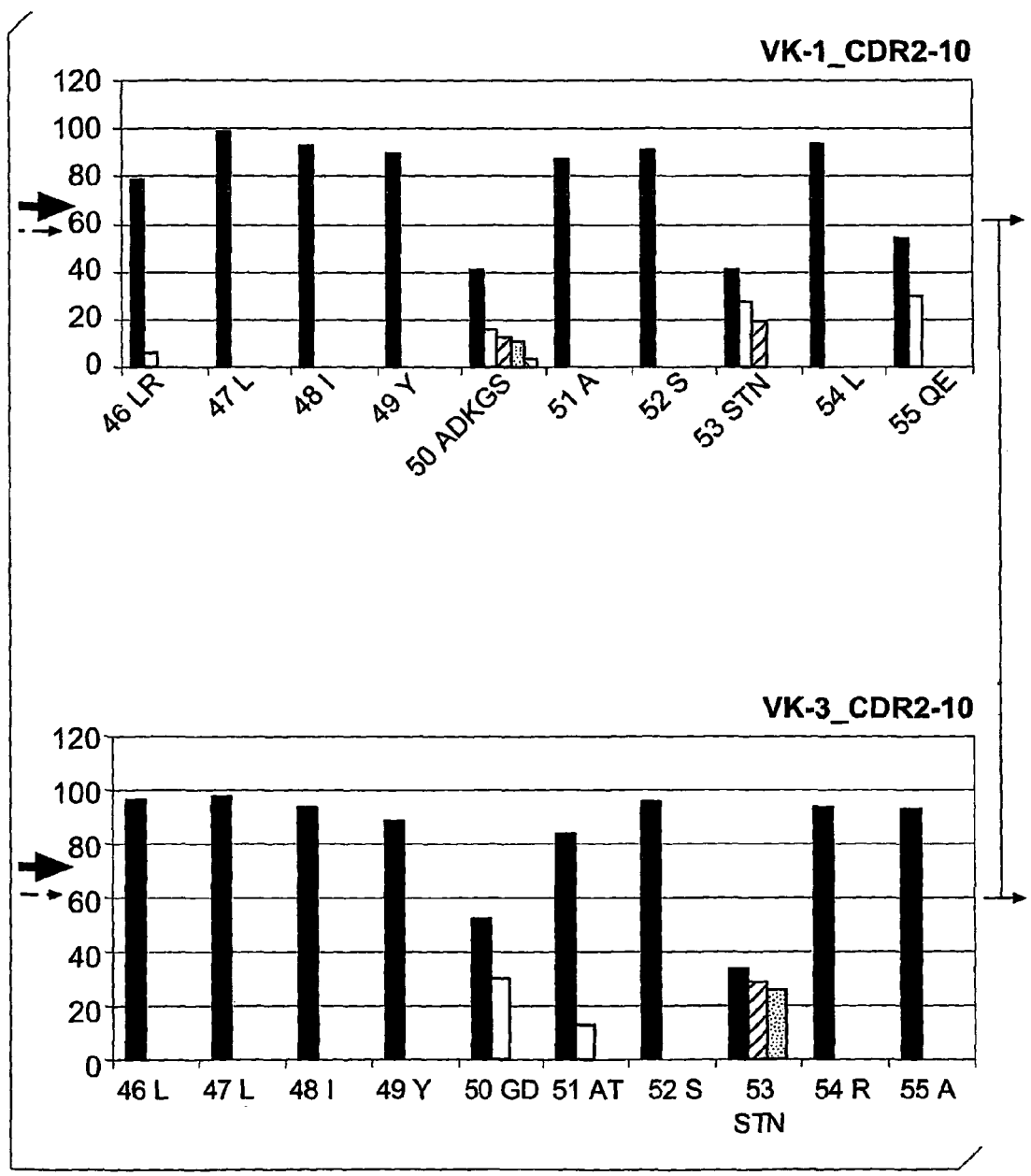
Figure 7D:
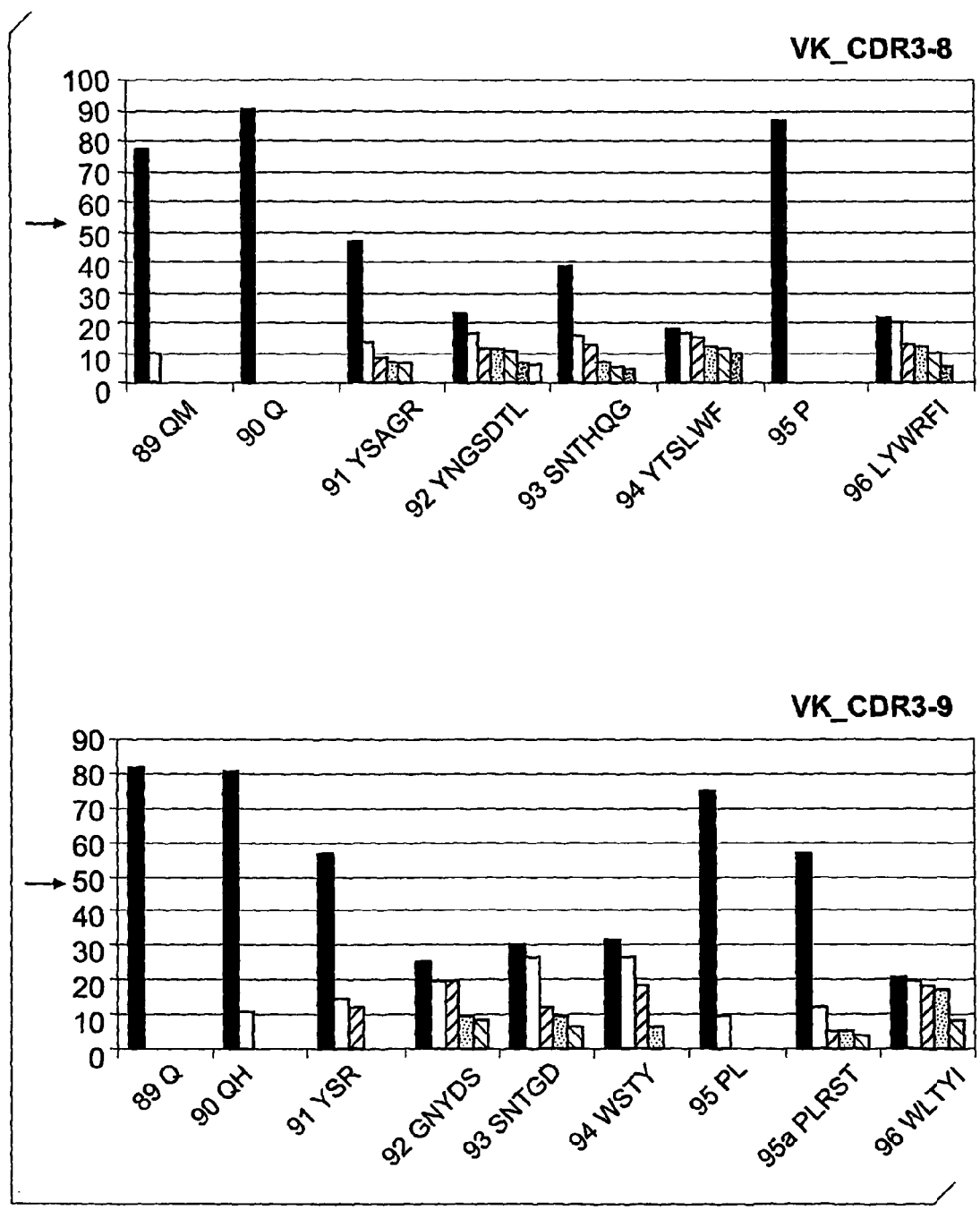
Figure 8A:
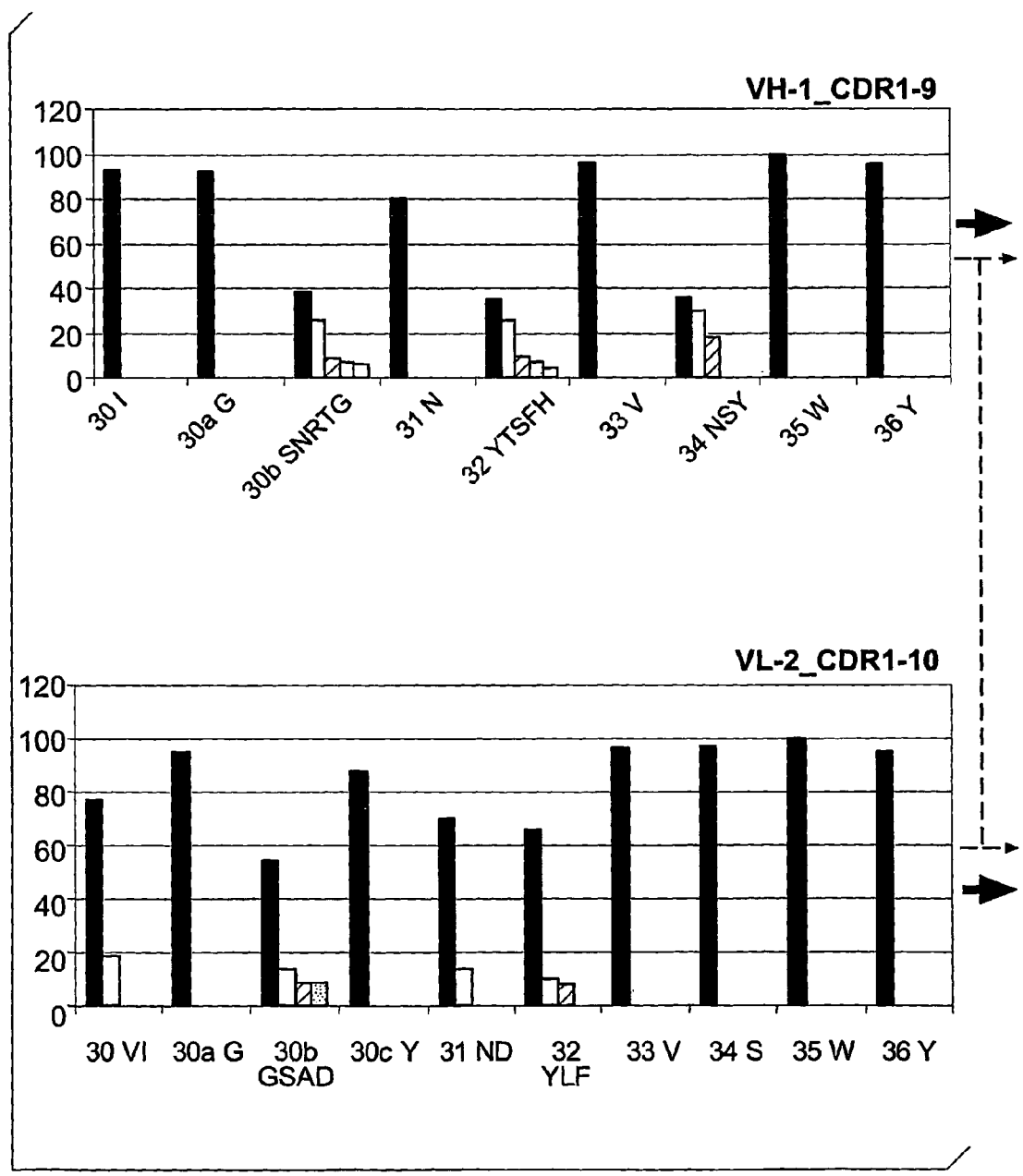
FIG. 8 shows the exemplary assembly of UAL lambda light chains, allowing for CDR1 and CDR2 framework crosses. VL-1_CDR2-10, VL-2_CDR2-10 and VL-3_CDR2-10 sequences disclosed as SEQ ID NO: 280.
Figure 8B:
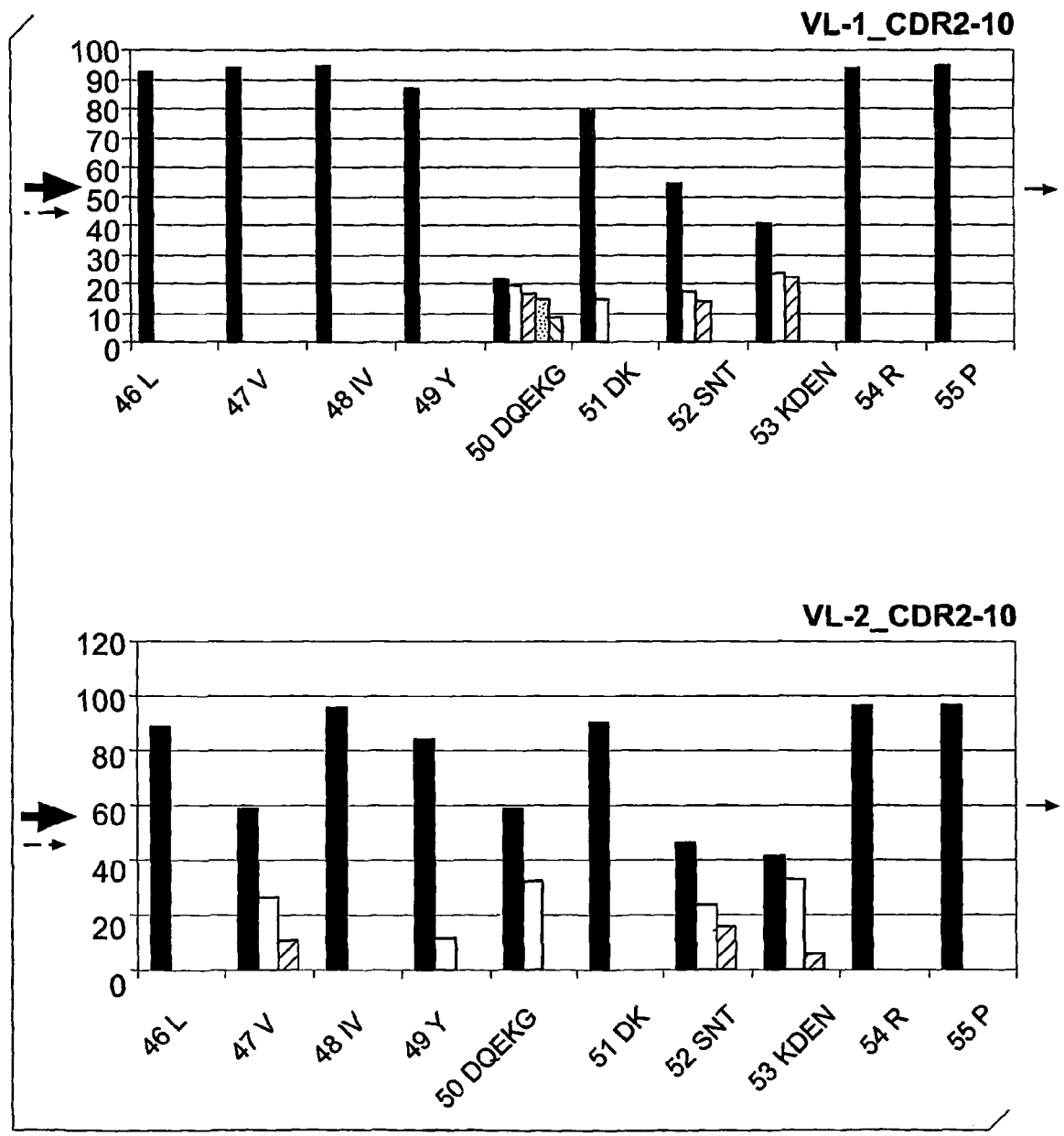
Figure 8C:
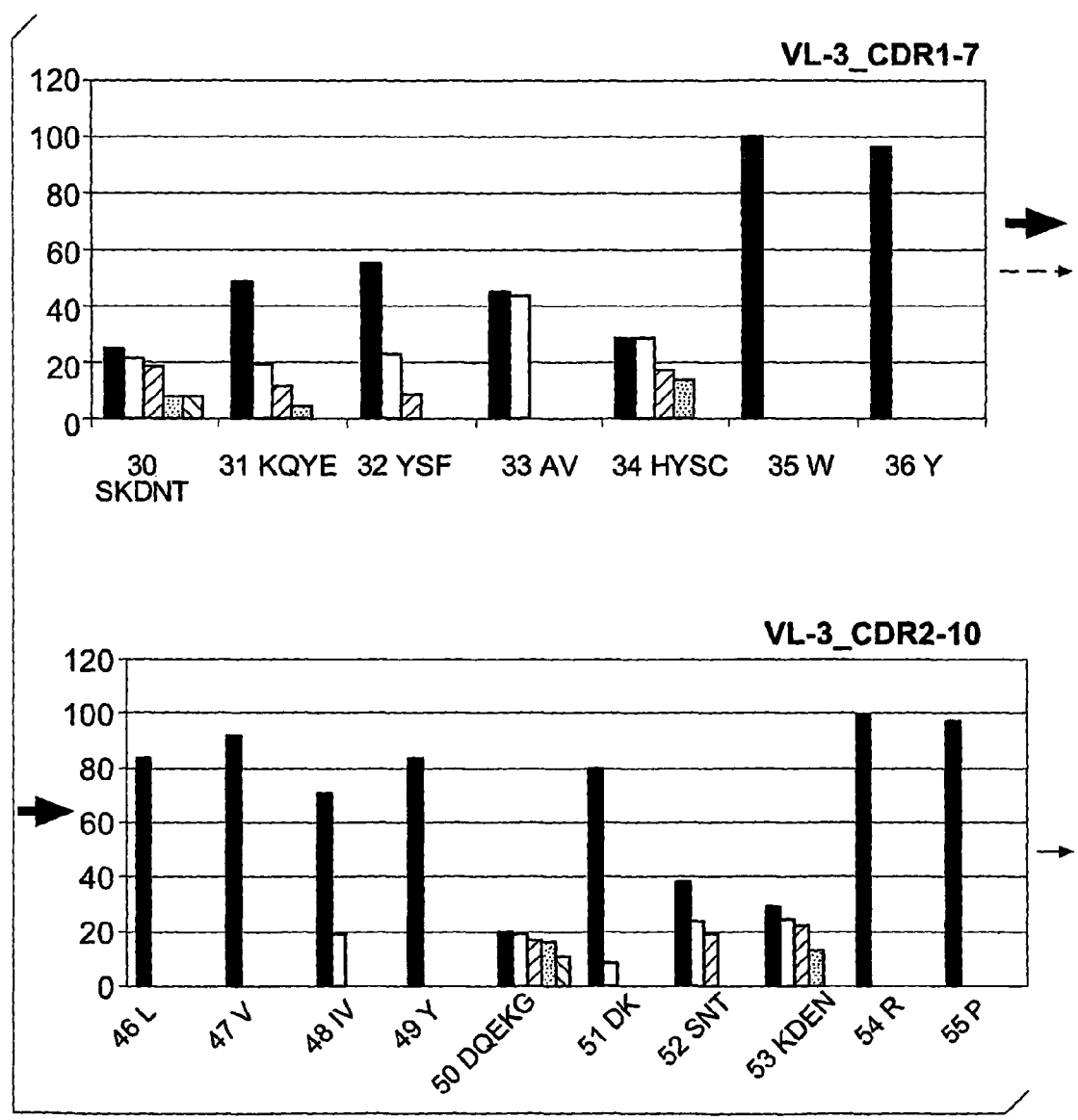
Figure 8D:
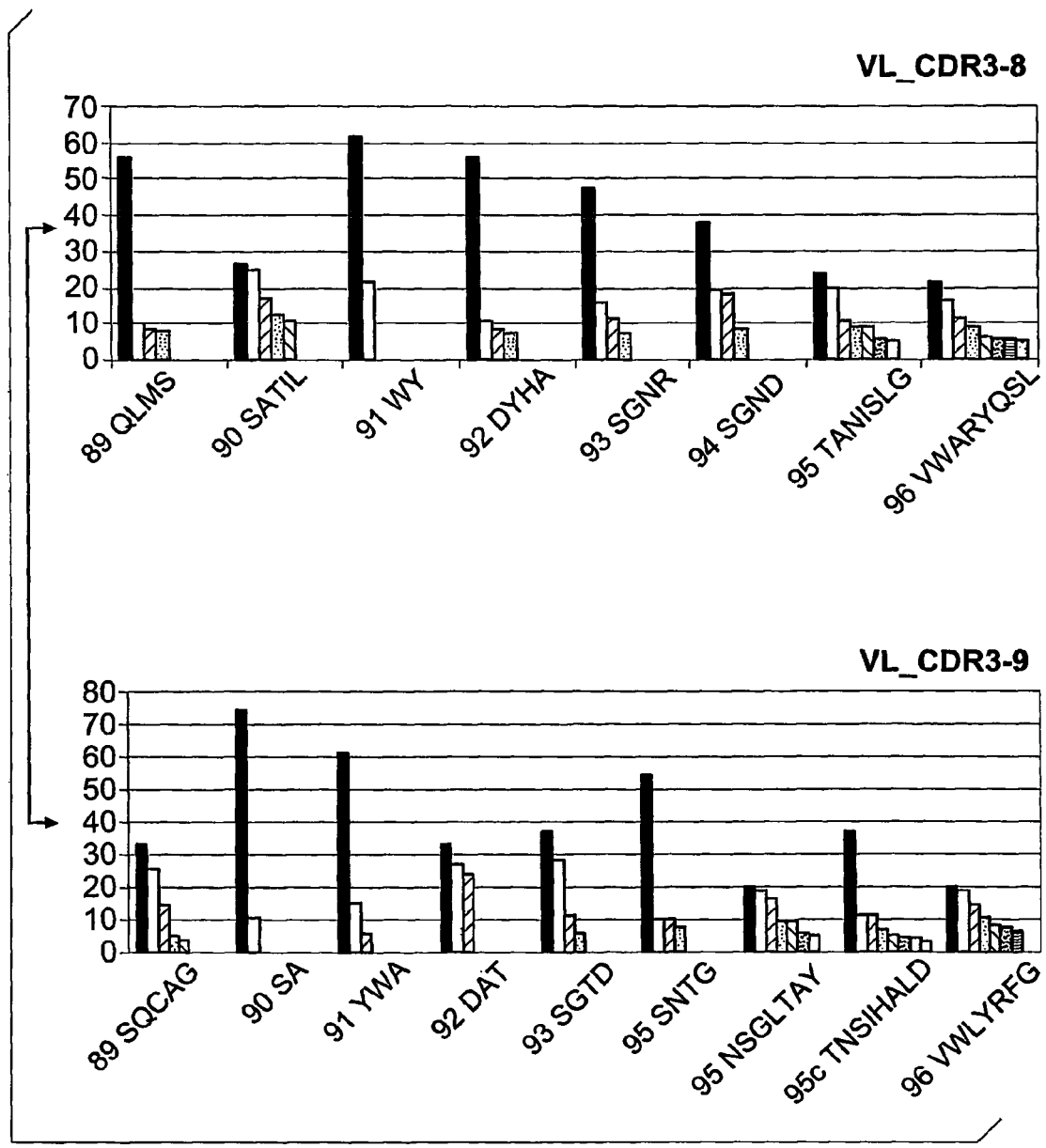
Figure 8E:
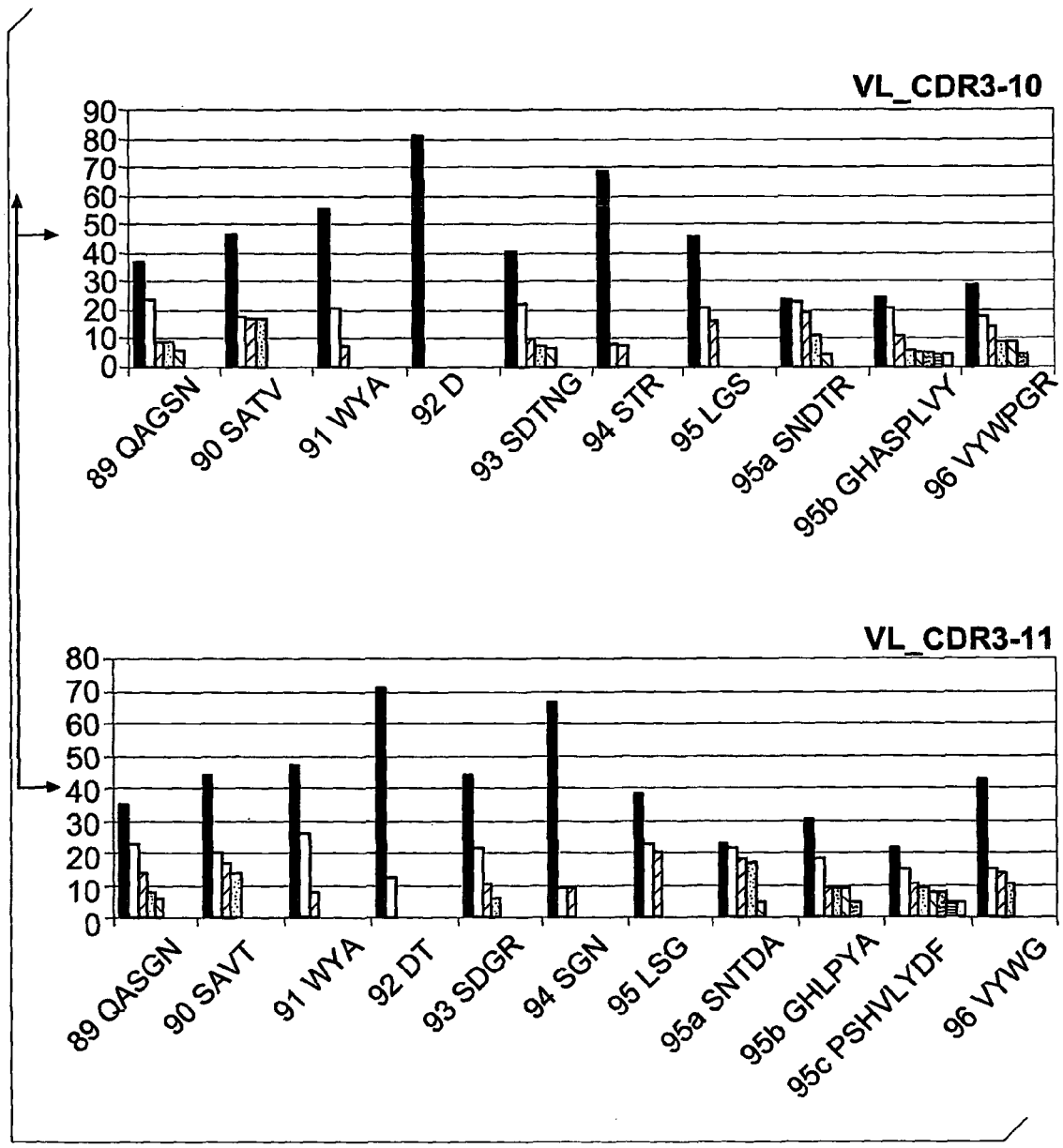

The matching of a CDR class to its natural framework can be used to delimit the range of sequence represented in CDR reference libraries. Such grouping of framework and CDR sequences for exemplary V☐, V☐ and V☐ sequences is shown in FIG. 5. Combination of CDR reference library sequences may then be performed to yield UALs. FIG. 6 depicts an exemplary assembly of heavy chain sequence into heavy chain UALs, via a process that allows for mixing of framework isotypes (termed "framework crosses") between VH-1 and VH-3 classes for CDR1 and CDR2. Likewise, FIG. 7 depicts the exemplary assembly of V☐ light chain UALs from CDR reference sequences, employing a process that allows for framework crosses between VK-1 and VK-3 classes for CDR1 and CDR2. Finally, FIG. 8 depicts the exemplary assembly of V☐ light chain UALs from CDR reference sequences, employing a process that allows for framework crosses between VL-1, VL-2 and VL-3 classes of CDR1 and CDR2 sequences.

Figure 9A:
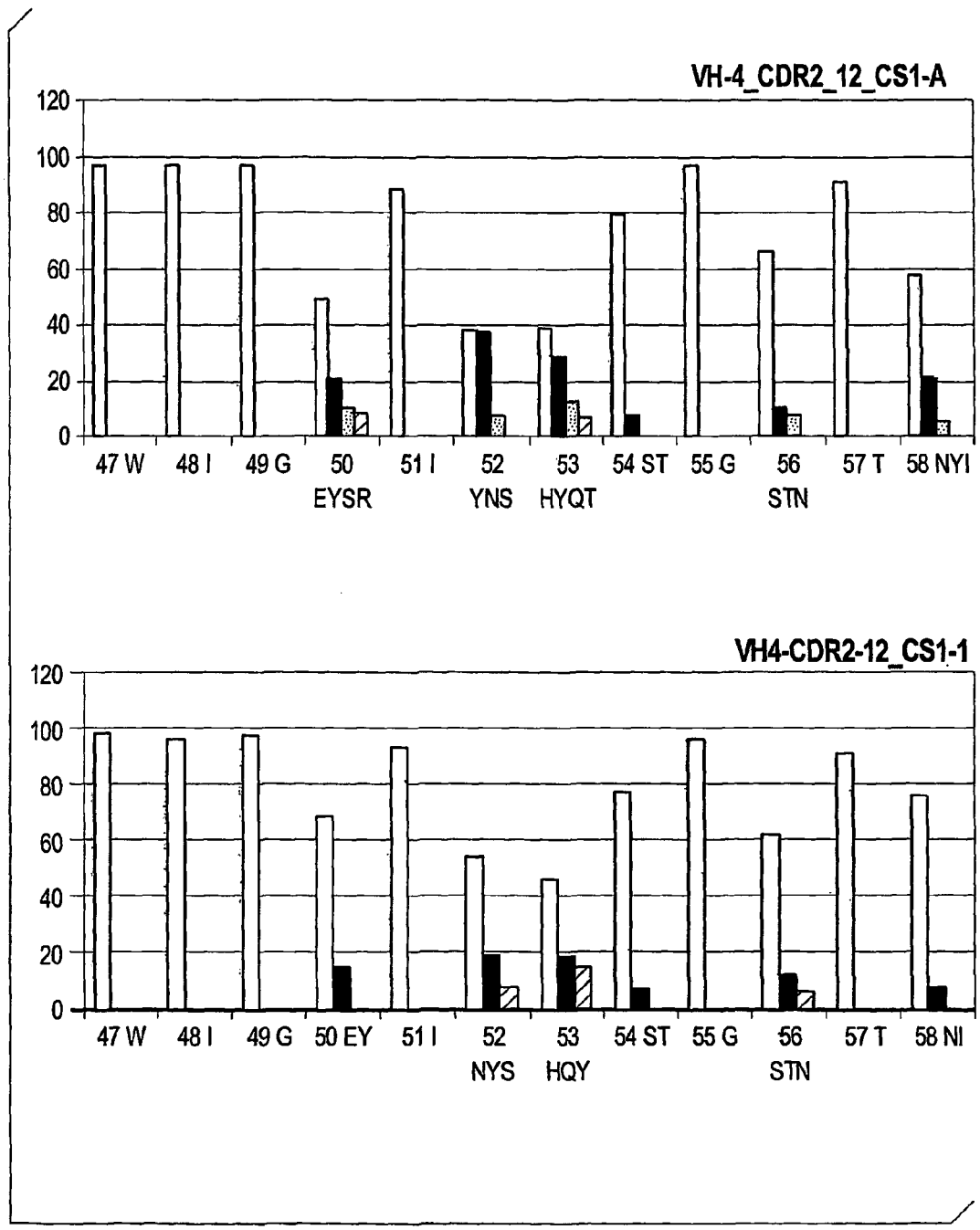
FIG. 9 shows histograms of position-by-position amino acid residue population prevalence for the four canonical structures (FIG. 9A shows CS1-A (SEQ ID NO: 636) and CS1-1 (SEQ ID NO: 637), while FIG. 9B shows CS1-2 (SEQ ID NO: 638) and CS1-3 (SEQ ID NO: 639)) identified for VH-4 isotype class CDR2 sequences of 12 residues in length. Distributions of population prevalences are observed to vary among the four subclasses at variable residue positions.

Subclassification of antibody sequence information into canonical classes can also be performed, with the effect of further altering the range of sequence that is represented in resultant CDR reference libraries. For example, for VH-4 CDR2 libraries of 12 amino acids in length, there exist four distinct canonical structures, and each canonical structure reveals differing population prevalence values for those CDR residue positions that display variability in the population (refer to FIG. 9).

Example 4

Identification and Generation of an Exemplary Anti-VEGF Cohort Antibody Library from Mouse Probe CDR Domains Selection of a cohort library from a reference library, e.g., a universal antibody library (UAL), proceeds via alignment and comparison of a query CDR peptide sequence to reference library (e.g., UAL) CDR peptide sequence(s). Any monoclonal antibody (including multiple monoclonal antibodies) can provide query CDR sequence(s) for assembling such a cohort library. In this example, cohort CDR libraries, which may be assembled into cohort antibody libraries, were made using an exemplary mouse anti-VEGF monoclonal antibody (Avastin A4.6.1). Identity criteria were used for all residue comparisons during assembly of the resulting cohort libraries.

The mouse Avastin A4.6.1 monoclonal antibody CDR1 sequence was determined to be "TNYGMN" (SEQ ID NO: 13). CDR1 in this case was defined according to contact definition. This CDR1 sequence was used as a query peptide sequence for comparison against CDR1 domain diversity present in two separate Universal Antibody Libraries (UALs), VH-1 and VH-3. The results of these comparisons are summarized in FIG. 10 and Tables 1 and 2.

TABLE 1

Mouse Avastin A4.6.1 Heavy Chain CDR1 Aligned with UAL VH-1 CDR1 Sequence Diversity
VH-1 CDR1

|  |   | S | A |   |   |   |   |
|---|---|---|---|---|---|---|---|
|  |   | G | Y |   |   | H |   |
| UAL | T | N | G | I | S |   |   |
| constituents | S | D | Y | D | M | N |   |
| mouse probe (SEQ ID NO: 13) | T | N | Y | G | M | N |   |
| library encodes (SEQ ID NO: 14) | T | N | Y | G | M | N | No Diversity |
| possible residues | 1 | 1 | 1 | 1 | 1 | 1 | Product 1 |

TABLE 2

Mouse Avastin A4.6.1 Heavy Chain CDR1 Aligned with UAL VH-3 CDR1 Sequence Diversity
VH-3 CDR1

|  |   | S | A |   |   |   |   |
|---|---|---|---|---|---|---|---|
|  |   | N | Y | G |   | S |   |
| UAL | S | D | A | W |   | H |   |
| constituents | N | T | S | Y | M | N |   |
| mouse probe (SEQ ID NO: 13) | T | N | Y | G | M | N |   |
| library encodes (SEQ ID NO: 15) | S or N | N | Y | G | M | N |   |
| possible residues | 2 | 1 | 1 | 1 | 1 | 1 | Product 2 |

Performance of the above-tabulated alignments involved separate, position-by-position comparisons of query sequence with known, prevalent sequence diversity found within two reference UALs, VH-1 and VH-3. For the comparisons shown in Table 1, each residue of mouse query sequence ("mouse probe") "TNYGMN" (SEQ ID NO: 13) was found at a corresponding position in the surveyed reference UAL, and thus represented a known, prevalent residue at that CDR1 position. The entire "TNYGMN" (SEQ ID NO: 14) sequence was therefore present in the reference UAL, and the comparison yielded a result in which no additional UAL-selected diversity was required to generate an optimal CDR1 cohort library corresponding to the query sequence. (It is important to note that although each residue of mouse probe "TNYGMN" (SEQ ID NO: 13) sequence was identical to a known residue present at the same position in the human CDR1 VH-1 UAL, this finding did not indicate that the entire "TNYGMN" (SEQ ID NO: 14) sequence was a naturally-occurring human CDR1 sequence. Thus, a finding that the surveyed reference UAL contains a "perfect match" with the query sequence does not mean that the query sequence was a known, naturally-occurring sequence prior to assembly of the reference UAL.)

A comparison was also performed between query sequence "TNYGMN" (SEQ ID NO: 13) and the reference VH-3 CDR1 UAL (Table 2). For this comparison, the reference VH-3 CDR1 UAL did not contain a Threonine (T) residue in the first position of CDR1, instead containing only Serine (S) and Asparagine (N) residues. Optimal CDR1 cohort library diversity was therefore achieved using the sequences "SNYGMN" (SEQ ID NO: 246) and "NNYGMN" (SEQ ID NO: 579), thus constituting a diversity of 2 for the cohort library derived from the reference VH-3 CDR1 UAL for the mouse Avastin A4.6.1 monoclonal antibody.

The Avastin A4.6.1 monoclonal antibody CDR2 sequence, "WMGWINTYTGEPT" (SEQ ID NO: 16), was additionally used as a query sequence to generate CDR2 cohort libraries. The sequence was aligned with CDR2 diversity present in reference VH-1 and VH-3 UALs, respectively, with results of these comparisons shown in FIG. 11 and Tables 3 and 4:

TABLE 3

Mouse Avastin A4.6.1 Heavy Chain CDR2 Aligned
with UAL VH-1 CDR2 Sequence Diversity

VH-1 CDR2

| UAL constituents | W | M | G | R | I | S | A | I N S Y P G M G | F S N G | G | T N G S D | T A | N K S G |
|---|---|---|---|---|---|---|---|---|---|---|---|---|---|
| mouse probe (SEQ ID NO: 16) | W M G W I N T Y T G E P T |
| library encodes (SEQ ID NO: 17) | W M G W I N P/A Y F/S/ N/G G T/N/G/ S/D T/A N/K/ S/G |
| possible residues | 1 1 1 1 1 1 2 1 4 1 5 2 4 Product 320 |

TABLE 4

Mouse Avastin A4.6.1 Heavy Chain CDR2 Aligned with
UAL VH-3 CDR2 Sequence Diversity

VH-3 CDR2

| UAL constituents | W | V | S A | V A N G Y S S T | S K W T | I N | G Y S Q W N F F | D N | S N | G S D D | S T G E T Y K I | T | Y N S T Y N F F H |
|---|---|---|---|---|---|---|---|---|---|---|---|---|---|
| Mouse probe (SEQ ID NO: 16) | W M G W I N T Y T G E P T |
| library encodes (SEQ ID NO: 18) | W V S/A/V/A/N/G/ Y/S/T S I N G/Y/S/Q/ W/N/F D/ S/N G/S G E T/ K/I Y/N/ F/H |
| Possible residues | 1 1 2 7 1 1 7 3 2 1 1 3 4 Product 70 |

As shown above in Table 3, alignment of mouse Avastin A4.6.1 heavy chain CDR2 with CDR2 domains of the VH-1 UAL revealed the presence of identical residues at the same position in the UAL for the first six, eighth and tenth residues of CDR2 query sequence. The UAL did not contain a Threonine (T) as a residue prevalently used at the seventh position, instead containing Proline (P) and Alanine (A) at this position, for a net impact on diversity of 2 at this position. The Threonine (T) residue at the ninth CDR2 query sequence position also failed to match a residue present in the UAL at this position, with the UAL instead containing Phenylalanine (F), Serine (S), Arginine (N) and Glycine (G) as residues commonly present at this position. For the purpose of generating a cohort library from this reference UAL, the diversity impact of this mismatch is 4. Consideration of the final three CDR2 query sequence residues yields diversity impacts of 5 (query sequence Glutamate (E) does not match UAL Threonine (T), Arginine (N), Glycine (G), Serine (S), or Aspartate (D) residues at this position), 2 (query sequence Proline (P) does not match UAL Threonine (T) or Alanine (A) residues at this position) and 4 (query sequence Threonine (T) does not match UAL Arginine (N), Lysine (K), Serine (S) or Glycine (G) residues at this position), respectively. An optimal cohort library derived from the human VH-1 CDR2 UAL therefore has the sequence "W-M-G-W-I-N-P/A-Y-F/S/N/G-G-T/N/G/S/D-T/A-N/K/S/G" (SEQ ID NO: 17) and can be generated using walk-through or look-through mutagenesis or other such techniques. The total diversity of such a cohort library represents the result of independent assortment of the variable residues within this sequence (the seventh, ninth and eleventh through thirteenth), resulting in the product of 2×4×5×2×4=320. The advantages of using the methods of the invention to query a UAL (or related form of reference library) in assembling a cohort library are illustrated when one considers that randomization of the five variable sites within this cohort library sequence would yield $3.2 \times 10^8$ distinct sequences, and this 10,000-fold increase in diversity would likely only add noise in the form of potentially immunoreactive CDR2 sequences.

Use of the methods of the invention in performing a comparison of the mouse Avastin A4.6.1 heavy chain CDR2 query sequence with the CDR2 domains of the VH-3 UAL yielded the sequence "W-V-S/A-V/A/N/G/Y/S/T-I-N-G/Y/S/Q/M/N/F-D/S/N-G/S-G-E-T/K/I-Y/N/F/H" (SEQ ID NO: 18).

The cohort library represented by this sequence has a diversity of 7056. Details of the alignment producing this result are shown in Table 4 above.

The methods of the invention were also applied to Avastin A4.6.1 heavy chain CDR3 query sequence to identify the cohort sequence "A-K-G/D/E/R/A/H/V/T-P-H-Y-Y-G-S-S-H-W-Y-F-D" (SEQ ID NO: 20) from a VH CDR3 UAL. This cohort sequence contains a diversity of 8. Details of the alignment producing this result are presented in Table 5:

TABLE 5

Mouse Avastin A4.6.1 Heavy Chain CDR3 Aligned
with UAL VH CDR3 Sequence Diversity
VH-CDR3

```
                                      G
                                   Y S       G Y
                                   G A Y     Y G Y
                                   R S G S S G S S N
                              G    S R D G G S T N G Y
                              D    P E E Y T Y P R S G
                              E    W T A D Y T L V W W
                              R    L F C R D R F A H P
                              A    Y L T T R A V C D F F D
                              H    A W F P V H K R A L P
UAL                    R      V    T H N A A D M D A L M G
constituents           A K    T    V I I L E W W H Q H D H mouse probe            A K    Y    P H Y Y G S S H W Y F D
(SEQ ID NO: 19)

library encodes        A K G/D/E/R/A/H/V/T  P H Y Y G S S H W Y F D
(SEQ ID NO: 20)

possible residues      1 1    8    1 1 1 1 1 1 1 1 1 1 1 1  Product
```

Application of the methods of the invention to light chain CDR sequences of the Avastin A4.6.1 monoclonal antibody yielded CDR cohort library sequences for all such light chain CDR domains. Kappa light chain CDR1, CDR2 and CDR3 sequences for the mouse Avastin A4.6.1 antibody are "SNYL-NWY" (SEQ ID NO: 21), "VLIYFTSSLH" (SEQ ID NO: 23), and "QQYSTVPW" (SEQ ID NO: 26), respectively. Use of the methods of the invention with the mouse Avastin A4.6.1 kappa chain CDR1 query sequence yielded cohort library sequences of "S-N-Y-L-N-W-Y" (SEQ ID NO: 22) (no diversity) and "S-N-Y-L-A-W-Y" (SEQ ID NO: 249) (diversity 1) when the query sequence was compared with a human VK-1 CDR1 UAL and a VK-3 CDR1 UAL, respectively. Implementation of the invention to query mouse Avastin A4.6.1 kappa chain CDR2 sequence against a human VK-1 CDR2 UAL yielded a cohort library sequence with diversity 20, "L/R-L-I-Y-A/D/K/G/S-A-S-S-L-Q/E" (SEQ ID NO: 24), while comparison of the kappa chain CDR2 probe sequence with a human VK-3 CDR2 UAL by the methods of the invention produced a cohort CDR2 library sequence of diversity 2, "L-L-I-Y-G/D-T-S-S-R-A" (SEQ ID NO: 25). Use of the mouse ACZ885 CDR3 as query sequence produced a cohort library CDR3 sequence of "Q-Q-Y-S-T-Y/T/S/L/W/F-P-W" (SEQ ID NO: 27) when aligned with a VK CDR3 UAL. This kappa chain CDR3 library had a diversity of 6.

The production of a final cohort antibody (or fragment thereof, e.g., Fab, scFv, etc.) library from the various cohort CDR libraries can be performed via independent assortment of cohort CDR library sequences with one another to build both heavy (e.g., IgG, IgM, IgA, IgD, IgE) and light (e.g., kappa or lambda) chains, and complete antibodies (or fragments thereof), from the cohort CDR libraries identified by the methods of the invention. Such independent assortment of cohort CDR library sequences results in chain and whole antibody cohort library diversities as shown in FIG. 12 and Table 6 for those cohort libraries generated using mouse Avastin A4.6.1 query sequences:

TABLE 6

Chain and Whole Antibody Diversities of Combined Cohort CDR
Libraries Generated Using Mouse Avastin A4.6.1 Probes

| Chain Diversity | | | |
|---|---|---|---|
| H1 Cohorts | H3 Cohorts | K1 Cohorts | K3 Cohorts |
| 2560 | 112896 | 120 | 12 |

| mAb diversity | K1 | K3 |
|---|---|---|
| H1 | $3.1 \times 10^5$ | $3.1 \times 10^4$ |
| H3 | $1.4 \times 10^7$ | $1.4 \times 10^6$ |

Even the most diverse of these antibody libraries is of a size (e.g., diversity substantially less than about $10^{12}$) that can be readily displayed and/or screened using currently available methods. Synthesis of such libraries can be performed using techniques such as e.g., look-through and/or walk-through mutagenesis, and synthesis of whole chains and/or antibodies can employ techniques such as gene single overlap extension (SOE) PCR, Kunkel mutagenesis or other known techniques for making such fusion proteins.

Example 5

Identification and Generation of Kappa Light Chain
CDR Cohort Libraries from Mouse Probe Anti-HIV
gp41 Monoclonal 41-S-2-L CDR Domains Kappa light chain sequences were obtained for mouse anti-HIV gp41 monoclonal antibody 41-S-2-L. A catalytic triad was identified in these light chain sequences, and included residues within kappa chain CDR1 and CDR3 domains.

Kappa chain CDR1, CDR2 and CDR3 sequences for this antibody are "LYSNGNTYLYWF" (SEQ ID NO: 29), "LLIYRLFHLA" (SEQ ID NO: 30), and "MQHLEYPYT" (SEQ ID NO: 31), respectively, with catalytic triad residues underlined (refer to FIG. 14A). To preserve the catalytic triad, it was determined that cohort library sequences would fix these residues (underlined) as the mouse query sequence residues at these positions in CDR1 and CDR3. Further, gapped alignment revealed that the mouse CDR1 query sequence for this antibody contained an insertion of five, residues ("YSNGN") (SEQ ID NO: 580) when compared with human kappa chain CDR1 UAL constituents of seven amino acid residues in length. Cohort libraries of sequence "S/R/G/N/Y-YSNGN-N-Y-L-A/N-W-Y" (SEQ ID NO: 33) and "S/G/N-YSNGN-T-Y-L-A-W-Y" (SEQ ID NO: 34) were obtained via application of the methods of the invention to the mouse CDR1 query sequence when compared to reference VK-1 CDR1-7 and VK-3 CDR1-7 UALs, respectively (refer to FIGS. 14B-C). Diversities of these cohort libraries were 10 and 3, respectively. The insertion found in mouse anti-HIV gp41 CDR1 also allowed for comparison of the sequence with CDR1 UAL constituents of 8 peptides in length. This comparison between the mouse CDR1 query sequence and reference library VK-3 CDR1-8 yielded a cohort library CDR1 sequence of "S-YSNG-N-T-Y-L-A-W-Y" (SEQ ID NO: 36) (FIG. 14C). Comparisons of mouse anti-HIV gp41 kappa light chain CDR2 query sequences with human VK-1 and VK-3 CDR2 reference libraries were also performed by the methods of the invention, yielding cohort kappa chain CDR2 libraries of sequence "L-L-I-Y-A/D/K/G/S-A-S-I/S/T/N-L-Q/E" (SEQ ID NO: 37) and "L-L-I-Y-G/D-A/T-S-S/T/N-R-A" (SEQ ID NO: 38), respectively (FIG. 14D). These cohort libraries had diversities of 40 and 12, respectively. Parallel comparison of mouse anti-HIV gp41 kappa light chain CDR3 query sequence with a human VK CDR39 reference library yielded a kappa chain CDR3 cohort library of sequence "Q-Q-H-S/D/Y/N/G-D/G/T/N/S-Y-P-P/L/R/S/T-T" (SEQ ID NO: 39) (with the Histidine residue at the third position fixed to preserve the catalytic triad; FIG. 14E. Note that when this Histidine residue is fixed, a discontinuous alignment is performed between query and reference library sequences (constituting comparison of only residues 1,2, and 4 through 9 between query and reference library sequences). Also note that were the choice made to fix the first three residues of CDR3 to the query sequence residues, "M-Q-H", an alignment of only residues 4 through 9 of query and reference libraries would have been desirable, thus constituting a partial alignment). This CDR3 cohort library had a diversity of 125.

In the present example, catalytic activity resides in the light chain of the antibody, thus heavy chain residues were left unaltered in the cohort library. The overall diversity values of cohort libraries generated for this antibody were therefore represented by the diversity values of the light chain, which were 50,000 and 4500 for K1 and K3 cohorts, respectively.

Example 6

Figure 15A:
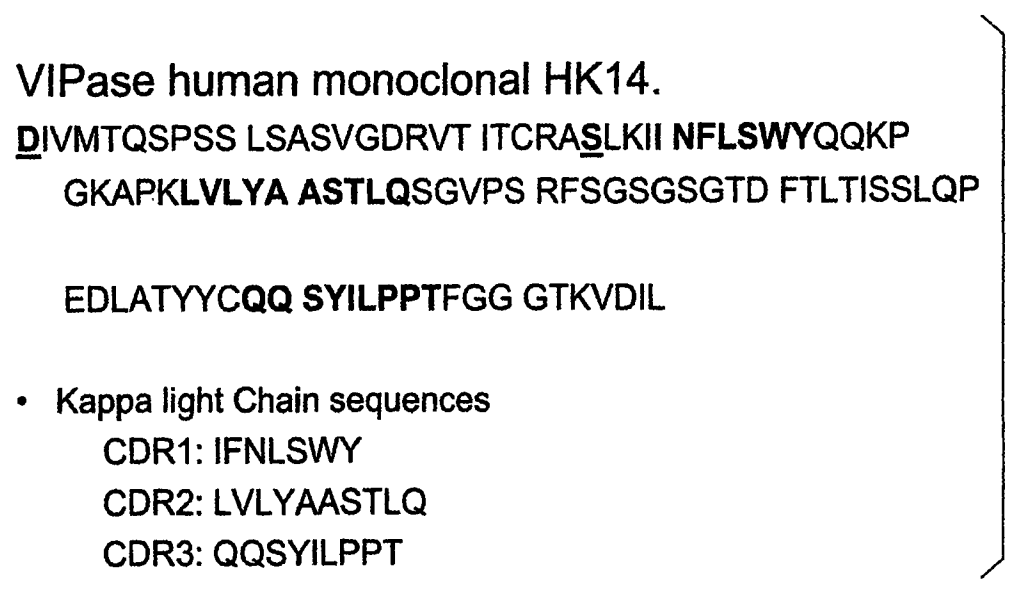

Identification and Generation of Kappa Light Chain CDR Cohort Libraries from Human Probe HK14 CDR Domains Kappa light chain CDR1, CDR2 and CDR3 sequences for a human HK14 antibody are "IFNLSWY" (SEQ ID NO: 41), "LVLYAASTLQ" (SEQ ID NO: 42), and "QQSYILPPT" (SEQ ID NO: 43), respectively (FIG. 15A). Use of the methods of the invention with the kappa chain CDR1 query sequence yielded a cohort library sequence of "S/R/G/N/Y-N-Y/W/D/S-L-A/N-W-Y" (SEQ ID NO: 581) when the query sequence was compared with a human VK-1 CDR1 UAL. This cohort library sequence had a diversity of 40. Comparison of the "IFNLSWY" (SEQ ID NO: 41) CDR1 sequence with a human VK-3 CDR1-7 UAL using the invention yielded a cohort sequence of diversity 9, "S/G/N-S/N/T-N-L-A-W-Y" (SEQ ID NO: 44) (FIG. 15B). Implementation of the invention to query kappa chain CDR2 sequence against a human VK-1 CDR2 UAL yielded a cohort library sequence identical to the query sequence, "L-L-I-Y-A-A-S-T-L-Q" (SEQ ID NO: 635), while query of the same sequence against a VK-3 CDR2 library yielded a sequence with diversity 2, "L-L-I-Y-G/D-A-S-T-R-A" SEQ ID NO: 45) (FIG. 15C). Use of the HK14 CDR3 as query sequence produced a cohort library CDR3 sequence of "Q-Q-S-Y-S/N/T/G/D-Y/T/S/W-P-P-T" (SEQ ID NO: 46) when aligned with a VK CDR3 UAL (FIG. 15D). This kappa chain CDR3 library had a diversity of 20.

As for the 41-S-2-L antibody above, catalytic activity resides in the light chain of the antibody, thus heavy chain residues were left unaltered in the cohort library. The overall diversity values of cohort libraries generated for this antibody were therefore represented by the diversity values of the light chain, which were 800 and 360 for K1 and K3 cohorts, respectively.

Example 7

Figures 3, 16A:
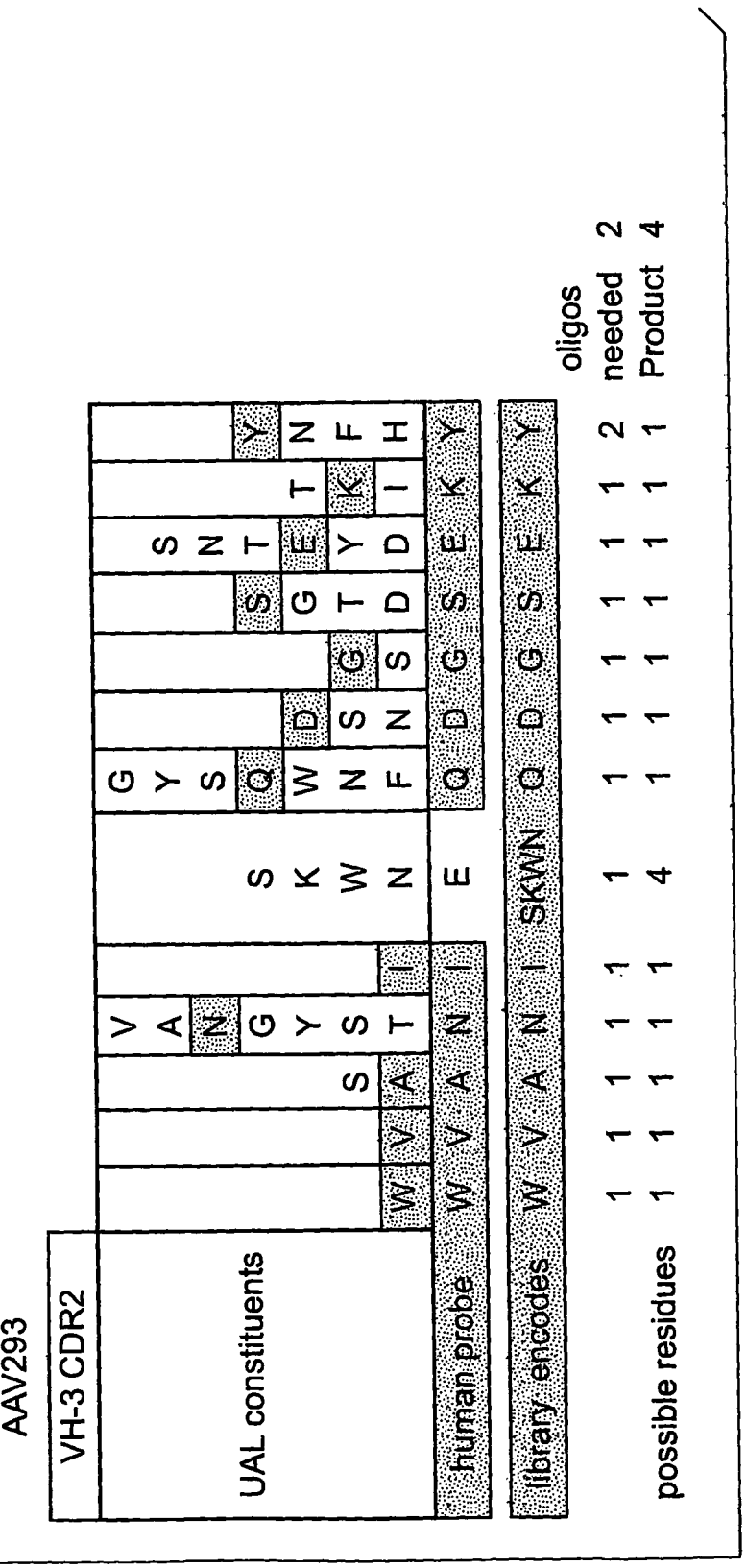

Identification and Generation of an AAV293 MCP-1 Cohort Antibody Library from Probe CDR Domains Heavy chain CDR1, CDR2 and CDR3 sequences for a human AAV293 MCP-1 antibody are "SHYWMS" (SEQ ID NO: 47), "WVANIEQDGSEKY" (SEQ ID NO: 51), and "ARDLDGYTD" (SEQ ID NO: 54), respectively. Use of the methods of the invention with the heavy chain CDR1 query sequence yielded cohort library sequences of "S-S/N/D/T-Y-W-M-S" (SEQ ID NO: 48) (diversity 4) and "S-S/G/N/D-Y-A/Y/G/D-M-S" (SEQ ID NO: 50) (diversity 16) when the query sequence was compared with a human VH-3 CDR1 UAL and a human VH-1 CDR1 UAL, respectively (FIG. 16A). Implementation of the invention to query heavy chain CDR2 sequence against a human VH-1 CDR2 UAL yielded a cohort library sequence with diversity of 4320, "W-M-G-W/G/R-I-N/I/S-P/A-I/N/S/Y/G/M-G-G-T/N/G/S/D-T/A-N/K/S/G" (SEQ ID NO: 52), while comparison of the heavy chain CDR2 probe sequence with a human VH-3 CDR2 UAL by the methods of the invention produced a cohort CDR2 library sequence of diversity 4, "W-V-A-N-I-S/K/W/N-Q-D-G-S-E-K-Y" (SEQ ID NO: 53). Use of the AAV293 MCP-1 CDR3 as query sequence produced a cohort library CDR3 sequence of "A-R-D-L-G/S/V/Y/R/T/N/I/L/Q-G-Y-F/L/G/S/M/A/I/P-D" (SEQ ID NO: 55) when aligned with a VH CDR3 UAL. This heavy chain CDR3 cohort library had a diversity of 80.

Figures 2, 16B:
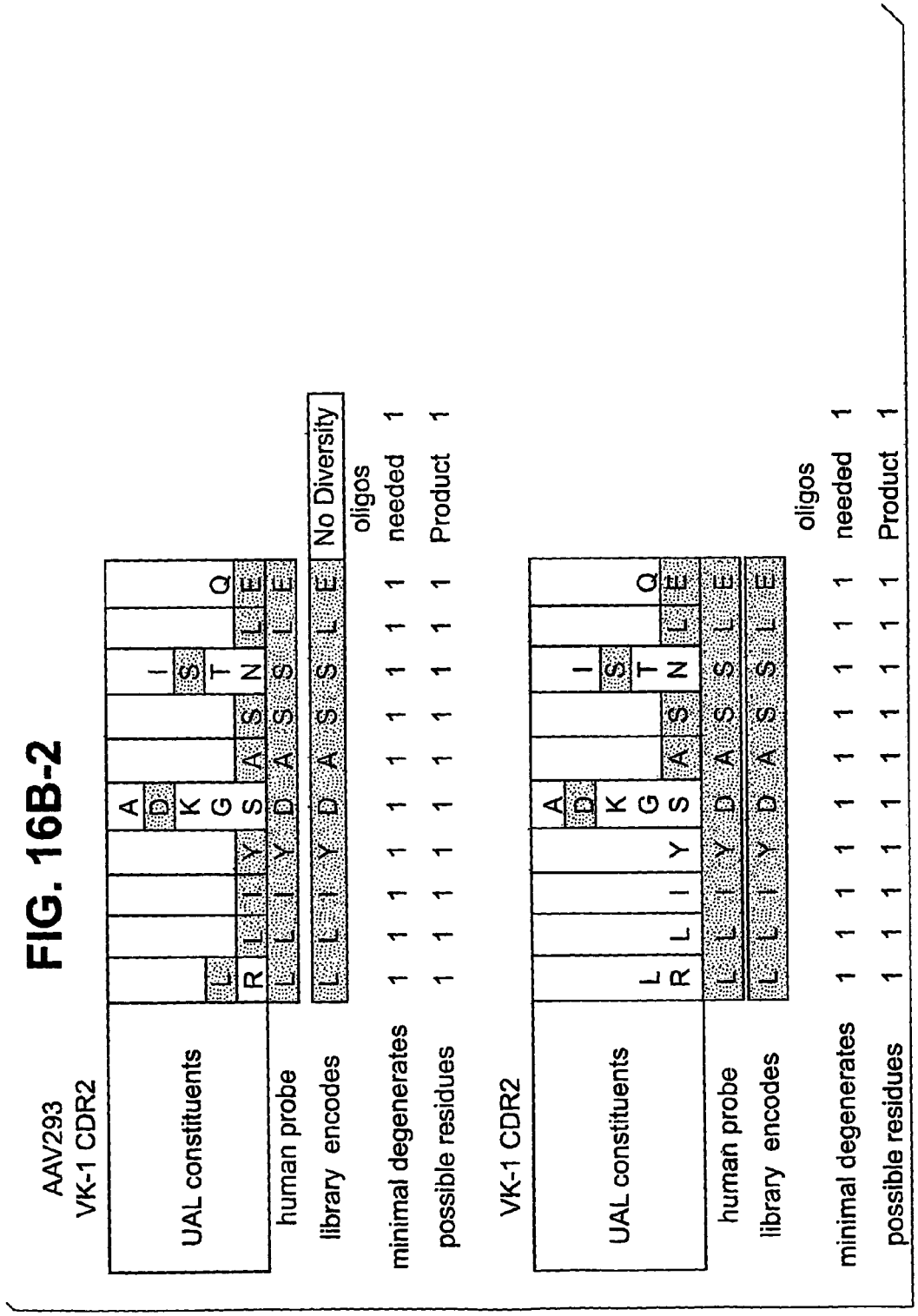
Figures 3, 16B:
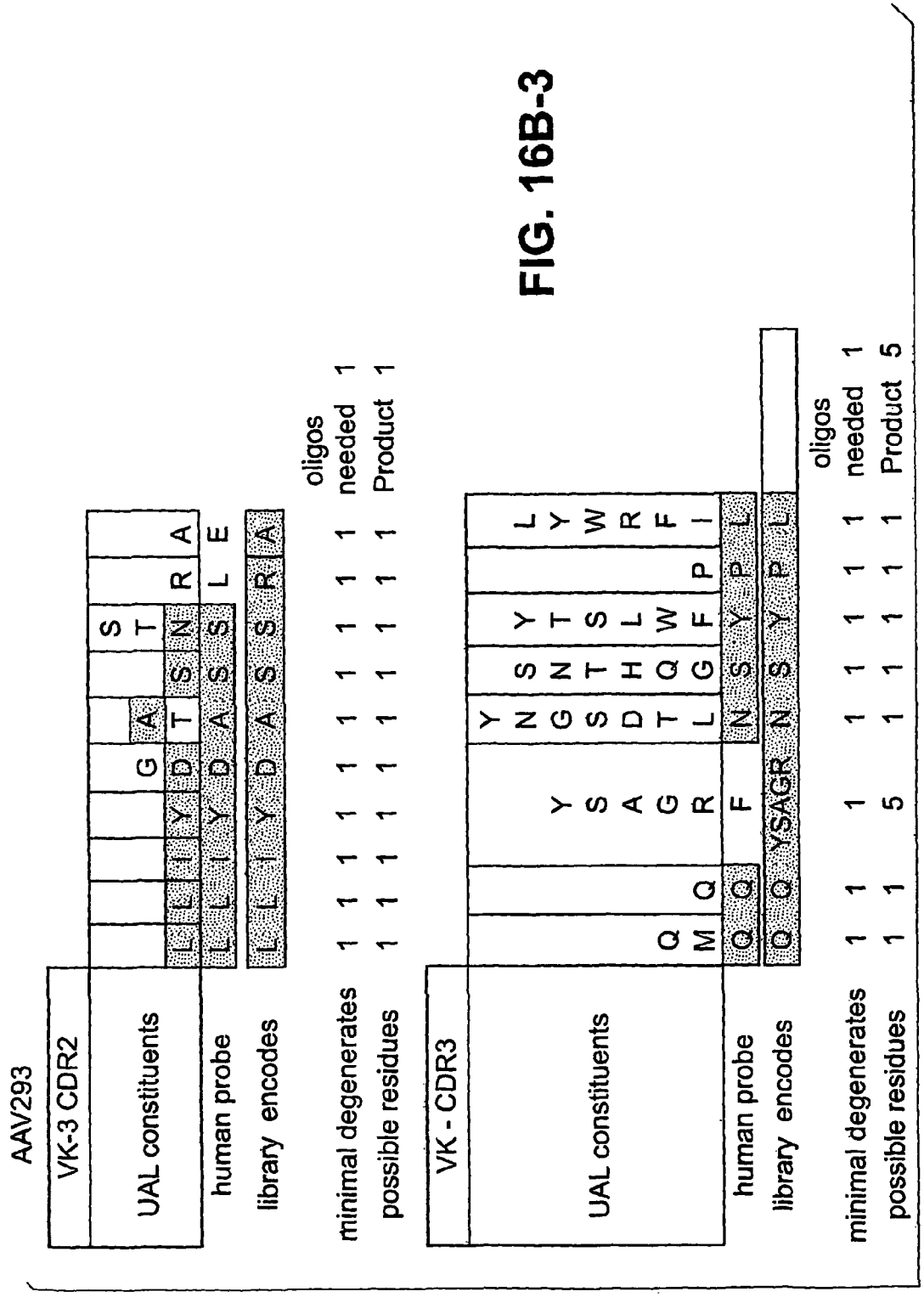

Kappa light chain CDR1, CDR2 and CDR3 sequences for a human AAV293 MCP-1 antibody are "SSALAWY" (SEQ ID NO: 56), "LLIYDASSLE" (SEQ ID NO: 59), and "QQFNSYPL" (SEQ ID NO: 61), respectively. Use of the methods of the invention with the kappa chain CDR1 query sequence yielded cohort library sequences of "S-S-Y/W/D/S-L-A-W-Y" (SEQ ID NO: 57) (diversity 4) and "S-S-N/Y-L-A-W-Y" (SEQ ID NO: 58) (diversity 2) when the query sequence was compared with a human VK-1 CDR1 UAL and a VK-3 CDR1 UAL, respectively (FIG. 16B). Implementation of the invention to query kappa chain CDR2 sequence against a human VK-1 CDR2 UAL yielded a cohort library sequence identical to the query sequence, "L-L-I-Y-D-A-S-S-L-E" (SEQ ID NO: 60), while comparison of the kappa chain CDR2 probe sequence with a human VK-3 CDR2 UAL by the methods of the invention produced a cohort CDR2 library sequence of diversity 1, "L-L-I-Y-D-A-S-S-R-A" (SEQ ID NO: 582). Use of the AAV293 CDR3 as query sequence produced a cohort library CDR3 sequence of "Q-Q-Y/S/A/G/R-N-S-Y-P-L" (SEQ ID NO: 62) when aligned with a VK CDR3 UAL. This kappa chain CDR3 library had a diversity of 5.

Again, the production of a final cohort antibody (or fragment thereof, e.g., Fab, scFv, etc.) library from the various cohort CDR libraries could be performed via independent assortment of cohort CDR library sequences with one another to build both heavy and light chains, and complete antibodies (or fragments thereof), from the cohort CDR libraries identified by the methods of the invention. Such independent assortment of cohort CDR library sequences results in chain and whole antibody cohort library diversities as shown in Table 7 for those cohort libraries generated using human AAV293 MCP-1 antibody query sequences:

TABLE 7

Chain and Whole Antibody Diversities of Combined Cohort CDR Libraries Generated Using Human AAV293 MCP-1 Antibody Probes

| Chain Diversity | | | |
|---|---|---|---|
| H1 Cohorts | H3 Cohorts | K1 Cohorts | K3 Cohorts |
| 5,529,600 | 1,280 | 20 | 10 |
| mAb diversity | | K1 | K3 |
| H1 | | 110,592,000 | 55,296,000 |
| H3 | | 25,600 | 12,800 |

As for other antibodies assessed via the methods of the present invention, even the most diverse of these antibody libraries is of a size (e.g., diversity substantially less than about $10^{12}$) that can be readily displayed and/or screened using currently available methods.

Example 8

Figures 2, 17A:
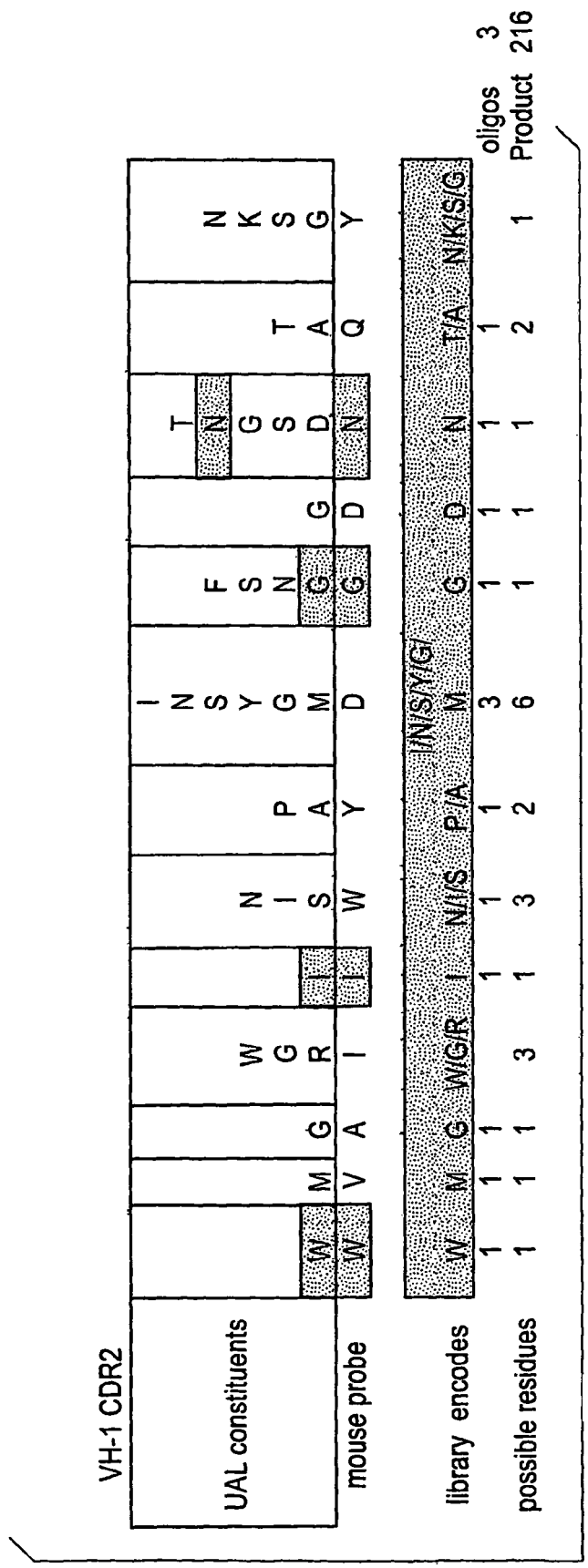
Figures 3, 17A:
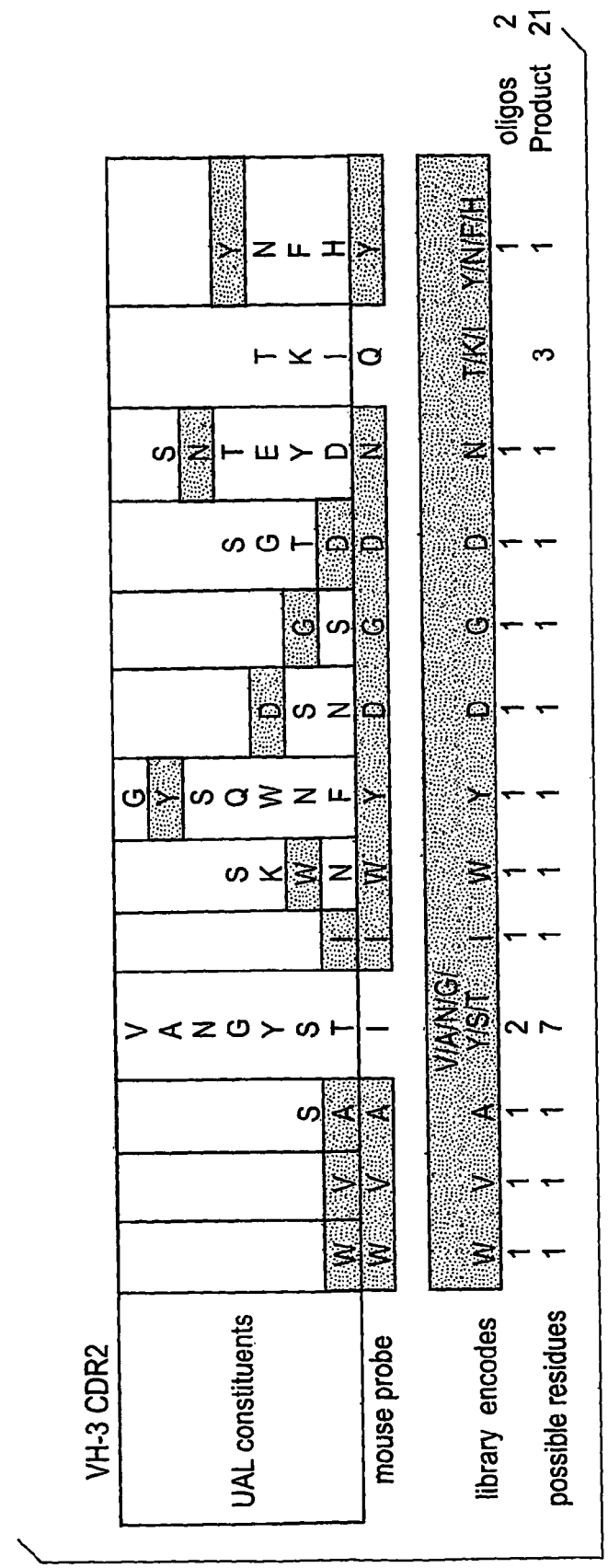
Figures 4, 17A:
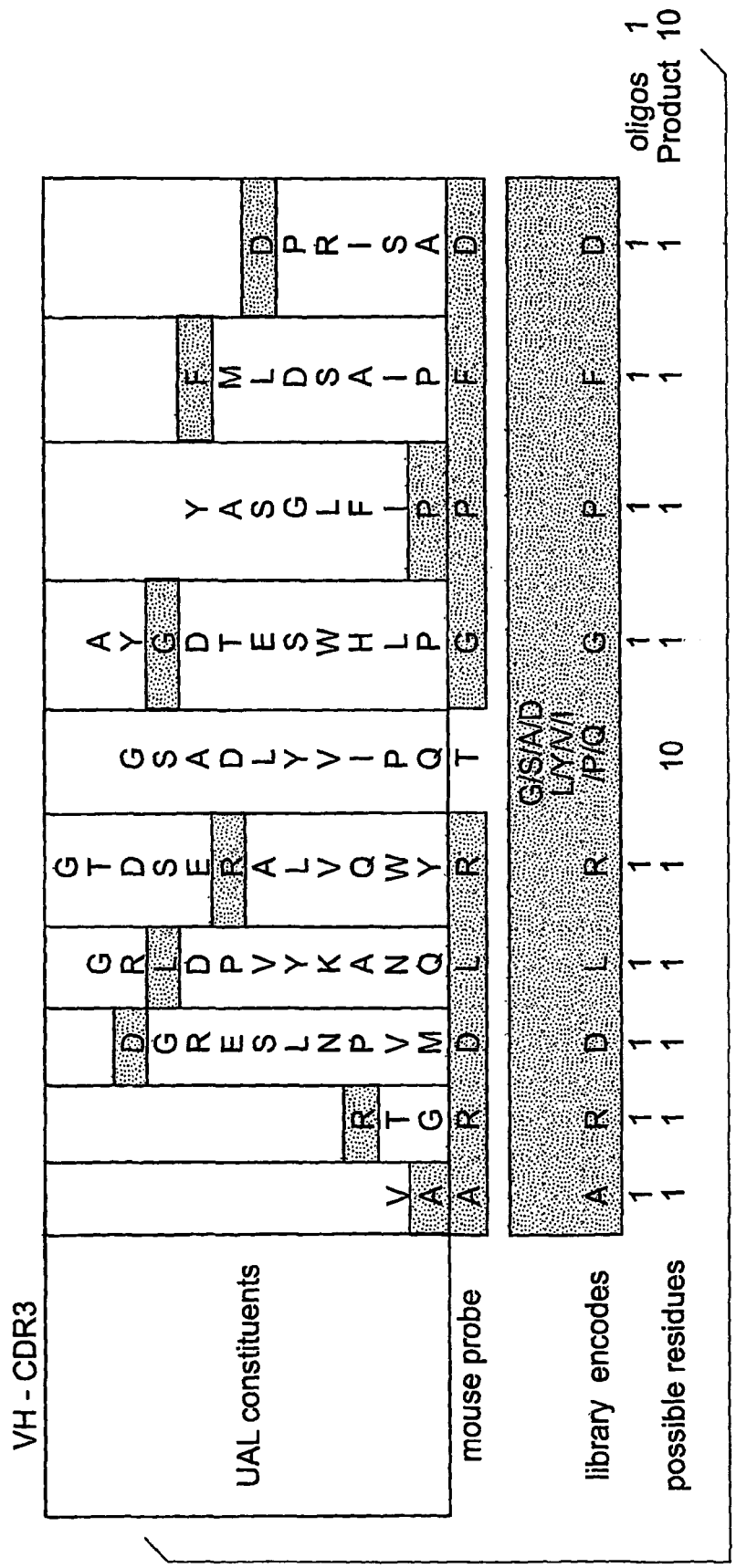

Identification and Generation of a Human ACZ885 Cohort Antibody Library from Mouse Probe CDR Domains Heavy chain CDR1, CDR2 and CDR3 sequences for a mouse ACZ885 antibody are "SVYGMN" (SEQ ID NO: 63), "WVAIIWYDGDNQY" (SEQ ID NO: 66), and "ARDLRT-GPFD" (SEQ ID NO: 69), respectively. Use of the methods of the invention with the mouse ACZ885 heavy chain CDR1 query sequence yielded cohort library sequences of "S-S/N/D/T-Y-G-M-N" (SEQ ID NO: 64) (diversity 4) and "S-S/G/N/D-Y-G-M-N" (SEQ ID NO: 65) (diversity 4) when the query sequence was compared with a human VH-3 CDR1 UAL and a human VH-1 CDR1 UAL, respectively (FIG. 17A). Implementation of the invention to query heavy chain CDR2 sequence against a human VH-1 CDR2 UAL yielded a cohort library sequence with diversity of 216, "W-M-G-W/G/R-I-N/I/S-P/A-I/N/S/Y/G/M-G-D-N-T/A-N/K/S/G" (SEQ ID NO: 67), while comparison of the heavy chain CDR2 probe sequence with a human VH-3 CDR2 UAL by the methods of the invention produced a cohort CDR2 library sequence of diversity 21, "W-V-A-V/A/N/G/N/S/T-I-W-Y-D-G-D-N-T/K/I-Y" (SEQ ID NO: 583). Use of the mouse ACZ885 heavy chain CDR3 as query sequence produced a cohort library CDR3 sequence of "A-R-D-L-R-G/S/A/D/L/Y/V/I/P/Q-G-P-F-D" (SEQ ID NO: 70) when aligned with a VH CDR3 UAL. This heavy chain CDR3 cohort library had a diversity of 10.

Figures 3, 17B:
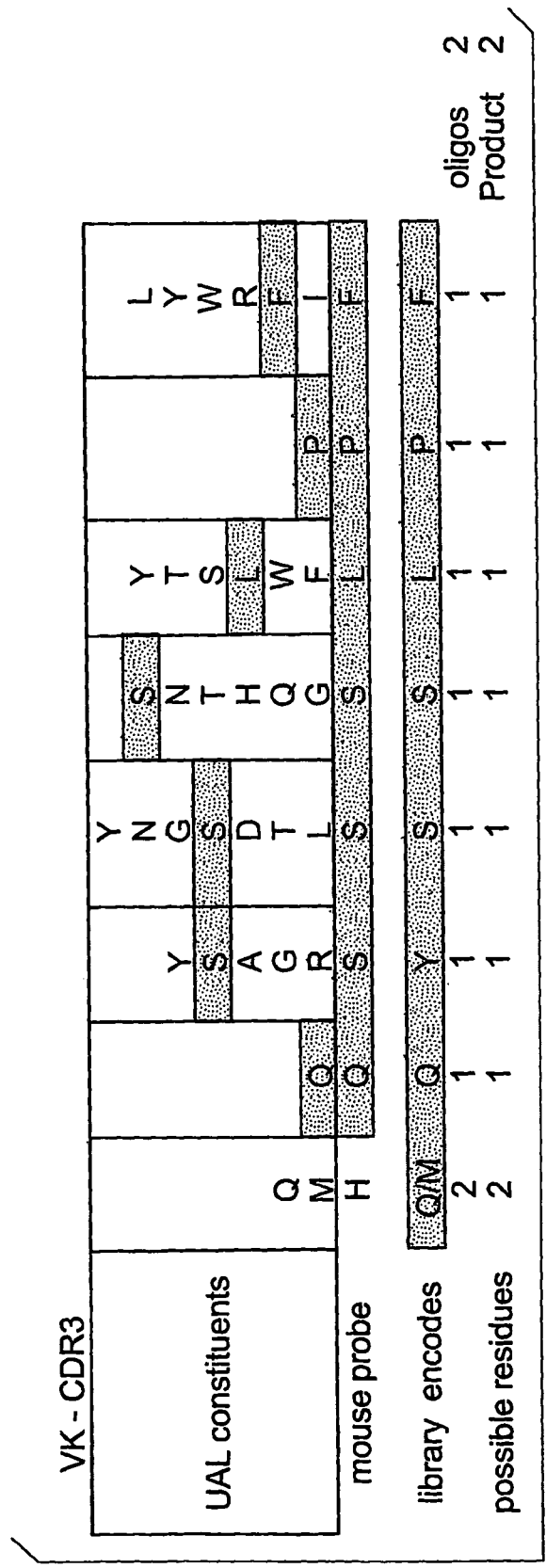

Kappa light chain CDR1, CDR2 and CDR3 sequences for the mouse ACZ885 antibody are "GSSLHWY" (SEQ ID NO: 71), "LLIKYASQSF" (SEQ ID NO: 74), and "HQSSSLPF" (SEQ ID NO: 77), respectively. Use of the methods of the invention with the mouse ACZ885 kappa chain CDR1 query sequence yielded cohort library sequences of "S/R/G/N/Y-S-S-L-A/N-W-Y" (SEQ ID NO: 72) (diversity 10) and "G-S-N/Y-L-A-W-Y" (SEQ ID NO: 73) (diversity 2) when the query sequence was compared with a human VK-1 CDR1 UAL and a VK-3 CDR1 UAL, respectively (FIG. 17B). Implementation of the invention to query kappa chain CDR2 sequence against a human VK-1 CDR2 UAL yielded a cohort library sequence with diversity 40, "L-L-I-Y-A/D/K/G/S-A-S-I/S/T/N-L-Q/E" (SEQ ID NO: 75), while comparison of the kappa chain CDR2 probe sequence with a human VK-3 CDR2 UAL by the methods of the invention produced a cohort CDR2 library sequence of diversity 6, "L-L-I-Y-G/D-A-S-S/T/N-R-A" (SEQ ID NO: 76). Use of the mouse ACZ885 CDR3 as query sequence produced a cohort library CDR3 sequence of "Q/M-Q-S-S-S-L-P-F" (SEQ ID NO: 78) when aligned with a VK CDR3 UAL. This kappa chain CDR3 library had a diversity of 2.

Again, the production of a final cohort antibody (or fragment thereof, e.g., Fab, scFv, etc) library from the various cohort CDR libraries could be performed via independent assortment of cohort CDR library sequences with one another to build both heavy and light chains, and complete antibodies (or fragments thereof), from the cohort CDR libraries identified by the methods of the invention. Such independent assortment of cohort CDR library sequences results in chain and whole antibody cohort library diversities as shown in Table 8 for those cohort libraries generated using mouse ACZ885 antibody query sequences:

TABLE 8

Chain and Whole Antibody Diversities of Combined Cohort CDR Libraries Generated Using Mouse ACZ885 Antibody Probes

| Chain Diversity | | | |
|---|---|---|---|
| H1 Cohorts | H3 Cohorts | K1 Cohorts | K3 Cohorts |
| 8,640 | 840 | 800 | 24 |
| mAb diversity | | K1 | K3 |
| H1 | | 6,912,000 | 207,360 |
| H3 | | 672,000 | 20,160 |

As for other antibodies assessed via the methods of the present invention, even the most diverse of these antibody libraries is of a size (e.g., diversity substantially less than about $10^{12}$) that can be readily displayed and/or screened using currently available methods.

Example 9

Figures 1, 18A:
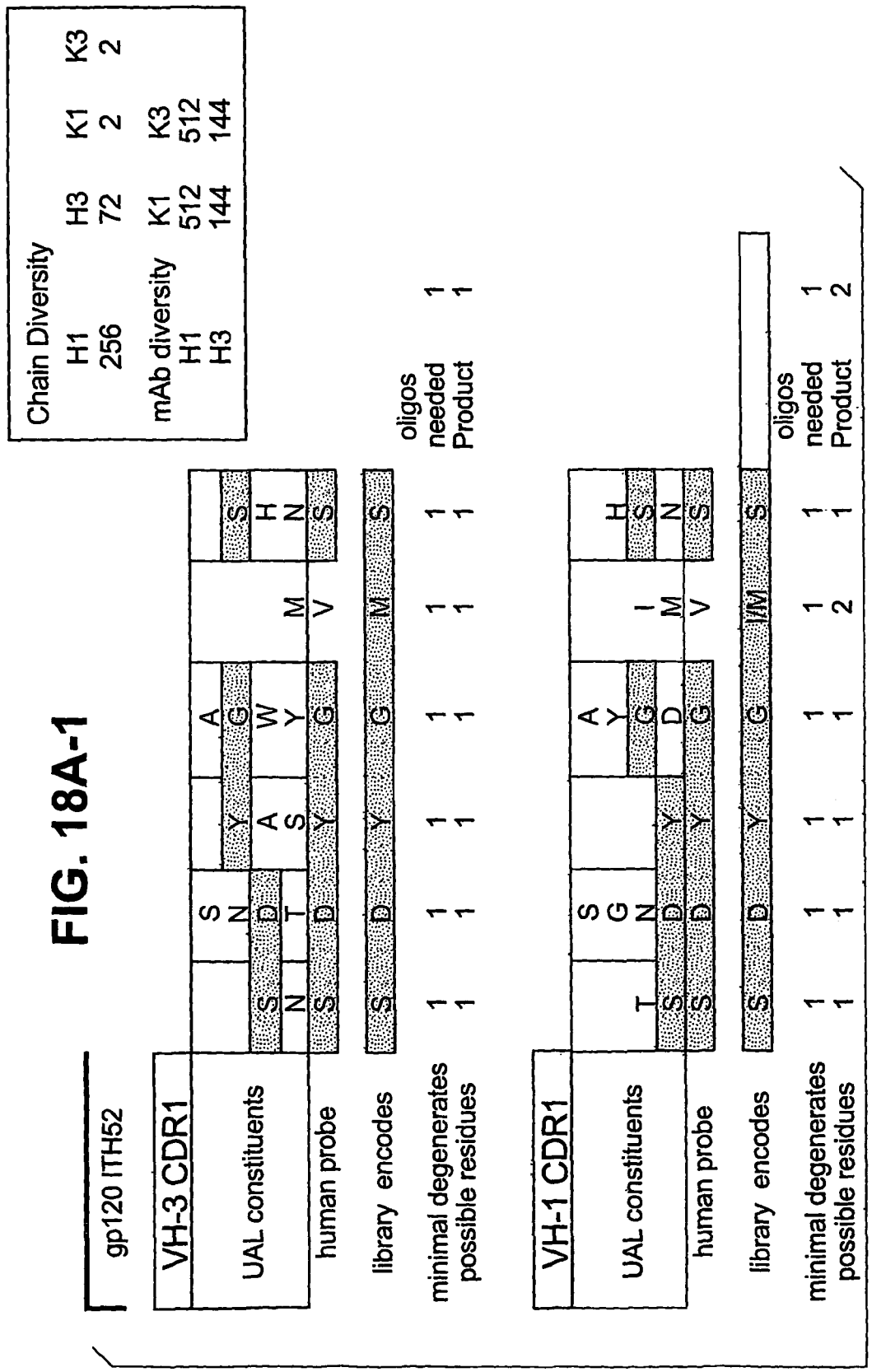
Figures 2, 18A:
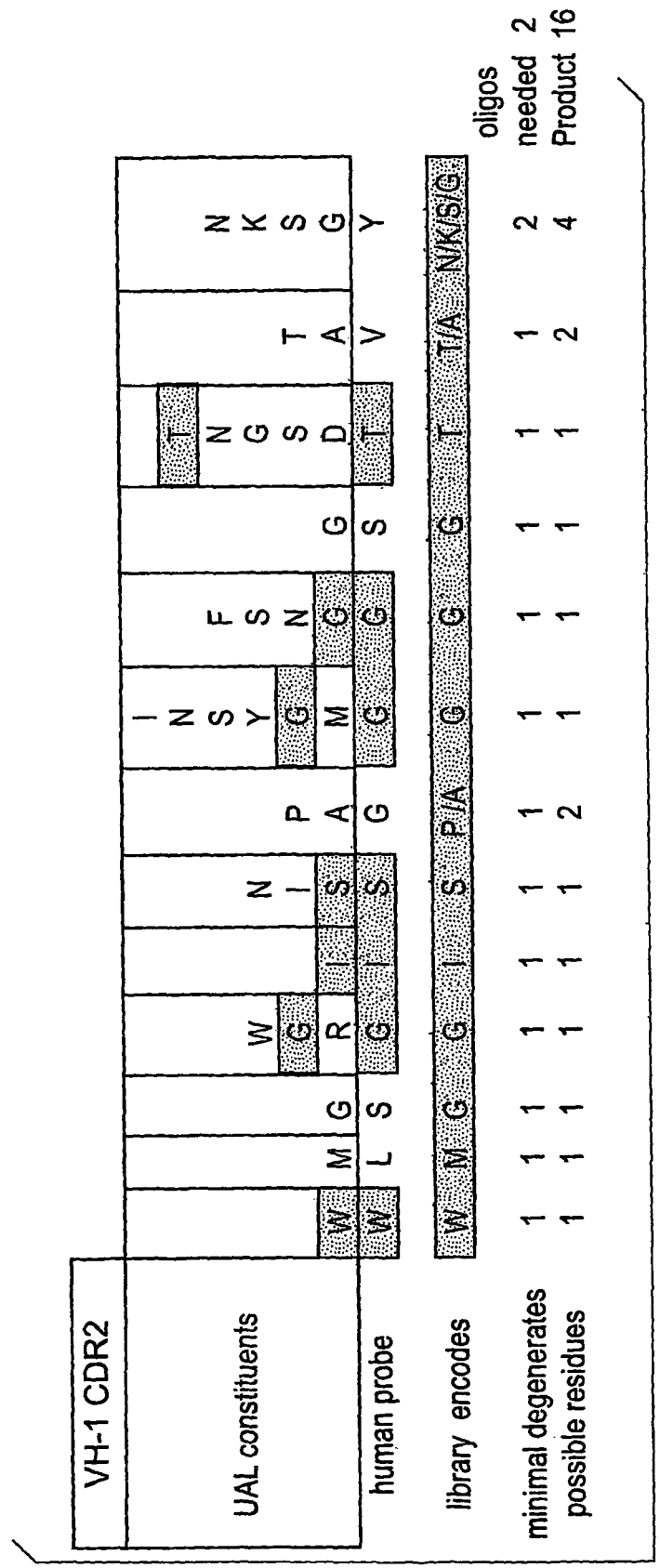
Figures 3, 18A:
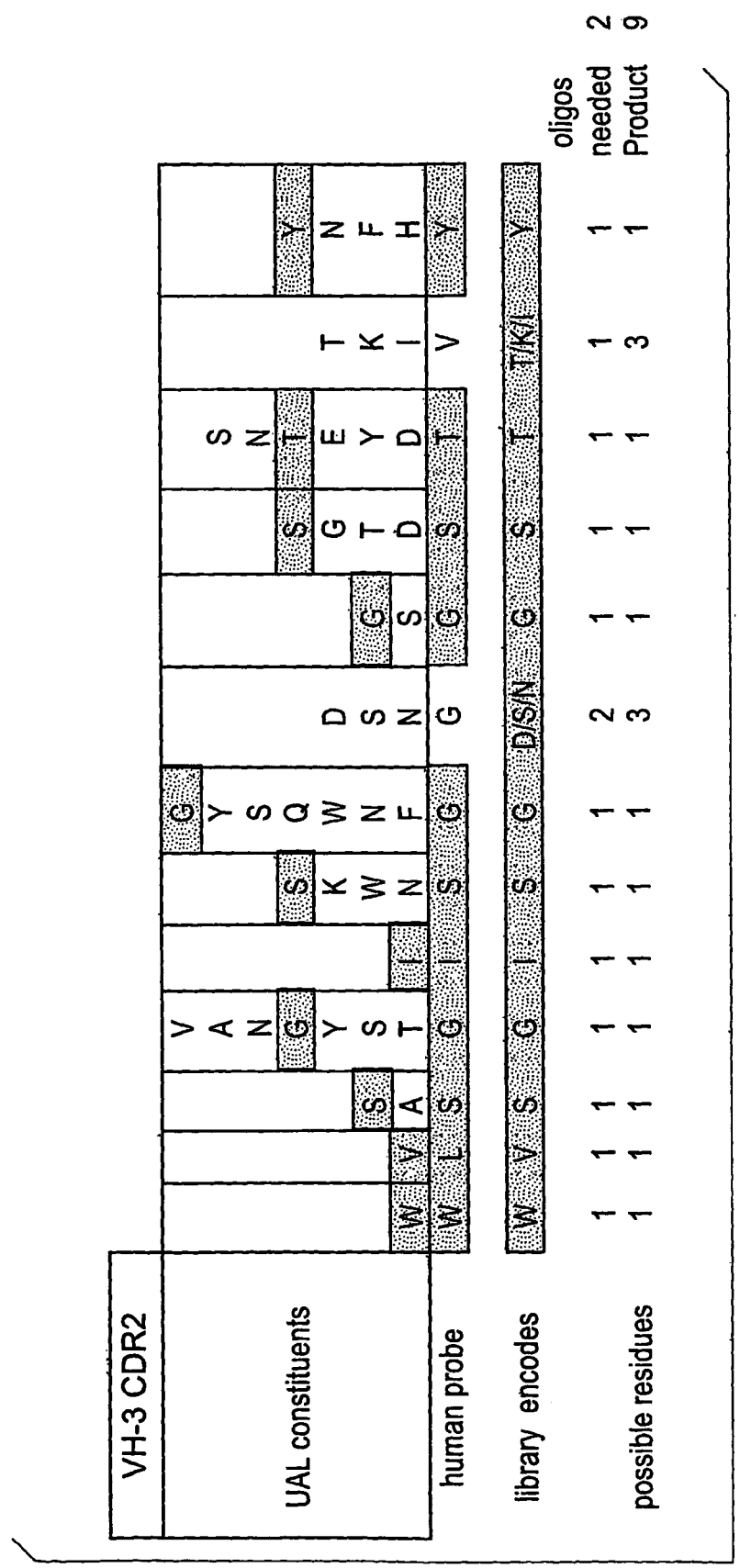
Figures 4, 18A:
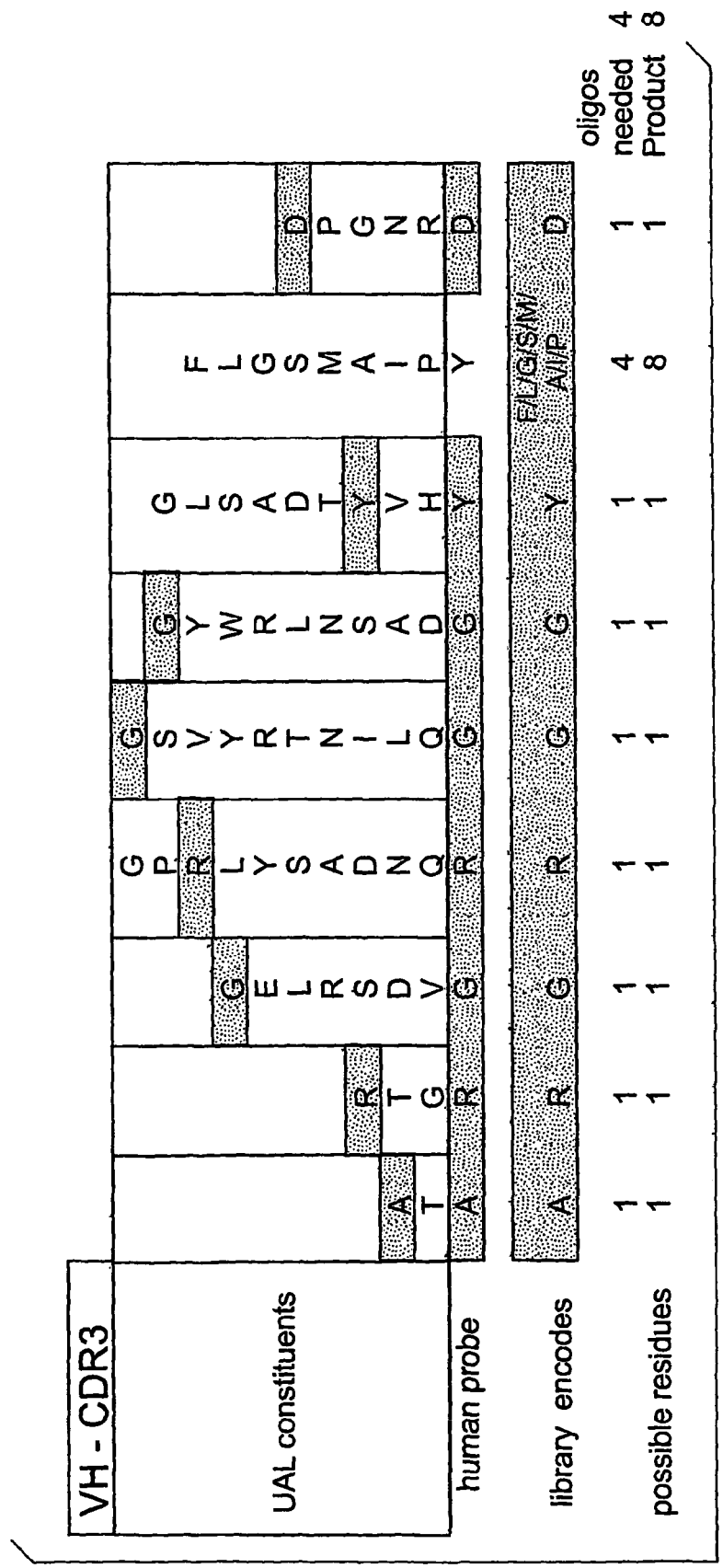

Identification and Generation of a Human gp120 ITH52 Oligo Cohort Antibody Library from Probe CDR Domains Heavy chain CDR1, CDR2 and CDR3 sequences for a human gp120 ITH52 oligo antibody are "SDYGVS" (SEQ ID NO: 79), "WLSGISGGGSTVY" (SEQ ID NO: 82), and "ARDLRTGPFD" (SEQ ID NO: 85), respectively. Use of the methods of the invention with the gp120 ITH52 oligo antibody heavy chain CDR1 query sequence yielded cohort library sequences of "S-D-Y-G-M-S" (SEQ ID NO: 80) (diversity 1) and "S-D-Y-G-I/M-S" (SEQ ID NO: 81) (diversity 2) when the query sequence was compared with a human VH-3 CDR1 UAL and a human VH-1 CDR1 UAL, respectively (FIG. 18A). Implementation of the invention to query heavy chain CDR2 sequence against a human VH-1 CDR2 UAL yielded a cohort library sequence with diversity of 16, "W-M-G-G-I-S-P/A-G-G-G-T-T/A-N/K/S/G" (SEQ ID NO: 83), while comparison of the heavy chain CDR2 probe sequence with a human VH-3 CDR2 UAL by the methods of the invention produced a cohort CDR2 library sequence of diversity 9, "W-V-S-G-I-S-G-D/S/N-G-T-T/K/I-Y" (SEQ ID NO: 84). Use of the gp120 ITH52 oligo antibody heavy chain CDR3 as query sequence produced a cohort library CDR3 sequence of "A-R-G-R-G-G-Y-F/L/G/S/M/A/I/P-D" (SEQ ID NO: 86) when aligned with a VH CDR3 UAL. This heavy chain CDR3 cohort library had a diversity of 8.

Figures 1, 18B:
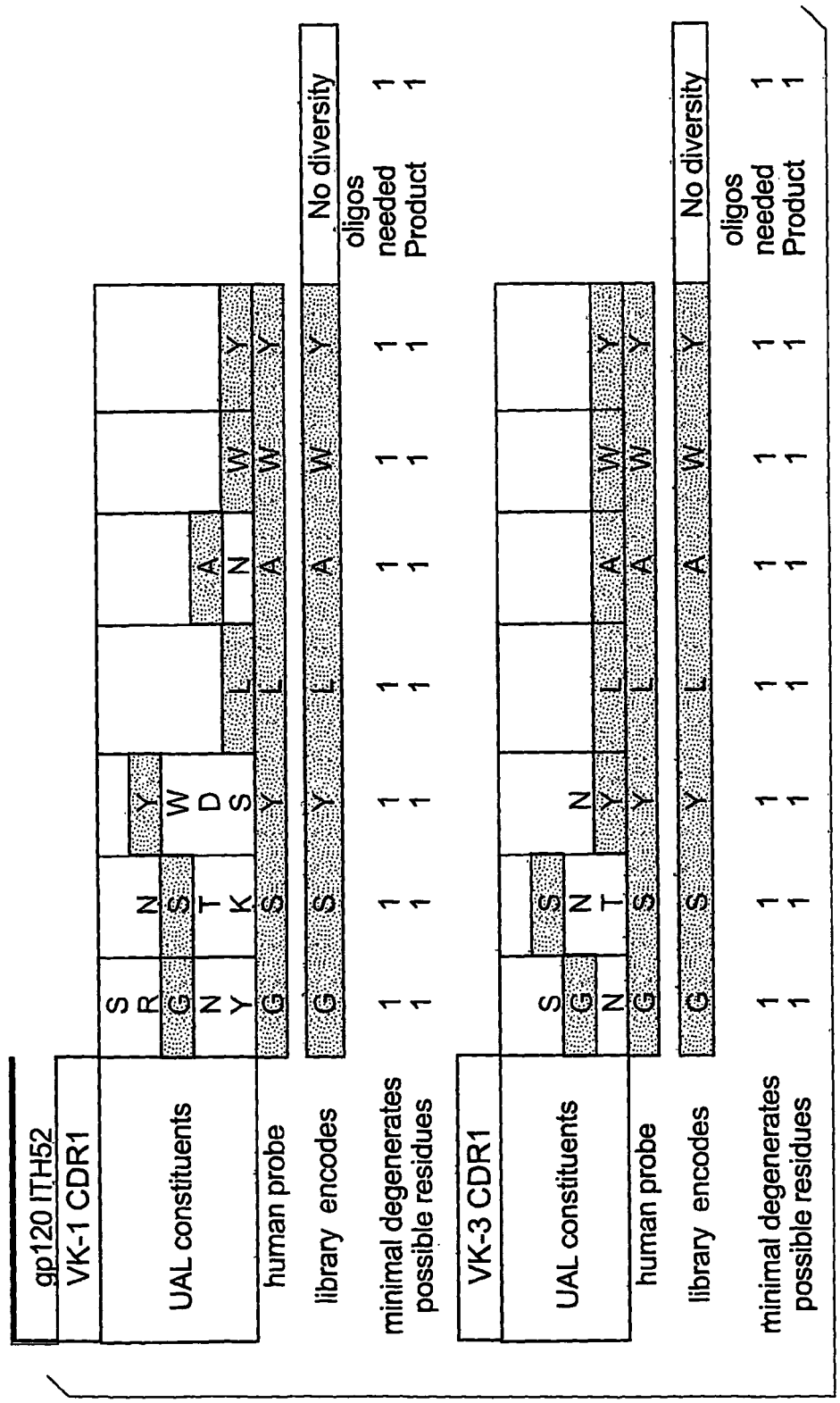
Figures 3, 18B:
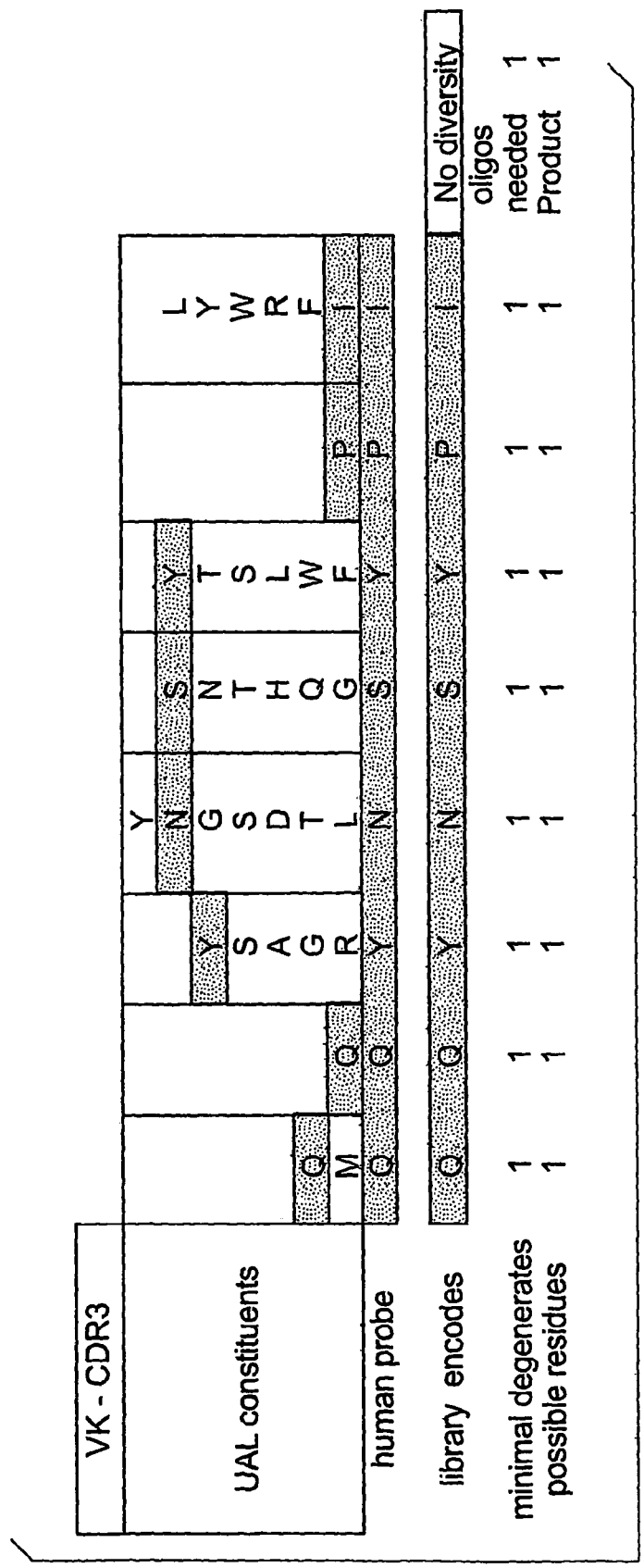

Kappa light chain CDR1, CDR2 and CDR3 sequences for the human gp120 ITH52 oligo antibody are "GSYLAWY" (SEQ ID NO: 87), "SLIYAASSLQ" (SEQ ID NO: 89), and "QQYNSYPI" (SEQ ID NO: 92), respectively. Use of the methods of the invention with the gp120 ITH52 oligo antibody kappa chain CDR1 query sequence yielded identical cohort library sequences of "G-S-Y-L-A-W-Y" (SEQ ID NO: 88) (no diversity) when the query sequence was compared with a human VK-1 CDR1 UAL and a VK-3 CDR1 UAL (FIG. 18B). Implementation of the invention to query kappa chain CDR2 sequence against a human VK-1 CDR2 UAL yielded a cohort library sequence with diversity 2, "L/R-L-I-Y-A-A-S-S-L-Q" (SEQ ID NO: 90), while comparison of the kappa chain CDR2 probe sequence with a human VK-3 CDR2 UAL by the methods of the invention produced a cohort CDR2 library sequence of diversity 2, "L-L-I-Y-G/D-A-S-S-R-A" (SEQ ID NO: 91). Use of the gp120 ITH52 oligo antibody CDR3 as query sequence produced an identical cohort library CDR3 sequence with no additional diversity of "Q-Q-Y-N-S-Y-P-I" (SEQ ID NO: 93) when aligned with a VK CDR3 UAL.

Again, the production of a final cohort antibody (or fragment thereof, e.g., Fab, scFv, etc.) library from the various cohort CDR libraries could be performed via independent assortment of cohort CDR library sequences with one another to build both heavy and light chains, and complete antibodies (or fragments thereof), from the cohort CDR libraries identified by the methods of the invention. Such independent assortment of cohort CDR library sequences results in chain and whole antibody cohort library diversities as shown in Table 9 for those cohort libraries generated using human gp120 ITH52 oligo antibody query sequences:

TABLE 9

Chain and Whole Antibody Diversities of Combined Cohort CDR Libraries Generated Using Human gp120 ITH52 Oligo Antibody Probes

| Chain Diversity | | | |
|---|---|---|---|
| H1 Cohorts | H3 Cohorts | K1 Cohorts | K3 Cohorts |
| 256 | 72 | 2 | 2 |

| mAb diversity | K1 | K3 |
|---|---|---|
| H1 | 512 | 512 |
| H3 | 144 | 144 |

As for other antibodies assessed via the methods of the present invention, even the most diverse of these antibody libraries is of a size (e.g., diversity substantially less than about $10^{12}$) that can be readily displayed and/or screened using currently available methods.

Example 10

Figures 2, 19A:
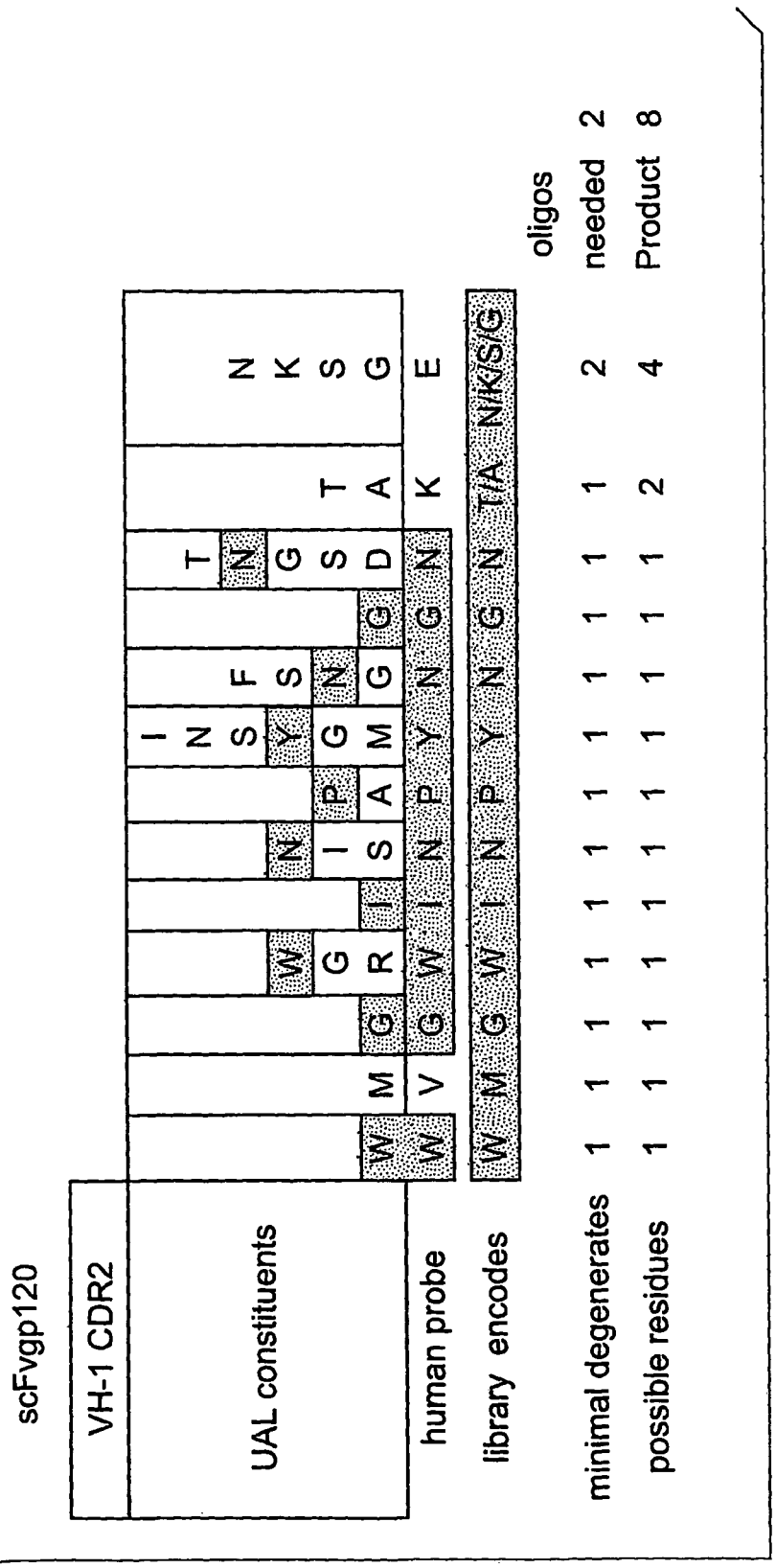

Identification and Generation of a Human scFv gp120 Cohort Antibody Library from Probe CDR Domains Heavy chain CDR1, CDR2 and CDR3 sequences for a human scFv gp120 antibody are "SNFVIH" (SEQ ID NO: 94), "WVGWINPYNGNKE" (SEQ ID NO: 97), and "ARVGPYSWDDSPQDNYYMD" (SEQ ID NO: 100), respectively. Use of the methods of the invention with the scFv gp120 antibody heavy chain CDR1 query sequence yielded cohort library sequences of "S-N-Y/A/S-A/G/W/Y-M-H" (SEQ ID NO: 95) (diversity 12) and "S-N-Y-A/Y/G/D-I-H" (SEQ ID NO: 96) (diversity 4) when the query sequence was compared with a human VH-3 CDR1 UAL and a human VH-1 CDR1 UAL, respectively (FIG. 19A). Implementation of the invention to query heavy chain CDR2 sequence against a human VH-1 CDR2 UAL yielded a cohort library sequence with diversity of 8, "W-M-G-W-I-N-P-Y-N-G-N-T/A-N/K/S/G" (SEQ ID NO: 98), while comparison of the heavy chain CDR2 probe sequence with a human VH-3 CDR2 UAL by the methods of the invention produced a cohort CDR2 library sequence of diversity 7056, "W-V-S/A-V/A/N/G/Y/S/T-I-N-G/Y/S/Q/W/N/F-D/S/N-G/S-G-N-K-Y/N/F/H" (SEQ ID NO: 99). Use of the scFv gp120 antibody heavy chain CDR3 as query sequence produced an identical cohort library CDR3 sequence of "A-R-V-G-P-Y-S-W-D-D-S-P-Q-D-N-Y-Y-M-D" (SEQ ID NO: 101) (no diversity) when aligned with a VH CDR3 UAL.

Figure 19B-2:
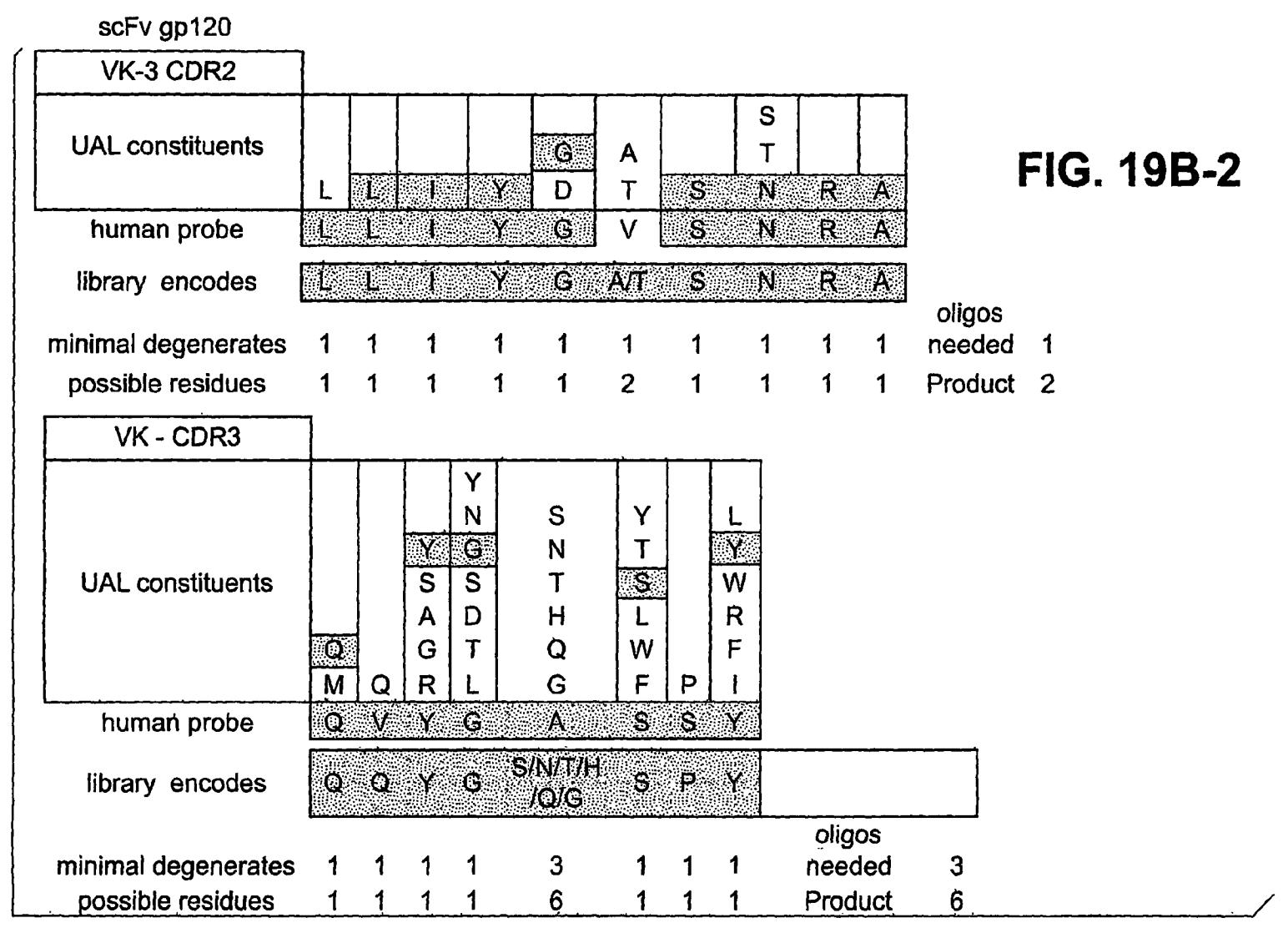

Kappa light chain CDR1, CDR2 and CDR3 sequences for the scFv gp120 antibody are "RSRRVAWY" (SEQ ID NO: 102), "LLIYGVSNRA" (SEQ ID NO: 104), and "QVYGA-SSY" (SEQ ID NO: 107), respectively. Use of the methods of the invention with the scFv gp120 antibody kappa chain CDR1 query sequence yielded a cohort library sequence of "S/N-S/N-S/N/T-Y-L-A-W-Y" (SEQ ID NO: 103) (diversity 12) when the query sequence was compared with a human VK-3 CDR1 UAL. Implementation of the invention to query kappa chain CDR2 sequence against a human VK-3 CDR2 UAL yielded a cohort library sequence with diversity 2, "L-L-I-Y-G-A/T-S-N-R-A" (SEQ ID NO: 106), while a query of the sequence against a human VK-1 CDR2 UAL yielded a distinct cohort library sequence of diversity 2, "L-L-I-Y-G-A-S-N-L-Q/E" (SEQ ID NO: 105) (FIG. 19B). Use of the scFv gp120 antibody CDR3 as query sequence produced a cohort library CDR3 sequence of "Q-Q-Y-G-S/N/T/H/Q/G-S-P-Y" (SEQ ID NO: 108) when aligned with a VK CDR3 UAL. This kappa chain CDR3 library had a diversity of 6.

Again, the production of a final cohort antibody (or fragment thereof, e.g., Fab, scFv, etc.) library from the various cohort CDR libraries could be performed via independent assortment of cohort CDR library sequences with one another to build both heavy and light chains, and complete antibodies (or fragments thereof), from the cohort CDR libraries identified by the methods of the invention. Such independent assortment of cohort CDR library sequences results in chain and whole antibody cohort library diversities as shown in Table 10 for those cohort libraries generated using scFv gp120 antibody query sequences:

TABLE 10

Chain and Whole Antibody Diversities of Combined Cohort CDR
Libraries Generated Using Human scFv gp120 Antibody Probes

| Chain Diversity | | |
|---|---|---|
| H1 Cohorts | H3 Cohorts | K3 Cohorts |
| 32 | 84,672 | 144 |

| mAb diversity | K3 |
|---|---|
| H1 | 4,608 |
| H3 | 12,192,768 |

As for other antibodies assessed via the methods of the present invention, even the most diverse of these antibody libraries is of a size (e.g., diversity substantially less than about $10^{12}$) that can be readily displayed and/or screened using currently available methods.

Example 11

Figure 20A-1:
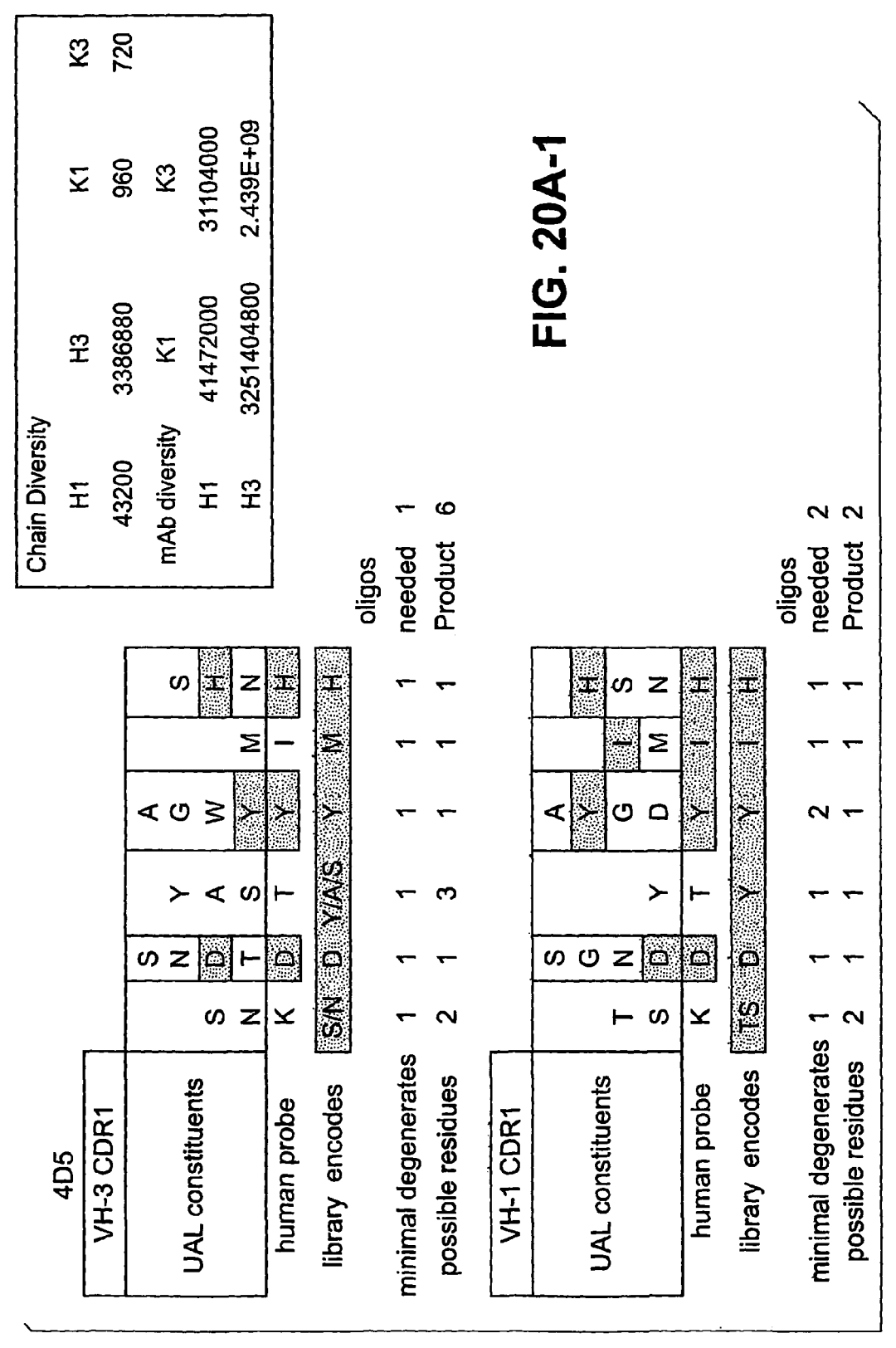
Figure 20A-3:
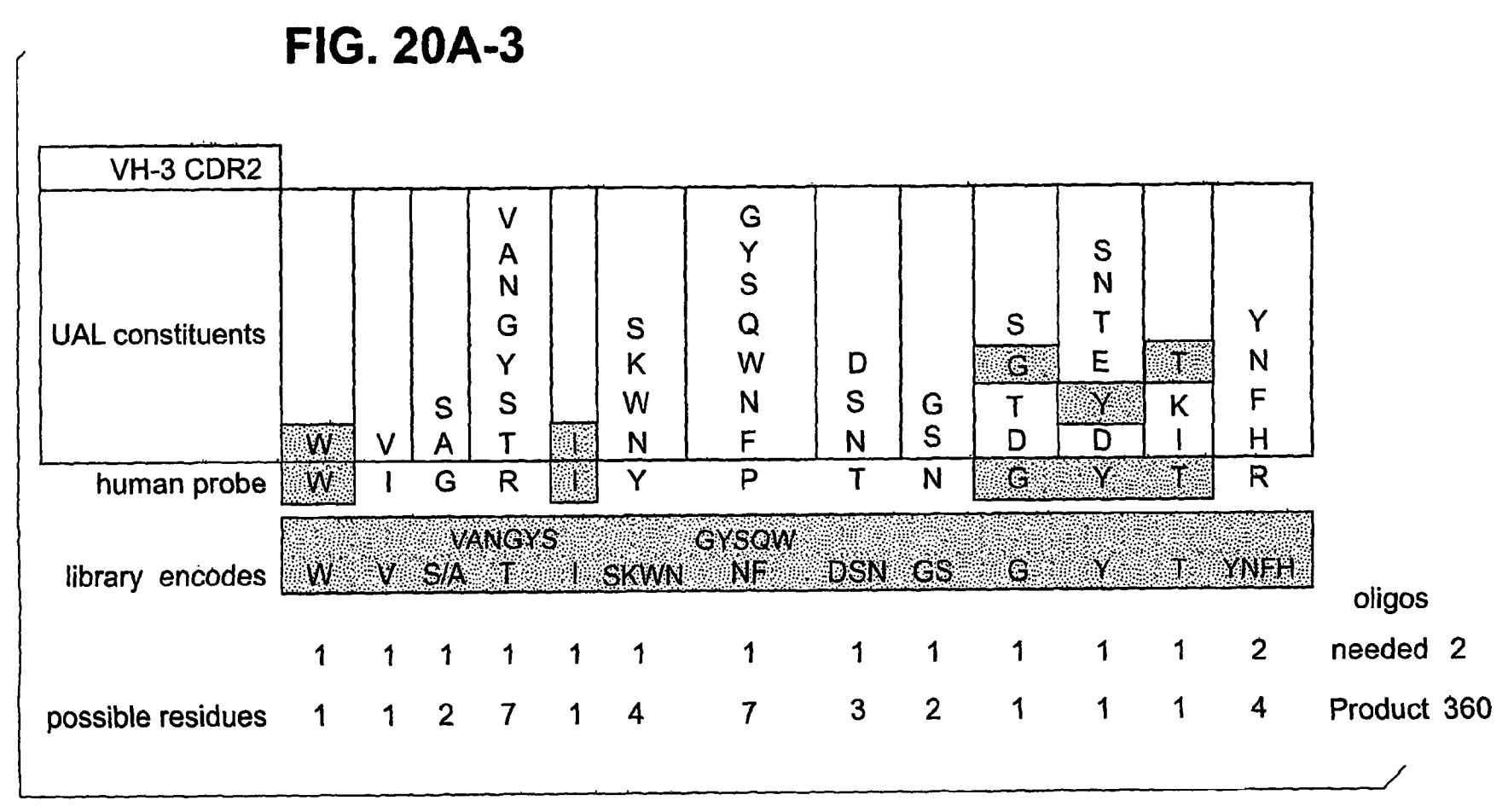

Identification and Generation of a Herceptin 4D5 Cohort Antibody Library from Probe CDR Domains Heavy chain CDR1, CDR2 and CDR3 sequences for a human Herceptin 4D5 antibody are "KDTYIH" (SEQ ID NO: 109), "WIGRIYPTNGYTR" (SEQ ID NO: 112), and "SRWGGDGFYAMD" (SEQ ID NO: 115), respectively. Use of the methods of the invention with the heavy chain CDR1 query sequence yielded cohort library sequences of "S/N-D-Y/A/S-Y-M-H" (SEQ ID NO: 110) (diversity 6) and "T/S-D-Y-Y-I-H" (SEQ ID NO: 111) (diversity 2) when the query sequence was compared with a human VH3 CDR1 UAL and a human VH-1 CDR1 UAL, respectively (FIG. 20A). Implementation of the invention to query heavy chain CDR2 sequence against a human VH-1 CDR2 UAL yielded a cohort library sequence with diversity of 360, "W-M-G-R-I-N/I/S-P-I/N/S/Y/G/M-N-G-T/N/G/S/D-T-N/K/S/G" (SEQ ID NO: 113), while comparison of the heavy chain CDR2 probe sequence with a human VH-3 CDR2 UAL by the methods of the invention produced a cohort CDR2 library sequence of diversity 9408, "W-V-S/A-V/A/N/G/Y/S/T-I-S/K/W/N-G/Y/S/Q/W/N/F-D/S/N-G/S-G-Y-T-Y/N/F/H" (SEQ ID NO: 114). Use of the Herceptin 4D5 heavy chain CDR3 as query sequence produced a cohort library CDR3 sequence of "A-R-G/D/E/R/V/A-G-G-D-G-S/G/Y/L/T/A/R/D/E/N-Y-A-M-D" (SEQ ID NO: 116) when aligned with a VH CDR3 UAL. This heavy chain CDR3 cohort library had a diversity of 60.

Figures 3, 20B:
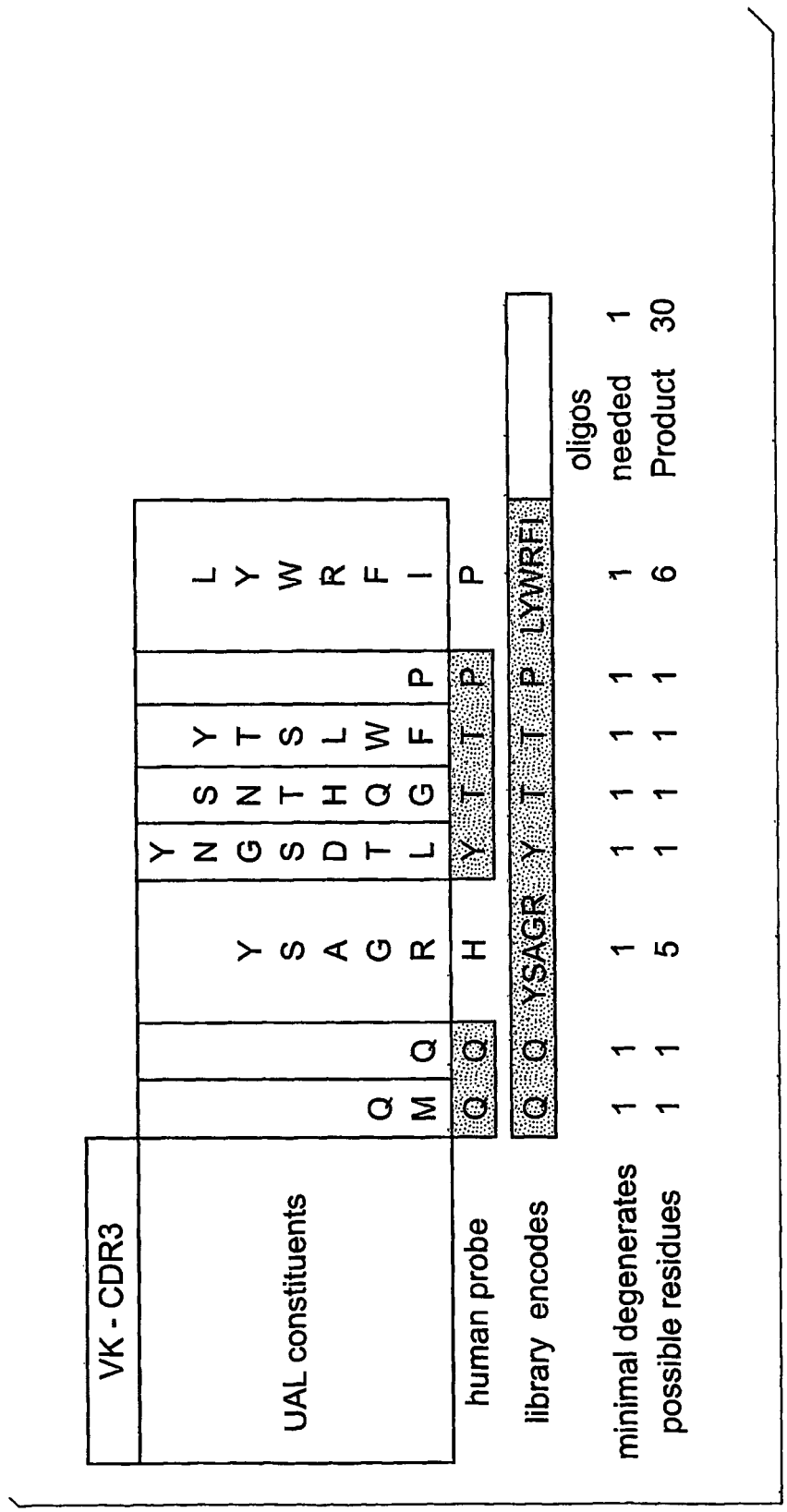

Kappa light chain CDR1, CDR2 and CDR3 sequences for the Herceptin 4D5 antibody are "NTAVAWY" (SEQ ID NO: 117), "LLIYSASFRY" (SEQ ID NO: 120), and "QQHYTTPP" (SEQ ID NO: 122), respectively. Use of the methods of the invention with the kappa chain CDR1 query sequence yielded cohort library sequences of "N-T-Y/W/D/S-L-A-W-Y" (SEQ ID NO: 118) (diversity 4) and "N-T-N-L-A-W-Y" (SEQ ID NO: 119) (diversity 2) when the query sequence was compared with a human VK-1 CDR1 UAL and a VK-3 CDR1 UAL, respectively (FIG. 20B). Implementation of the invention to query kappa chain CDR2 sequence against a human VK-1 CDR2 UAL yielded a cohort library sequence with diversity 8, "L-L-I-Y-S-A-S-I/S/T/N-L-Q/E" (SEQ ID NO: 121), while comparison of the kappa chain CDR2 probe sequence with a human VK-3 CDR2 UAL by the methods of the invention produced a cohort CDR2 library sequence of diversity 12, "L-L-I-Y-G/D-A/T-S-S/T/N-R-A" (SEQ ID NO: 122). Use of the Herceptin 4D5 CDR3 as query sequence produced a cohort library CDR3 sequence of "Q-Q-Y/S/A/G/R-Y-T-T-P-L/Y/W/R/F/I" (SEQ ID NO: 124) when aligned with a VK CDR3 UAL. This kappa chain CDR3 library had a diversity of 30.

Again, the production of a final cohort antibody (or fragment thereof, e.g., Fab, scFv, etc.) library from the various cohort CDR libraries could be performed via independent assortment of cohort CDR library sequences with one another to build both heavy and light chains, and complete antibodies (or fragments thereof), from the cohort CDR libraries identified by the methods of the invention. Such independent assortment of cohort CDR library sequences results in chain and whole antibody cohort library diversities as shown in Table 11 for those cohort libraries generated using human Herceptin 4D5 antibody query sequences:

TABLE 11

Chain and Whole Antibody Diversities of Combined Cohort CDR
Libraries Generated Using Human Herceptin 4D5 Antibody Probes

| Chain Diversity | | | |
|---|---|---|---|
| H1 Cohorts | H3 Cohorts | K1 Cohorts | K3 Cohorts |
| 43,200 | 3,386,880 | 960 | 360 |

| mAb diversity | K1 | K3 |
|---|---|---|
| H1 | 41,472,000 | 15,552,000 |
| H3 | $3.251 \times 10^9$ | $1.219 \times 10^9$ |

As for other antibodies assessed via the methods of the present invention, even the most diverse of these antibody libraries is of a size (e.g., diversity substantially less than about $10^{12}$) that can be readily displayed and/or screened using currently available methods.

Example 12

Figures 2, 21A:
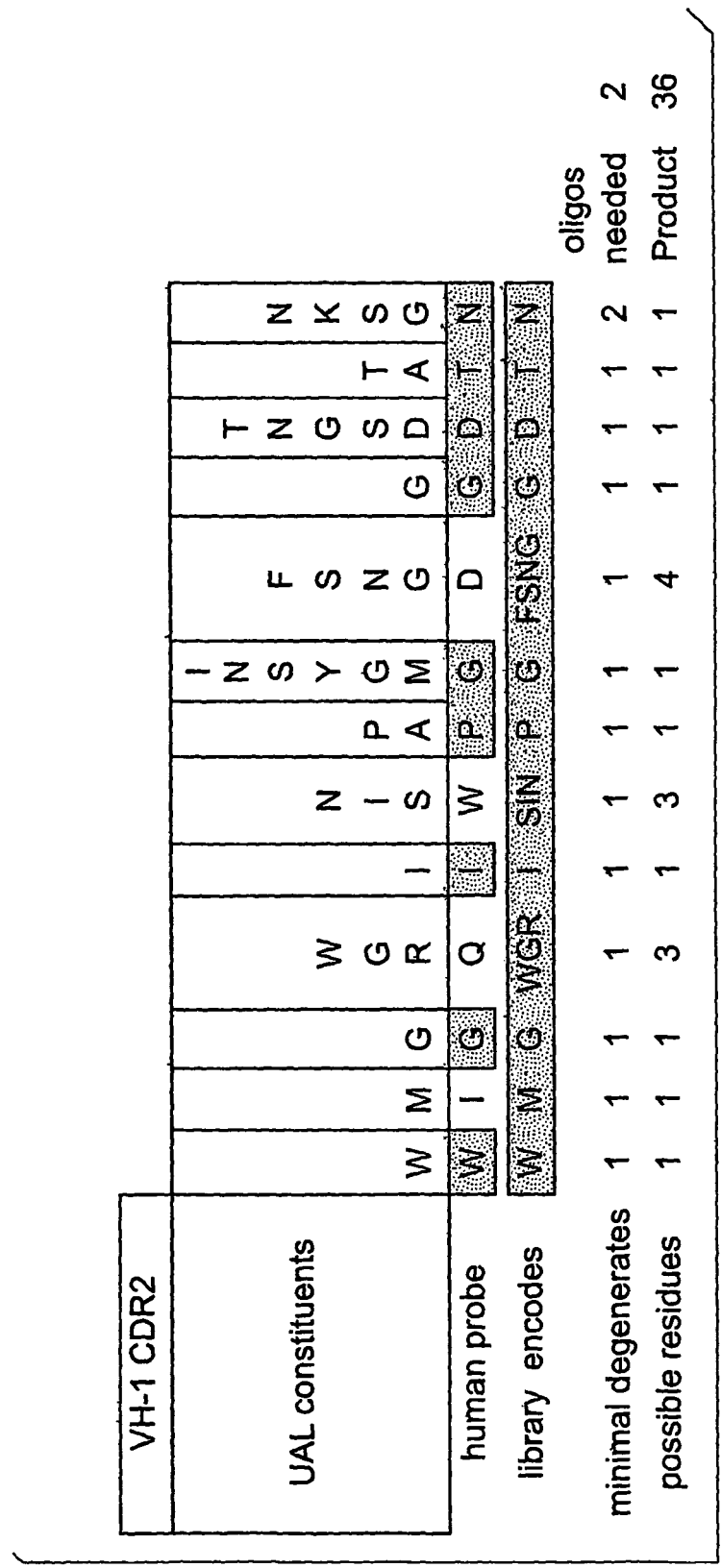

Identification and Generation of a CD19 HD37 Cohort Antibody Library from Probe CDR Domains Heavy chain CDR1, CDR2 and CDR3 sequences for a human CD19 HD37 antibody are "SSYWMN" (SEQ ID NO: 125), "WIGQIWPGDGDTN" (SEQ ID NO: 128), and "ARRETTTVGRYYYAMD" (SEQ ID NO: 131), respectively. Use of the methods of the invention with the heavy chain CDR1 query sequence yielded cohort library sequences of "S-S-Y-W-M-N" (SEQ ID NO: 126) (no diversity) and "S-Y-A/Y/G/D-M-N" (SEQ ID NO: 127) (diversity 4) when the query sequence was compared with a human VH-3 CDR1 UAL and a VH-1 CDR1 UAL, respectively (FIG. 21A). Implementation of the invention to query heavy chain CDR2 sequence against a human VH-1 CDR2 UAL yielded a cohort library sequence with diversity of 36, "W-M-G-W/G/R-I-N/I/S-P-G-F/S/N/G-G-D-T-N" (SEQ ID NO: 129), while comparison of the heavy chain CDR2 probe sequence with a human VH-3 CDR2 UAL by the methods of the invention produced a cohort CDR2 library sequence of diversity 2352, "W-V-S/A-V/A/N/G/Y/S/T-I-S/K/W/N-G/Y/S/Q/W/N/F-D/S/N-G/S-G-D-T-N" (SEQ ID NO: 130). Use of the CD19 HD37 heavy chain CDR3 as query sequence produced a cohort library CDR3 sequence of diversity 9, "A-R-R-E-T-T-G/S/Y/A/T/D/R/F/W-G-R-Y-Y-Y-A-M-D" (SEQ ID NO: 132) when aligned with a VH CDR3 UAL.

Figures 3, 21B:
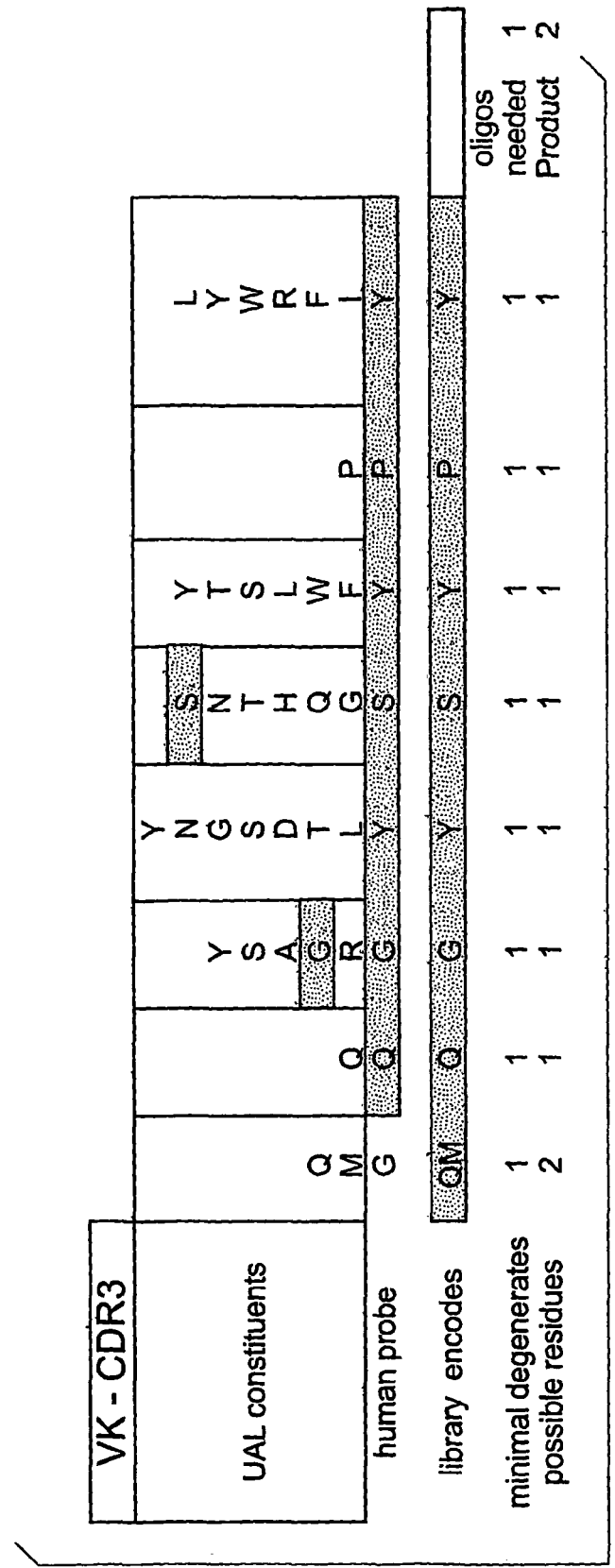

Kappa light chain CDR1, CDR2 and CDR3 sequences for the CD19 HD37 antibody are "VTYVSWY" (SEQ ID NO: 133), "LLIYGASNRY" (SEQ ID NO: 136), and "GQGYSYPY" (SEQ ID NO: 139), respectively. Use of the methods of the invention with the kappa chain CDR1 query sequence yielded cohort library sequences of "S/R/G/N/Y-T-Y-L-A/N-W-Y" (SEQ ID NO: 134) (diversity 10) and "S/G/N-T-Y-L-A-W-Y" (SEQ ID NO: 135) (diversity 3) when the query sequence was compared with a human VK-1 CDR1 UAL and a VK-3 CDR1 UAL, respectively (FIG. 21B). Implementation of the invention to query kappa chain CDR2 sequence against a human VK-1 CDR2 UAL yielded a cohort library sequence with diversity 2, "L-L-I-Y-G-A-S-N-L-Q/E" (SEQ ID NO: 137), while comparison of the kappa chain CDR2 probe sequence with a human VK-3 CDR2 UAL by the methods of the invention produced a cohort CDR2 library sequence of diversity 1, "L-L-I-Y-G-A-S-N-R-A" (SEQ ID NO: 138). Use of the CD19 HD37 CDR3 as query sequence produced a cohort library CDR3 sequence of "Q/M-Q-G-Y-S-Y-P-Y" (SEQ ID NO: 140) when aligned with a VK CDR3 UAL. This kappa chain CDR3 library had a diversity of 2.

Again, the production of a final cohort antibody (or fragment thereof, e.g., Fab, scFv, etc.) library from the various cohort CDR libraries could be performed via independent assortment of cohort CDR library sequences with one another to build both heavy and light chains, and complete antibodies (or fragments thereof), from the cohort CDR libraries identified by the methods of the invention. Such independent assortment of cohort CDR library sequences results in chain and whole antibody cohort library diversities as shown in Table 12 for those cohort libraries generated using human CD19 HD37 antibody query sequences:

TABLE 12

Chain and Whole Antibody Diversities of Combined Cohort CDR Libraries Generated Using Human CD19 HD37 Antibody Probes

| Chain Diversity | | | |
|---|---|---|---|
| H1 Cohorts | H3 Cohorts | K1 Cohorts | K3 Cohorts |
| 1,296 | 5,292 | 20 | 6 |

| mAb diversity | K1 | K3 |
|---|---|---|
| H1 | 25,920 | 7,776 |
| H3 | 105,840 | 31,752 |

As for other antibodies assessed via the methods of the present invention, even the most diverse of these antibody libraries is of a size (e.g., diversity substantially less than about $10^{12}$) that can be readily displayed and/or screened using currently available methods.

Example 13

Identification and Generation of a Human CD8 g10-1 Cohort Antibody Library from Mouse Probe CDR Domains Heavy chain CDR1, CDR2 and CDR3 sequences for a mouse CD8 g10-1 antibody are "TDYYMK" (SEQ ID NO: 141), "WIGHINPNNDDTF" (SEQ ID NO: 144), and "VRD-DYDGGWFA" (SEQ ID NO: 147), respectively. Use of the methods of the invention with the heavy chain CDR1 query sequence yielded cohort library sequences of "S/N-D-Y-Y-M-S/H/N" (SEQ ID NO: 142) (diversity 6) and "T-D-Y-Y-M-S/H/N" (SEQ ID NO: 143) (diversity 3) when the query sequence was compared with a human VH-3 CDR1 UAL and a human VH-1 CDR1 UAL, respectively (FIG. 22A). Implementation of the invention to query heavy chain CDR2 sequence against a human VH-1 CDR2 UAL yielded a cohort library sequence with diversity of 12, "W-M-G-W/G/R-I-N-P-N-N-G-D-T-N/K/S/G" (SEQ ID NO: 145), while comparison of the heavy chain CDR2 probe sequence with a human VH-3 CDR2 UAL by the methods of the invention produced a cohort CDR2 library sequence of diversity 196, "W-V-S/A-V/A/N/G/Y/S/T-I-N-G/Y/S/Q/W/N/F-N-G/S-D-D-T-F" (SEQ ID NO: 146). Use of the CD8 g10-1 heavy chain CDR3 as query sequence produced a cohort library CDR3 sequence of "V-R-D-D-Y-D-G-G-W-F-D/G" (SEQ ID NO: 148) when aligned with a VH CDR3 UAL. This heavy chain CDR3 cohort library had a diversity of 2.

Kappa light chain CDR1, CDR2 and CDR3 sequences for the CD8 g10-1 antibody are "NNYLNWY" (SEQ ID NO: 149), "LLIYTSRSSY" (SEQ ID NO: 152), and "QQGK-TLPW" (SEQ ID NO: 155), respectively. Use of the methods of the invention with the kappa chain CDR1 query sequence yielded cohort library sequences of "N-N-Y-L-N-W-Y" (SEQ ID NO: 156) (no diversity) and "N-N-Y-L-A-W-Y" (SEQ ID NO: 151) (diversity 1) when the query sequence was compared with a human VK-1 CDR1 UAL and a VK-3 CDR1 UAL, respectively (FIG. 22B). Implementation of the invention to query kappa chain CDR2 sequence against a human VK-1 CDR2 UAL yielded a cohort library sequence with diversity 10, "L-L-I-Y-A/D/K/G/S-A-S-S-L-Q/E" (SEQ ID NO: 153), while comparison of the kappa chain CDR2 probe sequence with a human VK-3 CDR2 UAL by the methods of the invention produced a cohort CDR2 library sequence of diversity 4, "L-L-I-Y-G/D-A/T-S-S-R-A" (SEQ ID NO: 154). Use of the CD8 g10-1 kappa chain CDR3 as query sequence produced a cohort library CDR3 sequence of "Q-Q-G-Y/N/G/S/D/T/L-T-L-P-W" (SEQ ID NO: 156) when aligned with a VK CDR3 UAL. This kappa chain CDR3 library had a diversity of 7.

Again, the production of a final cohort antibody (or fragment thereof, e.g., Fab, scFv, etc.) library from the various cohort CDR libraries could be performed via independent assortment of cohort CDR library sequences with one another to build both heavy and light chains, and complete antibodies (or fragments thereof), from the cohort CDR libraries identified by the methods of the invention. Such independent assortment of cohort CDR library sequences results in chain and whole antibody cohort library diversities as shown in Table 13 for those cohort libraries generated using human CD8 g10-1 antibody query sequences:

TABLE 13

Chain and Whole Antibody Diversities of Combined Cohort CDR Libraries Generated Using Human CD8 g10-1 Antibody Probes

| Chain Diversity | | | |
|---|---|---|---|
| H1 Cohorts | H3 Cohorts | K1 Cohorts | K3 Cohorts |
| 72 | 2352 | 70 | 28 |

| mAb diversity | K1 | K3 |
|---|---|---|
| H1 | 5,040 | 2,016 |
| H3 | 164,640 | 65,856 |

As for other antibodies assessed via the methods of the present invention, even the most diverse of these antibody libraries is of a size (e.g., diversity substantially less than about $10^{12}$) that can be readily displayed and/or screened using currently available methods.

Example 14

Figures 1, 23A:
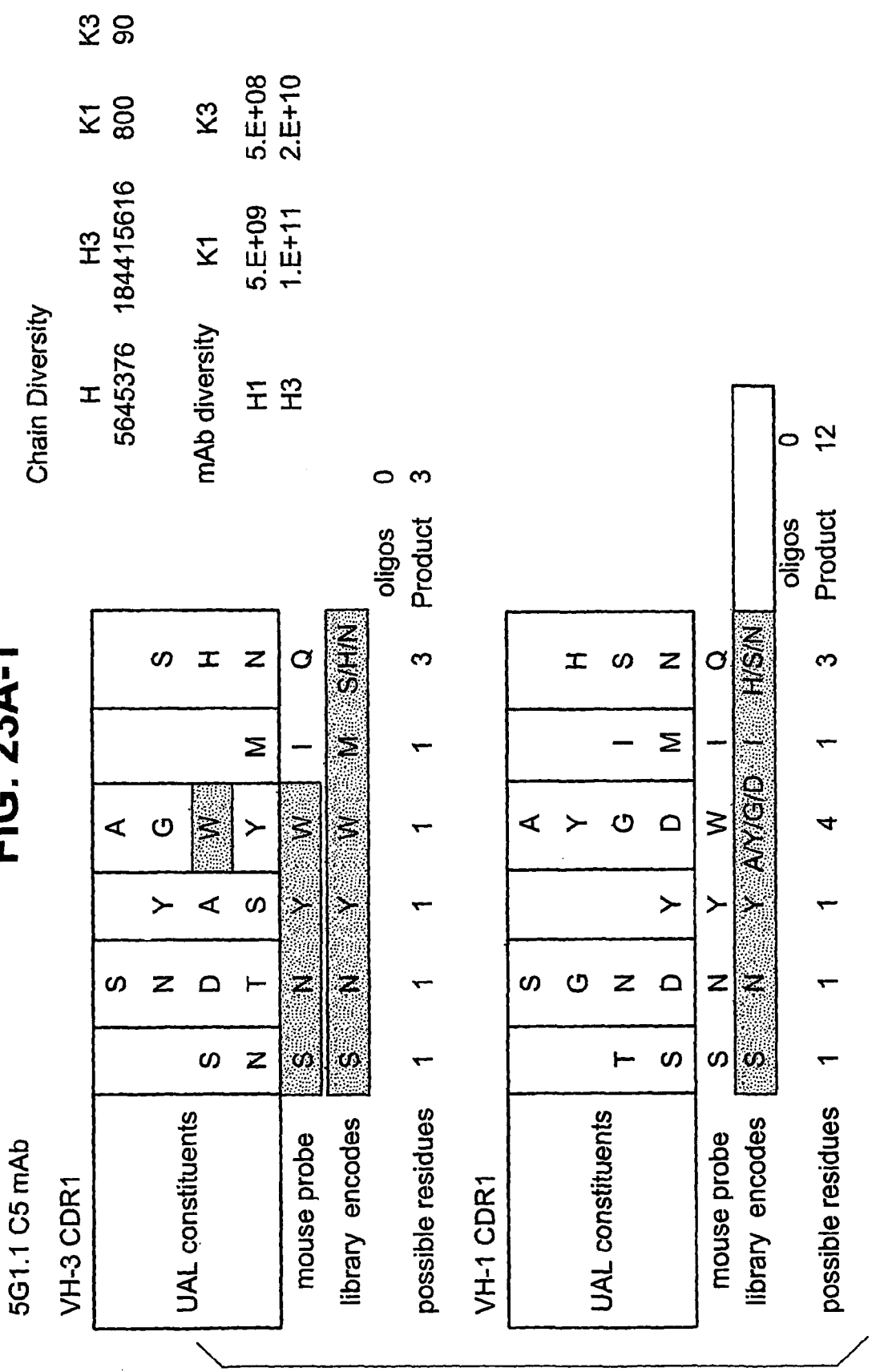
Figures 2, 23A:
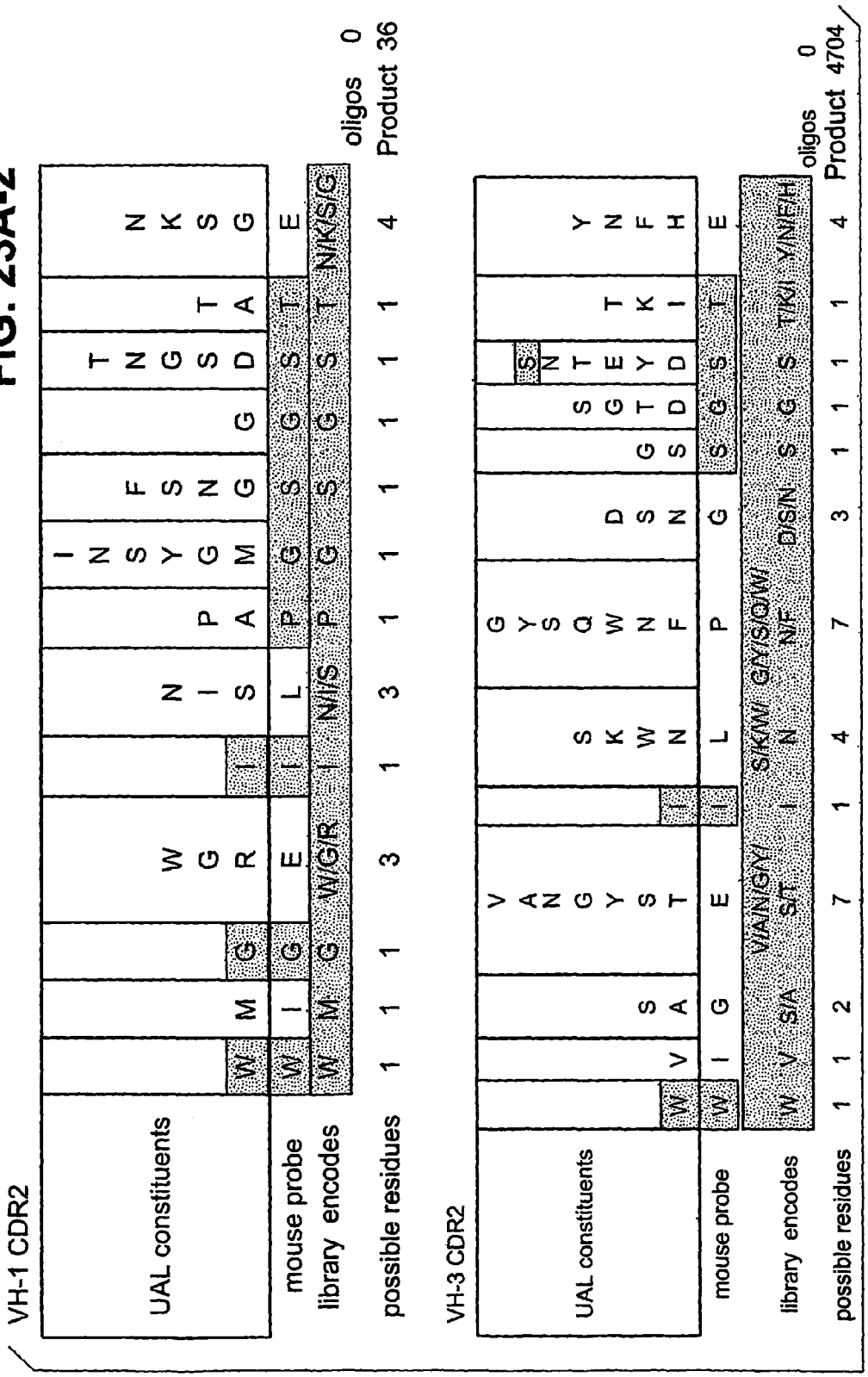

Identification and Generation of a Human 5G1.1 C5 Cohort Antibody Library from Mouse Probe CDR Domains Heavy chain CDR1, CDR2 and CDR3 sequences for a mouse 5G1.1 C5 antibody are "SNYWIQ" (SEQ ID NO: 157), "WIGEILPGSGSTE" (SEQ ID NO: 160), and "ARYFFGSSPNWYFD" (SEQ ID NO: 163), respectively. Use of the methods of the invention with the heavy chain CDR1 query sequence yielded cohort library sequences of "S-N-Y-W-M-S/H/N" (SEQ ID NO: 158) (diversity 3) and "S-N-Y-A/Y/G/D-I-H/S/N" (SEQ ID NO: 159) (diversity 12) when the query sequence was compared with a human VH-3 CDR1 UAL and a human VH-1 CDR1 UAL, respectively (FIG. 23A). Implementation of the invention to query heavy chain CDR2 sequence against a human VH-1 CDR2 UAL yielded a cohort library sequence with diversity of 36, "W-M-G-W/G/R-I-N/I/S-P-G-S-G-S-T-N/K/S/G" (SEQ ID NO: 161), while comparison of the heavy chain CDR2 probe sequence with a human VH-3 CDR2 UAL by the methods of the invention produced a cohort CDR2 library sequence of diversity 4704, "W-V-S/A-V/A/N/G/Y/S/T-I-S/K/W/N-G/Y/S/Q/W/N/F-D/S/N-S-G-S-T-Y/N/F/H" (SEQ ID NO: 162). Use of the mouse 5G1.1 C5 heavy chain CDR3 as query sequence produced a cohort library CDR3 sequence of "A-R-D/G/E/A/S/R/T/V/H-R/G/L/P/S/A/T/Q/H/I/K-G/Y/L/R/I/V/A/P/S/D/T/E-G-S-S-P-Y/G/D/S/T/F/A/P/E/L/R-W-Y-F-D" (SEQ ID NO: 164) when aligned with a VH CDR3 UAL. This heavy chain CDR3 cohort library had a diversity of 13,068.

Figures 3, 23B:
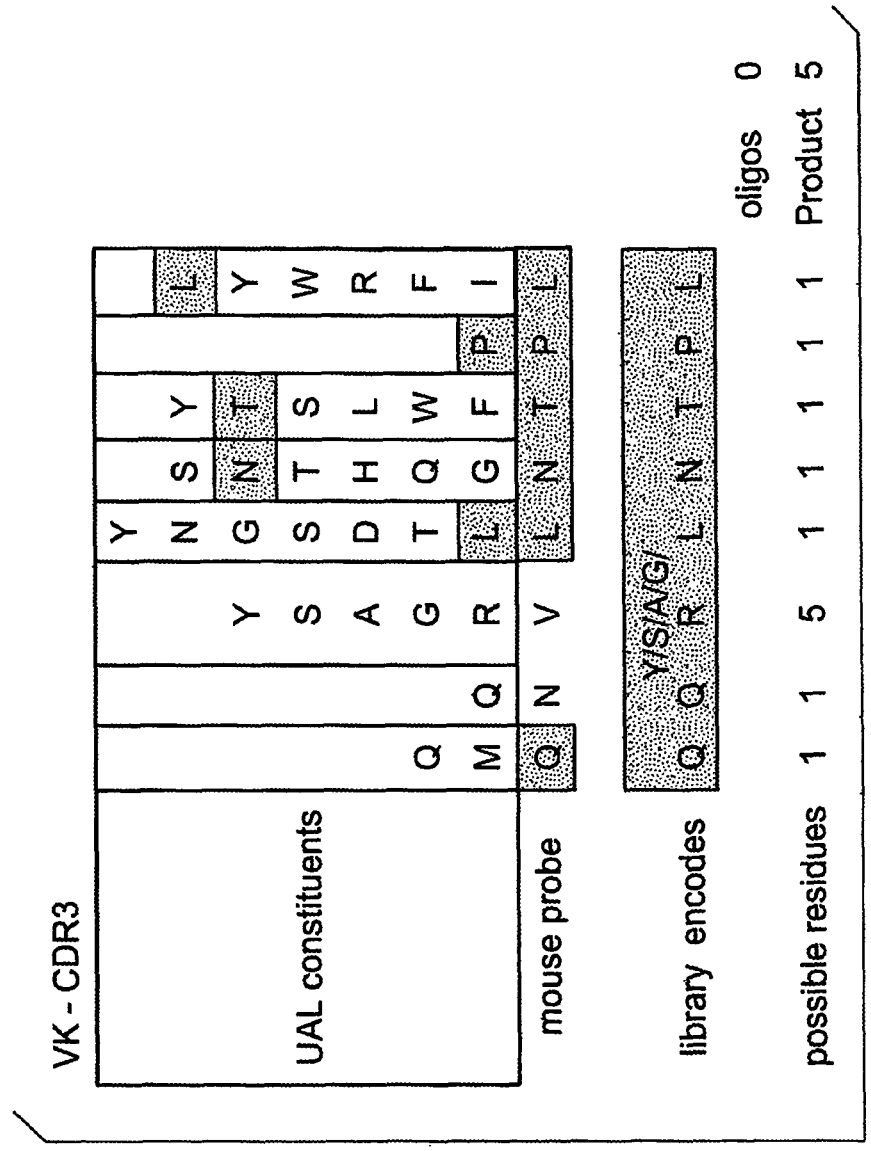

Kappa light chain CDR1, CDR2 and CDR3 sequences for the mouse 5G1.1 C5 antibody are "TGALNWY" (SEQ ID NO: 165), "LLIYGATNLA" SEQ ID NO: 168), and "QNVLNTPL" (SEQ ID NO: 171), respectively. Use of the methods of the invention with the kappa chain CDR1 query sequence yielded cohort library sequences of "S/R/G/N/Y-N/S/T/K-Y/W/D/S-L-N-W-Y" (SEQ ID NO: 166) (diversity 80) and "S/G/N-S/N/T-N/Y-L-A-W-Y" (SEQ ID NO: 167) (diversity 18) when the query sequence was compared with a human VK-1 CDR1 UAL and a VK-3 CDR1 UAL, respectively (FIG. 23B). Implementation of the invention to query kappa chain CDR2 sequence against a human VK-1 CDR2 UAL yielded a cohort library sequence with diversity 2, "L-L-I-Y-G-A-S-N-L-Q/E" (SEQ ID NO: 169), while comparison of the kappa chain CDR2 probe sequence with a human VK-3 CDR2 UAL by the methods of the invention produced a cohort CDR2 library sequence of diversity 1, "L-L-I-Y-G-A-S-N-R-A" (SEQ ID NO: 170). Use of the mouse 5G1.1 C5 kappa chain CDR3 as query sequence produced a cohort library CDR3 sequence of "Q-Y/S/A/G/R-L-N-T-P-L" (SEQ ID NO: 172) when aligned with a VK CDR3 UAL. This kappa chain CDR3 library had a diversity of 5.

Again, the production of a final cohort antibody (or fragment thereof, e.g., Fab, scFv, etc.) library from the various cohort CDR libraries could be performed via independent assortment of cohort CDR library sequences with one another to build both heavy and light chains, and complete antibodies (or fragments thereof), from the cohort CDR libraries identified by the methods of the invention. Such independent assortment of cohort CDR library sequences results in chain and whole antibody cohort library diversities as shown in Table 14 for those cohort libraries generated using mouse 5G1.1 C5 antibody query sequences:

TABLE 14

Chain and Whole Antibody Diversities of Combined Cohort CDR Libraries Generated Using Mouse 5G1.1 C5 Antibody Probes

| Chain Diversity | | | |
|---|---|---|---|
| H1 Cohorts | H3 Cohorts | K1 Cohorts | K3 Cohorts |
| 5,645,376 | 184,415,616 | 800 | 90 |

| mAb diversity | K1 | K3 |
|---|---|---|
| H1 | $4.52 \times 10^9$ | $5.08 \times 10^8$ |
| H3 | $1.48 \times 10^{11}$ | $1.66 \times 10^{10}$ |

As for other antibodies assessed via the methods of the present invention, even the most diverse of these antibody libraries is of a size (e.g., diversity less than about $10^{12}$) that can be readily displayed and/or screened using currently available methods.

Example 15

Figures 3, 24A:
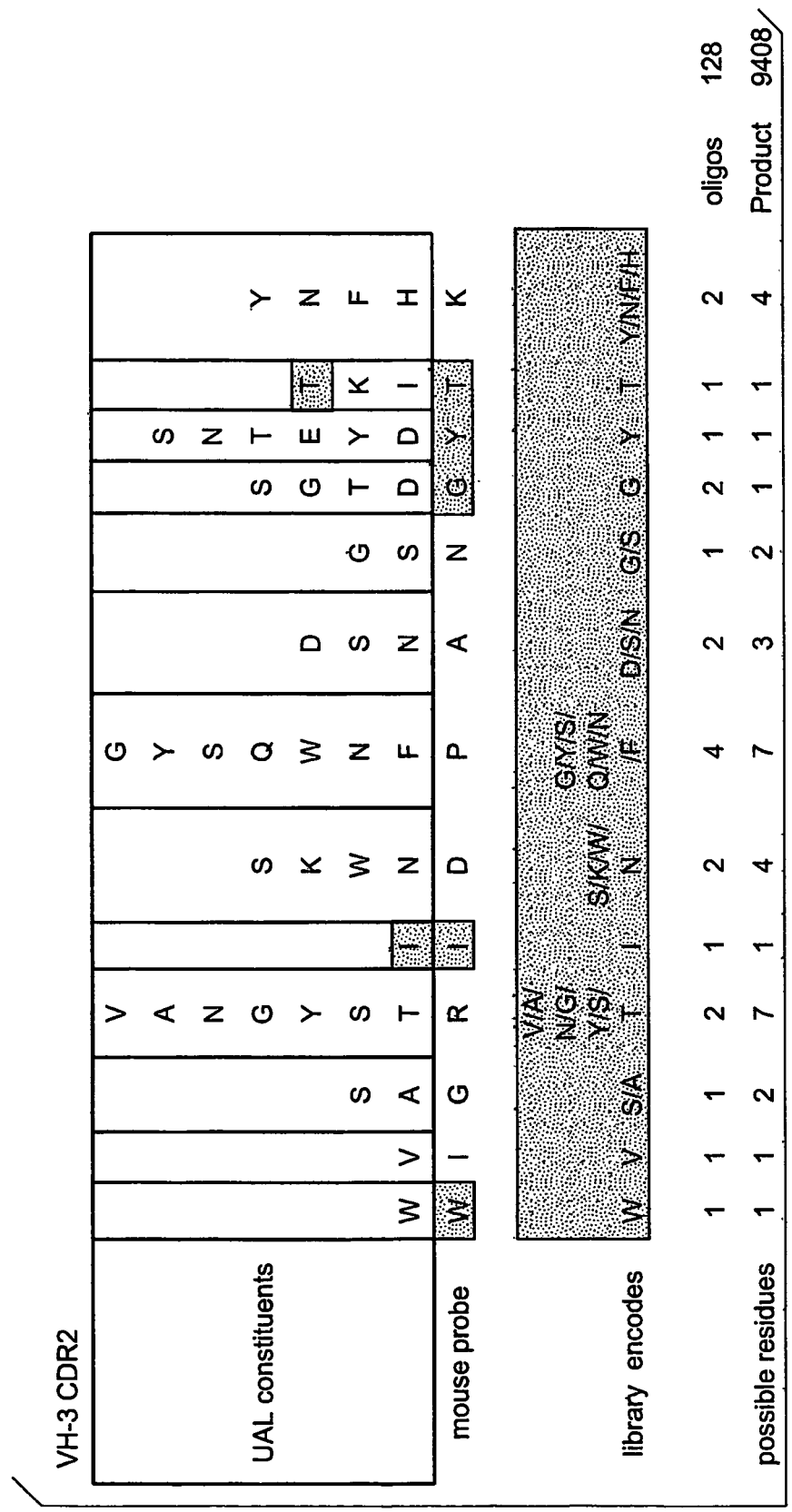

Identification and Generation of a Human Reopro 7E3 Cohort Antibody Library from Mouse Probe CDR Domains Heavy chain CDR1, CDR2 and CDR3 sequences for a mouse Reopro 7E3 antibody are "KDTYVH" (SEQ ID NO: 173), "WIGRIDPANGYTK" (SEQ ID NO: 176), and "VRPLYDYYAMD" (SEQ ID NO: 179), respectively. Use of the methods of the invention with the heavy chain CDR1 query sequence yielded cohort library sequences of "S/N-D-Y/A/S-Y-M-H" (SEQ ID NO: 174) (diversity 6) and "T/S-D-Y-Y-I/M-H" (SEQ ID NO: 175) (diversity 4) when the query sequence was compared with a human VH-3 CDR1 UAL and a human VH-1 CDR1 UAL, respectively (FIG. 24A). Implementation of the invention to query heavy chain CDR2 sequence against a human VH-1 CDR2 UAL yielded a cohort library sequence with diversity of 90, "W-M-G-R-I-N/I/S-P-I/N/S/Y/G/M-N-G-T/N/G/S/D-T-K" (SEQ ID NO: 177), while comparison of the heavy chain CDR2 probe sequence with a human VH-3 CDR2 UAL by the methods of the invention produced a cohort CDR2 library sequence of diversity 9408, "W-V-S/A-V/A/N/G/Y/S/T-I-S/K/W/N-G/Y/S/Q/W/N/F-D/S/N-G/S-G-Y-T-Y/N/F/H" (SEQ ID NO: 178). Use of the mouse Reopro 7E3 heavy chain CDR3 as query sequence produced a cohort library CDR3 sequence of "V-R-D/K/G/I/A/E/L/R/N-L-Y-D-Y-Y-A-M-D" (SEQ ID NO: 180) when aligned with a VH CDR3 UAL. This heavy chain CDR3 cohort library had a diversity of 9.

Kappa light chain CDR1, CDR2 and CDR3 sequences for the mouse Reopro 7E3 antibody are "SSNIGWL" (SEQ ID NO: 181), "GLIYYGTNLV" (SEQ ID NO: 184), and "VQYAQLPY" (SEQ ID NO: 187), respectively. Use of the methods of the invention with the kappa chain CDR1 query sequence yielded cohort library sequences of "S-S-Y/W/D/S-L-A/N-W-Y" (SEQ ID NO: 182) (diversity 8) and "S-S-N-L-A-W-Y" (SEQ ID NO: 183) (diversity 1) when the query sequence was compared with a human VK-1 CDR1 UAL and a VK-3 CDR1 UAL, respectively (FIG. 24B). Implementation of the invention to query kappa chain CDR2 sequence against a human VK-1 CDR2 UAL yielded a cohort library sequence with diversity 20, "L/R-L-I-Y-A/D/K/G/S-A-S-N-

L-Q/E" (SEQ ID NO: 185), while comparison of the kappa chain CDR2 probe sequence with a human VK-3 CDR2 UAL by the methods of the invention produced a cohort CDR2 library sequence of diversity 4, "L-L-I-Y-G/D-T/A-S-N-R-A" (SEQ ID NO: 186). Use of the mouse Reopro 7E3 kappa chain CDR3 as query sequence produced a cohort library CDR3 sequence of "Q/M-Q-Y-Y/N/G/S/D/T/L-Q-L-P-Y" (SEQ ID NO: 188) when aligned with a VK CDR3 UAL. This kappa chain CDR3 library had a diversity of 14.

Again, the production of a final cohort antibody (or fragment thereof, e.g., Fab, scFv, etc.) library from the various cohort CDR libraries could be performed via independent assortment of cohort CDR library sequences with one another to build both heavy and light chains, and complete antibodies (or fragments thereof), from the cohort CDR libraries identified by the methods of the invention. Such independent assortment of cohort CDR library sequences results in chain and whole antibody cohort library diversities as shown in Table 15 for those cohort libraries generated using mouse Reopro 7E3 antibody query sequences:

TABLE 15

Chain and Whole Antibody Diversities of Combined Cohort CDR Libraries Generated Using Mouse 5G1.1 C5 Antibody Probes

| Chain Diversity | | | |
|---|---|---|---|
| H1 Cohorts | H3 Cohorts | K1 Cohorts | K3 Cohorts |
| 3,240 | 508,032 | 2,240 | 56 |

| mAb diversity | K1 | K3 |
|---|---|---|
| H1 | 7,257,600 | 181,440 |
| H3 | 1,137,991,680 | 28,449,792 |

As for other antibodies assessed via the methods of the present invention, even the most diverse of these antibody libraries is of a size (e.g., diversity substantially less than about $10^{12}$) that can be readily displayed and/or screened using currently available methods.

Example 16

Figures 3, 25A:
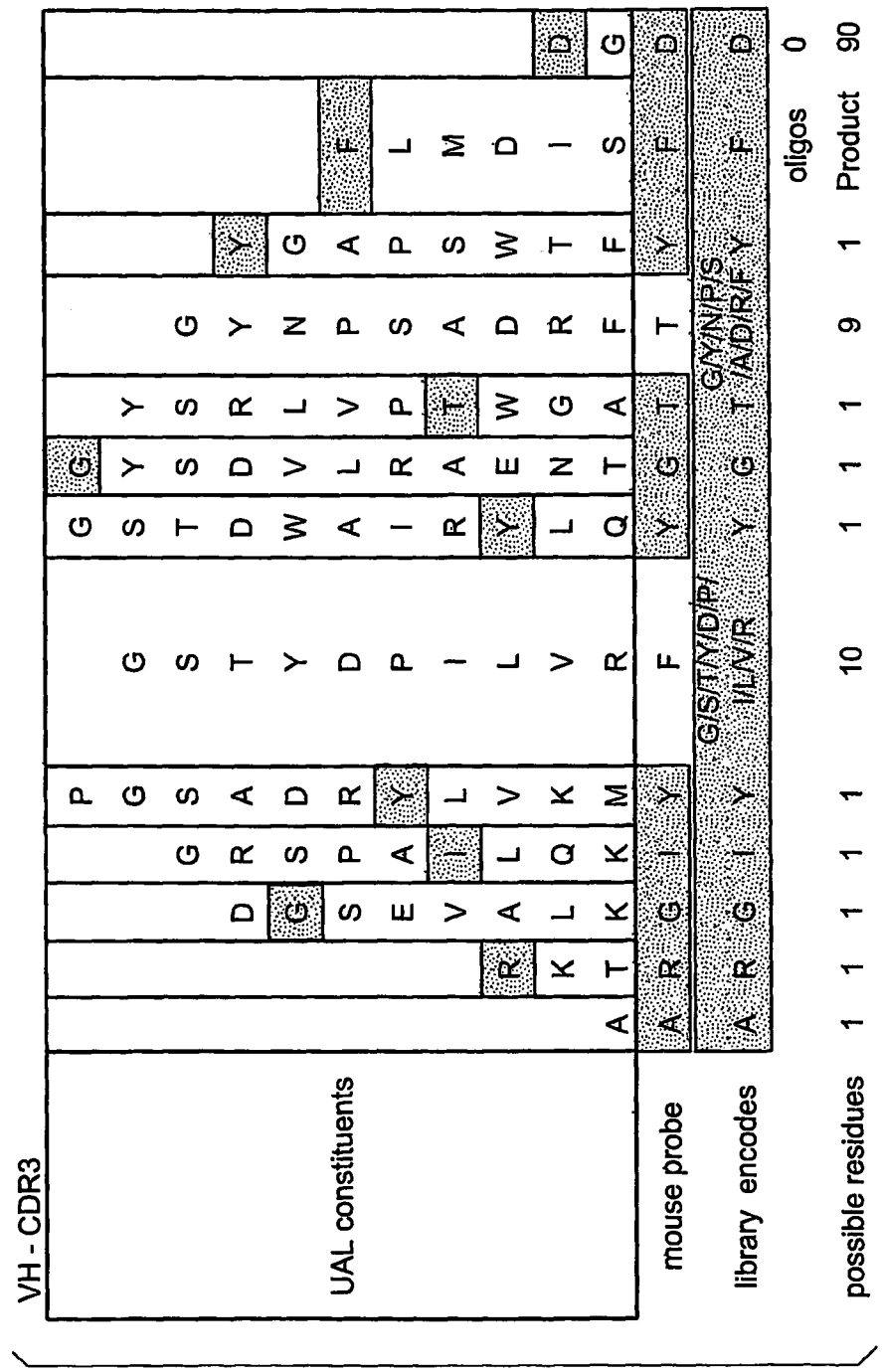

Identification and Generation of a Human Raptiva MHM24 Cohort Antibody Library from Mouse Probe CDR Domains Heavy chain CDR1, CDR2 and CDR3 sequences for a mouse Raptiva MHM24 antibody are "TGHWMN" (SEQ ID NO: 189), "WIGMIHPSDSETR" (SEQ ID NO: 192), and "ARGIYFYGTTYFD" (SEQ ID NO: 195), respectively. Use of the methods of the invention with the heavy chain CDR1 query sequence yielded cohort library sequences of "S/N-S/N/D/T-Y/A/S-W-M-N" (diversity 24) and "T-G-Y-A/Y/G/D-M-N" (SEQ ID NO: 191) (diversity 4) when the query sequence was compared with a human VH-3 CDR1 UAL and a human VH-1 CDR1 UAL, respectively (FIG. 25A). Implementation of the invention to query heavy chain CDR2 sequence against a human VH-1 CDR2 UAL yielded a cohort library sequence with diversity of 720, "W-M-G-W/G/R-I-N/I/S-P-S-F/S/N/G-G-T/N/G/S/D-T-N/K/S/G" (SEQ ID NO: 193), while comparison of the heavy chain CDR2 probe sequence with a human VH-3 CDR2 UAL by the methods of the invention produced a cohort CDR2 library sequence of diversity 3136, "W-V-S/A-V/A/N/G/Y/S/T-I-S/K/W/N-G/Y/S/Q/W/N/F-S-G/S-S-E-T-Y/N/F/H" (SEQ ID NO: 194). Use of the mouse Raptiva MHM24 heavy chain CDR3 as query sequence produced a cohort library CDR3 sequence of "A-R-G-I-Y-G/S/T/Y/D/P/I/L/V/R-Y-G-T-G/Y/N/P/S/A/D/R/F-Y-F-D" (SEQ ID NO: 196) when aligned with a VH CDR3 UAL. This heavy chain CDR3 cohort library had a diversity of 90.

Figures 3, 25B:
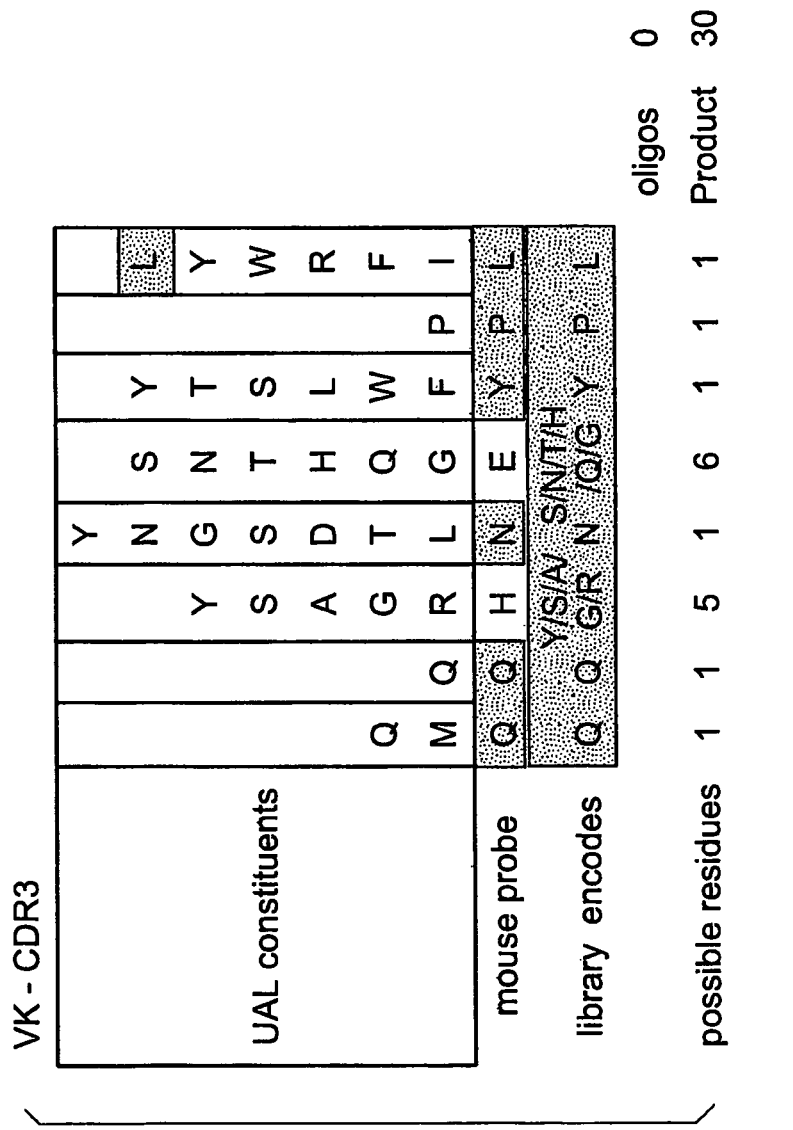

Kappa light chain CDR1, CDR2 and CDR3 sequences for the mouse Raptiva MHM24 antibody are "SKYLAWY" (SEQ ID NO: 197), "LLIYSGSTLQ" (SEQ ID NO: 200), and "QQHNEYPL" (SEQ ID NO: 203), respectively. Use of the methods of the invention with the kappa chain CDR1 query sequence yielded cohort library sequences of "S-K-Y-L-A-W-Y" (SEQ ID NO: 198) (no diversity) and "S-S/N/T-Y-L-A-W-Y" (SEQ ID NO: 199) (diversity 3) when the query sequence was compared with a human VK-1 CDR1 UAL and a VK-3 CDR1 UAL, respectively (FIG. 25B). Implementation of the invention to query kappa chain CDR2 sequence against a human VK-1 CDR2 UAL yielded a cohort library sequence with diversity 1, "L-L-I-Y-S-A-S-T-L-Q" (SEQ ID NO: 201), while comparison of the kappa chain CDR2 probe sequence with a human VK-3 CDR2 UAL by the methods of the invention produced a cohort CDR2 library sequence of diversity 4, "L-L-I-Y-G/D-T/A-S-T-R-A" (SEQ ID NO: 202). Use of the mouse Raptiva MHM24 kappa chain CDR3 as query sequence produced a cohort library CDR3 sequence of "Q-Q-Y/S/A/G/R-N-S/N/T/H/Q/G-Y-P-L" (SEQ ID NO: 204) when aligned with a VK CDR3 UAL. This kappa chain CDR3 library had a diversity of 30.

Again, the production of a final cohort antibody (or fragment thereof, e.g., Fab, scFv, etc.) library from the various cohort CDR libraries could be performed via independent assortment of cohort CDR library sequences with one another to build both heavy and light chains, and complete antibodies (or fragments thereof), from the cohort CDR libraries identified by the methods of the invention. Such independent assortment of cohort CDR library sequences results in chain and whole antibody cohort library diversities as shown in Table 16 for those cohort libraries generated using mouse Raptiva MHM24 antibody query sequences:

TABLE 16

Chain and Whole Antibody Diversities of Combined Cohort CDR Libraries Generated Using Mouse Raptiva MHM24 Antibody Probes

| Chain Diversity | | | |
|---|---|---|---|
| H1 Cohorts | H3 Cohorts | K1 Cohorts | K3 Cohorts |
| 259,200 | 6,773,760 | 30 | 360 |

| mAb diversity | K1 | K3 |
|---|---|---|
| H1 | 7,776,000 | 93,312,000 |
| H3 | 203,212,800 | 2,438,553,600 |

As for other antibodies assessed via the methods of the present invention, even the most diverse of these antibody libraries is of a size (e.g., diversity substantially less than about $10^{12}$) that can be readily displayed and/or screened using currently available methods.

Example 17

Identification and Generation of a Mouse Ovalbumin Cohort Antibody Library from Probe CDR Domains Heavy chain CDR1, CDR2 and CDR3 sequences for a mouse ovalbumin antibody are "TDYNMD" (SEQ ID NO:

205), "WIGDINPSNGYTI" (SEQ ID NO: 209), and "ARS-GYGSRHPPGFA" (SEQ ID NO: 212), respectively. Use of the methods of the invention with the heavy chain CDR1 query sequence yielded cohort library sequences of "S/N-D-Y-A/G/W/Y-M-S/H/N" (diversity 24) and "T-D-Y-A/Y/G/D-M-H/S/N" (SEQ ID NO: 585) (diversity 12) when the query sequence was compared with a human VH-3 CDR1 UAL and a human VH-1 CDR1 UAL, respectively (FIG. 26A). Implementation of the invention to query heavy chain CDR2 sequence against a human VH-1 CDR2 UAL yielded a cohort library sequence with diversity of 60, "W-M-G-W/G/R-I-N-P-S-N-G-T/N/G/S/D-T-N/K/S/G" (SEQ ID NO: 210), while comparison of the heavy chain CDR2 probe sequence with a human VH-3 CDR2 UAL by the methods of the invention produced a cohort CDR2 library sequence of diversity 2352, "W-V-S/A-V/A/N/G/Y/S/T-I-N-G/Y/S/Q/W/N/F-S-G/S-G-Y-T-Y/N/F/H" (SEQ ID NO: 211). Use of the ovalbumin heavy chain CDR3 as query sequence produced a cohort library CDR3 sequence of "A-R-S-G-Y-G-S-N/D/A/V/L/Y/T/S/G-V/I/E/P/L/T/A/Y/S/G-P-T/A/W/D/R/N/S/G/Y-G-F-A" (SEQ ID NO: 213) when aligned with a VH CDR3 UAL. This heavy chain CDR3 cohort library had a diversity of 810.

Figure 26B-1:
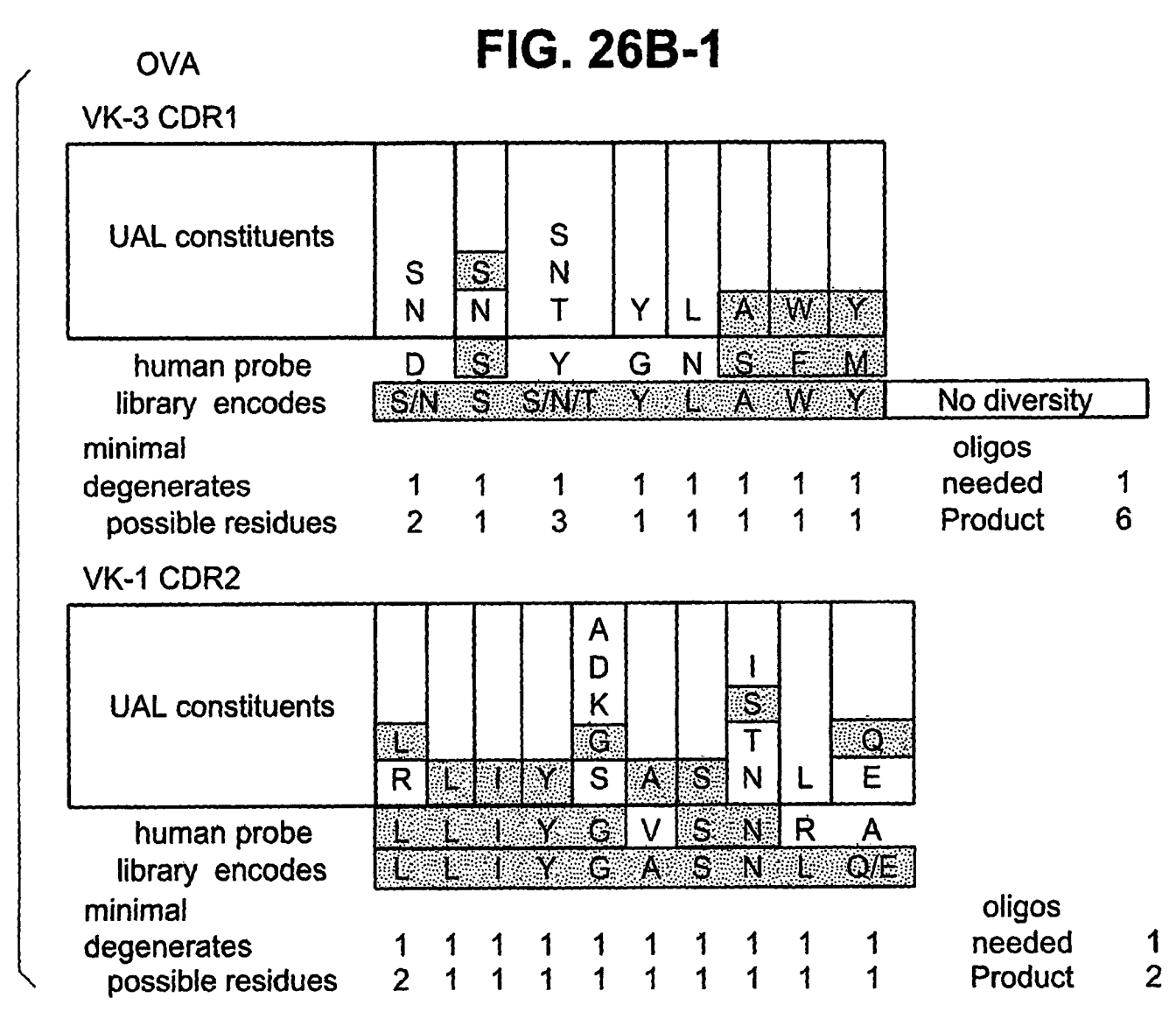

Kappa light chain CDR1, CDR2 and CDR3 sequences for the ovalbumin antibody are "DSYGNSFMHWY" (SEQ ID NO: 586), "LLIYLASNLE" (SEQ ID NO: 587), and "QQNIEDPF" (SEQ ID NO: 588), respectively. Because anti-ovalbumin CDR1 possesses 11 amino acids, either insertional analysis or use of framework-matched germline CDR sequences (for CDR1, "SNYLAWF" (SEQ ID NO: 589)) could have been performed. Thus, no cohort sequence or diversity information was generated by the methods of the invention for VK-1 CDR1. Use of the methods of the invention with the kappa chain CDR1 query sequence yielded a cohort library sequence of "S/N-S-S/N/T-Y-L-A-W-Y" (SEQ ID NO: 215) (diversity 6) when the query sequence was compared with a human VK-3 CDR1 UAL (FIG. 26B). Implementation of the invention to query kappa chain CDR2 sequence against a human VK-1 CDR2 UAL yielded a cohort library sequence with diversity 2, "L-L-I-Y-G-A-S-N-L-Q/E" (SEQ ID NO: 217), while comparison of the kappa chain CDR2 probe sequence with a human VK-3 CDR2 UAL by the methods of the invention produced a cohort CDR2 library sequence of diversity 2, "L-L-I-Y-G-A/T-S-N-R-A" (SEQ ID NO: 218). Use of the ovalbumin antibody kappa chain CDR3 as query sequence produced a cohort library CDR3 sequence of "Q-Q-Y-G-S/N/T/H/Q/G-S-P-Y" (SEQ ID NO: 220) when aligned with a VK CDR3 UAL. This kappa chain CDR3 library had a diversity of 6.

Again, the production of a final cohort antibody (or fragment thereof, e.g., Fab, scFv, etc.) library from the various cohort CDR libraries could be performed via independent assortment of cohort CDR library sequences with one another to build both heavy and light chains, and complete antibodies (or fragments thereof), from the cohort CDR libraries identified by the methods of the invention. Such independent assortment of cohort CDR library sequences results in chain and whole antibody cohort library diversifies as shown in Table 17 for those cohort libraries generated using ovalbumin antibody query sequences:

TABLE 17

Chain and Whole Antibody Diversities of Combined Cohort CDR Libraries Generated Using Ovalbumin Antibody Probes

| Chain Diversity | | |
|---|---|---|
| H1 Cohorts | H3 Cohorts | K3 Cohorts |
| 583,200 | 45,722,880 | 72 |
| mAb diversity | | K3 |
| H1 | | 41,990,400 |
| H3 | | 3,292,047,360 |

As for other antibodies assessed via the methods of the present invention, even the most diverse of these antibody libraries is of a size (e.g., diversity substantially less than about $10^{12}$) that can be readily displayed and/or screened using currently available methods.

Example 18

Figures 1, 27A:
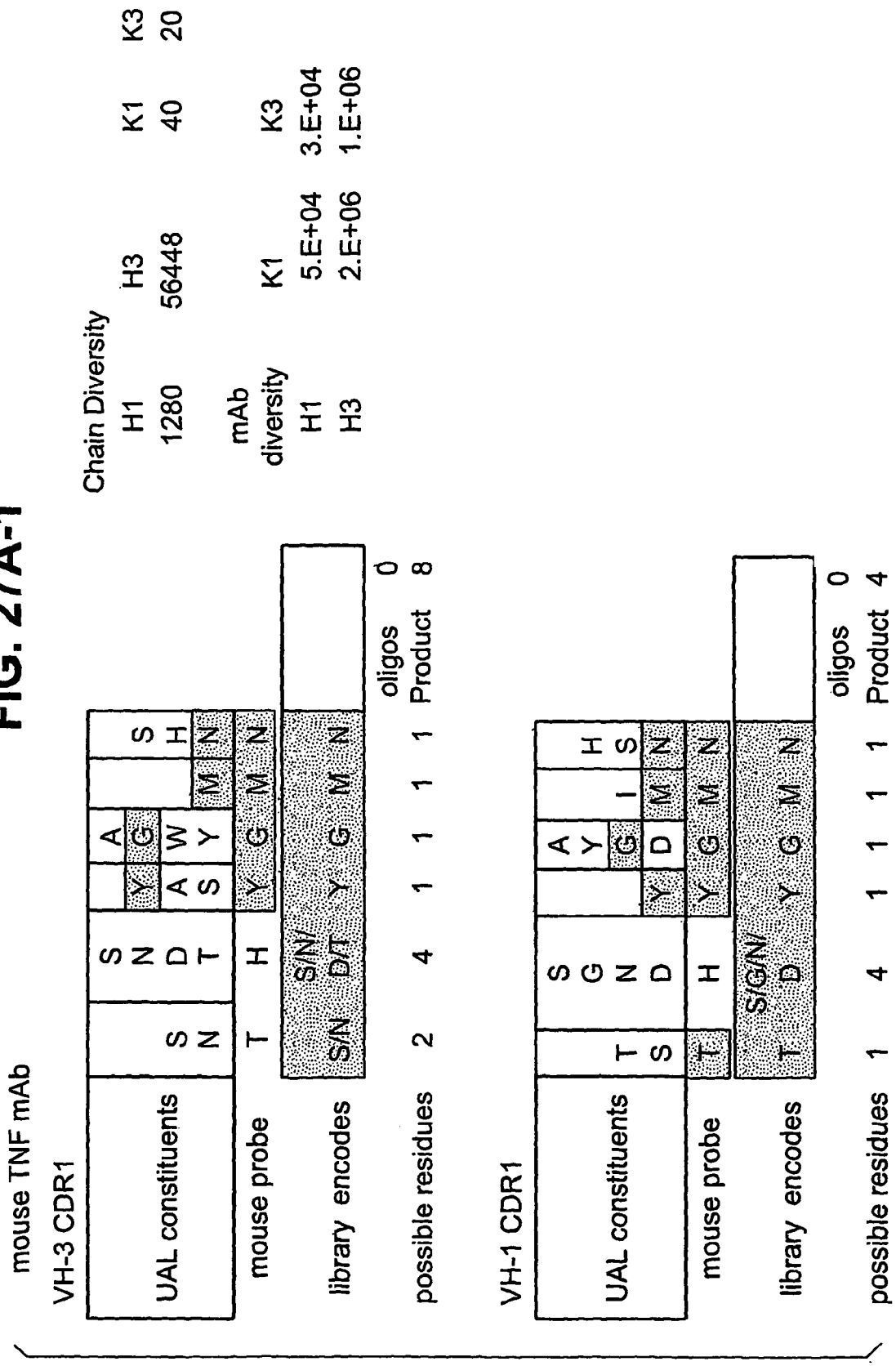
Figures 2, 27A:
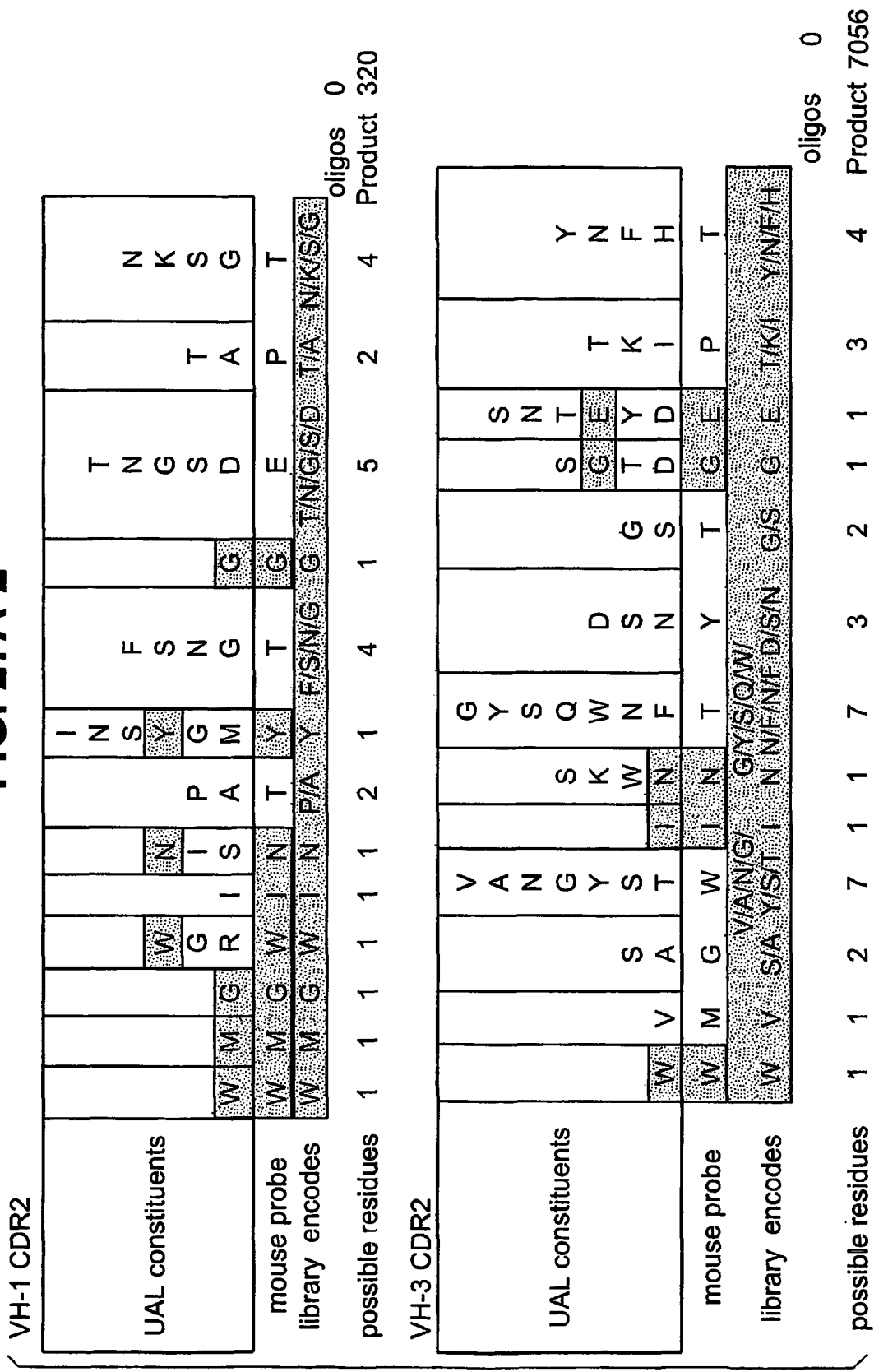

Identification and Generation of a Human TNF-□ Cohort Antibody Library from Mouse Probe CDR Domains Heavy chain CDR1, CDR2 and CDR3 sequences for a mouse TNF-□ monoclonal antibody are "THYGMN" (SEQ ID NO: 221), "WMGWINTYTGEPT" (SEQ ID NO: 224), and "ARERGDAMD" (SEQ ID NO: 227), respectively. Use of the methods of the invention with the heavy chain CDR1 query sequence yielded cohort library sequences of "S/N-S/N/D/T-Y-G-M-N" (SEQ ID NO: 222) (diversity 8) and "T-S/G/N/D-Y-G-M-N" (SEQ ID NO: 223) (diversity 4) when the query sequence was compared with a human VH-3 CDR1 UAL and a human VH-1 CDR1 UAL, respectively (FIG. 27A). Implementation of the invention to query heavy chain CDR2 sequence against a human VH-1 CDR2 UAL yielded a cohort library sequence with diversity of 320, "W-M-G-W-I-N-P/A-Y-F/S/N/G-G-T/N/G/S/D-T/A-N/K/S/G" (SEQ ID NO: 225), while comparison of the heavy chain CDR2 probe sequence with a human VH-3 CDR2 UAL by the methods of the invention produced a cohort CDR2 library sequence of diversity 7056, "W-V-S/A-V/A/N/G/Y/S/T-I-N-G/Y/S/Q/W/N/F-D/S/N-G/S-G-E-T/K/I-Y/N/F/H" (SEQ ID NO: 226). Use of the mouse TNF-□ heavy chain CDR3 as query sequence produced an identical (no diversity) cohort library CDR3 sequence of "A-R-E-R-G-D-A-M-D" (SEQ ID NO: 228) when aligned with a VH. CDR3 UAL.

Kappa light chain CDR1, CDR2 and CDR3 sequences for the mouse TNF-□ antibody are "SNDVVWY" (SEQ ID NO: 229), "MLMYSAFNRY" (SEQ ID NO: 232), and "QQDYNSPR" (SEQ ID NO: 235), respectively. Use of the methods of the invention with the kappa chain CDR1 query sequence yielded cohort library sequences of "S-N-D-L-A/N-W-Y" (SEQ ID NO: 230) (diversity 2) and "S-N-N/Y-L-A-W-Y" (SEQ ID NO: 231) (diversity 2) when the query sequence was compared with a human VK-1 CDR1 UAL and a VK-3 CDR1 UAL, respectively (FIG. 27B). Implementation of the invention to query kappa chain CDR2 sequence against a human VK-1 CDR2 UAL yielded a cohort library sequence with diversity 4, "L/R-L-I-Y-S-A-S-N-L-Q/E" (SEQ ID NO: 233), while comparison of the kappa chain CDR2 probe sequence with a human VK-3 CDR2 UAL by the methods of the invention produced a cohort CDR2 library sequence of diversity 2, "L-L-I-Y-G/D-A-S-N-R-A" (SEQ ID NO: 234). Use of the mouse TNF-☐ kappa chain CDR3 as query sequence produced a cohort library CDR3 sequence of "Q-Q-Y/S/A/G/R-Y-N-S-P-R" (SEQ ID NO: 236) when aligned with a VK CDR3 UAL. This kappa chain CDR3 library had a diversity of 5.

Again, the production of a final cohort antibody (or fragment thereof, e.g., Fab, scFv, etc.) library from the various cohort CDR libraries could be performed via independent assortment of cohort CDR library sequences with one another to build both heavy and light chains, and complete antibodies (or fragments thereof), from the cohort CDR libraries identified by the methods of the invention. Such independent assortment of cohort CDR library sequences results in chain and whole antibody cohort library diversities as shown in Table 18 for those cohort libraries generated using mouse TNF-☐ antibody query sequences:

TABLE 18

Chain and Whole Antibody Diversities of Combined Cohort CDR Libraries Generated Using Mouse TNF-☐ Antibody Probes Chain Diversity

| H1 Cohorts | H3 Cohorts | K1 Cohorts | K3 Cohorts |
|---|---|---|---|
| 1,280 | 56,448 | 40 | 20 |

| mAb diversity | K1 | K3 |
|---|---|---|
| H1 | 51,200 | 25,600 |
| H3 | 2,257,920 | 1,128,960 |

As for other antibodies assessed via the methods of the present invention, even the most diverse of these antibody libraries is of a size (e.g., diversity substantially less than about $10^{12}$) that can be readily displayed and/or screened using currently available methods.

Example 19

Use of Similarity Criteria in Generation of Cohort Antibody Libraries

The methods of the present invention allow for implementation of divergent selection criteria at one or more amino acid residue positions within a CDR sequence during generation of cohort antibody library sequences. As described above in Example 5 (for catalytic triad residues of mouse anti-HIV gp41 monoclonal antibody 41-S-2-L), certain residues of a query CDR sequence may be "fixed" and thus incorporated in cohort library sequence(s) regardless of the amino acid usage present in a reference library at that residue position. The methods of the invention may additionally implement similarity-based (as opposed to identity-based) criteria at one or more residue positions of a CDR sequence during selection of cohort antibody sequence(s). In most embodiments, distinctions between similarity criteria and identity criteria may be summarized as follows: for identity criteria, residues of a query CDR sequence that also appear in a reference library at the same position are locked (the identical amino acid appears in the resulting cohort library sequence), and residues lacking corresponding positional matches are substituted with all amino acid constituents of the reference library at that position; in contrast, for similarity criteria, residues of a query CDR sequence that also appear in a reference library at the same position are once again locked, but residues lacking corresponding positional matches may be substituted with a subset of amino acid residues from the reference library at that position if a component amino acid of the reference library is found to be "similar" to the query sequence at that residue (for those residue positions where no such similarity exists, all residues of the reference library are incorporated at that position).

For the present example, naturally-occurring amino acids were placed within the seven following similarity classes on the basis of side chain chemistry (classes are also tabulated in FIG. 28):

Small Side Chains: Glycine (G), Alanine (A)

Nucleophilic: Serine (S), Threonine (T), Cysteine (C), Histidine (H)

Hydrophobic, Valine (V), Leucine (L), Isoleucine (I), Methionine (M), Praline (P)

Aromatic: Phenylalanine (F), Tyrosine (Y), Tryptophan (W)

Acidic: Aspartate (D), Glutamate (E)

Amide: Asparagine (N), Glutamine (Q)

Basic: Lysine (K), Arginine (R)

Figure 29:
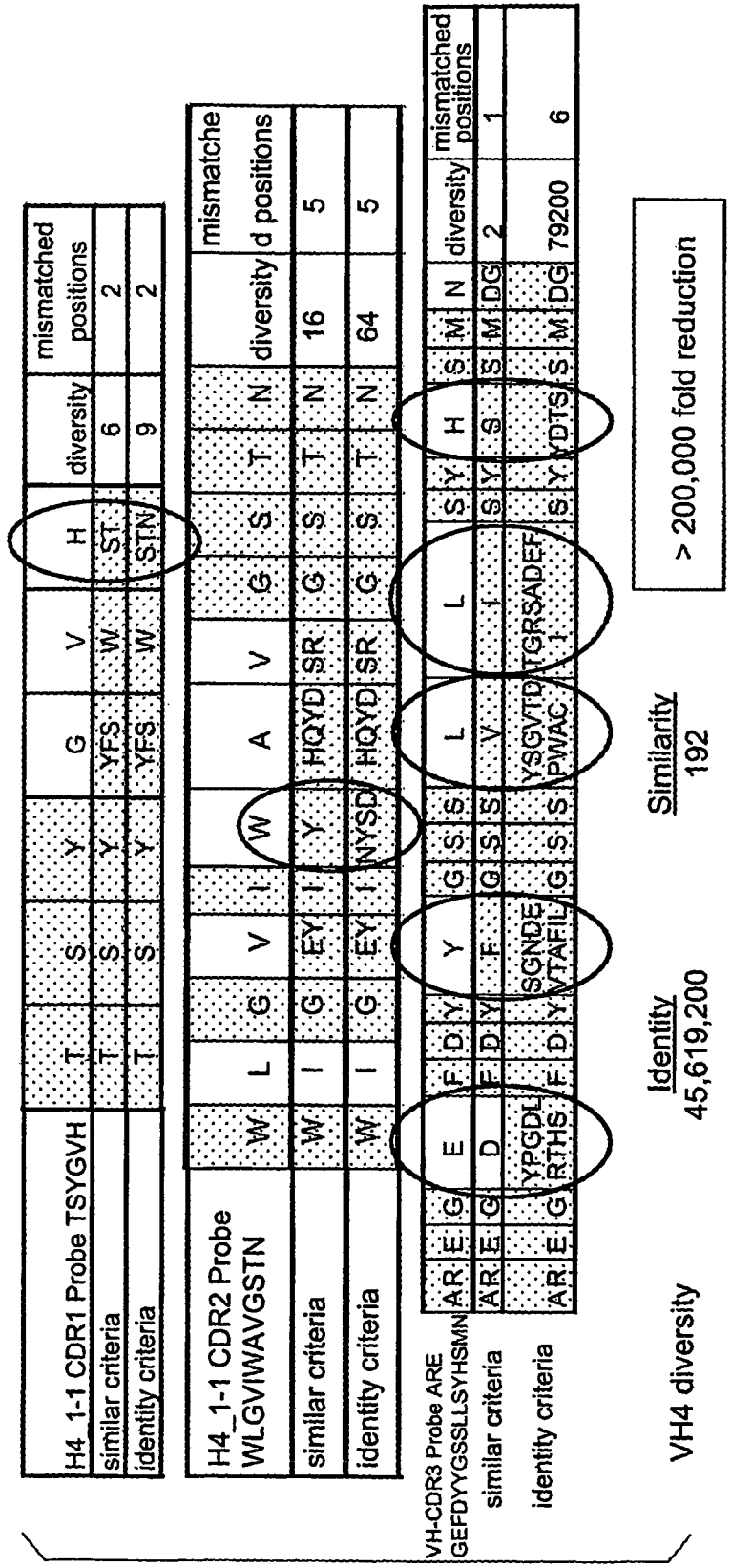
FIG. 29 shows comparison of cohort sequences obtained for a 4H6 anti-DR4 CDR1 query sequence under similarity criteria or identity criteria for comparison against a $V_H 4$ CDR1 reference library using the methods of the invention. First table discloses SEQ ID NOS 237-239, respectively, in order or appearance. Second table discloses SEQ ID NOS 240-242, respectively, in order or appearance. Third table discloses SEQ ID NOS 243-245, respectively, in order or appearance.

The distinction between similarity and identity criteria is illustrated via parallel application of both criteria to a mouse 4H6 anti-DR4 antibody. Heavy chain CDR1, CDR2 and CDR3 sequences for a mouse 4H6 anti-DR4 monoclonal antibody are "TSYGVH" (SEQ ID NO: 237), "WLGVI-WAVGSTN" (SEQ ID NO: 240), and "AREGEFDYYGSS-LLSYHSMN" (SEQ ID NO: 243), respectively. Use of the methods of the invention with the heavy chain CDR1 query sequence using similarity criteria yielded a cohort library sequence of "T-S-Y-Y/F/S-W-S/T" (SEQ ID NO: 238) (diversity 6) when the query sequence was compared with a human VH4_1-1 CDR1 UAL (FIG. 29). In contrast, use of the methods of the invention using the same CDR1 query sequence under identity criteria yielded the cohort library sequence "T-S-Y-Y/F/S-W-S/T/N" (SEQ ID NO: 239) (diversity). Use of similarity criteria thus allowed for rational omission of asparagine at the final position of CDR1 in the cohort library sequence, as histidine was deemed similar to reference library components serine and threonine, but not similar to asparagine. Implementation of the invention using similarity criteria to query heavy chain CDR2 sequence against a human VH4_1-1 CDR2 UAL yielded a cohort library sequence with diversity of 16, "W-I-G-E/Y-I-Y-H/Q/Y/D-S/R-G-S-T-N" (SEQ ID NO: 241), while parallel implementation of identity criteria yielded a cohort library sequence with diversity 64, "W-I-G-E/Y-I-N/Y/S/D-H/Q/Y/D-S/R-G-S-T-N" (SEQ ID NO: 242). Using similarity criteria to query heavy chain CDR3 sequence against a human VH UAL yielded a cohort library sequence of diversity 2, "A-R-E-G-D-F-D-Y-F-G-S-S-V-I-S-Y-S-S-M-D/G" (SEQ ID NO: 244), while identity criteria yielded a cohort library sequence of diversity 79,200, "A-R-E-G-Y/P/G/D/L/R/T/H/S-F-D-Y-S/G/N/D/E/V/T/A/F/I/L-G-S-S-Y/S/G/V/T/D/P/W/A/C-T/G/R/S/A/D/E/F/I-S-Y-Y/D/T/S-S-M-D/G" (SEQ ID NO: 245). Total heavy chain diversity of the resulting cohort libraries using similarity criteria was therefore 192, while total diversity of resulting cohort libraries designed in parallel using identity criteria was 45,619,200. Use of similarity criteria therefore rationally produced a greater than 200,000-fold reduction in total diversity.

Figure 30A:
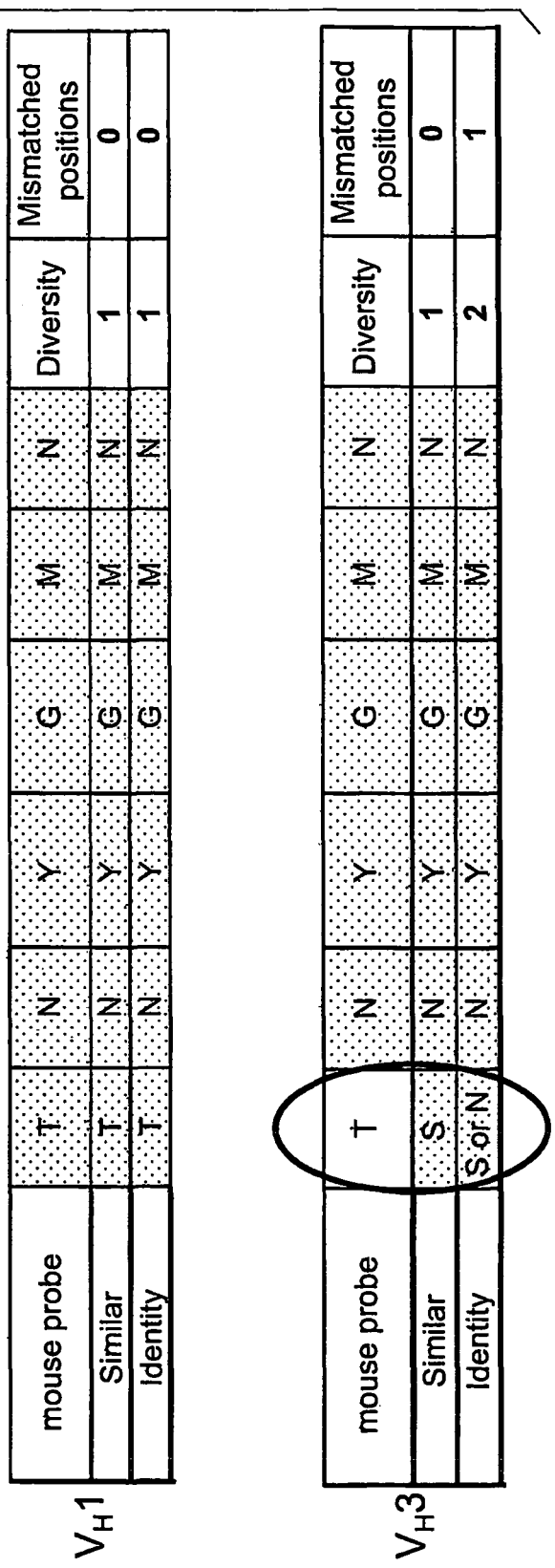
FIG. 30 (panels A-G) shows the cohort library sequences obtained under similarity and identity criteria using a mouse monoclonal anti-VEGF A4.6.1 antibody as a probe antibody. Panel A: Mouse Probe $V_H$ CDR1 "TNYGMN." (SEQ ID NO: 13). Similar and identity sequences disclosed as SEQ ID NO: 14 in the first table and SEQ ID NOS 246 and 15, respectively, in the second table. Panel B: Mouse Probe $V_H$ CDR2 "WMG-WINTYTGEPT." (SEQ ID NO: 16). Similar and identity sequences disclosed as SEQ ID NOS 247 and 17, respectively, in the first table and SEQ ID NOS 248 and 18, respectively, in the second table. Panel C: Mouse Probe $V_H$ CDR3 "AKYPHYYGSSHWYFD." (SEQ ID NO: 19). Similar and identity sequences disclosed as SEQ ID NO: 20. Panel D: Mouse Probe $V_L$ CDR1 "SNYLNWY." (SEQ ID NO: 21). Similar and identity sequences disclosed as SEQ ID NO: 22 in the first table and SEQ ID NO: 249 in the second table and SEQ ID NOS 250 and 251, respectively, in the third table. Panel E: Mouse Probe $V_L$ CDR2 "VLIYFTSSLH." (SEQ ID NO: 23). Similar and identity sequences disclosed as SEQ ID NOS 252 and 24, respectively, in the first table, SEQ ID NOS 253 and 25, respectively, in the second table and SEQ ID NOS 254 and 255, respectively, in the third table. Panel F: Mouse Probe $V_L$ CDR3 "QQYSTVPW." (SEQ ID NO: 26). Similar and identify sequences disclosed as SEQ ID NOS 256 and 27, respectively, in the first table and similar sequence disclosed as SEQ ID NO: 257, in the second table. Panel G: Combinatorial cohort diversity and similarity fold-reduction values.

Comparative implementation of similarity and identity criteria was also performed for heavy and light chain CDR sequences of mouse ant-VEGF monoclonal antibody A4.6.1. Heavy chain CDR1, CDR2 and CDR3 sequences for the mouse A4.6.1 anti-VEGF monoclonal antibody are "TNYGMN" (SEQ ID NO: 13), "WMGWINTYTGEPT" (SEQ ID NO: 16), and "AKYPHYYGSSHWYFD" (SEQ ID NO: 19), respectively. Use of the methods of the invention with the heavy chain CDR1 query sequence using similarity or identity criteria yielded a cohort library sequence of "T-N-Y-G-M-N" (SEQ ID NO: 14) (diversity 1) when the query sequence was compared with a human VH1 UAL (FIG. 30A). Comparison of the same query sequence with a human VH3 UAL using similarity criteria yielded a cohort library sequence of diversity 1, "S-N-Y-G-M-N" (SEQ ID NO: 246), while the same comparison using identity criteria yielded a cohort library sequence of diversity 2, "S/N-N-Y-G-M-N" (SEQ ID NO: 15). Application of the methods of the invention to heavy chain CDR2 using similarity criteria yielded cohort antibody library sequences of "W-M-G-W-I-N-P/A-Y-S-G-D-T/A-S" (SEQ ID NO: 247) (diversity 4) and "W-V-A-Y-I-N-S-D/S/N-S-G-E-I-H" (SEQ ID NO: 248) (diversity 3), when compared with $V_H1$ and $V_H3$ reference libraries, respectively (FIG. 30B). Parallel application of the methods of the invention to heavy chain CDR2 using identity criteria yielded cohort antibody library sequences of "W-M-G-W-I-N-P/A-Y-F/S/N/G-G-T/N/G/S/D-T/A-N/K/S/G" (SEQ ID NO: 17) (diversity 320) and "W-V-S/A-V/A/N/G/Y/S/T-I-N-G/Y/S/Q/W/N/F-D/S/N-G/S-G-E-T/K/I-Y/N/F/H" (SEQ ID NO: 18) (diversity 7056), when compared with $V_H1$ and $V_H3$ reference libraries, respectively. Application of the methods of the invention to heavy chain CDR3 using similarity and identity criteria for comparison with a $V_H$CDR3 UAL yielded identical cohort library sequences of diversity 8, "A-K-G/D/E/R/A/H/V/T-P-H-Y-Y-G-S-S-H-W-Y-F-D" (SEQ ID NO: 20) (FIG. 30C).

Light chain CDR1, CDR2 and CDR3 sequences for the mouse A4.6.1 anti-VEGF monoclonal antibody are "SNYLNWY" (SEQ ID NO: 21), "VLIYFTSSLH" (SEQ ID NO: 23), and "QQYSTVPW" (SEQ ID NO: 26), respectively. Light chain CDR1 comparisons yielded cohort libraries of "S-N-Y-L-N-W-Y" (SEQ ID NO: 22) (diversity 1) and "S-N-Y-L-A-W-Y" (SEQ ID NO: 249) (diversity 1) for comparison of the light chain CDR1 query sequence with $V_{L\square}1$ and $V_{L\square}3$ CDR1 UALs, respectively, regardless of whether similarity or identity criteria were employed (FIG. 30D). When the query light chain CDR1 sequence was compared with a $V_{L\square}3$ CDR1 UAL, similarity criteria yielded the cohort library "S-K/Q/Y/E-Y-V-H/Y/S/C-W-Y" (SEQ ID NO: 250) (diversity 16), while identity criteria yielded the cohort library "S-K/Q/Y/E-Y-A/V-H/Y/S/C-W-Y" (SEQ ID NO: 251) (diversity 32). Light chain CDR2 comparisons with a $V_{L\square}1$ CDR2 UAL yielded cohort libraries of "L-L-I-Y-A/D/K/G/S-A-S-S-L-Q/E" (SEQ ID NO: 252) (diversity 10) and "L/R-L-I-Y-A/D/K/G/S-A-S-S-L-Q/E" (SEQ ID NO: 24) (diversity 20) under similarity and identity criteria, respectively (FIG. 30E). Light chain CDR2 comparisons with $V_{L\square}3$ and $V_{L\square}3$ CDR2 reference libraries yielded cohort library sequences of "L-L-I-Y-G/D-T-S-S-R-A" (SEQ ID NO: 253) (diversity 2) and "L-V-I-Y-D/Q/E/K-D/K-S-K/D/E/N-R-P" (SEQ ID NO: 254) (diversity 40) under both similarity and identity criteria. For light chain CDR3, comparison of the query sequence with a $V_L\square$ CDR3 reference library yielded cohort library sequences of "Q-Q-Y-S-T-L-P-W" (SEQ ID NO: 256) (diversity 1) and "Q-Q-Y-S-T-Y/T/S/L/W/F-P-W" (SEQ ID NO: 27) (diversity 6) using similarity and diversity criteria, respectively. Comparison of this CDR3 query sequence with a $V_L\square$ CDR3 reference library yielded cohort library sequences of "Q-S/A/T/I/L-Y-D/Y/H/A-S-S/G/N/D-I/L-W" (SEQ ID NO: 257) (diversity 160) and "Q-S/A/T/I/L-Y-D/Y/H/A-S/G/N/R-S/G/N/D-T/A/N/I/S/L/G-W" (diversity 2240) using similarity and diversity criteria, respectively (FIG. 30F). Total diversity values of cohort library sequences under identity and similarity criteria are summarized in FIG. 30G and below in Table 19:

TABLE 19

Diversity of Cohort Library Sequences for Mouse A4.6.1 Monoclonal Antibody - Identity and Similarity Criteria Compared

| Chain Diversity Under Identity Criteria | | | | |
|---|---|---|---|---|
| H1 | H3 | K1 | K3 | L3 |
| 2560 | 112896 | 120 | 12 | 2867200 |

| Antibody Diversity Under Identity Criteria | | | |
|---|---|---|---|
| mAb diversity | K1 | K3 | L3 |
| H1 | 3.1E+05 | 3.1E+04 | 7.3E+09 |
| H3 | 1.4E+07 | 1.4E+06 | 3.2E+11 |

| Chain Diversity Under Similarity Criteria | | | | |
|---|---|---|---|---|
| H1 | H3 | K1 | K3 | L3 |
| 32 | 72 | 10 | 2 | 102400 |

| Antibody Diversity Under Similarity Criteria | | | |
|---|---|---|---|
| mAb diversity | K1 | K3 | L3 |
| H1 | 320 | 64 | 3276800 |
| H3 | 720 | 144 | 7372800 |
| Fold Reduction In Diversity Under Similarity Criteria | | | |
| H1 | 960 | 480 | 2240 |
| H3 | 18816 | 9408 | 43904 |

While the above implementation of similarity criteria incorporated one or more similar residues into cohort library sequence only if no identity match was found between query and reference library sequences at any individual residue position, similarity criteria can also be applied at positions where identity exists between query and reference library sequences. In such an implementation, a query sequence residue for which a reference library contains both an identity match and one or more similar residues yields cohort sequences comprising the identical residue plus one or more such similar residues at that position. Thus, application of this "all similar" criteria may be used to expand the diversity of a cohort library in a rational manner, achieving total diversity levels greater than for use of the standard similarity criteria described above, and possibly resulting in even greater total, rationally-derived diversity than that achieved using only identity criteria. The effect of using an "all similar" criteria as a component of the present invention was exemplified through application of identity, similarity and "all similar" criteria to the same anti-VEGF monoclonal antibody as above (A4.6.1). When "all similar" criteria were applied to heavy chain CDR1 sequence "TNYGMN" (SEQ ID NO: 13), a cohort library sequence of "T/S-N-Y-G-M-N" (SEQ ID NO: 259) (diversity 2) was obtained for when comparison was made between the query sequence and a $V_H1$ reference library (FIG. 31A). Thus, while a perfect match residue exists for the first residue of query sequence and the reference library (T), the "all similar" criteria results in usage of either T or the similar amino acid, S, in the first position of resultant CDR1 cohort library sequences. Use of "all similar" criteria for comparison of heavy chain CDR1 query sequence and the $V_H3$ CDR1 reference library yielded the cohort library sequence "S-N-Y-G/A-M-N" (SEQ ID NO: 261). The sequence of heavy chain CDR2 of the A4.6.1 antibody is "WMGWINTYTGEPT" (SEQ ID NO: 16). Comparison of this query CDR2 sequence using the methods of the invention while employing "all similar" criteria yielded cohort library sequences of "W-M-G-W-I-N-P/A-Y-S-G-D-T/A-S" (SEQ ID NO: 263) (diversity 4) and "W-V-A-Y-I-N-D/S/N-S-G-E/D-I-H" (SEQ ID NO: 265) (diversity 6) when query sequence was compared with $V_H1$ and $V_H3$ CDR2 reference libraries, respectively (FIG. 31B). Under "all similar" criteria, comparison of the heavy chain CDR3 query sequence, "AKYPHYYGSSHWYFD" (SEQ ID NO: 19), with a $V_H$ CDR3 reference library yielded the cohort library sequence "A-R/K-G/D/E/R/A/H/V/T-P/V/L-S/T/H-Y/F-Y/W-G/A-S/T-S/T-S/H-Y/W-Y/W-F-D" (diversity 36,864; FIG. 31C).

Application of "all similar" criteria to the A4.6.1 light chain CDR1, CDR2 and CDR3 sequences ("SNYLNWY" (SEQ ID NO: 21), "VLIYFTSSLH" (SEQ ID NO: 23), and "QQYSTVPW" (SEQ ID NO: 26), respectively) yielded the following cohort library sequences: "S-N-Y/W-L-N-W-Y" (SEQ ID NO: 269) (diversity 2), "S-N-Y-L-A-W-Y" (SEQ ID NO: 271) (diversity 1) and "S/T-K/Q/Y/E-Y/F-V-H/Y/S/C-W-Y" (diversity 64) for comparisons of CDR1 query sequence with $V_L\square 1$, $V_L\square 3$, and $V_L\square 3$ reference libraries, respectively (FIG. 31D); "L-L-I-Y-A/D/K/G/S-A-S-S/T-L-Q/E" (SEQ ID NO: 275) (diversity 20), "L-L-I-Y-G/D-T-S-S/T-R-A" (SEQ ID NO: 277) (diversity 4), and "L-V-I/V-Y-D/Q/E/K/G-D/K-S/T-K/D/E/N-R-P" (SEQ ID NO: 280) (diversity 160) for comparisons of CDR2 query sequence with $V_L\square 1$, $V_L\square^{3}$, and $V_L\square 3$ reference libraries, respectively (FIG. 31E); and "Q-Q-Y-S/T-S/T/H-L-P-Y/W/F" (SEQ ID NO: 281) (diversity 18) and "Q-S/A/T/I/L-W/Y-H-S-S/G/N/D-I/L-W" (SEQ ID NO: 283) (diversity 80) for comparisons of CDR3 query sequence with $V_L\square$ and $V_L\square$ reference libraries, respectively (FIG. 31F). As for previously considered antibody sequences, the production of a final cohort antibody (or fragment thereof, e.g., Fab, scFv, etc.) library from the various cohort CDR libraries can be performed via independent assortment of cohort CDR library sequences with one another to build both heavy and light chains, and complete antibodies (or fragments thereof), from the cohort CDR libraries identified by the methods of the invention. Table 20 summarizes diversity data for cohort libraries and antibodies of the invention that resulted from application of identity, similarity or "all similar" criteria across the CDR sequences of the mouse A4.6.1 monoclonal antibody.

TABLE 20

Diversity Produced Using Identity, Similarity and "All Similar" Criteria for Mouse A4.6.1 CDR Query Sequences Chain Diversity Under Identity Criteria

| H1 | H3 | K1 | K3 | L3 |
|---|---|---|---|---|
| 2560 | 112896 | 120 | 12 | 2867200 |

Antibody Diversity Under Identity Criteria

| mAb diversity | K1 | K3 | L3 |
|---|---|---|---|
| H1 | 3.1E+05 | 3.1E+04 | 7.3E+09 |

TABLE 20-continued

Diversity Produced Using Identity, Similarity and "All Similar" Criteria for Mouse A4.6.1 CDR Query Sequences

| H3 | 1.4E+07 | 1.4E+06 | 3.2E+11 |
|---|---|---|---|

Chain Diversity Under Similarity Criteria

| H1 | H3 | K1 | K3 | L3 |
|---|---|---|---|---|
| 32 | 72 | 10 | 2 | 102400 |

Antibody Diversity Under Similarity Criteria

| mAb diversity | K1 | K3 | L3 |
|---|---|---|---|
| H1 | 320 | 64 | 3276800 |
| H3 | 720 | 144 | 7372800 |

Chain Diversity Under "All Similar" Criteria

| H1 | H3 | K1 | K3 | L3 |
|---|---|---|---|---|
| 294,912 | 442,368 | 720 | 72 | 819,200 |

| mAb diversity | K1 | K3 | L3 |
|---|---|---|---|

Antibody Diversity Under "All Similar" Criteria

| | | | |
|---|---|---|---|
| H1 | 2.1E+08 | 2.1E+07 | 2.4E+11 |
| H3 | 3.2E+08 | 3.2E+07 | 3.6E+11 |

Fold Reduction In Whole Antibody Diversity Under Similarity v. Identity Criteria

| | | | |
|---|---|---|---|
| H1 | 960 | 480 | 2240 |
| H3 | 18816 | 9408 | 43904 |

Fold Expansion In Whole Antibody Diversity Under "All Similar" v. Similarity Criteria

| | | | |
|---|---|---|---|
| H1 | 663,552 | 331,776 | 73,728 |
| H3 | 442,368 | 221,184 | 49,152 |

Example 20

Methods for Genetically Engineering a Cohort Antibody Library

In this example, the steps for making and assembling a cohort antibody library using genetic engineering techniques are described.

The scFv format consists of the functional antigen binding units ($V_H$ and $V_L$ regions) joined together. Briefly, the $V_L$ and $V_H$ fragments of the antibodies are cloned using standard molecular biology techniques. The oligonucleotides encoding the framework and CDRs of the variable regions are assembled by the single overlap polymerase chain reaction (SOE-PCR). The separate $V_L$ and $V_H$ fragments are then subsequently linked with a polyGly-Ser linker (typically GGGGSGGGGSGGGGS) (SEQ ID NO: 590) to generate single chain antibodies (scFv). The full-length molecules are then amplified using flanking 5' and 3' primers containing restriction sites that facilitate cloning into the expression-display vector(s). The total diversity of the libraries generated depends on the number of framework sequences and number of positions in the CDRs chosen for mutagenesis, e.g., using WTM.

Typically, for synthesis of a complete reference universal antibody reference library, the average diversity of the VH library, using 9 amino acids to conduct WTM™, is $3.5 \times 10^6$ (6 frameworks×9 amino acids×(22 for CDR1×$2^6$ for CDR2×$2^8$ for the 13 amino acids CDR3)). The diversity of the $V_H$ library is an upper limit and the diversity of the $V_\lambda$ and $V_k$ libraries is significantly smaller, thereby limiting the combined diversity of the complete scFv library from $10^{10}$ to $10^{11}$ which is within the range of the transformation efficiencies of bacterial systems.

Figure 33:
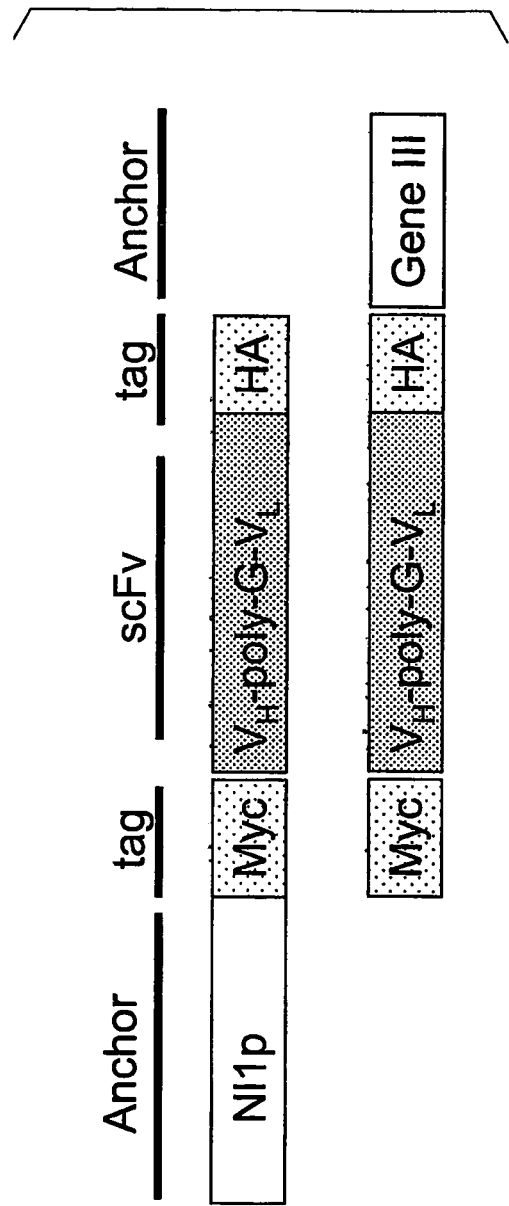
FIG. 33 shows various schematic representative scFv chimeric molecules that are formed in accordance with the present invention. The chimeric scFv constructs can be comprised of an N-terminal leader sequence for bacterial periplasmic export and retention. The alternative scFv C-terminal chimeric construct utilizes a Gene III anchoring signal to retain the scFv protein.

Accordingly, for generation of reference universal antibody libraries, 90 oligonucleotides were synthesized to encompass the frameworks of the various $V_H$, $V_\lambda$, and $V_k$ libraries (see FIGS. 62A-62E) along with 2 oligonucleotides that encoded for His and Myc immunotags at, respectively, the N- and C-termini (FIG. 33). In addition, a subset of 30-60 degenerate oligonucleotides representing the diversity in CDRs 1, 2, and 3 of each of the three libraries were synthesized (total 90-180). These oligonucleotides were assembled by the SOE-PCR method to generate the libraries that included the necessary $V_H$-$V_\lambda$ and $V_H$-$V_k$ combinations. Random clones from each library were then chosen for sequence verification and assessment of library quality.

Figure 34:
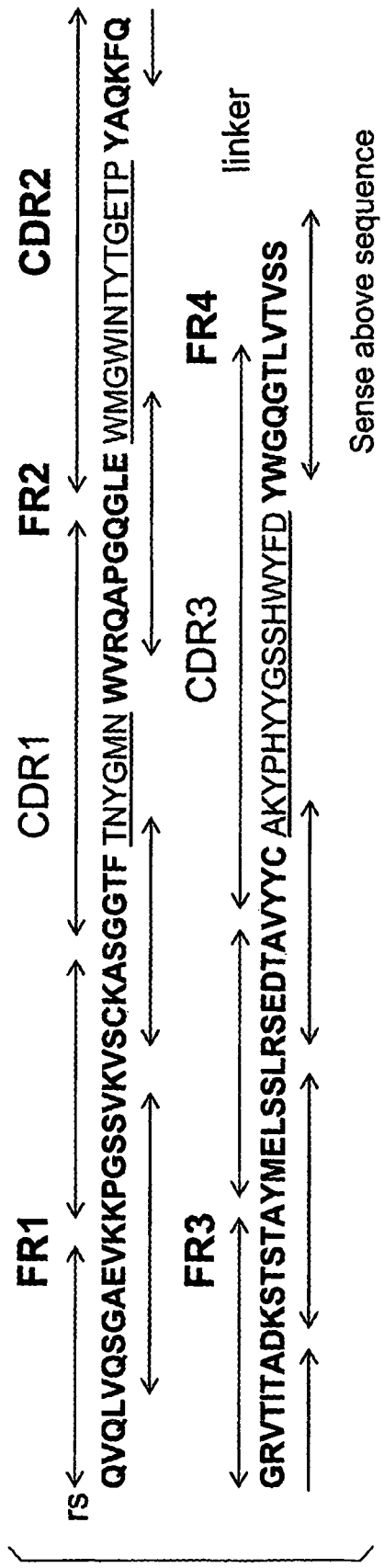
FIG. 34 shows the construction of the wildtype anti-VEGF A4.6.1 heavy chain library using a combination of overlapping nondegenerate oligonucleotides which can be converted to double-stranded nucleic acids using the single overlap extension polymerase chain reaction (SOE-PCR). Figure discloses SEQ ID NO: 285.
Figure 35:
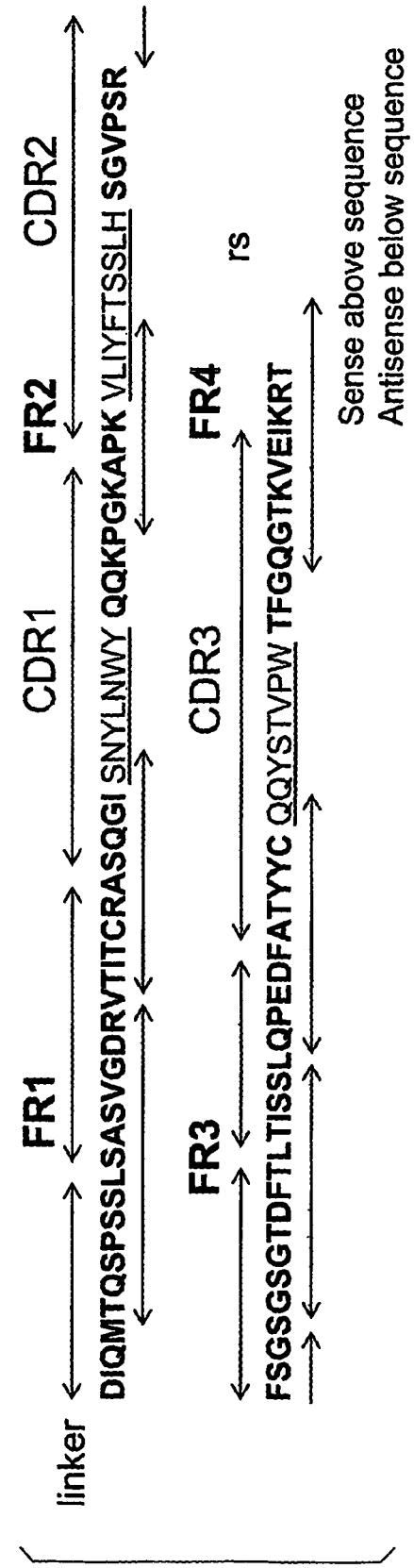
FIG. 35 shows the construction of the wildtype anti-VEGF A4.6.1 light chain library using a combination of overlapping nondegenerate oligonucleotides which can be converted to double-stranded nucleic acids using the single overlap extension polymerase chain reaction (SOE-PCR). Figure discloses SEQ ID NO: 286.

Synthesis of cohort CDR and antibody libraries of the invention were performed by the same process as described for UALs. Synthesis of cohort antibody libraries featured the added advantage that such cohort libraries would have lower diversity than reference libraries, thus rendering cohort libraries easier to generate, often requiring fewer oligonucleotides than a reference library. For each target antibody cohort library generation, a set of oligonucleotides of the wild type antibody sub-family member $V_L$ and $V_H$, CDR 1, 2, and 3 sequences were synthesized (FIGS. 62G-H). These $V_H$, $V_L$, and CDR oligonucleotides were also assembled by SOE-PCR to generate the initial necessary $V_H$-$V_L$ combinations for the base scFv mutagenesis template. Generation of the starting wild type antibody for positive controls was essentially carried out in similar fashion. See FIGS. 34 and 35 for anti-VEGF A4.6.1 framework and CDR amino adds coded and assembled by SOE-PCR oligonucleotides (FIGS. 62G-1).

The introduction of stop codons in the $V_L$ and $V_H$, CDRs 1, 2, and 3 (see below and the others in FIGS. 62G-I) was an additional feature of the wild type mutagenesis template employed to increase the screening efficiency of the cohort library. As an example, the $V_H$ CDR1 H1e_1_VEGF stop codon oligonucleotide had two in frame stops (TAA TAA) in place of the tyrosine and glycine (TAC GGG) residues at corresponding CDR positions of the wild type sequence, as shown below.

```
                                         (SEQ ID NO: 529)
H1e_1_VEGFstop: 5'-AGGCTTCCGGTGGCACATTC ACC AAC
TAA TAA ATG AAC TGGGTTAGACAGGCACCTGG-3'

(SEQ ID NO: 591)
H1e_1_VEGF: 5'AGGCTTCCGGTGGCACATTC ACC AAC TAC GGG
ATG AAC TGGGTTAGACAGGCACCTGG-3'.
```

Using the in-frame stop codon, any non-mutagenized $V_L$ and $V_H$, CDR templates would not be fully translated and/or exported to the bacterial periplasmic space. By limiting subsequent FACS to only functional scFvs, the background signal to noise level of antigen binding to wild-type scFvs was therefore minimized.

Regarding CDR diversity, LTM may be used to explore small perturbations within the antibody CDR loops (e.g., one change per loop). For further improvement, WTM, which allows for the incorporation of more than one substitution within a CDR, may be subsequently used to exhaustively screen the chemical landscape of the CDR(s). Using WTM, the wildtype amino acid and the desired amino acid variants are explored in targeted CDR positions by manipulating oligonucleotide synthesis. A mixed pool of oligonucleotides is synthesized where a subset of the oligonucleotides code for the wildtype and another subset code for the targeted mutation in a specific position. In the WTM procedure, at each step of the synthesis, the growing oligonucleotide chain is extended by one of two bases. One base encodes for the wild-type codon, while the other base belongs to a codon for the desired mutation.

By integrating wild type CDRs with different $V_H$ and $V_L$ frameworks, added diversity was generated beyond that of LTM and WTM CDR mutations (see Example 2X below). The total diversity of the cohort libraries generated depended on both the number of CDR positions mutated and how many amino acids were substituted based on the matched variability profile. The variability profile for each starting template was dependent upon the surrounding $V_L$ and $V_H$ framework.

Example 21

Creation of Cohort $V_H$, $V_\lambda$, and $V_K$ scFv Libraries by Walk Through Mutagenesis A. Preparation of scFv Single Stranded Template for Kunkel Mutagenesis Target scFv expression constructs were cloned in PBSKII for the preparation of scFv single-stranded DNA. The *E. coli* hosts CJ236 were grown in 2YT/Amp liquid medium until the OD600 reached approximately 0.2 to 0.5 Absorbance Units (AU). At this timepoint, 1 mL of M13 K07 helper phage was added to the bacterial culture for continued incubation at 37° C. After 30 minutes, the bacteria and phage culture was transferred to a larger volume of 2YT/Amp liquid medium (30 mL) containing 0.25 ug/mL uridine for overnight growth.

The next day, the culture medium was clarified by centrifugation (10 minutes at 10,000× g), after which the supernatant was collected and ⅕ volume of PEG-NaCl added for 30 minutes. The mixture was further centrifuged twice more, but after each centrifugation, the supernatant was discarded in favor of the retained PEG/phage pellet. The PEG/phage pellet was then resuspended in PBS (1 mL), re-centrifuged (5 minutes at 14,000×g). The supernatant was collected and then applied to DNA purification column (QIAprep Spin M13, Qiagen) to elute single-stranded scFv uridinylated-DNA.

B. Walk Through Mutagenesis (WTM) Oligonucleotides

Synthetic oligonucleotides were synthesized on a 3900 Oligosynthesizer (Syngen Inc., San Carlos, Calif.) as per manufacturer directions, and primer quality was verified by PAGE electrophoresis prior to PCR or Kunkel mutagenesis use. The Walk Through Mutagenesis (WTM) oligonucleotide annealed to uridinylated single stranded template and was designed to mutate specific position(s) with predetermined amino acids (see Patent Application No. PCT/US2004/020306, incorporated herein by reference in its entirety). This precision and control of amino acid substitutions was distinct from other stochastic mutagenesis techniques that allow for multiple specific CDR substitutions.

Using WTM, the wild-type amino acid and the desired amino acid variants were explored in targeted CDR positions by manipulating oligonucleotide synthesis. A mixed pool of oligonucleotides was synthesized, wherein a subset of the oligonucleotides coded for the wild-type codon and another subset coded for the targeted mutation at a specific position. In the WTM procedure, at each step of the synthesis, the growing oligonucleotide chain was extended by one of two bases. One base encoded for the wild-type codon, while the other base was designed to insert the desired mutant codon.

C. Ultra-Humanization Mutagenesis with CDR Oligonucleotides from Avastin Anti-VEGF $V_H$ CDR Blasting For the process of ultra-humanization, particular CDR positions were replaced by amino acids chosen based on their in vivo frequency (see Example 4 above, and results below). During humanization of murine-derived Avastin A4.6.1 into the first human $V_H1$ framework, there were no CDR1 amino add replacements based on the corresponding variability profile (table below). The oligonucleotide H1e_1_VEGF01 CDR1, (see Figure XE), consisted of the sequence: 5'-AGGCTTCCGGTGGCACATTC ACC AAC TAC GGG ATG AAC TGGGTTAGACAGGCACCTGG-3' (SEQ ID NO: 592). The $V_H1$ CDR1 coding sequence, 5'-ACC AAC TAC GGG ATG AAC-3' (SEQ ID NO: 593) was flanked by the DNA sequences 5'-AGGCTTCCGGTGGCACATTC (SEQ ID NO: 594) and TGGGTTAGACAGGCACCTGG-3' (SEQ ID NO: 595), which extended respectively into the surrounding $V_H1$ framework region.

TABLE 21

Avastin VH-1 CDR1 Mouse Probe Alignment
Mouse probe and library encodes sequences disclosed as SEQ ID NOS 13 and 14, respectively.
VH-1 CDR1

|  |  | S<br>G | | A<br>Y | | H |
|---|---|---|---|---|---|---|
|  | T | N | | G | I | S |
| UAL constituents | S | D | Y | D | M | N |
| mouse probe | T | N | Y | G | M | N |
| library encodes | T | N | Y | G | M | N |
| possible residues | 1 | 1 | 1 | 1 | 1 | 1 |

To re-iterate CDR-framework shuffling, this humanized $V_H1$ CDR1 coding sequence could also be integrated into the context of another framework (of sub-family $V_H1$ members, $V_H3$, $V_H4$ or others) by juxtaposition of subfamily sequence specific framework extension. The $V_H1$ CDR1 coding sequence could instead be flanked by the upstream $V_H3$-07 framework sequences 5'-GCCAGCGGCTTTACCTTCTCT (SEQ ID NO: 596) and downstream GCTGGGTTAGACAGGCACCT-3' (SEQ ID NO: 597) extensions into the surrounding $V_H3$ framework region.

During $V_H1$ CDR2 Avastin A4.6.1 blasting, five of the 13 wild-type amino acids (T, T, E, P, and T) were replaced with human preferred amino acids (respectively P/A, F/S/N/T, T/N/G/S/D, AND N,K,S,G) based on the $V_H1$ CDR2 variability profile (see open boxes in the variability profile table below). Here, the CDR2 wildtype amino acid sequence WMGWINTYTGEPT (SEQ ID NO: 16) was encoded by: 5'-TTG ATG GGA TTG ATA AAC CCA TAC TTC GGA ACA AAC-3' (SEQ ID NO: 598) which was flanked by the $V_H1$ framework 5'-CACCTGGTCAGGGCTTGGAG (SEQ ID NO: 599) and TACGCTCAGAAATTCCAGGG-3' (SEQ ID NO: 600) sequences.

TABLE 21

Avastin VH-1 CDR2 Mouse Probe Alignment
Mouse probe and library encodes sequences disclosed as SEQ ID NOS: 16 and 601, respectively.
VH-1 CDR2

|  |  |  |  |  |  |  |  | I<br>N<br>S<br>W<br>G | | | F<br>Y<br>S<br>N | | T<br>N<br>G<br>S | | N<br>K<br>G |
|---|---|---|---|---|---|---|---|---|---|---|---|---|---|---|---|
| UAL constituents | W | M | G | R | I | S | A | M | G | G | D | A | G |
| mouse probe | W | M | G | W | I | N | T | Y | T | G | E | P | T |
| library encodes | W | M | G | W | I | N | P/A | Y | F/S/N/T | G | T/N/G/S/D | T/A | N/K/S/G |
| minimal degenerate | 1 | 1 | 1 | 1 | 1 | 1 | 1 | 1 | 3 | 1 | 2 | 1 | 2 |
| possible residues | 1 | 1 | 1 | 1 | 1 | 1 | 2 | 1 | 4 | 1 | 5 | 2 | 4 |

These A4.6.1 $V_H$1CDR2 humanization substitutions for P/A, F/S/N/T, T/N/G/S/D, AND N,K,S,G thereby required a minimum of 12 oligonucleotides to generate the 320 possible unique replacement variations. Based on the above table, the needed humanization substitutions at CDR2 positions that were performed are shown by the italic degenerate base mixtures where S is (C or G) and R is (A or G) (see H1e_2_VEGF01-12 oligonucleotide sequences below).

TABLE 22

Avastin VH-1 CDR2 Degenerate Base Humanization Oligonucleotides

| | | |
|---|---|---|
| H1e_2_VEGF01 | 5'-CACCTGGTCAGGGCTTGGAGTTGATGGGCTTGATCAAC*S*CCTACTTCGG CAC*CRCCR*GCTACGCTCAGAAATTCCAGGG-3' | (SEQ ID NO: 602) |
| H1e_2_VEGF02 | 5'-CACCTGGTCAGGGCTTGGAGTTGATGGGCTTGATCAAC*S*CCTACTTCGG CAC*CRCCAAS*TACGCTCAGAAATTCCAGGG-3' | (SEQ ID NO: 603) |
| H1e_2_VEGF03 | 5'-CACCTGGTCAGGGCTTGGAGTTGATGGGCTTGATCAAC*S*CCTAC*R*GCGG CAC*CRCCR*GCTACGCTCAGAAATTCCAGGG-3' | (SEQ ID NO: 604) |
| H1e_2_VEGF04 | 5'-CACCTGGTCAGGGCTTGGAGTTGATGGGCTTGATCAAC*S*CCTAC*R*GCGG CAC*CRCCAAS*TACGCTCAGAAATTCCAGGG-3' | (SEQ ID NO: 605) |
| H1e_2_VEGF05 | 5'-CACCTGGTCAGGGCTTGGAGTTGATGGGCTTGATCAAC*S*CCTACAACGG CAC*CRCCR*GCTACGCTCAGAAATTCCAGGG-3' | (SEQ ID NO: 606) |
| H1e_2_VEGF06 | 5'-CACCTGGTCAGGGCTTGGAGTTGATGGGCTTGATCAAC*S*CCTACAACGG CAC*CRCCAAS*TACGCTCAGAAATTCCAGGG-3' | (SEQ ID NO: 607) |
| H1e_2_VEGF07 | 5'-CACCTGGTCAGGGCTTGGAGTTGATGGGCTTGATCAAC*S*CCTACTTCGG C*RRCRCCR*GCTACGCTCAGAAATTCCAGGG-3' | (SEQ ID NO: 608) |
| H1e_2_VEGF08 | 5'-CACCTGGTCAGGGCTTGGAGTTGATGGGCTTGATCAAC*S*CCTACTTCGG C*RRCRCCAAS*TACGCTCAGAAATTCCAGGG-3' | (SEQ ID NO: 609) |
| H1e_2_VEGF09 | 5'-CACCTGGTCAGGGCTTGGAGTTGATGGGCTTGATCAAC*S*CCTAC*R*GCGG C*RRCRCCR*GCTACGCTCAGAAATTCCAGGG-3' | (SEQ ID NO: 610) |
| H1e_2_VEGF10 | 5'-CACCTGGTCAGGGCTTGGAGTTGATGGGCTTGATCAAC*S*CCTAC*R*GCGG C*RRCRCCAAS*TACGCTCAGAAATTCCAGGG-3' | (SEQ ID NO: 611) |
| H1e_2_VEGF11 | 5'-CACCTGGTCAGGGCTTGGAGTTGATGGGCTTGATCAAC*S*CCTACAACGG C*RRCRCCR*GCTACGCTCAGAAATTCCAGGG-3' | (SEQ ID NO: 612) |
| H1e_2_VEGF12 | 5'-CACCTGGTCAGGGCTTGGAGTTGATGGGCTTGATCAAC*S*CCTACAACGG C*RRCRCCAAS*TACGCTCAGAAATTCCAGGG-3' | (SEQ ID NO: 613) |

For $V_H$ CDR3, there were no originating subfamilies, as CDR3 was formed from the recombinational joining of the immunoglobulin D and J segment genes. Using the above-described variability profile analysis, only one position of the CDR3 length size 15 was replaced with the 8 human preferred amino acids. Specifically, the CDR3 wild-type amino acid sequence, AKYPHYYGSSHWYPD (SEQ ID NO: 19) was humanized by the sequence A-K-G/D/E/R/A/H/Y/T-P-H-Y-Y-G-S-S-H-W-Y-P-D (SEQ ID NO: 20). In this case, only four degenerate oligonucleotides were needed for the A4.6.1 $V_H$1CDR3 humanization replacements (see H1e_3_VEGF01-4 sequences below).

TABLE 23

Avastin VH CDR3 Degenerate Base Humanization Oligonucleotides

| | | |
|---|---|---|
| H1e_3_VEGF01 | 5'-ATACCGCCGTGTATTACTGTGCCAAG*R*GACCCCACTACTACGG CAGCAGCCACTTGTACTTCGACTACTGGGGTCAGGGCACTCT-3' | (SEQ ID NO: 614) |
| H1e_3_VEGF02 | 5'-ATACCGCCGTGTATTACTGTGCCAAG*S*ACCCCACTACTACGG CAGCAGCCACTTGTACTTCGACTACTGGGGTCAGGGCACTCT-3' | (SEQ ID NO: 615) |
| H1e_3_VEGF03 | 5'-ATACCGCCGTGTATTACTGTGCCAAGG*W*GCCCCACTACTACGG CAGCAGCCACTTGTACTTCGACTACTGGGGTCAGGGCACTCT-3' | (SEQ ID NO: 616) |
| H1e_3_VEGF04 | 5'-ATACCGCCGTGTATTACTGTGCCAAG*R*CCCCCACTACTACGG CAGCAGCCACTTGTACTTCGACTACTGGGGTCAGGGCACTCT-3' | (SEQ ID NO: 617) |

The CDR3 was encoded by: 5'-GCC AAG (RGA OR SAC OR GWG OR RCC) CCC CAC TAC TAC GGC AGC AGC CAC TTG TAC TTC GAC-3' (SEQ ID NO: 618) which is flanked by the $V_H1$ framework 5'-ATACCGCCGTGTAT-TACTGT (SEQ ID NO: 619) and TACTGGGGT-CAGGGCACTCT-3' (SEQ ID NO: 620) sequences. The CDR3 degenerate positions are indicated by the bold degenerate base mixtures where S is (C or G), R is (A or G), and W is (A or T).

For $V_H3$ CDR1 and CDR2 humanization of A4.6.1, the replacement tables and CDR coding oligonucleotides are listed below (see FIG. 62I for the complete oligonucleotide listings). For $V_H3$, four distinct family members were employed, 3-30, 3-07, 3-11 and 3-23. Therefore, flanking the respective degenerate CDR1 and CDR2 coding sequences were $V_H3$: 3-30, 3-07, 3-11 and 3-23 framework-specific sequences for precise annealing to their respective starting $V_H3$ mutagenic scFv templates.

TABLE 24

Avastin VH-3 CDR1 Mouse Probe Alignment
Mouse probe and library encodes sequences disclosed as SEQ ID NOS: 13 and 15, respectively.
VH-3 CDR1

| | | S | | A | | | | |
|---|---|---|---|---|---|---|---|---|
| | | N | Y | G | | S | | |
| | S | D | A | W | | H | | |
| UAL constituents | N | T | S | Y | M | N | | |
| mouse probe | T | N | Y | G | M | N | | |
| library encodes | S or N | N | Y | G | M | N | | |
| possible residues | 2 | 1 | 1 | 1 | 1 | 1 | Diversity | 2 |

TABLE 25

Avastin VH-3 CDR2 Mouse Probe Alignment
Mouse probe and library encodes sequences disclosed as SEQ ID NOS: 16 and 18, respectively.
VH-3 CDR2

| | | | | V | | G | | | | | | | | |
|---|---|---|---|---|---|---|---|---|---|---|---|---|---|---|
| | | | | A | | Y | | | | S | | | | |
| | | | | N | | S | | | | N | | | | |
| | | | | G | | D | | | | S | T | | Y | |
| | | | | Y | | W | | | | G | E | T | N | |
| | | | G | S | K | W | D | | G | T | Y | K | F | |
| UAL constituents | W | V | A | T | I | N | F | N | G | D | D | I | H | |
| mouse probe | W | M | G | W | I | N | T | Y | T | G | E | P | T | |
| library encodes | W | V | S/A | V/A/N/G/Y/S/T | I | N | G/Y/S/Q/W/N/F | D/S/N | G/S | G | E | T/K/I | Y/N/F/H | |
| possible residues | 1 | 1 | 2 | 7 | 1 | 1 | 7 | 7 | 2 | 1 | 3 | 4 | Product | 7056 |

TABLE 26

Avastin VK-1 CDR1 Mouse Probe Alignment
Mouse probe and library encodes sequences disclosed as SEQ ID NOS: 21 and 22, respectively.
VK-1 CDR1

| | | S | | | | | | |
|---|---|---|---|---|---|---|---|---|
| | | R | N | Y | | | | |
| | | G | S | W | | | | |
| | | N | T | D | A | | | |
| UAL constituents | Y | K | S | L | N | W | Y | |
| mouse probe | S | N | Y | L | N | W | Y | |
| library encodes | S | N | Y | L | N | W | Y | No diversity |
| possible residues | 1 | 1 | 1 | 1 | 1 | 1 | 1 | Product 1 |

TABLE 27

Avastin VK-3 CDR1 Mouse Probe Alignment
Mouse probe and library encodes sequences disclosed as SEQ ID NOS: 21 and 249, respectively.
VK-3 CDR1

| | | S | S | | | | | |
|---|---|---|---|---|---|---|---|---|
| | | G | N | N | | | | |
| UAL constituents | N | T | Y | L | A | W | Y | |
| mouse probe | S | N | Y | L | N | W | Y | |
| library encodes | S | N | Y | L | A | W | Y | |
| possible residues | 1 | 1 | 1 | 1 | 1 | 1 | 1 | Product 1 |

The resulting VK-1 and VK-3 CDR1 oligonucleotides identified are respectively shown below (see K1__1_VEGF01 and K3__1_VEGF01):

D. Avastin Anti-VEGF $V_L$ CDR Blasting

In a related manner, ultra-humanization substitutions for the $V_L$ kappa and $V_L$ lambda light chains were established from their respective variability profiles. For example, use of $V_L$ kappa I and $V_L$ kappa III family members was determined, specifically $V_L$ kappa-L1, $V_L$ kappa III-A27 and $V_L$ kappa III-L6. The resulting ultra-humanization VK-1 and VK-3 replacement tables identified are shown below. In both VK-1 and VK-3 cases, there were no ultra-humanization VK-1 and VK-3 replacements needed.

```
                                           (SEQ ID NO: 621)
K1_1_VEGF01: 5'-GCAGAGCTTCTCAGGGTATC-AGC AAC TAC
CTG AAC TTG TAC - CAACAGAAGCCTGGTAAAGC-3'.

(SEQ ID NO: 622)
K3_1_VEGF01: 5'-GCAGAGCTTCTCAGTCCGTG AGC AAC TAC
CTG GCC TTG TAC - CAACAGAAACCTGGTCAGGC-3'.
```

Ultra-humanization for $V_L$ kappa I and $V_L$ kappa III CDR2 established from their respective variability profiles replacement tables as shown below. In VK-1 and VK-3 cases, there were four CDR positions that required humanization substitutions. However, the diversity tables demonstrated that even with the same number of replacements (four positions), actual VK-1 and VK-3 diversity created were 20 and 2, respectively. This illustrated the property that different variability profiles yielded different levels of diversity when the same input template was used for alignment.

TABLE 28

Avastin VK-1 CDR2 Mouse Probe Alignment
Mouse probe and library encodes sequences disclosed as SEQ ID
NOS: 23 and 24, respectively.

VK-1 CDR2

| UAL constituents | L<br>R | L | I | Y | A<br>D<br>K<br>G<br>S | A | S | I<br>S<br>T<br>N | L | Q<br>E | |
|---|---|---|---|---|---|---|---|---|---|---|---|
| mouse probe | V | L | I | Y | F | T | S | S | L | H | |
| library encodes | L/R | L | I | Y | A/D/K<br>G/S | A | S | S | L | Q/E | |
| possible residues | 2 | 1 | 1 | 1 | 5 | 1 | 1 | 1 | 1 | 2 | Product 20 |

TABLE 29

Avastin VK-3 CDR2 Mouse Probe Alignment
Mouse probe and library encodes sequences disclosed as SEQ
ID NOS: 23 and 25, respectively.

VK-3 CDR2

| UAL constit-uents | L | L | I | Y | G<br>D | A<br>T | S<br>S | N | R | A | |
|---|---|---|---|---|---|---|---|---|---|---|---|
| mouse probe | V | L | I | Y | F | T | S | S | L | H | |
| library encodes | L | L | I | Y | G/D | T | S | S | R | A | |
| possible residues | 1 | 1 | 1 | 1 | 2 | 1 | 1 | 1 | 1 | 1 | Product 2 |

The VK-1 CDR2 ultrahumanization oligonucleotides are as below (refer to Table 30, sequences K1_2_VEGF01-3). The 5' and 3' VK-1 flanking framework sequences around CDR2 are respectively: 5'-AGCCTGGTAAAGC-CCCTAAG-3' (SEQ ID NO: 623) and 5'-TCCGGCGTTC-CTAGCAGATT-3' (SEQ ID NO: 624).

TABLE 30

Avastin VK-1 CDR2 Degenerate Base Humanization Oligonucleotides

| K1_2_VEGF01 | 5'-AGCCTGGTAAAGCCCCT<br>AAGCKGCTGATCTACAAGGCCA<br>GCAGCCTGSAGTCCGGCGTTCC<br>TAGCAGATT-3' | (SEQ ID NO: 625) |
|---|---|---|
| K1_2_VEGF02 | 5'-AGCCTGGTAAAGCCCCTAA<br>GCKGCTGATCTACGMCGCCAG<br>CAGCCTGSAGTCCGGCGTTCCT<br>AGCAGATT-3' | (SEQ ID NO: 626) |
| K1_2_VEGF03 | 5'-AGCCTGGTAAAGCCCCTAA<br>GCKGCTGATCTACAAGRGCAGC<br>AGCCTGSAGTCCGGCGTTCCTA<br>GCAGATT-3' | (SEQ ID NO: 627) |

For VK-3 CDR2, the CDR2 oligonucleotide humanization coding sequence was 5'-CTG CTG ATC TAC GRC ACC AGC AGC AGG GCC-3' (SEQ ID NO: 628). However, as there were two VK-3 subfamily members to be utilized, specifically A27 and L6, the differences (bold italics) in the 5' and 3' flanking framework sequences around VK-3 CDR2 were respectively:

(SEQ ID NOS 629 and 630, respectively)
VK-3 A27: 5'-AACCTGGTCAGGCCCCT*CC*. . . CAGG*C*ATCCC TG*ATAT*ATT-3',
and (SEQ ID NOS 631 and 632, respectively)
VK-3 L6: 5'-AACCTGGTCAGGCCCCT*AGA*. . . CAGG*T*ATCCCT G*CCAG*ATT-3'.

TABLE 31

Avastin VK-3 CDR2 Humanization Oligonucleotides

| K3A27_2_VEGF01 | AACCTGGTCAGGCCCCTCG<br>CCTGCTGATCTACGRCACC<br>AGCAGCAGGGCC ACAGGC<br>ATCCCTGATATATT | (SEQ ID NO: 633) |
|---|---|---|
| K3L6_2_VEGF01 | AACCTGGTCAGGCCCCTAG<br>ACTGCTGATCTACGRCACC<br>AGCAGCAGGGCC ACAGGT<br>ATCCCTGCCAGATT | (SEQ ID NO: 634) |

E. Mutagenesis of the scFv Template

Figure 59:
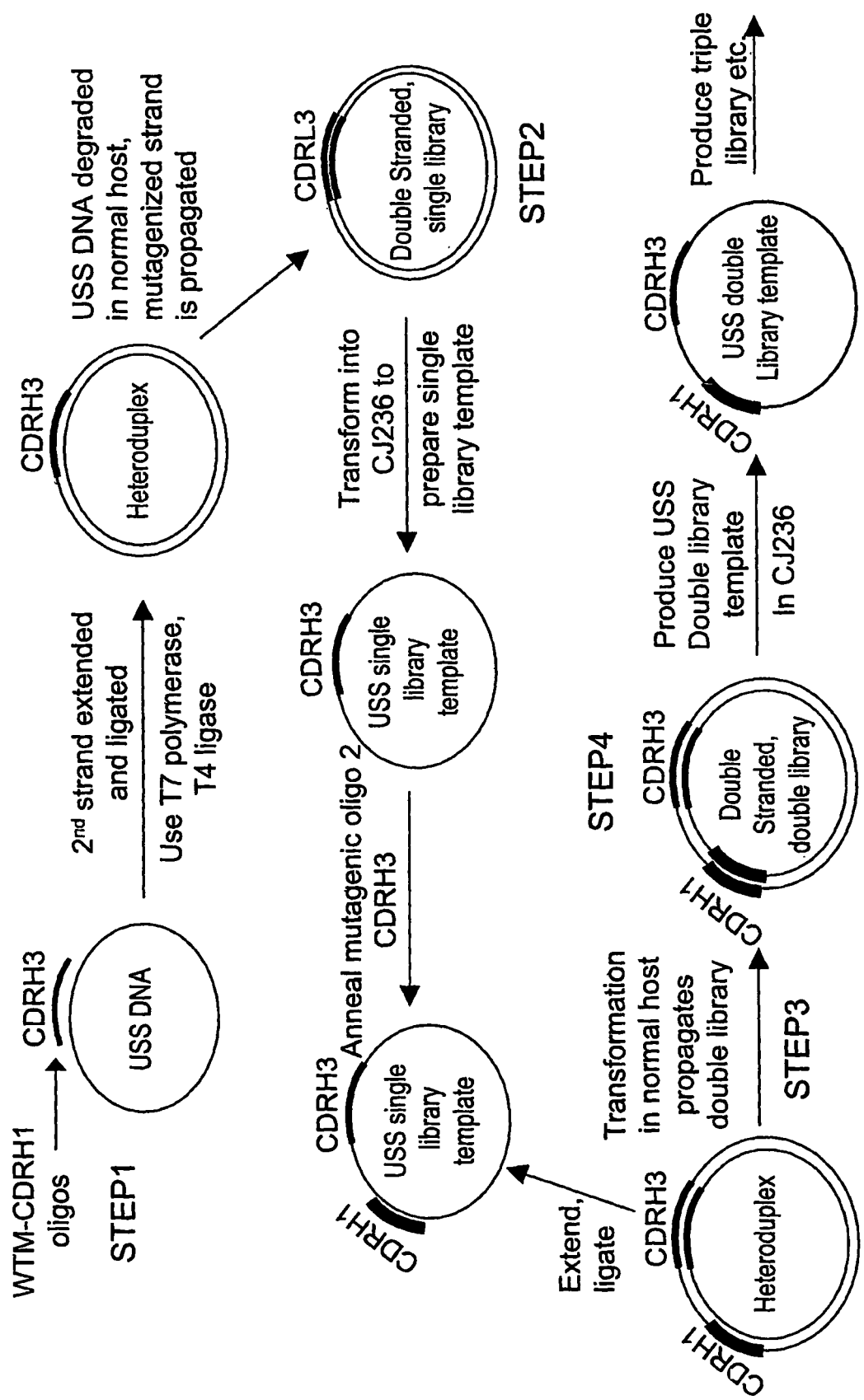
FIG. 59 illustrates the Kunkel mutagenesis method as applied in the present invention for generating CDR coding mutations using a single oligonucleotide annealing reaction. For the process shown, the first modified WTM-CDRH3 template was re-isolated and re-annealed with a second different CDRH1 oligonucleotide to generate two distinct WTM-CDR mutations in the same linear sequence. These iterations were then repeated until all the desired CDR mutations were incorporated.

For cohort libraries, multiply mutated CDRs within each scFv are needed to fully explore the effects of human preferred amino acid CDR sequences within the antigen binding pocket. Starting with the wild-type target scFv gene as the Kunkel template, a first WTM-CDR library template is generated (FIG. 59). As an example, CDRH3 is replaced with the appropriate human preferred amino acids as are identified from the respective CDRH3 $V_H1$, $V_H3$, $V_H4$ variability profiles. These first-made WTM-CDRH3 scFvs are used as subsequent templates to which are then annealed the appropriate set of WTM-CDRH1 oligonucleotides to generate the double mutation WTM-CDRH1 and WTM-CDRH3 region cohort library. This double WTM-CDRH1 and WTM-CDRH3 library can then be used as templates to incorporate other remaining WTM-CDRH2 oligonucleotides to make the triple WTM-CDR $V_H$ libraries. By progressive iterative combination of the rest of either the $V_\lambda$, and $V_k$ light chain CDRL1, CDRL2, and CDRL3 WTM oligonucleotides, complex arrays of $V_H$ ($V_H1$, $V_H3$, $V_H4$) and $V_L$ ($V_\lambda$, and $V_k$) cohort CDR libraries are developed.

F. Simultaneous Kunkel Double, Triple, Quadruple Mutation of scFv CDRs

There is an alternative to the step-wise building from the single WTM-CDR library into double WTM-CDR constructions and then subsequent triple WTM-CDR libraries. This alternative strategy is based upon recent experimental observations that multiple oligonucleotides can be simultaneously annealed to the same scFv template at different locations on the same genetic construct (FIG. 58). For example, two sets of CDRH1, CDRH2 and CDRH3 WTM oligonucleotides can be introduced in the reaction mixture to anneal at all three $V_H$ CDRS. Multiple WTM-CDR oligonucleotide incorporations were observed to occur for levels as high as five simultaneous annealing reactions.

The single stranded template incorporates all three WTM-CDRH1, WTM-CDRH2 and WTM-CDRH3 oligonucleotides. After one annealing round, however, there was about 50% frequency of recovery of scFv products in which all three CDRH1, CDRH2 and CDRH3 WTM modifications had been achieved. Typically, to generate a higher proportion of multiply mutated CDR scFvs, the reaction product from the first annealing reaction is recovered and then "re-annealed" with the same multiple WTM-CDR oligonucleotides. After this re-annealing, the percentage of multiply mutated CDR scFvs increased by yet another 50% for a population total of 75% of having multiply mutated CDRs.

This method has been termed "enrichment" for its ability to reintroduce multiple WTM-CDR oligonucleotides to the previously mutated template. Thus, by incorporating two or three further rounds of "enrichment", a population proportion of multiply mutated CDRs scFv template reaches 90%. One surprising aspect of "enrichment" is that the annealing of multiple adjacent oligonucleotides still introduces the desired substitutions even if the oligonucleotide ends overlap by a few bases. This was unexpected, as during the ligation process, the phosphate-diester bonds between 5' and 3' ends of the two oligonucleotides would not be easily formed if not directly next to each other. If there is any overlap, one oligonucleotide would be expected to "ride up" on the other (see FIG. 58).

G. $V_H$ and $V_L$ CDR Interfamily Crossing to Generate Increased Diversity

Figure 42:
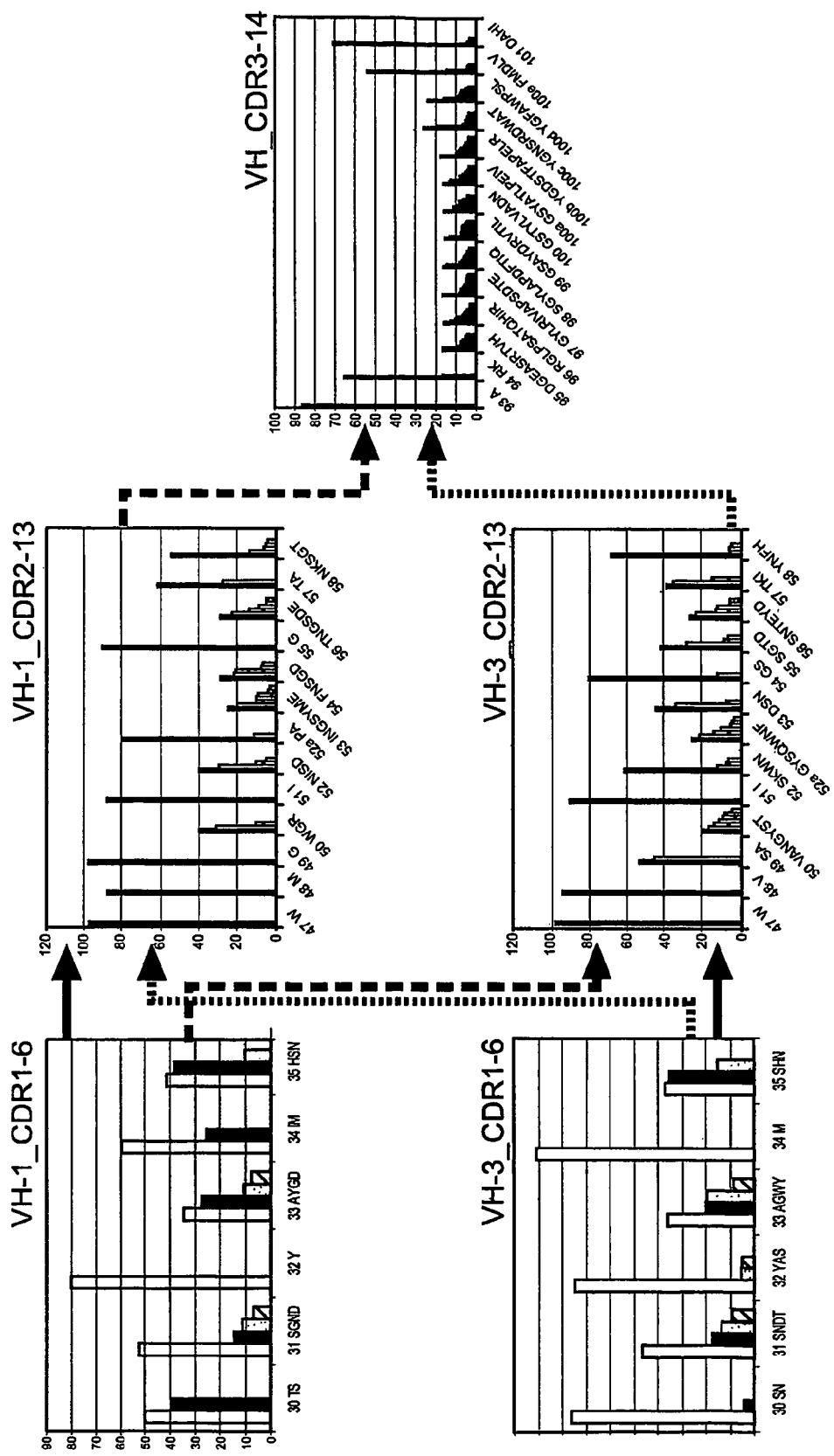
FIG. 42 shows $V_H1$ and $V_H3$ CDR1 and CDR2 design crosses with joining to a common CDR3 domain.
Figure 43:
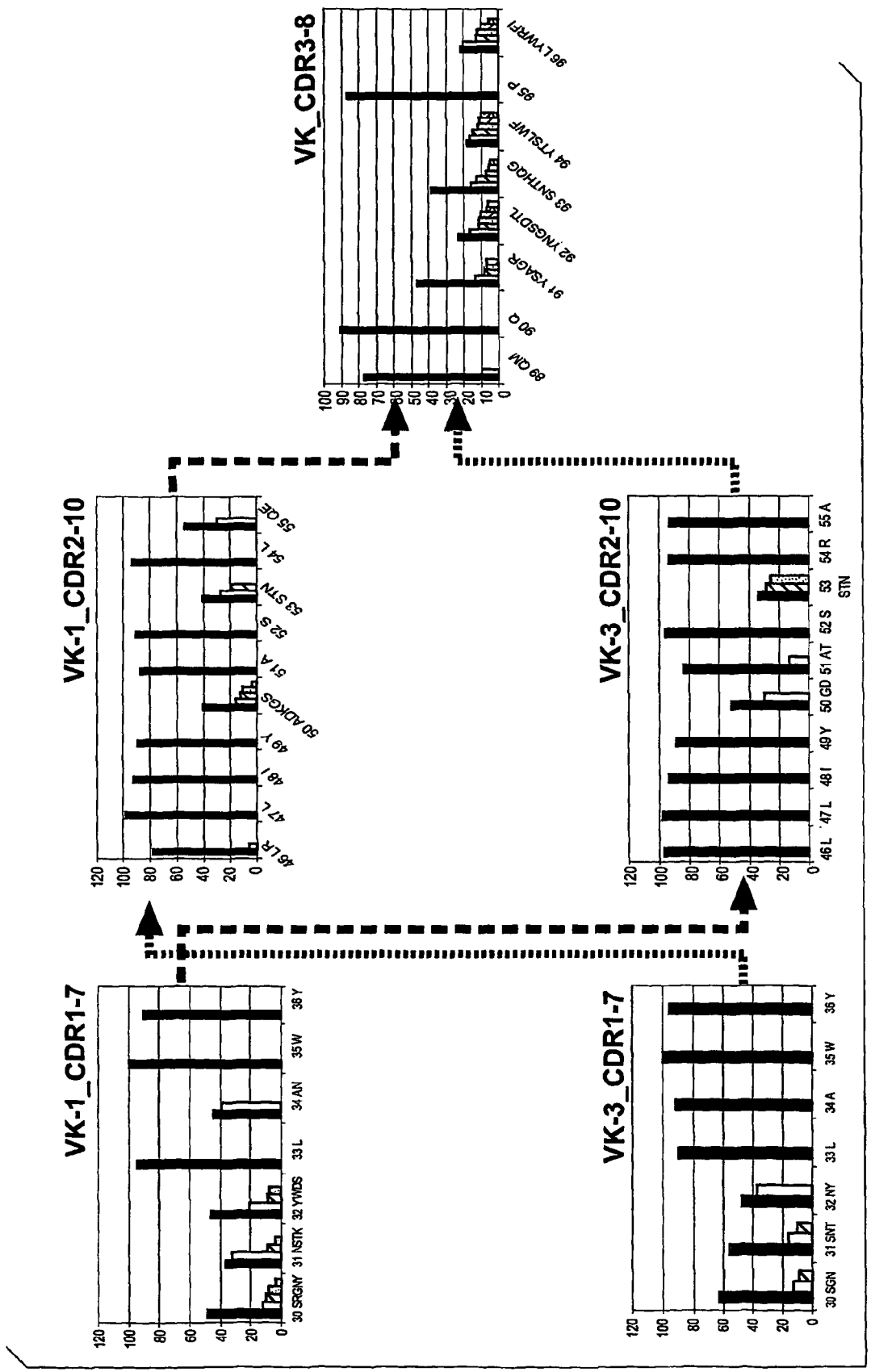
FIG. 43 shows $V_K1$ and $V_K3$ CDR1 and CDR2 design crosses with joining to a common CDR3 domain. VK-1_CDR2-10, VK-3_CDR1-7 and VK-3_CDR2-10 sequences disclosed as SEQ ID NOS 276, 167 and 278, respectively.

FIGS. 42 and 43 depict the various possible CDR combinations available in reconstructing a human anti-VEGF A4.6.1 scFv after CDR matching of the respective $V_H$ 1,3 and $V_L$ kappa, lambda variability profiles. For example, FIG. 42 demonstrates that the human anti-VEGF. $V_H$1 CDR1 cohort sequences can be combined with the expected human anti-VEGF $V_H$1 CDR2 cohort sequences (solid black arrow) and then with the common anti-VEGF $V_H$1 CDR3 cohort sequences. The complete ant-VEGF $V_H$1 CDR1, 2 and 3 cohort sequences are then expressed in relation with their natural $V_H$1 1-e framework sequences. Likewise for the collected anti-VEGF $V_H$3 CDR1, 2 and 3 cohort sequences, they can be expressed with the enumerated natural $V_H$3 3-07, 3-11, 3-23, and 3-30 framework sequences (FIG. 5).

Antibody diversity was able to be increased based on the featured in vitro genetic methodologies of the invention. With manipulative techniques, artificial CDR—framework combinations could be created. In the case of $V_H$, $V_H$3 CDRs can be assembled with $V_H$1 frameworks and vice versa. Thus, the separate CDR1, 2, and 3 variability profile results of $V_H$1 could also be paired with $V_H$3 3-07, 3-11, 3-23, and 3-30 frameworks to explore the antigen binding context in four other structural formats (dotted and dashed lines of FIG. 42). Similarly, for the $V_L$, it was possible to mix and match the variability profiles of CDR $V_{\square}$1, $V_{\square}$2, and $V_{\square}$3 with $V_{\square}$1 and $V_{\square}$3 (dotted and dashed lines of FIG. 43). The amalgamated CDRs could then be expressed in any of the following $V_L$ frameworks: $V_{\square}$1-1b, $V_{\square}$2 2a2, and $V_{\square}$3 3r, 3l with $V_{\square}$iL1 and $V_{\square}$3 A27 and L20 (FIG. 5). These CDR1 and CDR2 design crosses are then a subset of the overall collated UAL libraries (FIGS. 6, 7 and 8). The distinction in the cohort library is that only one CDR3 size is chosen, based upon the wild type antibody CDR3 length.

Example 22

Methods for the Expression and Display of a Reference Universal Antibody Library The approaches for enabling expression and display of universal antibody libraries are readily applicable to any of the reference and cohort antibody libraries of the present invention. Such libraries augment the diversity of the natural repertoire and once constructed can be repeatedly screened for other antigens.

The scFv library is transfected into the recipient bacterial hosts using standard techniques. The expressed fusion-scFv proteins are expressed at an outer surface location which permits binding of fluorescently labeled antigens. Library members expressing suitable scFv clones that efficiently bind antigen are then enriched for, using FACS. This population of cells is then re-grown and subjected to subsequent rounds of selection using increased levels of stringency to isolate a smaller subset of clones that recognize the target with higher specificity and affinity. The libraries are readily amenable to high-throughput formats, using, e.g., FITC labeled anti Myc-tag antibodies and FACS analysis for quick identification and confirmation.

Candidate clones are then isolated and plasmid preparations are performed to obtain scFv sequence information. The approach allows for a hypothesis-driven rational replacement of codons necessary to determine and optimize amino acid functionality in the complementarity determining regions (CDRs) of the $V_H$ and $V_L$ regions of the antibody. Comparative sequence analysis and individual clone affinity/specificity profiles then determine which clones undergo affinity maturation.

A. scFv APEx Surface Expression

The essential goal in the screening process was for each bacterial cell to express a scFv-fusion protein Host strain *E. coli* DH12S™ (Invitrogen™) was transformed with the modified pAPEx1 or pAK200 scFv constructs. Transformed cells were inoculated in Terrific Broth supplemented with 2% glucose and ampicillin at 50 µg/ml and allowed to grow to an $OD_{800}$ of 0.1. After induction, the cellular outer membrane was permeabilized. Briefly, cells (equivalent to ≈1 ml of 20 $OD_{600}$) were pelleted and resuspended in 350 µl of ice-cold solution of 0.75 M sucrose/0.1 M Tris-HCl, pH 8.0/100 µg/ml hen egg lysozyme. Then 700 µl of ice-cold 1 mM EDTA was gently added and the cell suspension was left on ice for 10 minutes; 50 µl of 0.5 M MgCl was then added, and the mix was left on ice for a further 10 minutes.

The resulting cells were gently pelleted and resuspended in 1×PBS at room temperature for 45 minutes before evaluation by FACS. The cells were then analyzed on ARLA/FACSscan (Becton Dickinson) using CellQuest software as per manufacturer's directions. Periplasmic expression of scFv can be determined by the addition of anti-human anti-scFv phycoerytherin antibody, or by also staining for the Myc or HA tags (all PharMingen, San Diego, Calif.).

After scFv periplasmic expression on the APEx library cells was confirmed, the next task was to verify that the scFv constructs were capable of binding their target antigen. Functional antigen binding is essential for subsequent FACS of cohort clones. To investigate, *E. coli* cells expressing the original wild-type scFv were collected as above and incubated with either biotin, phycoerytherin or FITC fluorescently labeled protein. Wild-type and functional cohort variants bind the labeled protein and yield higher fluorescence readings, as compared to vector control cells. The protocols below describe the procedures used for biotin labeling of VEGF proteins, although direct phycoerytherin or FITC conjugation can also be achieved.

B. Expression and Display of a Cohort scFv Antibody Library

In this example, methods for expressing and displaying a cohort antibody library for screening against target antigens are described. The scFv library was transfected into the recipient bacterial hosts using standard techniques. Briefly, a bacterial expression and display system was used which had a demonstrated reliability for expressing scFv molecules from libraries. The scFv was joined to small linker peptides derived from the NIpA lipoprotein or the phage gene three (Gene II) minor coat protein of M13 at either the N-terminal or C-terminal respectively, for export and display in the bacterial periplasmic space (FIG. 33). *E. coli* bacteria are surrounded by two membranes, an inner and outer with the periplasmic space in between. In APEx, scFv proteins are tethered to the inner membrane by either the NIpA lipoprotein or Gene III and then the outer membrane is chemically dissolved by lysozyme EDTA treatment to allow access to the fluorescently tagged targets.

Members of the cohort library expressing scFv clones that more efficiently bound the labeled antigens were then enriched through FACS. Target antigens were either directly or indirectly labeled via a biotin-streptavidin linkage with a secondary antibody. The scFv plasmid DNA was recovered using a standard alkaline lysis miniprep protocol (refer to Sambrook et al, sections 1.25-1.28), re-transformed and then re-grown and subjected to subsequent rounds of selection using increased levels of stringency to isolate a smaller subset of clones that recognize the target with higher specificity and affinity. Comparative sequence analysis and individual clone affinity/specificity profiles then determined which clones underwent affinity maturation (see Example 23).

C. Production and Purification of scFv Binding Proteins: VEGF Biotin Labeling

Bioactive VEGF protein is commercially available in a purified form (R and D System, San Diego, Calif.). Biotinylation of the VEGF protein can be accomplished by a variety of methods; however, over-biotinylation is undesirable, as it may block the epitope-antibody interaction site. The protocol used was adapted from Molecular Probes FluoReporter Biotin-XX Labeling Kit (cat#F-2610). Briefly, VEGF at stock concentration was added to 1M sodium bicarbonate Buffer and Biotin-XX solution (stock concentration Biotin-XX solution in DMSO). The mixture was incubated for 1 hour at 25° C. The solution was transferred to a micron centrifuge filter tube, centrifuged and washed repeatedly (four times) with PBS solution. The botinylated-VEGF solution was collected, purified over a Sephadex G-25 column, and the protein concentration determined by OD 280.

D. VEGF FITC Labeling

To one vial of FITC reagent, 850 μl of solvent reagent was added (Calbiochem, San Diego, Calif.) and mixed thoroughly, whereby the resultant FITC-solvent reagent was at a concentration of 1 mg/ml. The FITC mixture (500 μl) was then added to 2.5 mg of VEGF protein solution (2 mg/ml) and immediately vortexed. This reaction mixture provided a conjugation ratio of 200 μg FITC to 1 mg antibody/protein. The VEGF-FITC was mixed end-over-end for 2 hours at room temperature in a sealed container with aluminum foil to block out ambient light, while stirring. PBS buffer concentrate was diluted in distilled water and the VEGF-FITC conjugate was then transferred to dialysis tubing and dialyzed overnight at room temperature. The VEGF-FITC was then removed from dialysis tubing and protein concentration was re-determined.

E. ARIA-FACS Sorting and Recovery of scFv Variant Library Cells

The following methodology involves FACS screening scFv libraries for enrichment and isolation of cohort binding affinity variants. After growth in culture media, the above permeabilized *E. coli* cells were incubated with biotinylated VEGF at saturating concentrations (200 ng/mL) for 3 hours at 37° C. under gentle rotation. The *E. coli* cells were then twice washed with buffer to remove unbound biotinylated VEGF. The cells were then sorted on ARIA (Becton Dickinson) using CellQuest software as per manufacturer's directions.

Figure 38A:
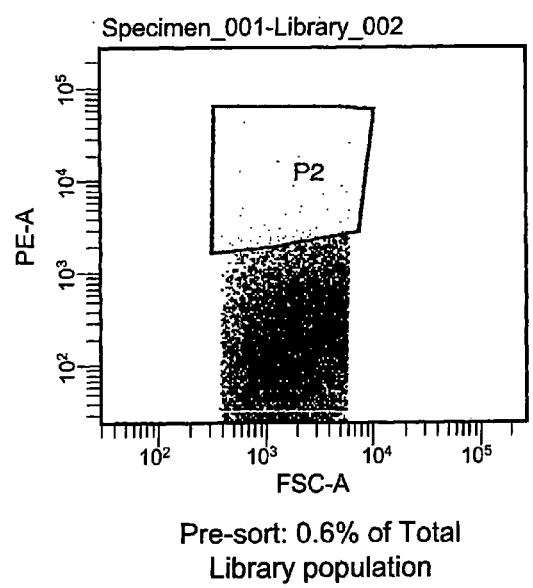
FIG. 38 is a FACS plot showing binding of biotinylated target antigen and streptavidin FITC to test candidate scFv. The left panel FACS plot shows a selection gate (the P2 trapezoid) for identifying only those clones that expressed the scFv fusion with a higher binding affinity to target antigen relative to the distribution of binding affinities of the total LTM library. The right FACS panel shows the post-sort FACS analysis which confirmed that >25% of the P2 pre-screen scFv clones were within the predetermined criteria of enhanced target antigen affinity.
Figure 38B:
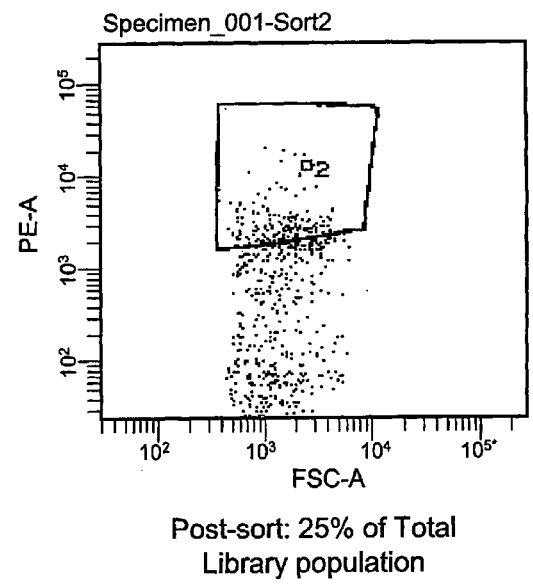

The sort gate could be adjusted to collect that fraction of the cohort population. For enhanced affinity of VEGF, the gate is set for higher florescence signals. FACS gating has now been demonstrated to enrich, by more than 80%, for a higher affinity sub-population in a test system with other cell lines and associated binding proteins (FIG. 38).

F. Recovery and Expression of Cohort-scFv

*E. coli* captured after the first sort were immediately resorted through the flow cytometer. Subsequently, the scFv genes in the sorted cell suspension were resorted, recovered, and retransformed at 37° C. The mutant scFv genes were then recloned into pAPEx1 vector, retransformed into, cells, and grown overnight on agar plates at 30° C. The resulting clones were subjected to a second round of sorting plus resorting as described above. Second/Third sort scFv genes were then subcloned into expression plasmid (pBAD) for the production of soluble scFv protein.

G. BIAcore Analysis

To assess functional scFv binding and gauge the preliminary affinities ($KD=k_d/k_a=k_{off}/k_{on}$), BIAcore-2000 surface plasmon resonance system analysis is employed (BIAcore, Inc. Piscatawy, N.J.). The ligand, e.g., mouse Avastin A4.6.1 anti-VEGF scFv, is immobilized on the BIAcore biosensor chip surface by covalent coupling using N-ethyl-N'-(3-dimethylaminopropyl)-carbo-diimide hydrochloride (EDC) and N-hydrosuccinimide (NHS) according to manufacturer's instructions (BIAcore, Inc). A solution of ethanolamine is injected as a blocking agent.

For the flow analysis, the target of the ligand, e.g., VEGF, is diluted in BIAcore running buffer (20 mM Hepes buffered Saline pH 7.0) into three aliquots of equal, e.g., 0.010 □M, concentration. The aliquots of target, e.g., VEGF, are injected at a flow rate of, e.g., 2 □l/minute for kinetic measurements. Dissociation can be observed in running buffer without dissociating agents. The kinetic parameters of the binding reactions are then determined using, e.g., BIAevaluation 2.1 software.

H. *E. coli* pBAD Expression

Competent *E. coli* host cells were prepared as per manufacturer's instructions (Invitrogen pBAD expression system). Briefly, 40 μl LMG 194 competent cells and 0.5 μl pBAD scFv construct (approximately 1 μg DNA) was incubated together on ice for 15 minutes after which, a one minute 42° C. heat shock was applied. The cells were then allowed to recover for 10 minutes at 37° C. in SOC media before plating onto LB-Ampicillin plates and 37° C. growth overnight. Single colonies were picked the next day for small-scale liquid cultures to initially determine optimal L-arabinose induction concentrations for scFv production. Replicates of each clone after reaching an $OD_{600}$=0.5 were test induced with serial (1:10) titratons of L-arabinose (0.2% to 0.00002% final concentration) after overnight growth at room temperature. Test cultures (1 ml) were collected, pelleted and 100 µl 1×BBS buffer (10 mM, 160 mM NaCl, 200 mM Boric acid, pH=8.0) added to resuspend the cells before the addition of 50 µl of Lysozyme solution for 1 hour (37° C.). Cell supernatants from the lysozyme digestions were collected after centrifugation, and $MgSO_4$ was added to final concentration 40 mM. This solution was applied to PBS pre-equilibrated Ni-NTA columns. His-tagged bound scFv samples were twice washed with PBS buffer upon which elution was accomplished with the addition of 250 mM imidazole. Soluble scFvs expression was then examined by SDS-PAGE.

I. Purification of scFv from Large Scale *E. coli* Culture:

After determination of optimal growth conditions, large scale (volume) whole *E. coli* cell culture pellets were collected by centrifugation after overnight growth at 25° C. The pellets were then re-suspended in PBS buffer (0.1% Tween) and subjected to 5 rounds of repeated sonication (Virtis Ultrasonic cell Disrupter) to lyse the bacterial cell membrane and release the cytoplasmic contents. The suspension was first clarified by high speed centrifugation to collect the supernatant for further processing. This supernatant was applied to PBS pre equilibrated Ni-NTA columns. His-tagged bound scFv samples were twice washed with PBS buffer upon which elution was accomplished with the addition of 250 mM imidazole. The pH of the supernatant was then adjusted to 5.5 with 6 M HCl and before loading onto a SP Sepharose HP cation exchange column (Pharmacia). The scFv was eluted a salt (NaCl) gradient and fraction concentrations containing the scFv were determined by optical density at 280 nm and verified by PAGE. Fractions containing scFvs were then pooled and dialyzed with PBS.

J. BIAcore Analysis of VEGF Protein Binding to Mouse Avastin A4.6.1-scFv

To assess functional scFv binding and gauge the preliminary affinities ($KD=k_d/k_a=k_{off}/k_{on}$), BIAcore-2000 surface plasmon resonance system analysis was employed (BIAcore, Inc. Piscatawy, N.J.). The ligand, mouse Avastin A4.6.1 anti-VEGF scFv, was immobilized on the BIAcore biosensor chip surface by covalent coupling using N-ethyl-N'-(3-dimethylaminopropyl)-carbo-diimide hydrochloride (EDC) and N-hydrosuccinimide (NHS) according to manufacturer's instructions (BIAcore, Inc). A solution of ethanolamine was injected as a blocking agent.

For the flow analysis, VEGF was diluted in BIAcore running buffer (20 mM Hepes buffered Saline pH 7.0) into three aliquots of 0.010 □M concentration. The aliquots of VEGF were injected at a flow rate of 2 □l/minute for kinetic measurements. Dissociation was observed in running buffer without dissociating agents. The kinetic parameters of the binding reactions were then determined using BIAevaluation 2.1 software.

Figure 39:
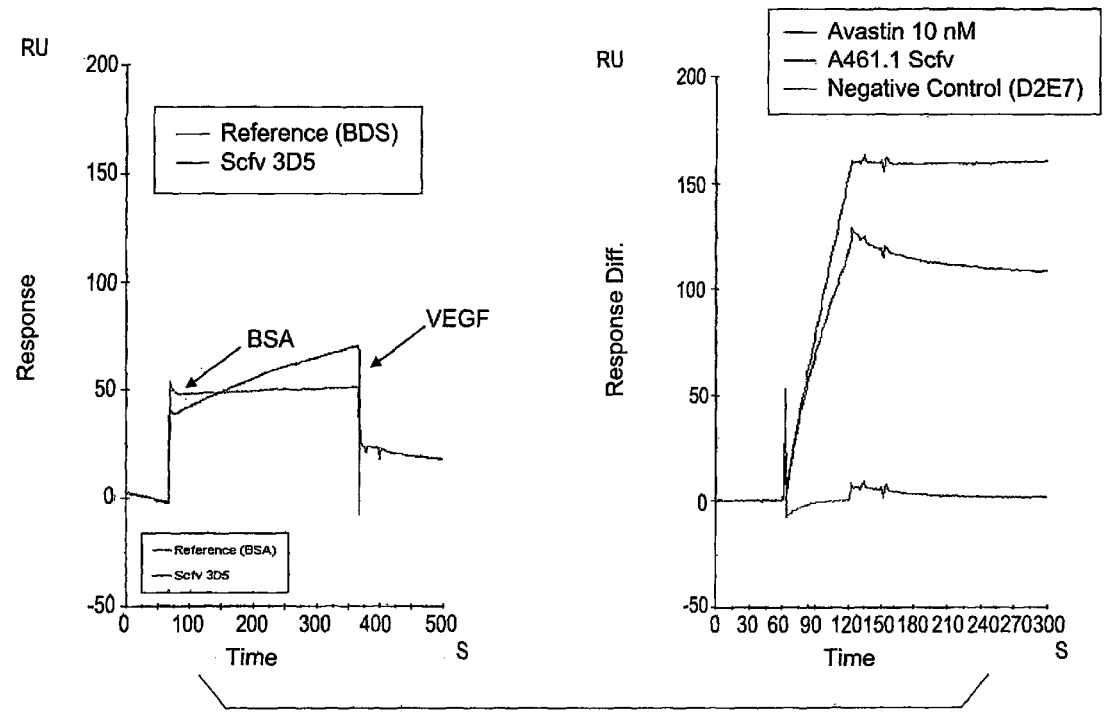
FIG. 39 shows Biacore binding kinetics for a 3D5 anti-VEGF scFv clone recovered from the A4.6.1 cohort library (left panel). The 3D5 anti-VEGF scFv done binds VEGF, as was demonstrated by the increase in response units (RU) as more VEGF antigen was added. In contrast, there was no increase in RU when non-specific BSA was added to 3D5 anti-VEGF scFv.

FIG. 39 displays BIAcore results from the VEGF binding to A4.6.1 anti-VEGF scFv. It was evident from these plots that the reconstituted VEGF bound the immobilized A4.6.1 anti-VEGF scFv, as indicated by the RU increase ($K_{on}$) in comparison to the negative control of heat-denatured protein. Furthermore, the RU increase was proportionate to the A4.6.1 anti-VEGF scFv protein concentration applied. The BIAcore profiles also displayed expected dissociation profiles for VEGF.

Example 23

Methods for Performing High-Throughput Affinity Maturation of Candidates from a Reference Universal Antibody Library This section describes exemplary steps for identification and further improvement of a candidate sequence from a cohort antibody library using WTM and/or Look Through Mutagenesis (LTM) affinity maturation. Look Through Mutagenesis (LTM) has been described previously in U.S. patent application Ser. No. 10/877,467 (published as US20050136428), the entire contents of which are incorporated herein by reference.

Briefly, in order to validate the power of the universal antibody library and the ability to take a candidate antibody molecule and refine the binding properties of the molecule, a commercially available antibody was designated as a test antibody and mutagenized (using, e.g., WTM™/LTM™ technology), expressed, displayed, and improved according to the methods of the invention. An exemplification of improving the binding properties of a candidate test reference antibody using LTM technology has been disclosed in U.S. Patent Application No. 60/586,487, the entire contents of which are incorporated herein by reference.

The test antibody was mutagenized in a scFv format and then expressed and displayed using yeast display, although any of the above-mentioned bacterial display systems could also be used. Kinetic selections of scFv yeast displayed libraries involve initial labeling of cells with biotinylated antigen followed by time-dependent chase in the presence of large excess of un-biotinylated antigen. Clones with slower dissociation kinetics are identified by SA-PE labeling after the chase period and sorted using a high speed FACS-sorter. Dotplots of the wild-type control and sorting gate, the library and the number of clones in the sorting gate and the clones isolated from the library post-sorting were generated (FIG. 38).

The tabulated sequence data from a test antibody LTM analysis indicated a diverse collection of 29 separate mutations that increased the affinity of the parent molecule by 1.5-fold or better. These mutations were found to occur in all six CDRs of the test antibody. Several of these changes were isolated multiple times, for example in CDR3, three separate S to K changes, and two S to Q changes were found. By contrast, changes in some CDR positions were never found to increase the affinity for the antigen. The next step involved the combination of all the discovered LTM single mutations into a single subsequent library. After this step, scFv clones were then capable of incorporating more than one LTM mutation per CDR. In addition to incorporating multiple mutations in one CDR, these scFv clones were also designed to have more than one mutagenized CDR in each scFv. This merging of distinct, single LTM mutations into a single linear sequence has been termed "combinatorial beneficial mutation" (CBM) analysis. This process was detailed in related U.S. Patent Application No. 60/585,918, the entire contents of which are incorporated herein by reference. The combination of all the discovered LTM single mutations into one library facilitated the isolation of clones that exhibited improved avidity among these high affinity mutations.

Figure 37:
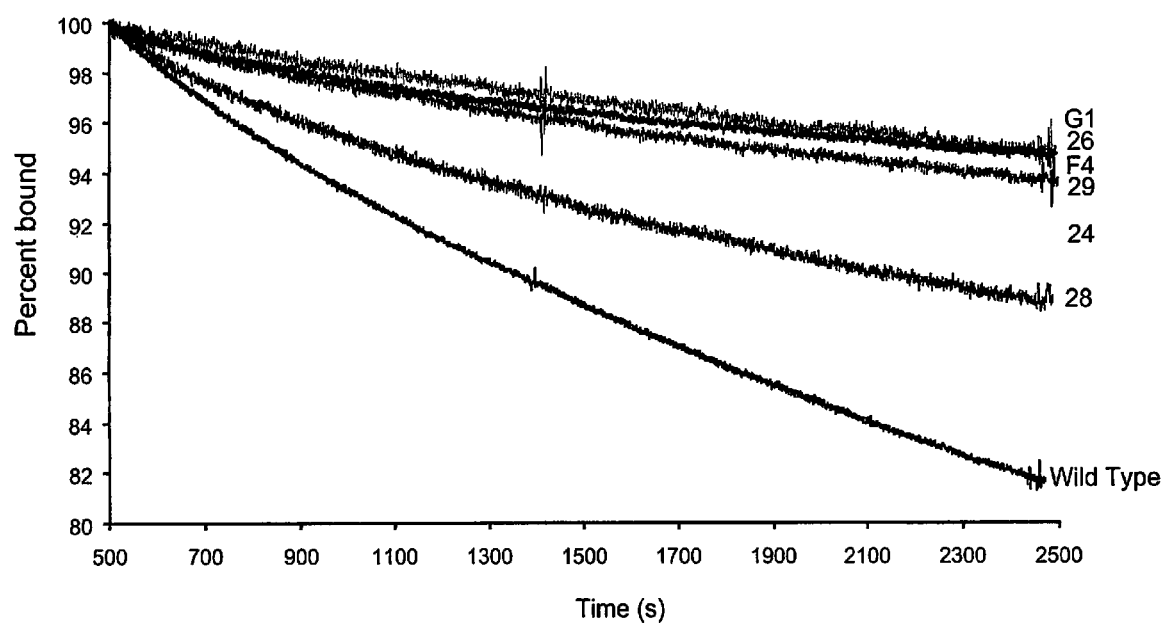
FIG. 37 shows a Biacore determination of binding $K_{off}$ kinetics for six affinity-enhanced CBM clones from FIG. 36 in comparison with the parental wild type done kinetics.

Expression screening of this CBM library further facilitated the isolation of clones that exhibited improved avidity through synergistic interactions among these high affinity mutations. FIG. 36 shows exemplary candidate clones recovered from CBM analysis. Furthermore, FIG. 37 displays BIAcore scFv results from the reference wild-type scFv and six affinity-enhanced $K_{off}$ clones. These data were fitted to a single exponential curve to determine the dissociation rate constants ($k_{off}$). It was evident from these plots that the reference wild-type scFv, when compared with all six clones, displayed a noticeably sharper decaying slope, indicative of a faster $K_{off}$.

The above-described techniques of affinity maturation can be readily applied to the selected cohort libraries of the present invention.

Example 24

Methods for Generating Positional Variability Profiles (VP) for Antibody CDRs Using Bioinformatics This example describes the determination of the Positional Variability Profiles (VP) for CDRs of in vivo expressed antibodies. The Positional Variability Profiles represented the cataloging of the different amino acids, and their respective rates of occurrence (population prevalence), present at a particular position in a dataset of aligned sequences of naturally-expressed antibodies. (See U.S. Patent Application No. 60/585,931 (PCT/US2005/024002), the entire contents of which are incorporated herein by reference.) The main purpose of generating the UAL CDR variability profile was to best match framework sequences with CDR canonical structures and their variable sequences therein to obtain the most stable and functional configurations.

Figure 4:
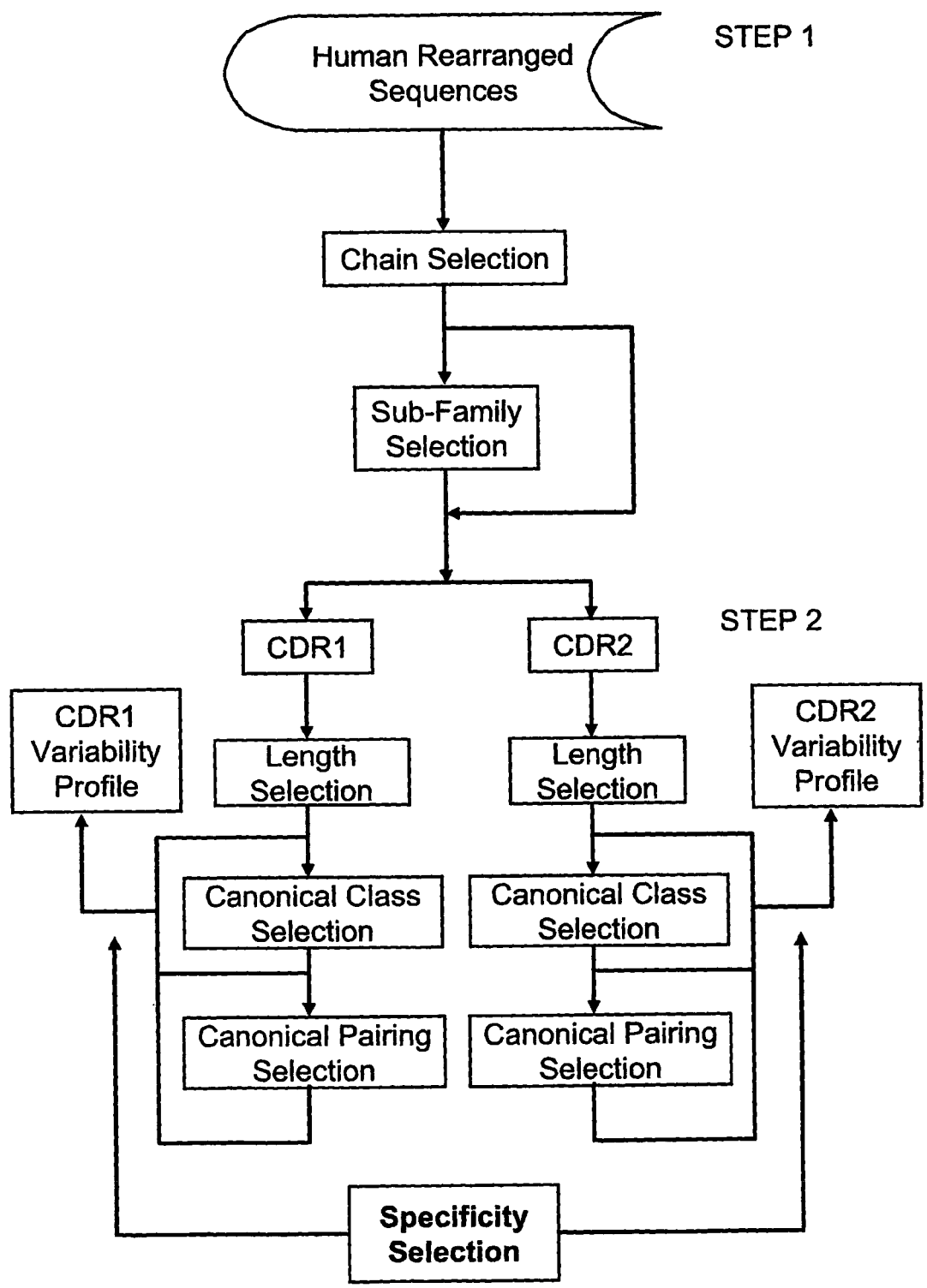
FIG. 4 provides an overview of the process by which CDR1 and CDR2 frequency tables are generated.

Therefore, determination of VP entailed two steps, e.g., STEP 1): collection and selection of (a dataset of) aligned amino acid sequences that shared one or more defined properties of interest to create a dataset. Separately aligned CDR1, CDR2, and CDR3 sequences from either the $V_H$ or $V_L$ formed the initial datasets for typical purposes. In STEP 2, several approaches in deriving CDR datasets with corresponding VP outcomes were available. Typically, for conducting STEP 2, (CDR) datasets were enumerated for amino acid variability and their relative frequencies for each aligned position (FIG. 4). The VP for each CDR dataset then identified the desired characteristics of a given CDR position for further introduction of diversity representation.

For conducting STEP 1, a UAL database of aligned sequences was assembled. The starting input dataset could be derived from a prior compilation of previously characterized and grouped sequences such as the Kabat database of endogenously expressed mature antibodies. From the Kabat database, human immunoglobulin and, in particular, VH sequences were selectively-collected for the starting base dataset Typically, the root germline origin for each rearranged human VH sequence was determined by comparative sequence analysis. In this manner, for example, the expressed antibody was attributed (STEP 1: Chain selection) to either $V_H1$, $V_H2$, $V_H3$, $V_H4$, or $V_H6$ etc families. The corresponding specific germline foundation was termed the "originating Sub-Family" (STEP 1 in FIG. 4). Additional CDRs in the VH sequences using the parameters set forth by Contact Definition within this starting "base dataset" could then be identified and delineated. The designation of CDRs and their comprising amino acids could also be described by Kabat, Chothia or any other suitable definitions (STEP 2 in FIG. 4).

Figure 40:
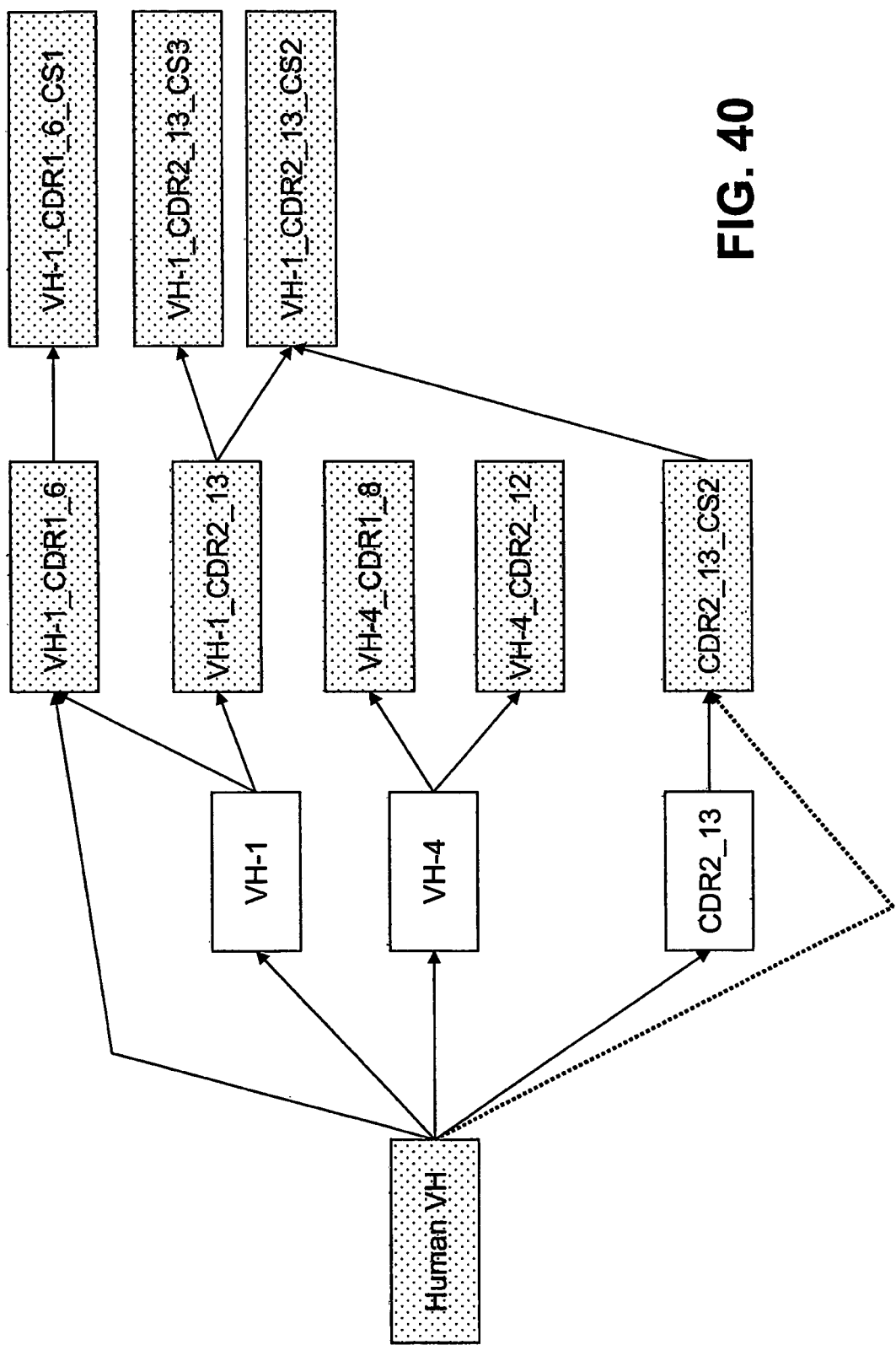
FIG. 40 shows the selection process for subgroup pools of heavy chain sequences, subclass partitioning of subgroup sequences, and further partitioning of subclass populations on the basis of canonical structure, as detailed in Example 2.
Figure 41:
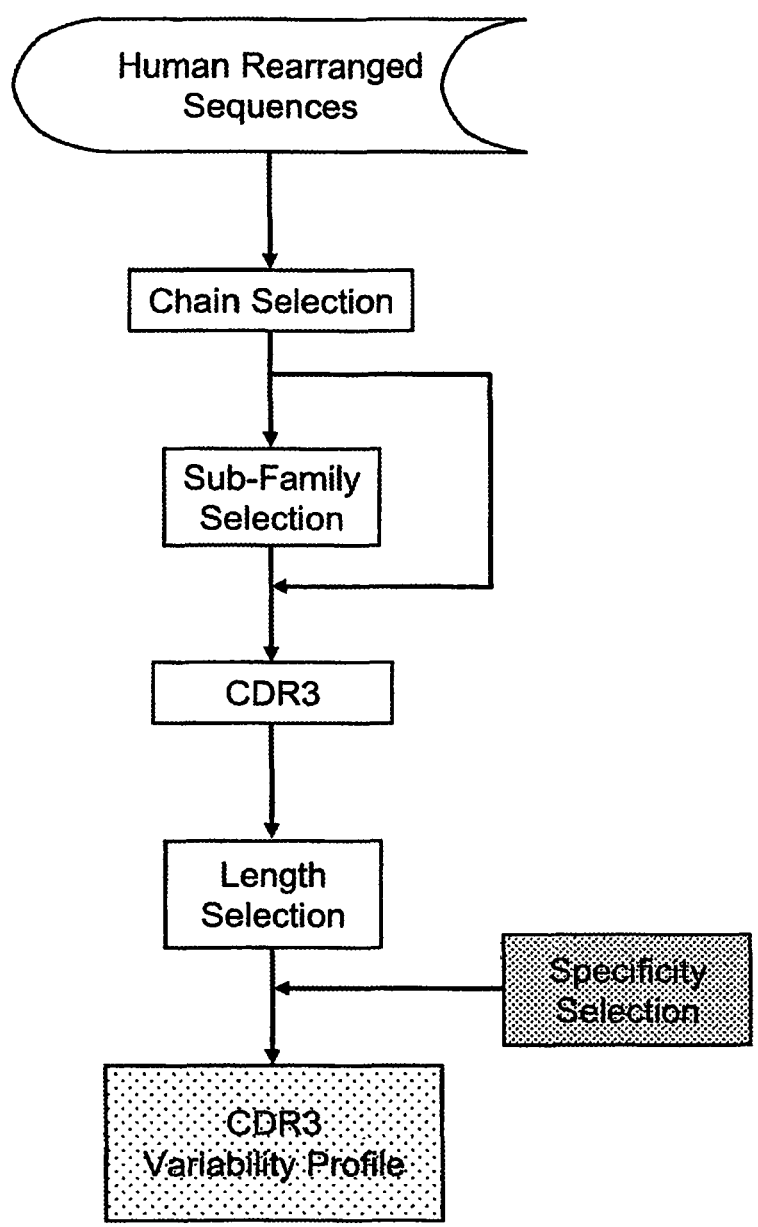
FIG. 41 shows a flow chart depicting CDR3 variability profile selection, as detailed in Example 2.

Within the starting human VH sequence "base dataset", the compiled VH sequences were still likely to possess vastly different characteristics. The VH framework sequences tend to vary in the following regards: 1—family groupings ($V_H1$, $V_H2$, $V_H3$, $V_H4$ etc). 2—"originating subfamilies" (e.g. $V_H3$ 3-07, 3-11, 3-23, 3-30), 3—CDR lengths, 4—CDR canonical structure classes, 5—antigen specificity among others. Due to sequence disparity among the "base dataset" members, the process of deriving a coherent analysis can require further selection from the starting "base dataset" such that datasets that share one or more elected properties of interest can be identified. Constituent members sharing those respective properties can produce a more "standardized" set of sequences for meaningful comparative analysis within the subgroup. This process can be iterated, resulting in the generation of smaller datasets of higher degree of relationship, and such is exemplified in FIG. 40. FIG. 41 diagrams the similar processes employed to derive the CDR3 database for VH and VL.

CDRs can be classified as follows. Beginning with the non-redundant "base dataset" of all human VH sequences, only sequences generating VH1 sequences were further selected (FIG. 40). Non-redundancy filtering removed duplicate antibody sequence deposited against the same antigen. If there were different antibodies raised against the same antigen, these sequences were retained in the database. Within the VH1 sub-group, CDR1 and CDR2 sequences were identified and then further partitioned as CDR1 or CDR2 subgroups. It should be noted that in CDR partitioning within VH families, the CDR1 or CDR2 sub-groups could still be populated with CDRs of different lengths. VH1 CDR2 occurred in both 13 and also 15 amino acid lengths. For CDR1 and CDR2, lengths of 6 and 13 amino acids were selected, respectively, and the generated datasets were respectively named VH-1_CDR1_6 and VH-1_CDR2_13, accordingly.

Figure 60:
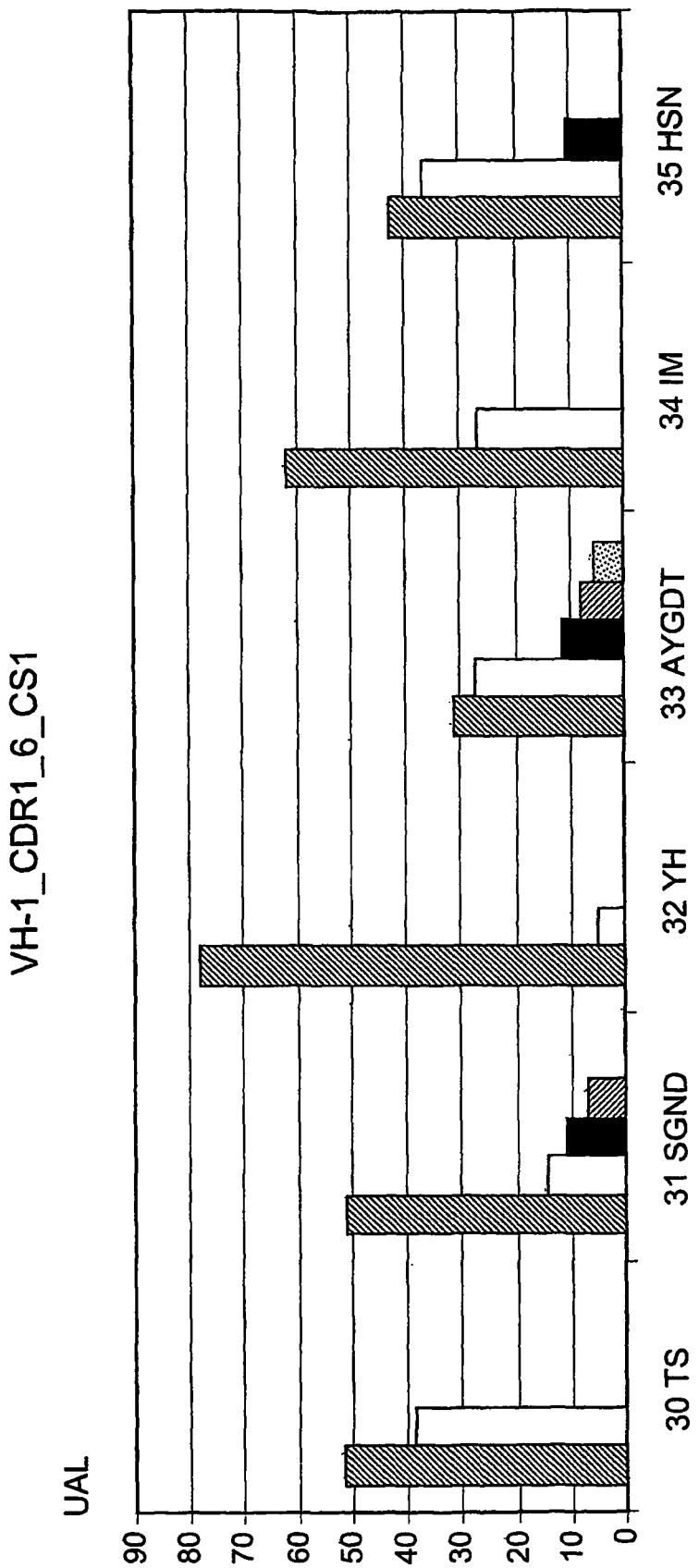
FIG. 60 shows a histogram of position-by-position amino acid residue frequencies for a VH-1 CDR1 universal antibody library (UAL) of length 6, canonical structure 1.
Figure 61A:
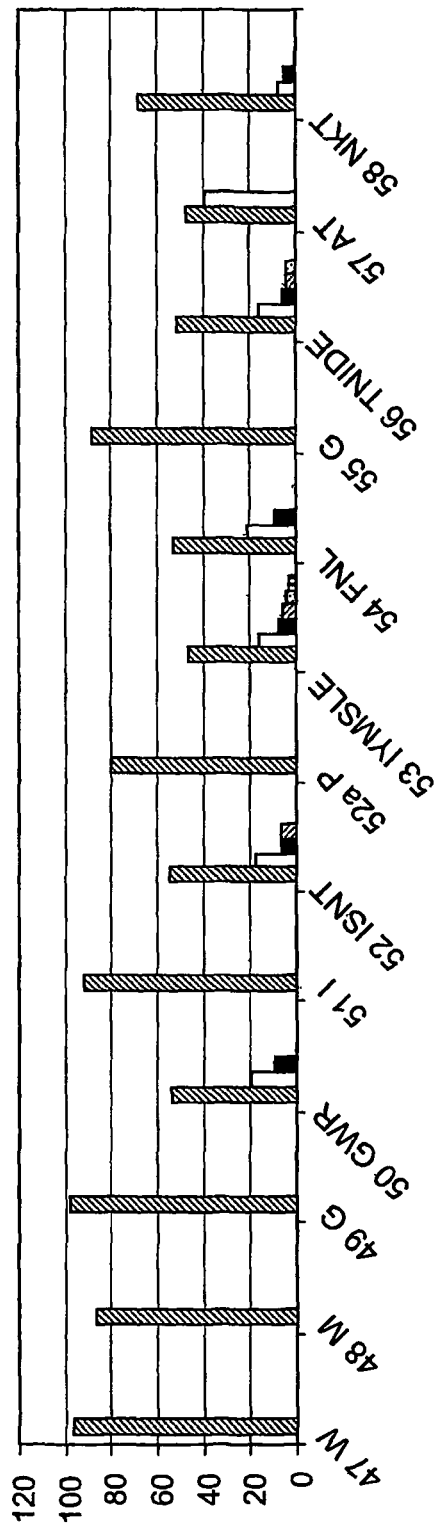
FIG. 61 shows a histogram of position-by-position amino acid residue frequencies for VH-1 CDR2 universal antibody libraries (UALs) of length 13, canonical structures 2 (panel A) and 3 (panel B).
Figure 61B:
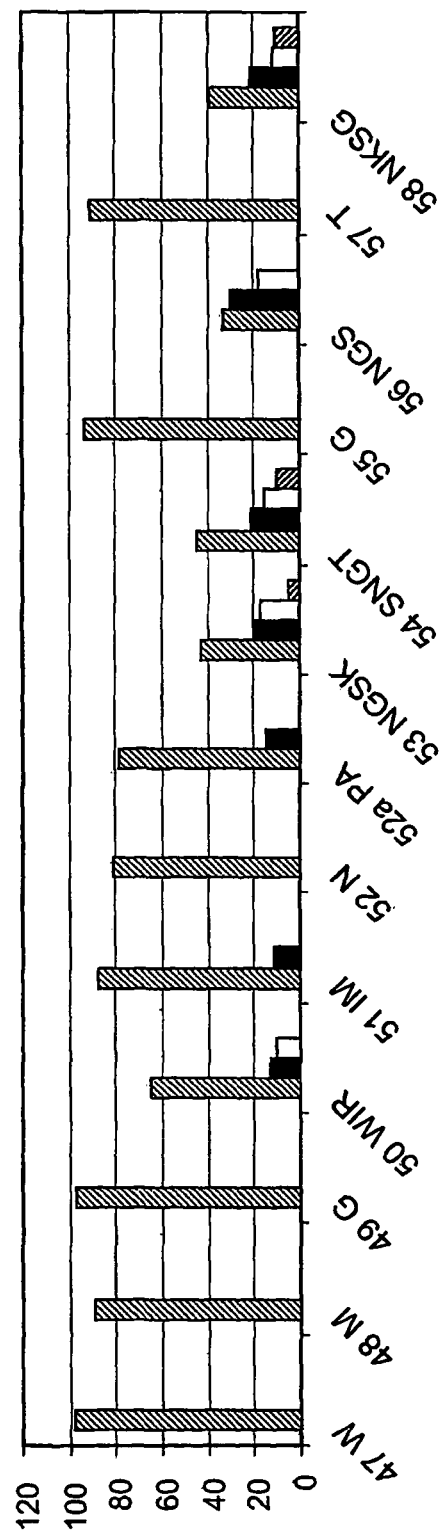
Figure 63:
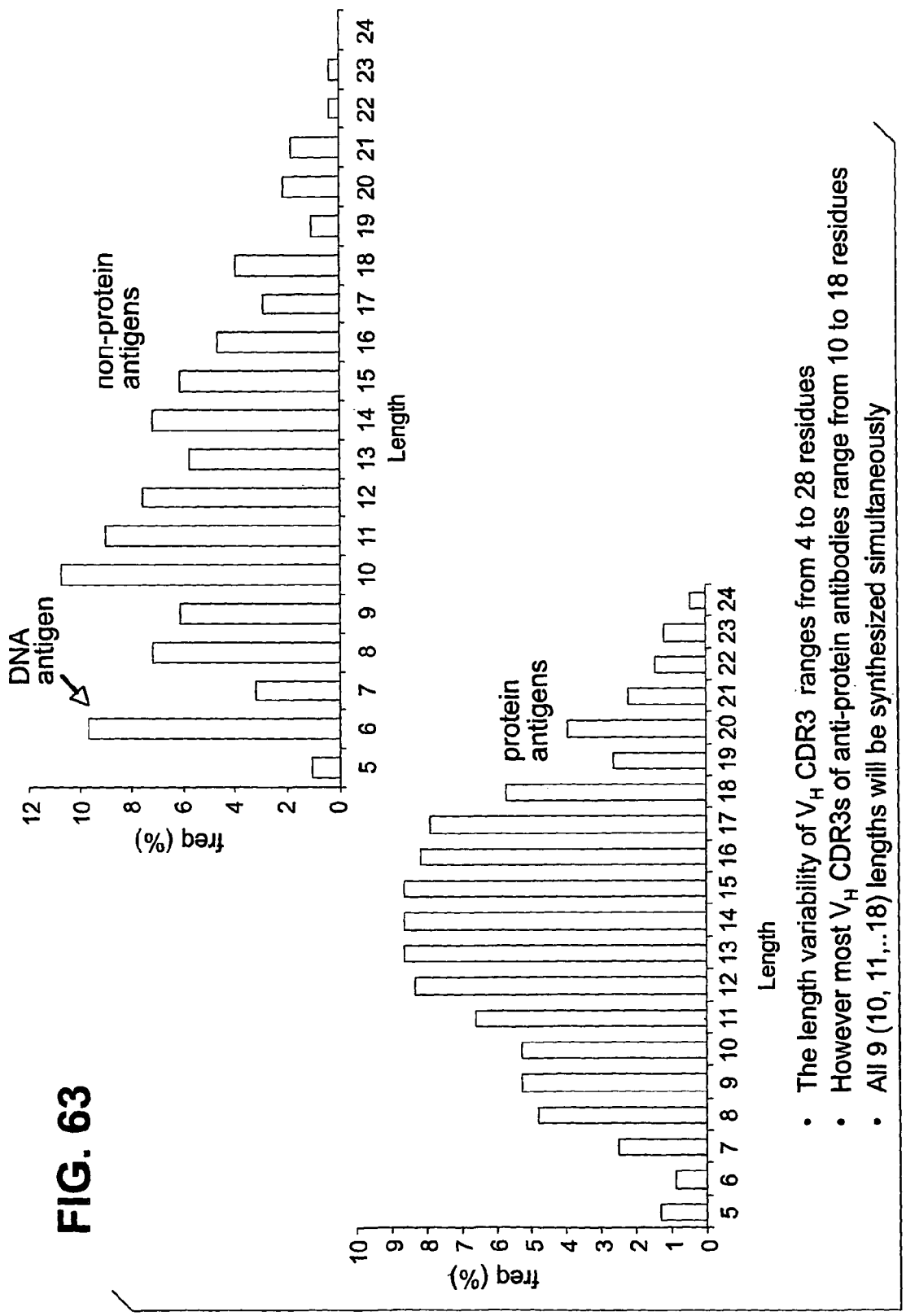
FIG. 63 shows histograms of VH CDR3 length analyses for protein (power left panel) and non-protein (upper right panel) antigens.

When even more stringent UAL datasets were necessary, grouping could be performed based on canonical structures. For example, within the VH1 CDR2 sequences, another subgroup partitioning to filter between those that were either of canonical structure 2 (CS2) or canonical structure (CS3), was performed. Canonical structures can be defined by distinguishing signature residues at key positions in the framework. For example, VH1 CDR2 sequences incorporating a V,A,L or T at amino acid position 71 denoted canonical structure 2, whereas an R at the same amino acid position signified canonical structure 3. These operations generated variability profile datasets named, respectively, VH-1_CDR2_13_CS2 and VH-1_CDR2_13_CS3 (FIG. 61). Likewise, VH1 CDR1 was of canonical class 1 (CS1) with the length requirement of six amino acid residues. In this case, CDR1 CS1-distinguishing key amino acid signatures included, for example, a T, A, V, G, or S at position 24; a G at amino acid position 26; and either a I, F, L, V, or S at position 29. Thus, it was possible that the VH-1_CDR1_6 dataset could contain sequences not belonging to CS1, as some six amino acid CDR variants did not have the requisite signature sequences. Once screened, a variability profile for VH1 CDR1 canonical class 1 (CS1) was then generated as VH-1_CDR1_6_CS1 (FIG. 60).

The above results demonstrated that depending on both the CDR1 and CDR2 canonical structures chosen for use as the acceptors, amino acid usage could be "fine-tuned." Such fine tuning would depend upon which amino acids were to be introduced in the various CDR amino acid positions for purpose of replicating the employed natural diversity of the reference library by matching sequences most likely to be found with particular classes of antigens. CDR antigen classification was performed in the following manner. Once grouped based on structural classifications, the collected CDR sequence members can also be sub-classified on the basis of antigen specificity (FIG. 40). A correlation of preferred amino acids within the CDRs for a given antigen class can exist, similar to what was observed for antigen class preference for certain frameworks. Thus, an additional parameter, antigen specificity, can be added during the partitioning of CDR sequences to generate antigen-specific variability profiles.

Figure 45A:
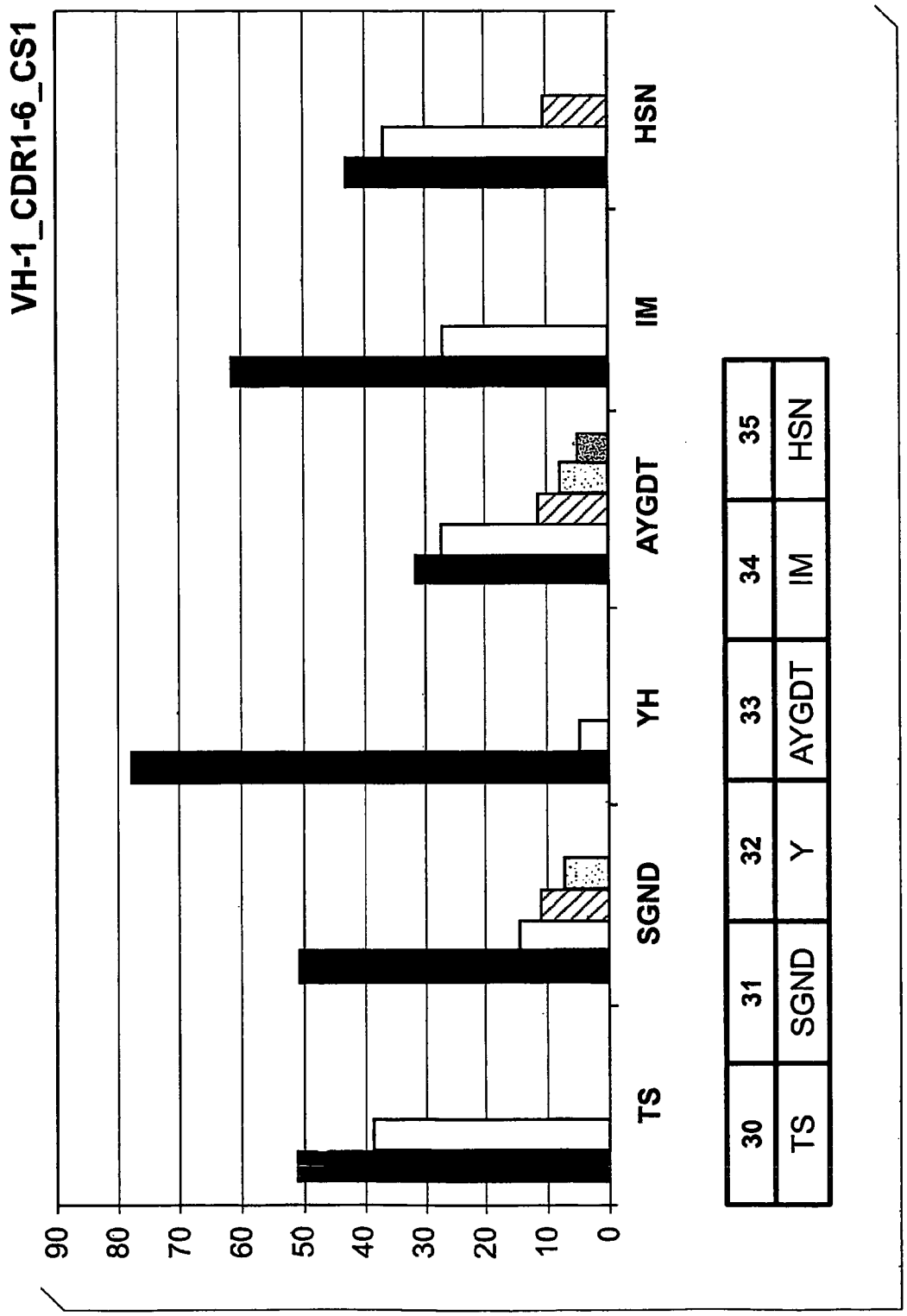
FIG. 45 shows the enumerated variability profiles of CDR1 length size 6 from VH-1 (panel A), VH-3 (panel B), and VH-4 (panel C) heavy chains, as determined from the Kabat database of deposited immunological sequences. The boundaries of listed CDRs were delineated according to Contact CDR definition prior to sequence alignment. The vertical (Y) axis denotes the frequency of occurrence of particular amino acids at that CDR position of in vivo expressed antibodies. The generated CDR1 variability profile (FIG. 44) then instructed the potential diversity that could be substituted at each CDR position to mimic host species preferences.
Figure 45B:
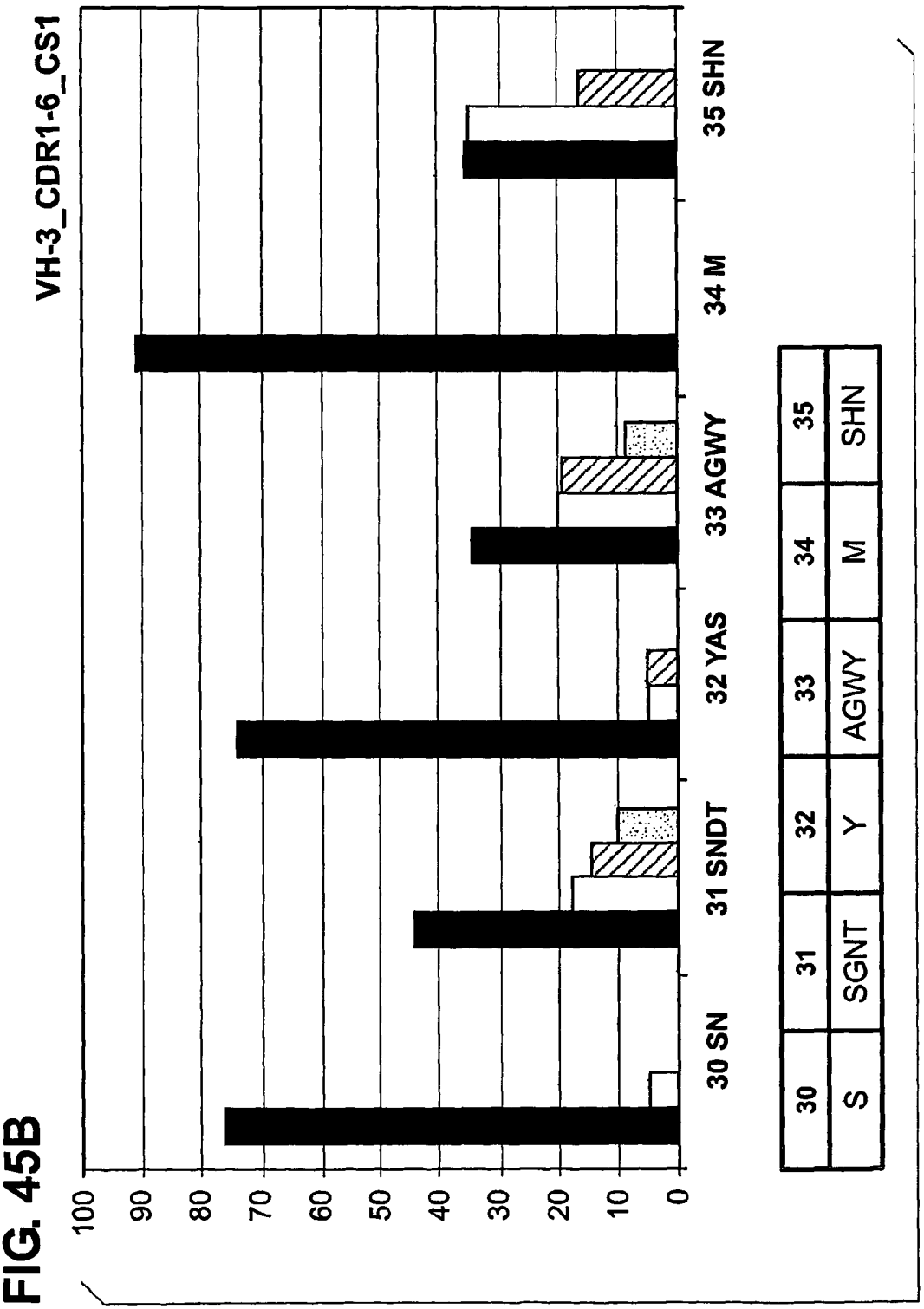
Figure 45C:
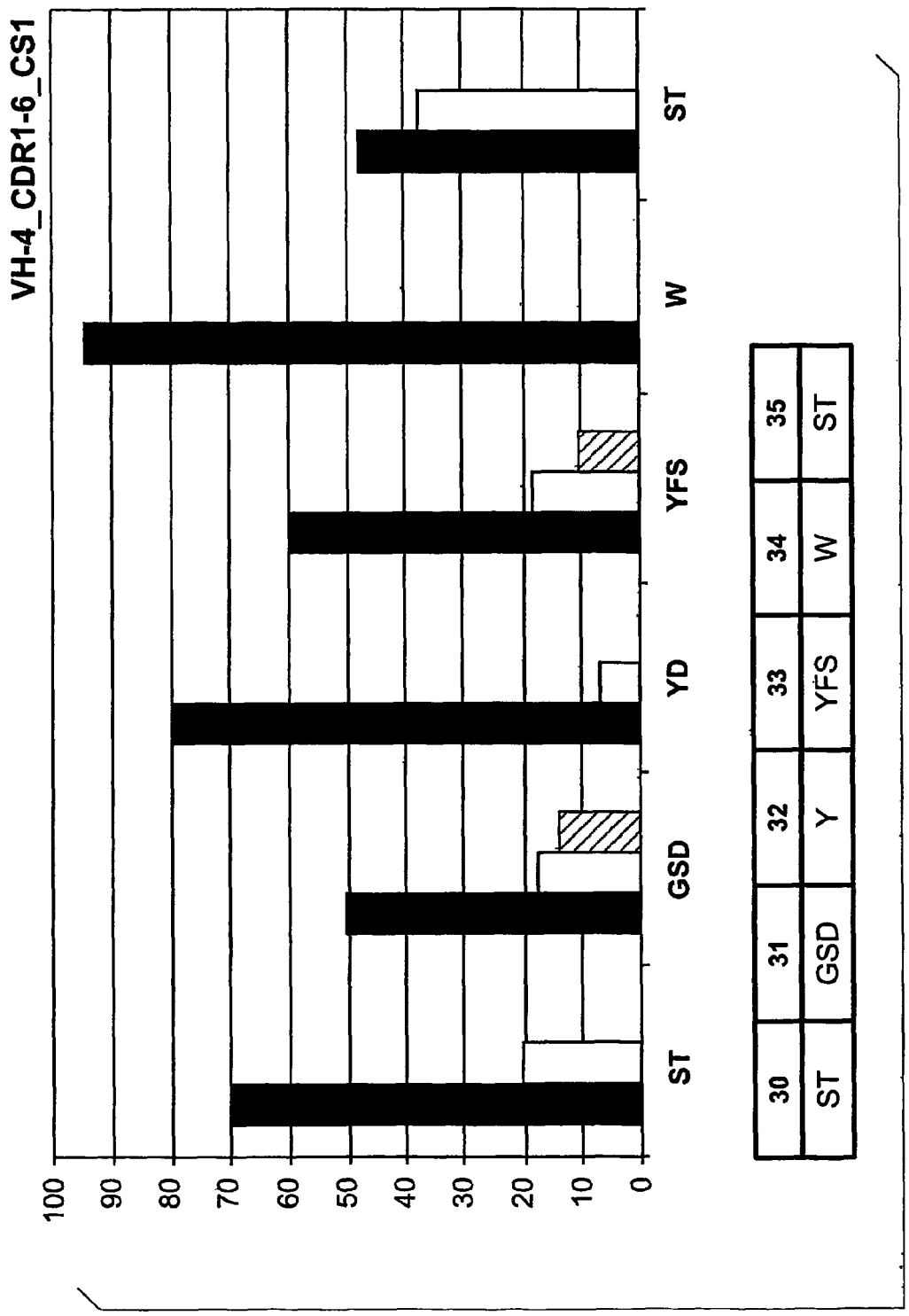

The important advantage of this process is that many different "selection" or "collection" paths were possible and each generated a different dataset and hence a different variability profile (VP). This was exemplified when the variability profiles for CDR1 were compared between the separated VH1, VH3 and VH4 (FIG. 45) datasets. The tables under each bar graph enumerate the available humanization replacement amino acids based on the above-described "80 percent" parameter. Overall the VPs were somewhat similar, as the "Y" was "fixed" at position 30 for VH1, VH3 and VH4 subfamilies. There were, however, differences observed. In VH3, an "S" can be fixed at position 30 whereas for VH1 and VH4, the VP indicated that "T and S" can be substituted at position 30. Other examples of VP differences occurred at position 34. In VH4, a "W" was fixed, while in VH3 an "M" was fixed. In contrast, in VH1, "I and M" was available for cohort CDR design.

As these CDR1 VPs differed between the VH subfamilies, the cohort library design can vary depending on which VH framework is chosen. For example, if the CDR1 amino acid target antibody at position 33 does not match any of the listed amino acids of VH1, VH3, or VH4 then their respective VPs are substituted. Thus, in target antibody CDR1 grafts into VH1, the amino acids A,Y,G, and D were chosen for incorporation at position 33. In CDR1 grafts to VH3 frameworks, the VP directed that A, G, W, and Y are to be used. Likewise, in CDR1 grafts to VH4 frameworks, the VP directed that Y, F, and S are to be substituted in position 33.

Figure 44:
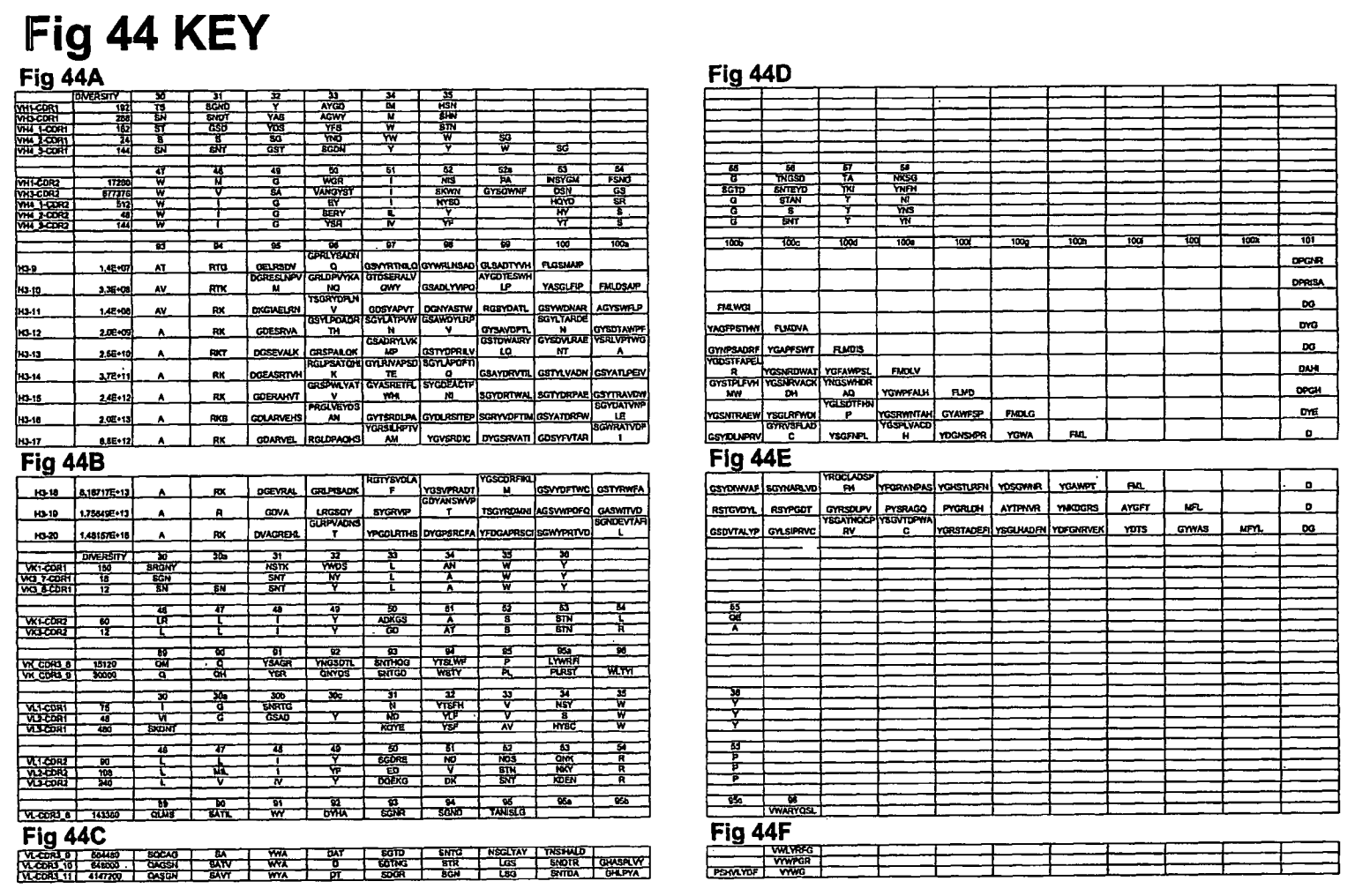

FIG. 44 shows the diverse VPs available for cohort antibody library generation. In this embodiment of the invention, the respective VPs were NOT pre-filtered based on canonical structure, in order to collect a broader collection of available amino acids in the resultant VP. For example, in canonical structure 2 at position 53 of VH-1 CDR2, the amino acids I, Y, M, S, L and E were identified for VH-1_CDR2_13_CS2 VP (FIG. 61). In canonical structure 3 at the same position 53, the VP of VH-1_CDR2_13_CS3 instead had N, G, S and K. Therefore, the VP of VH-1_CDR2_13 without the canonical structure splits would have had I, Y, M, S, E, N, G, and K available (top panel of FIG. 46). The "L" amino acid was not part of the VP collection, as the frequency of occurrence of the first seven amino acids had met the "80%" threshold. This extra set could therefore function to increase the cohort library diversity of that position 53 (and, thus, the resultant CDR) by nine-fold were "identity" criteria chosen.

Figure 46A:
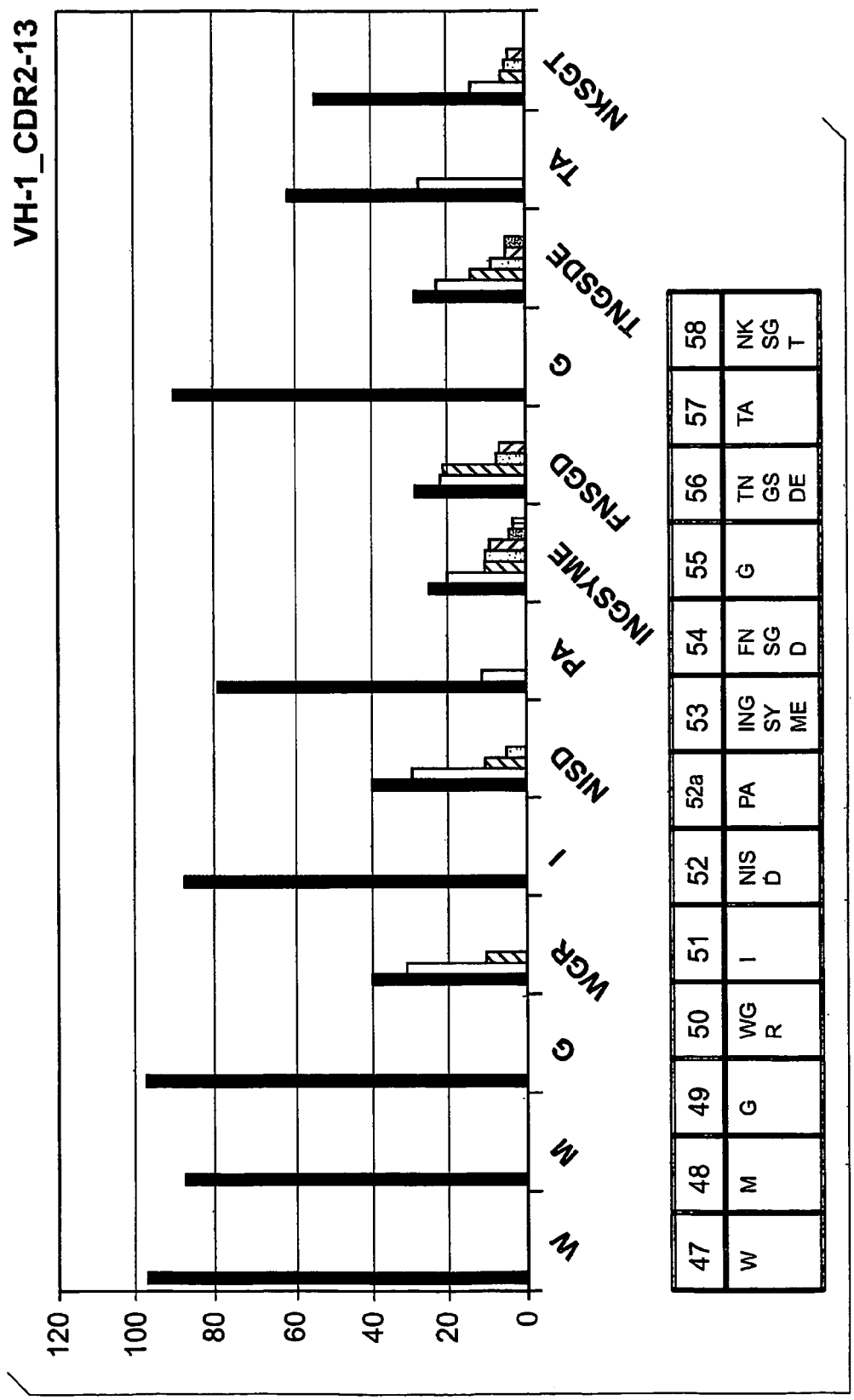
FIG. 46 shows the enumerated variability profiles of CDR2 length size 13 from VH-1 (panel A), VH-3 (panel B), and CDR2 length size 12 of VH-4 (panel C) heavy chains as determined from the Kabat database of deposited immunological sequences. The boundaries of listed CDRs were delineated according to Contact CDR definition prior to sequence alignment. The vertical (Y) axis denotes the frequency of occurrence of particular amino acids at that CDR position of in vivo expressed antibodies. The generated CDR1 variability profiles (FIG. 44) then instructed the potential diversity that could be substituted at each CDR position to mimic host species preferences.
Figure 46B:
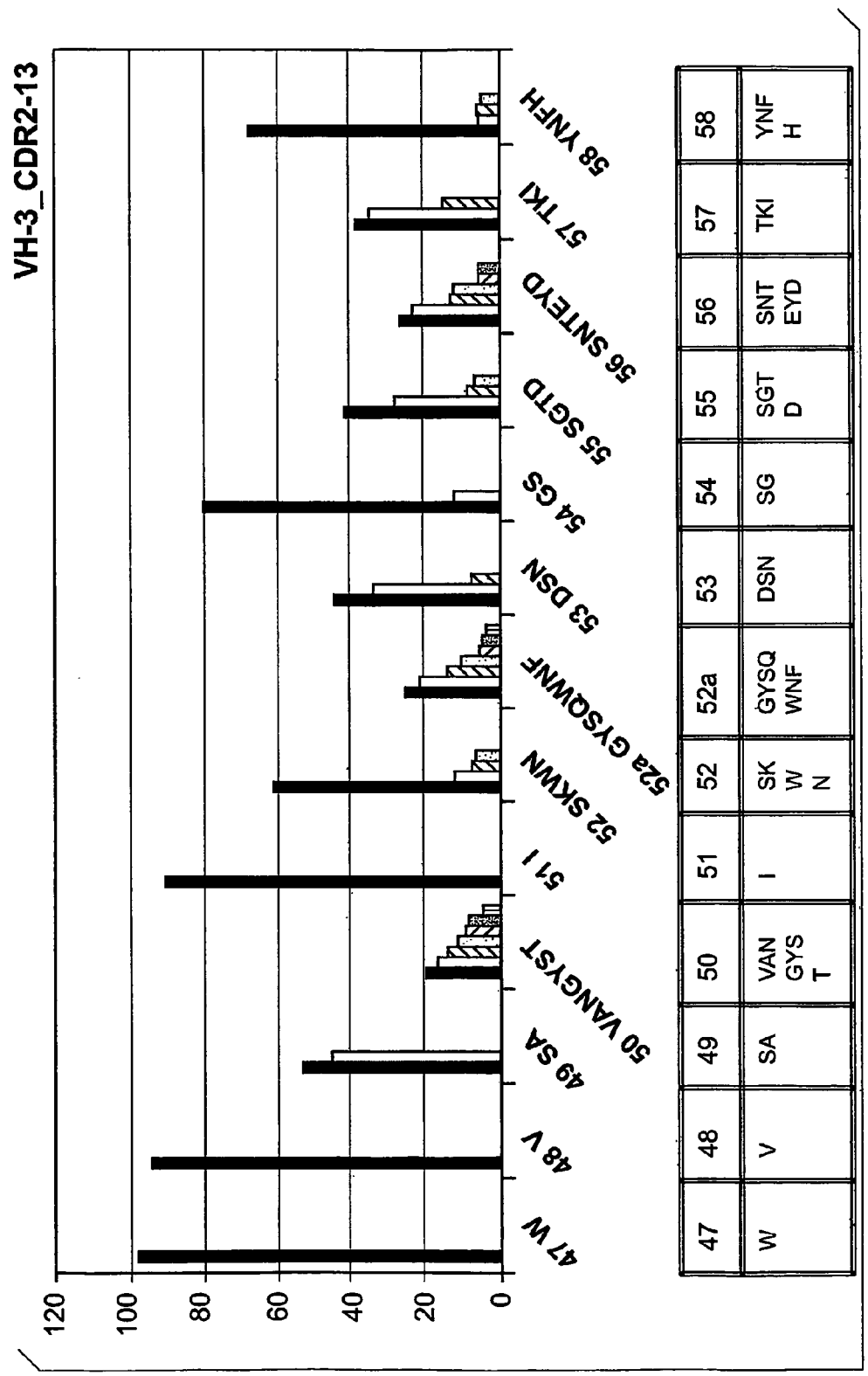
Figure 46C:
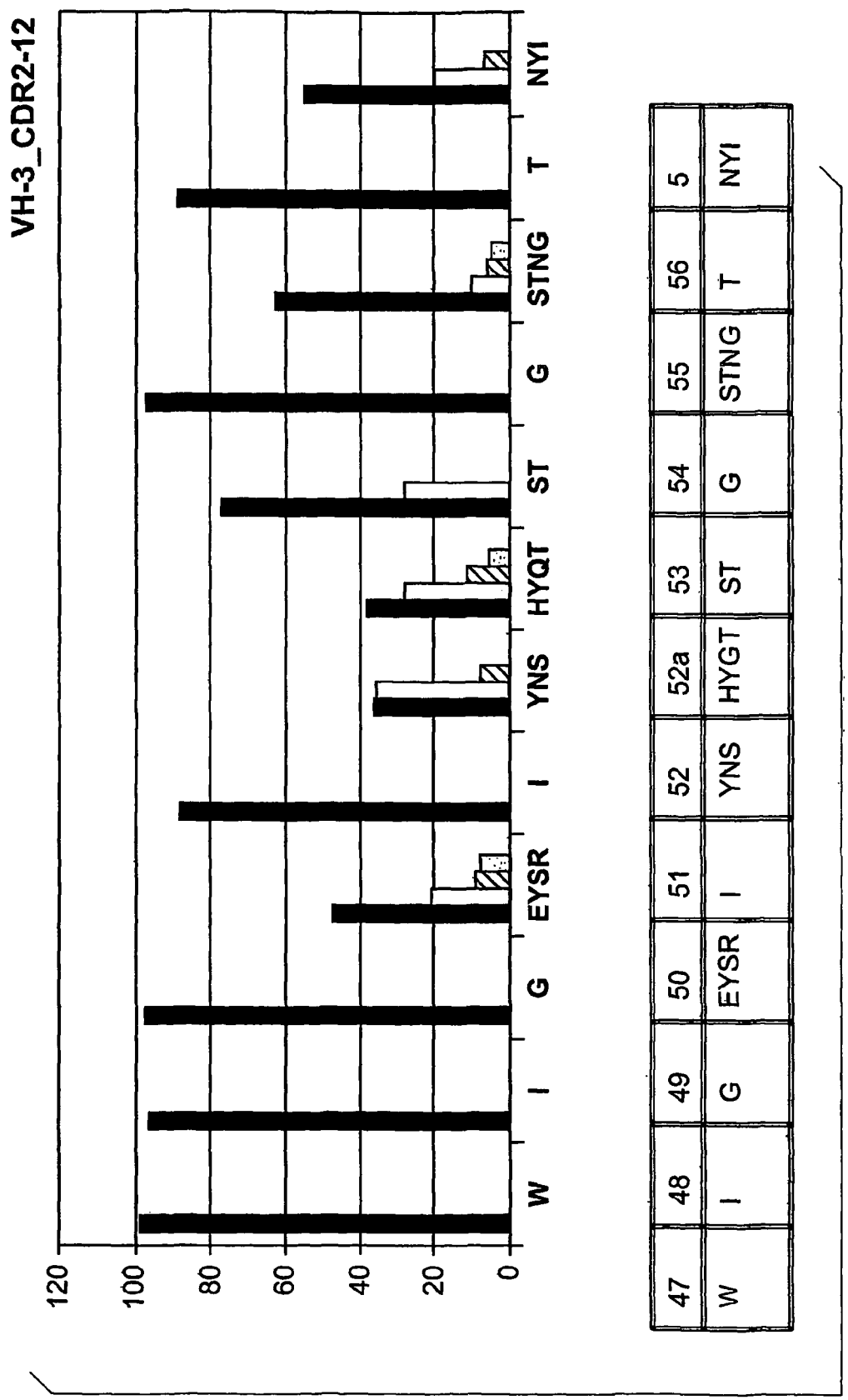
Figure 47B:
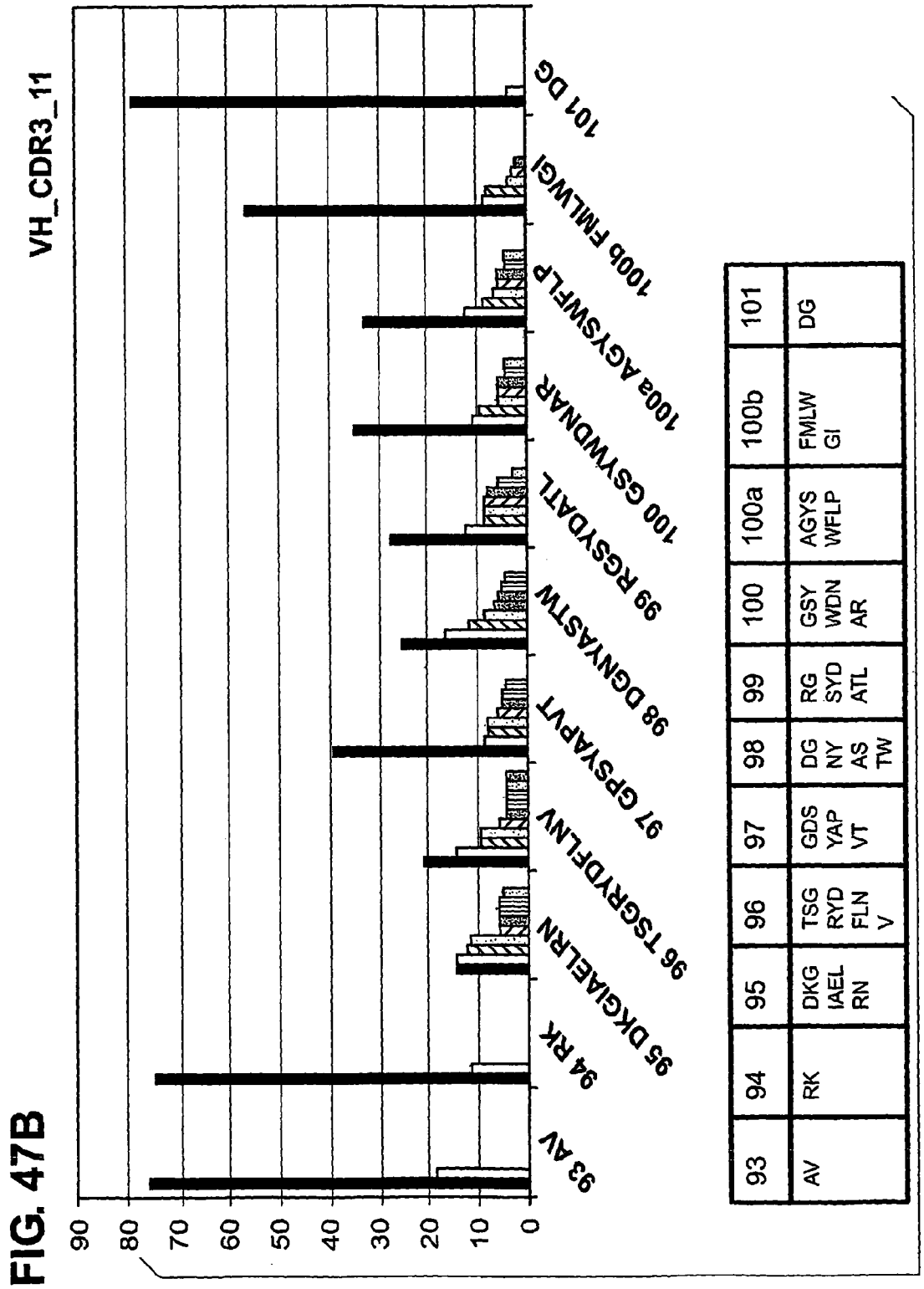
FIG. 47 shows the enumerated variability profiles of VH CDR3 length sizes 10 (panel A), and CDR3 length size 11 (panel B) as determined from the Kabat database of deposited immunological sequences. Irrespective of their original VH families, the VH CDR3 sequences were aligned according to Contact CDR definition for amino add profile enumeration. The vertical (Y) axis denotes the frequency of occurrence of particular VH CDR3 position amino acids. The generated VH CDR3 variability profiles (FIG. 44) then instructed the potential diversity that could be substituted at each VH CDR3 position of length sizes 10 and 11.
Figure 48A:
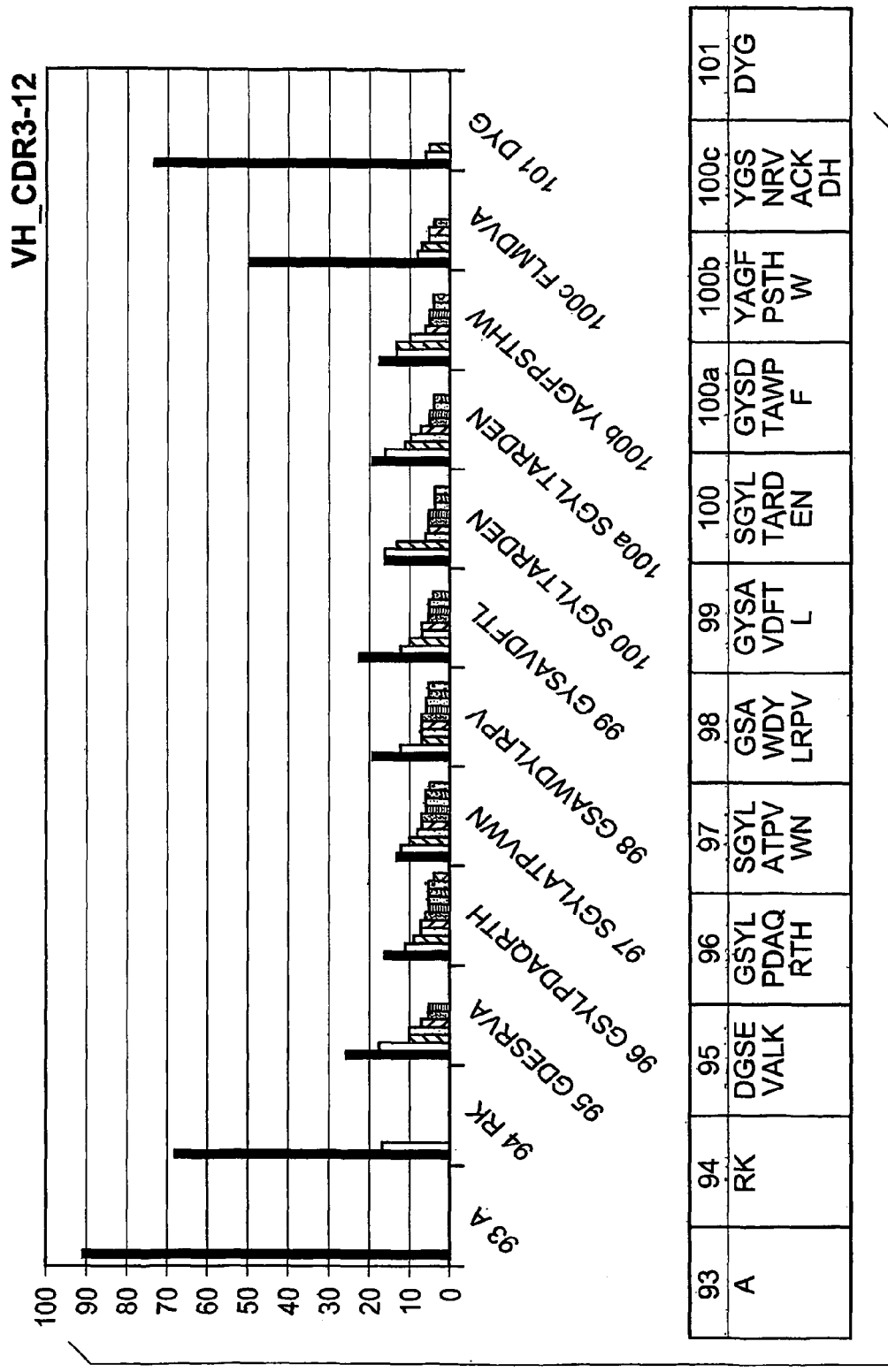
FIG. 48 shows the enumerated variability profiles of VH CDR3 length sizes 12 (panel A), and CDR3 length size 13 (panel B) as determined from the Kabat database of deposited immunological sequences. Irrespective of their original VH families, the VH CDR3 sequences were aligned according to Contact CDR definition for amino acid profile enumeration. The vertical (Y) axis denotes the frequency of occurrence of particular VH CDR3 position amino acids. The generated VH CDR3 variability profiles (FIG. 44) then instructed the potential diversity that could be substituted at each VH CDR3 position of length sizes 12 and 13.
Figure 48B:
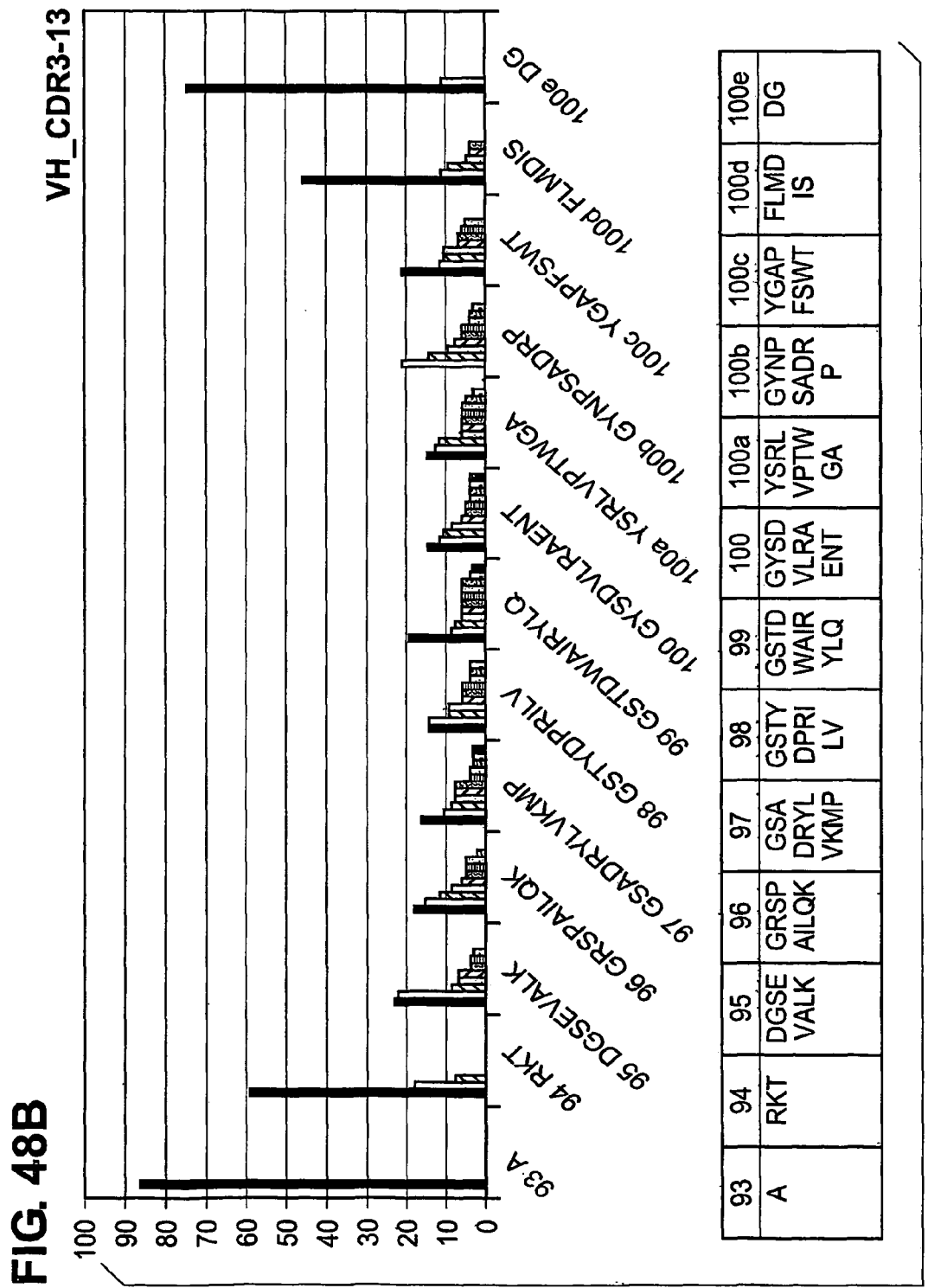
Figure 49A:
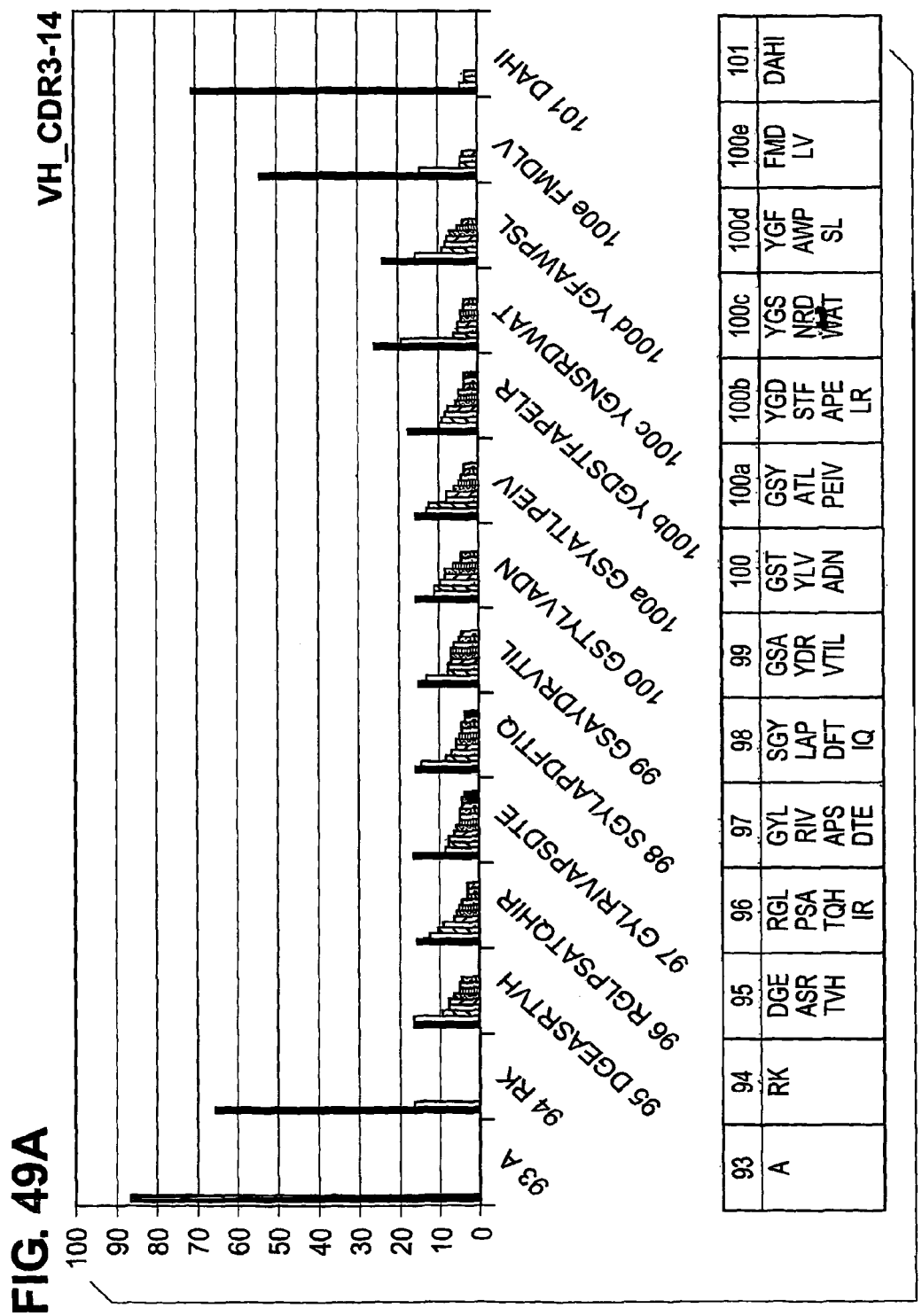
FIG. 49 shows the enumerated variability profiles of VH CDR3 length sizes 14 (panel A), and CDR3 length size 15 (panel B) as determined from the Kabat database of deposited immunological sequences. Irrespective of their original VH families, the VH CDR3 sequences were aligned according to Contact CDR definition for amino acid profile enumeration. The vertical (Y) axis denotes the frequency of occurrence of particular VH CDR3 position amino acids. The generated VH CDR3 variability profiles (FIG. 44) then instructed the potential diversity that could be substituted at each VH CDR3 position of length sizes 14 and 15.
Figure 49B:
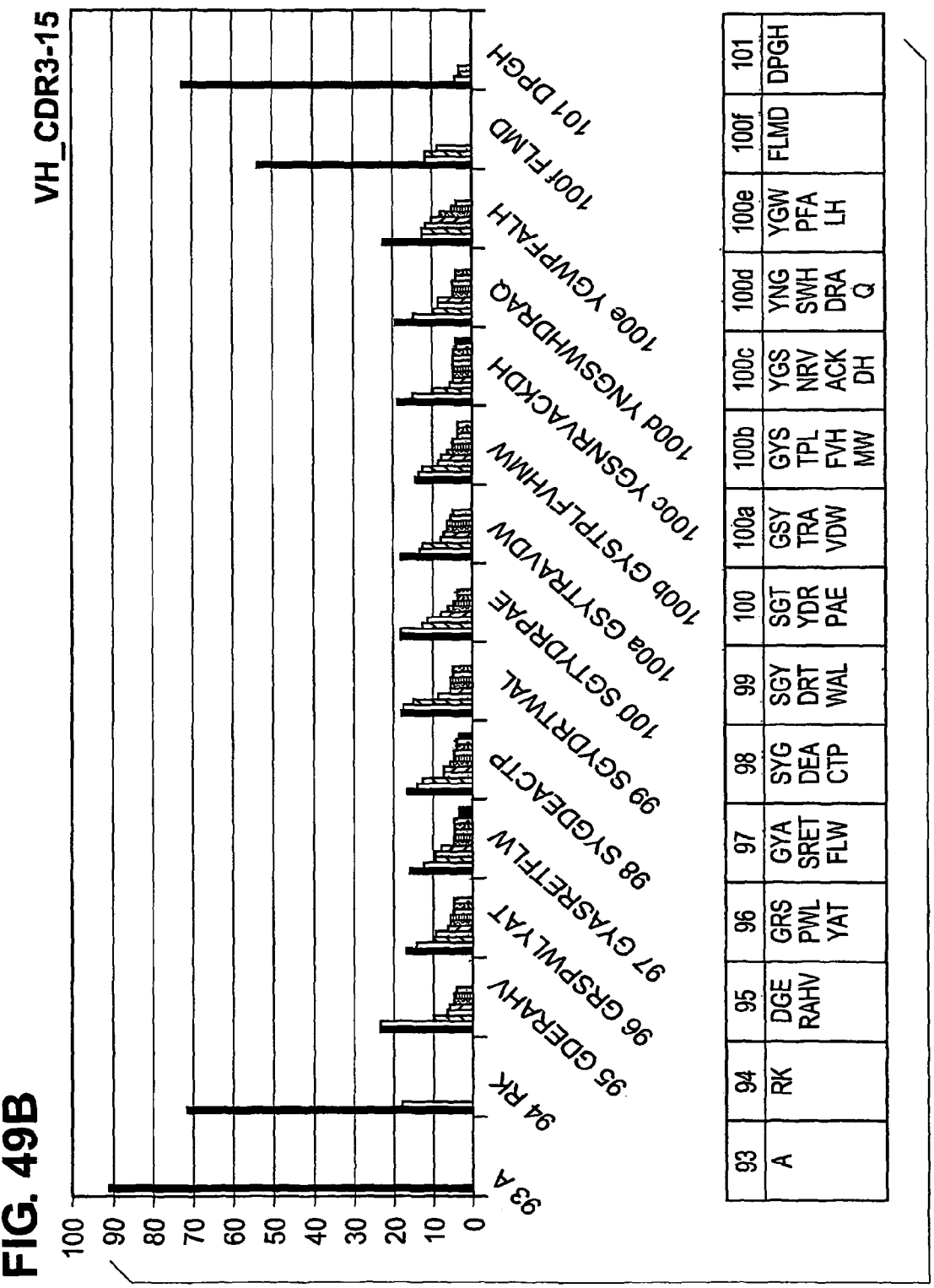
Figure 50A:
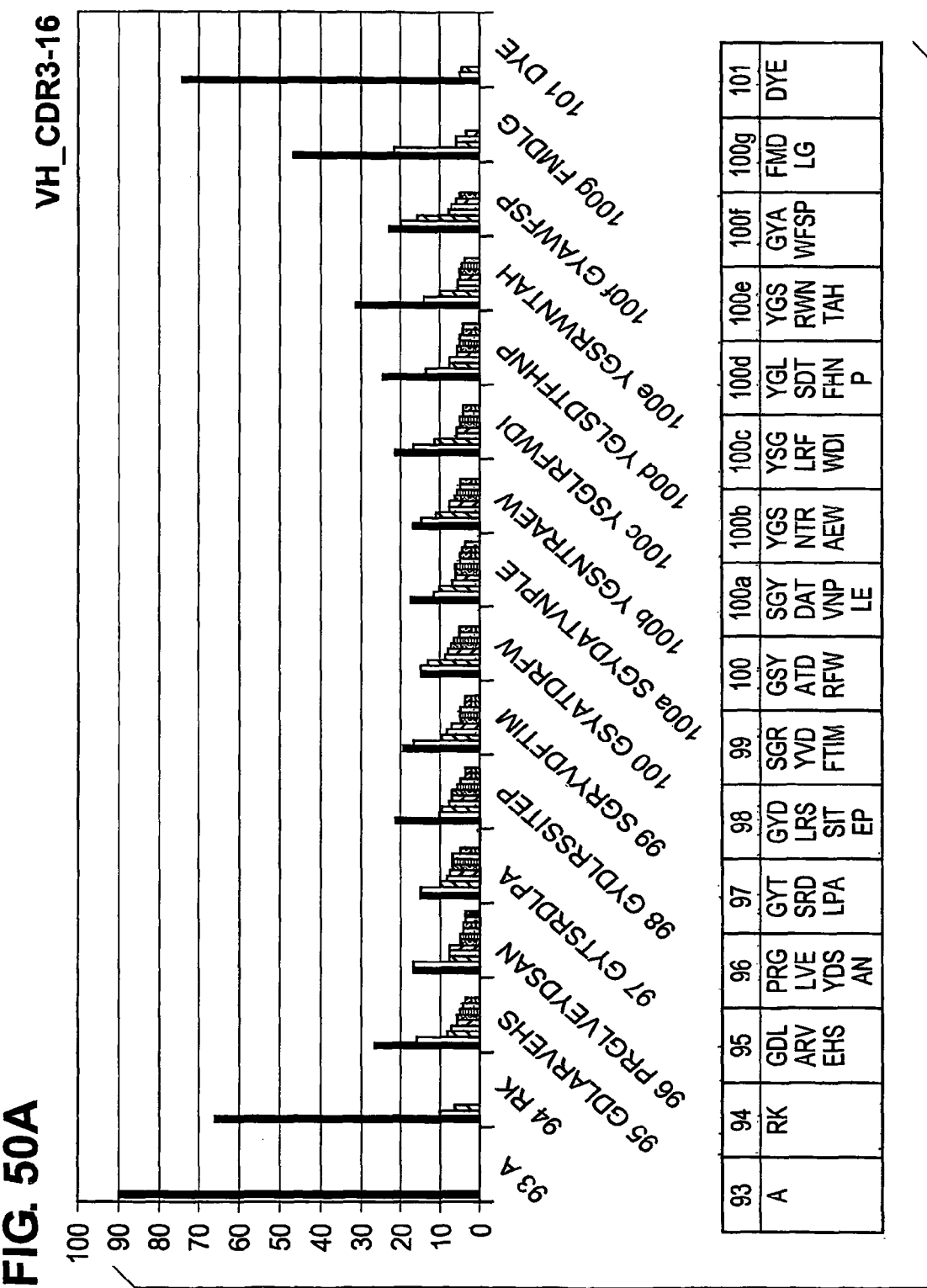
FIG. 50 shows the enumerated variability profiles of VH CDR3 length sizes 16 (panel A), and CDR3 length size 17 (panel B) as determined from the Kabat database of deposited immunological sequences. Irrespective of their original VH families, the VH CDR3 sequences were aligned according to Contact CDR definition for amino acid profile enumeration. The vertical (Y) axis denotes the frequency of occurrence of particular VH CDR3 position amino acids. The generated VH CDR3 variability profiles (FIG. 44) then instructed the potential diversity that could be substituted at each VH CDR3 position of length sizes 16 and 17.
Figure 50B:
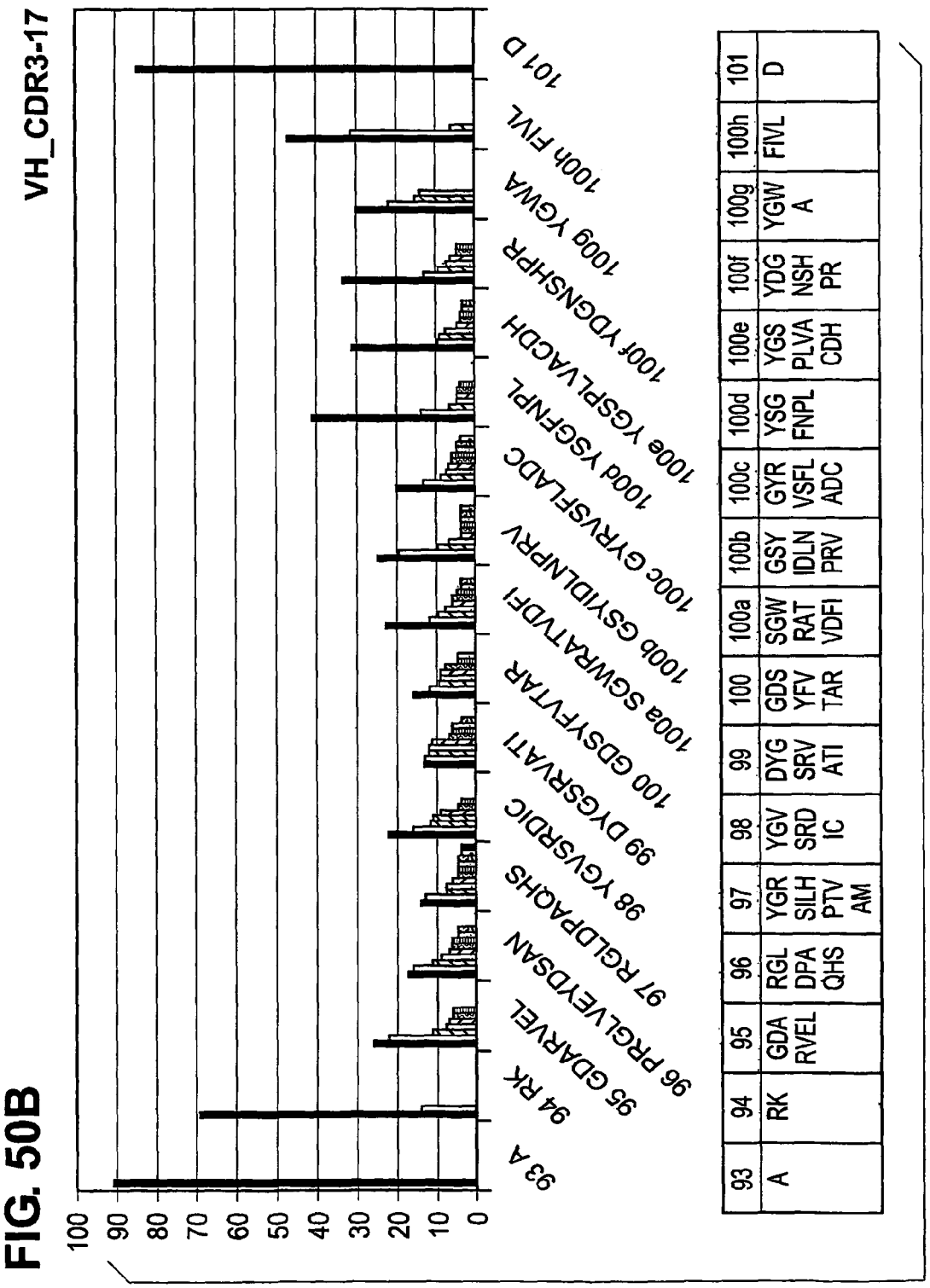
Figure 51A:
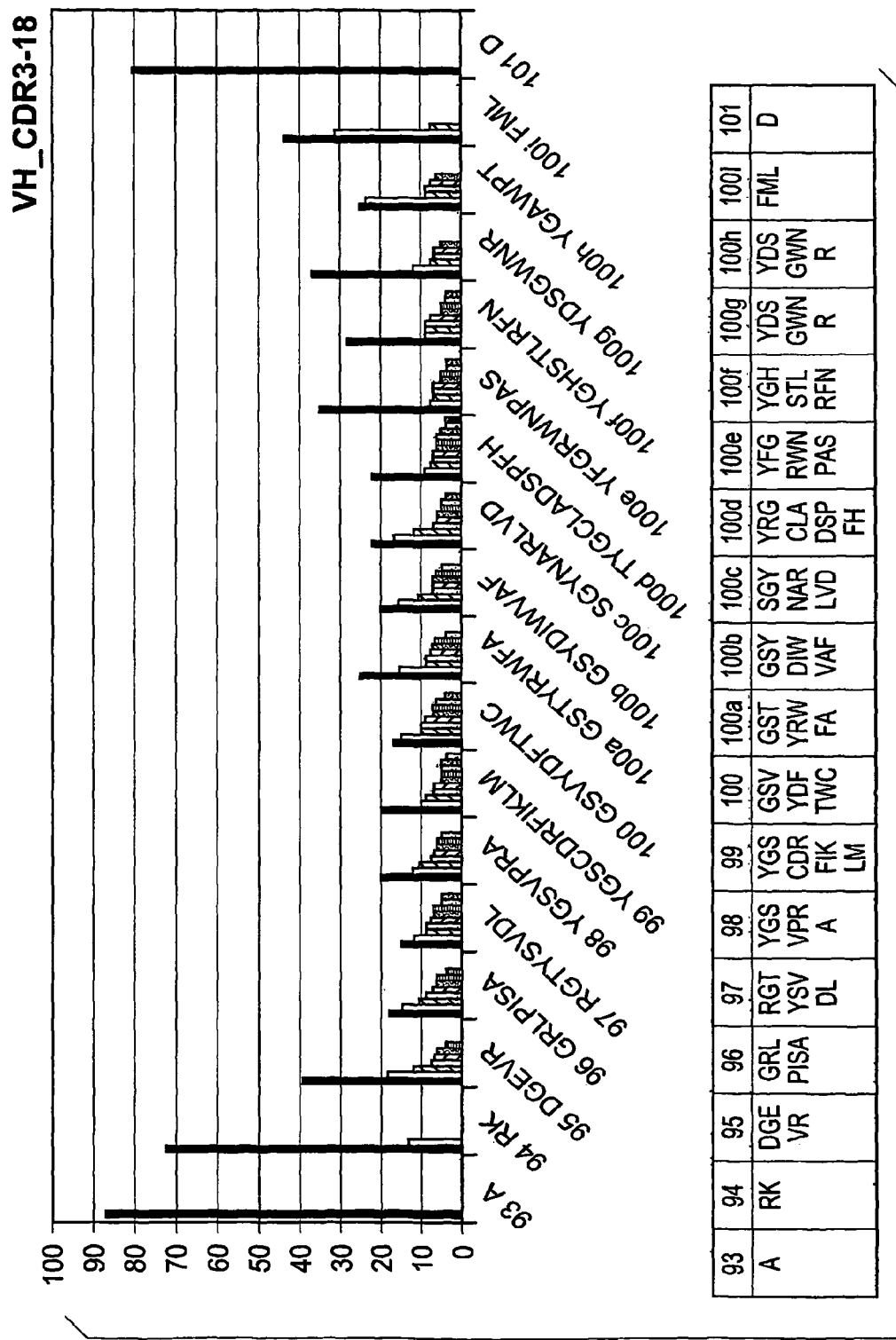
FIG. 51 shows the enumerated variability profiles of VH CDR3 length sizes 18 (panel A), and CDR3 length size 19 (panel B) as determined from the Kabat database of deposited immunological sequences. Irrespective of their original VH families, the VH CDR3 sequences were aligned according to Contact CDR definition for amino acid profile enumeration. The vertical (Y) axis denotes the frequency of occurrence of particular VH CDR3 position amino acids. The generated VH CDR3 variability profiles (FIG. 44) then instructed the potential diversity that could be substituted at each VH CDR3 position of length sizes 18 and 19.
Figure 51B:
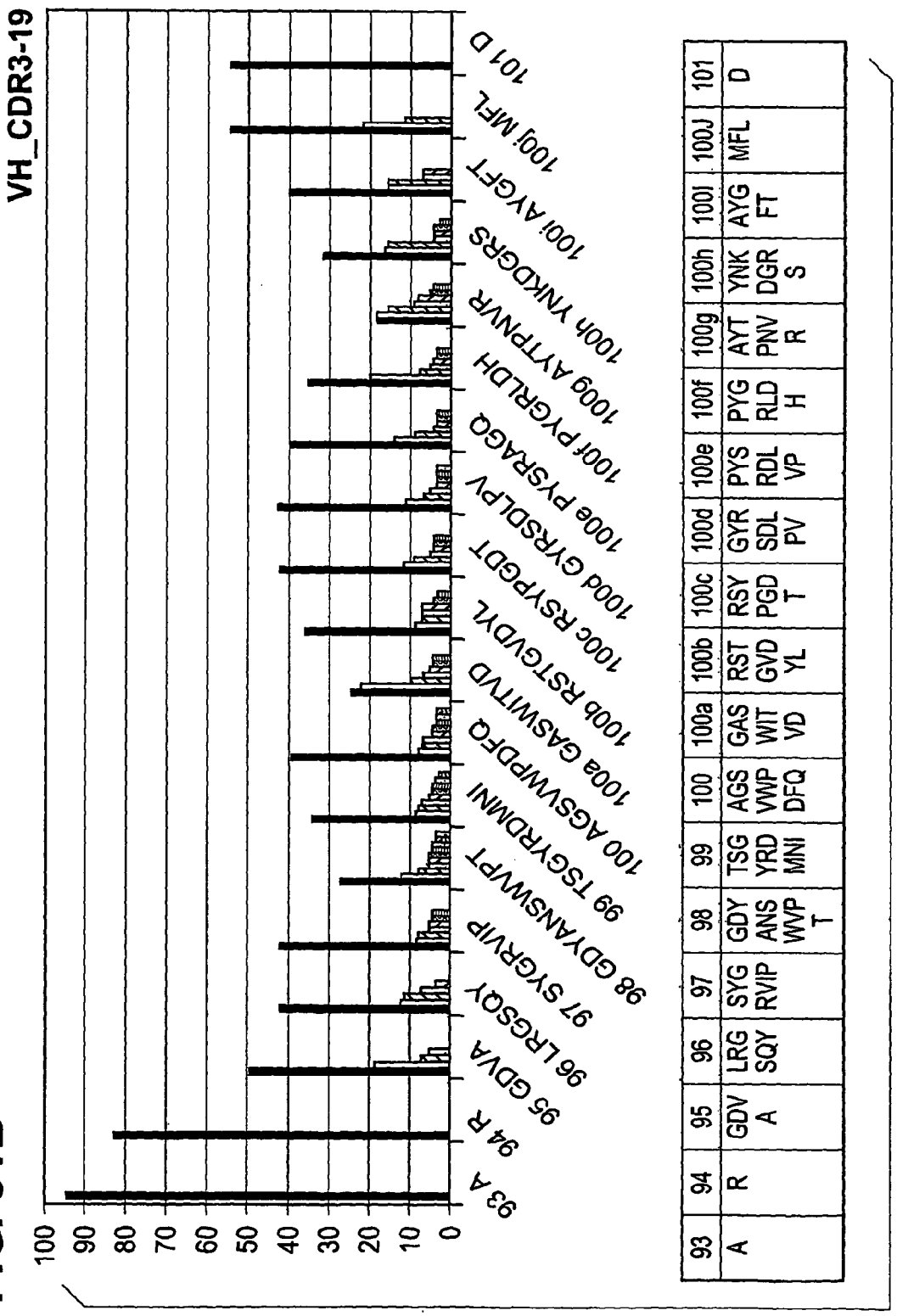
Figure 52:
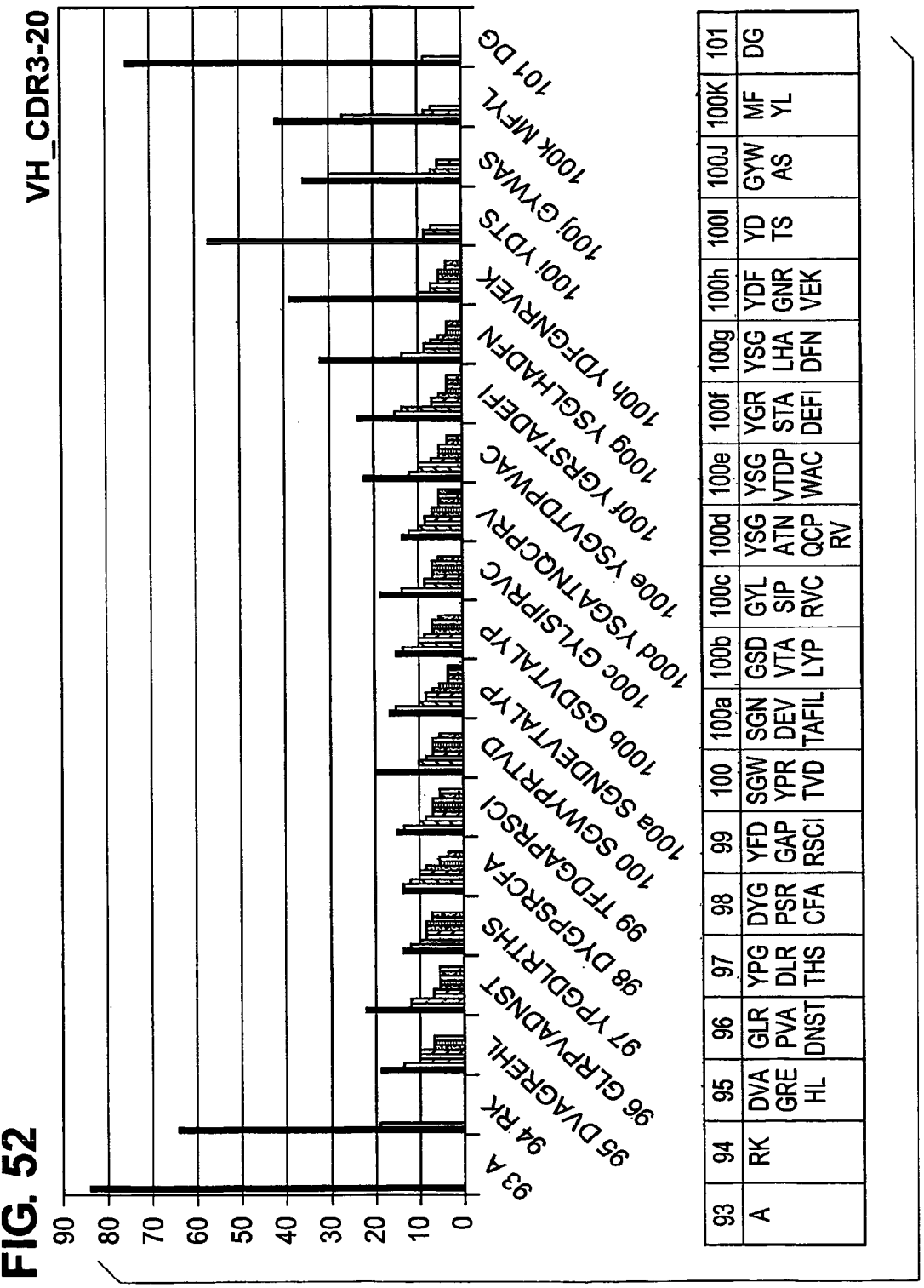
FIG. 52 shows the enumerated variability profiles of VH CDR3 length size 20 as determined from the Kabat database of deposited immunological sequences. Irrespective of their original VH families, the VH CDR3 sequences were aligned according to Contact CDR definition for amino acid profile enumeration. The vertical (Y) axis denotes the frequency of occurrence of particular VH CDR3 position amino acids. The generated VH CDR3 variability profiles (FIG. 44) then instructed the potential diversity that could be substituted at each VH CDR3 position of length size 20.

In contrast, when "similarity" criteria was used, cohort library diversity was reduced, as it was more likely to find a substitutable amino acid also belonging in the predetermined (e.g. aliphatic, polar, etc) groups. Thus, the database for FIG. 46 illustrates the VP sequence differences between VH1, VH3, and VH4 for CDR2 length 13. Another embodiment of the invention used to collect an even broader VP profile was to derive a general VH CDR2. The basic idea was to avoid pre-dividing based on the various VH1, VH3, VH4, and other subfamilies, and instead simply assemble all the VH CDR2 sequences of length 13 for enumeration. CDR blasting with the VP of VH CDR2_13 then obviated the need to perform CDR2 cross designs of the various VH1, VH3, and VH4 cohort libraries, as nearly all possible combinations could be generated in one larger cohort library.

This idea of a general VP assembly was what occurred in VH CDR3, where the eventual expressed CDR3 sequences could not be specifically assigned to originating sub-families. FIGS. 47-52 demonstrate the VPs of VH CDR3 of length sizes 10 to 20.

Figure 53:
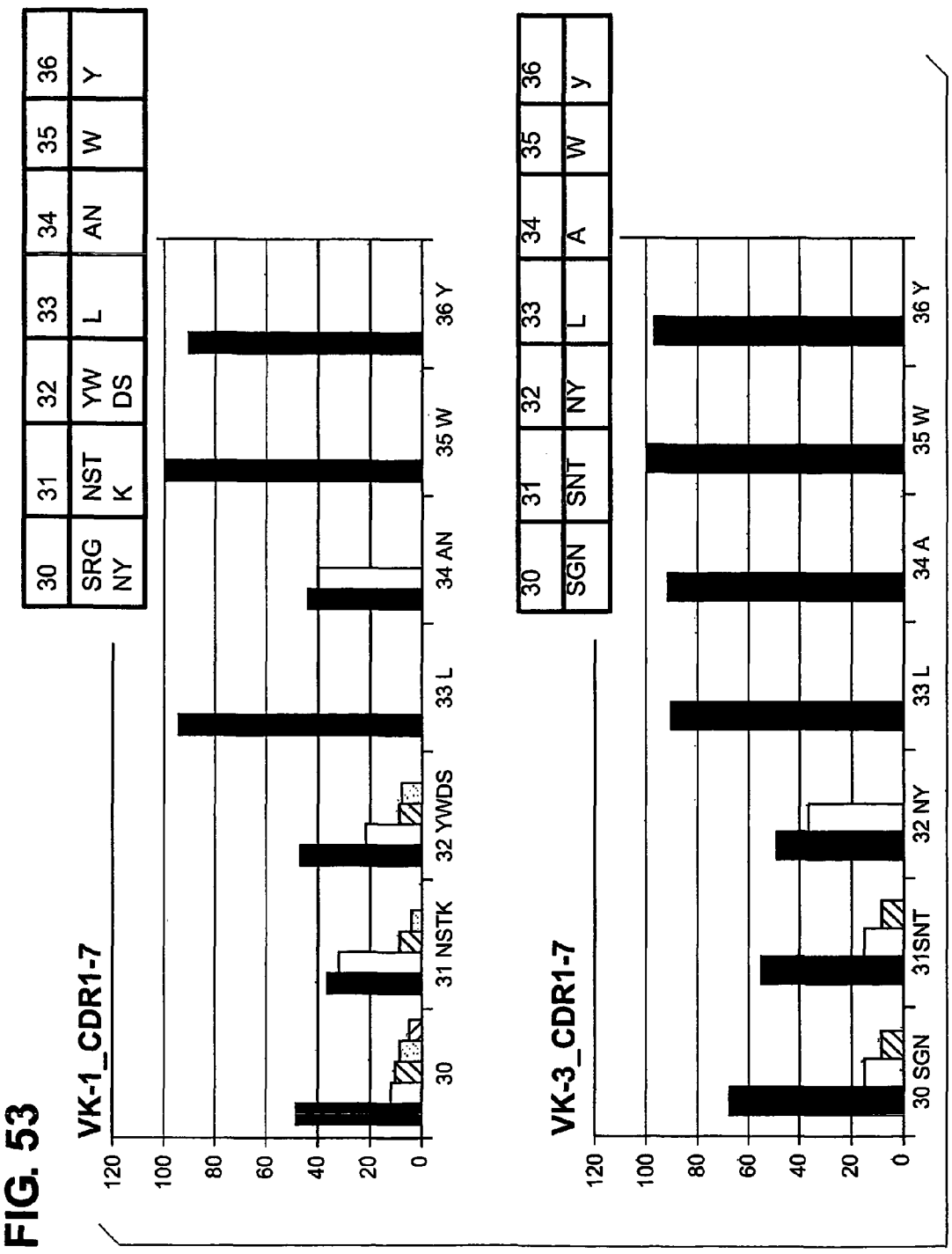
FIG. 53 shows the enumerated variability profiles of V kappa-1 (top panel) and V kappa-3 (bottom panel) CDR1 length size 7 as determined from the Kabat database of deposited immunological sequences. Irrespective of their original V kappa families, the V kappa CDR1 sequences were aligned according to Contact CDR definition for amino acid profile enumeration. The vertical (Y) axis denotes the frequency of occurrence of particular V kappa CDR1 position amino acids. The generated V kappa CDR1 variability profiles (FIG. 44, tabulated below each graph) then instructed the potential diversity that could be substituted at each V kappa CDR1 position of length size 7. VK-3_CDR1-7 sequence disclosed as SEC ID NO: 167.
Figure 54A:
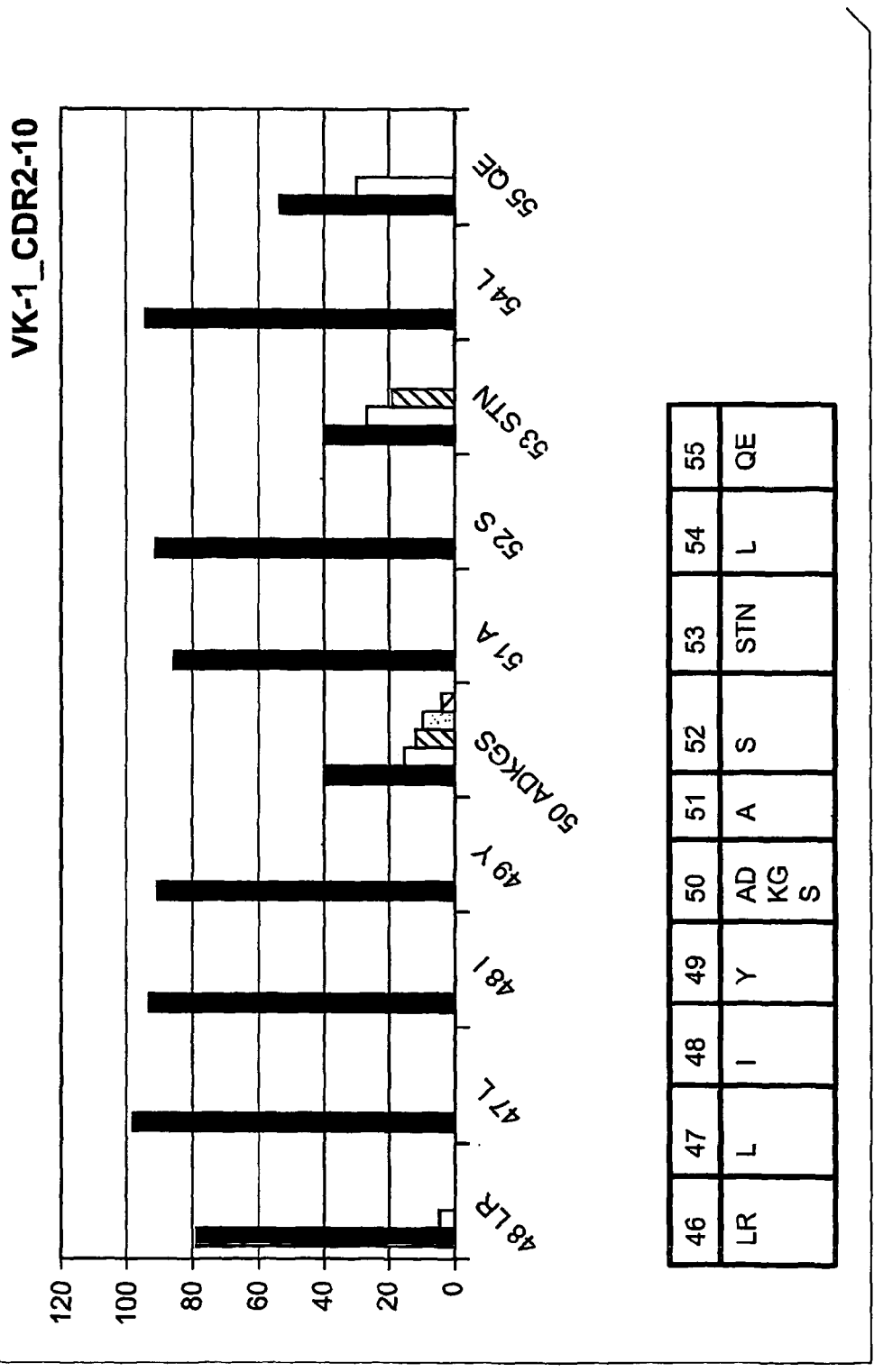
FIG. 54 shows the enumerated variability profiles of V kappa-1 (SEQ ID NO: 276) (panel A) and V kappa-3 (SEQ ID NO: 278) (panel B) CDR2 length size 10 as determined from the Kabat database of deposited immunological sequences. Irrespective of their original V kappa families, the V kappa CDR2 sequences were aligned according to Contact CDR definition for amino acid profile enumeration. The vertical (Y) axis denotes the frequency of occurrence of particular V kappa CDR2 position amino acids. The generated V kappa CDR2 variability profiles (FIG. 44, tabulated below each graph) then instructed the potential diversity that could be substituted at each V kappa CDR1 position of length size 10.
Figure 54B:
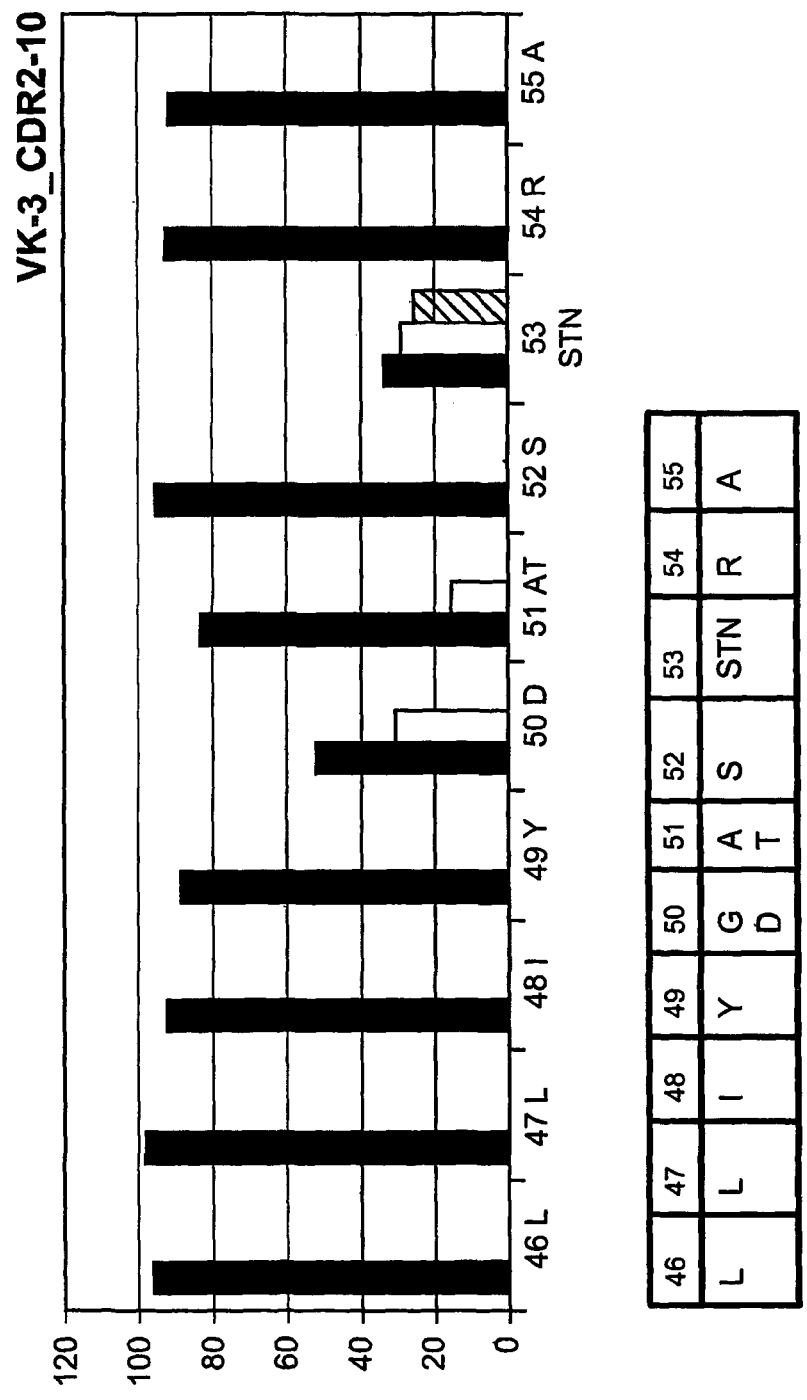
Figure 55A:
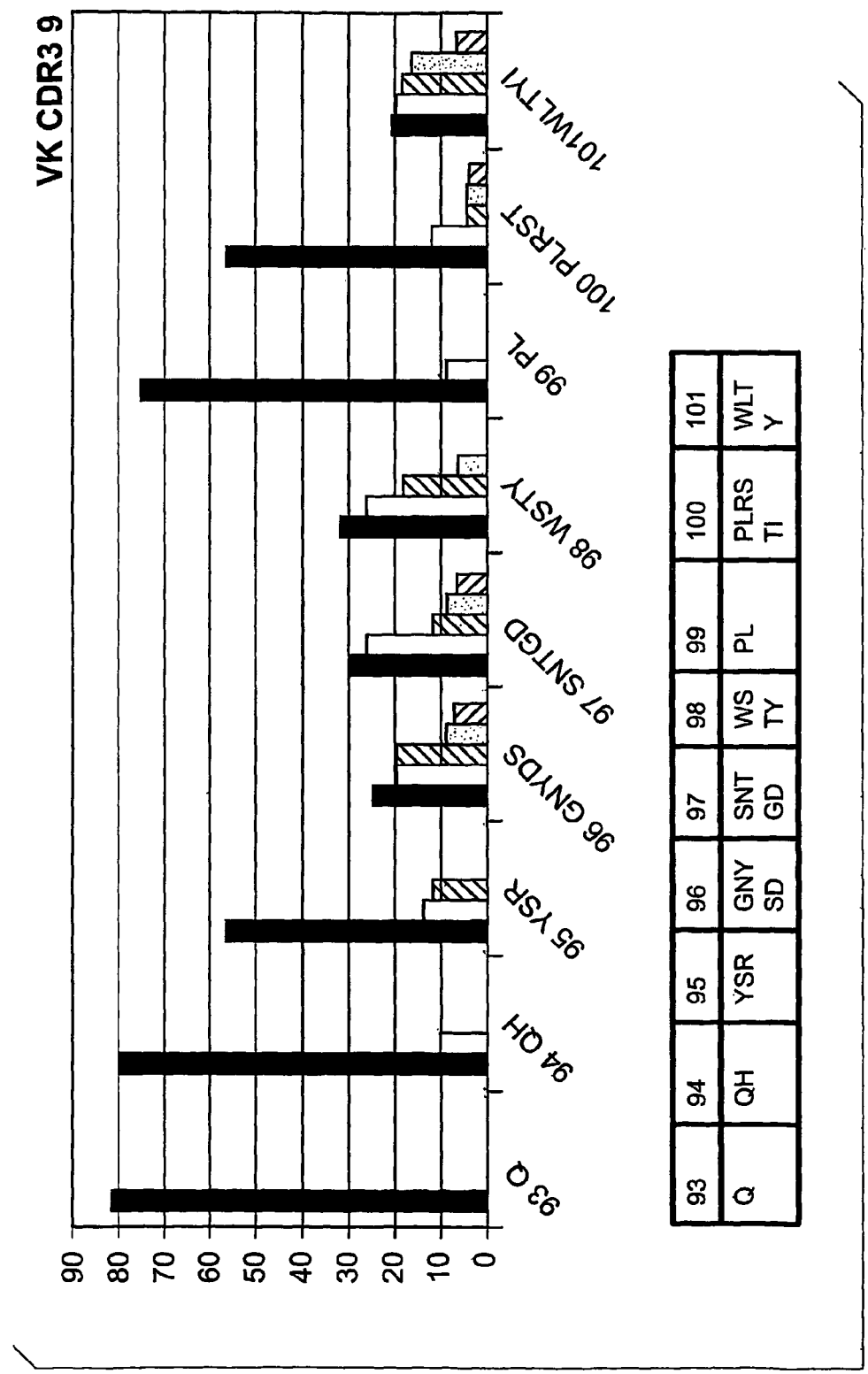
FIG. 55 shows the enumerated variability profiles of Vkappa (panel A) and Vlambda (panel B) CDR3 length size 9 as determined from the Kabat database of deposited immunological sequences. Irrespective of their original Vkappa and Vlambda sub-families, the CDR3 sequences were aligned according to Contact CDR definition for amino acid profile enumeration. The vertical (Y) axis denotes the frequency of occurrence of particular VL CDR3 position amino acids The generated Vkappa and Vlambda CDR3 variability profiles (FIG. 44, tabulated below each graph) then instructed the potential diversity that could be substituted at each VL CDR3 position of length size 9.
Figure 55B:
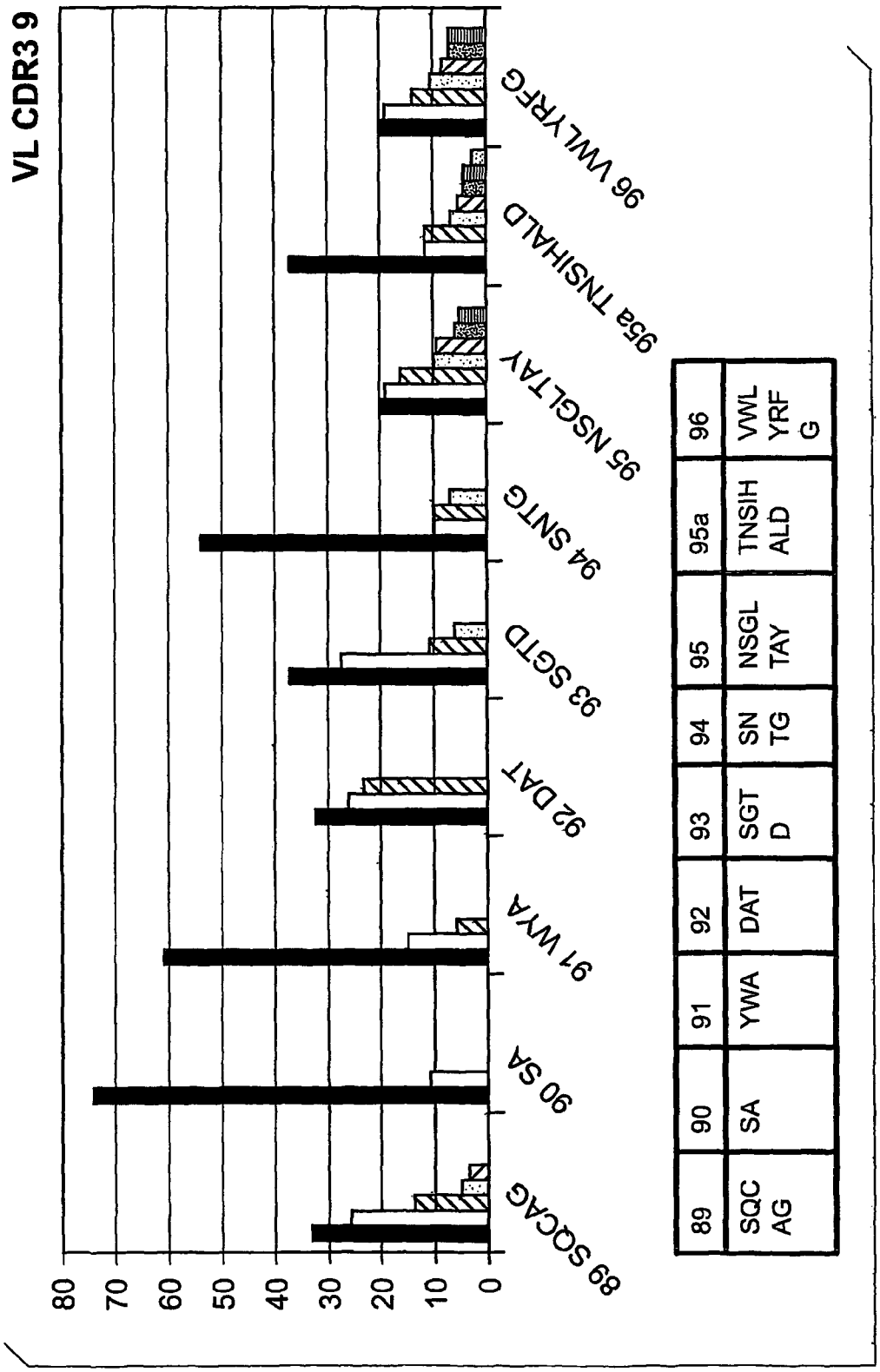
Figure 56A:
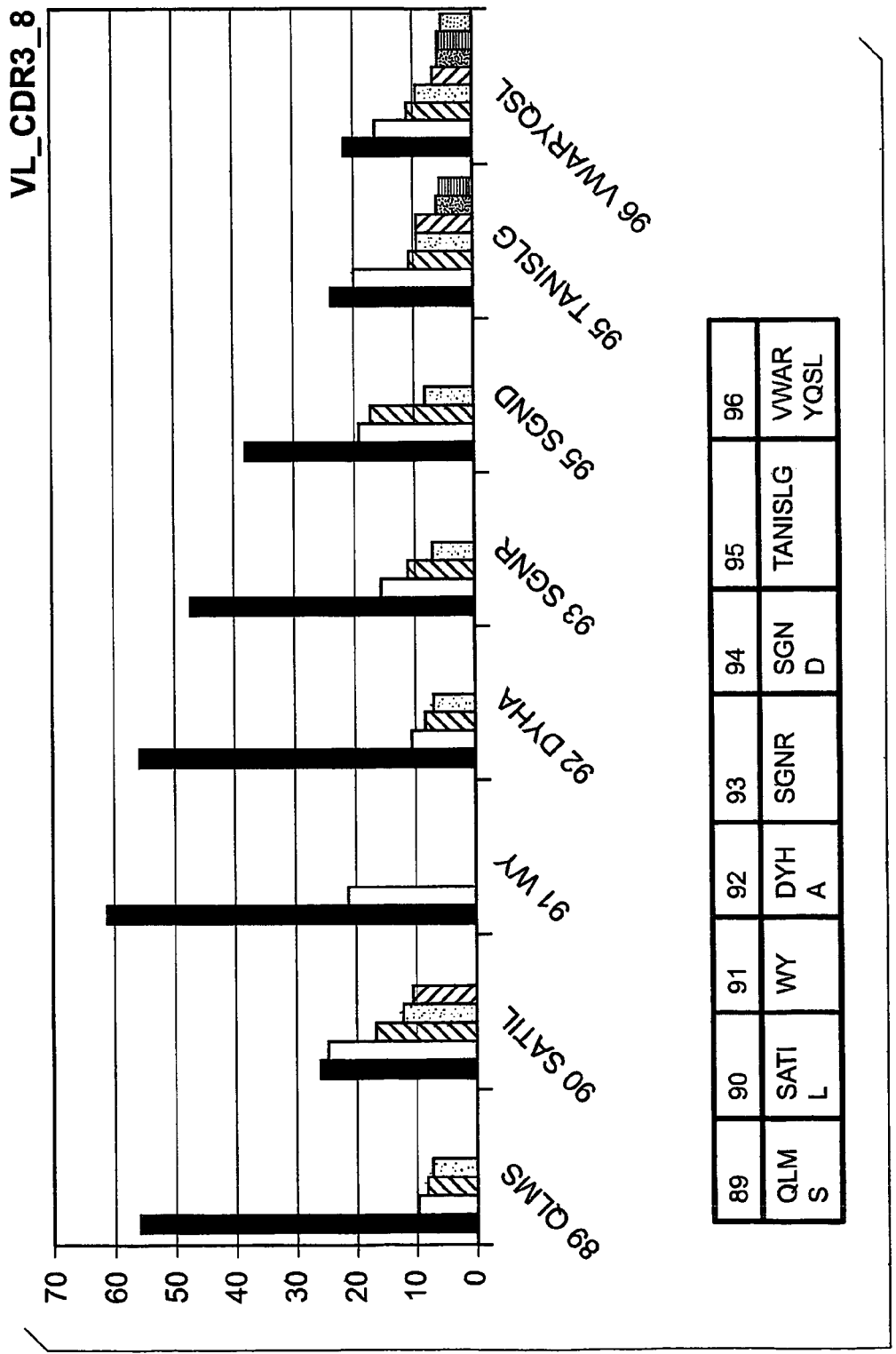
FIG. 56 shows the enumerated variability profiles of VL (both kappa and lambda) CDR3 length size 8 (panel A) and CDR3 length size 10 (panel B) as determined from the Kabat database of deposited immunological sequences. Irrespective of their original Vkappa and Vlambda families, the CDR3 sequences were aligned according to Contact CDR definition for amino acid profile enumeration. The vertical (Y) axis denotes the frequency of occurrence of particular VL CDR3 position amino acids. The generated VL CDR3 variability profiles (FIG. 44, tabulated below each graph) then instructed the potential diversity that could be substituted at each VL CDR3 position for length sizes 8 and 10.
Figure 56B:
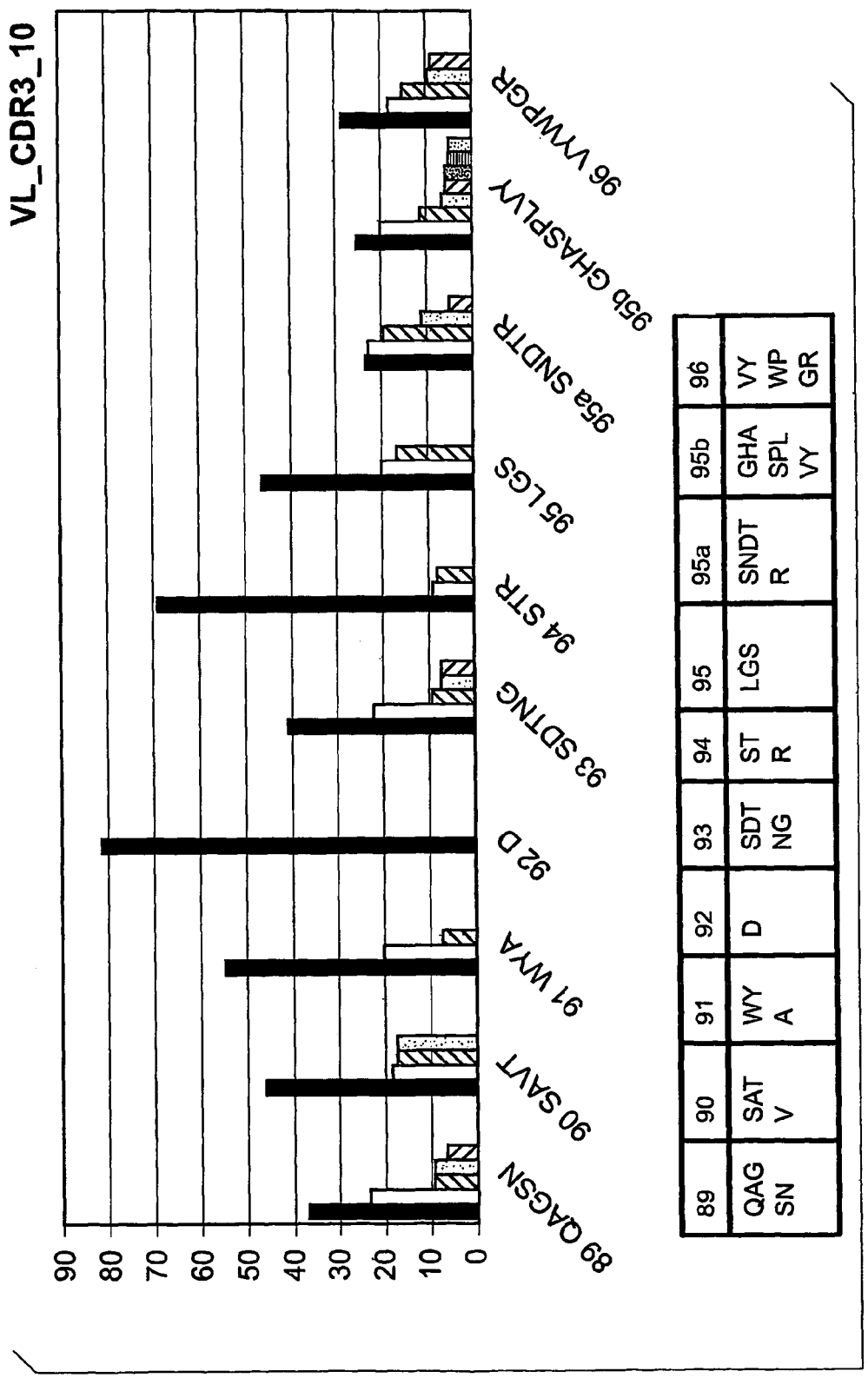
Figure 57:
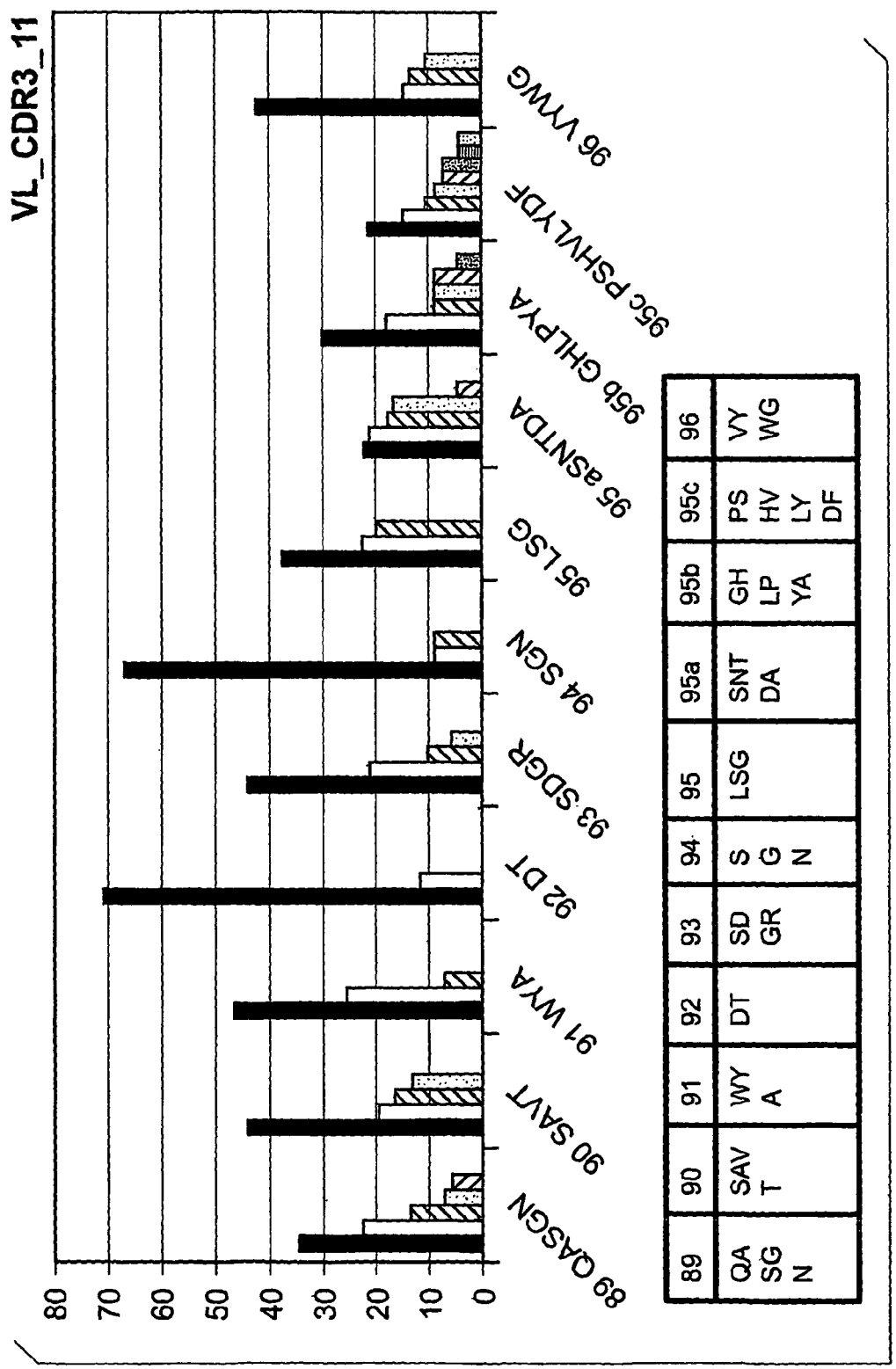
FIG. 57 shows the enumerated variability profiles of VL (both kappa and lambda) CDR3 length size 11 as determined from the Kabat database of deposited immunological sequences. Irrespective of their original Vkappa and Vlambda families, the CDR3 sequences were aligned according to Contact CDR definition for amino acid profile enumeration. The vertical (Y) axis denotes the frequency of occurrence of particular VL CDR3 position amino acids. The generated VL CDR3 variability profiles (FIG. 44, tabulated below each graph) then instructed the potential diversity that could be substituted at each VL CDR3 position for length size 11.

The same analyses were also performed with respect to VL kappa and lambda. In FIG. 53, the difference in the VPs of CDR1 length 7 between $V_k1$ and $V_k3$ are illustrated. FIG. 54 illustrates the VPs of CDR2 length 10 between $V_k1$ and $V_k3$. For FIG. 55, the VPs of CDR3 length 9 were derived for Vkappa and Vlambda. FIGS. 56 and 57 also demonstrate the broader Vlambda VPs of CDR3 length 8, 10 and 11 derived from the UAL database.

EQUIVALENTS

Those skilled in the art will recognize, or be able to ascertain using no more than routine experimentation, many equivalents to the specific embodiments of the invention described herein. Such equivalents are intended to be encompassed by the following claims.

---

The invention claimed is:

1. A method of producing a library of polynucleotides encoding at least one complementarity determining region (CDR), wherein the method comprises:

(a) determining the CDR amino acid sequence variation present in a reference antibody library that comprises naturally-occurring CDR amino acid regions, wherein the CDR sequence variation is determined at each amino acid residue position of the CDR;

(b) aligning a query CDR peptide sequence from an antibody against a target antigen with the CDR sequences of a reference antibody library; and (c) synthesizing a library of polynucleotides encoding CDR sequences, wherein for the majority of library CDR sequences synthesized:

(i) the amino acid residue encoded at any single position within a CDR sequence is identical to an amino acid residue at the corresponding aligned position of the query CDR peptide sequence from an antibody against a candidate antigen; or (ii) is a predetermined amino acid residue(s) if an identical amino acid residue for the query CDR peptide sequence at the position being aligned does not occur in the reference library;

wherein the library of polynucleotides encodes CDR analogs comprising CDR-HI, CDR-H2, and CDR-H3 sequences as shown in any of CDR-H1, CDR-H2, and CDR-H3 cohort library sequences, respectively, in any of FIG. 13 and FIG. 16-27; and wherein the library of polynucleotides encodes CDR analogs comprising CDR-L1, CDR-L2, and CDR-L3 sequences as shown in any of CDR-L1, CDR-L2, CDR-L3 cohort library sequences, respectively, in any of FIG. 13 and FIG. 16-27; and whereby a library of polynucleotides is provided that encodes CDR analogs of the query CDR peptide sequence from an antibody against a target antigen, the CDR analogs being enriched for naturally occurring amino acid residues at one or more residue positions.

2. The method of claim 1:

wherein the predetermined amino acid residue is (i) a small side chain amino acid residue selected from the group consisting of Glycine (G) and Alanine (A);

(ii) a nucleophilic side chain amino acid residue selected from the group consisting of Serine (S), Threonine (T), Cysteine (C), and Histidine (H);

(iii) a hydrophobic side chain amino acid residue selected from the group consisting of Valine (V), Leucine (L), Isoleucine (I), Methionine (M), and Proline (P);

(iv) an aromatic side chain amino acid residue selected from the group consisting of Phenylalanine (F), Tyrosine (Y), and Tryptophan (W);

(v) an acidic side chain amino acid residue selected from the group consisting of Aspartate (D), and Glutamate (E);

(vi) an amide side chain amino acid residue selected from the group consisting of Asparagine (N) and Glutamine (Q); and/or (vii) a basic side chain amino acid residue selected from the group consisting of Lysine (K), and Arginine (R).

* * * * *